(12) United States Patent
Corkey et al.

(10) Patent No.: US 9,682,998 B2
(45) Date of Patent: Jun. 20, 2017

(54) FUSED HETEROCYCLIC COMPOUNDS AS ION CHANNEL MODULATORS

(71) Applicant: Gilead Sciences, Inc., Foster City, CA (US)

(72) Inventors: Britton Kenneth Corkey, Redwood City, CA (US); Elfatih Elzein, Fremont, CA (US); Michael Graupe, Pacifica, CA (US); Juan Guerrero, Concord, CA (US); Robert H. Jiang, Cupertino, CA (US); Rao V. Kalla, Cupertino, CA (US); Tetsuya Kobayashi, Pleasanton, CA (US); Dmitry Koltun, Foster City, CA (US); Xiaofen Li, Mountain View, CA (US); Ruben Martinez, San Diego, CA (US); Gregory Notte, San Mateo, CA (US); Eric Q. Parkhill, San Francisco, CA (US); Thao Perry, San Jose, CA (US); Chandrasekar Venkataramani, Redwood City, CA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/188,701

(22) Filed: Jun. 21, 2016

(65) Prior Publication Data

US 2016/0362421 A1 Dec. 15, 2016

Related U.S. Application Data

(62) Division of application No. 14/808,296, filed on Jul. 24, 2015, now Pat. No. 9,403,782, which is a division
(Continued)

(51) Int. Cl.
| | |
|---|---|
| C07D 255/04 | (2006.01) |
| C07D 403/04 | (2006.01) |
| C07D 403/06 | (2006.01) |
| C07D 403/08 | (2006.01) |
| C07D 403/14 | (2006.01) |
| C07D 401/14 | (2006.01) |
| A61K 31/53 | (2006.01) |
| A61P 25/08 | (2006.01) |
| C07D 498/10 | (2006.01) |
| C07D 498/04 | (2006.01) |
| C07D 263/58 | (2006.01) |
| C07D 237/32 | (2006.01) |
| C07D 239/88 | (2006.01) |

(Continued)

(52) U.S. Cl.
CPC ......... *C07D 498/10* (2013.01); *C07D 217/26* (2013.01); *C07D 237/32* (2013.01); *C07D 239/88* (2013.01); *C07D 239/90* (2013.01); *C07D 253/08* (2013.01); *C07D 263/58* (2013.01); *C07D 265/22* (2013.01); *C07D 279/08* (2013.01); *C07D 401/04* (2013.01); *C07D 401/06* (2013.01); *C07D 401/12* (2013.01); *C07D 401/14* (2013.01); *C07D 403/04* (2013.01); *C07D 403/06* (2013.01); *C07D 403/08* (2013.01); *C07D 403/12* (2013.01); *C07D 403/14* (2013.01); *C07D 405/12* (2013.01); *C07D 413/06* (2013.01); *C07D 413/12* (2013.01); *C07D 413/14* (2013.01); *C07D 417/06* (2013.01); *C07D 417/12* (2013.01); *C07D 417/14* (2013.01); *C07D 498/04* (2013.01)

(58) Field of Classification Search
CPC .............................. C07D 255/04; A61K 31/53
USPC ........................................... 544/183; 514/243
See application file for complete search history.

(56) References Cited

U.S. PATENT DOCUMENTS

| | | | |
|---|---|---|---|
| 2,826,575 A | 3/1958 | Rigterink | |
| 2,867,618 A | 1/1959 | Rigterink | |

(Continued)

FOREIGN PATENT DOCUMENTS

| | | |
|---|---|---|
| CA | 2068255 A1 | 11/1992 |
| CN | 1735605 A | 2/2006 |

(Continued)

OTHER PUBLICATIONS

Baldwin et al. Bioorganic & Medicinal Chemistry Letters 18 (2008) 5285-5289.*

(Continued)

*Primary Examiner* — Venkataraman Balasubramanian
(74) *Attorney, Agent, or Firm* — Francis O. Ginah

(57) ABSTRACT

The present disclosure relates to compounds that are sodium channel inhibitors and to their use in the treatment of various disease states, including cardiovascular diseases and diabetes. In particular embodiments, the structure of the compounds is given by Formula I:

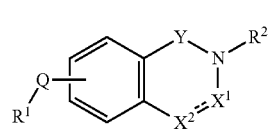

wherein Q, $R^1$, $X^1$, $X^2$, Y and $R^2$ are as described herein, to methods for the preparation and use of the compounds and to pharmaceutical compositions containing the same.

12 Claims, No Drawings

Related U.S. Application Data of application No. 13/466,995, filed on May 8, 2012, now Pat. No. 9,115,096.

(60) Provisional application No. 61/503,543, filed on Jun. 30, 2011, provisional application No. 61/484,500, filed on May 10, 2011.

(51) Int. Cl.

| | | |
|---|---|---|
| C07D 239/90 | (2006.01) | |
| C07D 253/08 | (2006.01) | |
| C07D 265/22 | (2006.01) | |
| C07D 401/04 | (2006.01) | |
| C07D 401/06 | (2006.01) | |
| C07D 401/12 | (2006.01) | |
| C07D 403/12 | (2006.01) | |
| C07D 405/12 | (2006.01) | |
| C07D 413/06 | (2006.01) | |
| C07D 413/14 | (2006.01) | |
| C07D 417/06 | (2006.01) | |
| C07D 417/14 | (2006.01) | |
| C07D 217/26 | (2006.01) | |
| C07D 413/12 | (2006.01) | |
| C07D 279/08 | (2006.01) | |
| C07D 417/12 | (2006.01) | |

(56) References Cited

U.S. PATENT DOCUMENTS

| | | |
|---|---|---|
| 3,441,649 A | 4/1969 | Bacaner |
| 3,483,193 A | 12/1969 | Gall et al. |
| 3,594,372 A | 7/1971 | Santilli et al. |
| 4,062,881 A | 12/1977 | Kugele |
| 4,230,705 A | 10/1980 | Allen, Jr. et al. |
| 4,242,515 A | 12/1980 | Trust et al. |
| 4,244,953 A | 1/1981 | Trust et al. |
| 4,326,525 A | 4/1982 | Swanson et al. |
| 4,654,343 A | 3/1987 | Albright et al. |
| 4,746,655 A | 5/1988 | Cale, Jr. |
| 4,812,565 A | 3/1989 | Cale, Jr. |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hseih |
| 5,565,449 A | 10/1996 | Blackburn et al. |
| 5,616,345 A | 4/1997 | Geoghegan et al. |
| 5,773,186 A * | 6/1998 | Takashima ............ G03C 1/002 430/138 |
| 5,939,412 A | 8/1999 | Bondinell et al. |
| 6,011,150 A | 1/2000 | Iwasaki et al. |
| 6,579,875 B1 | 6/2003 | Carling et al. |
| 6,908,917 B2 | 6/2005 | Ortwine |
| 6,998,408 B2 | 2/2006 | Pinto |
| 7,005,523 B2 | 2/2006 | Dombroski et al. |
| 7,122,677 B2 | 10/2006 | Reichard et al. |
| 7,157,490 B2 | 1/2007 | Colandrea et al. |
| 7,306,631 B2 | 12/2007 | Glenn, Jr. et al. |
| 7,456,187 B2 | 11/2008 | Ford et al. |
| 7,572,807 B2 | 8/2009 | Li et al. |
| 7,579,348 B2 | 8/2009 | Wang et al. |
| 7,790,741 B2 | 9/2010 | Calderwood et al. |
| 8,212,041 B2 | 7/2012 | Albrecht et al. |
| 8,252,810 B2 | 8/2012 | Ozaki et al. |
| 8,389,500 B2 | 3/2013 | Abelman et al. |
| 8,586,732 B2 | 11/2013 | Corkey et al. |
| 8,697,863 B2 | 4/2014 | Elzein et al. |
| 8,703,759 B2 | 4/2014 | Kobayashi et al. |
| 8,952,034 B2 | 2/2015 | Corkey et al. |
| 8,962,610 B2 | 2/2015 | Corkey et al. |
| 8,969,588 B2 | 3/2015 | Scott et al. |
| 9,079,901 B2 | 7/2015 | Kobayashi et al. |
| 9,115,096 B2 | 8/2015 | Corkey et al. |
| 9,139,570 B2 | 9/2015 | Mogalian et al. |
| 9,193,694 B2 | 11/2015 | Corkey et al. |
| 9,371,329 B2 | 6/2016 | Corkey et al. |
| 9,403,782 B2 | 8/2016 | Corkey et al. |
| 2004/0038974 A1 | 2/2004 | Ortwine |
| 2004/0063580 A1 | 4/2004 | Kuragano et al. |
| 2004/0204404 A1 | 10/2004 | Zelle et al. |
| 2004/0224959 A1 | 11/2004 | Ohkura et al. |
| 2004/0242572 A1* | 12/2004 | Stenkamp ............ C07C 233/78 514/227.2 |
| 2005/0239767 A1 | 10/2005 | Chan et al. |
| 2007/0066584 A1 | 3/2007 | Yao et al. |
| 2007/0066617 A1 | 3/2007 | Mita et al. |
| 2007/0142376 A1 | 6/2007 | Fleenor et al. |
| 2007/0249598 A1 | 10/2007 | Wang et al. |
| 2008/0176830 A1 | 7/2008 | Adams et al. |
| 2008/0293939 A1 | 11/2008 | Culshaw et al. |
| 2009/0012095 A1 | 1/2009 | Zelle et al. |
| 2009/0069300 A1 | 3/2009 | Zhou et al. |
| 2009/0124612 A1 | 5/2009 | Albrecht et al. |
| 2009/0131402 A1 | 5/2009 | Shirai et al. |
| 2009/0203707 A1 | 8/2009 | Rajamani et al. |
| 2009/0221555 A1 | 9/2009 | Ahmed et al. |
| 2009/0253689 A1 | 10/2009 | Baeschlin et al. |
| 2010/0056536 A1 | 3/2010 | Antzelevitch et al. |
| 2010/0099676 A1 | 4/2010 | Endoh et al. |
| 2010/0113449 A1 | 5/2010 | Abelman et al. |
| 2010/0113461 A1 | 5/2010 | Koltun et al. |
| 2010/0144715 A1 | 6/2010 | Hoyt et al. |
| 2010/0174065 A1 | 7/2010 | Heer et al. |
| 2010/0197684 A1 | 8/2010 | Abelman et al. |
| 2010/0240635 A1 | 9/2010 | Cordi et al. |
| 2011/0021521 A1 | 1/2011 | Corkey et al. |
| 2011/0076292 A1 | 3/2011 | Blaquiere et al. |
| 2011/0183990 A1 | 7/2011 | Antzelevitch et al. |
| 2012/0010192 A1 | 1/2012 | Kobayashi et al. |
| 2012/0289493 A1 | 11/2012 | Corkey et al. |
| 2013/0005706 A1 | 1/2013 | Corkey et al. |
| 2013/0012492 A1 | 1/2013 | Corkey et al. |
| 2013/0184255 A1 | 7/2013 | Corkey et al. |
| 2014/0135317 A1 | 5/2014 | Corkey et al. |
| 2014/0221286 A1 | 8/2014 | Belardinelli et al. |
| 2014/0303158 A1 | 10/2014 | Corkey et al. |
| 2015/0045305 A1 | 2/2015 | Belardinelli et al. |
| 2015/0080370 A1 | 3/2015 | Kobayashi et al. |
| 2015/0225383 A1 | 8/2015 | Chiu et al. |
| 2015/0225384 A1 | 8/2015 | Chiu et al. |
| 2015/0239904 A1 | 8/2015 | Corkey et al. |

FOREIGN PATENT DOCUMENTS

| | | |
|---|---|---|
| DE | 4010488 A1 | 10/1991 |
| DE | 10317526 A1 | 11/2004 |
| EP | 0017438 A1 | 10/1980 |
| EP | 0464572 A2 | 1/1992 |
| EP | 0477789 A1 | 4/1992 |
| EP | 0540334 A1 | 5/1993 |
| EP | 0597423 A2 | 5/1994 |
| EP | 0635488 A2 | 1/1995 |
| EP | 0999208 A1 | 5/2000 |
| EP | 1182195 A1 | 2/2002 |
| EP | 1333031 A1 | 8/2003 |
| EP | 1354602 A1 | 10/2003 |
| EP | 1803748 A1 | 7/2007 |
| JP | 5675428 B2 | 6/1981 |
| JP | 56075428 | 6/1981 |
| JP | 06-001779 | 1/1994 |
| JP | 06107647 | 4/1994 |
| JP | 09157262 | 6/1997 |
| JP | 11100394 | 4/1999 |
| JP | 2003277384 A | 10/2003 |
| JP | 2003321461 A | 11/2003 |
| JP | 2006-503875 A | 2/2006 |
| JP | 2006063064 A | 3/2006 |
| JP | 04209692 B2 | 1/2009 |
| JP | 5271069 B2 | 8/2013 |
| JP | 2014-509611 A | 4/2014 |
| TW | 200726765 | 7/2007 |
| TW | I490217 | 7/2015 |
| WO | WO-93/00095 A2 | 1/1993 |

(56) References Cited

FOREIGN PATENT DOCUMENTS

| | | |
|---|---|---|
| WO | WO-93/08174 A1 | 4/1993 |
| WO | WO-94/13272 A1 | 6/1994 |
| WO | WO-94/13292 A1 | 6/1994 |
| WO | WO-97/03975 A1 | 2/1997 |
| WO | WO-98/11890 A1 | 3/1998 |
| WO | WO-98/47885 A1 | 10/1998 |
| WO | WO-98/54135 A1 | 12/1998 |
| WO | WO-99/13038 A1 | 3/1999 |
| WO | WO-99/41246 A1 | 8/1999 |
| WO | WO-99/42456 A2 | 8/1999 |
| WO | WO-99/65904 A1 | 12/1999 |
| WO | WO-00/23451 A1 | 4/2000 |
| WO | WO-01/16110 A1 | 3/2001 |
| WO | WO-01/16263 A2 | 3/2001 |
| WO | WO-01/16274 A1 | 3/2001 |
| WO | WO-01/16275 A1 | 3/2001 |
| WO | WO-01/16276 A1 | 3/2001 |
| WO | WO-01/16277 A1 | 3/2001 |
| WO | WO-01/16278 A1 | 3/2001 |
| WO | WO-01/87883 A1 | 11/2001 |
| WO | WO-02/10135 A1 | 2/2002 |
| WO | WO-02/18377 A1 | 3/2002 |
| WO | WO-02/38562 A1 | 5/2002 |
| WO | WO-02/072579 A1 | 9/2002 |
| WO | WO-02/096873 A1 | 12/2002 |
| WO | WO-03/024941 A1 | 3/2003 |
| WO | WO-03/075858 A2 | 9/2003 |
| WO | WO-2004/014866 A1 | 2/2004 |
| WO | WO-2004/020440 A1 | 3/2004 |
| WO | WO-2004/024702 A1 | 3/2004 |
| WO | WO-2004/026292 A1 | 4/2004 |
| WO | WO-2004/037192 A2 | 5/2004 |
| WO | WO-2004/043940 A1 | 5/2004 |
| WO | WO-2004/062616 A2 | 7/2004 |
| WO | WO-2004/083190 A1 | 9/2004 |
| WO | WO-2004/094371 A2 | 11/2004 |
| WO | WO-2004/096767 A1 | 11/2004 |
| WO | WO-2004/101509 A2 | 11/2004 |
| WO | WO-2005/002520 A2 | 1/2005 |
| WO | WO-2005/011690 A1 | 2/2005 |
| WO | WO-2005/014558 A1 | 2/2005 |
| WO | WO-2005/060967 A1 | 7/2005 |
| WO | WO-2005/097052 A1 | 10/2005 |
| WO | WO-2006/002470 A1 | 1/2006 |
| WO | WO-2006/011669 A1 | 2/2006 |
| WO | WO-2006/020959 A2 | 2/2006 |
| WO | WO-2006/021544 A1 | 3/2006 |
| WO | WO-2006/023750 A2 | 3/2006 |
| WO | WO-2006/031676 A2 | 3/2006 |
| WO | WO-2006/032518 A1 | 3/2006 |
| WO | WO-2006/048727 A1 | 5/2006 |
| WO | WO-2006/091897 A2 | 8/2006 |
| WO | WO-2006/095014 A1 | 9/2006 |
| WO | WO-2006/113864 A2 | 10/2006 |
| WO | WO-2006/125119 A1 | 11/2006 |
| WO | WO-2006/125972 A1 | 11/2006 |
| WO | WO-2006/138549 A1 | 12/2006 |
| WO | WO-2006/138657 A1 | 12/2006 |
| WO | WO-2006/138695 A1 | 12/2006 |
| WO | WO-2007/004028 A2 | 1/2007 |
| WO | WO-2007/023750 A1 | 3/2007 |
| WO | WO-2007/038209 A2 | 4/2007 |
| WO | WO-2007/047604 A2 | 4/2007 |
| WO | WO-2007/058583 A2 | 5/2007 |
| WO | WO-2007/061677 A2 | 5/2007 |
| WO | WO-2007/061696 A2 | 5/2007 |
| WO | WO-2007/069986 A1 | 6/2007 |
| WO | WO-2007/070866 A2 | 6/2007 |
| WO | WO-2007/113226 A1 | 10/2007 |
| WO | WO-2007/146284 A2 | 12/2007 |
| WO | WO-2008/005338 A1 | 1/2008 |
| WO | WO-2008/005457 A2 | 1/2008 |
| WO | WO-2008/006540 A1 | 1/2008 |
| WO | WO-2008/007661 A1 | 1/2008 |
| WO | WO-2008/023336 A2 | 2/2008 |
| WO | WO-2008/055068 A2 | 5/2008 |
| WO | WO-2008/079570 A1 | 7/2008 |
| WO | WO-2008/080012 A1 | 7/2008 |
| WO | WO-2008/094909 A2 | 8/2008 |
| WO | WO-2008/108445 A1 | 9/2008 |
| WO | WO-2008/117061 A2 | 10/2008 |
| WO | WO-2008/118141 A2 | 10/2008 |
| WO | WO-2008/128086 A1 | 10/2008 |
| WO | WO-2008/134553 A1 | 11/2008 |
| WO | WO-2008/144483 A2 | 11/2008 |
| WO | WO-2009/005675 A1 | 1/2009 |
| WO | WO-2009/016462 A2 | 2/2009 |
| WO | WO-2009/026444 A1 | 2/2009 |
| WO | WO-2009/045753 A1 | 4/2009 |
| WO | WO-2009/085980 A1 | 7/2009 |
| WO | WO-2009/089027 A1 | 7/2009 |
| WO | WO-2009/091374 A2 | 7/2009 |
| WO | WO-2009/101917 A1 | 8/2009 |
| WO | WO-2009/112275 A1 | 9/2009 |
| WO | WO-2009/137462 A2 | 11/2009 |
| WO | WO-2009/137499 A1 | 11/2009 |
| WO | WO-2009/141026 A1 | 11/2009 |
| WO | WO-2009/148452 A1 | 12/2009 |
| WO | WO-2009/153589 A1 | 12/2009 |
| WO | WO-2010/006292 A1 | 1/2010 |
| WO | WO-2010/018686 A1 | 2/2010 |
| WO | WO-2010/022001 A1 | 2/2010 |
| WO | WO-2010/053757 A1 | 5/2010 |
| WO | WO-2010/056865 A1 | 5/2010 |
| WO | WO-2010/068461 A1 | 6/2010 |
| WO | WO-2010/074807 A1 | 7/2010 |
| WO | WO-2010/077680 A2 | 7/2010 |
| WO | WO-2010/077686 A1 | 7/2010 |
| WO | WO-2010/106249 A1 | 9/2010 |
| WO | WO-2010/111534 A1 | 9/2010 |
| WO | WO-2010/118208 A1 | 10/2010 |
| WO | WO-2011/014462 A1 | 2/2011 |
| WO | WO-2011/036280 A1 | 3/2011 |
| WO | WO-2011/042920 A1 | 4/2011 |
| WO | WO-2011/056985 A2 | 5/2011 |
| WO | WO-2011/075607 A1 | 6/2011 |
| WO | WO-2011/084733 A1 | 7/2011 |
| WO | WO-2012/003392 A1 | 1/2012 |
| WO | WO-2012/019071 A1 | 2/2012 |
| WO | WO-2012/019076 A1 | 2/2012 |
| WO | WO-2012/036233 A1 | 3/2012 |
| WO | WO-2012/037105 A1 | 3/2012 |
| WO | WO-2012/038813 A1 | 3/2012 |
| WO | WO-2012/050918 A2 | 4/2012 |
| WO | WO-2012/071509 A2 | 5/2012 |
| WO | WO-2012/154760 A1 | 11/2012 |
| WO | WO-2012/167212 A2 | 12/2012 |
| WO | WO-2013/004551 A1 | 1/2013 |
| WO | WO-2013/006400 A1 | 1/2013 |
| WO | WO-2013/006463 A1 | 1/2013 |
| WO | WO-2013/006485 A1 | 1/2013 |
| WO | WO-2013/043925 A1 | 3/2013 |
| WO | WO-2013/097052 A1 | 7/2013 |
| WO | WO-2013/098375 A1 | 7/2013 |
| WO | WO-2013/112932 A1 | 8/2013 |
| WO | WO-2013/185764 A2 | 12/2013 |
| WO | WO-2014/134419 A1 | 9/2014 |
| WO | WO-2015-123519 A2 | 8/2015 |

OTHER PUBLICATIONS

Witty et al. Bioorganic & Medicinal Chemistry Letters (2006), 16(18), 4872-4878.*
Ege et al. Justus Liebigs Annalen der Chemie (1976), (5), 946-68; CA 85;77216, 1976. CAPLUS Abstract provided.*
Armstrong et al. WO 2003033480,Apr. 24, 2003; CA 138:338173, 2003. CAPLUS Abstract provided.*
Abate et al., "Effects of bretylium tosylate on the atrio ventricular and intra ventricular conduction in man", Bollettino Della Societa Italiana di Cardiologia, Pensiero Scientifico, vol. 21, No. 4, 1975, pp. 601-608.

(56) References Cited

OTHER PUBLICATIONS

Agag et al., "Primary Amine-Functional Benzoxazine Monomers and Their Use for Amide-Containing Monomeric Benzoxazines," Macromolecules, 2010, 43(6):2748-2758.

Antoons, et al., "Late Na+ Current Inhibition by Ranolazine Reduces Torsades de Pointes in the Chronic Atrioventricular Block Dog Model," Journal of the American College of Cardiology, 55(8), 2010, pp. 801-809.

Banchs, et al., "Efficacy and safety of dofetilide in patients with atrial fibrillation and atrial flutter," J. Interv. Card. Electrophysiol, 23, 2008, pp. 111-115.

Banker, G.S. et al, "Modern Pharmaceutics, 3ed.", Marcel Dekker, New York. 1996, pp. 451 and 596.

Barsky et al., "Hypoglycemic Cyclic Amidines", J. Med. Chem., vol. 14, No. 1, 1971, pp. 40-44.

Belardinelli et al., "A Novel, Potent, and Selective Inhibitor of Cardiac Late Sodium Current Suppresses Experimental Arrhythmias," J. Pharm. Exp. Ther., 344(1), pp. 23-32, 2013.

Benson et al., "SUMO modification regulates inactivation of the voltage-gated potassium channel Kv1.5" Proc. Nat. Acad. Sci., 104(6), pp. 1805-1810, 2007.

Brady et al., "Synthesis of conformationally constrained benzoylureas as BH3-mimetics", Organic and Biomolecular Chemistry, vol. 10, No. 27, May 15, 2012 (May 15, 2012), pp. 5230-5237, XP002738888, DOI: 10.1039/C20B25618E.

Burashnikov et al., "Role of late sodium channel current block in the management of atrial fibrillation," Cardiovascular Drugs and Therapy / Sponsored by the International Society of Cardiovascular Pharmacotherapy, 27(1), pp. 79-89, 2013.

Caira, "Crystalline Polymorphism of Organic Compounds," Topics in Current Chemistry Springer, 198, 1998, pp. 163-208.

Chiu et al., "Cycloaddition of Alpha-Chloroformylarylhydrazines with Pyridines Afford 2-Aryl-2H-[1,2,4]triazolo[4,3-a]pyridine-3-ones", Journal of the Chinese Chemical Society, Chinese Electronic Periodical Services, China, vol. 48, 2001, pp. 1135-1142.

Chouhan et al., "Domino Ring-Opening/Carboxamidation Reactions of N-Tosyl Aziridines and 2-Halophenols/Pyridinol: Efficient Synthesis of 1,4-Benzo- and Pyrido-oxazepinones", Organic Letters, vol. 12. No. 1, pp. 192-195, 2010.

Chylinska et al., "Dihydro-1,3-oxazine Derivatives and Their Antitumor Activity," Journal of Medicinal Chemistry, 1963, vol. 6:484-487.

Clare et al, Drug Discovery Today 2000, vol. 5, No. 11, 506-520.

Cleator et al., "Synthesis of Novel Benzoxathiazepine-1,1-dioxides by Means of a One-pot Multicomponent Reaction", Tetrahedron Letters, 51, pp. 1079-1082, 2010.

Communication pursuant to Article 94(3) for European Application No. 12722595.1 dated Oct. 13, 2015.

Communication pursuant to Article 94(3) for European Application No. 12722595.1 dated Oct. 14, 2014.

Communication pursuant to Article 94(3) for European Application No. 12722595.1 dated Sep. 9, 2016. (3 pages).

Curran, "Potassium ion channels and human disease: phenotypes to drug targets?", Current Opinion in Biotechnology, vol. 9. No. 6, 1998, pp. 565-572.

Database WPI, Week 198132, Thomson Scientific, London, abstract, 1981, XP-002690413, JP56075428 (1 page).

Database WPI, Week 199346, Thomson Scientific, London, abstract, 1993, XP-002690414, JP5271069 (2 pages).

Dermer et al., Bio/Technology, 1994, 12:320.

Drici et al., "The bee venom peptide tertiapin underlines the role of IKACh in acetylcholine-induced artrioventricular blocks", British Journal of Pharmacology, vol. 131, No. 3, 2000, pp. 569-577.

Ege et al., "6-Fulor-Sowie 6-Nitro-3-phenyl-3,4-dihydro-1,2,3-benzo-triazin-4-on und deren Photolyse; nucleophile Substitution zur Erprobung der Fluor-Markierungsmethode von Suschitzky," Liabigs Ann. Chem. 1976, 946-968.

Elzein et al., "Novel 1,3-dipropyl-8-(1-heteroarylmethyl-1 H-pyrazol-4-yl)-xanthine derivatives as high affinity and selective A2B adenosine receptor antagonists," Bioorganic & Medicinal Chemistry Letters, 16:302-306 (2006).

Examination Report for Australian Application No. 2012253653 dated Aug. 26, 2015.

Examination Report for Gulf Cooperation Council Application No. 2012/21244 dated Jan. 18, 2016. (4 pages).

Examination Report for New Zealand Application No. 617987 dated Jul. 28, 2014.

Examination Report for New Zealand Application No. 716420 dated Feb. 16, 2016.

Foster, "Deuterium Isotope Effects in Studies of Drug Metabolism", Trends Pharmacol. Sci., 5(12):524-527, 1984.

Freshney et al., Culture of Animal Cells, A Manual of Basic Technique, Alan R. Liss, Inc., 1983, New York, pp. 1-6.

Hale et al., "Late sodium current inhibition as a new cardioprotective approach", Journal of Molecular and Cellular Cardiology, vol. 44 (2008), pp. 954-967.

Ilyin, et al., "One-step assembly of carbamoyl substituted annulated 1,4-oxazepines", Tetrahedron Letters, (2006), 47(15):2649-2653, Supplementary Data 3 pages.

International Preliminary Report on Patentability for International Application No. PCT/US2010/043264 (WO/2011/014462) dated Jan. 31, 2012.

International Preliminary Report on Patentability for International Application No. PCT/US2011/042700 dated Jan. 8, 2013.

International Preliminary Report on Patentability for International Application No. PCT/US2012/036976 (WO/2012/154760) dated Nov. 12, 2013. (8 pages).

International Preliminary Report on Patentability for International Application No. PCT/US2012/045021 dated Jan. 7, 2014.

International Preliminary Report on Patentability for International Application No. PCT/US2012/045086 dated Jan. 7, 2014.

International Preliminary Report on Patentability for International Application No. PCT/US2012/056419 dated Mar. 25, 2014.

International Preliminary Report on Patentability for International Application No. PCT/US2013/023291 dated Jul. 29, 2014.

International Preliminary Report on Patentability for International Application No. PCT/US2014/019351 dated Sep. 1, 2015.

International Preliminary Report on Patentability for International Application No. PCT/US2015/015814 dated Aug. 16, 2016.

International Search Report and Written Opinion for PCT/US2011/042700 dated Aug. 10, 2011.

International Search Report and Written Opinion for PCT/US2012/036976, dated Jun. 26, 2012.

International Search Report and Written Opinion for PCT/US2012/045021 dated Aug. 29, 2012.

International Search Report and Written Opinion for PCT/US2012/045086, dated Sep. 11, 2012.

International Search Report and Written Opinion for PCT/US2012/056419, dated Jan. 21, 2013.

International Search Report and Written Opinion for PCT/US2014/019351 dated Jun. 30, 2014.

International Search Report with Written Opinion for PCT/US2010/043264, dated Sep. 28, 2010.

International Search Report with Written Opinion for PCT/US2013/023291, dated Mar. 7, 2013.

International Search Report with Written Opinion for PCT/US2015/015814, dated Jul. 29, 2015.

Kamei et al., "Synthesis, SAR studies, and evaluation of 1,4-benzoxazepine derivatives as selective 5-HT1 A receptor agonists with neuroprotective effect: Discovery of Piclozotan", Bioorganic & Medicinal Chemistry, Pergamon, GB, vol. 14, No. 6, Mar. 15, 2006 (Mar. 15, 2006), pp. 1978-1992, XP027992458, ISSN: 0968-0896, DOI: 10.1016/j.bmc.2005.10.046.

Kerr et al., "Efficacy of azimilide for the maintenance of sinus rhythm in patients with paroxysmal atrial fibrillation in the presence and absence of structural heart disease", American Journal of Cardiology, vol. 98, No. 2, 2006, pp. 215-218.

Krafte et al., Current Opinion in Pharmacology 2008, 8:50-56.

Kumar et al., "New and emerging antiarrhythmic drugs for atrial fibrillation: what may become available to the clinician in the near future", Curr. Treat. Options Cardiovasc. Med., pp. 373-380 11(55), 2009.

(56) References Cited

OTHER PUBLICATIONS

Manikannan et al., "Chemoselective Reaction of Formalin with 2-(5-Substituted-2-hydroxpenzylamino)phenols: Synthesis of 6-Substituted 3-(2-hydroxyphenyl)-3,4-dihydro-2H-benzo[e][1,3]oxazines," Journal of Heterocyclic Chemistry, 2008, vol. 45:1207-1210.
Marc et al., "High Yield Phase Transfer N-Alkylation of Some Benzodiazepines by Esters of omega-Halo Acids," Syn. Comm. 1998, 28, pp. 1143-1157.
Murdock et al, "The Use of Oral Ranolazine to Convert New or Paroxysmal Atrial Fibrillation: A Review of Experience with Implications for Possible 'Pill in the Pocket' Approach to Atrial Fibrillation," Indian Pacing and Electrophysiology Journal, 9(5), 2009, pp. 260-267.
Nagashima et al., "Dual effects of disopyramide to the glycemic control in patients with diabetes mellitus", Diabetes, American Diabetes Association, vol. 53, No. Suppl. 2, 2004 (1 page).
Neumayr et al., "Ibutilide and sinus arrest", Herz Kardiovaskulare Erkrankungen, Urban & Vogel, vol. 32, No. 4, 2007, p. 342.
Ning et al., "Ranolazine Increases Beta-Cell Survival and Improves Glucose Homeostasis in Low-Dose Streptozotocin-induced Diabetes in Mice", J. Pharmacol. Exp. Ther., 337(1), 50-58, 2011.
Office Action and Search Report for Taiwan Application No. 101116359 dated Dec. 31, 2014.
Office Action and Search Report for Taiwan Application No. 101116359 dated May 12, 2014.
Office Action and Search Report for Taiwan Application No. 104130125 dated Aug. 22, 2016. (4 pages).
Office Action for Chinese Application No. 201280030042.9 dated Apr. 17, 2015. (9 pages).
Office Action for Panama Application No. 89690, dated Dec. 18, 2013.
Office Action for Bolivia Application No. SP-0152-2012, dated Aug. 7, 2015.
Office Action for Chinese Application No. 201280030042.9, dated Apr. 17, 2015.
Office Action for Chinese Application No. 201280030042.9, dated Nov. 4, 2014.
Office Action for Eurasian Application No. 201391532, dated Jan. 20, 2015.
Office Action for Eurasian Application No. 201391532 dated Dec. 19, 2016. (1 page).
Official Action for Eurasian Application No. 201391532 dated May 3, 2016. (3 pages).
Official Action for Eurasian Application No. 201391532 dated Sep. 21, 2015.
Official Action for Japanese Application No. 2014-510414 dated Dec. 11, 2015.
Official Notification for Israeli Application No. 229045 dated Jan. 29, 2015.
Official Notification for Israeli Application No. 229045 dated Jun. 14, 2016. (2 pages).
Rudolph et al., "Quinazolinone Derivatives as Orally Available Ghrelin Receptor Antagonists for the Treatment of Diabetes and Obesity", Journal of Medicinal Chemistry, vol. 50, No. 21, 2007, pp. 5202-5216.
Rush et al., Molecular Interventions 2007, vol. 4, issue 7, 192-195.
Scirica, "Ranolazine in patients with coronary artery disease", Expert Opinion Pharmacother (2007), 8(13): 2149-2157.
Seto, et al., "Design, synthesis, and evaluation of novel 2-substituted-4-aryl-6,7,8,9-tetrahydro-5H-pyrimido[4,5-b][1,5]oxazocin-5-ones as NK1 antagonists", Bioorganic & Medicinal Chemistry, (2005), 13(20):5717-5732.
Shin et al., "New Synthesis of Highly Potential Efficient Bluish-Green Electroluminescent Materials Based on 1,3,4-Oxadiazole Triazolopyridinone Carbazole Derivatives for Single-Layer Devices", Heteroatom Chemistry, Wiley Periodicals, Inc., vol. 17, No. 2, 2006, pp. 160-165.
Shin et al., "Synthesis and Characterization of New Bluish-Green Electroluminescent Materials Based on 1,3,4-Oxadiazole Triazolopyridinone Hybrids", Heteroatom Chemistry, Wiley Periodicals, Inc., vol. 10, No. 3, 2007, pp. 212-219.
Sircar, "Synthesis of new 1,2,4-triazolo[4,3-b]pyridazines and related compounds" Journal of Heterocyclic Chemistry 22(1):1045-1048 (1985). ISSN: 0022-152X.
Skidmore et al. (Journal of Medicinal Chemistry (2014), 57(24), 10424-10442).
Takahara et al., "Analysis of Arrhythmogenic profile in a canine model of chronic atrioventricular block by comparing in vitro effects of the class III antiarrhythmic drug nifekalant on the ventricular action potential indices between normal heart and atrioventricular block heart", Journal of Pharmacological Sciences, vol. 103, No. 2, Feb. 1, 2007 (Feb. 1, 2007), pp. 181-188.
Toussaint et al., "Late sodium current as a promising antiarrhythmic drug target for treatment of atrial fibrilolation?" Naunyn-Schmiedeberg's Archives of Pharmacology, 383(1), p. 61, 20117 77th Annual Meeting on German-Society-For Experimental-And-Clinical-Pharmacology-And Toxicology; Frankfurt, Germany; Mar. 30-Apr. 2, 2011.
Toyofuku et al. JP 06001779, Jan. 11, 1995; CA 122;10048, 1995. Abstract provided. JP06001779 (2 pages).
Ulrich J. Kirk-Othmer Encyclopedia of Chemical Technology, pp. 1-7, 2002.
Vadnais, et al., "Emerging Clinical Role of Ranolazine in the Management of Angina," Ther. Clin. Risk Management, 6, 2010, pp. 517-530.
Vippagunta et al., "Crystalline solids", Advanced Drug Delivery Reviews 48, pp. 3-26, (2001).
Wang et al., "Influence of Electronic Effects from Bridging Groups on Synthetic Reaction and Thermally Activated Polymerization of Bisphenol-Based Benzoxazines," Journal of Polymer Science: Part A: Polymer Chemistry, 2011, vol. 49(6):1443-1452.
Wolff, Manfred E., "Burger's Medicinal Chemistry, 5ed, Part 1" John Wiley & Sons, 1995, pp. 950-982.
Wu, et al., "Late Sodium Current Contributes to the Reverse Rate-Dependent Effect of I-KR Inhibition on Ventricular Repolarization", Circulation, 123(16), pp. 1713-1720, 2011.
Wunsche et al., "Skelettumlagerungen unter elektronenbeschuss-III: Benzotriazinone und 1,3-diphenyltriazene," Tetrahedron, 1969, 25: 5869-5877.
Yamada, "The role of muscarinic K+ channels in the negative chronotropic effect of a muscarinic agonist", Journal of Pharmacology and Experimental Therapeutics, vol. 300, No. 1, 2002, pp. 681-687.
Yamazaki et al., "Negative chronotropic and dromotropic effects of E-4031, an I-Kr blocker, on the atrioventricular node in anesthetized dog hearts", European Journal of Pharmacology, vol. 297, No. 3, 1996, pp. 233-239.
Yang, et al., "Synthesis of Dibenzo[b,f][1,4]oxazepin-11(10H)-ones via Intramolecular Cyclocarbonylation Reactions Using pfl2/Cytop 292 as the Catalytic System", Journal of Organic Chemistry, 75(18), 2010, pp. 6297-6299, S1-S12.
Zaza et al., "Pathophysiology and Pharmacology of the Cardiac "Late Sodium Current"," *Pharmacology and Therapeutics*, 119, pp. 326-339, 2008.

* cited by examiner

FUSED HETEROCYCLIC COMPOUNDS AS ION CHANNEL MODULATORS

CROSS REFERENCE TO RELATED APPLICATIONS

This application claims priority to U.S. Provisional Application Ser. No. 61/484,500, filed on May 10, 2011 and 61/503,543, filed on Jun. 30, 2011, the entirety of which are incorporated herein by reference.

FIELD

The present disclosure relates to novel compounds and to their use in the treatment of various diseases, including cardiovascular diseases and diabetes. The disclosure also relates to methods for preparation of the compounds and to pharmaceutical compositions containing such compounds.

BACKGROUND

The late sodium current (INaL) is a sustained component of the fast Na+ current of cardiac myocytes and neurons. Many common neurological and cardiac conditions are associated with abnormal INaL enhancement, which contributes to the pathogenesis of both electrical and contactile dysfunction in mammals. See, for example, Pathophysiology and Pharmacology of the Cardiac "Late Sodium Current", Pharmacology and Therapeutics 119 (2008) 326-339. Accordingly, compounds that selectively inhibit INaL in mammals are useful in treating such disease states.

One example of a selective inhibitor of INaL is RANEXA®, a compound approved by the FDA for the treatment of chronic stable angina pectoris. RANEXA® has also been shown to be useful for the treatment of a variety of cardiovascular diseases, including ischemia, reperfusion injury, arrhythmia, unstable angina, and diabetes. It would be desirable to provide novel compounds that selectively inhibit INaL in mammals and that have the same selectivity over peak INa inhibition as RANEXA®.

SUMMARY

Accordingly, in some embodiments the present disclosure provides novel compounds that function as late sodium channel blockers. In one embodiment, is provided compounds of Formula I:

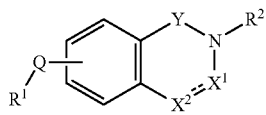

wherein:
the dotted line represents an optional double bond;
Y is —C($R^5$)$_2$— or —C(O)—;
$X^1$ is N and $X^2$ is N, $X^1$ is N and $X^2$ is $CR^3$, or $X^1$ is $CR^3$ and $X^2$ is N, and the dotted line is a double bond; or
$X^1$ is C($R^3$)$_2$ and $X^2$ is $NR^4$, —O—, —S—, —S(O)— or —S(O)$_2$—, or $X^1$ and $X^2$ are both C($R^3$)$_2$, and the dotted line is a single bond;
provided that:
when the dotted line is a single bond and Y is —C($R^5$)$_2$—; then both $X^1$ and $X^2$ are C($R^3$)$_2$; and
when the dotted line is a double bond; Y is —C(O)—;
Q is a covalent bond or $C_{2-4}$ alkynylene;
$R^1$ is $C_{3-6}$ cycloalkyl, $C_{3-6}$ cycloalkenyl, aryl, heterocyclyl or heteroaryl;
wherein said $C_{3-6}$ cycloalkyl, $C_{3-6}$ cycloalkenyl, aryl, heterocyclyl or heteroaryl are optionally substituted with one, two or three substituents independently selected from the group consisting of halo, —NO$_2$, CN, —SF$_5$, —Si(CH$_3$)$_3$, —O—$R^{20}$, —S—$R^{20}$, —C(O)—$R^{20}$, —C(O)—O$R^{20}$, —N($R^{20}$)($R^{22}$), —C(O)—N($R^{20}$)($R^{22}$), —N($R^{20}$)—C(O)—$R^{22}$, —N($R^{20}$)—S(O)$_2$—$R^{22}$, —S(O)$_2$—$R^{20}$, —S(O)$_2$—N($R^{20}$)($R^{22}$), $C_{1-4}$ alkyl, $C_{2-4}$ alkenyl, $C_{2-4}$ alkynyl, $C_{3-6}$ cycloalkyl, aryl, heteroaryl and heterocyclyl; and
wherein said $C_{1-4}$ alkyl, $C_{2-4}$ alkenyl, $C_{2-4}$ alkynyl, $C_{3-6}$ cycloalkyl, aryl, heteroaryl or heterocyclyl are optionally substituted with one, two or three substituents independently selected from the group consisting of halo, —NO$_2$, aryl, heterocyclyl, heteroaryl, $C_{1-4}$ alkyl, $C_{3-6}$ cycloalkyl, —N($R^{20}$)($R^{22}$), —C(O)—C(O)—O$R^{20}$, —C(O)—N($R^{20}$)($R^{22}$), —CN and —O—$R^{20}$;
$R^2$ is —$R^6$, —$C_{1-6}$ alkylene-$R^6$, —$C_{2-6}$ alkenylene-$R^6$, —$C_{2-6}$ alkynylene-$R^6$, -L-$R^6$, -L-$C_{1-6}$ alkylene-$R^6$, —$C_{1-6}$ alkylene-L-$R^6$ or —$C_{1-6}$ alkylene-L-$C_{1-6}$ alkylene-$R^6$;
L is —O—, —S—, —C(O)—, —S(O)$_2$—, —N$R^{20}$S(O)$_2$—, —S(O)$_2$N$R^{20}$—, —C(O)N$R^{20}$— or —N$R^{20}$C(O)—; provided that when Y is —C($R^5$)$_2$—, then L is —C(O)— or —S(O)$_2$—, and $R^2$ is -L-$R^6$, -L-$C_{1-6}$ alkylene-$R^6$, —$C_{1-6}$ alkylene-L-$R^6$ or —$C_{1-6}$ alkylene-L-$C_{1-6}$ alkylene-$R^6$;
each $R^3$ is independently hydrogen, $C_{1-6}$ alkyl, $C_{3-6}$ cycloalkyl, aryl, heteroaryl or heterocyclyl;
wherein said $C_{1-6}$ alkyl is optionally substituted with one, two or three substituents independently selected from the group consisting of halo, —NO$_2$, $C_{3-6}$ cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;
wherein said $C_{3-6}$ cycloalkyl, aryl, heterocyclyl and heteroaryl are optionally further substituted with one, two or three substituents independently selected from the group consisting of halo, —NO$_2$, $C_{1-6}$ alkyl, aralkyl, $C_{3-6}$ cycloalkyl, aryl, heterocyclyl, heteroaryl, —N($R^{20}$)($R^{22}$), —C(O)—$R^{20}$, —C(O)—O$R^{20}$, —C(O)—O$R^{20}$, —C(O)—N($R^{20}$)($R^{22}$), —CN and —O—$R^{20}$; and
wherein said $C_{1-6}$ alkyl, aralkyl, $C_{3-6}$ cycloalkyl, aryl, heterocyclyl and heteroaryl are optionally further substituted with one, two or three substituents independently selected from the group consisting of halo, —NO$_2$, —N($R^{20}$)($R^{22}$), —C(O)—C(O)—O$R^{20}$, —C(O)—N($R^{20}$)($R^{22}$), —CN and —O—$R^{20}$;
or when $X^1$ is C($R^3$)$_2$, two $R^3$ can join together with the with the carbon atom to which they are attached to form a $C_{3-6}$ cycloalkyl or heterocyclyl;
$R^4$ is hydrogen, $C_{1-6}$ alkyl, $C_{1-4}$ alkoxy, —C(O)—O$R^{20}$, —C(O)—N($R^{20}$)($R^{22}$), —N($R^{20}$)—S(O)$_2$—$R^{20}$, $C_{3-6}$ cycloalkyl, aryl, heteroaryl or heterocyclyl;
wherein said $C_{1-6}$ alkyl is optionally substituted with one, two or three substituents independently selected from the group consisting of halo, —NO$_2$, $C_{3-6}$ cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;

wherein said $C_{3-6}$ cycloalkyl, aryl, heterocyclyl or heteroaryl are optionally further substituted with one, two or three substituents independently selected from the group consisting of halo, —$NO_2$, $C_{1-6}$ alkyl, aralkyl, $C_{3-6}$ cycloalkyl, aryl, heterocyclyl, heteroaryl, —$N(R^{20})(R^{22})$, —C(O)—$R^{20}$, —C(O)—$OR^{20}$, —C(O)—$OR^{20}$, —C(O)—$N(R^{20})(R^{22})$, —CN, and —O—$R^{20}$; and wherein said $C_{1-6}$ alkyl, aralkyl, $C_{3-6}$ cycloalkyl, aryl, heterocyclyl, heteroaryl, are optionally further substituted with one, two or three substituents independently selected from the group consisting of hydroxyl, halo, —$NO_2$, —$N(R^{20})(R^{22})$, —C(O)—$R^{20}$, —C(O)—$OR^{20}$, —C(O)—$OR^{20}$, —C(O)—$N(R^{20})(R^{22})$, —CN and —O—$R^{20}$;

each $R^5$ is independently hydrogen or $C_{1-6}$ alkyl;

$R^6$ is $C_{3-6}$ cycloalkyl, aryl, heteroaryl or heterocyclyl;

wherein said $C_{3-6}$ cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, $C_{3-6}$ cycloalkyl, aryl, heterocyclyl, heteroaryl, —$N(R^{20})(R^{22})$, —$N(R^{20})$—$S(O)_2$—$R^{20}$, —$N(R^{20})$—C(O)—$R^{22}$, —C(O)—$R^{20}$, —C(O)—$OR^{20}$, —C(O)—$N(R^{20})(R^{22})$, —$S(O)_2$—$R^{20}$, —CN and —O—$R^{20}$;

wherein said $C_{1-6}$ alkyl, $C_{3-6}$ cycloalkyl, aryl, heterocyclyl or heteroaryl are optionally further substituted with one, two or three substituents independently selected from the group consisting of halo, —$NO_2$, $C_{1-6}$ alkyl, $C_{3-6}$ cycloalkyl, aryl, heterocyclyl, heteroaryl, —$N(R^{20})(R^{22})$, —C(O)—$R^{20}$, —C(O)—$OR^{20}$, —C(O)—$OR^{20}$, —C(O)—$N(R^{20})(R^{22})$, —CN and —O—$R^{20}$; and wherein said $C_{1-6}$ alkyl, $C_{3-6}$ cycloalkyl, aryl, heterocyclyl or heteroaryl are optionally further substituted with one, two or three substituents independently selected from the group consisting of $C_{1-6}$ alkyl, halo, aryl, —$NO_2$, —$CF_3$, —$N(R^{20})(R^{22})$, —C(O)—$R^{20}$, —C(O)—$OR^{20}$, —C(O)—$N(R^{20})(R^{22})$, —$S(O)_2$—$R^{20}$ and —O—$R^{20}$;

$R^{20}$ and $R^{22}$ are in each instance independently hydrogen, $C_{1-6}$ alkyl, $C_{2-6}$ alkenyl, $C_{2-6}$ alkynyl, $C_{3-6}$ cycloalkyl, heterocyclyl, aryl or heteroaryl; and wherein the $C_{1-6}$ alkyl, $C_{2-6}$ alkenyl, $C_{2-6}$ alkynyl, $C_{3-6}$ cycloalkyl, heterocyclyl, aryl or heteroaryl are optionally substituted with one, two or three substituents independently selected from the group consisting of hydroxyl, halo, $C_{1-4}$ alkyl, aralkyl, —$N(R^{26})(R^{28})$, aminoacyl, —$NO_2$, —$S(O)_2$—$R^{26}$, —CN, $C_{1-3}$ alkoxy, —$CF_3$, —$OCF_3$, —$OCH_2CF_3$, —C(O)—$NH_2$, —C(O)—$R^{26}$, —C(O)—$OR^{26}$, aryl, $C_{3-6}$ cycloalkyl, heterocyclyl, aryl and heteroaryl;

wherein said aralkyl, heterocyclyl or heteroaryl is optionally further substituted with $C_{1-4}$ alkyl, —$CF_3$, aryl or $C_{3-6}$ cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, alkyl, aralkyl, aryl, aryloxy, aralkyloxy, heteroaryloxy, substituted amino, aminoacyl, —$NO_2$, —$S(O)_2$—$R^{26}$, —CN, $C_{1-3}$ alkoxy, hydroxymethyl, —$CF_3$, —$OCF_3$, aryl, heteroaryl and $C_{3-6}$ cycloalkyl; and $R^{26}$ and $R^{28}$ are each independently selected from the group consisting of hydrogen, $C_{1-6}$ alkyl, $C_{1-6}$ alkenyl, $C_{3-6}$ cycloalkyl, aryl and heteroaryl; and wherein the $C_{1-6}$ alkyl, $C_{3-6}$ cycloalkyl, aryl or heteroaryl may be further substituted with from 1 to 3 substituents independently selected from the group consisting of hydroxyl, halo, $C_{1-4}$ alkoxy, —$CF_3$, —$OCF_3$ and $C_{3-6}$ cycloalkyl;

or a pharmaceutically acceptable salt, ester, hydrate, solvate, stereoisomer, tautomer, polymorph and/or prodrug thereof.

Some embodiments provide a method of using the compounds of Formula I in the treatment of a disease or condition in a mammal that is amenable to treatment by a late sodium channel blocker. The compounds of the disclosure and their pharmaceutically acceptable salt, ester, hydrate, solvate, stereoisomer, tautomer, polymorph and/or prodrug forms are potentially of use as medicaments for the treatment of certain diseases, such as, cardiovascular diseases such as atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease, and intermittent claudication. Such diseases may also include diabetes and conditions related to diabetes, e.g. diabetic peripheral neuropathy. Such diseases may also include conditions affecting the neuromuscular system resulting in pain, seizures, or paralysis.

In certain embodiments, the disclosure provides pharmaceutical compositions comprising a therapeutically effective amount of a compound of the disclosure (e.g. a compound of Formula I) and at least one pharmaceutically acceptable excipient.

In certain embodiments, the disclosure provides:

II-3   3-((3-methyl-1,2,4-oxadiazol-5-yl)methyl)-6-(4-(trifluoromethoxy)phenyl)benzo[d][1,2,3]triazin-4(3H)-one II-4   3-((5-chloropyrimidin-2-yl)methyl)-6-(4-(trifluoromethoxy)phenyl)benzo[d][1,2,3]triazin-4(3H)-one II-6   3-((5-methyl-1,2,4-oxadiazol-3-yl)methyl)-6-(4-(trifluoromethoxy)phenyl)benzo[d][1,2,3]triazin-4(3H)-one II-7   3-((3-methyl-1,2,4-oxadiazol-5-yl)methyl)-6-(4-phenoxyphenyl)benzo[d][1,2,3]triazin-4(3H)-one II-10   3-((3-phenylisoxazol-5-yl)methyl)-6-(4-(trifluoromethoxy)phenyl)benzo[d][1,2,3]triazin-4(3H)-one II-12   3-((3-benzyl-1,2,4-oxadiazol-5-yl)methyl)-6-(4-(trifluoromethoxy)phenyl)benzo[d][1,2,3]triazin-4(3H)-one II-13   3-(2-(1H-pyrazol-1-yl)ethyl)-6-(4-(trifluoromethoxy)phenyl)benzo[d][1,2,3]triazin-4(3H)-one II-14   3-((5-cyclopropyl-1,2,4-oxadiazol-3-yl)methyl)-6-(4-(trifluoromethoxy)phenyl)benzo[d][1,2,3]triazin-4(3H)-one II-15   3-(2-(pyridin-2-yl)ethyl)-6-(4-(trifluoromethoxy)phenyl)benzo[d][1,2,3]triazin-4(3H)-one II-16   6-(4-(4-chlorophenoxy)phenyl)-3-((3-methyl-1,2,4-oxadiazol-5-yl)methyl)benzo[d][1,2,3]triazin-4(3H)-one II-17   3-(2-(pyrimidin-4-yl)ethyl)-6-(4-(trifluoromethoxy)phenyl)benzo[d][1,2,3]triazin-4(3H)-one II-18   3-(2-(pyrimidin-2-yl)ethyl)-6-(4-(trifluoromethoxy)phenyl)benzo[d][1,2,3]triazin-4(3H)-one II-21   3-((5-phenyl-1H-tetrazol-1-yl)methyl)-6-(4-(trifluoromethoxy)phenyl)benzo[d][1,2,3]triazin-4(3H)-one II-22 3-cyclopropyl-6-(4-(trifluoromethoxy)phenyl)benzo[d][1,2,3]triazin-4(3H)-one
II-23 3-((4,5-dimethyloxazol-2-yl)methyl)-6-(4-(trifluoromethoxy)phenyl)benzo[d][1,2,3]triazin-4(3H)-one
II-24 3-(pyrimidin-2-ylmethyl)-6-(4-(trifluoromethoxy)phenyl)benzo[d][1,2,3]triazin-4(3H)-one
II-25 3-((3-methylisoxazol-5-yl)methyl)-6-(4-(trifluoromethoxy)phenyl)benzo[d][1,2,3]triazin-4(3H)-one
II-26 3-((5-methylisoxazol-3-yl)methyl)-6-(4-(trifluoromethoxy)phenyl)benzo[d][1,2,3]triazin-4(3H)-one
II-28 3-((2H-benzo[d][1,2,3]triazol-2-yl)methyl)-6-(4-(trifluoromethoxy)phenyl)benzo[d][1,2,3]triazin-4(3H)-one
II-29 3-(2-(1H-pyrazol-1-yl)ethyl)-6-(4-(4-chlorophenoxy)phenyl)benzo[d][1,2,3]triazin-4(3H)-one
II-32 3-(2-(pyrimidin-2-yloxy)ethyl)-6-(4-(trifluoromethoxy)phenyl)benzo[d][1,2,3]triazin-4(3H)-one
II-33 1-(4-oxo-6-(4-(trifluoromethoxy)phenyl)benzo[d][1,2,3]triazin-3(4H)-yl)cyclopropanecarbonitrile
II-34 3-((1-((2-methyl-1H-imidazol-1-yl)methyl)cyclopropyl)methyl)-6-(4-(trifluoromethoxy)phenyl)benzo[d][1,2,3]triazin-4(3H)-one
II-36 2-(2-(4-oxo-6-(4-(trifluoromethoxy)phenyl)benzo[d][1,2,3]triazin-3(4H)-yl)ethoxy)pyrimidine-4-carbonitrile
II-38 3-(piperidin-4-yl)-6-(4-(trifluoromethoxy)phenyl)benzo[d][1,2,3]triazin-4(3H)-one
II-39 3-(1-(pyrimidin-2-yl)piperidin-4-yl)-6-(4-(trifluoromethoxy)phenyl)benzo[d][1,2,3]triazin-4(3H)-one
II-40 3-((1-(morpholinomethyl)cyclopropyl)methyl)-6-(4-(trifluoromethoxy)phenyl)benzo[d][1,2,3]triazin-4(3H)-one
II-41 3-(2-oxo-2-(4-(pyrimidin-2-yl)piperazin-1-yl)ethyl)-6-(4-(trifluoromethoxy)phenyl)benzo[d][1,2,3]triazin-4(3H)-one
II-42 3-benzyl-6-(4-(trifluoromethoxy)phenyl)benzo[d][1,2,3]triazin-4(3H)-one
II-44 3-((4,6-dimethoxypyrimidin-2-yl)methyl)-6-(4-(trifluoromethoxy)phenyl)benzo[d][1,2,3]triazin-4(3H)-one
II-47 3-((5-(pyridin-2-yl)isoxazol-3-yl)methyl)-6-(4-(trifluoromethoxy)phenyl)benzo[d][1,2,3]triazin-4(3H)-one
II-50 1-(4-(4-oxo-3-(2-(pyrimidin-2-yloxy)ethyl)-3,4-dihydrobenzo[d][1,2,3]triazin-6-yl)phenyl)cyclopropanecarbonitrile
II-51 2-(2-(4-oxo-6-(4-(trifluoromethoxy)phenyl)benzo[d][1,2,3]triazin-3(4H)-yl)ethoxy)pyrimidine-5-carbonitrile
II-52 6-(4-(trifluoromethoxy)phenyl)-3-(2-(3-(trifluoromethyl)-1H-pyrazol-1-yl)ethyl)benzo[d][1,2,3]triazin-4(3H)-one
II-53 3-(1-(3-(pyrimidin-2-yl)-1,2,4-oxadiazol-5-yl)ethyl)-6-(4-(trifluoromethoxy)phenyl)benzo[d][1,2,3]triazin-4(3H)-one
II-54 3-((5-(pyridin-2-yl)-1,2,4-oxadiazol-3-yl)methyl)-6-(4-(trifluoromethoxy)phenyl)benzo[d][1,2,3]triazin-4(3H)-one
II-55 methyl 1-((4-oxo-6-(4-(trifluoromethoxy)phenyl)benzo[d][1,2,3]triazin-3(4H)-yl)methyl)cyclopropanecarboxylate
II-56 3-(pyrimidin-2-ylmethoxy)-6-(4-(trifluoromethoxy)phenyl)benzo[d][1,2,3]triazin-4(3H)-one
II-57 3-((1-(2-ethyl-1H-imidazol-1-yl)methyl)cyclopropyl)methyl)-6-(4-(trifluoromethoxy)phenyl)benzo[d][1,2,3]triazin-4(3H)-one
II-58 3-((1-((1H-imidazol-1-yl)methyl)cyclopropyl)methyl)-6-(4-(trifluoromethoxy)phenyl)benzo[d][1,2,3]triazin-4(3H)-one
II-59 3-(pyridin-3-ylmethoxy)-6-(4-(trifluoromethoxy)phenyl)benzo[d][1,2,3]triazin-4(3H)-one
II-60 3-(2-(4-(5-cyclopropyl-1,2,4-oxadiazol-3-yl)pyrimidin-2-yloxy)ethyl)-6-(4-(trifluoromethoxy)phenyl)benzo[d][1,2,3]triazin-4(3H)-one
II-63 3-((1-(pyrrolidin-1-ylmethyl)cyclopropyl)methyl)-6-(4-(trifluoromethoxy)phenyl)benzo[d][1,2,3]triazin-4(3H)-one
II-64 3-((1-((3,5-dimethyl-1H-pyrazol-1-yl)methyl)cyclopropyl)methyl)-6-(4-(trifluoromethoxy)phenyl)benzo[d][1,2,3]triazin-4(3H)-one
II-65 6-(4-(4-chlorophenoxy)phenyl)-3-(2-oxo-2-(4-(pyrimidin-2-yl)piperazin-1-yl)ethyl)benzo[d][1,2,3]triazin-4(3H)-one
II-66 3-((5-cyclopropyl-1,3,4-thiadiazol-2-yl)methyl)-6-(4-(trifluoromethoxy)phenyl)benzo[d][1,2,3]triazin-4(3H)-one
II-67 3-((5-cyclopropyl-1,3,4-oxadiazol-2-yl)methyl)-6-(4-(trifluoromethoxy)phenyl)benzo[d][1,2,3]triazin-4(3H)-one
II-71 3-(1-(2,2,2-trifluoroethyl)piperidin-4-yl)-6-(4-(trifluoromethoxy)phenyl)benzo[d][1,2,3]triazin-4(3H)-one
II-72 ethyl 4-oxo-3-(4-oxo-6-(4-(trifluoromethoxy)phenyl)benzo[d][1,2,3]triazin-3(4H)-yl)piperidine-1-carboxylate
II-73 6-(4-cyclopropylphenyl)-3-((3-methyl-1,2,4-oxadiazol-5-yl)methyl)benzo[d][1,2,3]triazin-4(3H)-one
II-75 3-((1-(hydroxymethyl)cyclopropyl)methyl)-6-(4-(trifluoromethoxy)phenyl)benzo[d][1,2,3]triazin-4(3H)-one
II-79 3-(1-(3-cyclopropyl-1,2,4-oxadiazol-5-yl)ethyl)-6-(4-(trifluoromethoxy)phenyl)benzo[d][1,2,3]triazin-4(3H)-one
II-80 3-((1-((pyrimidin-2-yloxy)methyl)cyclopropyl)methyl)-6-(4-(trifluoromethoxy)phenyl)benzo[d][1,2,3]triazin-4(3H)-one
II-84 3-(2,2-dimethyl-3-(pyrimidin-2-yloxy)propyl)-6-(4-(trifluoromethoxy)phenyl)benzo[d][1,2,3]triazin-4(3H)-one
II-95 3-((2-methyloxazol-5-yl)methyl)-6-(4-(trifluoromethoxy)phenyl)benzo[d][1,2,3]triazin-4(3H)-one
II-96 3-((5-methyloxazol-2-yl)methyl)-6-(4-(trifluoromethoxy)phenyl)benzo[d][1,2,3]triazin-4(3H)-one
II-97 3-((4-methyloxazol-2-yl)methyl)-6-(4-(trifluoromethoxy)phenyl)benzo[d][1,2,3]triazin-4(3H)-one
II-98 3-((2-cyclobutyloxazol-4-yl)methyl)-6-(4-(trifluoromethoxy)phenyl)benzo[d][1,2,3]triazin-4(3H)-one
II-99 3 42-methyloxazol-4-yl)methyl)-6-(4-(trifluoromethoxy)phenyl)benzo[d][1,2,3]triazin-4(3H)-one
II-100 3-((2-cyclopropyloxazol-4-yl)methyl)-6-(4-(trifluoromethoxy)phenyl)benzo[d][1,2,3]triazin-4(3H)-one
V-2 3-((5-methyl-1,2,4-oxadiazol-3-yl)methyl)-6-(6-(2,2,2-trifluoroethoxy)pyridin-3-yl)benzo[d][1,2,3]triazin-4(3H)-one
V-11 3-(2-(pyrimidin-2-yloxy)ethyl)-6-(6-(trifluoromethyl)pyridin-3-yl)benzo[d][1,2,3]triazin-4(3H)-one
V-12 6-(2-(piperidin-1-yl)pyrimidin-5-yl)-3-(2-(pyrimidin-2-yloxy)ethyl)benzo[d][1,2,3]triazin-4(3H)-one
VII-1 3-(2-(pyrimidin-2-yloxy)ethyl)-6-((4-(trifluoromethoxy)phenyl)ethynyl)benzo[d][1,2,3]triazin-4(3H)-one
III-2 2-((3-methyl-1,2,4-oxadiazol-5-yl)methyl)-7-(4-(trifluoromethoxy)phenyl)phthalazin-1(2H)-one
III-3 2-((5-methyl-1,2,4-oxadiazol-3-yl)methyl)-7-(4-(trifluoromethoxy)phenyl)phthalazin-1(2H)-one
III-5 2-(pyrimidin-2-ylmethyl)-7-(4-(trifluoromethoxy)phenyl)phthalazin-1(2H)-one
III-6 2-benzyl-7-(4-(trifluoromethoxy)phenyl)phthalazin-1(2H)-one
III-8 2-phenethyl-7-(4-(trifluoromethoxy)phenyl)phthalazin-1(2H)-one III-9 2-(2-(1H-pyrazol-1-yl)ethyl)-7-(4-(trifluoromethoxy)phenyl)phthalazin-1(2H)-one
III-10 2-(2-(1H-pyrrol-1-yl)ethyl)-7-(4-(trifluoromethoxy)phenyl)phthalazin-1(2H)-one
III-11 2-((4-methyl-1,2,5-oxadiazol-3-yl)methyl)-7-(4-(trifluoromethoxy)phenyl)phthalazin-1(2H)-one
III-12 6-((1-oxo-7-(4-(trifluoromethoxy)phenyl)phthalazin-2(1H)-yl)methyl)picolinonitrile
III-14 2-((2-bromopyridin-3-yl)methyl)-7-(4-(trifluoromethoxy)phenyl)phthalazin-1(2H)-one
III-17 2-(2-(3-methyl-1H-pyrazol-1-yl)ethyl)-7-(4-(trifluoromethoxy)phenyl)phthalazin-1(2H)-one
III-18 2-(2-(6-methylpyridin-2-yl)ethyl)-7-(4-(trifluoromethoxy)phenyl)phthalazin-1(2H)-one
III-19 2-((4,6-dimethoxypyrimidin-2-yl)methyl)-7-(4-(trifluoromethoxy)phenyl)phthalazin-1(2H)-one
III-20 2-((2-cyclopropylpyridin-3-yl)methyl)-7-(4-(trifluoromethoxy)phenyl)phthalazin-1(2H)-one
III-22 2-((4,6-dimethylpyrimidin-2-yl)methyl)-7-(4-(trifluoromethoxy)phenyl)phthalazin-1(2H)-one
III-23 2-((4-cyclopropylpyrimidin-2-yl)methyl)-7-(4-(trifluoromethoxy)phenyl)phthalazin-1(2H)-one
III-24 2-(2-(3,5-dimethyl-1H-pyrazol-1-yl)ethyl)-7-(4-(trifluoromethoxy)phenyl)phthalazin-1(2H)-one
III-25 2-(2-(1-methyl-1H-benzo[d]imidazol-2-yl)ethyl)-7-(4-(trifluoromethoxy)phenyl)phthalazin-1(2H)-one
III-26 2-(2-(1H-1,2,4-triazol-1-yl)ethyl)-7-(4-(trifluoromethoxy)phenyl)phthalazin-1(2H)-one
III-27 2-((4-(cyclopropylmethoxy)pyrimidin-2-yl)methyl)-7-(4-(trifluoromethoxy)phenyl)phthalazin-1(2H)-one
III-28 2-(2-(pyrimidin-2-yloxy)ethyl)-7-(4-(trifluoromethoxy)phenyl)phthalazin-1(2H)-one
III-29 2-(2-(4-cyclopropylpyrimidin-2-yloxy)ethyl)-7-(4-(trifluoromethoxy)phenyl)phthalazin-1(2H)-one
III-30 2-((4-methoxypyrimidin-2-yl)methyl)-7-(4-(trifluoromethoxy)phenyl)phthalazin-1(2H)-one
III-31 2-(2-(4-bromo-1H-pyrazol-1-yl)ethyl)-7-(4-(trifluoromethoxy)phenyl)phthalazin-1(2H)-one
III-32 2-(2-(5-methyl-1H-pyrazol-1-yl)ethyl)-7-(4-(trifluoromethoxy)phenyl)phthalazin-1(2H)-one
III-34 2-(2-(4-(2-methoxypyrimidin-5-yl)-1H-pyrazol-1-yl)ethyl)-7-(4-(trifluoromethoxy)phenyl)phthalazin-1(2H)-one
III-35 2-((5-chloropyrimidin-2-yl)methyl)-7-(4-(trifluoromethoxy)phenyl)phthalazin-1(2H)-one
III-36 2-(2-(pyrimidin-4-yl)ethyl)-7-(4-(trifluoromethoxy)phenyl)phthalazin-1(2H)-one
III-37 2-(2-(5-chloropyrimidin-2-yloxy)ethyl)-7-(4-(trifluoromethoxy)phenyl)phthalazin-1(2H)-one
III-38 2-(2-(1H-pyrazol-1-yl)propyl)-7-(4-(trifluoromethoxy)phenyl)phthalazin-1(2H)-one
III-39 2-(2-(pyrazin-2-yloxy)ethyl)-7-(4-(trifluoromethoxy)phenyl)phthalazin-1(2H)-one
III-40 2-(2-(pyridin-2-yloxy)ethyl)-7-(4-(trifluoromethoxy)phenyl)phthalazin-1(2H)-one
III-41 2-((5-(pyridin-2-yl)isoxazol-3-yl)methyl)-7-(4-(trifluoromethoxy)phenyl)phthalazin-1(2H)-one
IV-3 3-((4-methyl-1,2,5-oxadiazol-3-yl)methyl)-6-(4-(trifluoromethoxy)phenyl)quinazolin-4(3H)-one
IV-6 3-((3-methyl-1,2,4-oxadiazol-5-yl)methyl)-6-(4-(trifluoromethoxy)phenyl)quinazolin-4(3H)-one
IV-9 3-((5-methyl-1,2,4-oxadiazol-3-yl)methyl)-6-(4-(trifluoromethoxy)phenyl)quinazolin-4(3H)-one
VIII-1 3-(pyrimidin-2-ylmethyl)-6-(4-(trifluoromethyl)phenyl)-2H-benzo[e][1,3]oxazin-4(3H)-one
VIII-3 3-(pyridin-2-ylmethyl)-6-(4-(trifluoromethoxy)phenyl)-2H-benzo[e][1,3]oxazin-4(3H)-one
VIII-7 2-methyl-3-(pyrimidin-2-ylmethyl)-6-(4-(trifluoromethoxy)phenyl)-2H-benzo[e][1,3]oxazin-4(3H)-one
VIII-13 2,2-dimethyl-3-(pyridin-2-ylmethyl)-6-(4-(trifluoromethoxy)phenyl)-2H-benzo[e][1,3]oxazin-4(3H)-one
VIII-18 6-(2-fluoro-4-(trifluoromethyl)phenyl)-3-(pyrimidin-2-ylmethyl)-2H-benzo[e][1,3]oxazin-4(3H)-one
VIII-19 3-(pyrimidin-2-ylmethyl)-6-(4-(trifluoromethyl)phenyl)-2H-benzo[e][1,3]oxazin-4(3H)-one
VIII-20 3-(pyrimidin-2-ylmethyl)-6-(4-(trifluoromethoxy)phenyl)-2H-benzo[e][1,3]oxazin-4(3H)-one
VIII-21 3-benzyl-6-(4-(trifluoromethyl)phenyl)-2H-benzo[e][1,3]oxazin-4(3H)-one
VIII-22 3-benzyl-6-(2-fluoro-4-(trifluoromethyl)phenyl)-2H-benzo[e][1,3]oxazin-4(3H)-one
VIII-23 3-benzyl-6-(4-(trifluoromethoxy)phenyl)-2H-benzo[e][1,3]oxazin-4(3H)-one
X-1 3-(pyridin-2-ylmethyl)-6-(4-(trifluoromethoxy)phenyl)-2H-benzo[e][1,3]thiazin-4(3H)-one
X-2 3-(pyrimidin-2-ylmethyl)-6-(4-(trifluoromethoxy)phenyl)-2H-benzo[e][1,3]thiazin-4(3H)-one
X-3 3-(pyridin-2-ylmethyl)-6-(4-(trifluoromethyl)phenyl)-2H-benzo[e][1,3]thiazin-4(3H)-one
X-4 3-(pyrimidin-2-ylmethyl)-6-(4-(trifluoromethyl)phenyl)-2H-benzo[e][1,3]thiazin-4(3H)-one
X-5 3-(2-chlorobenzyl)-6-(4-(trifluoromethyl)phenyl)-2H-benzo[e][1,3]thiazin-4(3H)-one
X-6 3-((3-fluoropyridin-2-yl)methyl)-6-(4-(trifluoromethyl)phenyl)-2H-benzo[e][1,3]thiazin-4(3H)-one
X-9 3-((3-fluoropyridin-2-yl)methyl)-6-(4-(trifluoromethoxy)phenyl)-2H-benzo[e][1,3]thiazin-4(3H)-one
IX-1 2-(pyrimidin-2-ylmethyl)-7-(4-(trifluoromethoxy)phenyl)-3,4-dihydroisoquinolin-1(2H)-one
IX-2 2-(pyridin-2-ylmethyl)-7-(4-(trifluoromethoxy)phenyl)-3,4-dihydroisoquinolin-1(2H)-one
IX-3 2-(pyrimidin-2-ylmethyl)-7-(4-(trifluoromethyl)phenyl)-3,4-dihydroisoquinolin-1(2H)-one
IX-4 2-(pyrimidin-2-ylmethyl)-7-((4-(trifluoromethyl)phenyl)ethynyl)-3,4-dihydroisoquinolin-1(2H)-one
IX-5 2-(pyrimidin-2-ylmethyl)-7-((4-(trifluoromethoxy)phenyl)ethynyl)-3,4-dihydroisoquinolin-1(2H)-one
IX-6 pyridin-2-yl(7-(4-(trifluoromethyl)phenyl)-3,4-dihydroisoquinolin-2(1H)-yl)methanone
IX-7 pyrimidin-2-yl(7-(4-(trifluoromethyl)phenyl)-3,4-dihydroisoquinolin-2(1H)-yl)methanone
IX-11 pyrimidin-2-yl(7-(4-(trifluoromethoxy)phenyl)-3,4-dihydroisoquinolin-2(1H)-yl)methanone
IX-17 pyridazin-3-yl(7-(4-(trifluoromethyl)phenyl)-3,4-dihydroisoquinolin-2(1H)-yl)methanone
IX-22 (7-(2-fluoro-4-(trifluoromethyl)phenyl)-3,4-dihydroisoquinolin-2(1H)-yl)(pyrimidin-2-yl)methanone
IX-23 (7-(4-chloro-2-fluorophenyl)-3,4-dihydroisoquinolin-2(1H)-yl)(pyrimidin-2-yl)methanone
IX-24 (7-(4-chloro-3-fluorophenyl)-3,4-dihydroisoquinolin-2(1H)-yl)(pyrimidin-2-yl)methanone
IX-25 (3-fluoropyridin-2-yl)(7-(4-(trifluoromethyl)phenyl)-3,4-dihydroisoquinolin-2(1H)-yl)methanone
IX-26 (7-(4-(trifluoromethyl)phenyl)-3,4-dihydroisoquinolin-2(1H)-yl)(1,3,5-trimethyl-1H-pyrazol-4-yl)methanone
IX-27 (1-isopropyl-1H-pyrazol-4-yl)(7-(4-(trifluoromethyl)phenyl)-3,4-dihydroisoquinolin-2(1H)-yl)methanone
IX-28 (1,3-dimethyl-1H-pyrazol-4-yl)(7-(4-(trifluoromethyl)phenyl)-3,4-dihydroisoquinolin-2(1H)-yl)methanone
IX-29 2-(pyridin-2-yl)-1-(7-(4-(trifluoromethyl)phenyl)-3,4-dihydroisoquinolin-2(1H)-yl)ethanone IX-30 2-(pyrimidin-2-yl)-1-(7-(4-(trifluoromethyl)phenyl)-3,4-dihydroisoquinolin-2(1H)-yl)ethanone IX-31 (2-isopropylpyrimidin-4-yl)(7-(4-(trifluoromethyl)phenyl)-3,4-dihydroisoquinolin-2(1H)-yl)methanone IX-32 pyrimidin-4-yl(7-(4-(trifluoromethyl)phenyl)-3,4-dihydroisoquinolin-2(1H)-yl)methanone IX-33 pyrimidin-5-yl(7-(4-(trifluoromethyl)phenyl)-3,4-dihydroisoquinolin-2(1H)-yl)methanone IX-34 (2-amino-6-methylpyrimidin-4-yl)(7-(4-(trifluoromethyl)phenyl)-3,4-dihydroisoquinolin-2(1H)-yl)methanone IX-36 (1H-pyrazol-5-yl)(7-(4-(trifluoromethyl)phenyl)-3,4-dihydroisoquinolin-2(1H)-yl)methanone IX-39 (1-methyl-1H-imidazol-4-yl)(7-(4-(trifluoromethyl)phenyl)-3,4-dihydroisoquinolin-2(1H)-yl)methanone IX-41 N-benzyl-7-(4-(trifluoromethyl)phenyl)-3,4-dihydroisoquinoline-2(1H)-carboxamide IX-42 N-phenyl-7-(4-(trifluoromethyl)phenyl)-3,4-dihydroisoquinoline-2(1H)-carboxamide IX-44 N-cyclopropyl-7-(4-(trifluoromethyl)phenyl)-3,4-dihydroisoquinoline-2(1H)-carboxamide IX-48 N-(furan-2-ylmethyl)-7-(4-(trifluoromethyl)phenyl)-3,4-dihydroisoquinoline-2(1H)-carboxamide IX-50 N-methyl-N-phenyl-7-(4-(trifluoromethyl)phenyl)-3,4-dihydroisoquinoline-2(1H)-carboxamide IX-52 morpholino(7-(4-(trifluoromethyl)phenyl)-3,4-dihydroisoquinolin-2(1H)-yl)methanone IX-53 pyrrolidin-1-yl(7-(4-(trifluoromethyl)phenyl)-3,4-dihydroisoquinolin-2(1H)-yl)methanone IX-56 (1-methyl-1H-imidazol-5-yl)(7-(4-(trifluoromethyl)phenyl)-3,4-dihydroisoquinolin-2(1H)-yl)methanone IX-57 (1H-imidazol-2-yl)(7-(4-(trifluoromethyl)phenyl)-3,4-dihydroisoquinolin-2(1H)-yl)methanone IX-59 (4-fluoro-1H-imidazol-5-yl)(7-(4-(trifluoromethyl)phenyl)-3,4-dihydroisoquinolin-2(1H)-yl)methanone IX-77 N-cyclopentyl-7-(4-(trifluoromethyl)phenyl)-3,4-dihydroisoquinoline-2(1H)-carboxamide IX-80 (1-methyl-1H-imidazol-2-yl)(7-(4-(trifluoromethyl)phenyl)-3,4-dihydroisoquinolin-2(1H)-yl)methanone IX-88 azetidin-1-yl(7-(4-(trifluoromethyl)phenyl)-3,4-dihydroisoquinolin-2(1H)-yl)methanone IX-89 N-(pyrimidin-2-ylmethyl)-7-(4-(trifluoromethyl)phenyl)-3,4-dihydroisoquinoline-2(1H)-carboxamide IX-90 (3-methylpyrrolidin-1-yl)(7-(4-(trifluoromethyl)phenyl)-3,4-dihydroisoquinolin-2(1H)-yl)methanone IX-91 (3-hydroxypyrrolidin-1-yl)(7-(4-(trifluoromethyl)phenyl)-3,4-dihydroisoquinolin-2(1H)-yl)methanoneo IX-92 (3,3-difluoroazetidin-1-yl)(7-(4-(trifluoromethyl)phenyl)-3,4-dihydroisoquinolin-2(1H)-yl)methanone IX-93 (3-(pyridin-3-yloxy)azetidin-1-yl)(7-(4-(trifluoromethyl)phenyl)-3,4-dihydroisoquinolin-2(1H)-yl)methanone IX-94 (3-fluoropyrrolidin-1-yl)(7-(4-(trifluoromethyl)phenyl)-3,4-dihydroisoquinolin-2(1H)-yl)methanone IX-95 (3-fluoroazetidin-1-yl)(7-(4-(trifluoromethyl)phenyl)-3,4-dihydroisoquinolin-2(1H)-yl)methanone IX-98 2-(1-methyl-1H-imidazol-4-ylsulfonyl)-7-(4-(trifluoromethyl)phenyl)-1,2,3,4-tetrahydroisoquinoline IX-101 (R)-(3-(hydroxymethyl)pyrrolidin-1-yl)(7-(4-(trifluoromethyl)phenyl)-3,4-dihydroisoquinolin-2(1H)-yl)methanone IX-102 (S)-(2-(hydroxymethyl)pyrrolidin-1-yl)(7-(4-(trifluoromethyl)phenyl)-3,4-dihydroisoquinolin-2(1H)-yl)methanone IX-104 (3-(methylsulfonyl)azetidin-1-yl)(7-(4-(trifluoromethyl)phenyl)-3,4-dihydroisoquinolin-2(1H)-yl)methanone IX-105 ((2R,5R)-2,5-dimethylpyrrolidin-1-yl)(7-(4-(trifluoromethyl)phenyl)-3,4-dihydroisoquinolin-2(1H)-yl)methanone IX-106 ((2R,5S)-2,5-dimethylpyrrolidin-1-yl)(7-(4-(trifluoromethyl)phenyl)-3,4-dihydroisoquinolin-2(1H)-yl)methanone IX-107 (3-methylazetidin-1-yl)(7-(4-(trifluoromethyl)phenyl)-3,4-dihydroisoquinolin-2(1H)-yl)methanone IX-108 (3-hydroxyazetidin-1-yl)(7-(4-(trifluoromethyl)phenyl)-3,4-dihydroisoquinolin-2(1H)-yl)methanone IX-111 (3-amino-1H-1,2,4-triazol-5-yl)(7-(4-(trifluoromethyl)phenyl)-3,4-dihydroisoquinolin-2(1H)-yl)methanone IX-112 (3-hydroxy-3-methylazetidin-1-yl)(7-(4-(trifluoromethyl)phenyl)-3,4-dihydroisoquinolin-2(1H)-yl)methanone IX-113 (3-(hydroxymethyl)azetidin-1-yl)(7-(4-(trifluoromethyl)phenyl)-3,4-dihydroisoquinolin-2(1H)-yl)methanone IX-114 (R)-tert-butyl 2-(7-(4-(trifluoromethyl)phenyl)-1,2,3,4-tetrahydroisoquinoline-2-carbonyl)pyrrolidine-1-carboxylate IX-116 (1-phenyl-1H-1,2,3-triazol-5-yl)(7-(4-(trifluoromethyl)phenyl)-3,4-dihydroisoquinolin-2(1H)-yl)methanone IX-119 ethyl 2-(4-(7-(4-(trifluoromethyl)phenyl)-1,2,3,4-tetrahydroisoquinoline-2-carbonyl)-1H-1,2,3-triazol-1-yl)acetate IX-122 pyrrolidin-1-yl(7-(4-(trifluoromethoxy)phenyl)-3,4-dihydroisoquinolin-2(1H)-yl)methanone IX-123 N-(pyrimidin-2-ylmethyl)-7-(4-(trifluoromethoxy)phenyl)-3,4-dihydroisoquinoline-2(1H)-carboxamide or a pharmaceutically acceptable salt, ester, hydrate, solvate, stereoisomer, tautomer, polymorph and/or prodrug thereof.

DETAILED DESCRIPTION

1. Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms, or from 1 to 15 carbon atoms, or from 1 to 10 carbon atoms, or from 1 to 8 carbon atoms, or from 1 to 6 carbon atoms, or from 1 to 4 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, (in some embodiments, 1, 2 or 3 substituents) selected from the group consisting of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —SO$_2$-alkyl, —SO$_2$-cycloalkyl, —SO$_2$-heterocyclyl, —SO$_2$-aryl and —SO$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2; or 2) an alkyl group as defined above that is interrupted by 1-10 atoms (e.g. 1, 2, 3, 4 or 5 atoms) independently chosen from oxygen, sulfur and NR$^a$, where R$^a$ is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2; or 3) an alkyl group as defined above that has both 1, 2, 3, 4 or 5 substituents as defined above and is also interrupted by 1-10 atoms (e.g. 1, 2, 3, 4 or 5 atoms) as defined above.

The term "lower alkyl" refers to a monoradical branched or unbranched saturated hydrocarbon chain having 1, 2, 3, 4, 5 or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (in some embodiments, 1, 2 or 3 substituents), as defined for substituted alkyl or a lower alkyl group as defined above that is interrupted by 1, 2, 3, 4 or 5 atoms as defined for substituted alkyl or a lower alkyl group as defined above that has both 1, 2, 3, 4 or 5 substituents as defined above and is also interrupted by 1, 2, 3, 4 or 5 atoms as defined above.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "lower alkylene" refers to a diradical of a branched or unbranched saturated hydrocarbon chain, in some embodiments, having 1, 2, 3, 4, 5 or 6 carbon atoms.

The term "substituted alkylene" refers to an alkylene group as defined above having 1 to 5 substituents (in some embodiments, 1, 2 or 3 substituents) as defined for substituted alkyl.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —CH═CH$_2$), 1-propylene (or allyl, i.e. —CH$_2$CH═CH$_2$), isopropylene (—C(CH$_3$)═CH$_2$), and the like.

The term "lower alkenyl" refers to alkenyl as defined above having from 2 to 6 carbon atoms.

The term "substituted alkenyl" refers to an alkenyl group as defined above having 1 to 5 substituents (in some embodiments, 1, 2 or 3 substituents) as defined for substituted alkyl.

The term "alkenylene" refers to a diradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡CCH$_3$), and the like.

The term "substituted alkynyl" refers to an alkynyl group as defined above having 1 to 5 substituents (in some embodiments, 1, 2 or 3 substituents) as defined for substituted alkyl.

The term "alkynylene" refers to a diradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds.

The term "hydroxy" or "hydroxyl" refers to a group —OH.

The term "alkoxy" refers to the group R—O—, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl. This term is exemplified by groups such as methoxy, ethoxy, n-propoxy, iso-propoxy, n-butoxy, iso-butoxy, t-butoxy, n-hexyloxy, and the like.

The term "substituted alkoxy" refers to the group R—O—, where R is substituted alkyl or —Y—Z, in which Y is substituted alkylene and Z is substituted alkenyl or substituted alkynyl, where substituted alkyl, substituted alkenyl and substituted alkynyl are as defined herein.

The term "cycloalkyl" refers to cyclic alkyl groups of from 3 to 20 carbon atoms, or from 3 to 10 carbon atoms, having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO— cycloalkyl, —SO-heterocyclyl, —SO-aryl, —SO-heteroaryl, —SO$_2$-alkyl, —SO$_2$-cycloalkyl, —SO$_2$-heterocyclyl, —SO$_2$-aryl and —SO$_2$-heteroaryl. The term "substituted cycloalkyl" also includes cycloalkyl groups wherein one or more of the annular carbon atoms of the cycloalkyl group has an oxo group bonded thereto. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "cycloalkoxy" refers to the group cycloalkyl-O—.

The term "substituted cycloalkoxy" refers to the group substituted cycloalkyl-O—.

The term "cycloalkenyloxy" refers to the group cycloalkenyl-O—.

The term "substituted cycloalkenyloxy" refers to the group substituted cycloalkenyl-O—.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In some embodiments, aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —SO$_2$-alkyl, —SO$_2$-cycloalkyl, —SO$_2$-heterocyclyl, —SO$_2$-aryl and —SO$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —SO$_2$-alkyl, —SO$_2$-cycloalkyl, —SO$_2$-heterocyclyl, —SO$_2$-aryl and —SO$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Examples of heterocyclics include tetrahydrofuranyl, morpholino, piperidinyl, and the like.

The term "heterocyclooxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine.

The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

Unless otherwise constrained by the definition for the heteroaryl substituent, such heteroaryl groups can be optionally substituted with 1 to 5 substituents (in some embodiments, 1, 2 or 3 substituents) selected from the group consisting alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —SO$_2$-alkyl, —SO$_2$-cycloalkyl, —SO$_2$-heterocyclyl, —SO$_2$-aryl and —SO$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxynitrogen containing heteroaryl compounds.

The term "heteroaryloxy" refers to the group heteroaryl-O—.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen or a group —Y—Z, in which Y is optionally substituted alkylene and Z is alkenyl, cycloalkenyl or alkynyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkyl amine" refers to R—NH$_2$ in which R is optionally substituted alkyl.

The term "dialkyl amine" refers to R—NHR in which each R is independently an optionally substituted alkyl.

The term "trialkyl amine" refers to NR$_3$ in which each R is independently an optionally substituted alkyl.

The term "cyano" refers to the group —CN.

The term "azido" refers to a group

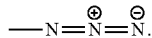

The term "keto" or "oxo" refers to a group =O.

The term "carboxy" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, CF$_3$, amino, substituted amino, cyano or —S(O)$_n$R$^a$, in which R$^a$ is alkyl, aryl or heteroaryl and n is 0, 1 or 2.

The term "acyl" denotes the group —C(O)R, in which R is hydrogen, alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aminocarbonyl" refers to the group —C(O)NRR where each R is independently hydrogen, alkyl, cycloalkyl, aryl, heteroaryl, or heterocyclyl, or where both R groups are joined to form a heterocyclic group (e.g., morpholino). Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "acyloxy" refers to the group —OC(O)—R, in which R is alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "acylamino" refers to the group —NRC(O)R where each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkoxycarbonylamino" refers to the group —N(R$^d$)C(O)OR in which R is alkyl and R$^d$ is hydrogen or alkyl. Unless otherwise constrained by the definition, each alkyl may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aminocarbonylamino" refers to the group —NR$^c$C(O)NRR, wherein R$^c$ is hydrogen or alkyl and each R is hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "thiol" refers to the group —SH.

The term "thiocarbonyl" refers to a group =S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl.

"Substituted sulfoxide" refers to a group —S(O)R, in which R is substituted alkyl, substituted cycloalkyl, substituted heterocyclyl, substituted aryl or substituted heteroaryl, as defined herein.

The term "sulfone" refers to a group —S(O)$_2$R, in which R is alkyl, cycloalkyl, heterocyclyl, aryl or heteroaryl. "Substituted sulfone" refers to a group —S(O)$_2$R, in which R is substituted alkyl, substituted cycloalkyl, substituted heterocyclyl, substituted aryl or substituted heteroaryl, as defined herein.

The term "aminosulfonyl" refers to the group —S(O)$_2$NRR, wherein each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

The phrase "the dotted line is a double bond" refers to compounds of Formula I having a double bond between X$^1$ and X$^2$. The phrase "the dotted line is a single bond" refers to compounds of Formula I having a single bond between X$^1$ and X$^2$.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to-substituted aryl-(substituted aryl)-substituted aryl.

A compound of a given formula (e.g. the compound of Formula I, which also includes Formulas II, III, IV, V, VI, IA, IB, IC, ID, IIA, IIIA, IVA, IVB, VA, VIA, VIIA, VIIIA and IXA) is intended to encompass the compounds of the disclosure, and the pharmaceutically acceptable salts, pharmaceutically acceptable esters, isomers, tautomers, solvates, isotopes, hydrates, polymorphs, and prodrugs of such compounds. Additionally, the compounds of the disclosure may possess one or more asymmetric centers, and can be produced as a racemic mixture or as individual enantiomers or diastereoisomers. The number of stereoisomers present in any given compound of a given formula depends upon the number of asymmetric centers present (there are 2$^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers. Non-limiting examples of amide-comprising and imidic acid-comprising tautomers are shown below:

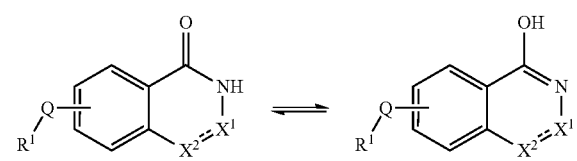

The term "polymorph" refers to different crystal structures of a crystalline compound. The different polymorphs may result from differences in crystal packing (packing polymorphism) or differences in packing between different conformers of the same molecule (conformational polymorphism).

The term "solvate" refers to a complex formed by the combining of a compound of Formula I, or any other formula as disclosed herein, and a solvent.

The term "hydrate" refers to the complex formed by the combining of a compound of Formula I, or any formula disclosed herein, and water.

The term "prodrug" refers to compounds of Formula I, or any formula disclosed herein, that include a chemical groups which, in vivo, can be converted and/or can be split off from the remainder of the molecule to provide for the active drug, a pharmaceutically acceptable salt thereof or a biologically active metabolite thereof.

Any formula or structure given herein, including Formula I, or any formula disclosed herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds of Formula I, or any formula disclosed herein, in which from 1 to "n" hydrogens attached to a carbon atom is/are replaced by deuterium, in which n is the number of hydrogens in the molecule. Such compounds exhibit increased resistance to metabolism and are thus useful for increasing the half life of any compound of Formula I when administered to a mammal. See, for example, Foster, "Deuterium Isotope Effects in Studies of Drug Metabolism", Trends Pharmacol. Sci. 5(12): 524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to absorption, distribution, metabolism and excretion (ADME). Substitution with heavier isotopes such as deuterium may afford certain therapeutic advantages resulting from greater metabolic stability, for example increased in vivo half-life or reduced dosage requirements. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the Formula I, or any formula disclosed herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The term "treatment" or "treating" refers to the administration of a compound as disclosed herein to a mammal for the purpose of:
 (i) preventing the disease, that is, causing the clinical symptoms of the disease not to develop;
 (ii) inhibiting the disease, that is, arresting the development of clinical symptoms; and/or
 (iii) relieving the disease, that is, causing the regression of clinical symptoms.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein monosubstituted amines have 2 of the three substituents on nitrogen ($R^{30}$, $R^{31}$ and $R^{32}$) as hydrogen, di-substituted amines have 1 of the three substituents on nitrogen ($R^{30}$, $R^{31}$ and $R^{32}$) as hydrogen, whereas tri-substituted amines have none of the three substituents on nitrogen ($R^{30}$, $R^{31}$ and $R^{32}$) as hydrogen. $R^{30}$, $R^{31}$ and $R^{32}$ are selected from a variety of substituents such as hydrogen, optionally substituted alkyl, aryl, heteroayl, cycloalkyl, cycloalkenyl, heterocyclyl and the like. The above-mentioned amines refer to the compounds wherein either one, two or three substituents on the nitrogen are as listed in the name. For example, the term "cycloalkenyl amine" refers to cycloalkenyl-NH$_2$, wherein "cycloalkenyl" is as defined herein. The term "diheteroarylamine" refers to NH(heteroaryl)$_2$, wherein "heteroaryl" is as defined herein and so on.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all diluents, solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

"Coronary diseases" or "cardiovascular diseases" refer to diseases of the cardiovasculature arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes and intermittent claudication.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs or calves when walking, climbing stairs or exercising. The pain is called intermittent claudication. When listing the symptom intermittent claudication, it is intended to include both PAD and PVD.

Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia and the ventricular tachycardias (VT5), including idiopathic ventricular tachycardia, ventricular fibrillation, pre-excitation syndrome and Torsade de Pointes (TdP).

2. Nomenclature

Names of compounds of the present disclosure are provided using ACD/Name software for naming chemical compounds (Advanced Chemistry Development, Inc., Toronto). Other compounds or radicals may be named with common names, or systematic or non-systematic names. The naming and numbering of the compounds of the disclosure is illustrated with a representative compound of Formula I:

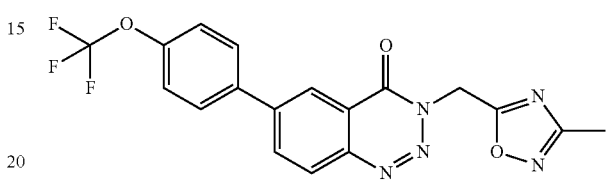

which is named 3-((3-methyl-1,2,4-oxadiazol-5-yl)methyl)-6-(4-(trifluoromethoxy)phenyl) benzo[d][1,2,3]triazin-4(3H)-one.

3. Compounds of Formula I

Accordingly, in typical embodiments the present disclosure provides compounds that function as sodium channel blockers. In typical embodiments the disclosure relates to compounds of Formula I:

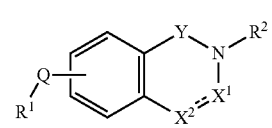

wherein:
the dotted line represents an optional double bond;
Y is —C(R$^5$)$_2$— or —C(O)—;
X$^1$ is N and X$^2$ is N, X$^1$ is N and X$^2$ is CR$^3$, or X$^1$ is CR$^3$ and X$^2$ is N, and the dotted line is a double bond; or
X$^1$ is C(R$^3$)$_2$ and X$^2$ is NR$^4$, —O—, —S—, —S(O)— or —S(O)$_2$—, or X$^1$ and X$^2$ are both C(R$^3$)$_2$, and the dotted line is a single bond;
provided that:
when the dotted line is a single bond and Y is —C(R$^5$)$_2$—; then both X$^1$ and X$^2$ are C(R$^3$)$_2$; and
when the dotted line is a double bond; Y is —C(O)—;
Q is a covalent bond or C$_{2-4}$ alkynylene;
R$^1$ is C$_{3-6}$ cycloalkyl, C$_{3-6}$ cycloalkenyl, aryl, heterocyclyl or heteroaryl;
wherein said C$_{3-6}$ cycloalkyl, C$_{3-6}$ cycloalkenyl, aryl, heterocyclyl or heteroaryl are optionally substituted with one, two or three substituents independently selected from the group consisting of halo, —NO$_2$, CN, —SF$_5$, —Si(CH$_3$)$_3$, —O—R$^{20}$, —S—R$^{20}$, —C(O)—R$^{20}$, —C(O)—OR$^{20}$, —N(R$^{20}$)(R$^{22}$), —C(O)—N(R$^{20}$)(R$^{22}$), —N(R$^{20}$)—C(O)—R$^{22}$, —N(R$^{20}$)—S(O)$_2$—R$^{22}$, —S(O)$_2$—R$^{20}$, —S(O)$_2$—N(R$^{20}$)(R$^{22}$), C$_{1-4}$ alkyl, C$_{2-4}$ alkenyl, C$_{2-4}$ alkynyl, C$_{3-6}$ cycloalkyl, aryl, heteroaryl and heterocyclyl; and
wherein said C$_{1-4}$ alkyl, C$_{2-4}$ alkenyl, C$_{2-4}$ alkynyl, C$_{3-6}$ cycloalkyl, aryl, heteroaryl or heterocyclyl are optionally substituted with one, two or three substituents independently selected from the group consisting of halo, —$NO_2$, aryl, heterocyclyl, heteroaryl, $C_{1-4}$ alkyl, $C_{3-6}$ cycloalkyl, —$N(R^{20})(R^{22})$, —C(O)—C(O)—$OR^{20}$, —C(O)—$N(R^{20})(R^{22})$, —CN and —O—$R^{20}$;

$R^2$ is —$R^6$, —$C_{1-6}$ alkylene-$R^6$, —$C_{2-6}$ alkenylene-$R^6$, —$C_{2-6}$ alkynylene-$R^6$, -L-$R^6$, -L-$C_{1-6}$ alkylene-$R^6$, —$C_{1-6}$ alkylene-L-$R^6$ or —$C_{1-6}$ alkylene-L-$C_{1-6}$ alkylene-$R^6$;

L is —O—, —S—, —C(O)—, —$S(O)_2$—, —$NR^{20}S(O)_2$—, —$S(O)_2NR^{20}$—, —$C(O)NR^{20}$— or —$NR^{20}C(O)$—; provided that when Y is —$C(R^5)_2$—, then L is —C(O)— or —$S(O)_2$—, and $R^2$ is -L-$R^6$, -L-$C_{1-6}$ alkylene-$R^6$, —$C_{1-6}$ alkylene-L-$R^6$ or —$C_{1-6}$ alkylene-L-$C_{1-6}$ alkylene-$R^6$;

each $R^3$ is independently hydrogen, $C_{1-6}$ alkyl, $C_{3-6}$ cycloalkyl, aryl, heteroaryl or heterocyclyl;
  wherein said $C_{1-6}$ alkyl is optionally substituted with one, two or three substituents independently selected from the group consisting of halo, —$NO_2$, $C_{3-6}$ cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$;
    wherein said $C_{3-6}$ cycloalkyl, aryl, heterocyclyl and heteroaryl are optionally further substituted with one, two or three substituents independently selected from the group consisting of halo, —$NO_2$, $C_{1-6}$ alkyl, aralkyl, $C_{3-6}$ cycloalkyl, aryl, heterocyclyl, heteroaryl, —$N(R^{20})(R^{22})$, —C(O)—$R^{20}$, —C(O)—$OR^{20}$, —C(O)—$OR^{20}$, —C(O)—$N(R^{20})(R^{22})$, —CN and —O—$R^{20}$; and
      wherein said $C_{1-6}$ alkyl, aralkyl, $C_{3-6}$ cycloalkyl, aryl, heterocyclyl and heteroaryl are optionally further substituted with one, two or three substituents independently selected from the group consisting of halo, —$NO_2$, —$N(R^{20})(R^{22})$, —C(O)—C(O)—$OR^{20}$, —C(O)—$N(R^{20})(R^{22})$, —CN and —O—$R^{20}$;

or when $X^1$ is $C(R^3)_2$, two $R^3$ can join together with the with the carbon atom to which they are attached to form a $C_{3-6}$ cycloalkyl or heterocyclyl;

$R^4$ is hydrogen, $C_{1-6}$ alkyl, $C_{1-4}$ alkoxy, —C(O)—$OR^{20}$, —C(O)—$N(R^{20})(R^{22})$, —$N(R^{20})$—$S(O)_2$—$R^{20}$, $C_{3-6}$ cycloalkyl, aryl, heteroaryl or heterocyclyl;
  wherein said $C_{1-6}$ alkyl is optionally substituted with one, two or three substituents independently selected from the group consisting of halo, —$NO_2$, $C_{3-6}$ cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$;
    wherein said $C_{3-6}$ cycloalkyl, aryl, heterocyclyl or heteroaryl are optionally further substituted with one, two or three substituents independently selected from the group consisting of halo, —$NO_2$, $C_{1-6}$ alkyl, aralkyl, $C_{3-6}$ cycloalkyl, aryl, heterocyclyl, heteroaryl, —$N(R^{20})(R^{22})$, —C(O)—$R^{20}$, —C(O)—$OR^{20}$, —C(O)—$OR^{20}$, —C(O)—$N(R^{20})(R^{22})$, —CN, and —O—$R^{20}$; and
      wherein said $C_{1-6}$ alkyl, aralkyl, $C_{3-6}$ cycloalkyl, aryl, heterocyclyl, heteroaryl, are optionally further substituted with one, two or three substituents independently selected from the group consisting of hydroxyl, halo, —$NO_2$, —$N(R^{20})$ ($R^{22}$), —C(O)—$R^{20}$, —C(O)—$OR^{20}$, —C(O)—$OR^{20}$, —C(O)—$N(R^{20})(R^{22})$, —CN and —O—$R^{20}$;

each $R^5$ is independently hydrogen or $C_{1-6}$ alkyl;

$R^6$ is $C_{3-6}$ cycloalkyl, aryl, heteroaryl or heterocyclyl;
  wherein said $C_{3-6}$ cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, $C_{3-6}$ cycloalkyl, aryl, heterocyclyl, heteroaryl, —$N(R^{20})(R^{22})$, —$N(R^{20})$—$S(O)_2$—$R^{20}$, —$N(R^{20})$—C(O)—$R^{22}$, —C(O)—$R^{20}$, —C(O)—$OR^{20}$, —C(O)—$N(R^{20})(R^{22})$, —$S(O)_2$—$R^{20}$, —CN and —O—$R^{20}$;
    wherein said $C_{1-6}$ alkyl, $C_{3-6}$ cycloalkyl, aryl, heterocyclyl or heteroaryl are optionally further substituted with one, two or three substituents independently selected from the group consisting of halo, —$NO_2$, $C_{1-6}$ alkyl, $C_{3-6}$ cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$; and
    wherein said $C_{1-6}$ alkyl, $C_{3-6}$ cycloalkyl, aryl, heterocyclyl or heteroaryl are optionally further substituted with one, two or three substituents independently selected from the group consisting of $C_{1-6}$ alkyl, halo, aryl, —$NO_2$, —$CF_3$, —$N(R^{20})(R^{22})$, —C(O)—$R^{20}$, —C(O)—$OR^{20}$, —C(O)—$N(R^{20})(R^{22})$, —$S(O)_2$—$R^{20}$ and —O—$R^{20}$;

$R^{20}$ and $R^{22}$ are in each instance independently hydrogen, $C_{1-6}$ alkyl, $C_{2-6}$ alkenyl, $C_{2-6}$ alkynyl, $C_{3-6}$ cycloalkyl, heterocyclyl, aryl or heteroaryl; and
  wherein the $C_{1-6}$ alkyl, $C_{2-6}$ alkenyl, $C_{2-6}$ alkynyl, $C_{3-6}$ cycloalkyl, heterocyclyl, aryl or heteroaryl are optionally substituted with one, two or three substituents independently selected from the group consisting of hydroxyl, halo, $C_{1-4}$ alkyl, aralkyl, —$N(R^{26})(R^{28})$, aminoacyl, —$NO_2$, —$S(O)_2$—$R^{26}$, —CN, $C_{1-3}$ alkoxy, —$CF_3$, —$OCF_3$, —$OCH_2CF_3$, —C(O)—$NH_2$, —C(O)—$R^{26}$, —C(O)—$OR^{26}$, aryl, $C_{3-6}$ cycloalkyl, heterocyclyl, aryl and heteroaryl;
    wherein said aralkyl, heterocyclyl or heteroaryl is optionally further substituted with $C_{1-4}$ alkyl, —$CF_3$, aryl or $C_{3-6}$ cycloalkyl; or
  when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, alkyl, aralkyl, aryl, aryloxy, aralkyloxy, heteroaryloxy, substituted amino, aminoacyl, —$NO_2$, —$S(O)_2$—$R^{26}$, —CN, $C_{1-3}$ alkoxy, hydroxymethyl, —$CF_3$, —$OCF_3$, aryl, heteroaryl and $C_{3-6}$ cycloalkyl; and $R^{26}$ and $R^{28}$ are each independently selected from the group consisting of hydrogen, $C_{1-6}$ alkyl, $C_{1-6}$ alkenyl, $C_{3-6}$ cycloalkyl, aryl and heteroaryl; and
  wherein the $C_{1-6}$ alkyl, $C_{3-6}$ cycloalkyl, aryl or heteroaryl may be further substituted with from 1 to 3 substituents independently selected from the group consisting of hydroxyl, halo, $C_{1-4}$ alkoxy, —$CF_3$, —$OCF_3$ and $C_{3-6}$ cycloalkyl;

or a pharmaceutically acceptable salt, ester, hydrate, solvate, stereoisomer, tautomer, polymorph and/or prodrug thereof.

In certain embodiments, the compound of Formula I is represented by Formula IA:

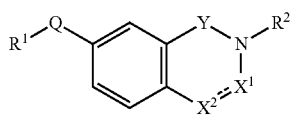
IA wherein the dotted line, Q, Y, $R^1$, $R^2$, $X^1$ and $X^2$ are as defined for Formula I.

In certain embodiments, the compound of Formula I is represented by Formula ID:

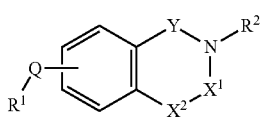
ID wherein Q, Y, $R^1$, $R^2$, $X^1$ and $X^2$ are as defined for Formula I.

In certain embodiments of Formula I or IA, Q is a bond.

In certain embodiments of Formula I or IA, $R^2$ is —$R^6$, —$C_{1-6}$ alkylene-$R^6$, -L-$R^6$, -L-$C_{1-6}$ alkylene-$R^6$, —$C_{1-6}$ alkylene-L-$R^6$ or —$C_{1-6}$ alkylene-L-$C_{1-6}$ alkylene-$R^6$.

In certain embodiments of Formula I or IA, $R^2$ is —$R^6$, —$C_{1-6}$ alkylene-$R^6$, -L-$R^6$, -L-$C_{1-6}$ alkylene-$R^6$ or —$C_{1-6}$ alkylene-L-$R^6$;

L is —O—, —C(O)—, —S(O)$_2$—, —S(O)$_2$N$R^{20}$— or —C(O)N$R^{20}$—; provided that when Y is —C($R^5$)$_2$—, then L is —C(O)— or —S(O)$_2$—, and $R^2$ is -L-$R^6$, alkylene-$R^6$ or —$C_{1-6}$ alkylene-L-$R^6$; and $R^6$ is $C_{3-6}$ cycloalkyl, aryl, heteroaryl or heterocyclyl;
  wherein said $C_{3-6}$ cycloalkyl, aryl, heteroaryl or heterocyclyl are optionally substituted with one, two or three substituents independently selected from the group consisting of $C_{1-6}$ alkyl, halo, $C_{3-6}$ cycloalkyl, aryl, heteroaryl, —N($R^{20}$)($R^{22}$), —C(O)—O$R^{20}$, —S(O)$_2$—$R^{20}$, —CN and —O—$R^{20}$;
    wherein said $C_{1-6}$ alkyl or heteroaryl are optionally further substituted with one, two or three substituents independently selected from the group consisting of halo, $C_{3-6}$ cycloalkyl, aryl, heterocyclyl, heteroaryl, —C(O)—O$R^{20}$ and —O—$R^{20}$; and
    wherein said heteroaryl is optionally further substituted with one, two or three $C_{1-6}$ alkyl.

In certain embodiments of Formula I or IA, $R^2$ is

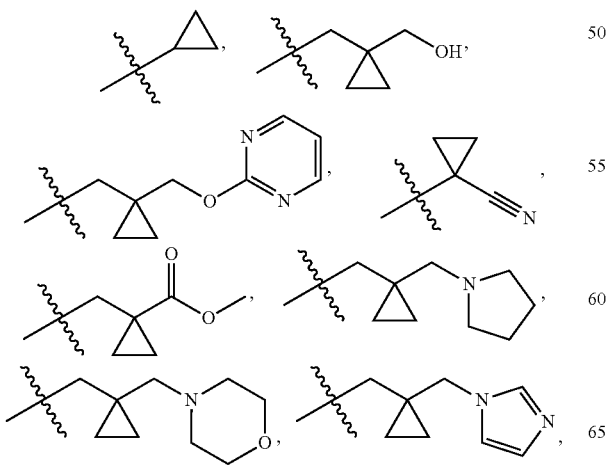

-continued

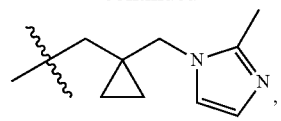

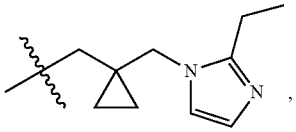

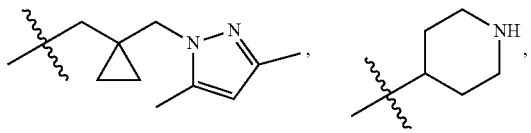

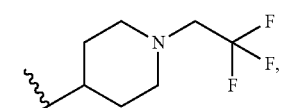

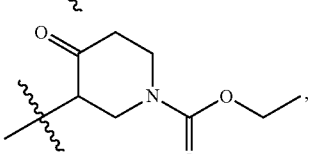

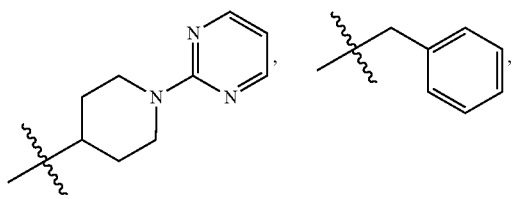

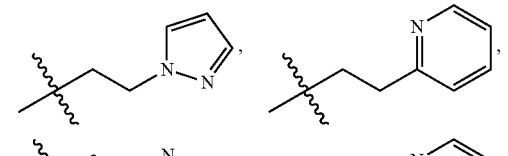

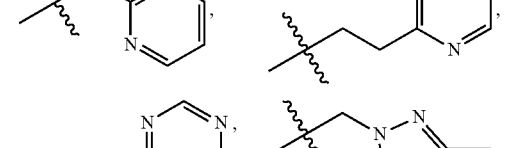

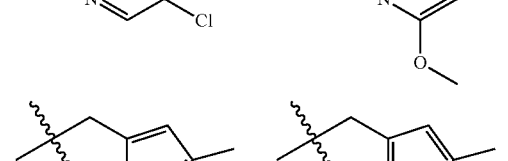

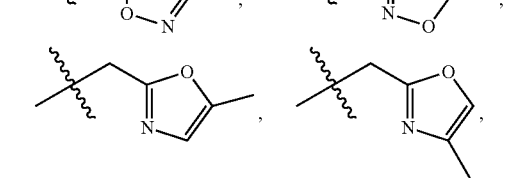

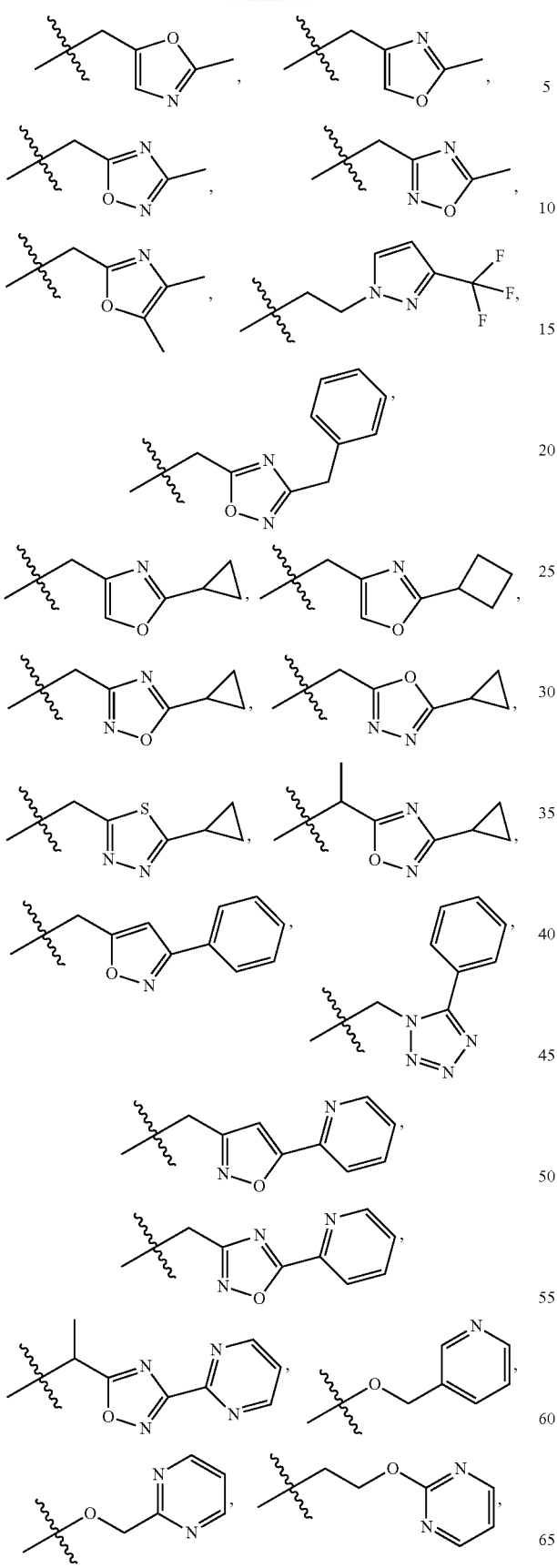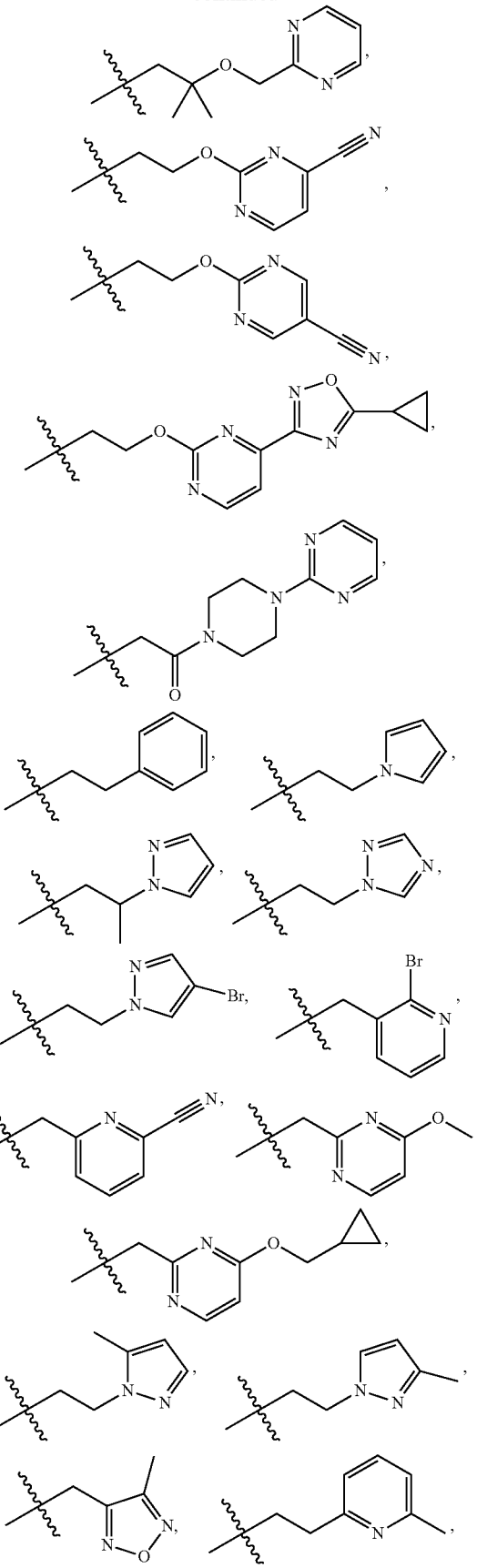

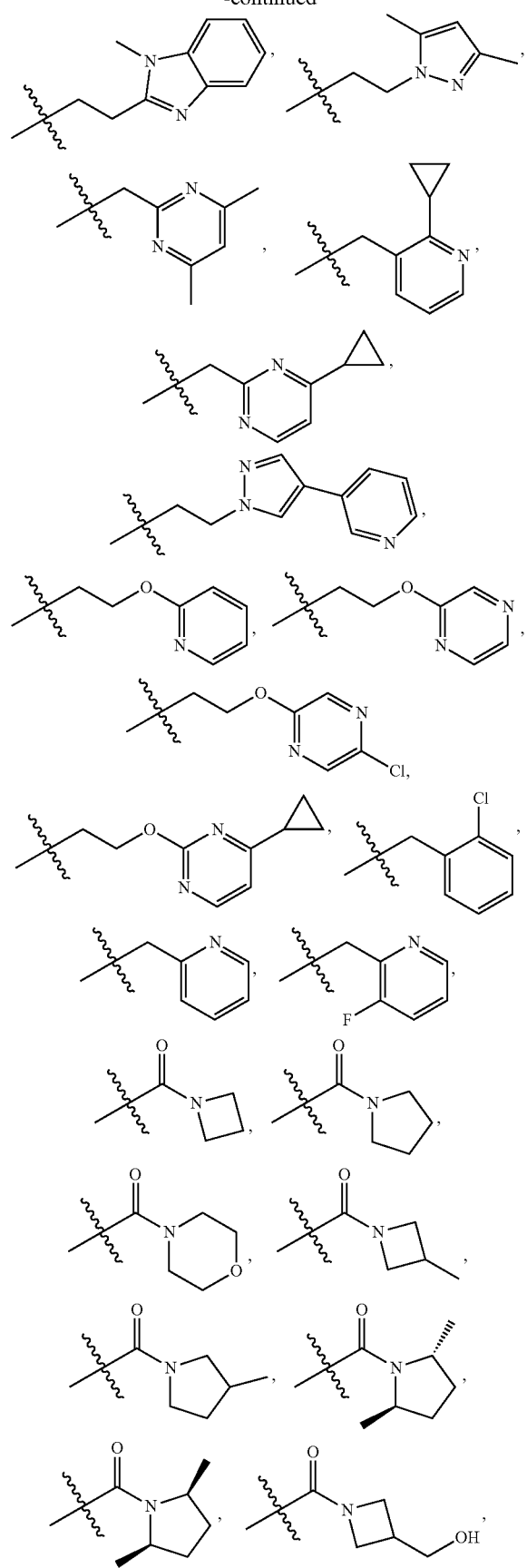
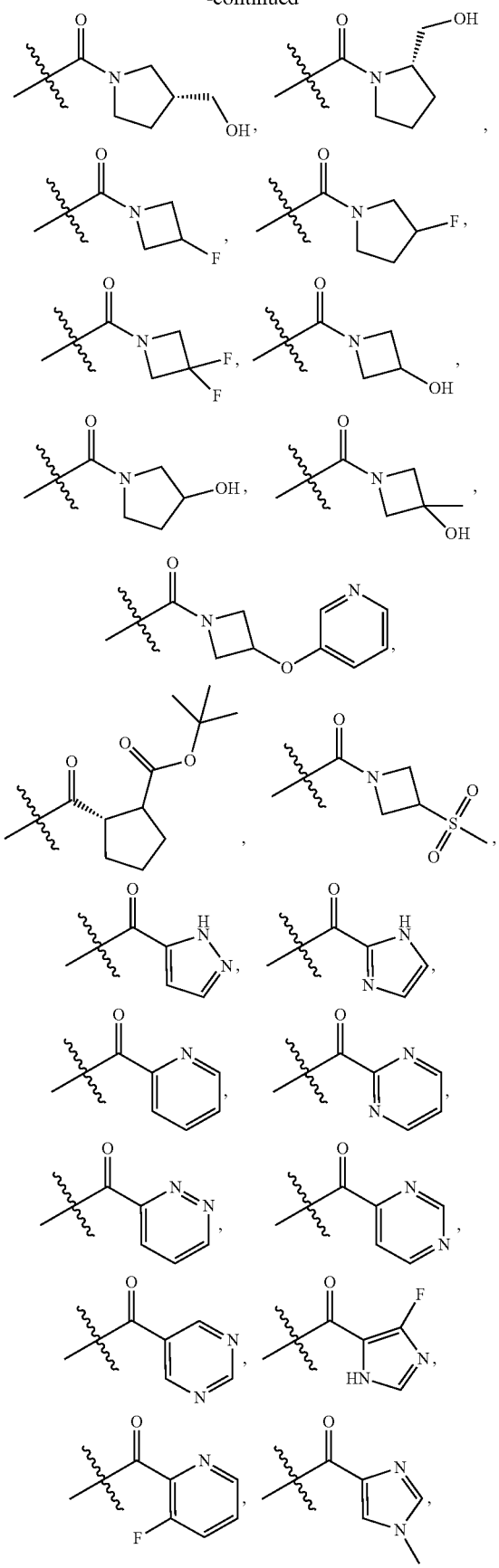

-continued

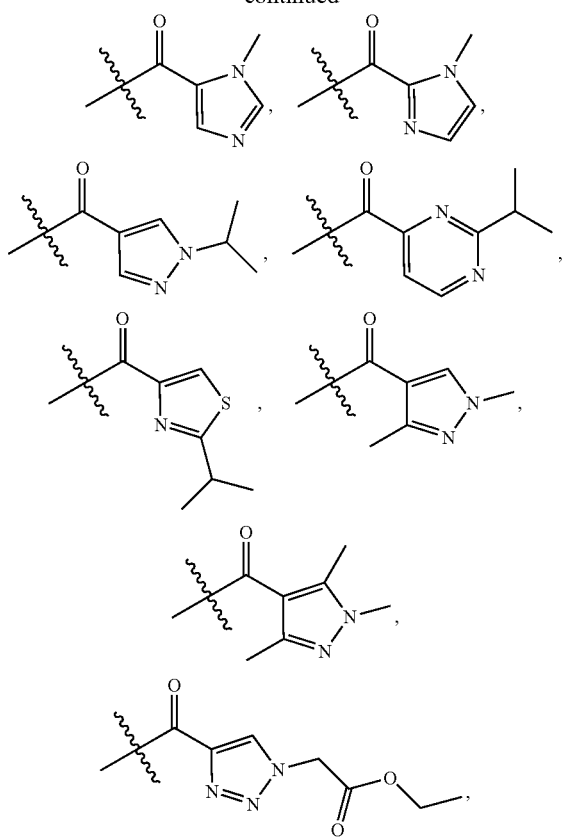

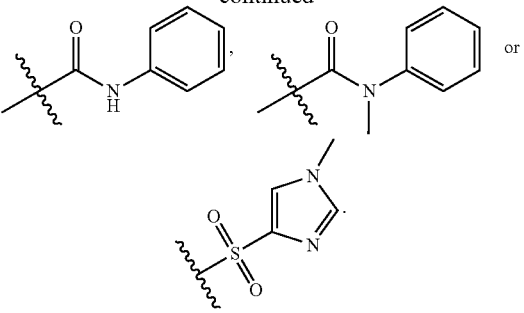

In certain embodiments of Formula I or IA, $R^1$ is aryl or heteroaryl.

In certain embodiments of Formula I or IA, $R^1$ is aryl or heteroaryl;
wherein said aryl or heteroaryl are optionally substituted with one, two or three substituents independently selected from the group consisting of halo, —O—$R^{20}$, $C_{1-4}$ alkyl, $C_{3-6}$ cycloalkyl and heterocyclyl; and
wherein said $C_{1-4}$ alkyl or $C_{3-6}$ cycloalkyl are optionally substituted with one, two or three substituents independently selected from the group consisting of halo and CN.

In certain embodiments of Formula I or IA, $R^1$ is aryl or heteroaryl optionally substituted with trifluoromethoxy or trifluoromethyl.

In certain embodiments, the compound of Formula I is represented by Formula II:

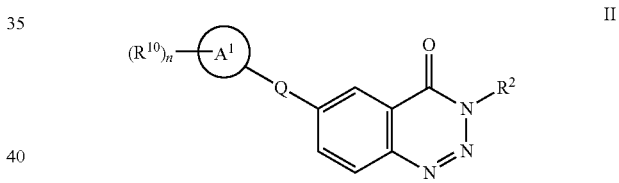

II wherein Q and $R^2$ are as defined in for Formula I;
$A^1$ is aryl or heteroaryl;
n is 0, 1, 2 or 3; and
$R^{10}$ is halo, —$NO_2$, CN, —$SF_5$, —$Si(CH_3)_3$, —O—$R^{20}$, —S—$R^{20}$, —C(O)—$R^{20}$, —C(O)—O$R^{20}$, —N($R^{20}$)($R^{22}$), —C(O)—N($R^{20}$)($R^{22}$), —N($R^{20}$)—C(O)—$R^{22}$, —N($R^{20}$)—S(O)$_2$—$R^{22}$, —S(O)$_2$—$R^{20}$, —S(O)$_2$—N($R^{20}$)($R^{22}$), $C_{1-4}$ alkyl, $C_{2-4}$ alkenyl, $C_{2-4}$ alkynyl, $C_{3-6}$ cycloalkyl, aryl, heteroaryl or heterocyclyl; and
wherein said $C_{1-4}$ alkyl, $C_{2-4}$ alkenyl, $C_{2-4}$ alkynyl, $C_{3-6}$ cycloalkyl, aryl, heteroaryl or heterocyclyl are optionally substituted with one, two or three substituents independently selected from the group consisting of halo, —$NO_2$, aryl, heterocyclyl, heteroaryl, $C_{1-4}$ alkyl, $C_{3-6}$ cycloalkyl, —N($R^{20}$)($R^{22}$), —C(O)—$R^{20}$, —C(O)—O$R^{20}$, —C(O)—N($R^{20}$)($R^{22}$), —CN and —O—$R^{20}$.

In some embodiments of Formula I, IA or II, Q is a bond.
In some embodiments of Formula I, IA or II, $R^2$ is —$R^6$, —$C_{1-6}$ alkylene-$R^6$ or -L-$C_{1-6}$ alkylene-$R^6$;
L is —O—, —C(O)— or —C(O)N$R^{20}$—;
$R^6$ is $C_{3-6}$ cycloalkyl, aryl, heteroaryl or heterocyclyl;
wherein said cycloalkyl, heteroaryl or heterocyclyl are optionally substituted with one, two or three substituents independently selected from the group consisting

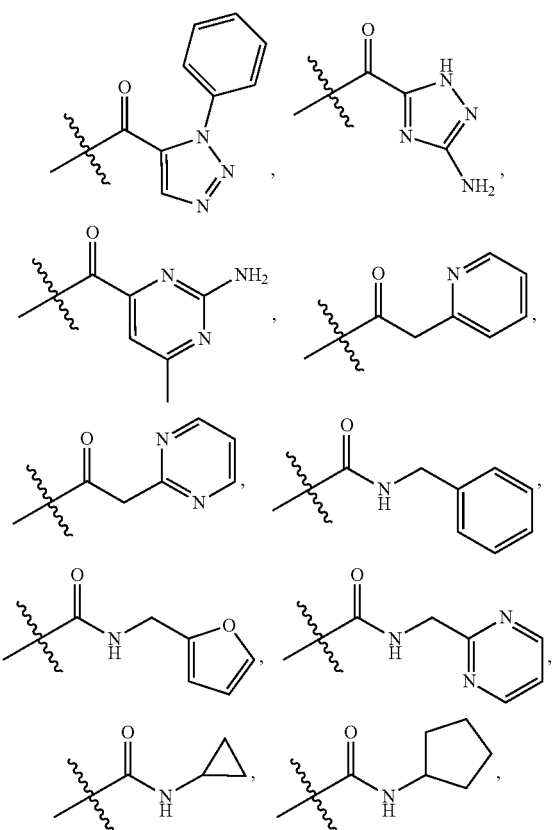

of $C_{1-6}$ alkyl, halo, $C_{3-6}$ cycloalkyl, aryl, heteroaryl, —C(O)—$OR^{20}$, —CN and —O—$R^{20}$;

wherein said $C_{1-6}$ alkyl or heteroaryl are optionally further substituted with one, two or three substituents independently selected from the group consisting of halo, $C_{3-6}$ cycloalkyl, aryl, heterocyclyl, heteroaryl, and —O—$R^{20}$; and wherein said heteroaryl is optionally further substituted with one, two or three $C_{1-6}$ alkyl.

In some embodiments of Formula I, IA or II, $R^2$ is

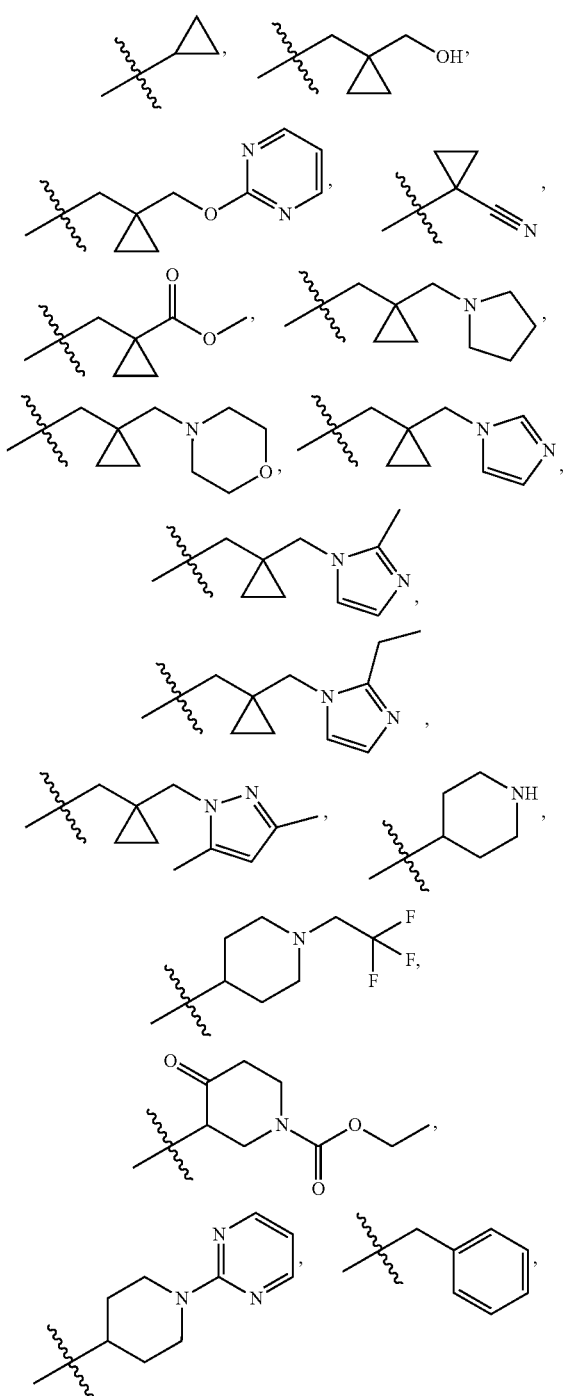

-continued

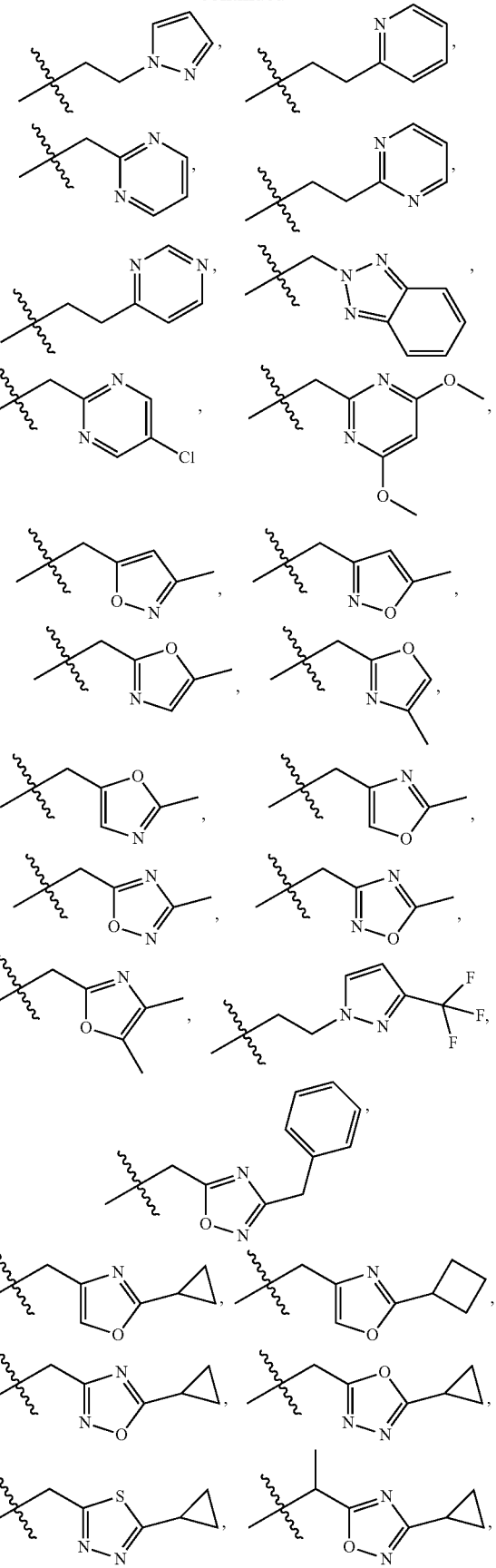

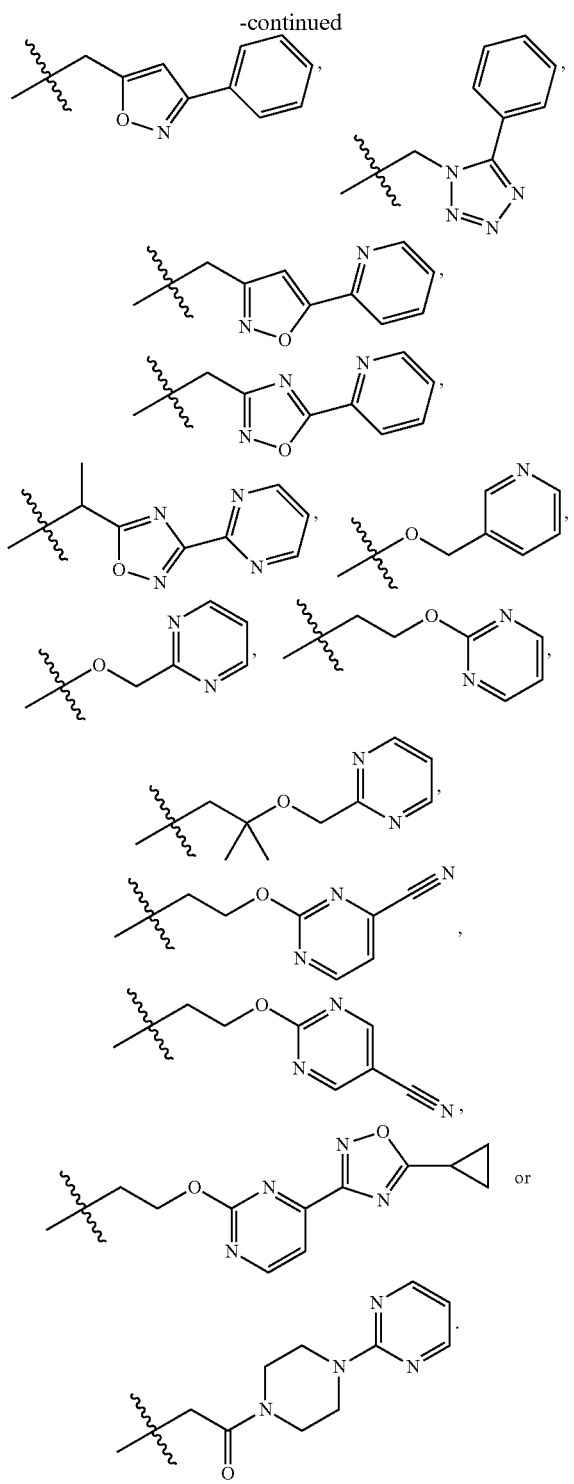

In some embodiments of Formula II, $R^{10}$ is —O—$R^{20}$, $C_{1-4}$ alkyl, $C_{3-6}$ cycloalkyl or heterocyclyl; and
wherein said $C_{1-4}$ alkyl or $C_{3-6}$ cycloalkyl are optionally substituted with one, two or three substituents independently selected from the group consisting of halo and —CN.

In some embodiments of Formula II, $R^{10}$ is 1-cyanocyclopropyl, 2,2,2-trifluoroethoxy, 4-chlorophenoxy, cyclopropyl, phenoxy, piperidin-1-yl, trifluoromethoxy or trifluoromethyl.

In certain embodiments, the compound of Formula I is represented by Formula III:

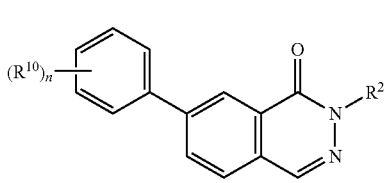

wherein $R^2$ is as defined for Formula I;
n is 0, 1, 2 or 3; and
$R^{10}$ is halo, —$NO_2$, CN, —$SF_5$, —$Si(CH_3)_3$, —O—$R^{20}$, —S—$R^{20}$, —C(O)—$R^{20}$, —C(O)—O$R^{20}$, —N($R^{20}$)($R^{22}$), —C(O)—N($R^{20}$)($R^{22}$), —N($R^{20}$)—C(O)—$R^{22}$, —N($R^{20}$)—S(O)$_2$—$R^{22}$, —S(O)$_2$—$R^{20}$, —S(O)$_2$—N($R^{20}$)($R^{22}$), $C_{1-4}$ alkyl, $C_{2-4}$ alkenyl, $C_{2-4}$ alkynyl, $C_{3-6}$ cycloalkyl, aryl, heteroaryl and heterocyclyl; and
wherein said $C_{1-4}$ alkyl, $C_{2-4}$ alkenyl, $C_{2-4}$ alkynyl, $C_{3-6}$ cycloalkyl, aryl, heteroaryl or heterocyclyl are optionally substituted with one, two or three substituents independently selected from the group consisting of halo, —$NO_2$, aryl, heterocyclyl, heteroaryl, $C_{1-4}$ alkyl, $C_{3-6}$ cycloalkyl, —N($R^{20}$)($R^{22}$), —C(O)—$R^{20}$, —C(O)—O$R^{20}$, —C(O)—N($R^{20}$)($R^{22}$), —CN and —O—$R^{20}$.

In some embodiments of Formula I, IA or III, $R^2$ is —$C_{1-6}$ alkylene-$R^6$ or —$C_{1-6}$ alkylene-L-$R^6$;
L is —O—; and
$R^6$ is aryl or heteroaryl;
wherein said heteroaryl is optionally substituted with one, two or three substituents independently selected from the group consisting of $C_{1-6}$ alkyl, halo, $C_{3-6}$ cycloalkyl, heteroaryl, —CN and —O—$R^{20}$.

In some embodiments of Formula I, IA or III, $R^2$ is

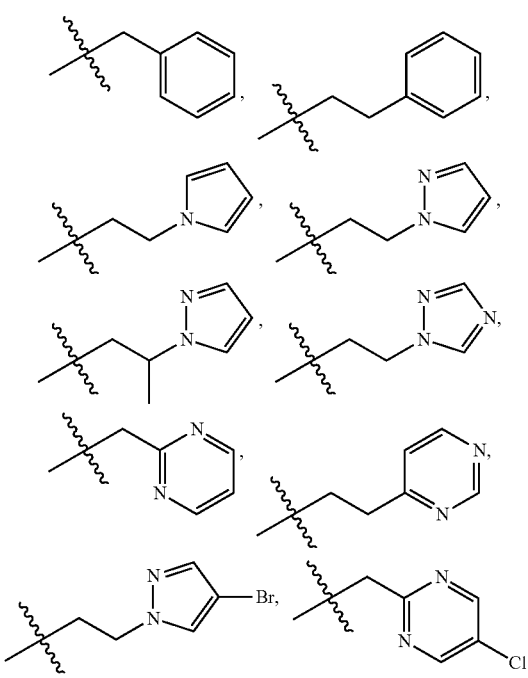

-continued

[chemical structures]

In some embodiments of Formula III, $R^{10}$ is trifluoromethoxy.

In certain embodiments, the compound of Formula I is represented by Formula IV:

$$(R^{10})_n \text{—[quinazolinone structure]—} R^2 \quad IV$$

wherein $R^2$ is as defined for Formula I;
n is 0, 1, 2 or 3; and
$R^{10}$ is halo, —$NO_2$, CN, —$SF_5$, —$Si(CH_3)_3$, —O—$R^{20}$, —S—$R^{20}$, —C(O)—$R^{20}$, —C(O)—O$R^{20}$, —N($R^{20}$)($R^{22}$), —C(O)—N($R^{20}$)($R^{22}$), —N($R^{20}$)—C(O)—$R^{22}$, —N($R^{20}$)—S(O)$_2$—$R^{22}$, —S(O)$_2$—$R^{20}$, —S(O)$_2$—N($R^{20}$)($R^{22}$), $C_{1-4}$ alkyl, $C_{2-4}$ alkenyl, $C_{2-4}$ alkynyl, $C_{3-6}$ cycloalkyl, aryl, heteroaryl or heterocyclyl; and
  wherein said $C_{1-4}$ alkyl, $C_{2-4}$ alkenyl, $C_{2-4}$ alkynyl, $C_{3-6}$ cycloalkyl, aryl, heteroaryl or heterocyclyl are optionally substituted with one, two or three substituents independently selected from the group consisting of halo, —$NO_2$, aryl, heterocyclyl, heteroaryl, $C_{1-4}$ alkyl, $C_{3-6}$ cycloalkyl, —N($R^{20}$)($R^{22}$), —C(O)—$R^{20}$, —C(O)—O$R^{20}$, —C(O)—N($R^{20}$)($R^{22}$), —CN and —O—$R^{20}$.

In some embodiments of Formula I, IA or IV, $R^2$ is —$C_{1-6}$ alkylene-$R^6$; and $R^6$ is heteroaryl;
wherein said heteroaryl is optionally substituted with $C_{1-6}$ alkyl.

In some embodiments of Formula I, IA or IV, $R^2$ is

[chemical structures] or [chemical structure].

In some embodiments of Formula IV, $R^{10}$ is trifluoromethoxy.

In certain embodiments, the compound of Formula I is represented by Formula V:

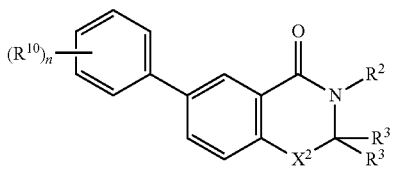

wherein $R^2$ and $R^3$ are as defined for Formula I;
$X^2$ is —O— or —S—;
n is 0, 1, 2 or 3; and
$R^{10}$ is halo, —$NO_2$, CN, —$SF_5$, —$Si(CH_3)_3$, —O—$R^{20}$, —S—$R^{20}$, —C(O)—$R^{20}$, —C(O)—$OR^{20}$, —$N(R^{20})(R^{22})$, —C(O)—$N(R^{20})(R^{22})$, —$N(R^{20})$—C(O)—$R^{22}$, —$N(R^{20})$—$S(O)_2$—$R^{22}$, —$S(O)_2$—$R^{20}$, —$S(O)_2$—$N(R^{20})(R^{22})$, $C_{1-4}$ alkyl, $C_{2-4}$ alkenyl, $C_{2-4}$ alkynyl, $C_{3-6}$ cycloalkyl, aryl, heteroaryl or heterocyclyl; and wherein said $C_{1-4}$ alkyl, $C_{2-4}$ alkenyl, $C_{2-4}$ alkynyl, $C_{3-6}$ cycloalkyl, aryl, heteroaryl or heterocyclyl are optionally substituted with one, two or three substituents independently selected from the group consisting of halo, —$NO_2$, aryl, heterocyclyl, heteroaryl, $C_{1-4}$ alkyl, $C_{3-6}$ cycloalkyl, —$N(R^{20})(R^{22})$, —C(O)—$R^{20}$, —C(O)—$OR^{20}$, —C(O)—$N(R^{20})(R^{22})$, —CN and —O—$R^{20}$.

In some embodiments of Formula I, IA or V, $X^2$ is —O—.
In some embodiments of Formula I, IA or V, $X^2$ is —S—.
In some embodiments of Formula I, IA or V, $R^2$ is —$C_{1-6}$ alkylene-$R^6$; and $R^6$ is aryl or heteroaryl;
wherein said aryl or heteroaryl are optionally substituted with one, two or three halo.
In some embodiments of Formula I, IA or V, $R^2$ is

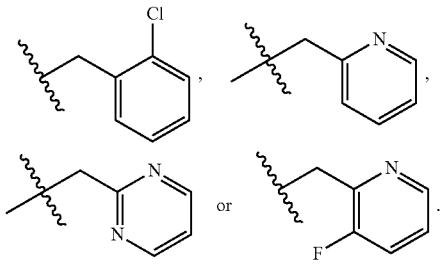

In some embodiments of Formula I, IA or V, $R^3$ is hydrogen or $C_{1-6}$ alkyl.
In some embodiments of Formula I, IA or V, $R^3$ is hydrogen or methyl.
In some embodiments of Formula V, $R^{10}$ is trifluoromethyl or trifluoromethoxy.
In certain embodiments, the compound of Formula I is represented by Formula VI:

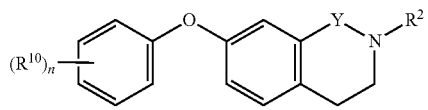

wherein Q, Y and $R^2$ are as defined for Formula I;
n is 0, 1, 2 or 3; and
$R^{10}$ is halo, —$NO_2$, CN, —$SF_5$, —$Si(CH_3)_3$, —O—$R^{20}$, —S—$R^{20}$, —C(O)—$R^{20}$, —C(O)—$OR^{20}$, —$N(R^{20})(R^{22})$, —C(O)—$N(R^{20})(R^{22})$, —$N(R^{20})$—C(O)—$R^{22}$, —$N(R^{20})$—$S(O)_2$—$R^{22}$, —$S(O)_2$—$R^{20}$, —$S(O)_2$—$N(R^{20})(R^{22})$, $C_{1-4}$ alkyl, $C_{2-4}$ alkenyl, $C_{2-4}$ alkynyl, $C_{3-6}$ cycloalkyl, aryl, heteroaryl or heterocyclyl; and wherein said $C_{1-4}$ alkyl, $C_{2-4}$ alkenyl, $C_{2-4}$ alkynyl, $C_{3-6}$ cycloalkyl, aryl, heteroaryl or heterocyclyl are optionally substituted with one, two or three substituents independently selected from the group consisting of halo, —$NO_2$, aryl, heterocyclyl, heteroaryl, $C_{1-4}$ alkyl, $C_{3-6}$ cycloalkyl, —$N(R^{20})(R^{22})$, —C(O)—$R^{20}$, —C(O)—$OR^{20}$, —C(O)—$N(R^{20})(R^{22})$, —CN and —O—$R^{20}$.

In some embodiments of Formula I, IA or III, $R^2$ is —$C_{1-6}$ alkylene-$R^6$, -L-$R^6$ or -L-$C_{1-6}$ alkylene-$R^6$; provided that when Y is —$C(R^5)_2$—, then $R^2$ is -L-$R^6$ or -L-$C_{1-6}$ alkylene-$R^6$; L is —C(O)—, —$S(O)_2$— or —C(O)$NR^{20}$—;
$R^6$ is $C_{3-6}$ cycloalkyl, aryl, heteroaryl or heterocyclyl;
wherein said heteroaryl or heterocyclyl are optionally substituted with one, two or three substituents independently selected from the group consisting of $C_{1-6}$ alkyl, halo, —C(O)—$OR^{20}$ and —O—$R^{20}$;
wherein said $C_{1-6}$ alkyl is optionally further substituted with one, two or three substituents independently selected from the group consisting of aryl, —$N(R^{20})(R^{22})$, —C(O)—$OR^{20}$ and —O—$R^{20}$.

In some embodiments of Formula I, IA or VI, $R^2$ is

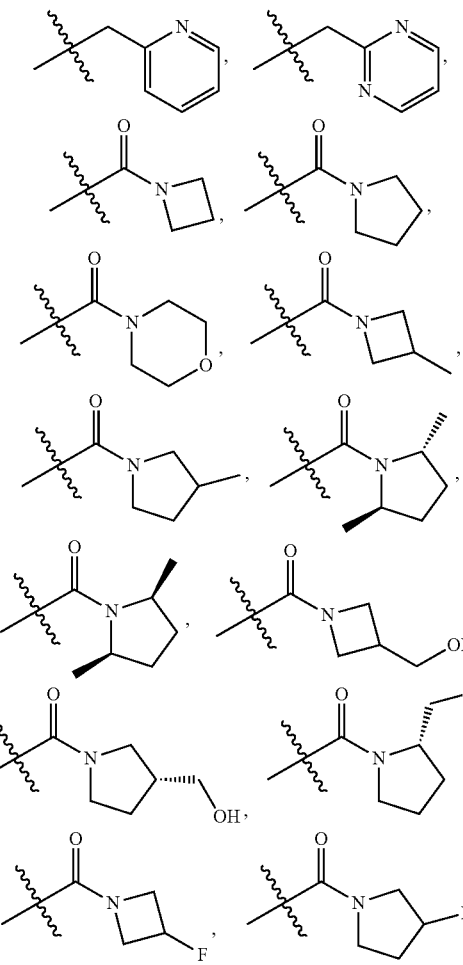

-continued
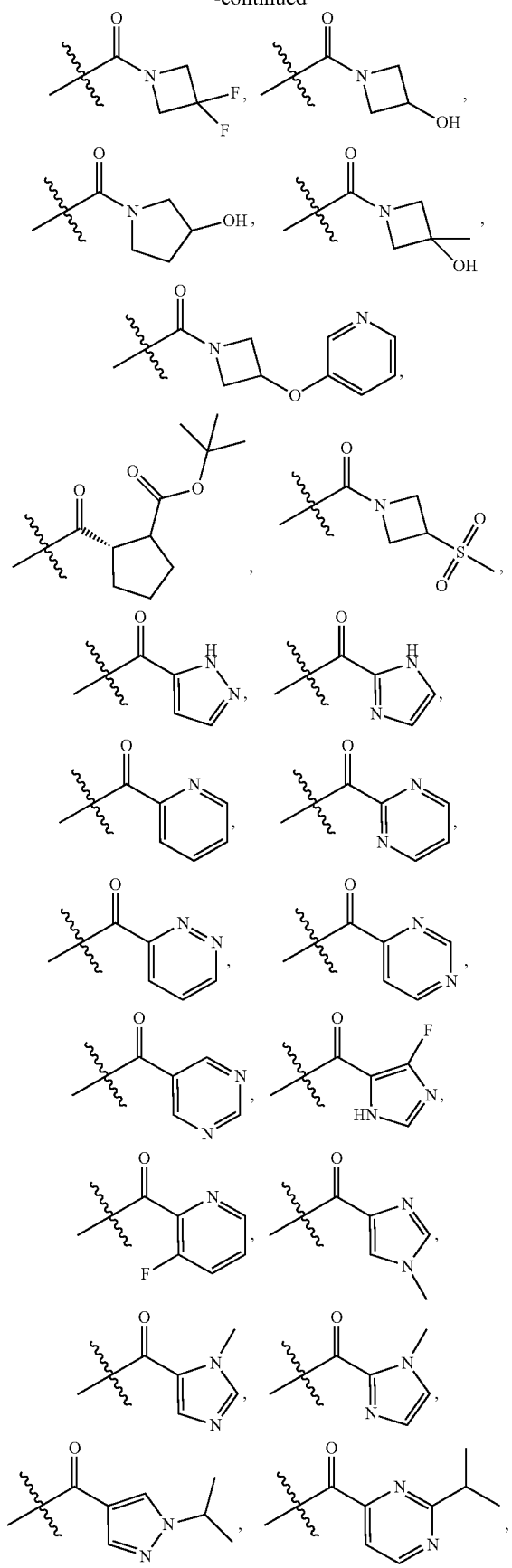
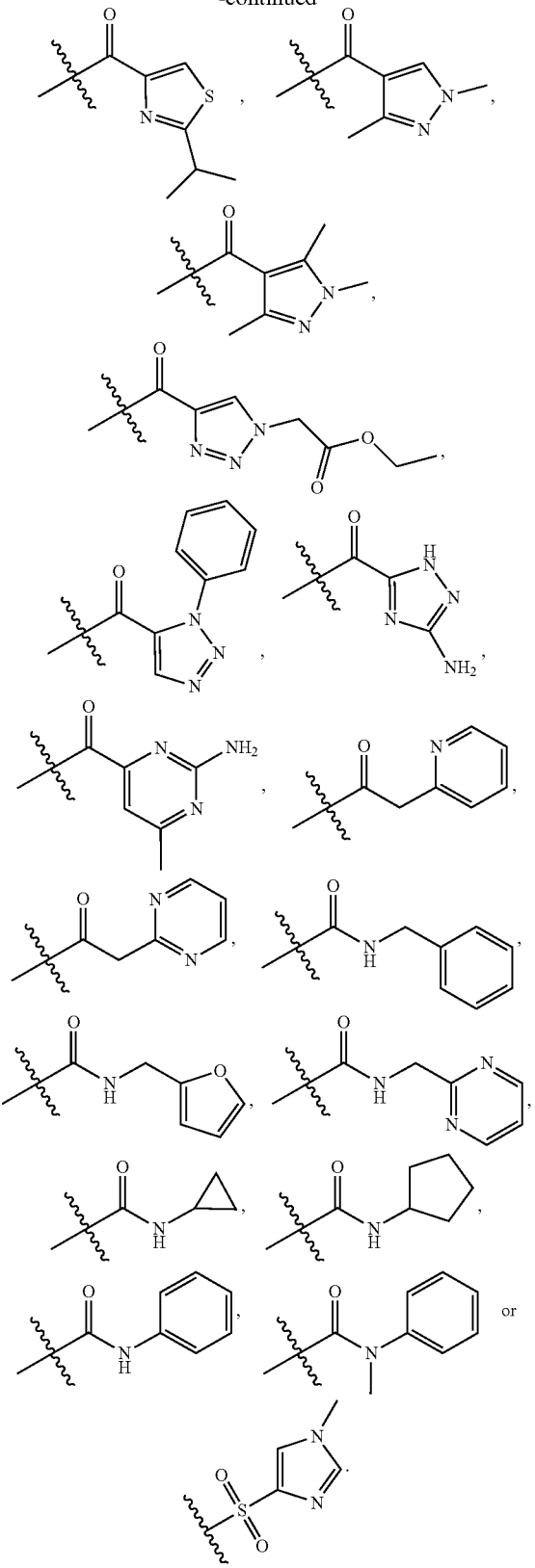
In some embodiments of Formula VI, each $R^{10}$ is independently chloro, fluoro, trifluoromethyl and trifluoromethoxy.

Other Embodiments

Accordingly, in other embodiments, the present disclosure provides compounds that function as sodium channel blockers. In typical embodiments the disclosure relates to compounds of Formula I:

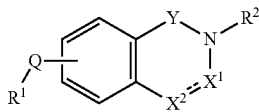

wherein:
the dotted line represents an optional double bond;
$R^1$ is selected from the group consisting of cycloalkyl, cycloalkenyl, aryl and heteroaryl;
  wherein said cycloalkyl, cycloalkenyl, aryl or heteroaryl are optionally substituted with one, two or three substituents independently selected from the group consisting of halo, —$NO_2$, CN, —$SF_5$, —$Si(CH_3)_3$, —O—$R^{20}$, —S—$R^{20}$, —C(O)—$R^{20}$, C(O)—$OR^{20}$, —N($R^{20}$)($R^{22}$), —C(O)—N($R^{20}$)($R^{22}$), —N($R^{20}$)—C(O)—$R^{22}$, —N($R^{20}$)—S($=O$)$_2$—$R^{26}$, —S($=O$)$_2$—$R^{20}$, —S($=O$)$_2$—N($R^{20}$)($R^{22}$), $C_{1-4}$ alkyl, $C_{2-4}$ alkenyl, $C_{2-4}$ alkynyl, cycloalkyl, aryl, heteroaryl and heterocyclyl; and
    wherein said $C_{1-4}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, aryl, heterocyclyl, heteroaryl, $C_{1-4}$ alkyl, cycloalkyl, —N($R^{20}$)($R^{22}$), —C(O)—$R^{20}$, —C(O)—$OR^{20}$, —C(O)—N($R^{20}$)($R^{22}$), —CN and —O—$R^{20}$;
$R^2$ is selected from the group consisting of hydrogen, $C_{1-15}$ alkyl, $C_{1-4}$ alkoxy, —C(O)—$R^{26}$, —C(O)—$OR^{26}$, —C(O)—N($R^{26}$)($R^{28}$), —N($R^{20}$)—S($=O$)$_2$—$R^{20}$, cycloalkyl, aryl, heteroaryl or heterocyclyl;
  wherein said $C_{1-15}$ alkyl, $C_{1-4}$ alkoxy, cycloalkyl aryl, heteroaryl or heterocyclyl are optionally substituted with one, two or three substituents independently selected from the group consisting of hydroxyl, $C_{1-15}$ alkyl, $C_{1-4}$ alkoxy, $C_{2-4}$ alkynyl, halo, —$NO_2$, cycloalkyl, aryl, heterocyclyl, heteroaryl, —N($R^{20}$)($R^{22}$), —C(O)—$R^{20}$, —C(O)—O—$R^{20}$, —C(O)—N($R^{20}$)($R^{22}$), —CN, oxo and —O—$R^{20}$;
    wherein said $C_{1-15}$ alkyl, $C_{1-4}$ alkoxy, cycloalkyl, aryl, heterocyclyl or heteroaryl are optionally further substituted with one, two or three substituents independently selected from the group consisting of hydroxyl, halo, —$NO_2$, $C_{1-6}$ alkyl, $C_{1-4}$ alkoxy, aralkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN, and —O—$R^{20}$; and
      wherein said $C_{1-6}$ alkyl, $C_{1-4}$ alkoxy, aralkyl, cycloalkyl, aryl, heterocyclyl or heteroaryl, are optionally further substituted with one, two or three substituents independently selected from the group consisting of hydroxyl, halo, —$NO_2$, —$CF_3$, —N($R^{20}$)($R^{22}$), —C(O)—$R^{20}$, —C(O)—O—$R^{20}$, —C(O)—N($R^{20}$)($R^{22}$), —CN, —S(O)$_2$—$R^{20}$ and —O—$R^{20}$;

Q is selected from the group consisting of a covalent bond and $C_{2-4}$ alkynylene;
Y is selected from the group consisting of —C($R^5$)$_2$— and —C(O)—; provided that when Y is —C($R^5$)$_2$—, then $R^2$ is —C(O)—$R^{26}$, —C(O)—O—$R^{26}$, or —C(O)—N($R^{26}$)($R^{28}$);
$X^1$ is N and $X^2$ is N, $X^1$ is N and $X^2$ is $CR^3$, or $X^1$ is $CR^3$ and $X^2$ is N, and the dotted line is a double bond; or
$X^1$ is C($R^3$)$_2$ and $X^2$ is $NR^4$, $X^1$ is C($R^3$)$_2$ and $X^2$ is —O—, or $X^1$ and $X^2$ are both C($R^3$)$_2$, and the dotted line is a single bond;
each $R^3$ is independently selected from the group consisting of hydrogen, $C_{1-15}$ alkyl, cycloalkyl, aryl, heteroaryl and heterocyclyl;
  wherein said $C_{1-15}$ alkyl is optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—O—$R^{20}$, —C(O)—N($R^{20}$)($R^{22}$), —CN and —O—$R^{20}$;
    wherein said cycloalkyl, aryl, heterocyclyl and heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and
      wherein said $C_{1-6}$ alkyl, aralkyl, cycloalkyl, aryl, heterocyclyl and heteroaryl are optionally further substituted with one, two or three substituents independently selected from the group consisting of halo, —$NO_2$, —N($R^{20}$)($R^{22}$), —C(O)—$R^{20}$, —C(O)—$OR^{20}$, —C(O)—N($R^{20}$)($R^{22}$), —CN and —O—$R^{20}$;
or when $X^1$ is C($R^3$)$_2$, two $R^3$ can join together with the with the carbon atom to which they are attached to form a cycloalkyl or heterocyclyl;
$R^4$ is selected from the group consisting of hydrogen, $C_{1-15}$ alkyl, $C_{1-4}$ alkoxy, —C(O)—O—$R^{26}$, —C(O)—N($R^{26}$)($R^{28}$), —N($R^{20}$)—S($=O$)$_2$—$R^{20}$, cycloalkyl, aryl, heteroaryl and heterocyclyl;
  wherein said $C_{1-15}$ alkyl is optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;
    wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—O—$R^{20}$, —C(O)—N($R^{20}$)($R^{22}$), —CN, and —O—$R^{20}$; and
      wherein said $C_{1-6}$ alkyl, aralkyl, cycloalkyl, aryl, heterocyclyl, heteroaryl, are optionally further substituted with one, two or three substituents independently selected from the group consisting of hydroxyl, halo, —$NO_2$, —N($R^{20}$)($R^{22}$), —N($R^{20}$)($R^{22}$), —C(O)—$R^{20}$, —C(O)—O—$R^{20}$, —C(O)—N($R^{20}$)($R^{22}$), —CN and —O—$R^{20}$;
each $R^5$ is independently selected from the group consisting of hydrogen and $C_{1-15}$ alkyl;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl; and wherein the $C_{1-15}$ alkyl, $C_{2-15}$ alkenyl, $C_{2-15}$ alkynyl, cycloalkyl, heterocyclyl, aryl or heteroaryl are optionally substituted with one, two or three substituents independently selected from the group consisting of hydroxyl, halo, $C_{1-4}$ alkyl, substituted amino, aminoacyl, —$NO_2$, —$SO_2R^{26}$, —CN, $C_{1-3}$ alkoxy, —$CF_3$, —$OCF_3$, —$OCH_2CF_3$, —C(O)—$NH_2$, aryl, cycloalkyl and heteroaryl;

wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryl, aryloxy, aralkyloxy, substituted amino, aminoacyl, —$NO_2$, —$SO_2R^{26}$, —CN, $C_{1-3}$ alkoxy, —$CF_3$, —$OCF_3$, aryl, heteroaryl and cycloalkyl; and $R^{26}$ and $R^{28}$ are in each instance independently selected from the group consisting of hydrogen, $C_{1-15}$ alkyl, cycloalkyl, aryl and heteroaryl; and wherein the $C_{1-15}$ alkyl, cycloalkyl, aryl or heteroaryl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, hydrate, solvate, stereoisomer, tautomer, polymorph and/or prodrug thereof.

In certain embodiments, the compound of formula I is represented by Formula IA:

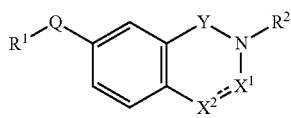

IA wherein:
the dotted line represents an optional double bond;
$R^1$ is selected from the group consisting of cycloalkyl, cycloalkenyl, aryl and heteroaryl;

wherein said cycloalkyl, cycloalkenyl, aryl or heteroaryl are optionally substituted with one, two or three substituents independently selected from the group consisting of halo, —$NO_2$, CN, —$SF_5$, —$Si(CH_3)_3$, —O—$R^{20}$, —S—$R^{20}$, —C(O)—$R^{20}$, C(O)—$OR^{20}$, —$N(R^{20})(R^{22})$, —C(O)—$N(R^{20})(R^{22})$, —$N(R^{20})$—C(O)—$R^{22}$, —$N(R^{20})$—S(=O)$_2$—$R^{26}$, —S(=O)$_2$—$R^{20}$, —S(=O)$_2$—$N(R^{20})(R^{22})$, $C_{1-4}$ alkyl, $C_{2-4}$ alkenyl, $C_{2-4}$ alkynyl, cycloalkyl, aryl, heteroaryl and heterocyclyl; and wherein said $C_{1-4}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, aryl, heterocyclyl, heteroaryl, $C_{1-4}$ alkyl, cycloalkyl, —$N(R^{20})(R^{22})$, —C(O)—$R^{20}$, —C(O)—$OR^{20}$, —C(O)—$N(R^{20})(R^{22})$, —CN and —O—$R^{20}$;

$R^2$ is selected from the group consisting of hydrogen, $C_{1-15}$ alkyl, $C_{1-4}$ alkoxy, —C(O)—$R^{26}$, —C(O)—$OR^{26}$, —C(O)—$N(R^{26})(R^{28})$, —$N(R^{20})$—S(=O)$_2$—$R^{20}$, cycloalkyl, aryl, heteroaryl or heterocyclyl;

wherein said $C_{1-15}$ alkyl, $C_{1-4}$ alkoxy, cycloalkyl aryl, heteroaryl or heterocyclyl are optionally substituted with one, two or three substituents independently selected from the group consisting of hydroxyl, $C_{1-15}$ alkyl, $C_{1-4}$ alkoxy, $C_{2-4}$ alkynyl, halo, —$NO_2$, cycloalkyl, aryl, heterocyclyl, heteroaryl, —$N(R^{20})(R^{22})$, —C(O)—$R^{20}$, —C(O)—O—$R^{20}$, —C(O)—$N(R^{20})(R^{22})$, —CN, oxo and —O—$R^{20}$;

wherein said $C_{1-15}$ alkyl, $C_{1-4}$ alkoxy, cycloalkyl, aryl, heterocyclyl or heteroaryl are optionally further substituted with one, two or three substituents independently selected from the group consisting of hydroxyl, halo, —$NO_2$, $C_{1-6}$ alkyl, $C_{1-4}$ alkoxy, aralkyl, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN, and —O—$R^{20}$; and wherein said $C_{1-6}$ alkyl, $C_{1-4}$ alkoxy, aralkyl, cycloalkyl, aryl, heterocyclyl or heteroaryl, are optionally further substituted with one, two or three substituents independently selected from the group consisting of hydroxyl, halo, —$NO_2$, —$CF_3$, —$N(R^{20})(R^{22})$, —C(O)—$R^{20}$, —C(O)—O—$R^{20}$, —C(O)—$N(R^{20})(R^{22})$, —CN, —S(O)$_2$—$R^{20}$ and —O—$R^{20}$;

Q is selected from the group consisting of a covalent bond and $C_{2-4}$ alkynylene;

Y is selected from the group consisting of —$C(R^5)_2$— and —C(O)—; provided that when Y is —$C(R^5)_2$—, then $R^2$ is —C(O)—$R^{26}$, —C(O)—O—$R^{26}$, or —C(O)—$N(R^{26})(R^{28})$;

$X^1$ is N and $X^2$ is N, $X^1$ is N and $X^2$ is $CR^3$, or $X^1$ is $CR^3$ and $X^2$ is N, and the dotted line is a double bond; or $X^1$ is $C(R^3)_2$ and $X^2$ is $NR^4$, $X^1$ is $C(R^3)_2$ and $X^2$ is —O—, or $X^1$ and $X^2$ are both $C(R^3)_2$, and the dotted line is a single bond;

each $R^3$ is independently selected from the group consisting of hydrogen, $C_{1-15}$ alkyl, cycloalkyl, aryl, heteroaryl and heterocyclyl;

wherein said $C_{1-15}$ alkyl is optionally substituted with one, two or three substituents independently selected from the group consisting of halo, —$NO_2$, cycloalkyl, aryl, heterocyclyl, heteroaryl, —$N(R^{20})(R^{22})$, —C(O)—$R^{20}$, —C(O)—O—$R^{20}$, —C(O)—$N(R^{20})(R^{22})$, —CN and —O—$R^{20}$;

wherein said cycloalkyl, aryl, heterocyclyl and heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$; and wherein said $C_{1-6}$ alkyl, aralkyl, cycloalkyl, aryl, heterocyclyl and heteroaryl are optionally further substituted with one, two or three substituents independently selected from the group consisting of halo, —$NO_2$, —$N(R^{20})(R^{22})$, —C(O)—$R^{20}$, —C(O)—O—$R^{20}$, —C(O)—$N(R^{20})(R^{22})$, —CN and —O—$R^{20}$;

or when $X^1$ is $C(R^3)_2$, two $R^3$ can join together with the with the carbon atom to which they are attached to form a cycloalkyl or heterocyclyl;

R⁴ is selected from the group consisting of hydrogen, $C_{1-15}$ alkyl, $C_{1-4}$ alkoxy, —C(O)—O—R²⁶, —C(O)—N(R²⁶)(R²⁸), —N(R²⁰)—S(=O)₂—R²⁰, cycloalkyl, aryl, heteroaryl and heterocyclyl;

wherein said $C_{1-15}$ alkyl is optionally substituted with one, two or three substituents independently selected from the group consisting of halo, —NO₂, cycloalkyl, aryl, heterocyclyl, heteroaryl, —N(R²⁰)(R²²), —C(O)—R²⁰, —C(O)—O—R²⁰, —C(O)—N(R²⁰)(R²²), —CN and —O—R²⁰;

wherein said cycloalkyl, aryl, heterocyclyl or heteroaryl are optionally further substituted with one, two or three substituents independently selected from the group consisting of halo, —NO₂, $C_{1-6}$ alkyl, aralkyl, cycloalkyl, aryl, heterocyclyl, heteroaryl, —N(R²⁰)(R²²), —C(O)—R²⁰, —C(O)—O—R²⁰, —C(O)—N(R²⁰)(R²²), —CN, and —O—R²⁰; and wherein said $C_{1-6}$ alkyl, aralkyl, cycloalkyl, aryl, heterocyclyl, heteroaryl, are optionally further substituted with one, two or three substituents independently selected from the group consisting of hydroxyl, halo, —NO₂, —N(R²⁰)(R²²), —N(R²⁰)(R²²), —C(O)—R²⁰, —C(O)—O—R²⁰, —C(O)—N(R²⁰)(R²²), —CN and —O—R²⁰;

each R⁵ is independently selected from the group consisting of hydrogen and $C_{1-15}$ alkyl;

R²⁰ and R²² are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl; and wherein the $C_{1-15}$ alkyl, $C_{2-15}$ alkenyl, $C_{2-15}$ alkynyl, cycloalkyl, heterocyclyl, aryl or heteroaryl are optionally substituted with one, two or three substituents independently selected from the group consisting of hydroxyl, halo, $C_{1-4}$ alkyl, substituted amino, aminoacyl, —NO₂, —SO₂R²⁶, —CN, $C_{1-3}$ alkoxy, —CF₃, —OCF₃, —OCH₂CF₃, —C(O)—NH₂, aryl, cycloalkyl and heterocyclyl;

wherein said heteroaryl is optionally further substituted with $C_{1-4}$ alkyl or cycloalkyl; or when R²⁰ and R²² are attached to a common nitrogen atom R²⁰ and R²² may join to form a heterocyclic or heteroaryl ring which is then optionally substituted with one, two or three substituents independently selected from the group consisting of hydroxyl, halo, $C_{1-4}$ alkyl, aralkyl, aryl, aryloxy, aralkyloxy, substituted amino, aminoacyl, —NO₂, —SO₂R²⁶, —CN, $C_{1-3}$ alkoxy, —CF₃, —OCF₃, aryl, heteroaryl and cycloalkyl; and R²⁶ and R²⁸ are in each instance independently selected from the group consisting of hydrogen, $C_{1-15}$ alkyl, cycloalkyl, aryl and heteroaryl; and wherein the $C_{1-15}$ alkyl, cycloalkyl, aryl or heteroaryl may be further substituted with from 1 to 3 substituents independently selected from the group consisting of hydroxyl, halo, $C_{1-4}$ alkoxy, —CF₃ and —OCF₃;

or a pharmaceutically acceptable salt, ester, hydrate, solvate, stereoisomer, tautomer, polymorph and/or prodrug thereof.

In some embodiments of Formula I or IA, R¹ is aryl or heteroaryl;

wherein said aryl or heteroaryl are optionally substituted with one, two or three substituents independently selected from the group consisting of —O—CF₃, —O—R²⁰, $C_{1-4}$ alkyl, cycloalkyl, and heterocyclyl; and wherein said alkyl, and cycloalkyl, are optionally substituted with one, two or three substituents independently selected from the group consisting of halo, and —CN; and R²⁰ in each instance is independently $C_{1-15}$ alkyl or aryl;

wherein the alkyl or aryl is optionally substituted with one, two or three halo.

In some embodiments of Formula I or IA, R¹ is selected from the group consisting of 6-CF₃-pyridin-3-yl, 6-(2,2,2-trifluoroethoxy)pyridin-3-yl, 4-phenoxy-phenyl, 4-OCF₃-phenyl, 4-cyclopropylphenyl, 4-(4-chlorophenoxy)phenyl, 4-(1-cyanocyclopropyl)phenyl and 2-(piperidin-1-yl)pyrimidin-5-yl.

In some embodiments of Formula I or IA, R² is hydrogen, $C_{1-15}$ alkyl, —C(O)—R²⁶, $C_{1-4}$ alkoxy, cycloalkyl or heterocyclyl;

wherein said $C_{1-15}$ alkyl, alkoxy, cycloalkyl, and heterocyclyl are optionally substituted with one, two or three substituents independently selected from the group consisting of hydroxyl, $C_{1-4}$ alkyl, alkoxy, alkynyl, aryl, heteroaryl, cycloalkyl, —N(R²⁰)(R²²), —C(O)—O—R²⁰, —C(O)—N(R²⁰)(R²²), —CN, oxo and —O—R²⁰;

wherein said alkyl, aryl or heteroaryl are optionally further substituted with one, two or three substituents independently selected from the group consisting of hydroxyl, halo, $C_{1-4}$ alkyl, $C_{1-4}$ alkoxy, heteroaryl, cycloalkyl, benzyl, aryl, —CN, and —O—R²⁰;

R²⁰ and R²² are in each instance independently selected from the group consisting of hydrogen, $C_{1-15}$ alkyl and heteroaryl; and wherein the alkyl, and heteroaryl are optionally substituted with one, two or three substituents independently selected from the group consisting of halo, —CN, cycloalkyl and heteroaryl;

wherein said heteroaryl is optionally further substituted with cycloalkyl; or when R²⁰ and R²² are attached to a common nitrogen atom R²⁰ and R²² may join to form a heterocyclic or heteroaryl ring which is then optionally substituted with one, two or three substituents independently selected from the group consisting of halo, $C_{1-15}$ alkyl, phenyl, —CF₃ and heteroaryl; and R²⁶ is heteroaryl.

In some embodiments of Formula I or IA, R² is hydrogen, methyl,

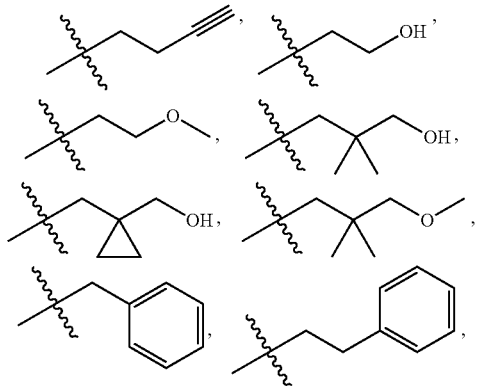

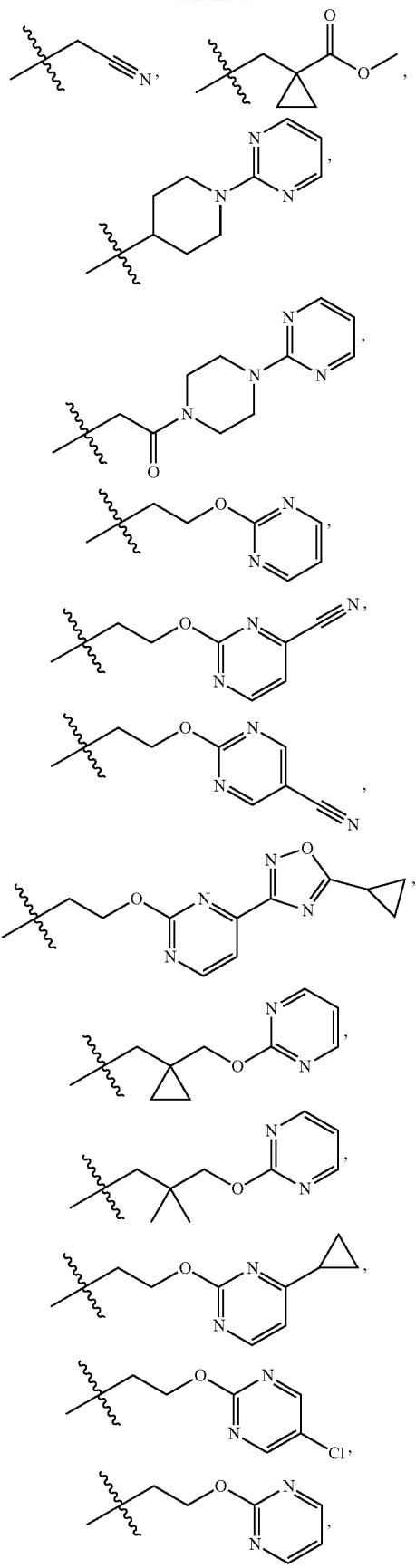
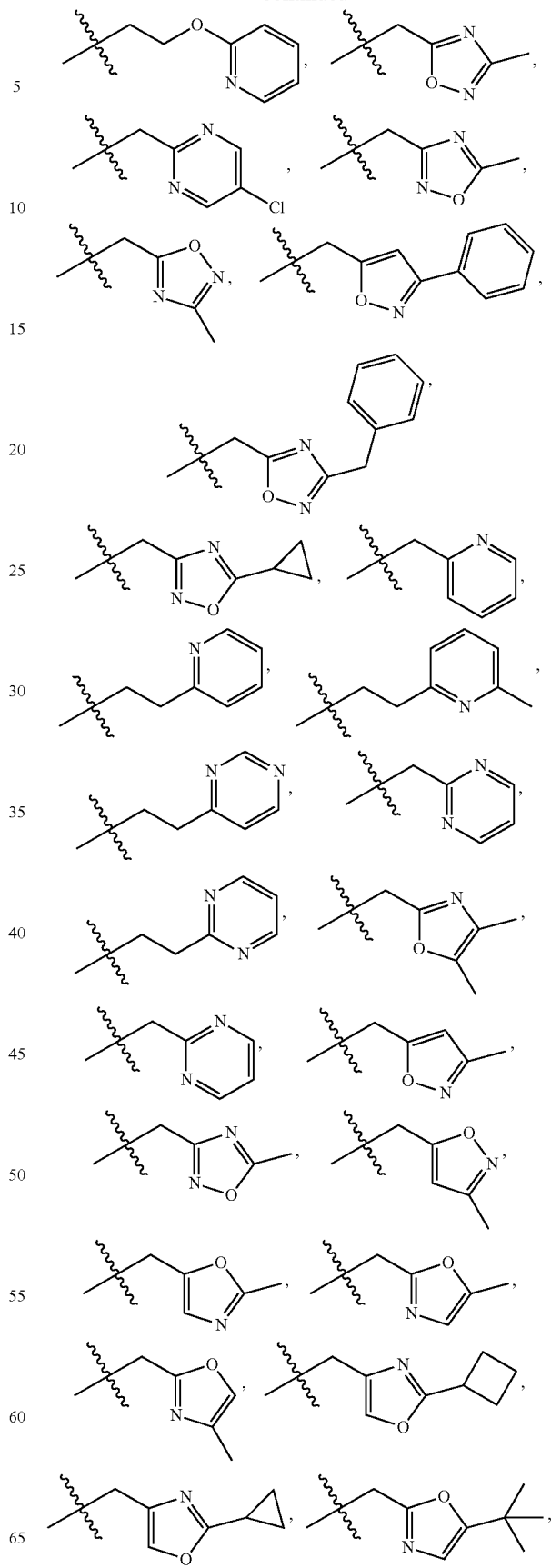

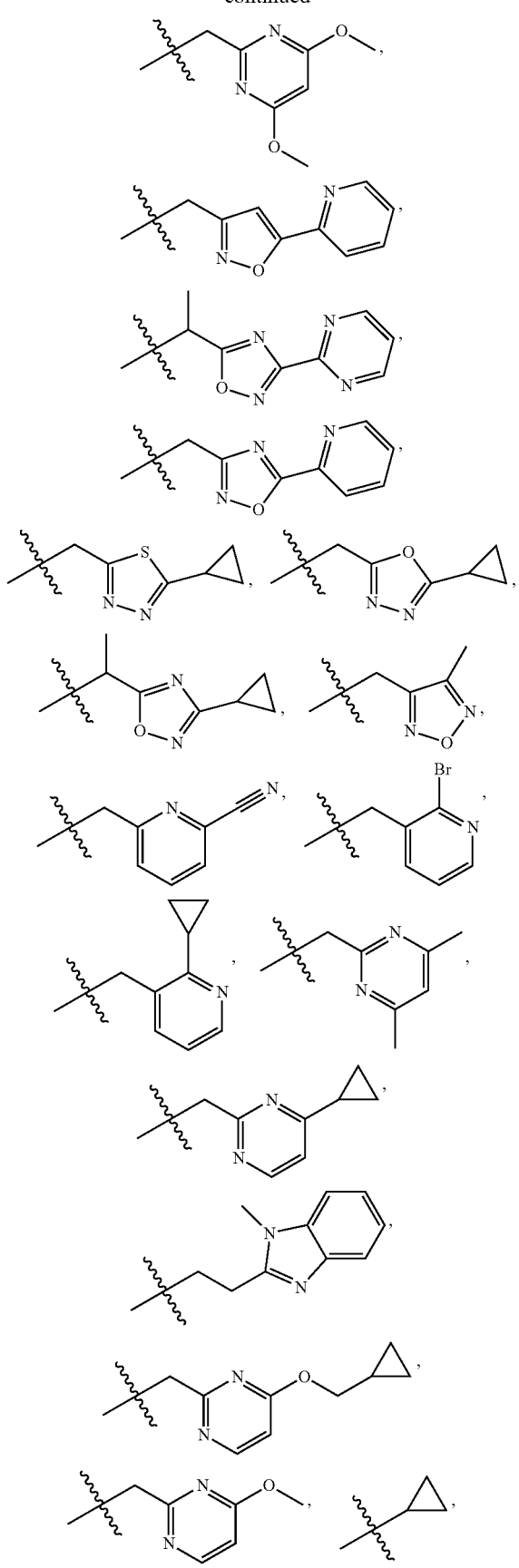
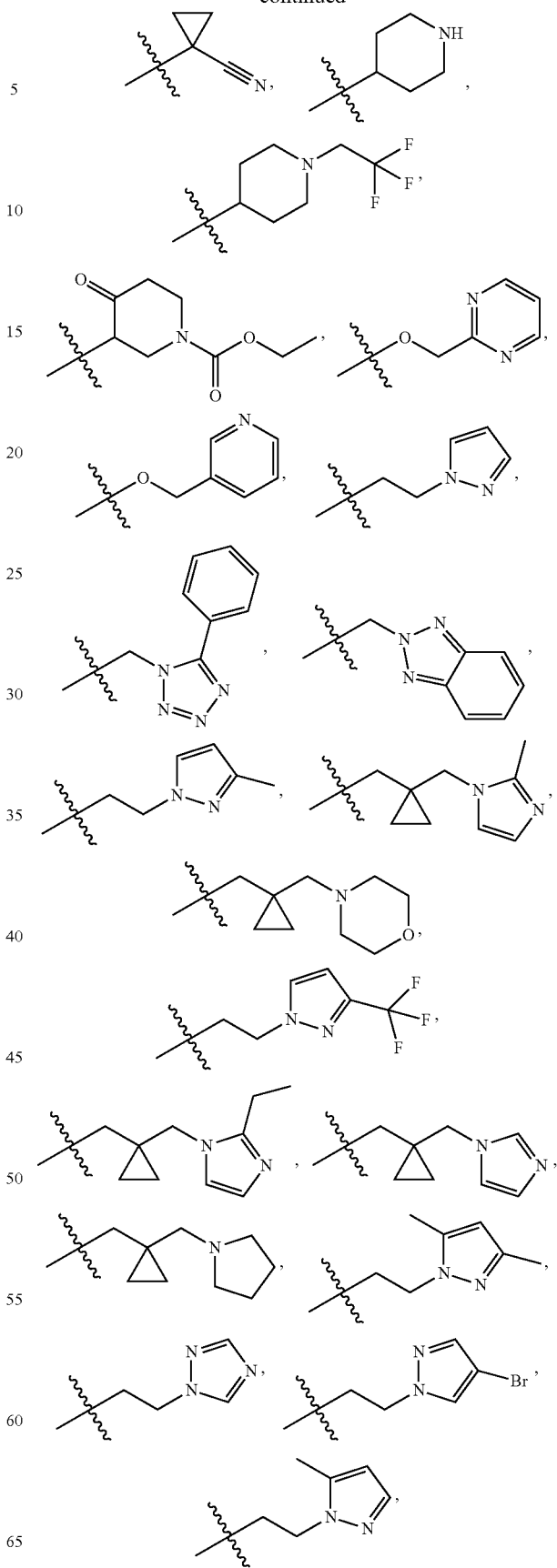

-continued

In certain embodiments, the compound of formula I is represented by Formula IIA:

IIA wherein:
n is 0, 1, 2, or 3;
$R^{10}$ is independently selected from the group consisting of halo, $-NO_2$, CN, $-SF_5$, $-Si(CH_3)_3$, $-O-R^{20}$, $-S-R^{20}$, $-C(O)-R^{20}$, $-C(O)-OR^{20}$, $-N(R^{20})(R^{22})$, $-C(O)-N(R^{20})(R^{22})$, $-N(R^{20})-C(O)-R^{22}$, $-N(R^{20})-S(=O)_2-R^{26}$, $-S(=O)_2-R^{20}$, $-S(=O)_2-N(R^{20})(R^{22})$, $C_{1-4}$ alkyl, $C_{2-4}$ alkenyl, $C_{2-4}$ alkynyl, cycloalkyl, aryl, heteroaryl and heterocyclyl; and
wherein said $C_{1-4}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, $-NO_2$, aryl, heterocyclyl, heteroaryl, $C_{1-4}$ alkyl, cycloalkyl, $-N(R^{20})(R^{22})$, $-C(O)-R^{20}$, $-C(O)-OR^{20}$, $-C(O)-N(R^{20})(R^{22})$, $-CN$ and $-O-R^{20}$;
$R^2$ is selected from the group consisting of hydrogen, $C_{1-15}$ alkyl, $C_{1-4}$ alkoxy, $-C(O)-R^{26}$, $-C(O)-OR^{26}$, $-C(O)-N(R^{26})(R^{28})$, $-N(R^{20})-S(=O)_2-R^{20}$, cycloalkyl, aryl, heteroaryl or heterocyclyl;
wherein said $C_{1-15}$ alkyl, $C_{1-4}$ alkoxy, cycloalkyl aryl, heteroaryl or heterocyclyl are optionally substituted with one, two or three substituents independently selected from the group consisting of hydroxyl, $C_{1-15}$ alkyl, $C_{1-4}$ alkoxy, $C_{2-4}$ alkynyl, halo, $-NO_2$, cycloalkyl, aryl, heterocyclyl, heteroaryl, $-N(R^{20})(R^{22})$, $-C(O)-R^{20}$, $-C(O)-O-R^{20}$, $-C(O)-N(R^{20})(R^{22})$, $-CN$, oxo and $-O-R^{20}$;
wherein said $C_{1-15}$ alkyl, $C_{1-4}$ alkoxy, cycloalkyl, aryl, heterocyclyl or heteroaryl are optionally further substituted with one, two or three substituents independently selected from the group consisting of hydroxyl, halo, $-NO_2$, $C_{1-6}$ alkyl, $C_{1-4}$ alkoxy, aralkyl, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$, and $-O-R^{20}$; and
wherein said $C_{1-6}$ alkyl, $C_{1-4}$ alkoxy, aralkyl, cycloalkyl, aryl, heterocyclyl or heteroaryl, are optionally further substituted with one, two or three substituents independently selected from the group consisting of hydroxyl, halo, $-NO_2$, $-CF_3$, $-N(R^{20})(R^{22})$, $-C(O)-R^{20}$, $-C(O)-O-R^{20}$, $-C(O)-N(R^{20})(R^{22})$, $-CN$, $-S(O)_2-R^{20}$ and $-O-R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl; and
wherein the $C_{1-15}$ alkyl, $C_{2-15}$ alkenyl, $C_{2-15}$ alkynyl, cycloalkyl, heterocyclyl, aryl or heteroaryl are optionally substituted with one, two or three substituents independently selected from the group consisting of hydroxyl, halo, $C_{1-4}$ alkyl, substituted amino, aminoacyl, $-NO_2$, $-SO_2R^{26}$, $-CN$, $C_{1-3}$ alkoxy, $-CF_3$, $-OCF_3$, $-OCH_2CF_3$, $-C(O)-NH_2$, aryl, cycloalkyl and heteroaryl;
wherein said heteroaryl is optionally further substituted with $C_{1-4}$ alkyl or cycloalkyl; or
when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryl, aryloxy, aralkyloxy, substituted amino, aminoacyl, $-NO_2$, $-SO_2R^{26}$, $-CN$, $C_{1-3}$ alkoxy, $-CF_3$, $-OCF_3$, aryl, heteroaryl and cycloalkyl; and
$R^{26}$ and $R^{28}$ are in each instance independently selected from the group consisting of hydrogen, $C_{1-15}$ alkyl, cycloalkyl, aryl and heteroaryl; and
wherein the $C_{1-15}$ alkyl, cycloalkyl, aryl or heteroaryl may be further substituted with from 1 to 3 substituents independently selected from the group consisting of hydroxyl, halo, $C_{1-4}$ alkoxy, $-CF_3$ and $-OCF_3$;
or a pharmaceutically acceptable salt, ester, hydrate, solvate, stereoisomer, tautomer, polymorph and/or prodrug thereof.

In some embodiments of Formula IIA, $R^2$ is selected from the group consisting of hydrogen, $C_{1-15}$ alkyl, $C_{1-4}$ alkoxy, cycloalkyl and heterocyclyl. In many embodiments the alkyl, alkoxy, cycloalkyl, and heterocyclyl moiety is further substituted with one, two or three substituents independently selected from the group consisting of hydroxyl, alkyl, alkoxy, alkynyl, aryl, heteroaryl, cycloalkyl, $-N(R^{20})(R^{22})$, $-C(O)-OR^{20}$, $-C(O)-N(R^{20})(R^{22})$, $-CN$, oxo and $-O-R^{20}$;
wherein said alkyl or heteroaryl are optionally further substituted with one, two or three substituents independently selected from the group consisting of halo, $C_{1-6}$ alkyl, $C_{1-4}$ alkoxy, benzyl, aryl, heteroaryl and cycloalkyl;
$R^{20}$ and $R^{22}$ are in each instance independently selected from the group consisting of hydrogen, $C_{1-15}$ alkyl and heteroaryl; and wherein the heteroaryl is optionally substituted with one, two or three substituents independently selected from the group consisting of —CN and heteroaryl;
  wherein said heteroaryl is optionally further substituted with cycloalkyl; or
when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of alkyl, phenyl, —$CF_3$ and heteroaryl.

Exemplary $R^2$ moieties of Formula IIA include, but are not limited to, hydrogen,

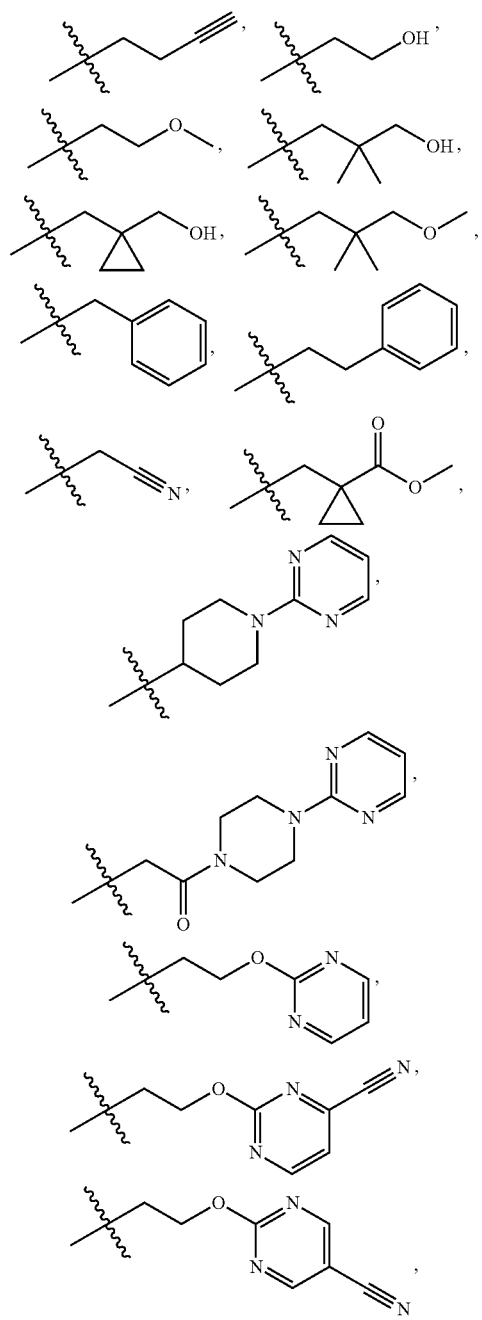

-continued

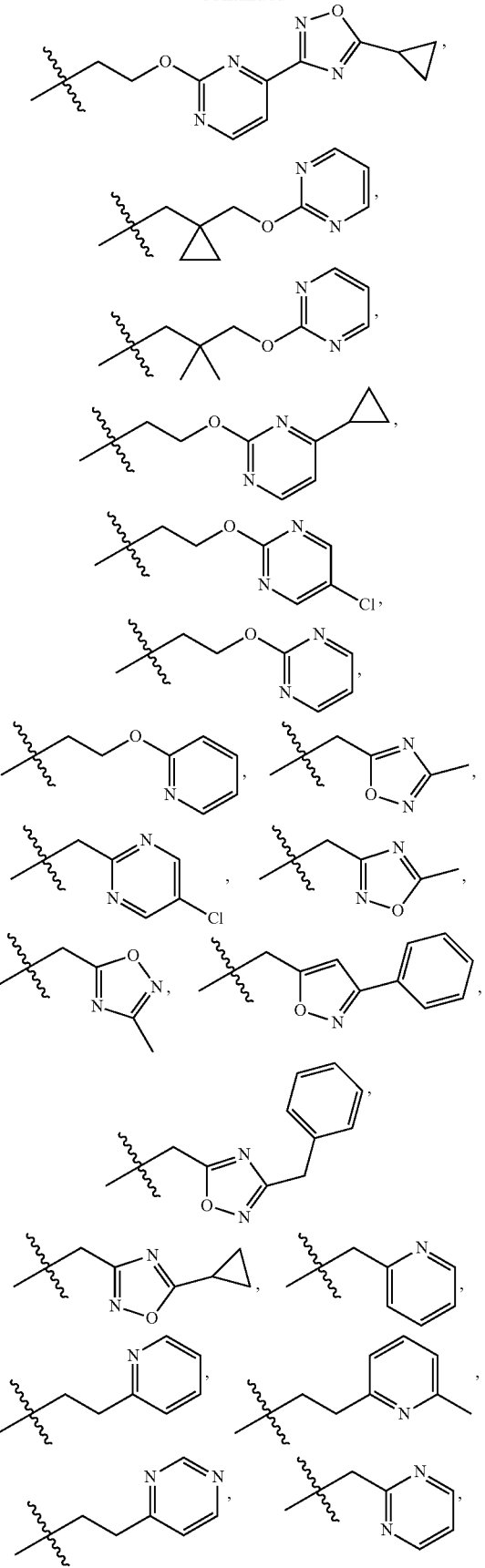

-continued
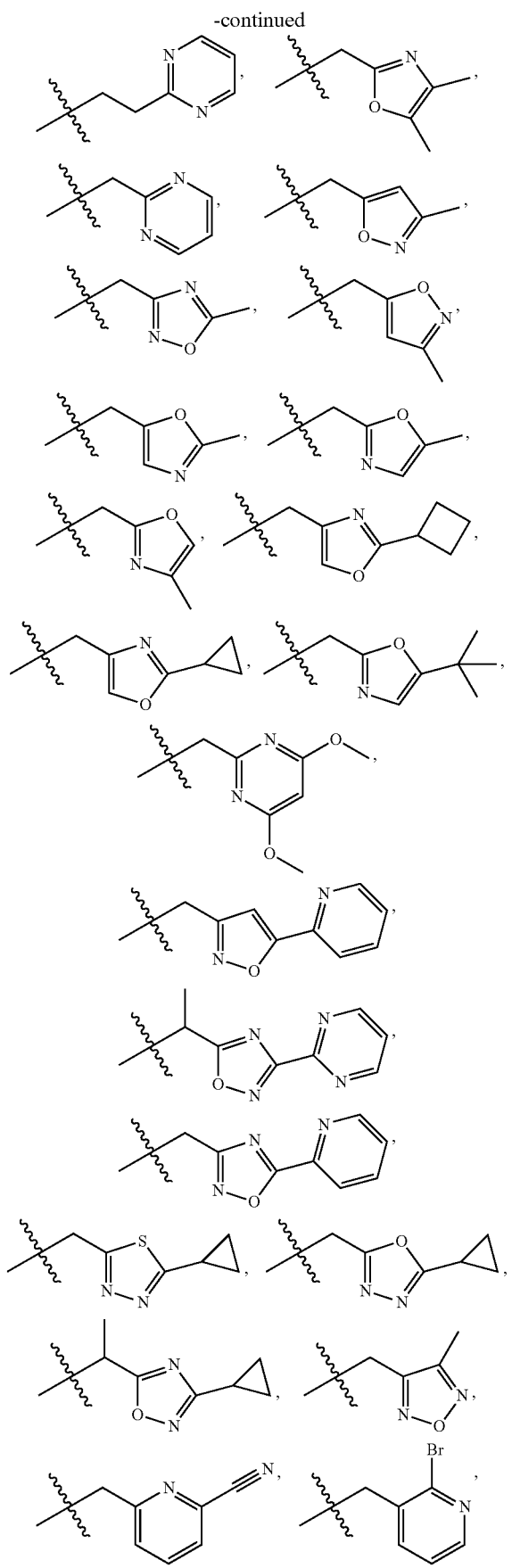
-continued
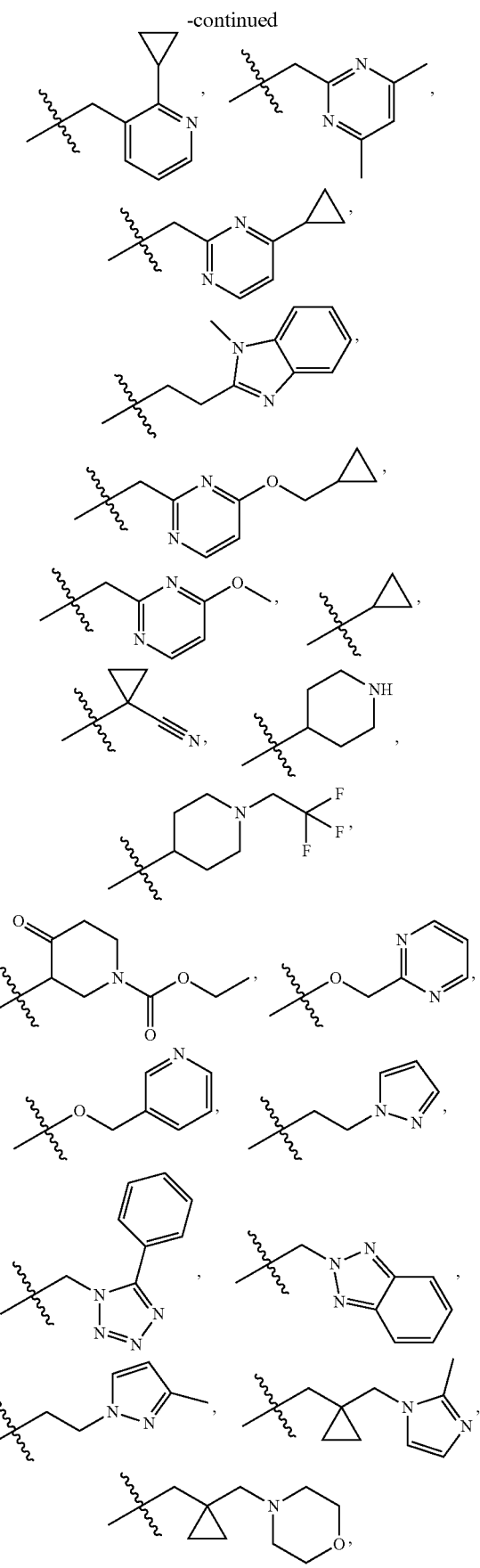

-continued

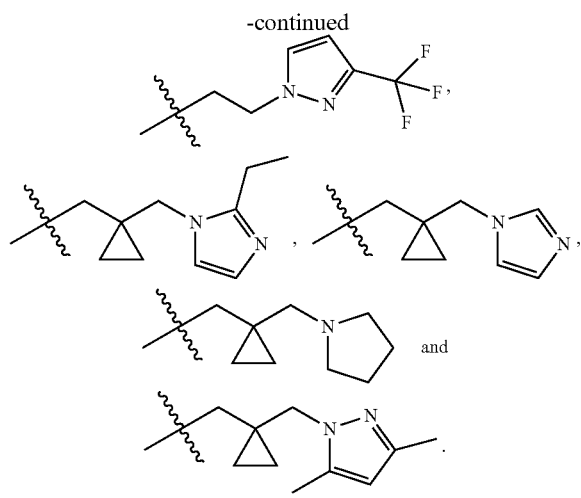

In some embodiments of Formula IIA, $R^{10}$ is selected from the group consisting of —$OCF_3$, cycloalkyl and —O—$R^{20}$; and $R^{20}$ is aryl. In many embodiments the cycloalkyl is optionally further substituted with —CN. In many embodiments $R^{20}$ is optionally substituted with halo.

Exemplary $R^{10}$ moieties of Formula IIA include, but are not limited to, —$OCF_3$, cyclopropyl, 1-cyanocyclopropyl, phenoxy and 4-chlorophenoxy.

Exemplary compounds of Formula IIA include
6-(4-(trifluoromethoxy)phenyl)benzo[d][1,2,3]triazin-4(3H)-one;
3-((3-methyl-1,2,4-oxadiazol-5-yl)methyl)-6-(4-(trifluoromethoxy)phenyl)benzo[d][1,2,3]triazin-4(3H)-one;
3-((5-chloropyrimidin-2-yl)methyl)-6-(4-(trifluoromethoxy)phenyl)benzo[d][1,2,3]triazin-4(3H)-one;
3-((5-methyl-1,2,4-oxadiazol-3-yl)methyl)-6-(4-(trifluoromethoxy)phenyl)benzo[d][1,2,3]triazin-4(3H)-one;
3-((3-methyl-1,2,4-oxadiazol-5-yl)methyl)-6-(4-phenoxyphenyl)benzo[d][1,2,3]triazin-4(3H)-one;
3-((3-phenylisoxazol-5-yl)methyl)-6-(4-(trifluoromethoxy)phenyl)benzo[d][1,2,3]triazin-4(3H)-one;
3-((3-benzyl-1,2,4-oxadiazol-5-yl)methyl)-6-(4-(trifluoromethoxy)phenyl)benzo[d][1,2,3]triazin-4(3H)-one;
3-(2-(1H-pyrazol-1-yl)ethyl)-6-(4-(trifluoromethoxy)phenyl)benzo[d][1,2,3]triazin-4(3H)-one;
3-((5-cyclopropyl-1,2,4-oxadiazol-3-yl)methyl)-6-(4-(trifluoromethoxy)phenyl)benzo[d][1,2,3]triazin-4(3H)-one;
3-(2-(pyridin-2-yl)ethyl)-6-(4-(trifluoromethoxy)phenyl)benzo[d][1,2,3]triazin-4(3H)-one;
6-(4-(4-chlorophenoxy)phenyl)-3-((3-methyl-1,2,4-oxadiazol-5-yl)methyl)benzo[d][1,2,3]triazin-4(3H)-one;
3-(2-(pyrimidin-4-yl)ethyl)-6-(4-(trifluoromethoxy)phenyl)benzo[d][1,2,3]triazin-4(3H)-one;
3-(2-(pyrimidin-2-yl)ethyl)-6-(4-(trifluoromethoxy)phenyl)benzo[d][1,2,3]triazin-4(3H)-one;
6-(4-(4-chlorophenoxy)phenyl)benzo[d][1,2,3]triazin-4(3H)-one;
3-((5-phenyl-1H-tetrazol-1-yl)methyl)-6-(4-(trifluoromethoxy)phenyl)benzo[d][1,2,3]triazin-4(3H)-one;
3-cyclopropyl-6-(4-(trifluoromethoxy)phenyl)benzo[d][1,2,3]triazin-4(3H)-one;
3 4-((4,5-dimethyloxazol-2-yl)methyl)-6-(4-(trifluoromethoxy)phenyl)benzo[d][1,2,3]triazin-4(3H)-one;
3-(pyrimidin-2-ylmethyl)-6-(4-(trifluoromethoxy)phenyl)benzo[d][1,2,3]triazin-4(3H)-one;
3-((3-methylisoxazol-5-yl)methyl)-6-(4-(trifluoromethoxy)phenyl)benzo[d][1,2,3]triazin-4(3H)-one;
3-((5-methylisoxazol-3-yl)methyl)-6-(4-(trifluoromethoxy)phenyl)benzo[d][1,2,3]triazin-4(3H)-one;
3-((2H-benzo[d][1,2,3]triazol-2-yl)methyl)-6-(4-(trifluoromethoxy)phenyl)benzo[d][1,2,3]triazin-4(3H)-one;
3-(2-(1H-pyrazol-1-yl)ethyl)-6-(4-(4-chlorophenoxy)phenyl)benzo[d][1,2,3]triazin-4(3H)-one;
2-(4-oxo-6-(4-(trifluoromethoxy)phenyl)benzo[d][1,2,3]triazin-3(4H)-yl)acetonitrile;
3-(2-(pyrimidin-2-yloxy)ethyl)-6-(4-(trifluoromethoxy)phenyl)benzo[d][1,2,3]triazin-4(3H)-one;
1-(4-oxo-6-(4-(trifluoromethoxy)phenyl)benzo[d][1,2,3]triazin-3(4H)-yl)cyclopropanecarbonitrile;
3-((1-((2-methyl-1H-imidazol-1-yl)methyl)cyclopropyl)methyl)-6-(4-(trifluoromethoxy)phenyl)benzo[d][1,2,3]triazin-4(3H)-one;
2-(2-(4-oxo-6-(4-(trifluoromethoxy)phenyl)benzo[d][1,2,3]triazin-3(4H)-yl)ethoxy)pyrimidine-4-carbonitrile;
3-(piperidin-4-yl)-6-(4-(trifluoromethoxy)phenyl)benzo[d][1,2,3]triazin-4(3H)-one;
3-(1-(pyrimidin-2-yl)piperidin-4-yl)-6-(4-(trifluoromethoxy)phenyl)benzo[d][1,2,3]triazin-4(3H)-one;
3-((1-(morpholinomethyl)cyclopropyl)methyl)-6-(4-(trifluoromethoxy)phenyl)benzo[d][1,2,3]triazin-4(3H)-one;
3-(2-oxo-2-(4-(pyrimidin-2-yl)piperazin-1-yl)ethyl)-6-(4-(trifluoromethoxy)phenyl)benzo[d][1,2,3]triazin-4(3H)-one;
3-benzyl-6-(4-(trifluoromethoxy)phenyl)benzo[d][1,2,3]triazin-4(3H)-one;
3-(2-methoxyethyl)-6-(4-(trifluoromethoxy)phenyl)benzo[d][1,2,3]triazin-4(3H)-one;
3 4-((4,6-dimethoxypyrimidin-2-yl)methyl)-6-(4-(trifluoromethoxy)phenyl)benzo[d][1,2,3]triazin-4(3H)-one;
3-(but-3-ynyl)-6-(4-(trifluoromethoxy)phenyl)benzo[d][1,2,3]triazin-4(3H)-one;
3-(2-hydroxyethyl)-6-(4-(trifluoromethoxy)phenyl)benzo[d][1,2,3]triazin-4(3H)-one;
3-((5-(pyridin-2-yl)isoxazol-3-yl)methyl)-6-(4-(trifluoromethoxy)phenyl)benzo[d][1,2,3]triazin-4(3H)-one;
1-(4-(4-oxo-3-(2-(pyrimidin-2-yloxy)ethyl)-3,4-dihydrobenzo[d][1,2,3]triazin-6-yl)phenyl)cyclopropanecarbonitrile;
2-(2-(4-oxo-6-(4-(trifluoromethoxy)phenyl)benzo[d][1,2,3]triazin-3(4H)-yl)ethoxy)pyrimidine-5-carbonitrile;
6-(4-(trifluoromethoxy)phenyl)-3-(2-(3-(trifluoromethyl)-1H-pyrazol-1-yl)ethyl)benzo[d][1,2,3]triazin-4(3H)-one;
3-(1-(3-(pyrimidin-2-yl)-1,2,4-oxadiazol-5-yl)ethyl)-6-(4-(trifluoromethoxy)phenyl)benzo[d][1,2,3]triazin-4(3H)-one;
3-((5-(pyridin-2-yl)-1,2,4-oxadiazol-3-yl)methyl)-6-(4-(trifluoromethoxy)phenyl)benzo[d][1,2,3]triazin-4(3H)-one;
methyl 1-((4-oxo-6-(4-(trifluoromethoxy)phenyl)benzo[d][1,2,3]triazin-3(4H)-yl)methyl)cyclopropanecarboxylate;
3-(pyrimidin-2-ylmethoxy)-6-(4-(trifluoromethoxy)phenyl)benzo[d][1,2,3]triazin-4(3H)-one;
3-((1-(2-ethyl-1H-imidazol-1-yl)methyl)cyclopropyl)methyl)-6-(4-(trifluoromethoxy)phenyl)benzo[d][1,2,3]triazin-4(3H)-one;
3-((1-((1H-imidazol-1-yl)methyl)cyclopropyl)methyl)-6-(4-(trifluoromethoxy)phenyl)benzo[d][1,2,3]triazin-4(3H)-one;
3-(pyridin-3-ylmethoxy)-6-(4-(trifluoromethoxy)phenyl)benzo[d][1,2,3]triazin-4(3H)-one;
3-(2-(4-(5-cyclopropyl-1,2,4-oxadiazol-3-yl)pyrimidin-2-yloxy)ethyl)-6-(4-(trifluoromethoxy)phenyl)benzo[d][1,2,3]triazin-4(3H)-one;
3-((1-(pyrrolidin-1-ylmethyl)cyclopropyl)methyl)-6-(4-(trifluoromethoxy)phenyl)benzo[d][1,2,3]triazin-4(3H)-one;

3-((1-(3,5-dimethyl-1H-pyrazol-1-yl)methyl)cyclopropyl)
  methyl)-6-(4-(trifluoromethoxy)phenyl)benzo[d][1,2,3]
  triazin-4(3H)-one;
6-(4-(4-chlorophenoxy)phenyl)-3-(2-oxo-2-(4-(pyrimidin-
  2-yl)piperazin-1-yl)ethyl)benzo[d][1,2,3]triazin-4(3H)-
  one;
3-((5-cyclopropyl-1,3,4-thiadiazol-2-yl)methyl)-6-(4-(trif-
  luoromethoxy)phenyl)benzo[d][1,2,3]triazin-4(3H)-one;
3-((5-cyclopropyl-1,3,4-oxadiazol-2-yl)methyl)-6-(4-(trif-
  luoromethoxy)phenyl)benzo[d][1,2,3]triazin-4(3H)-one;
3-(3-methoxy-2,2-dimethylpropyl)-6-(4-(trifluoromethoxy)
  phenyl)benzo[d][1,2,3]triazin-4(3H)-one;
3-(1-(2,2,2-trifluoroethyl)piperidin-4-yl)-6-(4-(trifluo-
  romethoxy)phenyl)benzo[d][1,2,3]triazin-4(3H)-one;
ethyl 4-oxo-3-(4-oxo-6-(4-(trifluoromethoxy)phenyl)benzo
  [d][1,2,3]triazin-3(4H)-yl)piperidine-1-carboxylate;
6-(4-cyclopropylphenyl)-3-((3-methyl-1,2,4-oxadiazol-5-
  yl)methyl)benzo[d][1,2,3]triazin-4(3H)-one;
3-((1-(hydroxymethyl)cyclopropyl)methyl)-6-(4-(trifluo-
  romethoxy)phenyl)benzo[d][1,2,3]triazin-4(3H)-one;
3-(1-(3-cyclopropyl-1,2,4-oxadiazol-5-yl)ethyl)-6-(4-(trif-
  luoromethoxy)phenyl)benzo[d][1,2,3]triazin-4(3H)-one;
3-((1-((pyrimidin-2-yloxy)methyl)cyclopropyl)methyl)-6-
  (4-(trifluoromethoxy)phenyl)benzo[d][1,2,3]triazin-4
  (3H)-one;
3-(3-hydroxy-2,2-dimethylpropyl)-6-(4-(trifluoromethoxy)
  phenyl)benzo[d][1,2,3]triazin-4(3H)-one;
3-(2,2-dimethyl-3-(pyrimidin-2-yloxy)propyl)-6-(4-(trifluo-
  romethoxy)phenyl)benzo[d][1,2,3]triazin-4(3H)-one;
3-((2-methyloxazol-5-yl)methyl)-6-(4-(trifluoromethoxy)
  phenyl)benzo[d][1,2,3]triazin-4(3H)-one;
3-((5-methyloxazol-2-yl)methyl)-6-(4-(trifluoromethoxy)
  phenyl)benzo[d][1,2,3]triazin-4(3H)-one;
3-((4-methyloxazol-2-yl)methyl)-6-(4-(trifluoromethoxy)
  phenyl)benzo[d][1,2,3]triazin-4(3H)-one;
3-((2-cyclobutyloxazol-4-yl)methyl)-6-(4-(trifluo-
  romethoxy)phenyl)benzo[d][1,2,3]triazin-4(3H)-one;
3-((2-methyloxazol-4-yl)methyl)-6-(4-(trifluoromethoxy)
  phenyl)benzo[d][1,2,3]triazin-4(3H)-one; and
3-((2-cyclopropyloxazol-4-yl)methyl)-6-(4-(trifluo-
  romethoxy)phenyl)benzo[d][1,2,3]triazin-4(3H)-one;
or a pharmaceutically acceptable salt, ester, hydrate, solvate, stereoisomer, tautomer, polymorph and/or prodrug thereof.

In certain embodiments, the compound of Formula I is represented by Formula IIIA:

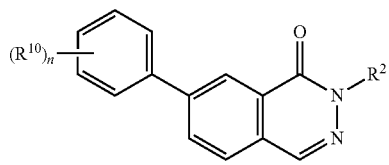

IIIA wherein:
n is 0, 1, 2, or 3;
$R^{10}$ is independently selected from the group consisting of halo, $-NO_2$, CN, $-SF_5$, $-Si(CH_3)_3$, $-O-R^{20}$, $-S-R^{20}$, $-C(O)-R^{20}$, $-C(O)-OR^{20}$, $-N(R^{20})(R^{22})$, $-C(O)-N(R^{20})(R^{22})$, $-N(R^{20})-C(O)-R^{22}$, $-N(R^{20})-S(=O)_2-R^{26}$, $-S(=O)_2-R^{20}$, $-S(=O)_2-N(R^{20})(R^{22})$, $C_{1-4}$ alkyl, $C_{2-4}$ alkenyl, $C_{2-4}$ alkynyl, cycloalkyl, aryl, heteroaryl and heterocyclyl; and wherein said $C_{1-4}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, $-NO_2$, aryl, heterocyclyl, heteroaryl, $C_{1-4}$ alkyl, cycloalkyl, $-N(R^{20})(R^{22})$, $-C(O)-R^{20}$, $-C(O)-OR^{20}$, $-C(O)-N(R^{20})(R^{22})$, $-CN$ and $-O-R^{20}$;

$R^2$ is selected from the group consisting of hydrogen, $C_{1-15}$ alkyl, $C_{1-4}$ alkoxy, $-C(O)-R^{26}$, $-C(O)-OR^{26}$, $-C(O)-N(R^{26})(R^{28})$, $-N(R^{20})-S(=O)_2-R^{20}$, cycloalkyl, aryl, heteroaryl or heterocyclyl;
wherein said $C_{1-15}$ alkyl, $C_{1-4}$ alkoxy, cycloalkyl aryl, heteroaryl or heterocyclyl are optionally substituted with one, two or three substituents independently selected from the group consisting of hydroxyl, $C_{1-15}$ alkyl, $C_{1-4}$ alkoxy, $C_{2-4}$ alkynyl, halo, $-NO_2$, cycloalkyl, aryl, heterocyclyl, heteroaryl, $-N(R^{20})(R^{22})$, $-C(O)-R^{20}$, $-C(O)-O-R^{20}$, $-C(O)-N(R^{20})(R^{22})$, $-CN$, oxo and $-O-R^{20}$;
wherein said $C_{1-15}$ alkyl, $C_{1-4}$ alkoxy, cycloalkyl, aryl, heterocyclyl or heteroaryl are optionally further substituted with one, two or three substituents independently selected from the group consisting of hydroxyl, halo, $-NO_2$, $C_{1-6}$ alkyl, $C_{1-4}$ alkoxy, aralkyl, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$, and $-O-R^{20}$; and
wherein said $C_{1-6}$ alkyl, $C_{1-4}$ alkoxy, aralkyl, cycloalkyl, aryl, heterocyclyl or heteroaryl, are optionally further substituted with one, two or three substituents independently selected from the group consisting of hydroxyl, halo, $-NO_2$, $-CF_3$, $-N(R^{20})(R^{22})$, $-C(O)-R^{20}$, $-C(O)-O-R^{20}$, $-C(O)-N(R^{20})(R^{22})$, $-CN$, $-S(O)_2-R^{20}$ and $-O-R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl; and
wherein the $C_{1-15}$ alkyl, $C_{2-15}$ alkenyl, $C_{2-15}$ alkynyl, cycloalkyl, heterocyclyl, aryl or heteroaryl are optionally substituted with one, two or three substituents independently selected from the group consisting of hydroxyl, halo, $C_{1-4}$ alkyl, substituted amino, aminoacyl, $-NO_2$, $-SO_2R^{26}$, $-CN$, $C_{1-3}$ alkoxy, $-CF_3$, $-OCF_3$, $-OCH_2CF_3$, $-C(O)-NH_2$, aryl, cycloalkyl and heteroaryl;
wherein said heteroaryl is optionally further substituted with $C_{1-4}$ alkyl or cycloalkyl; or
when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryl, aryloxy, aralkyloxy, substituted amino, aminoacyl, $-NO_2$, $-SO_2R^{26}$, $-CN$, $C_{1-3}$ alkoxy, $-CF_3$, $-OCF_3$, aryl, heteroaryl and cycloalkyl; and $R^{26}$ and $R^{28}$ are in each instance independently selected from the group consisting of hydrogen, $C_{1-15}$ alkyl, cycloalkyl, aryl and heteroaryl; and
wherein the $C_{1-15}$ alkyl, cycloalkyl, aryl or heteroaryl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, hydrate, solvate, stereoisomer, tautomer, polymorph and/or prodrug thereof.

In some embodiments of Formula IIIA, $R^2$ is hydrogen or $C_{1-15}$ alkyl. In many embodiments the alkyl moiety is further substituted with one, two or three substituents independently selected from the group consisting of hydroxyl, aryl, heteroaryl, —$N(R^{20})(R^{22})$, and —O—$R^{20}$; and wherein said aryl, or heteroaryl are optionally further substituted with one, two or three substituents independently selected from the group consisting of hydroxyl, halo, $C_{1-4}$ alkyl, $C_{1-4}$ alkoxy, heteroaryl, cycloalkyl, —CN, and —O—$R^{20}$;

$R^{20}$ and $R^{22}$ in each instance are independently selected from the group consisting of $C_{1-15}$ alkyl, and heteroaryl; and wherein the $C_{1-15}$ alkyl, and heteroaryl are optionally substituted with halo or cycloalkyl; or when $R^{20}$ and $R^{22}$ are attached to a common nitrogen atom $R^{20}$ and $R^{22}$ may join to form a heteroaryl ring which is then optionally substituted with one, two or three substituents independently selected from the group consisting of halo, $C_{1-6}$ alkyl, and heteroaryl.

Exemplary $R^2$ moieties of Formula IIIA include, but are not limited to, hydrogen, methyl,

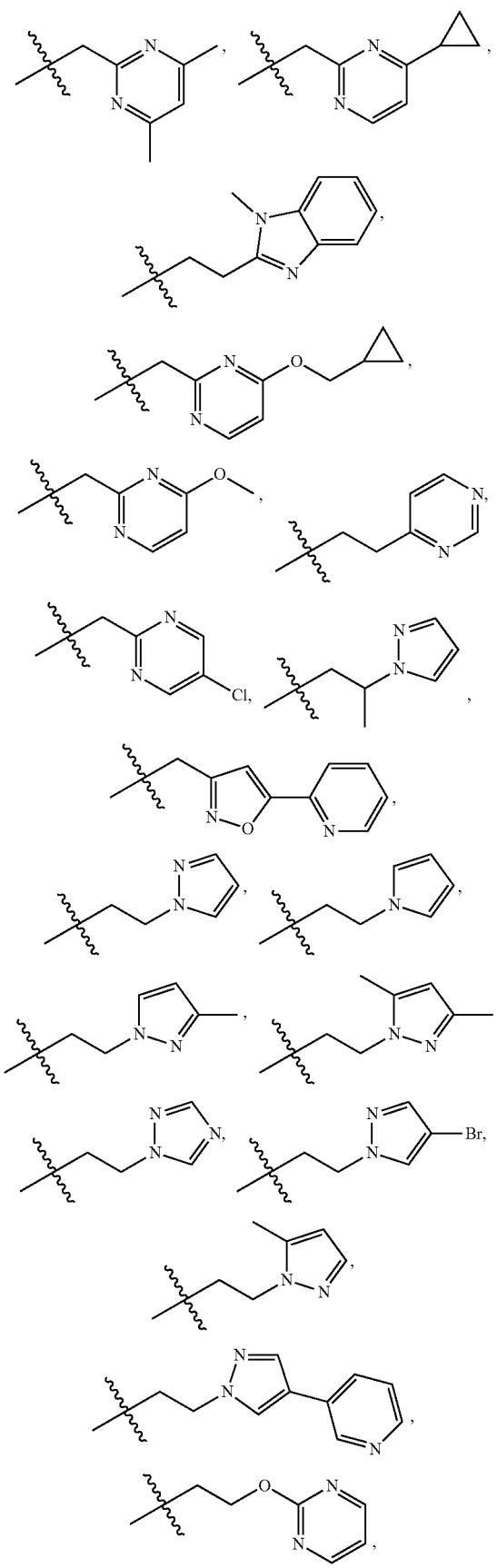

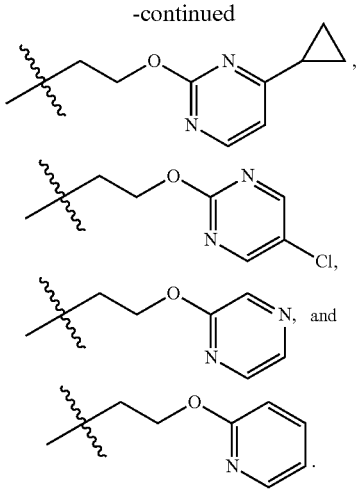

An exemplary R¹⁰ moiety of Formula IIIA includes —OCF₃.

Exemplary compounds of Formula IIIA include
7-(4-(trifluoromethoxy)phenyl)phthalazin-1(2H)-one;
2-((3-methyl-1;2;4-oxadiazol-5-yl)methyl)-7-(4-(trifluoromethoxy)phenyl)phthalazin-1(2H)-one;
2-((5-methyl-1;2;4-oxadiazol-3-yl)methyl)-7-(4-(trifluoromethoxy)phenyl)phthalazin-1(2H)-one;
2-methyl-7-(4-(trifluoromethoxy)phenyl)phthalazin-1(2H)-one;
2-(pyrimidin-2-ylmethyl)-7-(4-(trifluoromethoxy)phenyl)phthalazin-1(2H)-one;
2-benzyl-7-(4-(trifluoromethoxy)phenyl)phthalazin-1(2H)-one;
2-((1-oxo-7-(4-(trifluoromethoxy)phenyl)phthalazin-2(1H)-yl)methyl)benzonitrile;
2-phenethyl-7-(4-(trifluoromethoxy)phenyl)phthalazin-1(2H)-one;
2-(2-(1H-pyrazol-1-yl)ethyl)-7-(4-(trifluoromethoxy)phenyl)phthalazin-1(2H)-one;
2-(2-(1H-pyrrol-1-yl)ethyl)-7-(4-(trifluoromethoxy)phenyl)phthalazin-1(2H)-one;
2-((4-methyl-1;2;5-oxadiazol-3-yl)methyl)-7-(4-(trifluoromethoxy)phenyl)phthalazin-1(2H)-one;
6-((1-oxo-7-(4-(trifluoromethoxy)phenyl)phthalazin-2(1H)-yl)methyl)picolinonitrile;
7-(4-(trifluoromethoxy)phenyl)-2-((5-(3-(trifluoromethyl)phenyl)-1;2;4-oxadiazol-3-yl)methyl)phthalazin-1(2H)-one;
2-((2-bromopyridin-3-yl)methyl)-7-(4-(trifluoromethoxy)phenyl)phthalazin-1(2H)-one;
2-(3-hydroxypropyl)-7-(4-(trifluoromethoxy)phenyl)phthalazin-1(2H)-one;
2-(3-(pyridin-2-yloxy)propyl)-7-(4-(trifluoromethoxy)phenyl)phthalazin-1(2H)-one;
2-(2-(3-methyl-1H-pyrazol-1-yl)ethyl)-7-(4-(trifluoromethoxy)phenyl)phthalazin-1(2H)-one;
2-(2-(6-methylpyridin-2-yl)ethyl)-7-(4-(trifluoromethoxy)phenyl)phthalazin-1(2H)-one;
2-((4;6-dimethoxypyrimidin-2-yl)methyl)-7-(4-(trifluoromethoxy)phenyl)phthalazin-1(2H)-one;
2-((2-cyclopropylpyridin-3-yl)methyl)-7-(4-(trifluoromethoxy)phenyl)phthalazin-1(2H)-one;
7-(4-(trifluoromethoxy)phenyl)-2-((6-(trifluoromethyl)pyridin-2-yl)methyl)phthalazin-1(2H)-one;
2-((4;6-dimethylpyrimidin-2-yl)methyl)-7-(4-(trifluoromethoxy)phenyl)phthalazin-1(2H)-one;
2-((4-cyclopropylpyrimidin-2-yl)methyl)-7-(4-(trifluoromethoxy)phenyl)phthalazin-1(2H)-one;
2-(2-(3;5-dimethyl-1H-pyrazol-1-yl)ethyl)-7-(4-(trifluoromethoxy)phenyl)phthalazin-1(2H)-one;
2-(2-(1-methyl-1H-benzo[d]imidazol-2-yl)ethyl)-7-(4-(trifluoromethoxy)phenyl)phthalazin-1(2H)-one;
2-(2-(1H-1;2;4-triazol-1-yl)ethyl)-7-(4-(trifluoromethoxy)phenyl)phthalazin-1(2H)-one;
2-((4-(cyclopropylmethoxy)pyrimidin-2-yl)methyl)-7-(4-(trifluoromethoxy)phenyl)phthalazin-1(2H)-one;
2-(2-(pyrimidin-2-yloxy)ethyl)-7-(4-(trifluoromethoxy)phenyl)phthalazin-1(2H)-one;
2-(2-(4-cyclopropylpyrimidin-2-yloxy)ethyl)-7-(4-(trifluoromethoxy)phenyl)phthalazin-1(2H)-one;
2-((4-methoxypyrimidin-2-yl)methyl)-7-(4-(trifluoromethoxy)phenyl)phthalazin-1(2H)-one;
2-(2-(4-bromo-1H-pyrazol-1-yl)ethyl)-7-(4-(trifluoromethoxy)phenyl)phthalazin-1(2H)-one;
2-(2-(5-methyl-1H-pyrazol-1-yl)ethyl)-7-(4-(trifluoromethoxy)phenyl)phthalazin-1(2H)-one;
2-(2-(4-(pyridin-3-yl)-1H-pyrazol-1-yl)ethyl)-7-(4-(trifluoromethoxy)phenyl)phthalazin-1(2H)-one;
2-(2-(4-(2-methoxypyrimidin-5-yl)-1H-pyrazol-1-yl)ethyl)-7-(4-(trifluoromethoxy)phenyl)phthalazin-1(2H)-one;
2-((5-chloropyrimidin-2-yl)methyl)-7-(4-(trifluoromethoxy)phenyl)phthalazin-1(2H)-one;
2-(2-(pyrimidin-4-yl)ethyl)-7-(4-(trifluoromethoxy)phenyl)phthalazin-1(2H)-one;
2-(2-(5-chloropyrimidin-2-yloxy)ethyl)-7-(4-(trifluoromethoxy)phenyl)phthalazin-1(2H)-one;
2-(2-(1H-pyrazol-1-yl)propyl)-7-(4-(trifluoromethoxy)phenyl)phthalazin-1(2H)-one;
2-(2-(pyrazin-2-yloxy)ethyl)-7-(4-(trifluoromethoxy)phenyl)phthalazin-1(2H)-one;
2-(2-(pyridin-2-yloxy)ethyl)-7-(4-(trifluoromethoxy)phenyl)phthalazin-1(2H)-one; and
2-((5-(pyridin-2-yl)isoxazol-3-yl)methyl)-7-(4-(trifluoromethoxy)phenyl)phthalazin-1(2H)-one;
or a pharmaceutically acceptable salt, ester, hydrate, solvate, stereoisomer, tautomer, polymorph and/or prodrug thereof.

In certain embodiments, the compound of Formula I is represented by Formula IVA:

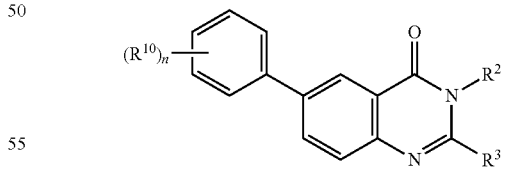

IVA wherein:
n is 0, 1, 2, or 3;
R¹⁰ is independently selected from the group consisting of halo, —NO₂, CN, —SF₅, —Si(CH₃)₃, —O—R²⁰, —S—R²⁰, —C(O)—R²⁰, —C(O)—OR²⁰, —N(R²⁰)(R²²), —C(O)—N(R²⁰)(R²²), —N(R²⁰)—C(O)—R²², —N(R²⁰)—S(=O)₂—R²⁶, —S(=O)₂—R²⁰, —S(=O)₂—N(R²⁰)(R²²), C₁₋₄ alkyl, C₂₋₄ alkenyl, C₂₋₄ alkynyl, cycloalkyl, aryl, heteroaryl and heterocyclyl; and wherein said $C_{1-4}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, aryl, heterocyclyl, heteroaryl, $C_{1-4}$ alkyl, cycloalkyl, —$N(R^{20})(R^{22})$, —$C(O)$—$R^{20}$, —$C(O)$—$OR^{20}$, —$C(O)$—$N(R^{20})(R^{22})$, —CN and —O—$R^{20}$;

$R^2$ is selected from the group consisting of hydrogen, $C_{1-15}$ alkyl, $C_{1-4}$ alkoxy, —$C(O)$—$R^{26}$, —$C(O)$—$OR^{26}$, —$C(O)$—$N(R^{26})(R^{28})$, —$N(R^{20})$—$S(=O)_2$—$R^{20}$, cycloalkyl, aryl, heteroaryl or heterocyclyl;

wherein said $C_{1-15}$ alkyl, $C_{1-4}$ alkoxy, cycloalkyl aryl, heteroaryl or heterocyclyl are optionally substituted with one, two or three substituents independently selected from the group consisting of hydroxyl, $C_{1-15}$ alkyl, $C_{1-4}$ alkoxy, $C_{2-4}$ alkynyl, halo, —$NO_2$, cycloalkyl, aryl, heterocyclyl, heteroaryl, —$N(R^{20})(R^{22})$, —$C(O)$—$R^{20}$, —$C(O)$—$O$—$R^{20}$, —$C(O)$—$N(R^{20})(R^{22})$, —CN, oxo and —O—$R^{20}$;

wherein said $C_{1-15}$ alkyl, $C_{1-4}$ alkoxy, cycloalkyl, aryl, heterocyclyl or heteroaryl are optionally further substituted with one, two or three substituents independently selected from the group consisting of hydroxyl, halo, —$NO_2$, $C_{1-6}$ alkyl, $C_{1-4}$ alkoxy, aralkyl, cycloalkyl, aryl, heterocyclyl, heteroaryl, —$N(R^{20})(R^{22})$, —$C(O)$—$R^{20}$, —$C(O)$—$OR^{20}$, —$C(O)$—$N(R^{20})(R^{22})$, —CN, and —O—$R^{20}$; and wherein said $C_{1-6}$ alkyl, $C_{1-4}$ alkoxy, aralkyl, cycloalkyl, aryl, heterocyclyl or heteroaryl, are optionally further substituted with one, two or three substituents independently selected from the group consisting of hydroxyl, halo, —$NO_2$, —$CF_3$, —$N(R^{20})(R^{22})$, —$C(O)$—$R^{20}$, —$C(O)$—$O$—$R^{20}$, —$C(O)$—$N(R^{20})(R^{22})$, —CN, —$S(O)_2$—$R^{20}$ and —O—$R^{20}$;

each $R^3$ is independently selected from the group consisting of hydrogen, $C_{1-15}$ alkyl, cycloalkyl, aryl, heteroaryl and heterocyclyl;

wherein said $C_{1-15}$ alkyl is optionally substituted with one, two or three substituents independently selected from the group consisting of halo, —$NO_2$, cycloalkyl, aryl, heterocyclyl, heteroaryl, —$N(R^{20})(R^{22})$, —$C(O)$—$R^{20}$, —$C(O)$—$O$—$R^{20}$, —$C(O)$—$N(R^{20})(R^{22})$, —CN and —O—$R^{20}$;

wherein said cycloalkyl, aryl, heterocyclyl and heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —$N(R^{20})(R^{22})$, —$C(O)$—$R^{20}$, —$C(O)$—$OR^{20}$, —$C(O)$—$N(R^{20})(R^{22})$, —CN and —O—$R^{20}$; and wherein said $C_{1-6}$ alkyl, aralkyl, cycloalkyl, aryl, heterocyclyl and heteroaryl are optionally further substituted with one, two or three substituents independently selected from the group consisting of halo, —$NO_2$, —$N(R^{20})(R^{22})$, —$C(O)$—$R^{20}$, —$C(O)$—$O$—$R^{20}$, —$C(O)$—$N(R^{20})(R^{22})$, —CN and —O—$R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl; and wherein the $C_{1-15}$ alkyl, $C_{2-15}$ alkenyl, $C_{2-15}$ alkynyl, cycloalkyl, heterocyclyl, aryl or heteroaryl are optionally substituted with one, two or three substituents independently selected from the group consisting of hydroxyl, halo, $C_{1-4}$ alkyl, substituted amino, aminoacyl, —$NO_2$, —$SO_2R^{26}$, —CN, $C_{1-3}$ alkoxy, —$CF_3$, —$OCF_3$, —$OCH_2CF_3$, —$C(O)$—$NH_2$, aryl, cycloalkyl and heteroaryl;

wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, alkyl, aralkyl, aryl, aryloxy, aralkyloxy, substituted amino, aminoacyl, —$NO_2$, —$SO_2R^{26}$, —CN, $C_{1-3}$ alkoxy, —$CF_3$, —$OCF_3$, aryl, heteroaryl and cycloalkyl; and $R^{26}$ and $R^{28}$ are in each instance independently selected from the group consisting of hydrogen, $C_{1-15}$ alkyl, cycloalkyl, aryl and heteroaryl; and wherein the $C_{1-15}$ alkyl, cycloalkyl, aryl or heteroaryl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, hydrate, solvate, stereoisomer, tautomer, polymorph and/or prodrug thereof.

In some embodiments of Formula IVA, $R^2$ is $C_{1-15}$ alkyl. In many embodiments the alkyl moiety is further substituted with heteroaryl; wherein said heteroaryl is optionally further substituted with $C_{1-6}$ alkyl.

Exemplary $R^2$ moieties of Formula IVA include, but are not limited to,

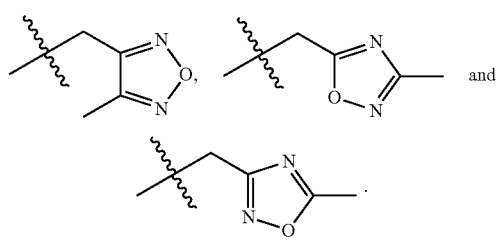

An exemplary $R^{10}$ moiety of Formula IVA includes —$OCF_3$.

Exemplary compounds of Formula IVA include 3-((4-methyl-1,2,5-oxadiazol-3-yl)methyl)-6-(4-(trifluoromethoxy)phenyl)quinazolin-4(3H)-one;

3-((3-methyl-1,2,4-oxadiazol-5-yl)methyl)-6-(4-(trifluoromethoxy)phenyl)quinazolin-4(3H)-one; and 3-((5-methyl-1,2,4-oxadiazol-3-yl)methyl)-6-(4-(trifluoromethoxy)phenyl)quinazolin-4(3H)-one;

or a pharmaceutically acceptable salt, ester, hydrate, solvate, stereoisomer, tautomer, polymorph and/or prodrug thereof.

In certain embodiments, the compound of Formula I is represented by Formula VA:

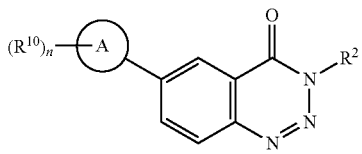

wherein:
A is heteroaryl;
n is 0, 1, 2, or 3;
$R^{10}$ is independently selected from the group consisting of halo, $-NO_2$, CN, $-SF_5$, $-Si(CH_3)_3$, $-O-R^{20}$, $-S-R^{20}$, $-C(O)-R^{20}$, $-C(O)-OR^{20}$, $-N(R^{20})(R^{22})$, $-C(O)-N(R^{20})(R^{22})$, $-N(R^{20})-C(O)-R^{22}$, $-N(R^{20})-S(=O)_2-R^{26}$, $-S(=O)_2-R^{20}$, $-S(=O)_2-N(R^{20})(R^{22})$, $C_{1-4}$ alkyl, $C_{2-4}$ alkenyl, $C_{2-4}$ alkynyl, cycloalkyl, aryl, heteroaryl and heterocyclyl; and wherein said $C_{1-4}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, $-NO_2$, aryl, heterocyclyl, heteroaryl, $C_{1-4}$ alkyl, cycloalkyl, $-N(R^{20})(R^{22})$, $-C(O)-R^{20}$, $-C(O)-OR^{20}$, $-C(O)-N(R^{20})(R^{22})$, $-CN$ and $-O-R^{20}$;

$R^2$ is selected from the group consisting of hydrogen, $C_{1-15}$ alkyl, $C_{1-4}$ alkoxy, $-C(O)-R^{26}$, $-C(O)-OR^{26}$, $-C(O)-N(R^{26})(R^{28})$, $-N(R^{20})-S(=O)_2-R^{20}$, cycloalkyl, aryl, heteroaryl or heterocyclyl;

wherein said $C_{1-15}$ alkyl, $C_{1-4}$ alkoxy, cycloalkyl aryl, heteroaryl or heterocyclyl are optionally substituted with one, two or three substituents independently selected from the group consisting of hydroxyl, $C_{1-15}$ alkyl, $C_{1-4}$ alkoxy, $C_{2-4}$ alkynyl, halo, $-NO_2$, cycloalkyl, aryl, heterocyclyl, heteroaryl, $-N(R^{20})(R^{22})$, $-C(O)-R^{20}$, $-C(O)-O-R^{20}$, $-C(O)-N(R^{20})(R^{22})$, $-CN$ oxo and $-O-R^{20}$;

wherein said $C_{1-15}$ alkyl, $C_{1-4}$ alkoxy, cycloalkyl, aryl, heterocyclyl or heteroaryl are optionally further substituted with one, two or three substituents independently selected from the group consisting of hydroxyl, halo, $-NO_2$, $C_{1-6}$ alkyl, $C_{1-4}$ alkoxy, aralkyl, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$, and $-O-R^{20}$; and wherein said $C_{1-6}$ alkyl, $C_{1-4}$ alkoxy, aralkyl, cycloalkyl, aryl, heterocyclyl or heteroaryl, are optionally further substituted with one, two or three substituents independently selected from the group consisting of hydroxyl, halo, $-NO_2$, $-CF_3$, $-N(R^{20})(R^{22})$, $-C(O)-R^{20}$, $-C(O)-O-R^{20}$, $-C(O)-N(R^{20})(R^{22})$, $-CN$, $-S(O)_2-R^{20}$ and $-O-R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl; and wherein the $C_{1-15}$ alkyl, $C_{2-15}$ alkenyl, $C_{2-15}$ alkynyl, cycloalkyl, heterocyclyl, aryl or heteroaryl are optionally substituted with one, two or three substituents independently selected from the group consisting of hydroxyl, halo, $C_{1-4}$ alkyl, substituted amino, aminoacyl, $-NO_2$, $-SO_2R^{26}$, $-CN$, $C_{1-3}$ alkoxy, $-CF_3$, $-OCF_3$, $-OCH_2CF_3$, $-C(O)-NH_2$, aryl, cycloalkyl and heteroaryl;

wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, alkyl, aralkyl, aryl, aryloxy, aralkyloxy, substituted amino, aminoacyl, $-NO_2$, $-SO_2R^{26}$, $-CN$, $C_{1-3}$ alkoxy, $-CF_3$, $-OCF_3$, aryl, heteroaryl and cycloalkyl; and $R^{26}$ and $R^{28}$ are in each instance independently selected from the group consisting of hydrogen, $C_{1-15}$ alkyl, cycloalkyl, aryl and heteroaryl; and wherein the $C_{1-15}$ alkyl, cycloalkyl, aryl or heteroaryl may be further substituted with from 1 to 3 substituents independently selected from the group consisting of hydroxyl, halo, $C_{1-4}$ alkoxy, $-CF_3$ and $-OCF_3$;

or a pharmaceutically acceptable salt, ester, hydrate, solvate, stereoisomer, tautomer, polymorph and/or prodrug thereof.

In some embodiments of Formula VA, A is selected from the group consisting of pyridin-3-yl and pyrimidin-5-yl.

In some embodiments of Formula VA, n is 1.

In some embodiments of Formula VA, $R^2$ is hydrogen or $C_{1-15}$ alkyl. In many embodiments the alkyl moiety is further substituted with heteroaryl; wherein said heteroaryl is optionally further substituted with one, two or three substituents independently selected from the group consisting of heteroaryl and $-O-R^{20}$; wherein said heteroaryl is optionally further substituted with $C_{1-6}$ alkyl; and $R^{20}$ is heteroaryl.

Exemplary $R^2$ moieties of Formula VA include, but are not limited to,

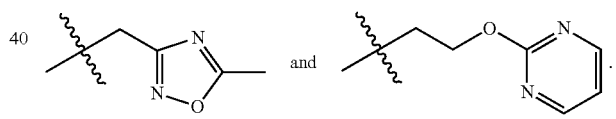

In some embodiments of Formula VA, $R^2$ is $-N(R^{20})(R^{22})$, $-O-R^{20}$, $C_{1-4}$ alkyl or heteroaryl; wherein $R^{20}$ and $R^{22}$ are in each instance independently $C_{1-15}$ alkyl, and the $C_{1-15}$ alkyl is optionally substituted with one, two or three halo; or $R^{20}$ and $R^{22}$ are attached to a common nitrogen atom $R^{20}$ and $R^{22}$ may join to form a heterocyclic ring. In many embodiments the $C_{1-15}$ alkyl or heteroaryl moiety of $R^2$ is further substituted with one, two or three substituents independently selected from the group consisting of halo, and $C_{1-6}$ alkyl.

Exemplary $R^{10}$ moieties of Formula VA include 2,2,2-trifluoroethoxy, $-CF_3$ and piperidin-1-yl.

Exemplary compounds of Formula VA include
3-((5-methyl-1,2,4-oxadiazol-3-yl)methyl)-6-(6-(2,2,2-trifluoroethoxy)pyridin-3-yl)benzo[d][1,2,3]triazin-4(3H)-one;
3-(2-(pyrimidin-2-yloxy)ethyl)-6-(6-(trifluoromethyl)pyridin-3-yl)benzo[d][1,2,3]triazin-4(3H)-one; and
6-(2-(piperidin-1-yl)pyrimidin-5-yl)-3-(2-(pyrimidin-2-yloxy)ethyl)benzo[d][1,2,3]triazin-4(3H)-one;
or a pharmaceutically acceptable salt, ester, hydrate, solvate, stereoisomer, tautomer, polymorph and/or prodrug thereof.

In certain embodiments, the compound of Formula I is represented by Formula VIA:

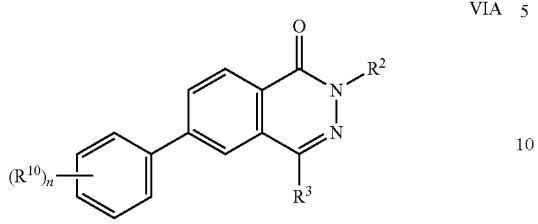

wherein:
n is 0, 1, 2, or 3;
$R^{10}$ is independently selected from the group consisting of halo, —$NO_2$, CN, —$SF_5$, —$Si(CH_3)_3$, —O—$R^{20}$, —S—$R^{20}$, —C(O)—$R^{20}$, —C(O)—$OR^{20}$, —$N(R^{20})(R^{22})$, —C(O)—$N(R^{20})(R^{22})$, —$N(R^{20})$—C(O)—$R^{22}$, —$N(R^{20})$—S(=O)$_2$—$R^{26}$, —S(=O)$_2$—$R^{20}$, —S(=O)$_2$—$N(R^{20})(R^{22})$, $C_{1-4}$ alkyl, $C_{2-4}$ alkenyl, $C_{2-4}$ alkynyl, cycloalkyl, aryl, heteroaryl and heterocyclyl; and wherein said $C_{1-4}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, aryl, heterocyclyl, heteroaryl, $C_{1-4}$ alkyl, cycloalkyl, —$N(R^{20})(R^{22})$, —C(O)—$R^{20}$, —C(O)—$OR^{20}$, —C(O)—$N(R^{20})(R^{22})$, —CN and —O—$R^{20}$;

$R^2$ is selected from the group consisting of hydrogen, $C_{1-15}$ alkyl, $C_{1-4}$ alkoxy, —C(O)—$R^{26}$, —C(O)—$OR^{26}$, —C(O)—$N(R^{26})(R^{28})$, —$N(R^{20})$—S(=O)$_2$—$R^{20}$, cycloalkyl, aryl, heteroaryl or heterocyclyl;

wherein said $C_{1-15}$ alkyl, $C_{1-4}$ alkoxy, cycloalkyl aryl, heteroaryl or heterocyclyl are optionally substituted with one, two or three substituents independently selected from the group consisting of hydroxyl, $C_{1-15}$ alkyl, $C_{1-4}$ alkoxy, $C_{2-4}$ alkynyl, halo, —$NO_2$, cycloalkyl, aryl, heterocyclyl, heteroaryl, —$N(R^{20})(R^{22})$, —C(O)—$R^{20}$, —C(O)—O—$R^{20}$, —C(O)—$N(R^{20})(R^{22})$, —CN, oxo and —O—$R^{20}$;

wherein said $C_{1-15}$ alkyl, $C_{1-4}$ alkoxy, cycloalkyl, aryl, heterocyclyl or heteroaryl are optionally further substituted with one, two or three substituents independently selected from the group consisting of hydroxyl, halo, —$NO_2$, $C_{1-6}$ alkyl, $C_{1-4}$ alkoxy, aralkyl, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN, and —O—$R^{20}$; and wherein said $C_{1-6}$ alkyl, $C_{1-4}$ alkoxy, aralkyl, cycloalkyl, aryl, heterocyclyl or heteroaryl, are optionally further substituted with one, two or three substituents independently selected from the group consisting of hydroxyl, halo, —$NO_2$, —$CF_3$, —$N(R^{20})(R^{22})$, —C(O)—$R^{20}$, —C(O)—O—$R^{20}$, —C(O)—$N(R^{20})(R^{22})$, —CN, —S(O)$_2$—$R^{20}$ and —O—$R^{20}$;

each $R^3$ is independently selected from the group consisting of hydrogen, $C_{1-15}$ alkyl, cycloalkyl, aryl, heteroaryl and heterocyclyl;
wherein said $C_{1-15}$ alkyl is optionally substituted with one, two or three substituents independently selected from the group consisting of halo, —$NO_2$, cycloalkyl, aryl, heterocyclyl, heteroaryl, —$N(R^{20})(R^{22})$, —C(O)—$R^{20}$, —C(O)—O—$R^{20}$, —C(O)—$N(R^{20})(R^{22})$, —CN and —O—$R^{20}$;

wherein said cycloalkyl, aryl, heterocyclyl and heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$; and wherein said $C_{1-6}$ alkyl, aralkyl, cycloalkyl, aryl, heterocyclyl and heteroaryl are optionally further substituted with one, two or three substituents independently selected from the group consisting of halo, —$NO_2$, —$N(R^{20})(R^{22})$, —C(O)—$R^{20}$, —C(O)—O—$R^{20}$, —C(O)—N$(R^{20})(R^{22})$, —CN and —O—$R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl; and wherein the $C_{1-15}$ alkyl, $C_{2-15}$ alkenyl, $C_{2-15}$ alkynyl, cycloalkyl, heterocyclyl, aryl or heteroaryl are optionally substituted with one, two or three substituents independently selected from the group consisting of hydroxyl, halo, $C_{1-4}$ alkyl, substituted amino, aminoacyl, —$NO_2$, —$SO_2R^{26}$, —CN, $C_{1-3}$ alkoxy, —$CF_3$, —$OCF_3$, —$OCH_2CF_3$, —C(O)—$NH_2$, aryl, cycloalkyl and heteroaryl;

wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, alkyl, aralkyl, aryl, aryloxy, aralkyloxy, substituted amino, aminoacyl, —$NO_2$, —$SO_2R^{26}$, —CN, $C_{1-3}$ alkoxy, —$CF_3$, —$OCF_3$, aryl, heteroaryl and cycloalkyl; and $R^{26}$ and $R^{28}$ are in each instance independently selected from the group consisting of hydrogen, $C_{1-15}$ alkyl, cycloalkyl, aryl and heteroaryl; and
wherein the $C_{1-15}$ alkyl, cycloalkyl, aryl or heteroaryl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, hydrate, solvate, stereoisomer, tautomer, polymorph and/or prodrug thereof.

In some embodiments of Formula VIA, $R^2$ is hydrogen. An exemplary $R^{10}$ moiety of Formula VIA includes —$OCF_3$.

In some embodiments of Formula VIA, $R^3$ is $C_{1-15}$ alkyl. An exemplary $R^3$ moiety of Formula VI includes methyl.

An exemplary compound of Formula VIA includes 4-methyl-6-(4-(trifluoromethoxy)phenyl)phthalazin-1(2H)-one;
or a pharmaceutically acceptable salt, ester, hydrate, solvate, stereoisomer, tautomer, polymorph and/or prodrug thereof.

In certain embodiments, the compound of Formula I is represented by Formula VIIA:

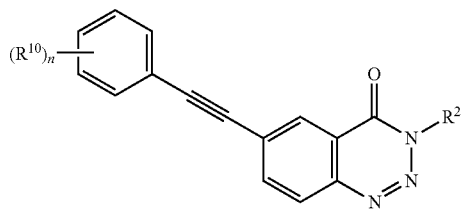

wherein:
n is 0, 1, 2, or 3;
R$^{10}$ is independently selected from the group consisting of halo, —NO$_2$, CN, —SF$_5$, —Si(CH$_3$)$_3$, —O—R$^{20}$, —S—R$^{20}$, —C(O)—R$^{20}$, —C(O)—OR$^{20}$, —N(R$^{20}$)(R$^{22}$), —C(O)—N(R$^{20}$)(R$^{22}$), —N(R$^{20}$)—C(O)—R$^{22}$, —N(R$^{20}$)—S(=O)$_2$—R$^{26}$, —S(=O)$_2$—R$^{20}$, —S(=O)$_2$—N(R$^{20}$)(R$^{22}$), C$_{1-4}$ alkyl, C$_{2-4}$ alkenyl, C$_{2-4}$ alkynyl, cycloalkyl, aryl, heteroaryl and heterocyclyl; and
wherein said C$_{1-4}$ alkyl, C$_{2-4}$ alkenyl, C$_{2-4}$ alkynyl, cycloalkyl, aryl, heteroaryl or heterocyclyl are optionally substituted with one, two or three substituents independently selected from the group consisting of halo, —NO$_2$, aryl, heterocyclyl, heteroaryl, C$_{1-4}$ alkyl, cycloalkyl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

R$^2$ is selected from the group consisting of hydrogen, C$_{1-15}$ alkyl, C$_{1-4}$ alkoxy, —C(O)—R$^{26}$, —C(O)—OR$^{26}$, —C(O)—N(R$^{26}$)(R$^{28}$), —N(R$^{20}$)—S(=O)$_2$—R$^{20}$, cycloalkyl, aryl, heteroaryl or heterocyclyl;
wherein said C$_{1-15}$ alkyl, C$_{1-4}$ alkoxy, cycloalkyl aryl, heteroaryl or heterocyclyl are optionally substituted with one, two or three substituents independently selected from the group consisting of hydroxyl, C$_{1-15}$ alkyl, C$_{1-4}$ alkoxy, C$_{2-4}$ alkynyl, halo, —NO$_2$, cycloalkyl, aryl, heterocyclyl, heteroaryl, —N(R$^{20}$)(R$^{22}$), —C(O)—R$^{20}$, —C(O)—O—R$^{20}$, —C(O)—N(R$^{20}$)(R$^{22}$), —CN, oxo and —O—R$^{20}$;
wherein said C$_{1-15}$ alkyl, C$_{1-4}$ alkoxy, cycloalkyl, aryl, heterocyclyl or heteroaryl are optionally further substituted with one, two or three substituents independently selected from the group consisting of hydroxyl, halo, —NO$_2$, C$_{1-6}$ alkyl, C$_{1-4}$ alkoxy, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN, and —O—R$^{20}$; and
wherein said C$_{1-6}$ alkyl, C$_{1-4}$ alkoxy, aralkyl, cycloalkyl, aryl, heterocyclyl or heteroaryl, are optionally further substituted with one, two or three substituents independently selected from the group consisting of hydroxyl, halo, —NO$_2$, —CF$_3$, —N(R$^{20}$)(R$^{22}$), —C(O)—R$^{20}$, —C(O)—O—R$^{20}$, —C(O)—N(R$^{20}$)(R$^{22}$), —CN, —S(O)$_2$—R$^{20}$ and —O—R$^{20}$;

R$^{20}$ and R$^{22}$ are in each instance independently selected from the group consisting of hydrogen, C$_{1-15}$ alkyl, C$_{2-15}$ alkenyl, C$_{2-15}$ alkynyl, cycloalkyl, heterocyclyl, aryl and heteroaryl; and
wherein the C$_{1-15}$ alkyl, C$_{2-15}$ alkenyl, C$_{2-15}$ alkynyl, cycloalkyl, heterocyclyl, aryl or heteroaryl are optionally substituted with one, two or three substituents independently selected from the group consisting of hydroxyl, halo, C$_{1-4}$ alkyl, substituted amino, aminoacyl, —NO$_2$, —SO$_2$R$^{26}$, —CN, C$_{1-3}$ alkoxy, —CF$_3$, —OCF$_3$, —OCH$_2$CF$_3$, —C(O)—NH$_2$, aryl, cycloalkyl and heteroaryl;
wherein said heteroaryl is optionally further substituted with C$_{1-4}$ alkyl or cycloalkyl; or
when R$^{20}$ and R$^{22}$ are attached to a common nitrogen atom R$^{20}$ and R$^{22}$ may join to form a heterocyclic or heteroaryl ring which is then optionally substituted with one, two or three substituents independently selected from the group consisting of hydroxyl, halo, alkyl, aralkyl, aryl, aryloxy, aralkyloxy, substituted amino, aminoacyl, —NO$_2$, —SO$_2$R$^{26}$, —CN, C$_{1-3}$ alkoxy, —CF$_3$, —OCF$_3$, aryl, heteroaryl and cycloalkyl; and
R$^{26}$ and R$^{28}$ are in each instance independently selected from the group consisting of hydrogen, C$_{1-15}$ alkyl, cycloalkyl, aryl and heteroaryl; and
wherein the C$_{1-15}$ alkyl, cycloalkyl, aryl or heteroaryl may be further substituted with from 1 to 3 substituents independently selected from the group consisting of hydroxyl, halo, C$_{1-4}$ alkoxy, —CF$_3$ and —OCF$_3$;
or a pharmaceutically acceptable salt, ester, hydrate, solvate, stereoisomer, tautomer, polymorph and/or prodrug thereof.

In some embodiments of Formula VIIA, R$^2$ is C$_{1-15}$ alkyl. In many embodiments the alkyl moiety is further substituted with with —O—R$^{20}$; wherein R$^{20}$ is heteroaryl.

An exemplary R$^2$ moiety of Formula VIIA includes

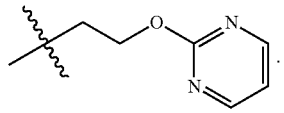

An exemplary R$^{10}$ moiety of Formula VIIA includes —OCF$_3$.

An exemplary compound of Formula VIIA includes 3-(2-(pyrimidin-2-yloxy)ethyl)-6-((4-(trifluoromethoxy)phenyl)ethynyl)benzo[d][1,2,3]triazin-4(3H)-one;
or a pharmaceutically acceptable salt, ester, hydrate, solvate, stereoisomer, tautomer, polymorph and/or prodrug thereof.

In certain embodiments, the compound of Formula I is represented by Formula VIIIA:

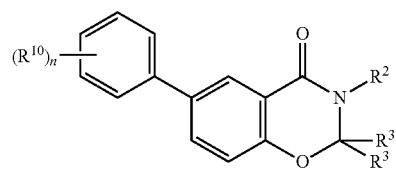

wherein:
n is 1, 2 or 3:
R$^{10}$ is independently selected from the group consisting of halo, —NO$_2$, CN, —SF$_5$, —Si(CH$_3$)$_3$, —O—R$^{20}$, —S—R$^{20}$, —C(O)—R$^{20}$, —C(O)—OR$^{20}$, —N(R$^{20}$)(R$^{22}$), —C(O)—N(R$^{20}$)(R$^{22}$), —N(R$^{20}$)—C(O)—R$^{22}$, —N(R$^{20}$)—S(=O)$_2$—R$^{26}$, —S(=O)$_2$—R$^{20}$, —S(=O)₂—N(R²⁰)(R²²), C₁₋₄ alkyl, C₂₋₄ alkenyl, C₂₋₄ alkynyl, cycloalkyl, aryl, heteroaryl and heterocyclyl; and wherein said C₁₋₄ alkyl, C₂₋₄ alkenyl, C₂₋₄ alkynyl, cycloalkyl, aryl, heteroaryl or heterocyclyl are optionally substituted with one, two or three substituents independently selected from the group consisting of halo, —NO₂, aryl, heterocyclyl, heteroaryl, C₁₋₄ alkyl, cycloalkyl, —N(R²⁰)(R²²), —C(O)—R²⁰, —C(O)—OR²⁰, —C(O)—N(R²⁰)(R²²), —CN and —O—R²⁰;

R² is selected from the group consisting of hydrogen, C₁₋₁₅ alkyl, C₁₋₄ alkoxy, —C(O)—R²⁶, —C(O)—OR²⁶, —C(O)—N(R²⁶)(R²⁸), —N(R²⁰)—S(=O)₂—R²⁰, cycloalkyl, aryl, heteroaryl or heterocyclyl;

wherein said C₁₋₁₅ alkyl, C₁₋₄ alkoxy, cycloalkyl aryl, heteroaryl or heterocyclyl are optionally substituted with one, two or three substituents independently selected from the group consisting of hydroxyl, C₁₋₁₅ alkyl, C₁₋₄ alkoxy, C₂₋₄ alkynyl, halo, —NO₂, cycloalkyl, aryl, heterocyclyl, heteroaryl, —N(R²⁰)(R²²), —C(O)—R²⁰, —C(O)—O—R²⁰, —C(O)—N(R²⁰)(R²²), —CN, oxo and —O—R²⁰;

wherein said C₁₋₁₅ alkyl, C₁₋₄ alkoxy, cycloalkyl, aryl, heterocyclyl or heteroaryl are optionally further substituted with one, two or three substituents independently selected from the group consisting of hydroxyl, halo, —NO₂, C₁₋₆ alkyl, C₁₋₄ alkoxy, aralkyl, cycloalkyl, aryl, heterocyclyl, heteroaryl, —N(R²⁰)(R²²), —C(O)—R²⁰, —C(O)—OR²⁰, —C(O)—N(R²⁰)(R²²), —CN, and —O—R²⁰; and wherein said C₁₋₆ alkyl, C₁₋₄ alkoxy, aralkyl, cycloalkyl, aryl, heterocyclyl or heteroaryl, are optionally further substituted with one, two or three substituents independently selected from the group consisting of hydroxyl, halo, —NO₂, —CF₃, —N(R²⁰)(R²²), —C(O)—R²⁰, —C(O)—O—R²⁰, —C(O)—N(R²⁰)(R²²), —CN, —S(O)₂—R²⁰ and —O—R²⁰;

each R³ is independently selected from the group consisting of hydrogen, C₁₋₁₅ alkyl, cycloalkyl, aryl, heteroaryl and heterocyclyl;

wherein said C₁₋₁₅ alkyl is optionally substituted with one, two or three substituents independently selected from the group consisting of halo, —NO₂, cycloalkyl, aryl, heterocyclyl, heteroaryl, —N(R²⁰)(R²²), —C(O)—R²⁰, —C(O)—O—R²⁰, —C(O)—N(R²⁰)(R²²), —CN and —O—R²⁰;

wherein said cycloalkyl, aryl, heterocyclyl and heteroaryl are optionally further substituted with one, two or three substituents independently selected from the group consisting of halo, —NO₂, C₁₋₆ alkyl, aralkyl, cycloalkyl, aryl, heterocyclyl, heteroaryl, —N(R²⁰)(R²²), —C(O)—R²⁰, —C(O)—OR²⁰, —C(O)—N(R²⁰)(R²²), —CN and —O—R²⁰; and wherein said C₁₋₆ alkyl, aralkyl, cycloalkyl, aryl, heterocyclyl and heteroaryl are optionally further substituted with one, two or three substituents independently selected from the group consisting of halo, —NO₂, —N(R²⁰)(R²²), —C(O)—R²⁰, —C(O)—O—R²⁰, —C(O)—N(R²⁰)(R²²), —CN and —O—R²⁰;

or two R³ can join together with the with the carbon atom to which they are attached to form a cycloalkyl or heterocyclyl;

R²⁰ and R²² are in each instance independently selected from the group consisting of hydrogen, C₁₋₁₅ alkyl, C₂₋₁₅ alkenyl, C₂₋₁₅ alkynyl, cycloalkyl, heterocyclyl, aryl and heteroaryl; and wherein the C₁₋₁₅ alkyl, C₂₋₁₅ alkenyl, C₂₋₁₅ alkynyl, cycloalkyl, heterocyclyl, aryl or heteroaryl are optionally substituted with one, two or three substituents independently selected from the group consisting of hydroxyl, halo, C₁₋₄ alkyl, substituted amino, aminoacyl, —NO₂, —SO₂R²⁶, —CN, C₁₋₃ alkoxy, —CF₃, —OCF₃, —OCH₂CF₃, —C(O)—NH₂, aryl, cycloalkyl and heteroaryl;

wherein said heteroaryl is optionally further substituted with C₁₋₄ alkyl or cycloalkyl; or when R²⁰ and R²² are attached to a common nitrogen atom R²⁰ and R²² may join to form a heterocyclic or heteroaryl ring which is then optionally substituted with one, two or three substituents independently selected from the group consisting of hydroxyl, halo, alkyl, aralkyl, aryl, aryloxy, aralkyloxy, substituted amino, aminoacyl, —NO₂, —SO₂R²⁶, —CN, C₁₋₃ alkoxy, —CF₃, —OCF₃, aryl, heteroaryl and cycloalkyl; and R²⁶ and R²⁸ are in each instance independently selected from the group consisting of hydrogen, C₁₋₁₅ alkyl, cycloalkyl, aryl and heteroaryl; and wherein the C₁₋₁₅ alkyl, cycloalkyl, aryl or heteroaryl may be further substituted with from 1 to 3 substituents independently selected from the group consisting of hydroxyl, halo, C₁₋₄ alkoxy, —CF₃ and —OCF₃;

or a pharmaceutically acceptable salt, ester, hydrate, solvate, stereoisomer, tautomer, polymorph and/or prodrug thereof.

In some embodiments of Formula VIIA, R² is C₁₋₁₅ alkyl; wherein said alkyl is optionally substituted with heteroaryl;

or a pharmaceutically acceptable salt, ester, hydrate, solvate, stereoisomer, tautomer, polymorph and/or prodrug thereof.

Exemplary R² moieties of Formula VIIA include

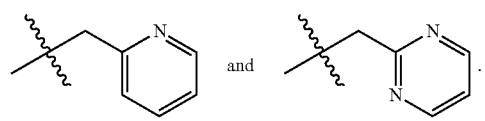

Exemplary R¹⁰ moieties of Formula VIIA include hydrogen, —CF₃ and —OCF₃.

Exemplary compounds of Formula VIIIA include
3-(pyridin-2-ylmethyl)-6-(4-(trifluoromethyl)phenyl)-2H-benzo[e][1,3]oxazin-4(3H)-one;
3-(pyridin-2-ylmethyl)-6-(4-(trifluoromethoxy)phenyl)-2H-benzo[e][1,3]oxazin-4(3H)-one;
2-methyl-3-(pyrimidin-2-ylmethyl)-6-(4-(trifluoromethoxy)phenyl)-2H-benzo[e][1,3]oxazin-4(3H)-one; and
2,2-dimethyl-3-(pyridin-2-ylmethyl)-6-(4-(trifluoromethoxy)phenyl)-2H-benzo[e][1,3]oxazin-4(3H)-one;
or a pharmaceutically acceptable salt, ester, hydrate, solvate, stereoisomer, tautomer, polymorph and/or prodrug thereof.

In certain embodiments, the compound of Formula I is represented by Formula IXA:

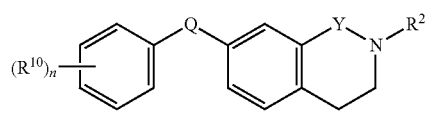

wherein:
n is 1, 2 or 3:
R¹⁰ is independently selected from the group consisting of halo, —NO₂, CN, —SF₅, —Si(CH₃)₃, —O—R²⁰, —S—R²⁰, —C(O)—R²⁰, —C(O)—OR²⁰, —N(R²⁰)(R²²), —C(O)—N(R²⁰)(R²²), —N(R²⁰)—C(O)—R²², —N(R²⁰)—S(=O)₂—R²⁶, —S(=O)₂—R²⁰, —S(=O)₂—N(R²⁰)(R²²), C₁₋₄ alkyl, C₂₋₄ alkenyl, C₂₋₄ alkynyl, cycloalkyl, aryl, heteroaryl and heterocyclyl; and wherein said C₁₋₄ alkyl, C₂₋₄ alkenyl, C₂₋₄ alkynyl, cycloalkyl, aryl, heteroaryl or heterocyclyl are optionally substituted with one, two or three substituents independently selected from the group consisting of halo, —NO₂, aryl, heterocyclyl, heteroaryl, C₁₋₄ alkyl, cycloalkyl, —N(R²⁰)(R²²), —C(O)—R²⁰, —C(O)—OR²⁰, —C(O)—N(R²⁰)(R²²), —CN and —O—R²⁰;

R² is selected from the group consisting of —C(O)—R²⁶, —C(O)—OR²⁶ and —C(O)—N(R²⁶)(R²⁸);

Q is selected from the group consisting of a covalent bond and C₂₋₄ alkynylene;

Y is selected from the group consisting of —C(R⁵)₂— and —C(O);

each R⁵ is independently selected from the group consisting of hydrogen and C₁₋₁₅ alkyl;

R²⁰ and R²² are in each instance independently selected from the group consisting of hydrogen, C₁₋₁₅ alkyl, C₂₋₁₅ alkenyl, C₂₋₁₅ alkynyl, cycloalkyl, heterocyclyl, aryl and heteroaryl; and wherein the C₁₋₁₅ alkyl, C₂₋₁₅ alkenyl, C₂₋₁₅ alkynyl, cycloalkyl, heterocyclyl, aryl or heteroaryl are optionally substituted with one, two or three substituents independently selected from the group consisting of hydroxyl, halo, C₁₋₄ alkyl, substituted amino, aminoacyl, —NO₂, —SO₂R²⁶, —CN, C₁₋₃ alkoxy, —CF₃, —OCF₃, —OCH₂CF₃, —C(O)—NH₂, aryl, cycloalkyl and heteroaryl;

wherein said heteroaryl is optionally further substituted with C₁₋₄ alkyl or cycloalkyl; or when R²⁰ and R²² are attached to a common nitrogen atom R²⁰ and R²² may join to form a heterocyclic or heteroaryl ring which is then optionally substituted with one, two or three substituents independently selected from the group consisting of hydroxyl, halo, C₁₋₄ alkyl, aralkyl, aryl, aryloxy, aralkyloxy, substituted amino, aminoacyl, —NO₂, —SO₂R²⁶, —CN, C₁₋₃ alkoxy, —CF₃, —OCF₃, aryl, heteroaryl and cycloalkyl; and R²⁶ and R²⁸ are in each instance independently selected from the group consisting of hydrogen, C₁₋₁₅ alkyl, cycloalkyl, aryl and heteroaryl; and wherein the C₁₋₁₅ alkyl, cycloalkyl, aryl or heteroaryl may be further substituted with from 1 to 3 substituents independently selected from the group consisting of hydroxyl, halo, C₁₋₄ alkoxy, —CF₃ and —OCF₃;

or a pharmaceutically acceptable salt, ester, hydrate, solvate, stereoisomer, tautomer, polymorph and/or prodrug thereof.

In some embodiments of Formula IXA, R² is C₁₋₁₅ alkyl; wherein said alkyl is optionally substituted with heteroaryl;

or a pharmaceutically acceptable salt, ester, hydrate, solvate, stereoisomer, tautomer, polymorph and/or prodrug thereof.

Exemplary R² moieties of Formula IXA include

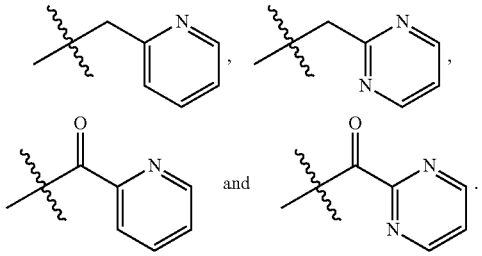

Exemplary R¹⁰ moieties of Formula IXA include hydrogen, —CF₃ and —OCF₃.

Exemplary compounds of Formula IXA include
2-(pyrimidin-2-ylmethyl)-7-(4-(trifluoromethoxy)phenyl)-3,4-dihydroisoquinolin-1(2H)-one;
2-(pyridin-2-ylmethyl)-7-(4-(trifluoromethoxy)phenyl)-3,4-dihydroisoquinolin-1(2H)-one;
2-(pyrimidin-2-ylmethyl)-7-(4-(trifluoromethyl)phenyl)-3,4-dihydroisoquinolin-1(2H)-one;
2-(pyrimidin-2-ylmethyl)-7-((4-(trifluoromethyl)phenyl)ethynyl)-3,4-dihydroisoquinolin-1(2H)-one;
2-(pyrimidin-2-ylmethyl)-7-((4-(trifluoromethoxy)phenyl)ethynyl)-3,4-dihydroisoquinolin-1(2H)-one;
pyridin-2-yl(7-(4-(trifluoromethyl)phenyl)-3,4-dihydroisoquinolin-2(1H)-yl)methanone; or
pyrimidin-2-yl(7-(4-(trifluoromethyl)phenyl)-3,4-dihydroisoquinolin-2(1H)-yl)methanone;
or a pharmaceutically acceptable salt, ester, hydrate, solvate, stereoisomer, tautomer, polymorph and/or prodrug thereof.

In one embodiment, at least one of the substituents (i.e., at least one of R¹, R², R³ is not hydrogen.

In other embodiments, the present disclosure provides compounds of Formula IB:

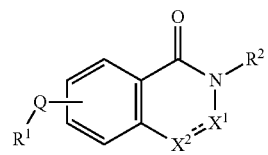

wherein:
the dotted line represents an optional double bond;
R¹ is aryl or heteroaryl;
wherein said aryl or heteroaryl are optionally substituted with one, two, or three substituents independently selected from the group consisting of halo, —NO₂, CN, —SF₅, —Si(CH₃)₃, —O—CF₃, —O—R²⁰, —S—R²⁰, —C(O)—R²⁰, C(O)OH, —N(R²⁰)(R²²), —C(O)—N(R²⁰)(R²²), —N(R²⁰)—C(O)—R²², —N(R²⁰)—S(=O)₂—R²⁶, —S(=O)₂—R²⁰, —S(=O)₂—N(R²⁰)

($R^{22}$), $C_{1-4}$ alkyl, $C_{2-4}$ alkenyl, $C_{2-4}$ alkynyl, cycloalkyl, aryl, heteroaryl, and heterocyclyl; and wherein said alkyl, alkenyl, alkynyl, aryl, heteroaryl, cycloalkyl, or heterocyclyl are optionally substituted with one, two, or three substituents independently selected from the group consisting of halo, —$NO_2$, —O—$CF_3$, —O—$CHF_2$, phenyl, heterocyclyl, heteroaryl, $C_{1-4}$ alkyl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$;

$R^2$ is hydrogen, $C_{1-15}$ alkyl, $C_{1-4}$ alkoxy, —C(O)—O—$R^{26}$, —C(O)—N($R^{26}$)($R^{28}$), —N($R^{20}$)—S(=O)$_2$—$R^{20}$, cycloalkyl, aryl, heteroaryl, or heterocyclyl;

wherein said alkyl, alkoxy, cycloalkyl, and heterocyclyl are optionally substituted with one, two, or three substituents independently selected from the group consisting of hydroxyl, alkyl, alkoxy, alkynyl, halo, —$NO_2$, —O—$CF_3$, —O—$CHF_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, oxo, and —O—$R^{20}$;

wherein said alkyl, alkoxy, cycloalkyl, aryl, heterocyclyl, or heteroaryl are optionally further substituted with one, two, or three substituents independently selected from the group consisting of hydroxyl, halo, —$NO_2$, —$CF_3$, —O—$CF_3$, $C_{1-6}$ alkyl, $C_{1-4}$ alkoxy, benzyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$; and wherein said $C_{1-6}$ alkyl, $C_{1-4}$ alkoxy, benzyl, aryl, heterocyclyl, heteroaryl, cycloalkyl, are optionally further substituted with one, two, or three substituents independently selected from the group consisting of hydroxyl, halo, —$NO_2$, —O—$CF_3$, —$CF_3$, —O—$CHF_2$, —N($R^{20}$)($R^{22}$), —C(O)—$R^{20}$, —C(O)—O—$R^{20}$, —C(O)—N($R^{20}$)($R^{22}$), —CN, —S(O)$_2$—$R^{20}$ and —O—$R^{20}$;

Q is a covalent bond or $C_{2-4}$ alkynylene;

$X^1$ is N and $X^2$ is N, $X^1$ is N and $X^2$ is $CR^3$, or $X^1$ is $CH_2$ and $X^2$ is $NR^4$;

$R^3$ is hydrogen, $C_{1-15}$ alkyl, $C_{1-4}$ alkoxy, cycloalkyl, aryl, heteroaryl, or heterocyclyl;

wherein said alkyl is optionally substituted with one, two, or three substituents independently selected from the group consisting of halo, —$NO_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$;

wherein said cycloalkyl, aryl, heterocyclyl, or heteroaryl are optionally further substituted with one, two, or three substituents independently selected from the group consisting of halo, —$NO_2$, $C_{1-6}$ alkyl, benzyl, aryl, heterocyclyl, heteroaryl, cycloalkyl, —N($R^{20}$)($R^{22}$), —C(O)—$R^{20}$, —C(O)—O$R^{20}$, —C(O)—N($R^{20}$)($R^{22}$), —CN, and —O—$R^{20}$; and wherein said $C_{1-6}$ alkyl, benzyl, aryl, heterocyclyl, heteroaryl, cycloalkyl, are optionally further substituted with one, two, or three substituents independently selected from the group consisting of halo, —$NO_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$;

$R^4$ is hydrogen, $C_{1-15}$ alkyl, $C_{1-4}$ alkoxy, —C(O)—O—$R^{26}$, —C(O)—N($R^{26}$)($R^{28}$), —N($R^{20}$)—S(=O)$_2$—$R^{20}$, cycloalkyl, aryl, heteroaryl, or heterocyclyl;

wherein said alkyl is optionally substituted with one, two, or three substituents independently selected from the group consisting of halo, —$NO_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$;

wherein said cycloalkyl, aryl, heterocyclyl, or heteroaryl are optionally further substituted with one, two, or three substituents independently selected from the group consisting of halo, —$NO_2$, $C_{1-6}$ alkyl, benzyl, aryl, heterocyclyl, heteroaryl, cycloalkyl, —N($R^{20}$)($R^{22}$), —C(O)—$R^{20}$, —C(O)—O$R^{20}$, —C(O)—N($R^{20}$)($R^{22}$), —CN, and —O—$R^{20}$; and wherein said $C_{1-6}$ alkyl, benzyl, aryl, heterocyclyl, heteroaryl, cycloalkyl, are optionally further substituted with one, two, or three substituents independently selected from the group consisting of halo, —$NO_2$, —N($R^{20}$)($R^{22}$), —N($R^{20}$)($R^{22}$), —C(O)—$R^{20}$, —C(O)—O—$R^{20}$, —C(O)—N($R^{20}$)($R^{22}$), —CN, and —O—$R^{20}$;

$R^{20}$ and $R^{22}$ are in each instance independently selected from the group consisting of hydrogen, $C_1$-$C_{15}$ alkyl, $C_2$-$C_{15}$ alkenyl, $C_2$-$C_{15}$ alkynyl, cycloalkyl, heterocyclyl, aryl, and heteroaryl; and wherein the alkyl, alkenyl, alkynyl, heterocyclyl, aryl, and heteroaryl are optionally substituted with one, two, or three substituents independently selected from the group consisting of hydroxyl, halo, $C_{1-4}$ alkyl, monoalkylamino, dialkylamino, alkyl amide, aryl amide, heteroaryl amide, —$NO_2$, —$SO_2R^{26}$, —CN, $C_{1-3}$ alkoxy, —$CF_3$, —$OCF_3$, —$OCH_2CF_3$, —C(O)—$NH_2$, aryl, cycloalkyl, and heteroaryl;

wherein said heteroaryl is optionally further substituted with $C_{1-4}$ alkyl, or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two, or three substituents independently selected from the group consisting of hydroxyl, halo, alkyl, benzyl, phenyl, phenoxy, benzyloxy, monoalkylamino, dialkylamino, alkyl amide, aryl amide, heteroaryl amide, —$NO_2$, —$SO_2R^{26}$, —CN, $C_{1-3}$ alkoxy, —$CF_3$, —$OCF_3$, aryl, heteroaryl and cycloalkyl;

$R^{25}$ is in each instance independently a covalent bond or $C_1$-$C_3$ alkylene optionally substituted with one or two $C_1$-$C_3$ alkyl groups; and $R^{26}$ and $R^{28}$ are in each instance independently selected from the group consisting of hydrogen, alkyl, and cycloalkyl; and wherein the alkyl, phenyl and cycloalkyl may be further substituted with from 1 to 3 substituents independently selected from the group consisting of hydroxyl, halo, $C_{1-4}$ alkoxy, —$CF_3$, and —$OCF_3$;

or a pharmaceutically acceptable salt, ester, hydrate, solvate, polymorph, and/or prodrug thereof.

In certain embodiments, the compound of formula TB is represented by Formula IC:

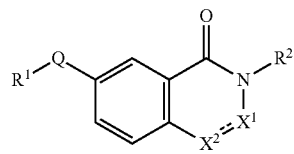

wherein:
the dotted line represents an optional double bond;
$R^1$ is aryl or heteroaryl;
  wherein said aryl or heteroaryl are optionally substituted with one, two, or three substituents independently selected from the group consisting of halo, —$NO_2$, CN, —$SF_5$, —$Si(CH_3)_3$, —O—$CF_3$, —O—$R^{20}$, —S—$R^{20}$, —C(O)—$R^{20}$, C(O)OH, —N($R_{20}$)($R_{22}$), —C(O)—N($R^{20}$)($R^{22}$), —N($R^{20}$)—C(O)—$R^{22}$, —N($R^{20}$)—S(=O)$_2$—$R^{26}$, —S(=O)$_2$—$R^{20}$, —S(=O)$_2$—N($R^{20}$)($R^{22}$), $C_{1-4}$ alkyl, $C_{2-4}$ alkenyl, $C_{2-4}$ alkynyl, cycloalkyl, aryl, heteroaryl, and heterocyclyl; and
  wherein said alkyl, alkenyl, alkynyl, aryl, heteroaryl, cycloalkyl, or heterocyclyl are optionally substituted with one, two, or three substituents independently selected from the group consisting of halo, —$NO_2$, —O—$CF_3$, —O—$CHF_2$, phenyl, heterocyclyl, heteroaryl, $C_{1-4}$ alkyl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$;
$R^2$ is hydrogen, $C_{1-15}$ alkyl, $C_{1-4}$ alkoxy, —C(O)—O—$R^{26}$, —C(O)—N($R^{26}$)($R^{28}$), —N($R^{20}$)—S(=O)$_2$—$R^{20}$, cycloalkyl, aryl, heteroaryl, or heterocyclyl;
  wherein said alkyl, alkoxy, cycloalkyl, and heterocyclyl are optionally substituted with one, two, or three substituents independently selected from the group consisting of hydroxyl, alkyl, alkoxy, alkynyl, halo, —$NO_2$, —O—$CF_3$, —O—$CHF_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, oxo, and —O—$R^{20}$;
  wherein said alkyl, alkoxy, cycloalkyl, aryl, heterocyclyl, or heteroaryl are optionally further substituted with one, two, or three substituents independently selected from the group consisting of hydroxyl, halo, —$NO_2$, —$CF_3$, —O—$CF_3$, $C_{1-6}$ alkyl, $C_{1-4}$ alkoxy, benzyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$; and
    wherein said $C_{1-6}$ alkyl, $C_{1-4}$ alkoxy, benzyl, aryl, heterocyclyl, heteroaryl, cycloalkyl, are optionally further substituted with one, two, or three substituents independently selected from the group consisting of hydroxyl, halo, —$NO_2$, —O—$CF_3$, —$CF_3$, —O—$CHF_2$, —N($R^{20}$)($R^{22}$), —C(O)—$R^{20}$, —C(O)—O—$R^{20}$, —C(O)—N($R^{20}$)($R^{22}$), —CN, —S(O)$_2$—$R^{20}$ and —O—$R^{20}$;
Q is a covalent bond or $C_{2-4}$ alkynylene;
$X^1$ is N and $X^2$ is N, $X^1$ is N and $X^2$ is $CR^3$, or $X^1$ is $CH_2$ and $X^2$ is $NR^4$;
$R^3$ is hydrogen, $C_{1-15}$ alkyl, $C_{1-4}$ alkoxy, cycloalkyl, aryl, heteroaryl, or heterocyclyl;
  wherein said alkyl is optionally substituted with one, two, or three substituents independently selected from the group consisting of halo, —$NO_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$;
  wherein said cycloalkyl, aryl, heterocyclyl, or heteroaryl are optionally further substituted with one, two, or three substituents independently selected from the group consisting of halo, —$NO_2$, $C_{1-6}$ alkyl, benzyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$ ($R^{22}$), —CN, and —O—$R^{20}$; and
  wherein said $C_{1-6}$ alkyl, benzyl, aryl, heterocyclyl, heteroaryl, cycloalkyl, are optionally further substituted with one, two, or three substituents independently selected from the group consisting of halo, —$NO_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$;
$R^4$ is hydrogen, $C_{1-15}$ alkyl, $C_{1-4}$ alkoxy, —C(O)—O—$R^{26}$, —C(O)—N($R^{26}$)($R^{28}$), —N($R^{20}$)—S(=O)$_2$—$R^{20}$, cycloalkyl, aryl, heteroaryl, or heterocyclyl;
  wherein said alkyl is optionally substituted with one, two, or three substituents independently selected from the group consisting of halo, —$NO_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$;
  wherein said cycloalkyl, aryl, heterocyclyl, or heteroaryl are optionally further substituted with one, two, or three substituents independently selected from the group consisting of hydroxyl, halo, —$NO_2$, $C_{1-6}$ alkyl, benzyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$; and
  wherein said $C_{1-6}$ alkyl, benzyl, aryl, heterocyclyl, heteroaryl, cycloalkyl, are optionally further substituted with one, two, or three substituents independently selected from the group consisting of halo, —$NO_2$, —N($R^{20}$)($R^{22}$), —C(O)—$R^{20}$, —C(O)—O—$R^{20}$, —C(O—N($R^{20}$ ($R^{22}$), —CN, and —O—$R^{20}$;
$R^{20}$ and $R^{22}$ are in each instance independently selected from the group consisting of hydrogen, $C_1$-$C_{15}$ alkyl, $C_2$-$C_{15}$ alkenyl, $C_2$-$C_{15}$ alkynyl, cycloalkyl, heterocyclyl, aryl, and heteroaryl; and
  wherein the alkyl, alkenyl, alkynyl, heterocyclyl, aryl, and heteroaryl are optionally substituted with one, two, or three substituents independently selected from the group consisting of hydroxyl, halo, $C_{1-4}$ alkyl, monoalkylamino, dialkylamino, alkyl amide, aryl amide, heteroaryl amide, —$NO_2$, —$SO_2R^{26}$, —CN, $C_{1-3}$ alkoxy, —$CF_3$, —$OCF_3$, —$OCH_2CF_3$, —C(O)—$NH_2$, aryl, cycloalkyl, and heteroaryl;
  wherein said heteroaryl is optionally further substituted with $C_{1-4}$ alkyl, or cycloalkyl; or
when $R^{20}$ and $R^{22}$ are attached to a common nitrogen atom $R^{20}$ and $R^{22}$ may join to form a heterocyclic or heteroaryl ring which is then optionally substituted with one, two, or three substituents independently selected from the group consisting of hydroxyl, halo, alkyl, benzyl, phenyl, phenoxy, benzyloxy, monoalkylamino, dialkylamino, alkyl amide, aryl amide, heteroaryl amide, —$NO_2$, —$SO_2R^{26}$, —CN, $C_{1-3}$ alkoxy, —$CF_3$, —$OCF_3$, aryl, heteroaryl and cycloalkyl;

R²⁵ is in each instance independently a covalent bond or C₁-C₃ alkylene optionally substituted with one or two C₁-C₃ alkyl groups; and R²⁶ and R²⁸ are in each instance independently selected from the group consisting of hydrogen, alkyl, and cycloalkyl; and wherein the alkyl, phenyl and cycloalkyl may be further substituted with from 1 to 3 substituents independently selected from the group consisting of hydroxyl, halo, C₁₋₄ alkoxy, —CF₃, and —OCF₃;

or a pharmaceutically acceptable salt, ester, hydrate, solvate, polymorph, and/or prodrug thereof.

In some embodiments of Formula IB or IC, R¹ is aryl or heteroaryl;
wherein said aryl or heteroaryl are optionally substituted with one, two, or three substituents independently selected from the group consisting of —O—CF₃, —O—R²⁰, C₁₋₄ alkyl, cycloalkyl, and heterocyclyl; and wherein said alkyl, and cycloalkyl, are optionally substituted with one, two, or three substituents independently selected from the group consisting of halo, and —CN; and R²⁰ in each instance is independently C₁-C₁₅ alkyl or aryl;
wherein the alkyl or aryl is optionally substituted with one, two, or three halo.

In some embodiments of Formula IB or IC, R¹ is selected from the group consisting of 6-CF₃-pyridin-3-yl, 6-(2,2,2-trifluoroethoxy)pyridin-3-yl, 4-phenoxy-phenyl, 4-OCF₃-phenyl, 4-cyclopropylphenyl, 4-(4-chlorophenoxy)phenyl, 4-(1-cyanocyclopropyl)phenyl, and 2-(piperidin-1-yl)pyrimidin-5-yl.

In some embodiments of Formula IB or IC, R² is hydrogen, C₁₋₁₅ alkyl, C₁₋₄ alkoxy, cycloalkyl, or heterocyclyl;
wherein said alkyl, alkoxy, cycloalkyl, and heterocyclyl are optionally substituted with one, two, or three substituents independently selected from the group consisting of hydroxyl, alkyl, alkoxy, alkynyl, aryl, heteroaryl, cycloalkyl, —N(R²⁰)(R²²), —C(O)—O—R²⁰, —C(O)—N(R²⁰)(R²²), CN, oxo, and —O—R²⁰;

wherein said alkyl, aryl or heteroaryl are optionally further substituted with one, two, or three substituents independently selected from the group consisting of hydroxyl, halo, C₁₋₆ alkyl, C₁₋₄ alkoxy, heteroaryl, cycloalkyl, benzyl, aryl, —CN, and —O—R²⁰;

R²⁰ and R²² are in each instance independently selected from the group consisting of hydrogen, C₁-C₁₅ alkyl, and heteroaryl; and wherein the alkyl, and heteroaryl are optionally substituted with one, two, or three substituents independently selected from the group consisting of halo, —CN, cycloalkyl and heteroaryl;

wherein said heteroaryl is optionally further substituted with cycloalkyl; or when R²⁰ and R²² are attached to a common nitrogen atom R²⁰ and R²² may join to form a heterocyclic or heteroaryl ring which is then optionally substituted with one, two, or three substituents independently selected from the group consisting of halo, alkyl, phenyl, —CF₃, and heteroaryl.

In some embodiments of Formula IB or IC, R² is hydrogen, methyl,

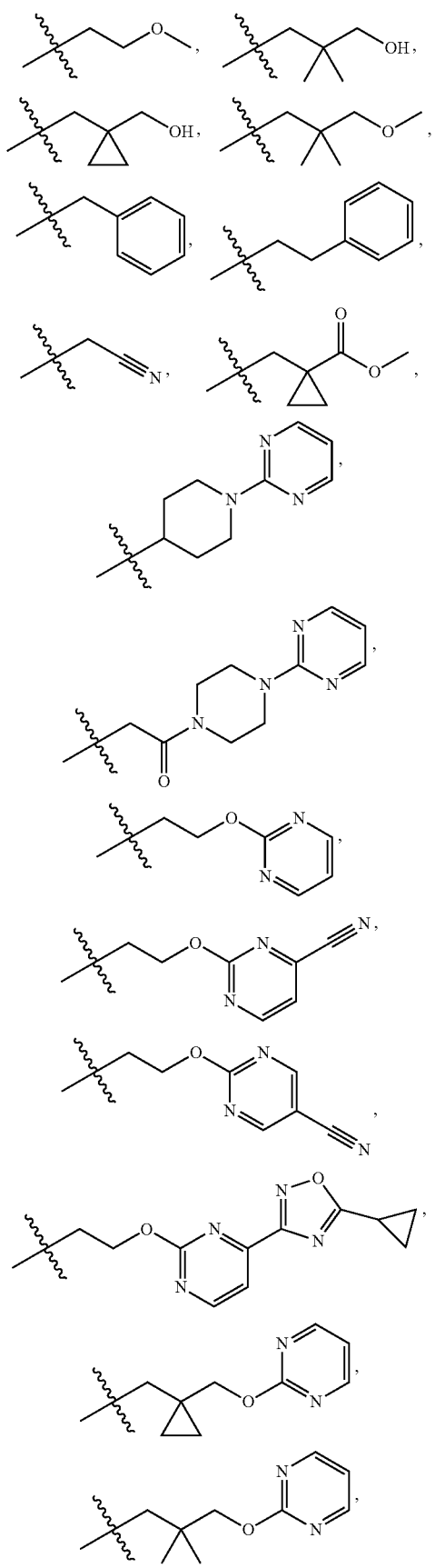

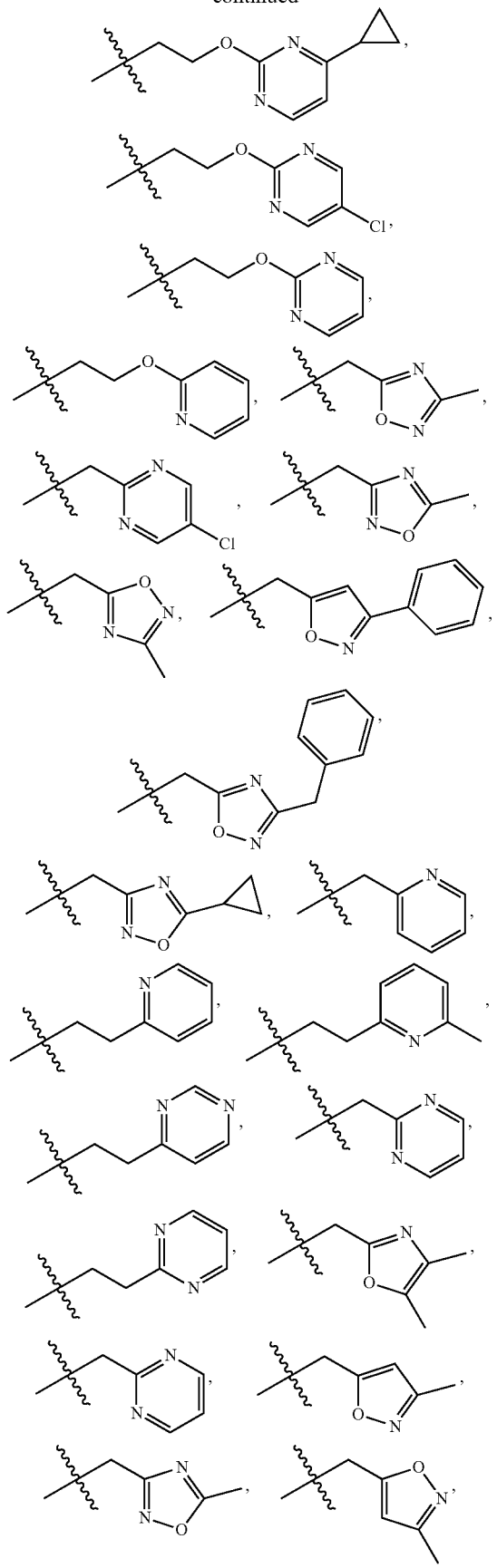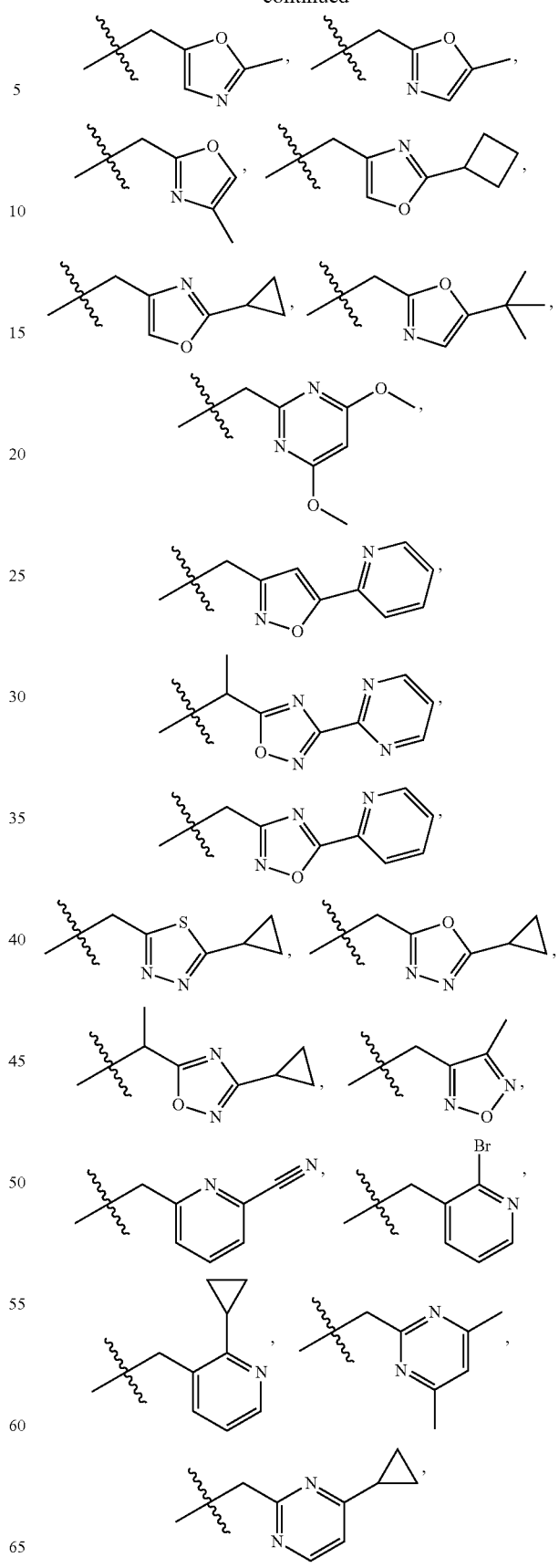

-continued

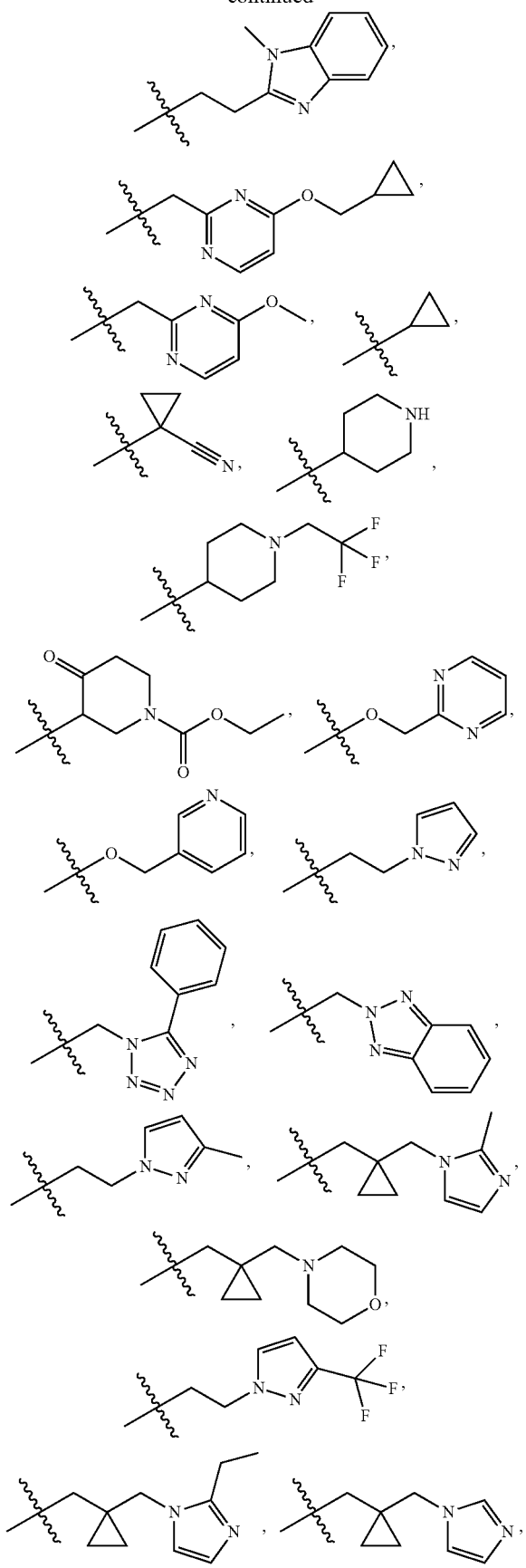

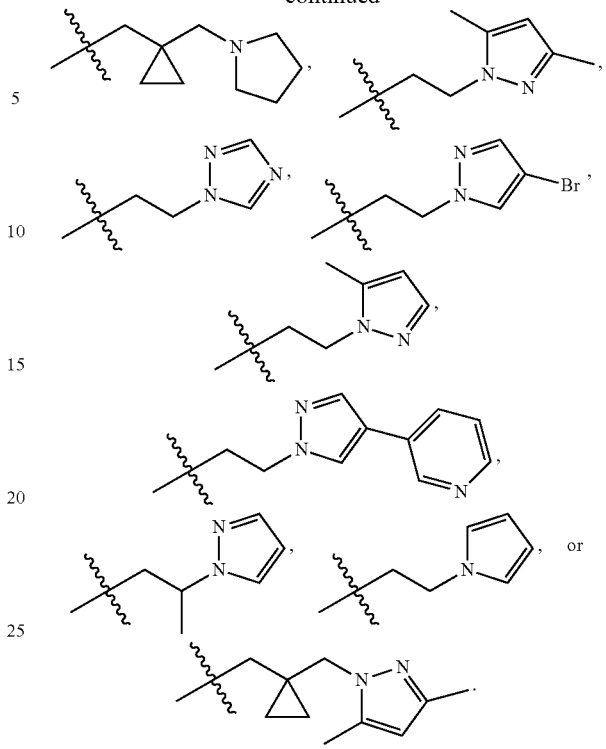

In certain embodiments, the compound of formula IB is represented by Formula IIA:

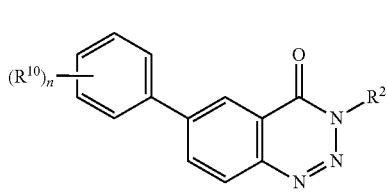

IIA wherein:
n is 0, 1, 2, or 3;
R[10] is independently selected from the group consisting of halo, —NO$_2$, CN, —SF$_5$, —Si(CH$_3$)$_3$, —O—CF$_3$, —O—R[20], —S—R[20], —C(O)—R[20], C(O)OH, —N(R[20])(R[22]), —C(O)—N(R[20])(R[22]), —N(R[20])—C(O)—R[22], —N(R[20])—S(=O)$_2$—R[26], —S(=O)$_2$—R[20], —S(=O)$_2$—N(R[20])(R[22]), C$_{1-4}$ alkyl, C$_{2-4}$ alkenyl, C$_{2-4}$ alkynyl, cycloalkyl, aryl, heteroaryl, and heterocyclyl; and
wherein said alkyl, alkenyl, alkynyl, aryl, heteroaryl, cycloalkyl, or heterocyclyl are optionally substituted with one, two, or three substituents independently selected from the group consisting of halo, —NO$_2$, —O—CF$_3$, —O—CHF$_2$, phenyl, heterocyclyl, heteroaryl, C$_{1-4}$ alkyl, cycloalkyl, —N(R[20])(R[22]), —C(O)—R[20], —C(O)—O—R[20], —C(O)—N(R[20])(R[22]), —CN, and —O—R[20];
R[2] is hydrogen, C$_{1-15}$ alkyl, C$_{1-4}$ alkoxy, —C(O)—O—R[26], —C(O)—N(R[26])(R[28]), —N(R[20])—S(=O)$_2$—R[20], cycloalkyl, aryl, heteroaryl, or heterocyclyl;
wherein said alkyl, alkoxy, cycloalkyl, and heterocyclyl are optionally substituted with one, two, or three substituents independently selected from the group consisting of hydroxyl, alkyl, alkoxy, alkynyl, halo, —NO$_2$, —O—CF$_3$, —O—CHF$_2$, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, oxo, and —O—R$^{20}$;

wherein said alkyl, alkoxy, cycloalkyl, aryl, heterocyclyl, or heteroaryl are optionally further substituted with one, two, or three substituents independently selected from the group consisting of hydroxyl, halo, —NO$_2$, —CF$_3$, —O—CF$_3$, C$_{1-6}$ alkyl, C$_{1-4}$ alkoxy, benzyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$; and wherein said C$_{1-6}$ alkyl, C$_{1-4}$ alkoxy, benzyl, aryl, heterocyclyl, heteroaryl, cycloalkyl, are optionally further substituted with one, two, or three substituents independently selected from the group consisting of hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, —S(O)$_2$—R$^{20}$ and —O—R$^{20}$;

R$^{20}$ and R$^{22}$ are in each instance independently selected from the group consisting of hydrogen, C$_1$-C$_{15}$ alkyl, C$_2$-C$_{15}$ alkenyl, C$_2$-C$_{15}$ alkynyl, cycloalkyl, heterocyclyl, aryl, and heteroaryl; and wherein the alkyl, alkenyl, alkynyl, heterocyclyl, aryl, and heteroaryl are optionally substituted with one, two, or three substituents independently selected from the group consisting of hydroxyl, halo, C$_{1-4}$ alkyl, monoalkylamino, dialkylamino, alkyl amide, aryl amide, heteroaryl amide, —NO$_2$, —SO$_2$R$^{26}$, —CN, C$_{1-3}$ alkoxy, —CF$_3$, —OCF$_3$, —OCH$_2$CF$_3$, —C(O)—NH$_2$, aryl, cycloalkyl, and heteroaryl;

wherein said heteroaryl is optionally further substituted with C$_{1-4}$ alkyl, or cycloalkyl; or when R$^{20}$ and R$^{22}$ are attached to a common nitrogen atom R$^{20}$ and R$^{22}$ may join to form a heterocyclic or heteroaryl ring which is then optionally substituted with one, two, or three substituents independently selected from the group consisting of hydroxyl, halo, alkyl, benzyl, phenyl, phenoxy, benzyloxy, monoalkylamino, dialkylamino, alkyl amide, aryl amide, heteroaryl amide, —NO$_2$, —SO$_2$R$^{26}$, —CN, C$_{1-3}$ alkoxy, —CF$_3$, —OCF$_3$, aryl, heteroaryl and cycloalkyl; and R$^{26}$ and R$^{28}$ are in each instance independently selected from the group consisting of hydrogen, alkyl, and cycloalkyl; and wherein the alkyl, phenyl and cycloalkyl may be further substituted with from 1 to 3 substituents independently selected from the group consisting of hydroxyl, halo, C$_{1-4}$ alkoxy, —CF$_3$, and —OCF$_3$;

or a pharmaceutically acceptable salt, ester, hydrate, solvate, polymorph, and/or prodrug thereof.

In some embodiments of Formula IIA, R$^2$ is selected from the group consisting of hydrogen, C$_{1-15}$ alkyl, C$_{1-4}$ alkoxy, cycloalkyl, and heterocyclyl. In many embodiments the alkyl, alkoxy, cycloalkyl, and heterocyclyl moiety is further substituted with one, two, or three substituents independently selected from the group consisting of hydroxyl, alkyl, alkoxy, alkynyl, aryl, heteroaryl, cycloalkyl, —N(R$^{20}$)(R$^{22}$), —C(O)—O—R$^{20}$, —C(O)—N(R$^{20}$)(R$^{22}$), —CN, oxo, and —O—R$^{20}$;

wherein said alkyl or heteroaryl are optionally further substituted with one, two, or three substituents independently selected from the group consisting of halo, C$_{1-6}$ alkyl, C$_{1-4}$ alkoxy, benzyl, aryl, heteroaryl and cycloalkyl;

R$^{20}$ and R$^{22}$ are in each instance independently selected from the group consisting of hydrogen, C$_1$-C$_{15}$ alkyl, and heteroaryl; and wherein the heteroaryl is optionally substituted with one, two, or three substituents independently selected from the group consisting of —CN and heteroaryl;

wherein said heteroaryl is optionally further substituted with cycloalkyl; or when R$^{20}$ and R$^{22}$ are attached to a common nitrogen atom R$^{20}$ and R$^{22}$ may join to form a heterocyclic or heteroaryl ring which is then optionally substituted with one, two, or three substituents independently selected from the group consisting of alkyl, phenyl, —CF$_3$, and heteroaryl.

Exemplary R$^2$ moieties of Formula IIA include, but are not limited to, hydrogen,

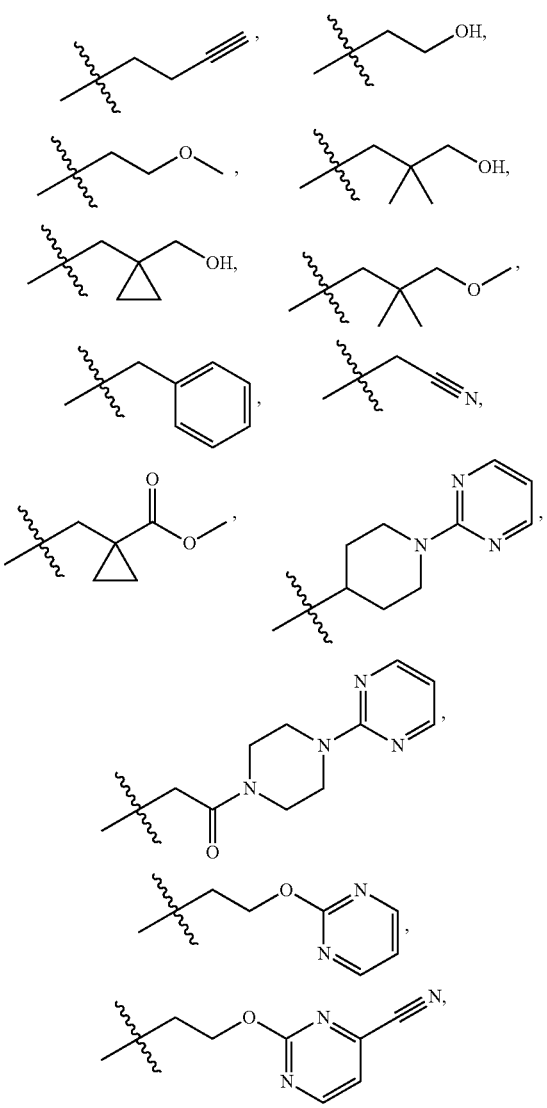

91
-continued
92
-continued
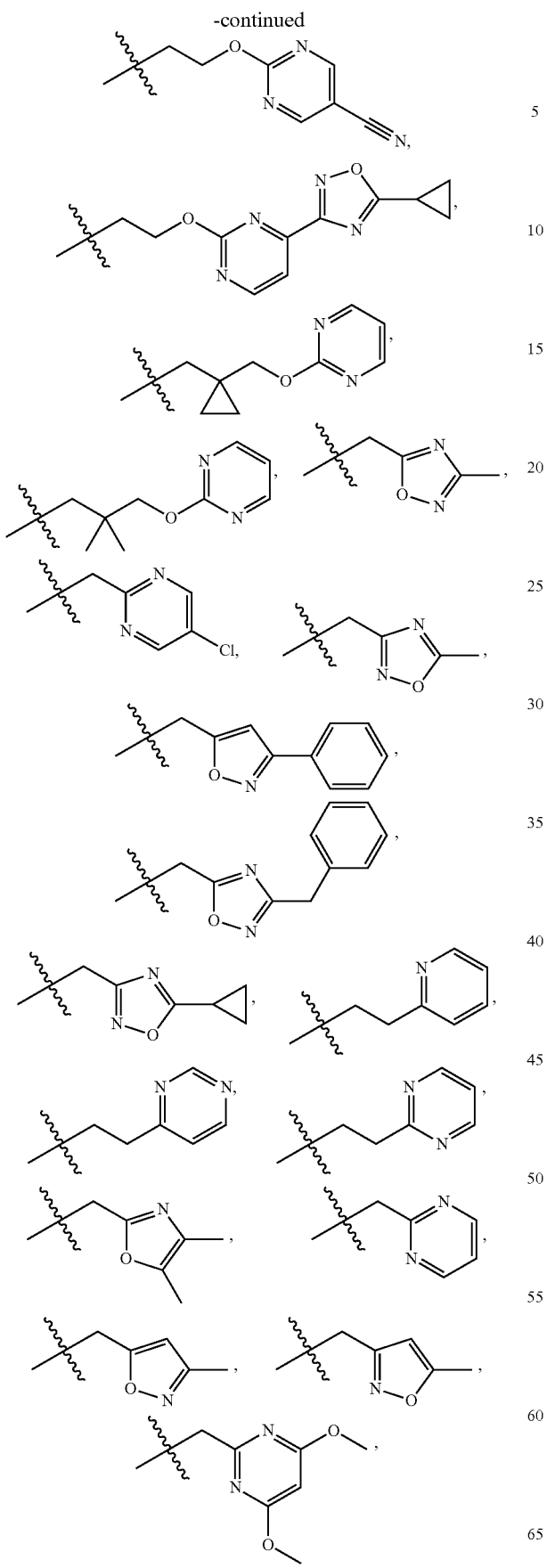
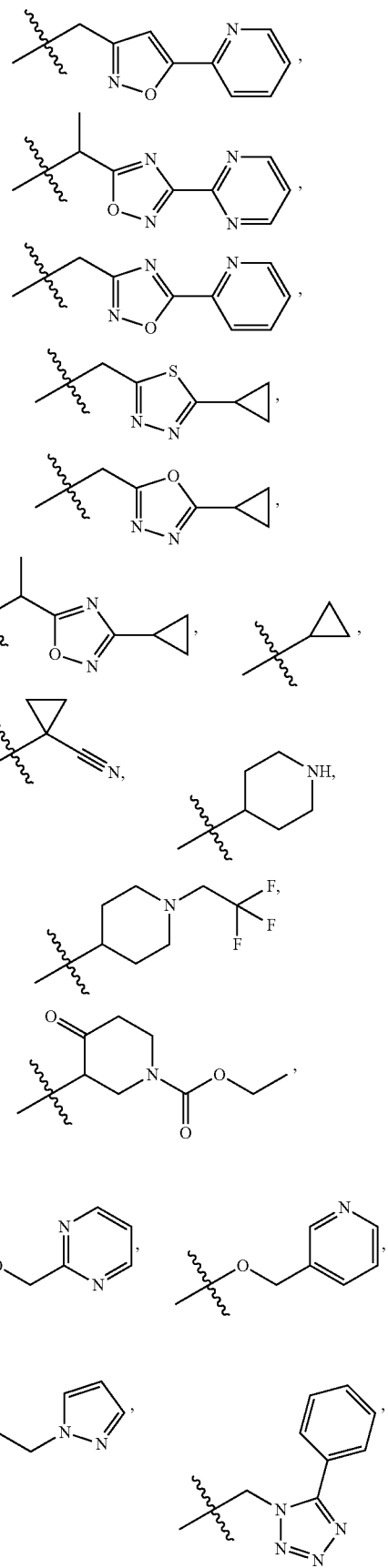

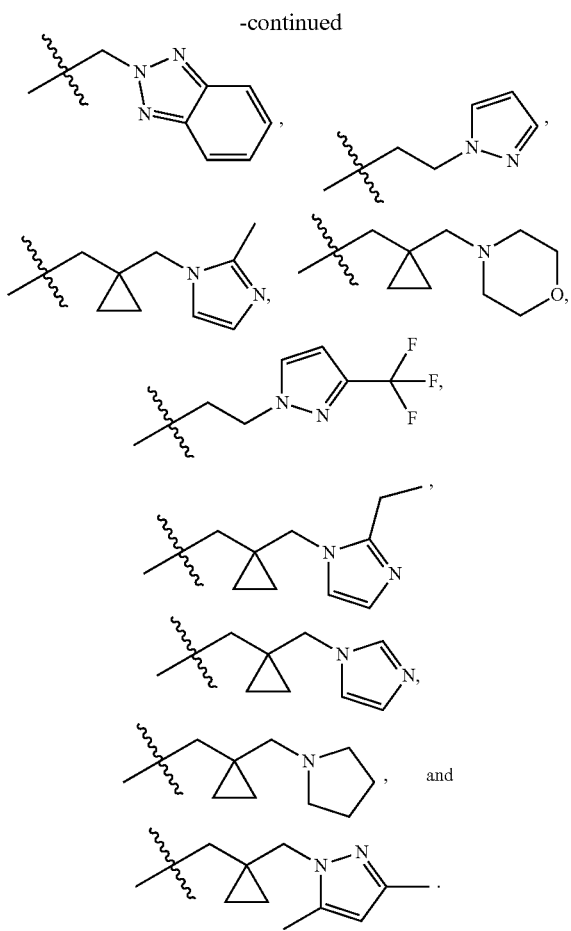

In some embodiments of Formula IIA, $R^{10}$ is selected from the group consisting of —$OCF_3$, cycloalkyl, and —O—$R^{20}$; and $R^{20}$ is aryl. In many embodiments the cycloalkyl is optionally further substituted with —CN. In many embodiments $R^{20}$ is optionally substituted with halo.

Exemplary $R^{10}$ moieties of Formula IIA include, but are not limited to, —$OCF_3$, cyclopropyl, 1-cyanocyclopropyl, phenoxy and 4-chlorophenoxy.

Exemplary compounds of Formula IIA include
6-(4-(trifluoromethoxy)phenyl)benzo[d][1,2,3]triazin-4(3H)-one;
3-((3-methyl-1,2,4-oxadiazol-5-yl)methyl)-6-(4-(trifluoromethoxy)phenyl)benzo[d][1,2,3]triazin-4(3H)-one;
3-((5-chloropyrimidin-2-yl)methyl)-6-(4-(trifluoromethoxy)phenyl)benzo[d][1,2,3]triazin-4(3H)-one;
3-((5-methyl-1,2,4-oxadiazol-3-yl)methyl)-6-(4-(trifluoromethoxy)phenyl)benzo[d][1,2,3]triazin-4(3H)-one;
3-((3-methyl-1,2,4-oxadiazol-5-yl)methyl)-6-(4-phenoxyphenyl)benzo[d][1,2,3]triazin-4(3H)-one;
3-((3-phenylisoxazol-5-yl)methyl)-6-(4-(trifluoromethoxy)phenyl)benzo[d][1,2,3]triazin-4(3H)-one;
3-((3-benzyl-1,2,4-oxadiazol-5-yl)methyl)-6-(4-(trifluoromethoxy)phenyl)benzo[d][1,2,3]triazin-4(3H)-one;
3-(2-(1H-pyrazol-1-yl)ethyl)-6-(4-(trifluoromethoxy)phenyl)benzo[d][1,2,3]triazin-4(3H)-one;
3-((5-cyclopropyl-1,2,4-oxadiazol-3-yl)methyl)-6-(4-(trifluoromethoxy)phenyl)benzo[d][1,2,3]triazin-4(3H)-one;
3-(2-(pyridin-2-yl)ethyl)-6-(4-(trifluoromethoxy)phenyl)benzo[d][1,2,3]triazin-4(3H)-one;
6-(4-(4-chlorophenoxy)phenyl)-3-((3-methyl-1,2,4-oxadiazol-5-yl)methyl)benzo[d][1,2,3]triazin-4(3H)-one;
3-(2-(pyrimidin-4-yl)ethyl)-6-(4-(trifluoromethoxy)phenyl)benzo[d][1,2,3]triazin-4(3H)-one;
3-(2-(pyrimidin-2-yl)ethyl)-6-(4-(trifluoromethoxy)phenyl)benzo[d][1,2,3]triazin-4(3H)-one;
6-(4-(4-chlorophenoxy)phenyl)benzo[d][1,2,3]triazin-4(3H)-one;
3-((5-phenyl-1H-tetrazol-1-yl)methyl)-6-(4-(trifluoromethoxy)phenyl)benzo[d][1,2,3]triazin-4(3H)-one;
3-cyclopropyl-6-(4-(trifluoromethoxy)phenyl)benzo[d][1,2,3]triazin-4(3H)-one;
3-((4,5-dimethyloxazol-2-yl)methyl)-6-(4-(trifluoromethoxy)phenyl)benzo[d][1,2,3]triazin-4(3H)-one;
3-(pyrimidin-2-ylmethyl)-6-(4-(trifluoromethoxy)phenyl)benzo[d][1,2,3]triazin-4(3H)-one;
3-((3-methylisoxazol-5-yl)methyl)-6-(4-(trifluoromethoxy)phenyl)benzo[d][1,2,3]triazin-4(3H)-one;
3-((5-methylisoxazol-3-yl)methyl)-6-(4-(trifluoromethoxy)phenyl)benzo[d][1,2,3]triazin-4(3H)-one;
3-((2H-benzo[d][1,2,3]triazol-2-yl)methyl)-6-(4-(trifluoromethoxy)phenyl)benzo[d][1,2,3]triazin-4(3H)-one;
3-(2-(1H-pyrazol-1-yl)ethyl)-6-(4-(4-chlorophenoxy)phenyl)benzo[d][1,2,3]triazin-4(3H)-one;
2-(4-oxo-6-(4-(trifluoromethoxy)phenyl)benzo[d][1,2,3]triazin-3(4H)-yl)acetonitrile;
3-(2-(pyrimidin-2-yloxy)ethyl)-6-(4-(trifluoromethoxy)phenyl)benzo[d][1,2,3]triazin-4(3H)-one;
1-(4-oxo-6-(4-(trifluoromethoxy)phenyl)benzo[d][1,2,3]triazin-3(4H)-yl)cyclopropanecarbonitrile;
3-((1-((2-methyl-1H-imidazol-1-yl)methyl)cyclopropyl)methyl)-6-(4-(trifluoromethoxy)phenyl)benzo[d][1,2,3]triazin-4(3H)-one;
2-(2-(4-oxo-6-(4-(trifluoromethoxy)phenyl)benzo[d][1,2,3]triazin-3(4H)-yl)ethoxy)pyrimidine-4-carbonitrile;
3-(piperidin-4-yl)-6-(4-(trifluoromethoxy)phenyl)benzo[d][1,2,3]triazin-4(3H)-one;
3-(1-(pyrimidin-2-yl)piperidin-4-yl)-6-(4-(trifluoromethoxy)phenyl)benzo[d][1,2,3]triazin-4(3H)-one;
3-((1-(morpholinomethyl)cyclopropyl)methyl)-6-(4-(trifluoromethoxy)phenyl)benzo[d][1,2,3]triazin-4(3H)-one;
3-(2-oxo-2-(4-(pyrimidin-2-yl)piperazin-1-yl)ethyl)-6-(4-(trifluoromethoxy)phenyl)benzo[d][1,2,3]triazin-4(3H)-one;
3-benzyl-6-(4-(trifluoromethoxy)phenyl)benzo[d][1,2,3]triazin-4(3H)-one;
3-(2-methoxyethyl)-6-(4-(trifluoromethoxy)phenyl)benzo[d][1,2,3]triazin-4(3H)-one;
3-((4,6-dimethoxypyrimidin-2-yl)methyl)-6-(4-(trifluoromethoxy)phenyl)benzo[d][1,2,3]triazin-4(3H)-one;
3-(but-3-ynyl)-6-(4-(trifluoromethoxy)phenyl)benzo[d][1,2,3]triazin-4(3H)-one;
3-(2-hydroxyethyl)-6-(4-(trifluoromethoxy)phenyl)benzo[d][1,2,3]triazin-4(3H)-one;
3-((5-(pyridin-2-yl)isoxazol-3-yl)methyl)-6-(4-(trifluoromethoxy)phenyl)benzo[d][1,2,3]triazin-4(3H)-one;
1-(4-(4-oxo-3-(2-(pyrimidin-2-yloxy)ethyl)-3,4-dihydrobenzo[d][1,2,3]triazin-6-yl)phenyl)cyclopropanecarbonitrile;
2-(2-(4-oxo-6-(4-(trifluoromethoxy)phenyl)benzo[d][1,2,3]triazin-3(4H)-yl)ethoxy)pyrimidine-5-carbonitrile;
6-(4-(trifluoromethoxy)phenyl)-3-(2-(3-(trifluoromethyl)-1H-pyrazol-1-yl)ethyl)benzo[d][1,2,3]triazin-4(3H)-one;
3-(1-(3-(pyrimidin-2-yl)-1,2,4-oxadiazol-5-yl)ethyl)-6-(4-(trifluoromethoxy)phenyl)benzo[d][1,2,3]triazin-4(3H)-one;
3-((5-(pyridin-2-yl)-1,2,4-oxadiazol-3-yl)methyl)-6-(4-(trifluoromethoxy)phenyl)benzo[d][1,2,3]triazin-4(3H)-one;

methyl 1-((4-oxo-6-(4-(trifluoromethoxy)phenyl)benzo[d] [1,2,3]triazin-3(4H)-yl)methyl)cyclopropanecarboxylate;
3-(pyrimidin-2-ylmethoxy)-6-(4-(trifluoromethoxy)phenyl) benzo[d][1,2,3]triazin-4(3H)-one;
3-((1-((2-ethyl-1H-imidazol-1-yl)methyl)cyclopropyl) methyl)-6-(4-(trifluoromethoxy)phenyl)benzo[d][1,2,3] triazin-4(3H)-one;
3-((1-((1H-imidazol-1-yl)methyl)cyclopropyl)methyl)-6-(4-(trifluoromethoxy)phenyl)benzo[d][1,2,3]triazin-4(3H)-one;
3-(pyridin-3-ylmethoxy)-6-(4-(trifluoromethoxy)phenyl) benzo[d][1,2,3]triazin-4(3H)-one;
3-(2-(4-(5-cyclopropyl-1,2,4-oxadiazol-3-yl)pyrimidin-2-yloxy)ethyl)-6-(4-(trifluoromethoxy)phenyl)benzo[d][1,2,3]triazin-4(3H)-one;
3-((1-(pyrrolidin-1-ylmethyl)cyclopropyl)methyl)-6-(4-(trifluoromethoxy)phenyl)benzo[d][1,2,3]triazin-4(3H)-one;
3-((1-(3,5-dimethyl-1H-pyrazol-1-yl)methyl)cyclopropyl) methyl)-6-(4-(trifluoromethoxy)phenyl)benzo[d][1,2,3] triazin-4(3H)-one;
6-(4-(4-chlorophenoxy)phenyl)-3-(2-oxo-2-(4-(pyrimidin-2-yl)piperazin-1-yl)ethyl)benzo[d][1,2,3]triazin-4(3H)-one;
3-((5-cyclopropyl-1,3,4-thiadiazol-2-yl)methyl)-6-(4-(trifluoromethoxy)phenyl)benzo[d][1,2,3]triazin-4(3H)-one;
3-((5-cyclopropyl-1,3,4-oxadiazol-2-yl)methyl)-6-(4-(trifluoromethoxy)phenyl)benzo[d][1,2,3]triazin-4(3H)-one;
3-(3-methoxy-2,2-dimethylpropyl)-6-(4-(trifluoromethoxy) phenyl)benzo[d][1,2,3]triazin-4(3H)-one;
3-(1-(2,2,2-trifluoroethyl)piperidin-4-yl)-6-(4-(trifluoromethoxy)phenyl)benzo[d][1,2,3]triazin-4(3H)-one;
ethyl 4-oxo-3-(4-oxo-6-(4-(trifluoromethoxy)phenyl)benzo [d][1,2,3]triazin-3(4H)-yl)piperidine-1-carboxylate;
6-(4-cyclopropylphenyl)-3-((3-methyl-1,2,4-oxadiazol-5-yl)methyl)benzo[d][1,2,3]triazin-4(3H)-one;
3-((1-(hydroxymethyl)cyclopropyl)methyl)-6-(4-(trifluoromethoxy)phenyl)benzo[d][1,2,3]triazin-4(3H)-one;
3-(1-(3-cyclopropyl-1,2,4-oxadiazol-5-yl)ethyl)-6-(4-(trifluoromethoxy)phenyl)benzo[d][1,2,3]triazin-4(3H)-one;
3-((1-((pyrimidin-2-yloxy)methyl)cyclopropyl)methyl)-6-(4-(trifluoromethoxy)phenyl)benzo[d][1,2,3]triazin-4 (3H)-one;
3-(3-hydroxy-2,2-dimethylpropyl)-6-(4-(trifluoromethoxy) phenyl)benzo[d][1,2,3]triazin-4(3H)-one; and
3-(2,2-dimethyl-3-(pyrimidin-2-yloxy)propyl)-6-(4-(trifluoromethoxy)phenyl)benzo[d][1,2,3]triazin-4(3H)-one;
or a pharmaceutically acceptable salt, ester, hydrate, solvate, polymorph, and/or prodrug thereof.

In certain embodiments, the compound of Formula IB is represented by Formula IIIA:

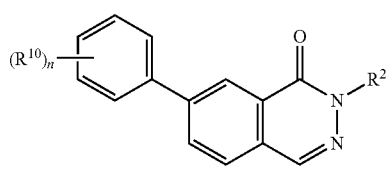

IIIA wherein:
n is 0, 1, 2, or 3;
$R^{10}$ is independently selected from the group consisting of halo, —$NO_2$, CN, —$SF_5$, —$Si(CH_3)_3$ —O—$CF_3$, —S—$R^{20}$, —C(O)—$R^{20}$, C(O)OH, —N($R^{20}$)($R^{22}$), —C(O)—N($R^{20}$)($R^{22}$), —N($R^{20}$)—C(O)—$R^{22}$, —N($R^{20}$)—S(=O)$_2$—$R^{26}$, —S(=O)$_2$—$R^{20}$, —S(=O)$_2$—N($R^{20}$)($R^{22}$), $C_{1-4}$ alkyl, $C_{2-4}$ alkenyl, $C_{2-4}$ alkynyl, cycloalkyl, aryl, heteroaryl, and heterocyclyl; and
wherein said alkyl, alkenyl, alkynyl, aryl, heteroaryl, cycloalkyl, or heterocyclyl are optionally substituted with one, two, or three substituents independently selected from the group consisting of halo, —$NO_2$, —O—$CF_3$, —O—$CHF_2$, phenyl, heterocyclyl, heteroaryl, $C_{1-4}$ alkyl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$;
$R^2$ is hydrogen, $C_{1-15}$ alkyl, $C_{1-4}$ alkoxy, —C(O)—O—$R^{26}$, —C(O)—N($R^{26}$)($R^{28}$), —N($R^{20}$)—S(=O)$_2$—$R^{20}$, cycloalkyl, aryl, heteroaryl, or heterocyclyl;
wherein said alkyl, alkoxy, cycloalkyl, and heterocyclyl are optionally substituted with one, two, or three substituents independently selected from the group consisting of hydroxyl, alkyl, alkoxy, alkynyl, halo, —$NO_2$, —O—$CF_3$, —O—$CHF_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, oxo, and —O—$R^{20}$;
wherein said alkyl, alkoxy, cycloalkyl, aryl, heterocyclyl, or heteroaryl are optionally further substituted with one, two, or three substituents independently selected from the group consisting of hydroxyl, halo, —$NO_2$, —$CF_3$, —O—$CF_3$, $C_{1-6}$ alkyl, $C_{1-4}$ alkoxy, benzyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$; and
wherein said $C_{1-6}$ alkyl, $C_{1-4}$ alkoxy, benzyl, aryl, heterocyclyl, heteroaryl, cycloalkyl, are optionally further substituted with one, two, or three substituents independently selected from the group consisting of hydroxyl, halo, —$NO_2$, —O—$CF_3$, —$CF_3$, —O—$CHF_2$, —N($R^{20}$) ($R^{22}$), —C(O)—$R^{20}$, —C(O)—O—$R^{20}$, —C(O)—N($R^{20}$)($R^{22}$), —CN, —S(O)$_2$—$R^{20}$ and —O—$R^{20}$;
$R^{20}$ and $R^{22}$ are in each instance independently selected from the group consisting of hydrogen, $C_1$-$C_{15}$ alkyl, $C_2$-$C_{15}$ alkenyl, $C_2$-$C_{15}$ alkynyl, cycloalkyl, heterocyclyl, aryl, and heteroaryl; and
wherein the alkyl, alkenyl, alkynyl, heterocyclyl, aryl, and heteroaryl are optionally substituted with one, two, or three substituents independently selected from the group consisting of hydroxyl, halo, $C_{1-4}$ alkyl, monoalkylamino, dialkylamino, alkyl amide, aryl amide, heteroaryl amide, —$NO_2$, —$SO_2R^{26}$, —CN, $C_{1-3}$ alkoxy, —$CF_3$, —$OCF_3$, —$OCH_2CF_3$, —C(O)—$NH_2$, aryl, cycloalkyl, and heteroaryl;
wherein said heteroaryl is optionally further substituted with $C_{1-4}$ alkyl, or cycloalkyl; or
when $R^{20}$ and $R^{22}$ are attached to a common nitrogen atom $R^{20}$ and $R^{22}$ may join to form a heterocyclic or heteroaryl ring which is then optionally substituted with one, two, or three substituents independently selected from the group consisting of hydroxyl, halo, alkyl, benzyl, phenyl, phenoxy, benzyloxy, monoalkylamino, dialkylamino, alkyl amide, aryl amide, heteroaryl amide, —$NO_2$, —$SO_2R^{26}$, —CN, $C_{1-3}$ alkoxy, —$CF_3$, —$OCF_3$, aryl, heteroaryl and cycloalkyl; and
$R^{26}$ and $R^{28}$ are in each instance independently selected from the group consisting of hydrogen, alkyl, and cycloalkyl; and wherein the alkyl, phenyl and cycloalkyl may be further substituted with from 1 to 3 substituents independently selected from the group consisting of hydroxyl, halo, $C_{1-4}$ alkoxy, —$CF_3$, and —$OCF_3$;

or a pharmaceutically acceptable salt, ester, hydrate, solvate, polymorph, and/or prodrug thereof.

In some embodiments of Formula IIIA, $R^2$ is hydrogen or $C_{1-15}$ alkyl. In many embodiments the alkyl moiety is further substituted with one, two, or three substituents independently selected from the group consisting of hydroxyl, aryl, heteroaryl, —$N(R^{20})(R^{22})$, and —O—$R^{20}$; and wherein said aryl, or heteroaryl are optionally further substituted with one, two, or three substituents independently selected from the group consisting of hydroxyl, halo, $C_{1-6}$ alkyl, $C_{1-4}$ alkoxy, heteroaryl, cycloalkyl, —CN, and —O—$R^{20}$;

$R^{20}$ and $R^{22}$ in each instance are independently selected from the group consisting of $C_1$-$C_{15}$ alkyl, and heteroaryl; and wherein the alkyl, and heteroaryl are optionally substituted with halo or cycloalkyl; or when $R^{20}$ and $R^{22}$ are attached to a common nitrogen atom $R^{20}$ and $R^{22}$ may join to form a heteroaryl ring which is then optionally substituted with one, two, or three substituents independently selected from the group consisting of halo, alkyl, and heteroaryl.

Exemplary $R^2$ moieties of Formula IIIA include, but are not limited to, hydrogen, methyl,

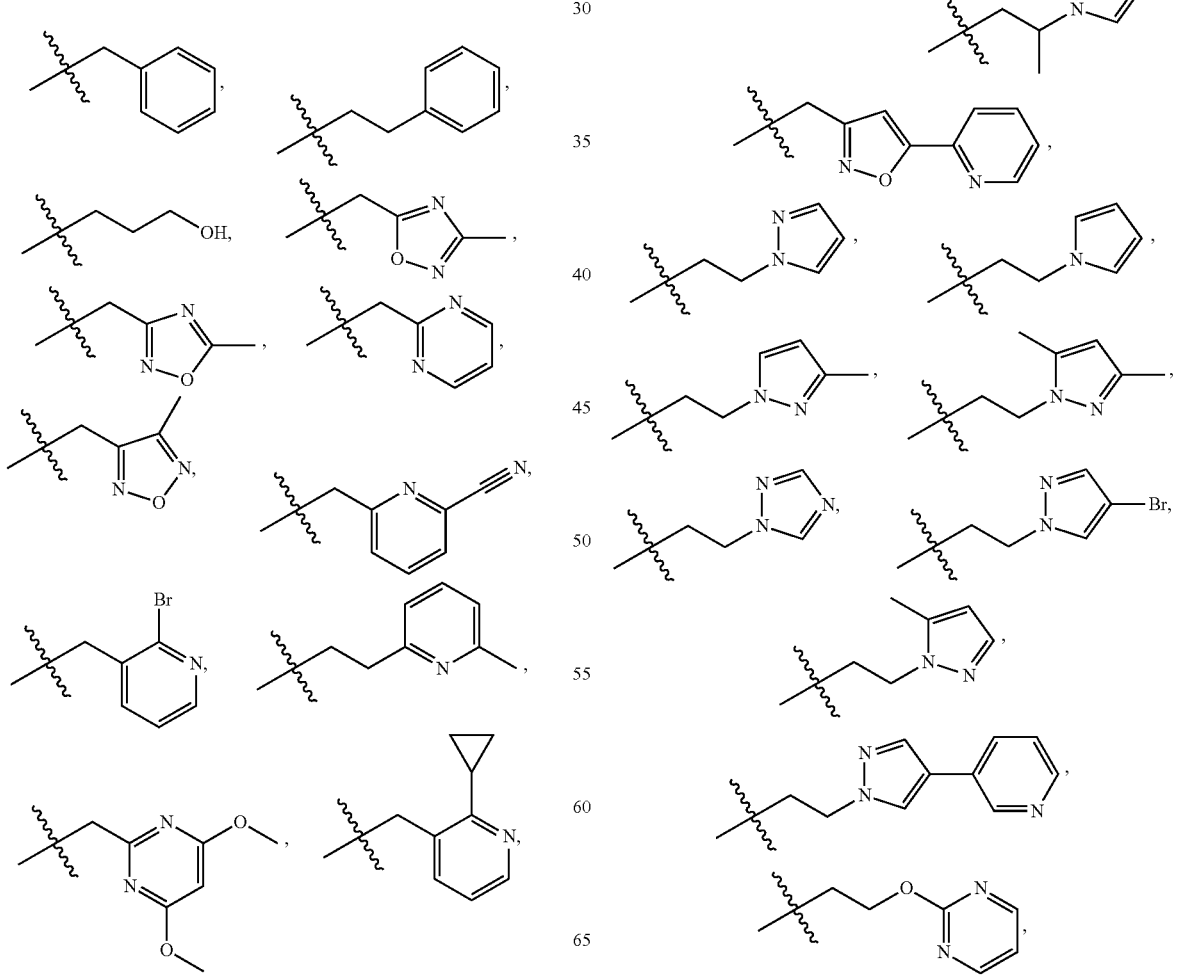

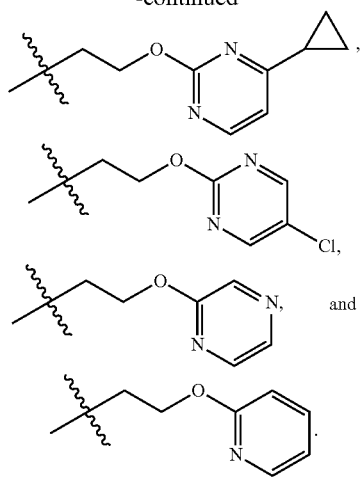

An exemplary R[10] moiety of Formula IIIA includes —OCF$_3$.

Exemplary compounds of Formula IIIA include
7-(4-(trifluoromethoxy)phenyl)phthalazin-1(2H)-one;
2-((3-methyl-1;2;4-oxadiazol-5-yl)methyl)-7-(4-(trifluoromethoxy)phenyl)phthalazin-1(2H)-one;
2-((5-methyl-1;2;4-oxadiazol-3-yl)methyl)-7-(4-(trifluoromethoxy)phenyl)phthalazin-1(2H)-one;
2-methyl-7-(4-(trifluoromethoxy)phenyl)phthalazin-1(2H)-one;
2-(pyrimidin-2-ylmethyl)-7-(4-(trifluoromethoxy)phenyl)phthalazin-1(2H)-one;
2-benzyl-7-(4-(trifluoromethoxy)phenyl)phthalazin-1(2H)-one;
2-((1-oxo-7-(4-(trifluoromethoxy)phenyl)phthalazin-2(1H)-yl)methyl)benzonitrile;
2-phenethyl-7-(4-(trifluoromethoxy)phenyl)phthalazin-1(2H)-one;
2-(2-(1H-pyrazol-1-yl)ethyl)-7-(4-(trifluoromethoxy)phenyl)phthalazin-1(2H)-one;
2-(2-(1H-pyrrol-1-yl)ethyl)-7-(4-(trifluoromethoxy)phenyl)phthalazin-1(2H)-one;
2-((4-methyl-1;2;5-oxadiazol-3-yl)methyl)-7-(4-(trifluoromethoxy)phenyl)phthalazin-1(2H)-one;
6-((1-oxo-7-(4-(trifluoromethoxy)phenyl)phthalazin-2(1H)-yl)methyl)picolinonitrile;
7-(4-(trifluoromethoxy)phenyl)-2-((5-(3-(trifluoromethyl)phenyl)-1;2;4-oxadiazol-3-yl)methyl)phthalazin-1(2H)-one;
2-((2-bromopyridin-3-yl)methyl)-7-(4-(trifluoromethoxy)phenyl)phthalazin-1(2H)-one;
2-(3-hydroxypropyl)-7-(4-(trifluoromethoxy)phenyl)phthalazin-1(2H)-one;
2-(3-(pyridin-2-yloxy)propyl)-7-(4-(trifluoromethoxy)phenyl)phthalazin-1(2H)-one;
2-(2-(3-methyl-1H-pyrazol-1-yl)ethyl)-7-(4-(trifluoromethoxy)phenyl)phthalazin-1(2H)-one;
2-(2-(6-methylpyridin-2-yl)ethyl)-7-(4-(trifluoromethoxy)phenyl)phthalazin-1(2H)-one;
2-((4;6-dimethoxypyrimidin-2-yl)methyl)-7-(4-(trifluoromethoxy)phenyl)phthalazin-1(2H)-one;
2-((2-cyclopropylpyridin-3-yl)methyl)-7-(4-(trifluoromethoxy)phenyl)phthalazin-1(2H)-one;
7-(4-(trifluoromethoxy)phenyl)-2-((6-(trifluoromethyl)pyridin-2-yl)methyl)phthalazin-1(2H)-one;
2-((4;6-dimethylpyrimidin-2-yl)methyl)-7-(4-(trifluoromethoxy)phenyl)phthalazin-1(2H)-one;
2-((4-cyclopropylpyrimidin-2-yl)methyl)-7-(4-(trifluoromethoxy)phenyl)phthalazin-1(2H)-one;
2-(2-(3;5-dimethyl-1H-pyrazol-1-yl)ethyl)-7-(4-(trifluoromethoxy)phenyl)phthalazin-1(2H)-one;
2-(2-(1-methyl-1H-benzo[d]imidazol-2-yl)ethyl)-7-(4-(trifluoromethoxy)phenyl)phthalazin-1(2H)-one;
2-(2-(1H-1;2;4-triazol-1-yl)ethyl)-7-(4-(trifluoromethoxy)phenyl)phthalazin-1(2H)-one;
2-((4-(cyclopropylmethoxy)pyrimidin-2-yl)methyl)-7-(4-(trifluoromethoxy)phenyl)phthalazin-1(2H)-one;
2-(2-(pyrimidin-2-yloxy)ethyl)-7-(4-(trifluoromethoxy)phenyl)phthalazin-1(2H)-one;
2-(2-(4-cyclopropylpyrimidin-2-yloxy)ethyl)-7-(4-(trifluoromethoxy)phenyl)phthalazin-1(2H)-one;
2-((4-methoxypyrimidin-2-yl)methyl)-7-(4-(trifluoromethoxy)phenyl)phthalazin-1(2H)-one;
2-(2-(4-bromo-1H-pyrazol-1-yl)ethyl)-7-(4-(trifluoromethoxy)phenyl)phthalazin-1(2H)-one;
2-(2-(5-methyl-1H-pyrazol-1-yl)ethyl)-7-(4-(trifluoromethoxy)phenyl)phthalazin-1(2H)-one;
2-(2-(4-(pyridin-3-yl)-1H-pyrazol-1-yl)ethyl)-7-(4-(trifluoromethoxy)phenyl)phthalazin-1(2H)-one;
2-(2-(4-(2-methoxypyrimidin-5-yl)-1H-pyrazol-1-yl)ethyl)-7-(4-(trifluoromethoxy)phenyl)phthalazin-1(2H)-one;
2-((5-chloropyrimidin-2-yl)methyl)-7-(4-(trifluoromethoxy)phenyl)phthalazin-1(2H)-one;
2-(2-(pyrimidin-4-yl)ethyl)-7-(4-(trifluoromethoxy)phenyl)phthalazin-1(2H)-one;
2-(2-(5-chloropyrimidin-2-yloxy)ethyl)-7-(4-(trifluoromethoxy)phenyl)phthalazin-1(2H)-one;
2-(2-(1H-pyrazol-1-yl)propyl)-7-(4-(trifluoromethoxy)phenyl)phthalazin-1(2H)-one;
2-(2-(pyrazin-2-yloxy)ethyl)-7-(4-(trifluoromethoxy)phenyl)phthalazin-1(2H)-one;
2-(2-(pyridin-2-yloxy)ethyl)-7-(4-(trifluoromethoxy)phenyl)phthalazin-1(2H)-one; and
2-((5-(pyridin-2-yl)isoxazol-3-yl)methyl)-7-(4-(trifluoromethoxy)phenyl)phthalazin-1(2H)-one;
or a pharmaceutically acceptable salt, ester, hydrate, solvate, polymorph, and/or prodrug thereof.

In certain embodiments, the compound of Formula IB is represented by Formula IVB:

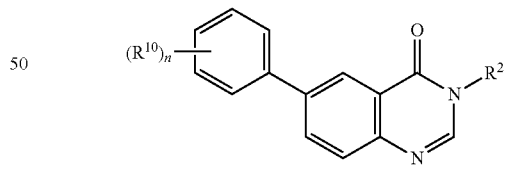

IVB wherein:
n is 0, 1, 2, or 3;
R[10] is independently selected from the group consisting of halo, —NO$_2$, CN, —SF$_5$, —Si(CH$_3$)$_3$, —O—CF$_3$, —O—R[20], —S—R[20], —C(O)—R[20], C(O)OH, —N(R[20])(R[22]), —C(O)—N(R[20])(R[22]), —N(R[20])—C(O)—R[22], —N(R[20])—S(=O)$_2$—R[26], —S(=O)$_2$—R[20], —S(=O)$_2$—N(R[20])(R[22]), C$_{1-4}$ alkyl, C$_{2-4}$ alkenyl, C$_{2-4}$ alkynyl, cycloalkyl, aryl, heteroaryl, and heterocyclyl; and
wherein said alkyl, alkenyl, alkynyl, aryl, heteroaryl, cycloalkyl, or heterocyclyl are optionally substituted with one, two, or three substituents independently selected from the group consisting of halo, —NO$_2$, —O—CF$_3$, —O—CHF$_2$, phenyl, heteroaryl, heteroaryl, C$_{1-4}$ alkyl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$;

R$^2$ is hydrogen, C$_{1-15}$ alkyl, C$_{1-4}$ alkoxy, —C(O)—O—R$^{26}$, —C(O)—N(R$^{26}$)(R$^{28}$), —N(R$^{20}$)—S(=O)$_2$—R$^{20}$, cycloalkyl, aryl, heteroaryl, or heterocyclyl;

wherein said alkyl, alkoxy, cycloalkyl, and heterocyclyl are optionally substituted with one, two, or three substituents independently selected from the group consisting of hydroxyl, alkyl, alkoxy, alkynyl, halo, —NO$_2$, —O—CF$_3$, —O—CHF$_2$, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, oxo, and —O—R$^{20}$;

wherein said alkyl, alkoxy, cycloalkyl, aryl, heterocyclyl, or heteroaryl are optionally further substituted with one, two, or three substituents independently selected from the group consisting of hydroxyl, halo, —NO$_2$, —CF$_3$, —O—CF$_3$, C$_{1-6}$ alkyl, C$_{1-4}$ alkoxy, benzyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$; and wherein said C$_{1-6}$ alkyl, C$_{1-4}$ alkoxy, benzyl, aryl, heterocyclyl, heteroaryl, cycloalkyl, are optionally further substituted with one, two, or three substituents independently selected from the group consisting of hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, —S(O)$_2$—R$^{20}$ and —O—R$^{20}$;

R$^{20}$ and R$^{22}$ are in each instance independently selected from the group consisting of hydrogen, C$_1$-C$_{15}$ alkyl, C$_2$-C$_{15}$ alkenyl, C$_2$-C$_{15}$ alkynyl, cycloalkyl, heterocyclyl, aryl, and heteroaryl; and wherein the alkyl, alkenyl, alkynyl, heterocyclyl, aryl, and heteroaryl are optionally substituted with one, two, or three substituents independently selected from the group consisting of hydroxyl, halo, C$_{1-4}$ alkyl, monoalkylamino, dialkylamino, alkyl amide, aryl amide, heteroaryl amide, —NO$_2$, —SO$_2$R$^{26}$, —CN, C$_{1-3}$ alkoxy, —CF$_3$, —OCF$_3$, —OCH$_2$CF$_3$, —C(O)—NH$_2$, aryl, cycloalkyl, and heteroaryl;

wherein said heteroaryl is optionally further substituted with C$_{1-4}$ alkyl, or cycloalkyl; or when R$^{20}$ and R$^{22}$ are attached to a common nitrogen atom R$^{20}$ and R$^{22}$ may join to form a heterocyclic or heteroaryl ring which is then optionally substituted with one, two, or three substituents independently selected from the group consisting of hydroxyl, halo, alkyl, benzyl, phenyl, phenoxy, benzyloxy, monoalkylamino, dialkylamino, alkyl amide, aryl amide, heteroaryl amide, —NO$_2$, —SO$_2$R$^{26}$, —CN, C$_{1-3}$ alkoxy, —CF$_3$, —OCF$_3$, aryl, heteroaryl and cycloalkyl; and R$^{26}$ and R$^{28}$ are in each instance independently selected from the group consisting of hydrogen, alkyl, and cycloalkyl; and wherein the alkyl, phenyl and cycloalkyl may be further substituted with from 1 to 3 substituents independently selected from the group consisting of hydroxyl, halo, C$_{1-4}$ alkyl, —CF$_3$, and —OCF$_3$;

or a pharmaceutically acceptable salt, ester, hydrate, solvate, polymorph, and/or prodrug thereof.

In some embodiments of Formula IVB, R$^2$ is C$_{1-15}$ alkyl. In many embodiments the alkyl moiety is further substituted with heteroaryl; wherein said heteroaryl is optionally further substituted with C$_{1-6}$ alkyl.

Exemplary R$^2$ moieties of Formula IVB include, but are not limited to,

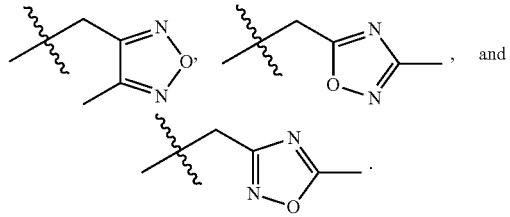

An exemplary R$^{10}$ moiety of Formula IVB includes —OCF$_3$.

Exemplary compounds of Formula IVB include
3-((4-methyl-1,2,5-oxadiazol-3-yl)methyl)-6-(4-(trifluoromethoxy)phenyl)quinazolin-4(3H)-one;
3-((3-methyl-1,2,4-oxadiazol-5-yl)methyl)-6-(4-(trifluoromethoxy)phenyl)quinazolin-4(3H)-one; and
3-((5-methyl-1,2,4-oxadiazol-3-yl)methyl)-6-(4-(trifluoromethoxy)phenyl)quinazolin-4(3H)-one;
or a pharmaceutically acceptable salt, ester, hydrate, solvate, polymorph, and/or prodrug thereof.

In certain embodiments, the compound of Formula IB is represented by Formula VA:

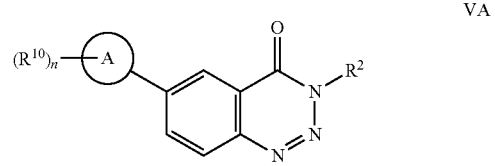

VA wherein:
A is heteroaryl;
n is 0, 1, 2, or 3;
R$^{10}$ is independently selected from the group consisting of halo, —NO$_2$, CN, —SF$_5$, —Si(CH$_3$)$_3$, —O—CF$_3$, —O—R$^{20}$, —S—R$^{20}$, —C(O)—R$^{20}$, C(O)OH, —N(R$^{20}$)(R$^{22}$), —C(O)—N(R$^{20}$)(R$^{22}$), —N(R$^{20}$)—C(O)—R$^{22}$, —N(R$^{20}$)—S(=O)$_2$—R$^{26}$, —S(=O)$_2$—R$^{20}$, —S(=O)$_2$—N(R$^{20}$)(R$^{22}$), C$_{1-4}$ alkyl, C$_{2-4}$ alkenyl, C$_{2-4}$ alkynyl, cycloalkyl, aryl, heteroaryl, and heterocyclyl; and wherein said alkyl, alkenyl, alkynyl, aryl, heteroaryl, cycloalkyl, or heterocyclyl are optionally substituted with one, two, or three substituents independently selected from the group consisting of halo, —NO$_2$, —O—CF$_3$, —O—CHF$_2$, phenyl, heterocyclyl, heteroaryl, C$_{1-4}$ alkyl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$;

R$^2$ is hydrogen, C$_{1-15}$ alkyl, C$_{1-4}$ alkoxy, —C(O)—O—R$^{26}$, —C(O)—N(R$^{26}$)(R$^{28}$), —N(R$^{20}$)—S(=O)$_2$—R$^{20}$, cycloalkyl, aryl, heteroaryl, or heterocyclyl;

wherein said alkyl, alkoxy, cycloalkyl, and heterocyclyl are optionally substituted with one, two, or three substituents independently selected from the group consisting of hydroxyl, alkyl, alkoxy, alkynyl, halo, —O₂, —O—CF₃, —O—CHF₂, aryl, heterocyclyl, heteroaryl, cycloalkyl, —(R²⁰)(R²²), —CF₃, —C(O)—R²⁰, —C(O)—O—R²⁰, —C(O)—N(R²⁰) (R²²), —N, oxo, and —O—R²⁰;

wherein said alkyl, alkoxy, cycloalkyl, aryl, heterocyclyl, or heteroaryl are optionally further substituted with one, two, or three substituents independently selected from the group consisting of hydroxyl, halo, —NO₂, —O—CF₃, $C_{1-6}$ alkyl, $C_{1-4}$ alkoxy, benzyl, aryl, heterocyclyl, heteroaryl, cycloalkyl, —N(R²⁰)(R²²), —C(O)—R²⁰, —C(O)—O—R²⁰, —C(O)—N(R²⁰)(R²²), —N, and —O—R²⁰; and wherein said $C_{1-6}$ alkyl, $C_{1-4}$ alkoxy, benzyl, aryl, heterocyclyl, heteroaryl, cycloalkyl, are optionally further substituted with one, two, or three substituents independently selected from the group consisting of hydroxyl, halo, —NO₂, —O—CF₃, —CF₃, —O—CHF₂, —(R²⁰)(R²²), —C(O)—R²⁰, —C(O)—O—R²⁰, —C(O)—N (R²⁰)(R²²), —CN, —S(O)₂—R²⁰ and —O—R²⁰;

R²⁰ and R²² are in each instance independently selected from the group consisting of hydrogen, $C_1$-$C_{15}$ alkyl, $C_2$-$C_{15}$ alkenyl, $C_2$-$C_{15}$ alkynyl, cycloalkyl, heterocyclyl, aryl, and heteroaryl; and wherein the alkyl, alkenyl, alkynyl, heterocyclyl, aryl, and heteroaryl are optionally substituted with one, two, or three substituents independently selected from the group consisting of hydroxyl, halo, $C_{1-4}$ alkyl, monoalkylamino, dialkylamino, alkyl amide, aryl amide, heteroaryl amide, —NO₂, —SO₂R²⁶, —CN, $C_{1-3}$ alkoxy, —CF₃, —OCF₃, —OCH₂CF₃, —C(O)—NH₂, aryl, cycloalkyl, and heteroaryl;

wherein said heteroaryl is optionally further substituted with $C_{1-4}$ alkyl, or cycloalkyl; or when R²⁰ and R²² are attached to a common nitrogen atom R²⁰ and R²² may join to form a heterocyclic or heteroaryl ring which is then optionally substituted with one, two, or three substituents independently selected from the group consisting of hydroxyl, halo, alkyl, benzyl, phenyl, phenoxy, benzyloxy, monoalkylamino, dialkylamino, alkyl amide, aryl amide, heteroaryl amide, —NO₂, —SO₂R²⁶, —CN, $C_{1-3}$ alkoxy, —CF₃, —OCF₃, aryl, heteroaryl and cycloalkyl; and R²⁶ and R²⁸ are in each instance independently selected from the group consisting of hydrogen, alkyl, and cycloalkyl; and wherein the alkyl, phenyl and cycloalkyl may be further substituted with from 1 to 3 substituents independently selected from the group consisting of hydroxyl, halo, $C_{1-4}$ alkoxy, —CF₃, and —OCF₃;

or a pharmaceutically acceptable salt, ester, hydrate, solvate, polymorph, and/or prodrug thereof.

In some embodiments of Formula VA, A is selected from the group consisting of pyridin-3-yl and pyrimidin-5-yl.

In some embodiments of Formula VA, n is 1.

In some embodiments of Formula VA, R² is hydrogen or $C_{1-15}$ alkyl. In many embodiments the alkyl moiety is further substituted with heteroaryl; wherein said heteroaryl is optionally further substituted with one, two, or three substituents independently selected from the group consisting of heteroaryl and —O—R²⁰; wherein said heteroaryl is optionally further substituted with $C_{1-6}$ alkyl; and R²⁰ is heteroaryl.

Exemplary R² moieties of Formula VA include, but are not limited to,

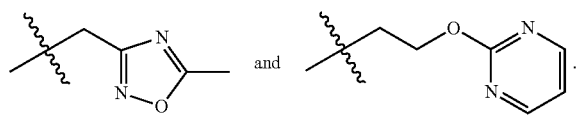

In some embodiments of Formula VA, R² is —N(R²⁰)(R²²) $C_{1-4}$ alkyl or heteroaryl; wherein R²⁰ and R²² are in each instance independently $C_1$-$C_{15}$ alkyl, and the alkyl is optionally substituted with one, two, or three halo; or R²⁰ and R²² are attached to a common nitrogen atom R²⁰ and R²² may join to form a heterocyclic ring. In many embodiments the alkyl or heteroaryl moiety of R² is further substituted with one, two, or three substituents independently selected from the group consisting of halo, and alkyl.

Exemplary R¹⁰ moieties of Formula VA include 2,2,2-trifluoroethoxy, —CF₃, and piperidin-1-yl.

Exemplary compounds of Formula VA include
3-((5-methyl-1,2,4-oxadiazol-3-yl)methyl)-6-(6-(2,2,2-trifluoroethoxy)pyridin-3-yl)benzo[d][1,2,3]triazin-4(3H)-one;

3-(2-(pyrimidin-2-yloxy)ethyl)-6-(6-(trifluoromethyl)pyridin-3-yl)benzo[d][1,2,3]triazin-4(3H)-one; and 6-(2-(piperidin-1-yl)pyrimidin-5-yl)-3-(2-(pyrimidin-2-yloxy)ethyl)benzo[d][1,2,3]triazin-4(3H)-one;

or a pharmaceutically acceptable salt, ester, hydrate, solvate, polymorph, and/or prodrug thereof.

In certain embodiments, the compound of Formula IA is represented by Formula VIA:

VIA

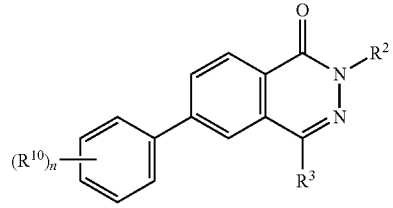

wherein:
n is 0, 1, 2, or 3;
R¹⁰ is independently selected from the group consisting of halo, —NO₂, CN, —SF₅, —Si(CH₃)₃, —O—CF₃, —O—R²⁰, —S—R²⁰, —C(O)—R²⁰, C(O)OH, —N(R²⁰)(R²²), —C(O)—N(R²⁰)(R²²), —N(R²⁰)—C (O)—R²², —N(R²⁰)—S(=O)₂—R²⁶, —S(=O)₂—R²⁰, —S(=O)₂—N(R²⁰)(R²²), $C_{1-4}$ alkyl, $C_{2-4}$ alkenyl, $C_{2-4}$ alkynyl, cycloalkyl, aryl, heteroaryl, and heterocyclyl; and wherein said alkyl, alkenyl, alkynyl, aryl, heteroaryl, cycloalkyl, or heterocyclyl are optionally substituted with one, two, or three substituents independently selected from the group consisting of halo, —NO₂, —O—CF₃, —O—CHF₂, phenyl, heterocyclyl, heteroaryl, $C_{1-4}$ alkyl, cycloalkyl, —N(R²⁰)(R²²), —C(O)—R²⁰, —C(O)—O—R²⁰, —C(O)—N(R²⁰) (R²²), —CN, and —O—R²⁰;

R² is hydrogen, $C_{1-15}$ alkyl, $C_{1-4}$ alkoxy, —C(O)—O—R²⁶, —C(O)—N(R²⁶)(R²⁸), —N(R²⁰)—S(=O)₂—R²⁰, cycloalkyl, aryl, heteroaryl, or heterocyclyl;

wherein said alkyl, alkoxy, cycloalkyl, and heterocyclyl are optionally substituted with one, two, or three substituents independently selected from the group consisting of hydroxyl, alkyl, alkoxy, alkynyl, halo, —$O_2$, —O—$CF_3$, —O—$CHF_2$, aryl, heterocyclyl, heteroaryl, cycloalkyl, —($R^{20}$)($R^{22}$), —C(O)—$R^{20}$, —C(O)—O—$R^{20}$, —C(O)—N($R^{20}$)($R^{22}$), —CN, oxo, and —O—$R^{20}$;
  wherein said alkyl, alkoxy, cycloalkyl, aryl, heterocyclyl, or heteroaryl are optionally further substituted with one, two, or three substituents independently selected from the group consisting of hydroxyl, halo, —$NO_2$, —$CF_3$, —O—$CF_3$, $C_{1-6}$ alkyl, $C_{1-4}$ alkoxy, benzyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —N, and —O—$R^{20}$; and
    wherein said $C_{1-6}$ alkyl, $C_{1-4}$ alkoxy, benzyl, aryl, heterocyclyl, heteroaryl, cycloalkyl, are optionally further substituted with one, two, or three substituents independently selected from the group consisting of hydroxyl, halo, —$NO_2$, —O—$CF_3$, —$CF_3$, —O—$CHF_2$, —($R^{20}$)($R^{22}$), —C(O)—$R^{20}$, —C(O)—O—$R^{20}$, —C(O)—N($R^{20}$)($R^{22}$), —CN, —S(O)$_2$—$R^{20}$ and —O—$R^{20}$;
$R^3$ is hydrogen, $C_{1-15}$ alkyl, cycloalkyl, aryl, heteroaryl, or heterocyclyl;
  wherein said alkyl is optionally substituted with one, two, or three substituents independently selected from the group consisting of hydroxyl, alkoxy, halo, —$NO_2$, —O—$CF_3$, —O—$CHF_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$;
    wherein said alkoxy, cycloalkyl, aryl, heterocyclyl, or heteroaryl are optionally further substituted with one, two, or three substituents independently selected from the group consisting of hydroxyl, halo, —$NO_2$, —O—$CF_3$, $C_{1-6}$ alkyl, $C_{1-4}$ alkoxy, benzyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$ ($R^{22}$), —CN, and —O—$R^{20}$; and
    wherein said $C_{1-6}$ alkyl, $C_{1-4}$ alkoxy, benzyl, aryl, heterocyclyl, heteroaryl, cycloalkyl, are optionally further substituted with one, two, or three substituents independently selected from the group consisting of hydroxyl, halo, —$NO_2$, —O—$CF_3$, —$CF_3$, —O—$CHF_2$, —N($R^{20}$) ($R^{22}$), —C(O)—$R^{20}$, —C(O)—O—$R^{20}$, —C(O)—N($R^{20}$ ($R^{22}$), —CN, and —O—$R^{20}$;
$R^{20}$ and $R^{22}$ are in each instance independently selected from the group consisting of hydrogen, $C_1$-$C_{15}$ alkyl, $C_2$-$C_{15}$ alkenyl, $C_2$-$C_{15}$ alkynyl, cycloalkyl, heterocyclyl, aryl, and heteroaryl; and
  wherein the alkyl, alkenyl, alkynyl, heterocyclyl, aryl, and heteroaryl are optionally substituted with one, two, or three substituents independently selected from the group consisting of hydroxyl, halo, $C_{1-4}$ alkyl, monoalkylamino, dialkylamino, alkyl amide, aryl amide, heteroaryl amide, —$NO_2$, —$SO_2R^{26}$, —CN, $C_{1-3}$ alkoxy, —$CF_3$, —$OCF_3$, —$OCH_2CF_3$, —C(O)—$NH_2$, aryl, cycloalkyl, and heteroaryl;
    wherein said heteroaryl is optionally further substituted with $C_{1-4}$ alkyl, or cycloalkyl; or
when $R^{20}$ and $R^{22}$ are attached to a common nitrogen atom $R^{20}$ and $R^{22}$ may join to form a heterocyclic or heteroaryl ring which is then optionally substituted with one, two, or three substituents independently selected from the group consisting of hydroxyl, halo, alkyl, benzyl, phenyl, phenoxy, benzyloxy, monoalkylamino, dialkylamino, alkyl amide, aryl amide, heteroaryl amide, —$NO_2$, —$SO_2R^{26}$, —CN, $C_{1-3}$ alkoxy, —$CF_3$, —$OCF_3$, aryl, heteroaryl and cycloalkyl; and
$R^{26}$ and $R^{28}$ are in each instance independently selected from the group consisting of hydrogen, alkyl, and cycloalkyl; and
  wherein the alkyl, phenyl and cycloalkyl may be further substituted with from 1 to 3 substituents independently selected from the group consisting of hydroxyl, halo, $C_{1-4}$ alkoxy, —$CF_3$, and —$OCF_3$;
or a pharmaceutically acceptable salt, ester, hydrate, solvate, polymorph, and/or prodrug thereof.

In some embodiments of Formula VIA, $R^2$ is hydrogen.

An exemplary $R^{10}$ moiety of Formula VIA includes —$OCF_3$.

In some embodiments of Formula VIA, $R^3$ is $C_{1-15}$ alkyl. An exemplary $R^3$ moiety of Formula VI includes methyl.

An exemplary compound of Formula VIA includes 4-methyl-6-(4-(trifluoromethoxy)phenyl)phthalazin-1(2H)-one;
or a pharmaceutically acceptable salt, ester, hydrate, solvate, polymorph, and/or prodrug thereof.

In certain embodiments, the compound of Formula IB is represented by Formula VIIA:

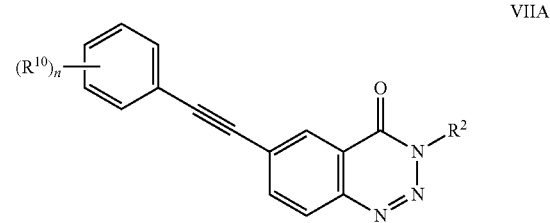

VIIA wherein:
n is 0, 1, 2, or 3;
$R^{10}$ is independently selected from the group consisting of halo, —$NO_2$, CN, —$SF_5$, —Si($CH_3$)$_3$, —O—$CF_3$, —O—$R^{20}$, —S—$R^{20}$, —C(O)—$R^{20}$, C(O)OH, —N($R^{20}$)($R^{22}$), —C(O)—N($R^{20}$)($R^{22}$), —N($R^{20}$)—C(O)—$R^{22}$, —N($R^{20}$)—S(=O)$_2$—$R^{26}$, —S(=O)$_2$—$R^{20}$, —S(=O)$_2$—N($R^{20}$)($R^{22}$), $C_{1-4}$ alkyl, $C_{2-4}$ alkenyl, $C_{2-4}$ alkynyl, cycloalkyl, aryl, heteroaryl, and heterocyclyl; and
  wherein said alkyl, alkenyl, alkynyl, aryl, heteroaryl, cycloalkyl, or heterocyclyl are optionally substituted with one, two, or three substituents independently selected from the group consisting of halo, —$NO_2$, —O—$CF_3$, —O—$CHF_2$, phenyl, heterocyclyl, heteroaryl, $C_{1-4}$ alkyl, cycloalkyl, —N($R^{20}$)($R^{22}$), —C(O)—$R^{20}$, —C(O)—O—$R^{20}$, —C(O)—N($R^{20}$) ($R^{22}$), —CN, and —O—$R^{20}$;
$R^2$ is hydrogen, $C_{1-15}$ alkyl, $C_{1-4}$ alkoxy, —C(O)—O—$R^{26}$, —C(O)—N($R^{26}$)($R^{28}$), —N($R^{20}$)—S(=O)$_2$—$R^{20}$, cycloalkyl, aryl, heteroaryl, or heterocyclyl;
  wherein said alkyl, alkoxy, cycloalkyl, and heterocyclyl are optionally substituted with one, two, or three substituents independently selected from the group consisting of hydroxyl, alkyl, alkoxy, alkynyl, halo, —$O_2$, —O—$CF_3$, —O—$CHF_2$, aryl, heterocyclyl, heteroaryl, cycloalkyl, ($R^{20}$)($R^{22}$), —C(O)—$R^{20}$, —C(O)—O—$R^{20}$, —C(O)—N($R^{20}$)($R^{22}$), —CN, oxo, and —O—$R^{20}$;
    wherein said alkyl, alkoxy, cycloalkyl, aryl, heterocyclyl, or heteroaryl are optionally further substituted with one, two, or three substituents independently selected from the group consisting of hydroxyl, halo, —NO$_2$, —CF$_3$, —O—CF$_3$, C$_{1-6}$ alkyl, C$_{1-4}$ alkoxy, benzyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$; and wherein said C$_{1-6}$ alkyl, C$_{1-4}$ alkoxy, benzyl, aryl, heterocyclyl, heteroaryl, cycloalkyl, are optionally further substituted with one, two, or three substituents independently selected from the group consisting of hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, —S(O)$_2$—R$^{20}$ and —O—R$^{20}$;

R$^{20}$ and R$^{22}$ are in each instance independently selected from the group consisting of hydrogen, C$_1$-C$_{15}$ alkyl, C$_2$-C$_{15}$ alkenyl, C$_2$-C$_{15}$ alkynyl, cycloalkyl, heterocyclyl, aryl, and heteroaryl; and wherein the alkyl, alkenyl, alkynyl, heterocyclyl, aryl, and heteroaryl are optionally substituted with one, two, or three substituents independently selected from the group consisting of hydroxyl, halo, C$_{1-4}$ alkyl, monoalkylamino, dialkylamino, alkyl amide, aryl amide, heteroaryl amide, —NO$_2$, —SO$_2$R$^{26}$, —CN, C$_{1-3}$ alkoxy, —CF$_3$, —OCF$_3$, —OCH$_2$CF$_3$, —C(O)—NH$_2$, —C(O)—NH$_2$, aryl, cycloalkyl, and heteroaryl;

wherein said heteroaryl is optionally further substituted with C$_{1-4}$ alkyl, or cycloalkyl; or when R$^{20}$ and R$^{22}$ are attached to a common nitrogen atom R$^{20}$ and R$^{22}$ may join to form a heterocyclic or heteroaryl ring which is then optionally substituted with one, two, or three substituents independently selected from the group consisting of hydroxyl, halo, alkyl, benzyl, phenyl, phenoxy, benzyloxy, monoalkylamino, dialkylamino, alkyl amide, aryl amide, heteroaryl amide, —NO$_2$, —SO$_2$R$^{26}$, —CN, C$_{1-3}$ alkoxy, —CF$_3$, —OCF$_3$, aryl, heteroaryl and cycloalkyl; and R$^{26}$ and R$^{28}$ are in each instance independently selected from the group consisting of hydrogen, alkyl, and cycloalkyl; and wherein the alkyl, phenyl and cycloalkyl may be further substituted with from 1 to 3 substituents independently selected from the group consisting of hydroxyl, halo, C$_{1-4}$ alkoxy, —CF$_3$, and —OCF$_3$;

or a pharmaceutically acceptable salt, ester, hydrate, solvate, polymorph, and/or prodrug thereof.

In some embodiments of Formula VIIA, R$^2$ is C$_{1-15}$ alkyl. In many embodiments the alkyl moiety is further substituted with with —O—R$^{20}$; wherein R$^{20}$ is heteroaryl.

An exemplary R$^2$ moiety of Formula VIIA includes

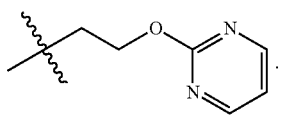 [SMILES: *CCOc1ncccn1]

An exemplary R$^{10}$ moiety of Formula VIIA includes —OCF$_3$.

An exemplary compound of Formula VIIA includes 3-(2-(pyrimidin-2-yloxy)ethyl)-6-((4-(trifluoromethoxy)phenyl)ethynyl)benzo[d][1,2,3]triazin-4(3H)-one;

or a pharmaceutically acceptable salt, ester, hydrate, solvate, polymorph, and/or prodrug thereof.

4. Further Embodiments

In some embodiments, the compounds provided by the present disclosure are effective in the treatment of conditions or diseases known to respond to administration of late sodium channel blockers, including but not limited to cardiovascular diseases such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, and myocardial infarction. In some embodiments, compounds provided by the present disclosure which function as late sodium channel blockers may be used in the treatment of diseases affecting the neuromuscular system resulting in pain, itching, seizures, or paralysis, or in the treatment of diabetes or reduced insulin sensitivity, and disease states related to diabetes, such as diabetic peripheral neuropathy.

Certain compounds of the disclosure may also possess a sufficient activity in modulating neuronal sodium channels, i.e., Na$_v$ 1.1., 1.2, 1.5, 1.7, and/or 1.8, and may have appropriate pharmacokinetic properties such that they may active with regard to the central and/or peripheral nervous system. Consequently, some compounds of the disclosure may also be of use in the treatment of epilepsy or pain or itching of a neuropathic origin.

In one embodiment, this disclosure provides a method of treating a disease state in a mammal that is alleviable by treatment with an agent capable of reducing late sodium current, comprising administering to a mammal in need thereof a therapeutically effective dose of a compound of Formula I as described above. In another embodiment, the disease state is a cardiovascular disease selected from one or more of atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease, pulmonary hypertension, and intermittent claudication. In another embodiment, the disease state is diabetes or diabetic peripheral neuropathy. In a further embodiment, the disease state results in one or more of neuropathic pain, epilepsy, seizures, or paralysis.

In one embodiment, this disclosure provides a method of treating diabetes in a mammal, comprising administering to a mammal in need thereof a therapeutically effective dose of a compound of Formula I as described above. Diabetes mellitus is a disease characterized by hyperglycemia; altered metabolism of lipids, carbohydrates and proteins; and an increased risk of complications from vascular disease. Diabetes is an increasing public health problem, as it is associated with both increasing age and obesity.

There are two major types of diabetes mellitus: 1) Type I, also known as insulin dependent diabetes (IDDM) and 2) Type II, also known as insulin independent or non-insulin dependent diabetes (NIDDM). Both types of diabetes mellitus are due to insufficient amounts of circulating insulin and a decrease in the response of peripheral tissue to insulin.

Type I diabetes results from the body's failure to produce insulin, the hormone that "unlocks" the cells of the body, allowing glucose to enter and fuel them. The complications of Type I diabetes include heart disease and stroke; retinopathy (eye disease); kidney disease (nephropathy); neuropathy (nerve damage); as well as maintenance of good skin, foot and oral health.

Type II diabetes results from the body's inability to either produce enough insulin or the cells inability to use the insulin that is naturally produced by the body. The condition where the body is not able to optimally use insulin is called insulin resistance. Type II diabetes is often accompanied by high blood pressure and this may contribute to heart disease. In patients with type II diabetes mellitus, stress, infection, and medications (such as corticosteroids) can also lead to severely elevated blood sugar levels. Accompanied by dehydration, severe blood sugar elevation in patients with type II diabetes can lead to an increase in blood osmolality (hyperosmolar state). This condition can lead to coma.

It has been suggested that ranolazine (RANEXA®, a selective inhibitor of INaL) may be an antidiabetic agent that causes β-cell preservation and enhances insulin secretion in a glucose-dependent manner in diabetic mice (see, Y. Ning et al. J Pharmacol Exp Ther. 2011, 337(1), 50-8). Therefore it is contemplated that the compounds of Formula I as disclosed herein can be used as antidiabetic agents for the treatment of diabetes.

Pharmaceutical Compositions and Administration

Compounds provided in accordance with the present disclosure are usually administered in the form of pharmaceutical compositions. This disclosure therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Preferably, for parenteral administration, sterile injectable solutions are prepared containing a therapeutically effective amount, e.g., 0.1 to 700 mg, of a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the disclosure can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616, 345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g, or alternatively, or 100 mg to 500 mg, of a compound described herein, and for parenteral administration, preferably from 0.1 mg to 700 mg, or alternatively, 0.1 mg to 100 mg, of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Combination Therapy

Patients being treated by administration of the late sodium channel blockers of the disclosure often exhibit diseases or conditions that benefit from treatment with other therapeutic agents. These diseases or conditions can be of the cardiovascular nature or can be related to pulmonary disorders, metabolic disorders, gastrointestinal disorders and the like. Additionally, some coronary patients being treated by administration of the late sodium channel blockers of the disclosure exhibit conditions that can benefit from treatment with therapeutic agents that are antibiotics, analgesics, and/or antidepressants and anti-anxiety agents.

Cardiovascular Agent Combination Therapy

Cardiovascular related diseases or conditions that can benefit from a combination treatment of the late sodium channel blockers of the disclosure with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the late sodium channel blockers of the disclosure with therapeutic agents suitable for treating cardiovascular related conditions allows enhancement in the standard of care therapy the patient is currently receiving.

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral®), atenolol (Tenormin®), betaxolol (Kerlone®), bisoprolol/hydrochlorothiazide (Ziac®), bisoprolol (Zebeta®), carteolol (Cartrol®), esmolol (Brevibloc®), labetalol (Normodyne®, Trandate®), metoprolol (Lopressor®, Toprol® XL), nadolol (Corgard®), propranolol (Inderal®), sotalol (Betapace®), and timolol (Blocadren®).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc®, Lotrel®), bepridil (Vascor®), diltiazem (Cardizem®, Tiazac®), felodipine (Plendil®), nifedipine (Adalat®, Procardia®), nimodipine (Nimotop®), nisoldipine (Sular), verapamil (Calan®, Isoptin®, Verelan®), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn®), furosemide (Lasix®), bumetanide (Bumex®), spironolactone (Aldactone®), and eplerenone (Inspra®).

Angiotensin converting enzyme (ACE) inhibitors reduce the workload on the heart by expanding the blood vessels and decreasing resistance to blood flow. Examples of ACE inhibitors include benazepril (Lotensin®), captopril (Capoten®), enalapril (Vasotec®), fosinopril (Monopril®), lisinopril Zestril®), moexipril (Univasc®), perindopril (Aceon®), quinapril (Accupril®), ramipril (Altace®), and trandolapril (Mavik®).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (Plavix®), prasugrel (Effient®), dipyridamole, cilostazol, persantine sulfinpyrazone, dipyridamole, indomethacin, and glycoprotein llb/llla inhibitors, such as abciximab, tirofiban, and eptifibatide (Integrelin®). Beta blockers and calcium channel blockers also have a platelet-inhibiting effect.

Anticoagulants prevent blood clots from growing larger and prevent the formation of new clots. Examples of anticoagulants include bivalirudin (Angiomax®), warfarin (Coumadin®), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest (see U.S. Patent Application Publication No. 2010/0056536 and U.S. Patent Application Publication No. 2011/0183990, the entirety of which are incorporated herein).

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot formation. Examples of antihypertensive agents include alpha-1-adrenergic antagonists, such as prazosin (Minipress®), doxazosin mesylate (Cardura®), prazosin hydrochloride (Minipress®), prazosin, polythiazide (Minizide®), and terazosin hydrochloride (Hytrin®); beta-adrenergic antagonists, such as propranolol (Inderal®), nadolol (Corgard®), timolol (Blocadren®), metoprolol (Lopressor®), and pindolol (Visken®); central alpha-adrenoceptor agonists, such as clonidine hydrochloride (Catapres®), clonidine hydrochloride and chlorthalidone (Clorpres®, Combipres®), guanabenz Acetate (Wytensin®), guanfacine hydrochloride (Tenex®), methyldopa (Aldomet®), methyldopa and chlorothiazide (Aldoclor®), methyldopa and hydrochlorothiazide (Aldoril®); combined alpha/beta-adrenergic antagonists, such as labetalol (Normodyne®, Trandate®), carvedilol (Coreg®); adrenergic neuron blocking agents, such as guanethidine (Ismelin®), reserpine (Serpasil®); central nervous system-acting antihypertensives, such as clonidine (Catapres®), methyldopa (Aldomet®), guanabenz (Wytensin®); anti-angiotensin II agents; ACE inhibitors, such as perindopril (Aceon®) captopril (Capoten®), enalapril (Vasotec®), lisinopril Zestril®); angiotensin-II receptor antagonists, such as candesartan (Atacand®), eprosartan (Teveten®), irbesartan (Avapro®), losartan (Cozaar®), telmisartan (Micardis®), valsartan (Diovan®); calcium channel blockers, such as verapamil (Calan®, Isoptin®), diltiazem (Cardizem®), nifedipine (Adalat®, Procardia®); diuretics; direct vasodilators, such as nitroprusside (Nipride®), diazoxide (Hyperstat® IV), hydralazine (Apresoline®), minoxidil (Loniten®), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip®), ciprofibrate (Modalim®), and statins, such as atorvastatin (Lipitor®), fluvastatin (Lescol®), lovastatin (Mevacor®, Altocor®), mevastatin, pitavastatin (Livalo®, Pitava®) pravastatin (Lipostat®), rosuvastatin (Crestor®), and simvastatin (Zocor®).

In this invention, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient a compound as disclosed herein (e.g., Formula I) in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire®, Bricanyl®), albuterol (Proventil®), salmeterol (Serevent®, Serevent Diskus®), theophylline, ipratropium bromide (Atrovent®), tiotropium (Spiriva®), methylprednisolone (Solu-Medrol®, Medrol®), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix®), lansoprazole (Prevacid®), esomeprazole (Nexium®), omeprazole (Prilosec®), rabeprazole; H2 blockers, such as cimetidine (Tagamet®), ranitidine (Zantac®), famotidine (Pepcid®), nizatidine (Axid®); prostaglandins, such as misoprostol (Cytotec®); sucralfate; and antacids.

Antibiotics, Analgesics, Antidepressants and Anti-Anxiety Agents Combination Therapy Patients presenting with an acute coronary disease event may exhibit conditions that benefit from administration of therapeutic agent or agents that are antibiotics, analgesics, antidepressant and anti-anxiety agents in combination with a compound as disclosed herein (e.g., Formula I).

Antibiotics

Antibiotics are therapeutic agents that kill, or stop the growth of, microorganisms, including both bacteria and fungi. Example of antibiotic agents include β-Lactam antibiotics, including penicillins (amoxicillin), cephalosporins, such as cefazolin, cefuroxime, cefadroxil (Duricef®), cephalexin (Keflex®), cephradine (Velosef®), cefaclor (Ceclor®), cefuroxime axtel (Ceftin®), cefprozil (Cefzil®), loracarbef (Lorabid®), cefixime (Suprax®), cefpodoxime proxetil (Vantin®), ceftibuten (Cedax®), cefdinir (Omnicef®), ceftriaxone (Rocephin®), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the late sodium channel blockers of the disclosure to treat neuropathic pain via inhibition of the $Na_V$ 1.7 and 1.8 sodium channels, combination with analgesics are particularly invisioned. See U.S. Patent Application Publication 20090203707.

Antidepressant and Anti-Anxiety Agents

Antidepressant and anti-anxiety agents include those agents used to treat anxiety disorders, depression, and those used as sedatives and tranquillers. Examples of antidepressant and anti-anxiety agents include benzodiazepines, such as diazepam, lorazepam, and midazolam; enzodiazepines; barbiturates; glutethimide; chloral hydrate; meprobamate; sertraline (Zoloft®, Lustral®, Apo-Sertral®, Asentra®, Gladem®, Serlift®, Stimuloton®); escitalopram (Lexapro®, Cipralex®); fluoxetine (Prozac®, Sarafem®, Fluctin®, Fontex®, Prodep®, Fludep®, Lovan®); venlafaxine (Effexor® XR, Efexor®); citalopram (Celexa®, Cipramil®, Talohexane®); paroxetine (Paxil®, Seroxat®, Aropax®); trazodone (Desyrer®); amitriptyline (Elavir®); and bupropion (Wellbutrin®, Zyban®).

Accordingly, one aspect of the disclosure provides for a composition comprising the late sodium channel blockers of the disclosure and at least one therapeutic agent. In an alternative embodiment, the composition comprises the late sodium channel blockers of the disclosure and at least two therapeutic agents. In further alternative embodiments, the composition comprises the late sodium channel blockers of the disclosure and at least three therapeutic agents, the late sodium channel blockers of the disclosure and at least four therapeutic agents, or the late sodium channel blockers of the disclosure and at least five therapeutic agents.

The methods of combination therapy include co-administration of a single formulation containing the the late sodium channel blockers of the disclosure and therapeutic agent or agents, essentially contemporaneous administration of more than one formulation comprising the late sodium channel blocker of the disclosure and therapeutic agent or agents, and consecutive administration of a late sodium channel blocker of the disclosure and therapeutic agent or agents, in any order, wherein preferably there is a time period where the late sodium channel blocker of the disclosure and therapeutic agent or agents simultaneously exert their therapeutic affect.

5. Synthesis of Example Compounds

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula I, may be accomplished as described in the following examples. If available, reagents may be purchased commercially, e.g. from Sigma Aldrich or other chemical suppliers.

General Syntheses

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present invention, inspection of the structure of the compound to be synthesized will provide the identity of each substituent group in view of the general schemes provided herein. The identity of the final product will generally render apparent the identity of the necessary starting materials by a simple process of inspection, given the examples herein.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis*, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula I

The compounds of Formula I are typically prepared by first providing the molecular core 1-2; which may be commercially obtained, for example 7-bromophthalazin-1(2H)-one, 6-bromophthalazin-1(2H)-one, and the like, or synthesized de novo, and then attaching the desired -Q-R$^1$ substituents using suitable coupling conditions (e.g., Suzuki coupling) and the desired —R$^2$ substituents using suitable substitution conditions. These processes are shown below in Scheme 1 for the synthesis of a compound of Formula I (or a compound of Formula IA, IB, IC, ID, II, IIA, III, IIIA, IV, IVA, IVB, V, VA, VI, VIA, VIIA, VIIIA, or IXA).

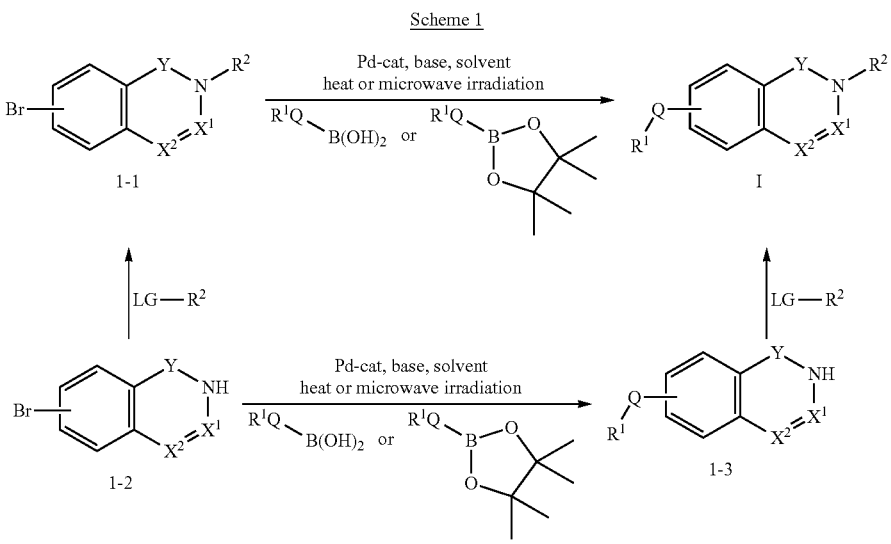

Scheme 1

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and In general, a halogenated compound of formula 1-1, in this case a brominated compound, is reacted with an appropriately substituted boronic acid derivative of formula R$^1$Q-B(OH)$_2$, or a boronic ester thereof, in an inert solvent, for example aqueous N,N-dimethylformamide, in the presence of a mild base, for example potassium carbonate or sodium bicarbonate. The reaction is typically conducted in the presence of a metal catalyst with an appropriate ligand, for example dichlorobis(triphenylphosphine) palladium(II), at a temperature of about 120-170° C., for about 10 minutes to about 1 hour or at a lower temperature, i.e., 90-110° C. for 2 to 5 days. When the reaction is substantially complete, the product of Formula I is isolated by conventional means.

It will be appreciated that the $R^2$ substituent can be modified or added either before (as shown in Scheme 1) or after the addition of the $R^1$ moiety. The $R^2$ moiety may be coupled to the core 1-2 under substitution reaction conditions with an appropriate reagent of formula LG-$R^2$ (where LG is a leaving group such as a halo, hydroxyl, alkoxy, and the like) as shown in Scheme 1. Typical substitution reaction conditions include the presence of a base, such as potassium carbonate, sodium bicarbonate, triethylamine, and the like, in a polar aprotic solvent, such as N,N-dimethylformamide, and optionally an elevated temperature of about 100-150° C., or in a microwave. Also, in the case where the $R^2$ substituent contains a heteroaryl ring, the heteroaryl ring may be synthesized and cyclized before or after addition of the -Q-$R^1$ portion.

Optional Core Synthesis

In certain embodiments, the core may be synthesized and cyclized before or after addition of the -Q-$R^1$ substituent (Scheme 2). For example, such alternative routes for the synthesis of benzo[d][1,2,3]triazin-4(3H)-one compounds of Formula 2-8 (i.e., Formula II, IIA, VA, and VIIA) are shown in Scheme 2, below.

sodium nitrite in the presence of an acid, such as hydrochloric acid, in a suitable solvent system, such as aqueous dioxane. Compounds of Formula 2-5 can be provided from compounds of Formula 2-4 via reaction with an appropriately substituted boronic acid derivative of formula $R^1$Q-B(OH)$_2$, or a boronic ester thereof, under typical coupling reaction conditions.

Typical coupling reaction conditions an inert solvent, for example aqueous N,N-dimethylformamide, in the presence of a mild base, for example potassium carbonate or sodium bicarbonate. The reaction is typically conducted in the presence of a metal catalyst with an appropriate ligand, for example dichlorobis(triphenylphosphine) palladium(II), at a temperature of about 120-170° C., for about 10 minutes to about 1 hour or at a lower temperature, i.e., 90-110° C. for 2 to 5 days. When the reaction is substantially complete, the compounds of Formula 2-5 can be isolated by conventional means.

In another embodiment, compounds of Formula 2-5 can be provided from compounds of Formula 2-6. For example, compounds of Formula 2-6 are coupled with an appropriately substituted boronic acid derivative of formula $R^1$Q-B(OH)$_2$, or a boronic ester thereof, under typical coupling reaction conditions as described hereinabove, to afford compounds of Formula 2-7. Compounds of Formula 2-7 are cyclized to afford compounds of Formula 2-5 using sodium

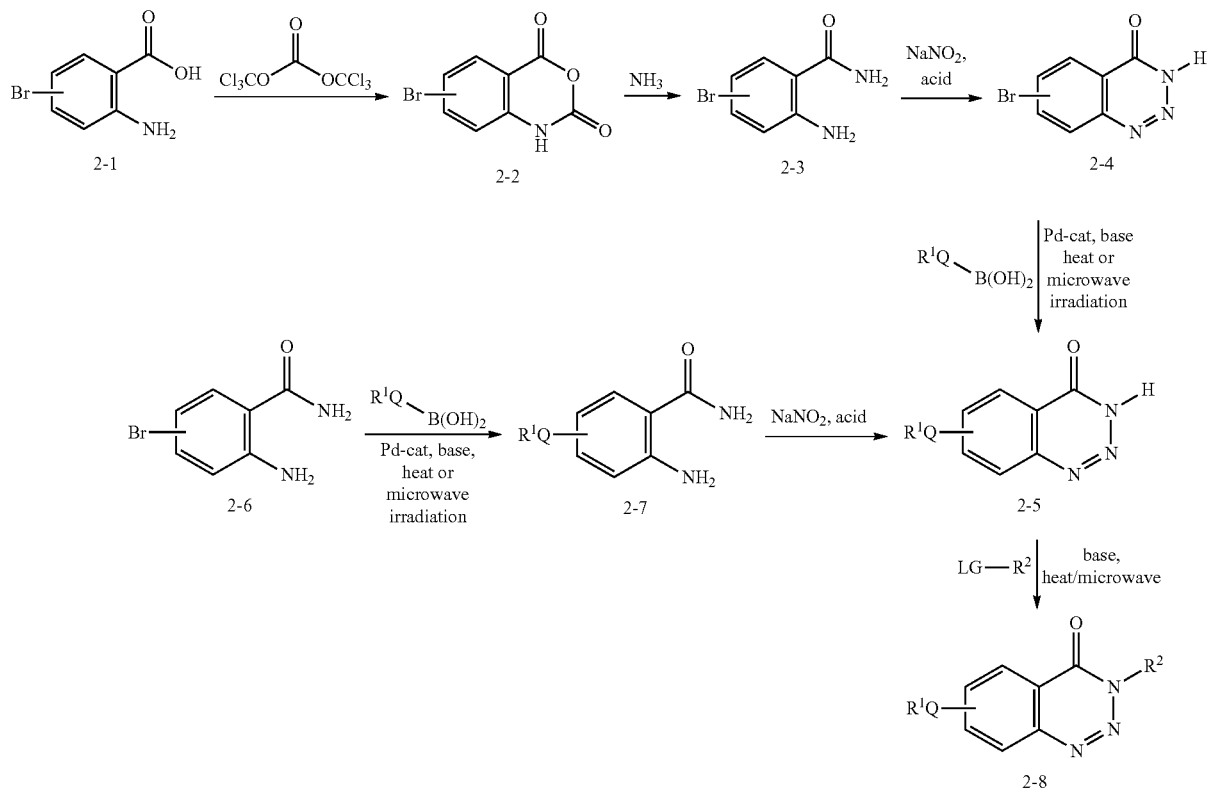

Scheme 2

In one embodiment, compounds of Formula 2-2 are prepared from commercially available compounds of Formula 2-1 using bis(trichloromethyl) carbonate. Reaction of compounds of Formula 2-2 with ammonia in a suitable solvent, such as THF affords compounds of Formula 2-3, which are converted to compounds of Formula 2-4 with nitrite in the presence of an acid, such as hydrochloric acid, in a suitable solvent system, such as aqueous dioxane.

The $R^2$ moiety may be coupled to compounds of Formula 2-5 under substitution reaction conditions with an appropriate reagent of formula LG-$R^2$ (where LG is a leaving group such as a halo, hydroxyl, alkoxy, or the like) as shown in Scheme 1 to afford benzo[d][1,2,3]triazin-4(3H)-one compounds of Formula 2-8. Typical substitution reaction conditions include the presence of a base, such as potassium carbonate, sodium bicarbonate, triethylamine, and the like, in a polar aprotic solvent, such as N,N-dimethylformamide, and optionally an elevated temperature of about 100-150° C., or in a microwave.

In other embodiments, the core may be synthesized and cyclized before or after addition of the $R^2$ substitutent (Scheme 3). For example, such an alternative route for the synthesis of benzo[d][1,2,3]triazin-4(3H)-one compounds of Formula 2-8 (i.e., Formula II, IIA, VA, and VIIA) are shown in Scheme 3, below.

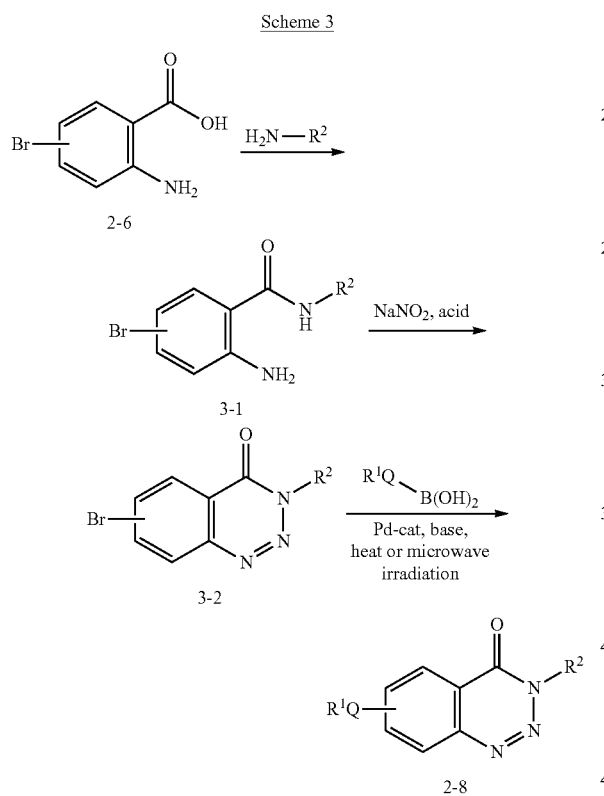

In Scheme 3, amides of Formula 3-1 can be prepared from the corresponding acid of Formula 2-6 using an appropriately substituted primary amine of formula $H_2N$—$R^2$ under standard reaction conditions, including, but not limited to, the use of a suitable base, such as diisopropylethylamine. In addition, the acid of Formula 2-6 can first be converted to the corresponding acid halide using, for example, thionylchloride, prior to reaction with the amine of formula $H_2N$—$R^2$. Compounds of Formula 3-1 are then cyclized to afford compounds of Formula 3-2 using sodium nitrite in the presence of an acid, such as hydrochloric acid, in a suitable solvent system, such as aqueous dioxane. Compounds of Formula 3-2 are then coupled with an appropriately substituted boronic acid derivative of formula $R^1Q$-$B(OH)_2$, or a boronic ester thereof, under typical coupling reaction conditions as described hereinabove, to afford compounds of Formula 2-8.

In certain embodiments, the core may be synthesized and cyclized before or after addition of the $R^2$ substitutent (Schemes 4 and 5). For example, the synthesis of 2H-benzo[e][1,3]oxazin-4(3H)-one compounds of Formula 4-4 (e.g., Formula V and VIIIA) are shown in Scheme 4, below.

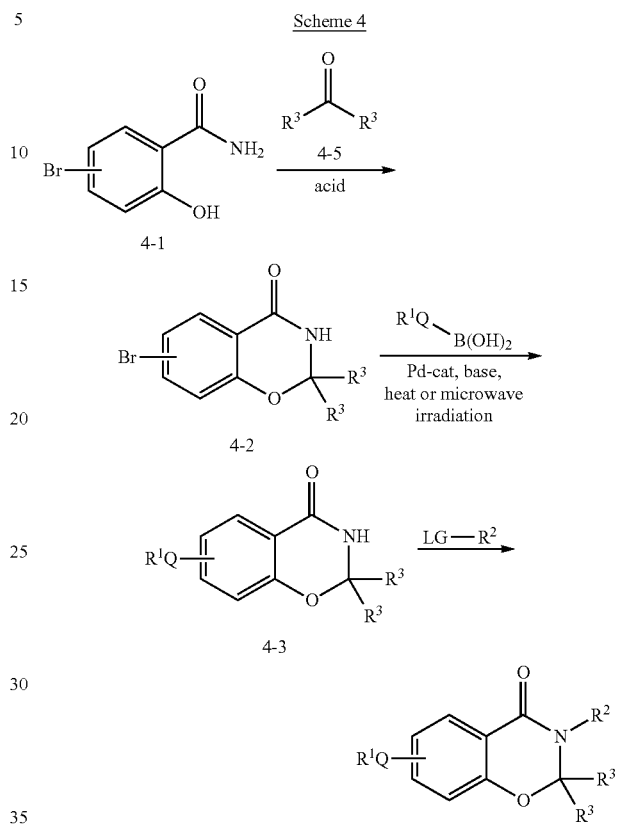

In Scheme 4, compounds of Formula 4-2 can be prepared from the corresponding amide of Formula 4-1 via cyclization using a reagent of Formula 4-5, or a protected version thereof, in the presence of an acid, such as para-toluenesulfonic acid or hydrochloric acid, in a suitable solvent system, such as toluene, to afford compounds of Formula 4-2. Compounds of Formula 4-2 can then be coupled with an appropriately substituted boronic acid derivative of formula $R^1Q$-$B(OH)_2$, or a boronic ester thereof, under typical coupling reaction conditions as described hereinabove, to afford compounds of Formula 4-3. The $R^2$ moiety may be coupled to compounds of Formula 4-3 under substitution reaction conditions with an appropriate reagent of formula LG-$R^2$ (where LG is a leaving group such as a halo, hydroxyl, alkoxy, or the like) as shown in Scheme 1 to afford compounds of Formula 4-4. Typical substitution reaction conditions include the presence of a base, such as potassium carbonate, sodium bicarbonate, triethylamine, and the like, in a polar aprotic solvent, such as N,N-dimethylformamide, and optionally an elevated temperature of about 100-150° C., or in a microwave.

In other embodiments, an alternative synthesis of 2H-benzo[e][1,3]oxazin-4(3H)-one compounds of Formula 4-4 (e.g., Formula V and VIIIA) is shown in Scheme 5, below.

Scheme 5

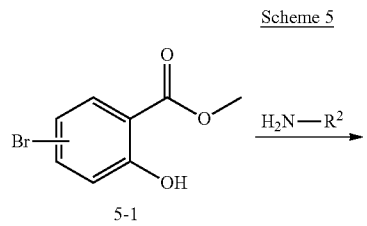

5-1

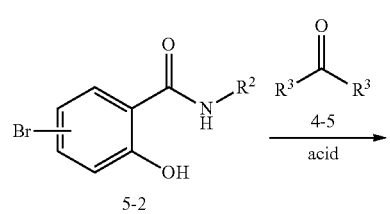

5-2

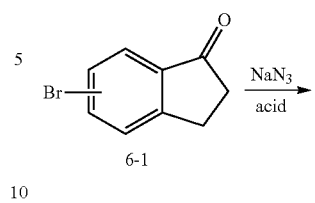

5-3

Scheme 6

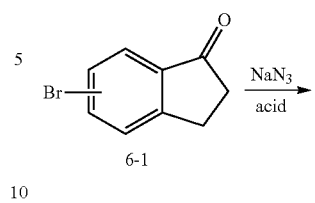

6-1

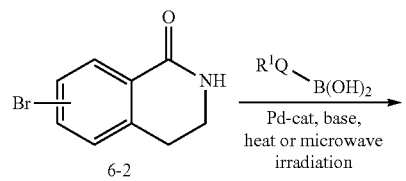

6-2

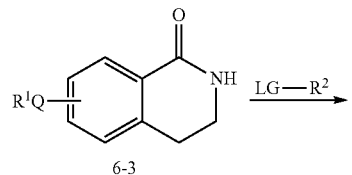

6-3

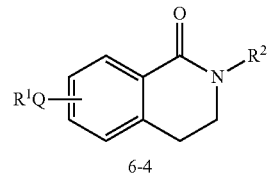

6-4

4-4

In Scheme 5, amides of Formula 5-2 can be prepared from the corresponding ester of Formula 5-1 using an appropriately substituted primary amine of formula H₂N—R² under standard reaction conditions, including, but not limited to, the use of a suitable base, such as diisopropylethylamine. Compounds of Formula 5-2 are then cyclized to afford compounds of Formula 5-3 using a reagent of Formula 4-5, or a protected version thereof, in the presence of an acid, such as para-toluenesulfonic acid or hydrochloric acid, in a suitable solvent system, such as toluene. Compounds of Formula 5-3 are then coupled with an appropriately substituted boronic acid derivative of formula R¹Q-B(OH)₂, or a boronic ester thereof, under typical coupling reaction conditions as described hereinabove, to afford compounds of Formula 4-4.

In another embodiment, compounds of Formula 6-4 (e.g., Formula VI and IXA) can be synthesized as shown in Scheme 6, below.

In Scheme 6, compounds of Formula 6-2 can be prepared from the corresponding 2,3-dihydro-1H-inden-1-one of Formula 6-1 using about a 1.5 molar excess of sodium azide in the presence of an acid, such as methanesulfonic acid, in an ice bath. Compounds of Formula 6-2 are then coupled with an appropriately substituted boronic acid derivative of formula R¹Q-B(OH)₂, or a boronic ester thereof, under typical coupling reaction conditions as described hereinabove, to afford compounds of Formula 6-3. The R² moiety may be coupled to compounds of Formula 6-3 under substitution reaction conditions with an appropriate reagent of formula LG-R² (where LG is a leaving group such as a halo, hydroxyl, alkoxy, or the like) to afford compounds of Formula 6-4. Typical substitution reaction conditions include the presence of a base, such as potassium carbonate, sodium bicarbonate, triethylamine, and the like, in a polar aprotic solvent, such as N,N-dimethylformamide, and optionally an elevated temperature of about 100-150° C., or in a microwave.

In certain embodiments, the core may be synthesized and cyclized before or after addition of the -Q-R¹ substitutent (Scheme 7). For example, such routes for the synthesis of quinazolin-4(3H)-one compounds of Formula 7-5 (i.e., Formula IV, IVA and IVB) are shown in Scheme 7, below.

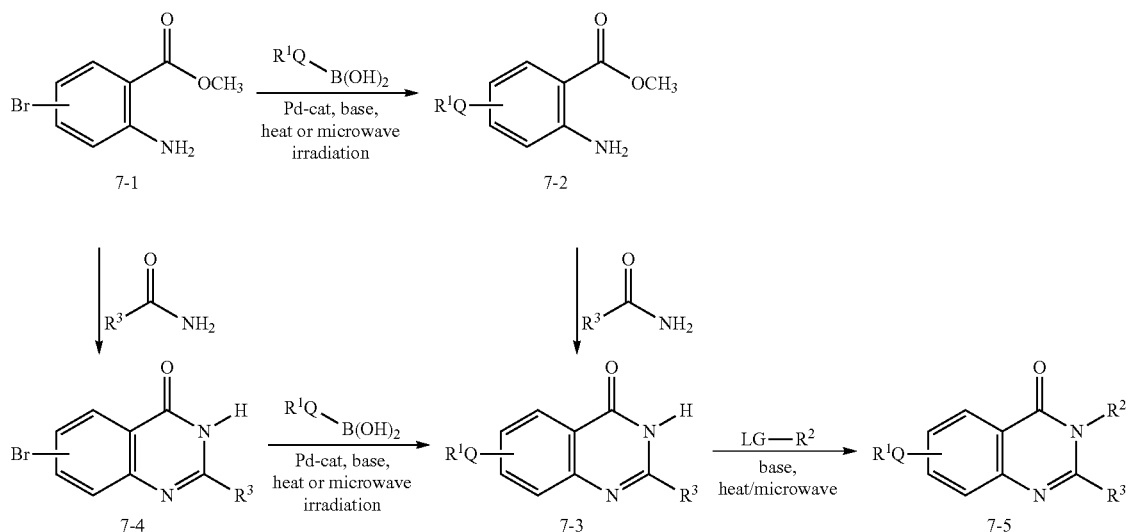

Scheme 7

In one embodiment, compounds of Formula 7-2 can be provided from compounds of Formula 7-1. For example, compounds of Formula 7-2 are coupled with an appropriately substituted boronic acid derivative of formula $R^1Q$-B$(OH)_2$, or a boronic ester thereof, under typical coupling reaction conditions as described hereinabove, to afford compounds of Formula 7-2. Compounds of Formula 7-2 are then cyclized using an excess of the appropriate amide to afford compounds of Formula 7-3.

In another embodiment, compounds of Formula 7-3 are prepared from compounds of Formula 7-1 by way of compounds of Formula 7-4. Reaction of compounds of Formula 7-1 with an excess of the appropriate amide affords compounds of Formula 7-4, which are then converted to compounds of Formula 7-3 via reaction with an appropriately substituted boronic acid derivative of formula $R^1Q$-B$(OH)_2$, or a boronic ester thereof, under typical coupling reaction conditions. Typical coupling reaction conditions an inert solvent, for example aqueous N,N-dimethylformamide, in the presence of a mild base, for example potassium carbonate or sodium bicarbonate. The reaction is typically conducted in the presence of a metal catalyst with an appropriate ligand, for example dichlorobis(triphenylphosphine) palladium(II), at a temperature of about 120-170° C., for about 10 minutes to about 1 hour or at a lower temperature, i.e., 90-110° C. for 2 to 5 days. When the reaction is substantially complete, the compounds of Formula 7-3 can be isolated by conventional means.

The $R^2$ moiety may be coupled to compounds of Formula 7-3 under substitution reaction conditions with an appropriate reagent of formula LG-$R^2$ (where LG is a leaving group such as a halo, hydroxyl, alkoxy, or the like) as shown in Scheme 1 to afford quinazolin-4(3H)-one compounds of Formula 7-5. Typical substitution reaction conditions include the presence of a base, such as potassium carbonate, sodium bicarbonate, triethylamine, and the like, in a polar aprotic solvent, such as N,N-dimethylformamide, and optionally an elevated temperature of about 100-150° C., or in a microwave.

In other embodiments, the core may be synthesized and cyclized before or after addition of the $R^2$ substitutent (Scheme 8). For example, such an alternative route for the synthesis of quinazolin-4(3H)-one compounds of Formula 7-5 (i.e., Formula IV and IVA) are shown in Scheme 8, below.

Scheme 8

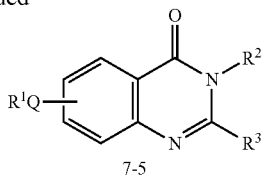

In Scheme 8, amides of Formula 3-1 can be prepared from the corresponding acid of Formula 2-6 using an appropriately substituted primary amine of formula $H_2N-R^2$ according to Scheme 3, hereinabove. Compounds of Formula 3-1 are then cyclized using triethyl orthoformate (i.e., $(EtO)_3CR^3$), or an appropriately substituted derivative thereof, to afford compounds of Formula 8-1. Compounds of Formula 8-1 are then coupled with an appropriately substituted boronic acid derivative of formula $R^1Q\text{-}B(OH)_2$, or a boronic ester thereof, under typical coupling reaction conditions as described hereinabove, to afford quinazolin-4(3H)-one compounds of Formula 7-5.

Alternatively, compounds of Formula 7-4 are coupled with an appropriately substituted boronic acid derivative of formula $R^1Q\text{-}B(OH)_2$, or a boronic ester thereof, under typical coupling reaction conditions as described hereinabove, to afford compounds of Formula 8-2, which can then be further substituted with $R^2$ using an appropriate reagent of formula $LG\text{-}R^2$ (where LG is a leaving group such as a halo, hydroxyl, alkoxy, or the like) as shown in Scheme 1 to afford quinazolin-4(3H)-one compounds of Formula 7-5.

In another embodiment, compounds of Formula 9-3 (e.g., Formula VI and IXA) can be synthesized as shown in Scheme 9, below.

Compounds of Formula 9-1 may be coupled to the $-C(O)-R^2$ moiety under typical peptide coupling reaction conditions with an appropriate reagent of formula $LG\text{-}C(O)-R^2$ (where LG is a leaving group such as a halo, hydroxyl, alkoxy, or the like) to afford compounds of Formula 9-2. Typical coupling reaction conditions include the presence of an activating agent, such as 2-(1H-7-azabenzotriazol-1-yl)-1,1,3,3-tetramethyl uronium hexafluorophosphate methanaminium (HATU) with N-methylmorpholine (NMM), and the like, in a polar aprotic solvent, such as N,N-dimethylformamide, and optionally an elevated temperature of about 100-150° C., or in a microwave. Compounds of Formula 9-1 can be purchased or synthesized according to known procedures. Compounds of Formula 9-2 are then coupled with an appropriately substituted boronic acid derivative of formula $R^1Q\text{-}B(OH)_2$, or a boronic ester thereof, under typical coupling reaction conditions as described hereinabove, to afford compounds of Formula 9-3.

In another embodiment, the synthesis of 2H-benzo[e][1,3]thiazin-4(3H)-one compounds of Formula 10-4 (e.g., Formula V) are shown in Scheme 10, below.

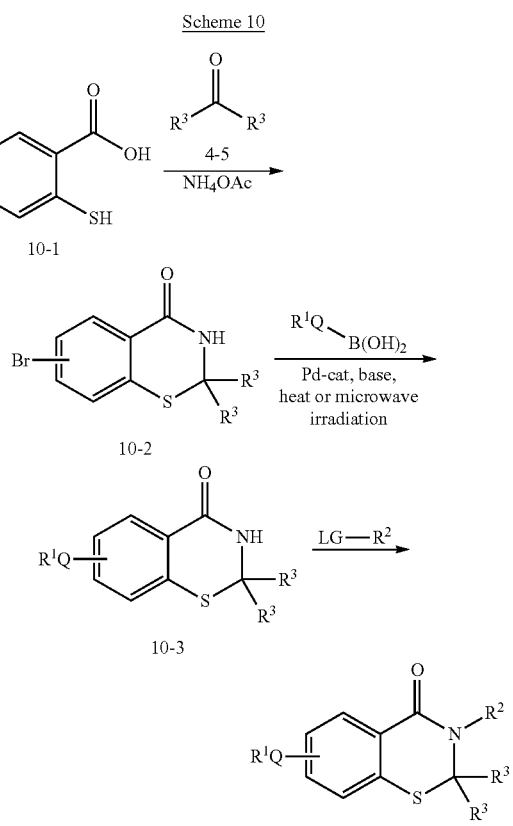

In Scheme 4, compounds of Formula 10-2 can be prepared from the corresponding amide of Formula 10-1 via cyclization using a reagent of Formula 4-5, or a protected version thereof, in the presence of ammonium acetate, in a suitable solvent system, such as toluene, to afford compounds of Formula 10-2. Compounds of Formula 10-2 can then be coupled with an appropriately substituted boronic acid derivative of formula $R^1Q\text{-}B(OH)_2$, or a boronic ester thereof, under typical coupling reaction conditions as described hereinabove, to afford compounds of Formula 10-3. The $R^2$ moiety may be coupled to compounds of Formula 10-3 under substitution reaction conditions with an appropriate reagent of formula $LG\text{-}R^2$ (where LG is a leaving group such as a halo, hydroxyl, alkoxy, or the like) to afford compounds of Formula 10-4. Typical substitution reaction conditions include the presence of a base, such as sodium hydride, potassium carbonate, sodium bicarbonate, triethylamine, and the like, in a polar aprotic solvent, such as N,N-dimethylformamide, at room temperature, or optionally an elevated temperature of about 100-150° C., or in a microwave.

In certain embodiments, the core may be commercially available or be synthesized or cyclized before the addition of the -Q-R¹ and/or R² substitutent. For example, the synthesis of bromophthalazinone compounds of Formula 11-3 (e.g., Formula III, IIIA and VIA) are shown in Scheme 11, below.

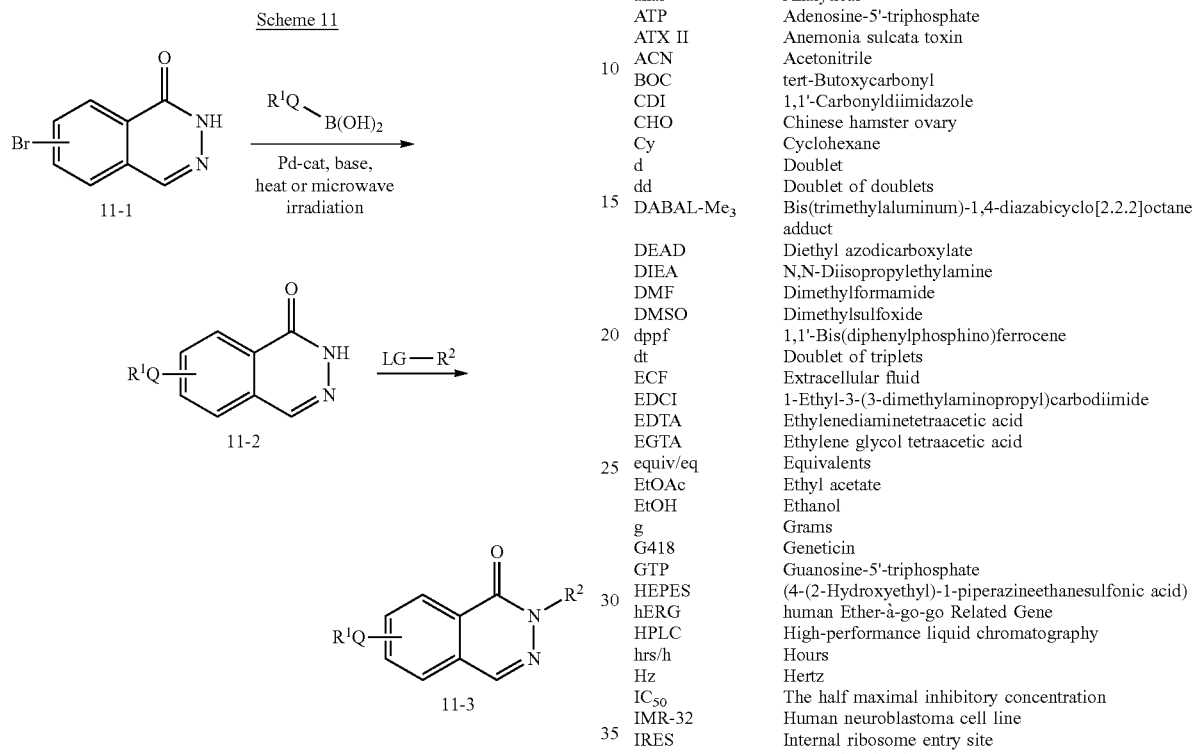

In Scheme 11, compounds of Formula 11-1 can then be coupled with an appropriately substituted boronic acid derivative of formula R¹Q-B(OH)₂, or a boronic ester thereof, under typical coupling reaction conditions as described hereinabove, to afford compounds of Formula 11-2. The R² moiety may be coupled to compounds of Formula 11-2 under substitution reaction conditions with an appropriate reagent of formula LG-R² (where LG is a leaving group such as a halo, hydroxyl, alkoxy, or the like) as shown in Scheme 1 to afford compounds of Formula 11-3. Typical substitution reaction conditions include the presence of a base, such as potassium carbonate, sodium bicarbonate, triethylamine, and the like, in a polar aprotic solvent, such as N,N-dimethylformamide, and optionally an elevated temperature of about 100-150° C., or in a microwave.

It will also be appreciated that the addition of any substituent may result in the production of a number of isomeric products any or all of which may be isolated and purified using conventional techniques.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

LIST OF ABBREVIATIONS AND ACRONYMS

| Abbreviation | Meaning |
| --- | --- |
| ° C. | Degree Celsius |
| anal | Analytical |
| ATP | Adenosine-5'-triphosphate |
| ATX II | Anemonia sulcata toxin |
| ACN | Acetonitrile |
| BOC | tert-Butoxycarbonyl |
| CDI | 1,1'-Carbonyldiimidazole |
| CHO | Chinese hamster ovary |
| Cy | Cyclohexane |
| d | Doublet |
| dd | Doublet of doublets |
| DABAL-Me₃ | Bis(trimethylaluminum)-1,4-diazabicyclo[2.2.2]octane adduct |
| DEAD | Diethyl azodicarboxylate |
| DIEA | N,N-Diisopropylethylamine |
| DMF | Dimethylformamide |
| DMSO | Dimethylsulfoxide |
| dppf | 1,1'-Bis(diphenylphosphino)ferrocene |
| dt | Doublet of triplets |
| ECF | Extracellular fluid |
| EDCI | 1-Ethyl-3-(3-dimethylaminopropyl)carbodiimide |
| EDTA | Ethylenediaminetetraacetic acid |
| EGTA | Ethylene glycol tetraacetic acid |
| equiv/eq | Equivalents |
| EtOAc | Ethyl acetate |
| EtOH | Ethanol |
| g | Grams |
| G418 | Geneticin |
| GTP | Guanosine-5'-triphosphate |
| HEPES | (4-(2-Hydroxyethyl)-1-piperazineethanesulfonic acid) |
| hERG | human Ether-à-go-go Related Gene |
| HPLC | High-performance liquid chromatography |
| hrs/h | Hours |
| Hz | Hertz |
| IC₅₀ | The half maximal inhibitory concentration |
| IMR-32 | Human neuroblastoma cell line |
| IRES | Internal ribosome entry site |
| IU | International unit |
| J | Coupling constant |
| Kg | Kilogram |
| kHz | Kilohertz |
| L | Liter |
| LCMS/LC-MS | Liquid chromatography-mass spectrometry |
| M | Molar |
| m | Meter |
| m/z | mass-to-charge ratio |
| M+ | Mass peak |
| M + H | Mass peak plus hydrogen |
| M + Na | Mass peak plus sodium |
| Me | Methyl |
| mg | Milligram |
| MHz | Megahertz |
| min | Minute |
| ml/mL | Milliliter |
| mM | Millimolar |
| mm | Millimeter |
| mmol | Millimole |
| mOsmol | Milliosmole |
| MRM | Magnetic Resonance Microscopy |
| MS | Metabolic Stability |
| MS | Mass spectroscopy |
| ms | Millisecond |
| mV | Millivolt |
| MW/mw | Microwave |
| N | Normal |
| nmol | Nanomole |
| NMR | Nuclear magnetic resonance |
| pA | Picoamps |
| Ph | Phenyl |
| prep | Preparative |
| q.s. | Quantity sufficient to achieve a stated function |
| Rf | Retention factor |
| RT/rt/R.T | Room temperature |
| s | Second |
| s | Singlet |

| Abbreviation | Meaning |
|---|---|
| SEM | Standard error of the mean |
| t | Triplet |
| TB | Tonic Block |
| TEA | Triethylamine |
| TFA | Trifluoroacetic acid |
| THF | Tetrahydrofuran |
| TLC | Thin layer chromatography |
| TTX | Tetrodotoxin |
| UDB | Use Dependent Block |
| WT | Wild type |
| δ | Chemical shift |
| μg | Microgram |
| μL/μl | Microliter |
| μM | Micromolar |
| μm | Micrometer |
| μmol | Micromole |

EXAMPLES

Example 1

6-(4-(Trifluoromethoxy)phenyl)benzo[d][1,2,3]triazin-4(3H)-one (Compound II-1)

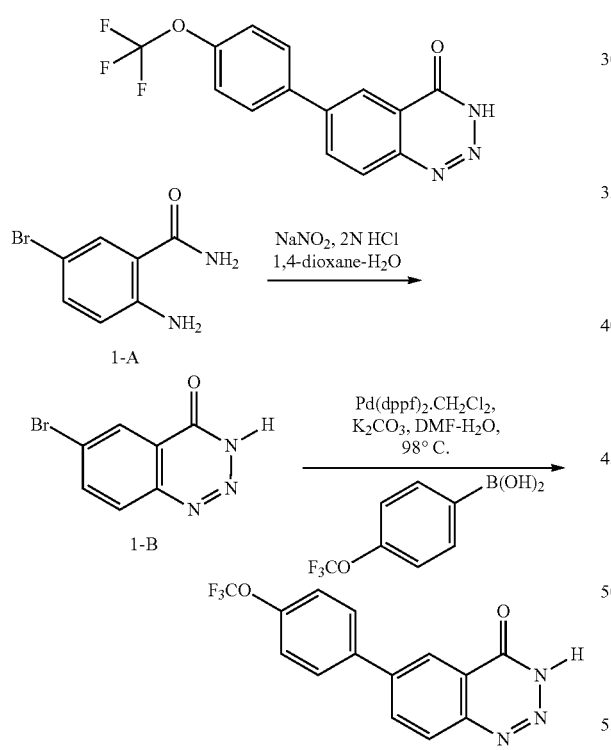

To a mixture of commercially available Compound 1-A (9.250 g, 43.03 mmol) and sodium nitrite (8.909 g, 129.11 mmol) in 1,4-dioxane (40 mL) was added dropwise 2N aqueous HCl (80 mL, 160.00 mmol) with vigorous stir over a period of 30 min, during which H$_2$O was added twice (40 mL each at 10th and 20th min). After completion of addition, the reaction mixture was stirred overnight, then diluted with H$_2$O (200 mL), sonicated, filtered, washed with H$_2$O (500 mL), dried to afford the desired product as 1-B. LCMS m/z 226.0 (M+H), 228.0 (M+H+2), anal HPLC >98%. $^1$H NMR (400 MHz; DMSO-d$_6$) δ 8.30 (d, J=2.3 Hz, 1H); 8.22 (dd, J=8.6, 2.0 Hz, 1H); 8.10 (d, J=9.0 Hz, 1H).

To a solution of 1-B (1.130 g, 5.0 mmol) and 4-trifluoromethylphenylboronic acid (1.544 g, 7.5 mmol) in DMF (30 mL) was added K$_2$CO$_3$ (2.073 g, 15.0 mmol) and H$_2$O (3 mL). The reaction mixture was stirred for 5 min under an atmosphere of dry N$_2$. PdCl$_2$(dppf) (146 mg, 0.20 mmol) was added, and the resulting mixture was heated at 98° C. until 1-B disappeared (LCMS). The reaction mixture was cooled, diluted with EtOAc (70 mL), filtered through a layer of celite, washed with 20% DMF in EtOAc (100 mL), transferred to a separation funnel, organic phase was washed with 0.5M K$_2$CO$_3$ (50 mL, 25.0 mmol), 30% aqueous NH$_4$Cl (100 mL) and brine (100 mL), dried and concentrated. To the crude product was added 10% EtOAc in n-hexane (10 mL), sonicated, filtered, washed with 10% EtOAc in n-hexane (20 mL) to afford the desired product as Compound 1, MS m/z 308.0 (M+H), HPLC purity >97%. $^1$H NMR matched the desired product. The combined filtrate was concentrated, subjected to Gilson's reverse-phase preparative HPLC with a gradient 0.1% TFA containing ACN/H$_2$O (10% to 90%) to afford additional desired product as Compound II-1. LCMS m/z 308.0 (M+H), anal HPLC >99%. The overall combined yield is 71%. $^1$H NMR (400 MHz; DMSO-d$_6$) δ 8.42 (m, 1H); 8.39 (d, J=2.3 Hz, 1H); 8.26 (d, J=8.2 Hz, 1H); 8.00 (m, 2H); 7.52 (d, J=8.2 Hz, 2H). $^{19}$F NMR (400 MHz; DMSO-d$_6$) δ □–57.2 (s, 3F).

Example 2

6-(6-(2,2,2-trifluoroethoxy)pyridin-3-yl)benzo[d][1,2,3]triazin-4(3H)-one (Compound V-1)

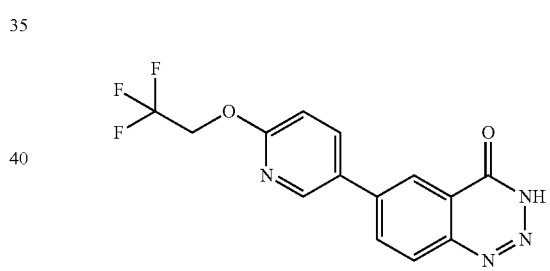

Compound V-1 was prepared using a similar procedure as that described for Compound II-1 with the appropriate starting materials.

Example 3

6-(2-methoxypyrimidin-5-yl)benzo[d][1,2,3]triazin-4(3H)-one (Compound V-4)

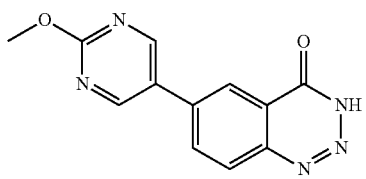 [SMILES: COc1ncc(-c2ccc3nn[nH]c(=O)c3c2)cn1]

Compound V-4 was prepared using a similar procedure as that described for Compound II-1 with the appropriate starting materials.

Example 4

6-(2-(trifluoromethyl)pyrimidin-5-yl)benzo[d][1,2,3]triazin-4(3H)-one (Compound V-7)

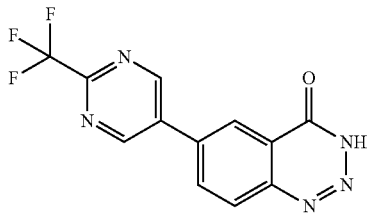 [SMILES: O=c1[nH]nnc2ccc(-c3cnc(C(F)(F)F)nc3)cc12]

Compound V-7 was prepared using a similar procedure as that described for Compound II-1 with the appropriate starting materials.

Example 5

6-(2-(dimethylamino)pyrimidin-5-yl)benzo[d][1,2,3]triazin-4(3H)-one (Compound V-9)

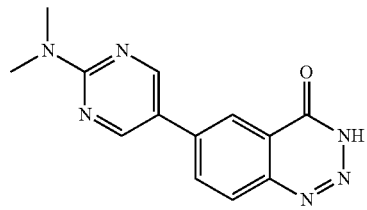 [SMILES: CN(C)c1ncc(-c2ccc3nn[nH]c(=O)c3c2)cn1]

Compound V-9 was prepared using a similar procedure as that described for Compound II-1 with the appropriate starting materials.

Example 6

6-(4-(4-chlorophenoxy)phenyl)benzo[d][1,2,3]triazin-4(3H)-one (Compound II-20)

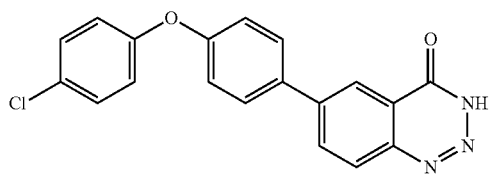 [SMILES: O=c1[nH]nnc2ccc(-c3ccc(Oc4ccc(Cl)cc4)cc3)cc12]

Compound II-20 was prepared using a similar procedure as that described for Compound II-1 with the appropriate starting materials.

Example 7

3-((5-cyclopropyl-1,2,4-oxadiazol-3-yl)methyl)-6-(4-(trifluoromethoxy)phenyl)benzo[d][1,2,3]triazin-4(3H)-one (Compound II-14)

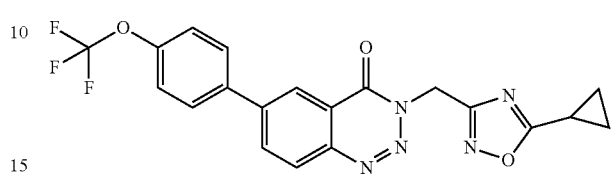

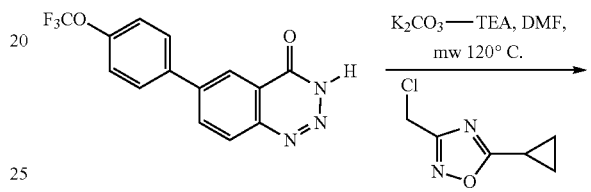

To a solution of Compound 1 (2.446 g, 7.96 mmol), 3-(chloromethyl)-5-cyclopropyl-1,2,4-oxadiazole (1.660 g, 10.47 mmol) in DMF (15 mL) in a Biotage microwave tube (20 mL capacity) was added potassium carbonate (1.881 g, 13.61 mmol) and triethyl amine (2 mL) with stir. The reaction mixture was stirred at room temperature for 5 min, and then subjected to microwave heating at 120° C. until Compound 1 disappeared in LCMS. The mixture was cooled, diluted with 20% DMF in EtOAc (50 mL), filtered, washed with 20% DMF in EtOAc (100 mL). The combined filtrate was concentrated in vacuo, dissolved mostly in dichloromethane (20 mL), filtered, and the filtrated was subjected to Yamazen chromatography over Universal column, eluted with a gradient EtOAc in n-hexane to afford, after drying, Compound 14, anal HPLC 97%. Compound II-14 was recrystallized from EtOAc/n-hexane and dried to give Compound II-14: MS m/z 430.1 (M+H), 452.1 (M+Na), Analytical HPLC purity >99%.

$^1$H NMR (400 MHz; DMSO-$d_6$) δ 8.46 (m, 2H); 8.35 (d, J=9.0 Hz, 1H); 8.20 (d, J=7.6 Hz, 2H); 7.53 (d, J=7.8 Hz, 2H); 5.71 (s, 2H); 2.31 (m, 1H); 1.21 (m, 2H); 1.06 (m, 2H). $^{19}$F NMR (400 MHz; DMSO-$d_6$) δ −57.2 (s, 3F).

Example 8

3-((5-methyl-1,2,4-oxadiazol-3-yl)methyl)-6-(6-(2,2,2-trifluoroethoxy)pyridin-3-yl)benzo[d][1,2,3]triazin-4(3H)-one (Compound V-2)

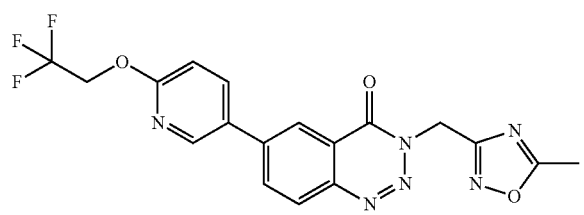 [SMILES: Cc1nc(Cn2nnc3ccc(-c4ccc(OCC(F)(F)F)nc4)cc3c2=O)no1]

Compound V-2 was prepared using a similar procedure as that described for Compound II-14 with the appropriate starting materials.

Example 9

3-((3-tert-butyl-1,2,4-oxadiazol-5-yl)methyl)-6-(4-(trifluoromethoxy)phenyl)benzo[d][1,2,3]triazin-4(3H)-one (Compound II-2)

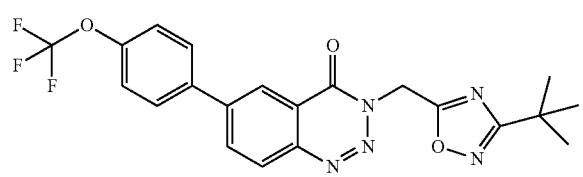 [SMILES: CC(C)(C)c1noc(Cn2nnc3ccc(-c4ccc(OC(F)(F)F)cc4)cc3c2=O)n1]

Compound II-2 was prepared using a similar procedure as that described for Compound II-14 with the appropriate starting materials.

Example 10

3-((3-methyl-1,2,4-oxadiazol-5-yl)methyl)-6-(4-(trifluoromethoxy)phenyl)benzo[d][1,2,3]triazin-4(3H)-one (Compound II-3)

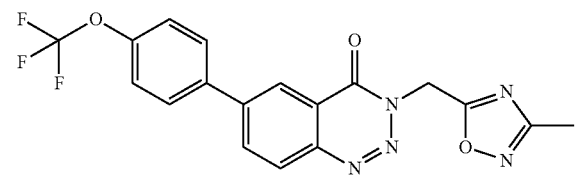

Compound II-3 was prepared using a similar procedure as that described for Compound II-14 with the appropriate starting materials.

Example 11

3-((5-chloropyrimidin-2-yl)methyl)-6-(4-(trifluoromethoxy)phenyl)benzo[d][1,2,3]triazin-4(3H)-one (Compound II-4)

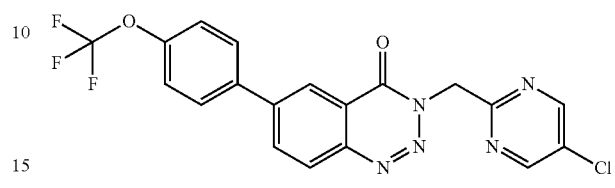

Compound II-4 was prepared using a similar procedure as that described for Compound II-14 with the appropriate starting materials.

Example 12

3-(1-(3-(pyridin-4-yl)-1,2,4-oxadiazol-5-yl)ethyl)-6-(4-(trifluoromethoxy)phenyl)benzo[d][1,2,3]triazin-4(3H)-one (Compound II-5)

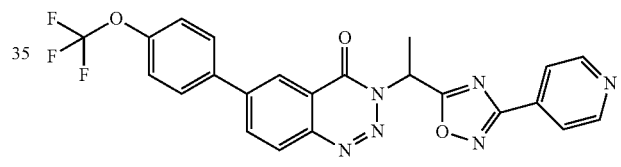

Compound II-5 was prepared using a similar procedure as that described for Compound II-14 with the appropriate starting materials.

Example 13

3-((5-methyl-1,2,4-oxadiazol-3-yl)methyl)-6-(4-(trifluoromethoxy)phenyl)benzo[d][1,2,3]triazin-4(3H)-one (Compound II-6)

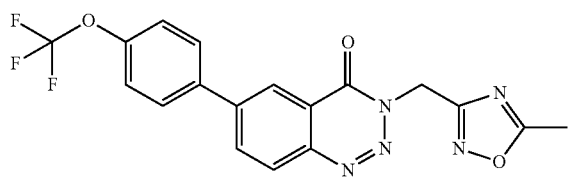 [SMILES: Cc1nc(Cn2nnc3ccc(-c4ccc(OC(F)(F)F)cc4)cc3c2=O)no1]

Compound II-6 was prepared using a similar procedure as that described for Compound II-14 with the appropriate starting materials.

Example 14

3-((3-methyl-1,2,4-oxadiazol-5-yl)methyl)-6-(4-phenoxyphenyl)benzo[d][1,2,3]triazin-4(3H)-one (Compound II-7)

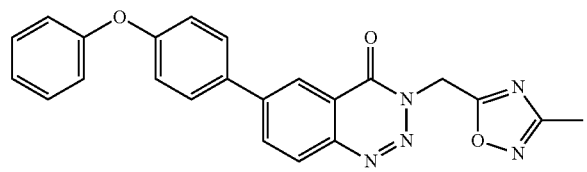 [SMILES: Cc1noc(Cn2nnc3ccc(-c4ccc(Oc5ccccc5)cc4)cc3c2=O)n1]

Compound II-7 was prepared using a similar procedure as that described for Compound II-14 with the appropriate starting materials.

Example 15

3-((3-((pyridin-2-ylsulfonyl)methyl)-1,2,4-oxadiazol-5-yl)methyl)-6-(4-(trifluoromethoxy)phenyl)benzo[d][1,2,3]triazin-4(3H)-one (Compound II-8)

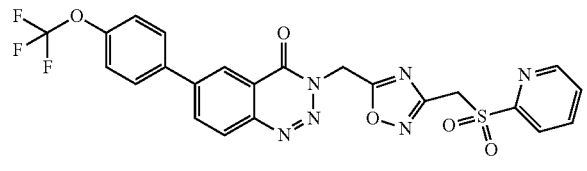 [SMILES: O=c1c2cc(-c3ccc(OC(F)(F)F)cc3)ccc2nnn1Cc1nc(CS(=O)(=O)c2ccccn2)no1]

Compound II-8 was prepared using a similar procedure as that described for Compound II-14 with the appropriate starting materials.

Example 16

3-((3-phenylisoxazol-5-yl)methyl)-6-(4-(trifluoromethoxy)phenyl)benzo[d][1,2,3]triazin-4(3H)-one (Compound II-10)

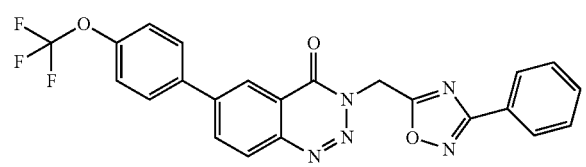 [SMILES: O=c1c2cc(-c3ccc(OC(F)(F)F)cc3)ccc2nnn1Cc1nc(-c2ccccc2)no1]

Compound II-10 was prepared using a similar procedure as that described for Compound II-14 with the appropriate starting materials.

Example 17

N-(2,6-dimethylphenyl)-2-(4-oxo-6-(4-(trifluoromethoxy)phenyl)benzo[d][1,2,3]triazin-3(4H)-yl)acetamide (Compound II-11)

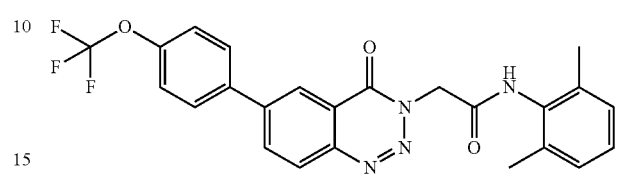

Compound II-11 was prepared using a similar procedure as that described for Compound II-14 with the appropriate starting materials.

Example 18

3-((3-benzyl-1,2,4-oxadiazol-5-yl)methyl)-6-(4-(trifluoromethoxy)phenyl)benzo[d][1,2,3]triazin-4(3H)-one (Compound II-12)

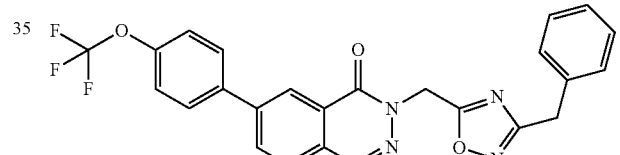

Compound II-12 was prepared using a similar procedure as that described for Compound II-14 with the appropriate starting materials.

Example 19

3-(2-(1H-pyrazol-1-yl)ethyl)-6-(4-(trifluoromethoxy)phenyl)benzo[d][1,2,3]triazin-4(3H)-one (Compound II-13)

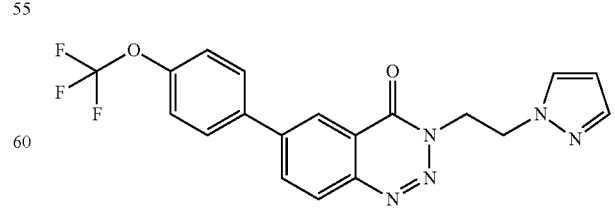

Compound II-13 was prepared using a similar procedure as that described for Compound II-14 with the appropriate starting materials.

Example 20

6-(4-(4-chlorophenoxy)phenyl)-3-((3-methyl-1,2,4-oxadiazol-5-yl)methyl)benzo[d][1,2,3]triazin-4(3H)-one (Compound II-16)

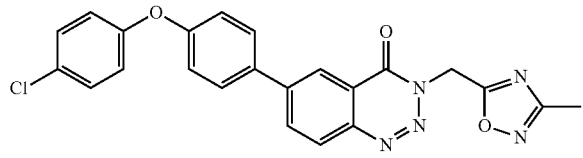 [SMILES: Cc1noc(Cn2nnc3ccc(-c4ccc(Oc5ccc(Cl)cc5)cc4)cc3c2=O)n1]

Compound II-16 was prepared using a similar procedure as that described for Compound II-14 with the appropriate starting materials.

Example 21

3-((4,5-dimethyloxazol-2-yl)methyl)-6-(4-(trifluoromethoxy)phenyl)benzo[d][1,2,3]triazin-4(3H)-one (Compound II-23)

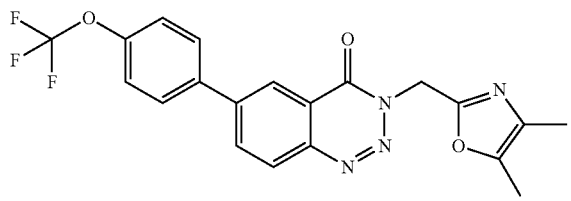 [SMILES: Cc1nc(Cn2nnc3ccc(-c4ccc(OC(F)(F)F)cc4)cc3c2=O)oc1C]

Compound II-23 was prepared using a similar procedure as that described for Compound II-14 with the appropriate starting materials.

Example 22

3-(pyrimidin-2-ylmethyl)-6-(4-(trifluoromethoxy)phenyl)benzo[d][1,2,3]triazin-4(3H)-one (Compound II-24)

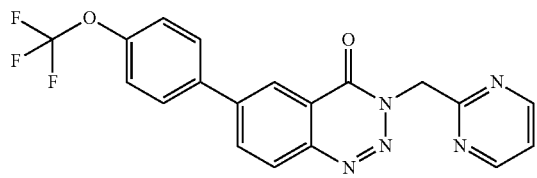 [SMILES: O=c1c2cc(-c3ccc(OC(F)(F)F)cc3)ccc2nnn1Cc1ncccn1]

Compound II-24 was prepared using a similar procedure as that described for Compound II-14 with the appropriate starting materials.

Example 23

3-((3-methylisoxazol-5-yl)methyl)-6-(4-(trifluoromethoxy)phenyl)benzo[d][1,2,3]triazin-4(3H)-one (Compound II-25)

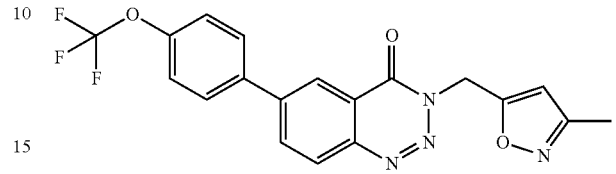

Compound II-25 was prepared using a similar procedure as that described for Compound II-14 with the appropriate starting materials.

Example 24

3-((5-methylisoxazol-3-yl)methyl)-6-(4-(trifluoromethoxy)phenyl)benzo[d][1,2,3]triazin-4(3H)-one (Compound II-26)

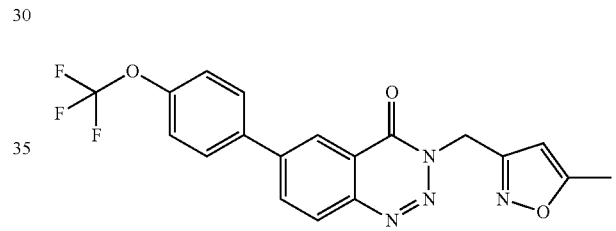

Compound II-26 was prepared using a similar procedure as that described for Compound II-14 with the appropriate starting materials.

Example 25

4-((4-oxo-6-(4-(trifluoromethoxy)phenyl)benzo[d][1,2,3]triazin-3(4H)-yl)methyl)benzonitrile (Compound II-27)

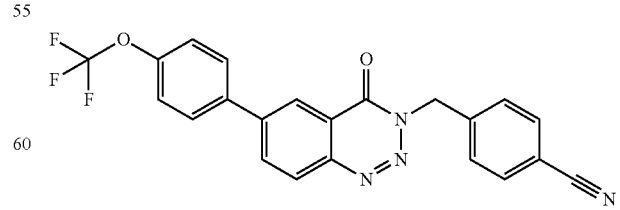

Compound II-27 was prepared using a similar procedure as that described for Compound II-14 with the appropriate starting materials.

Example 26

3-(2-(1H-pyrazol-1-yl)ethyl)-6-(4-(4-chlorophenoxy)phenyl)benzo[d][1,2,3]triazin-4(3H)-one (Compound II-29)

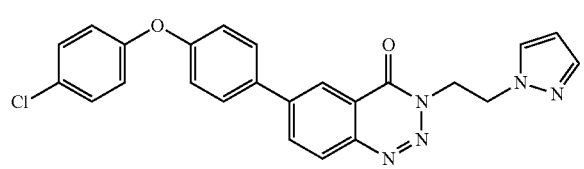 [SMILES: O=c1c2cc(-c3ccc(Oc4ccc(Cl)cc4)cc3)ccc2nnn1CCn1cccn1]

Compound II-29 was prepared using a similar procedure as that described for Compound II-14 with the appropriate starting materials.

Example 27

2-(4-oxo-6-(4-(trifluoromethoxy)phenyl)benzo[d][1,2,3]triazin-3(4H)-yl)acetonitrile (Compound II-30)

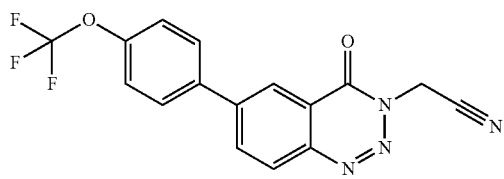 [SMILES: N#CCn1nnc2ccc(-c3ccc(OC(F)(F)F)cc3)cc2c1=O]

Compound II-30 was prepared using a similar procedure as that described for Compound II-14 with the appropriate starting materials.

Example 28

3-((1H-imidazol-2-yl)methyl)-6-(4-(trifluoromethoxy)phenyl)benzo[d][1,2,3]triazin-4(3H)-one (Compound II-35)

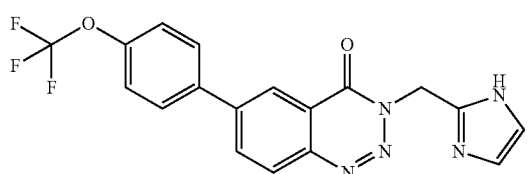

Compound II-35 was prepared using a similar procedure as that described for Compound II-14 with the appropriate starting materials.

Example 29

3-benzyl-6-(4-(trifluoromethoxy)phenyl)benzo[d][1,2,3]triazin-4(3H)-one (Compound II-42)

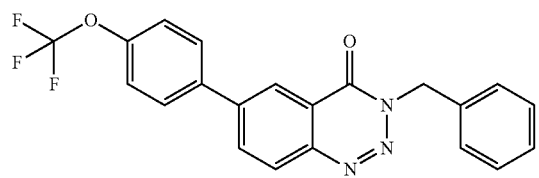 [SMILES: O=c1c2cc(-c3ccc(OC(F)(F)F)cc3)ccc2nnn1Cc1ccccc1]

Compound II-42 was prepared using a similar procedure as that described for Compound II-14 with the appropriate starting materials.

Example 30

3-((5-cyclopropyl-1,2,4-oxadiazol-3-yl)methyl)-6-(2-(trifluoromethyl)pyrimidin-5-yl)benzo[d][1,2,3]triazin-4(3H)-one (Compound V-8)

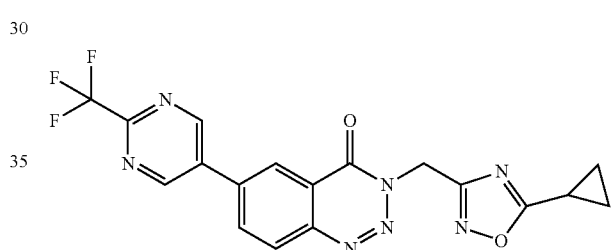

Compound V-8 was prepared using a similar procedure as that described for Compound II-14 with the appropriate starting materials.

Example 31

3-(but-3-ynyl)-6-(4-(trifluoromethoxy)phenyl)benzo[d][1,2,3]triazin-4(3H)-one (Compound II-45)

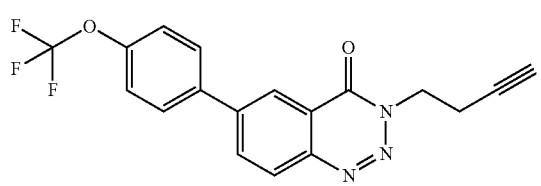 [SMILES: C#CCCn1nnc2ccc(-c3ccc(OC(F)(F)F)cc3)cc2c1=O]

Compound II-45 was prepared using a similar procedure as that described for Compound II-14 with the appropriate starting materials.

Example 32

3-(1-(3-(pyrimidin-2-yl)-1,2,4-oxadiazol-5-yl)ethyl)-6-(4-(trifluoromethoxy)phenyl)benzo[d][1,2,3]triazin-4(3H)-one (Compound II-53)

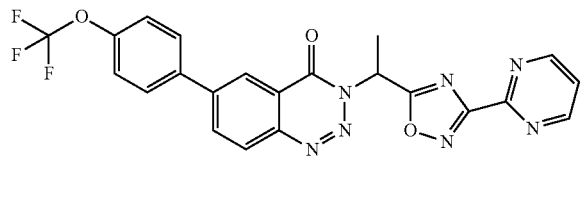 [SMILES: CC(c1nc(-c2ncccn2)no1)n1nnc2ccc(-c3ccc(OC(F)(F)F)cc3)cc2c1=O]

Compound II-53 was prepared using a similar procedure as that described for Compound II-14 with the appropriate starting materials.

Example 33

3-((5-cyclopropyl-1,3,4-thiadiazol-2-yl)methyl)-6-(4-(trifluoromethoxy)phenyl)benzo[d][1,2,3]triazin-4(3H)-one (Compound II-66)

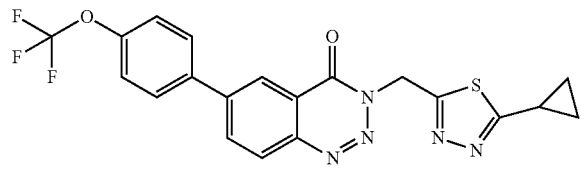

Compound II-66 was prepared using a similar procedure as that described for Compound II-14 with the appropriate starting materials.

Example 34

3-((5-cyclopropyl-1,3,4-oxadiazol-2-yl)methyl)-6-(4-(trifluoromethoxy)phenyl)benzo[d][1,2,3]triazin-4(3H)-one (Compound II-67)

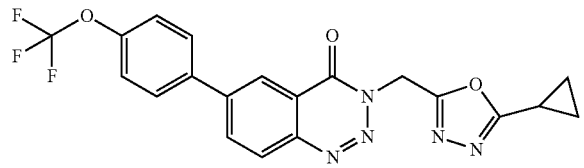 [SMILES: O=c1c2cc(-c3ccc(OC(F)(F)F)cc3)ccc2nnn1Cc1nnc(C2CC2)o1]

Compound II-67 was prepared using a similar procedure as that described for Compound II-14 with the appropriate starting materials.

Example 35

3-((3-methyl-1,2,4-oxadiazol-5-yl)methyl)-6-(4-(trifluoromethyl)phenyl)benzo[d][1,2,3]triazin-4(3H)-one (Compound II-78)

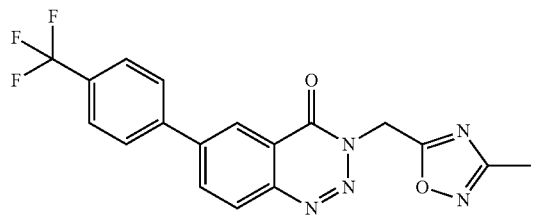 [SMILES: Cc1noc(Cn2nnc3ccc(-c4ccc(C(F)(F)F)cc4)cc3c2=O)n1]

Compound II-78 was prepared using a similar procedure as that described for Compound II-14 with the appropriate starting materials.

Example 36

3-(1-(3-cyclopropyl-1,2,4-oxadiazol-5-yl)ethyl)-6-(4-(trifluoromethoxy)phenyl)benzo[d][1,2,3]triazin-4(3H)-one (Compound II-79)

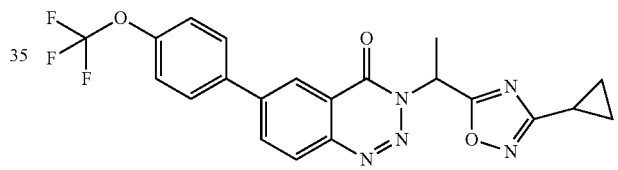

Compound II-79 was prepared using a similar procedure as that described for Compound II-14 with the appropriate starting materials.

Example 37

3-((3-cyclopropyl-1,2,4-oxadiazol-5-yl)methyl)-6-(4-(trifluoromethyl)phenyl)benzo[d][1,2,3]triazin-4(3H)-one (Compound II-91)

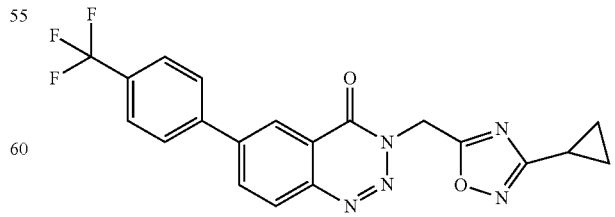

Compound II-91 was prepared using a similar procedure as that described for Compound II-14 with the appropriate starting materials.

Example 38

3-(pyrimidin-2-ylmethoxy)-6-(4-(trifluoromethoxy)phenyl)benzo[d][1,2,3]triazin-4(3H)-one (Compound II-56)

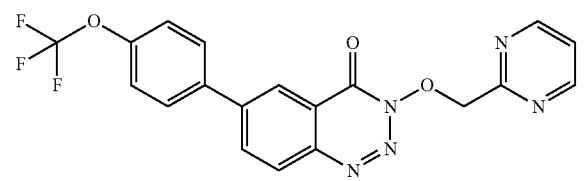

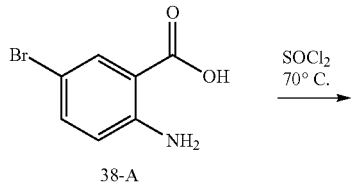

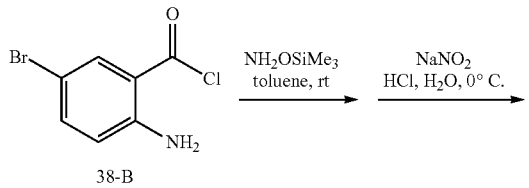

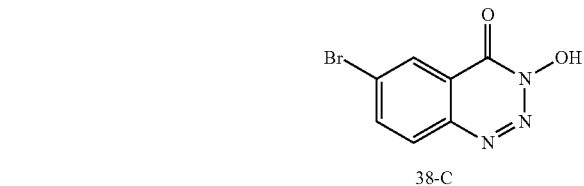

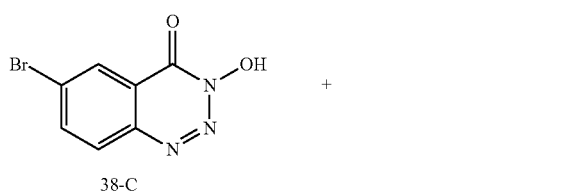

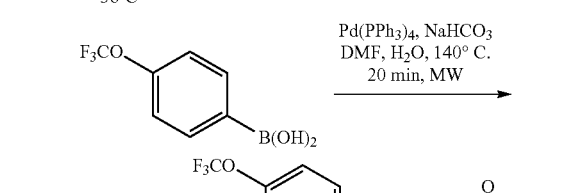

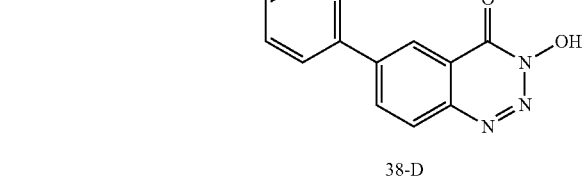

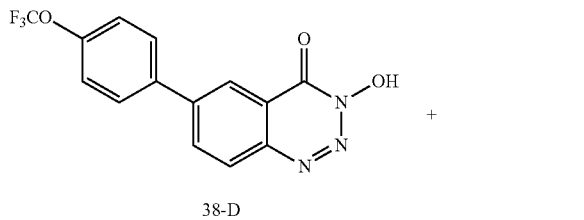

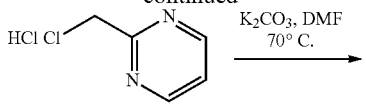

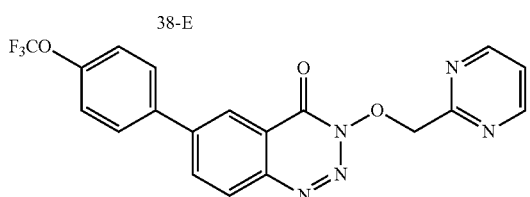

2-Amino-5-bromobenzoic acid 38-A (1.4 g, 6.48 mmol) in thionyl chloride (8 mL) was stirred at 70° C. for 2 hrs. After removing the extra solvent the residue was suspended in toluene. O-(trimethylsilyl)hydroxylamine (1.98 mL, 16.2 mmol) was then added, and the mixture was stirred at room temperature overnight. The solvent was evaporated and the residue was suspended in concentrated HCl (2 mL) and H$_2$O (15 mL). A solution of NaNO$_2$ (0.89 g, 12.96 mmol) in H$_2$O (5 mL) was then added slowly in an ice-bath. The resulting mixture was stirred at 0° C. for 1 h. The precipitate was collected by filtration and washed with H$_2$O to afford 38-C.

To a stirred suspension of 38-C (145 mg, 0.6 mmol) and 4-(trifluoromethoxy)phenylboronic acid (247 mg, 1.2 mmol) in DMF (3.5 mL) was added NaHCO$_3$ (302 mg, 3.6 mmol) and H$_2$O (0.4 mL). Under N$_2$ atmosphere tetrakis(triphenylphosphine)palladium (35 mg, 5%) was added. The resulting mixture was put onto microwave at 140° C. for 20 min. The mixture was diluted with EtOAc, filtered through celite and further washed with EtOAc. The filtrate was concentrated and followed by purification with HPLC to afford 38-D.

To a stirred solution of 38-D (75 mg, 0.232 mmol) in DMF (6 mL) was added K$_2$CO$_3$ (128 mg, 0.928 mmol), followed by 38-E (57 mg, 0.348 mmol). The resulting mixture was stirred at 70° C. overnight. Diluted the reaction mixture with EtOAc and washed with H$_2$O. The organic layer was dried over Na$_2$SO$_4$ and evaporated in vacuo. The residue was then purified by column chromatography (EtOAc:hexanes=2:3) to afford Compound II-56.

Example 39

3-(pyridin-3-ylmethoxy)-6-(4-(trifluoromethoxy)phenyl)benzo[d][1,2,3]triazin-4(3H)-one (Compound II-59)

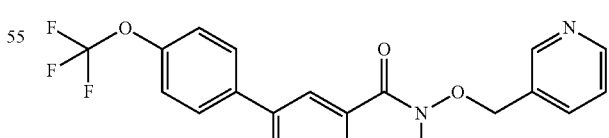

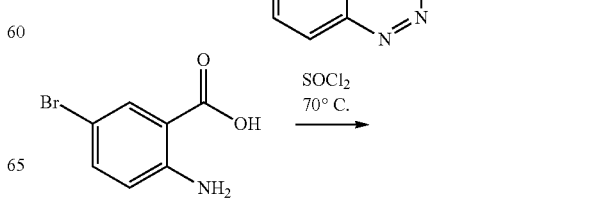

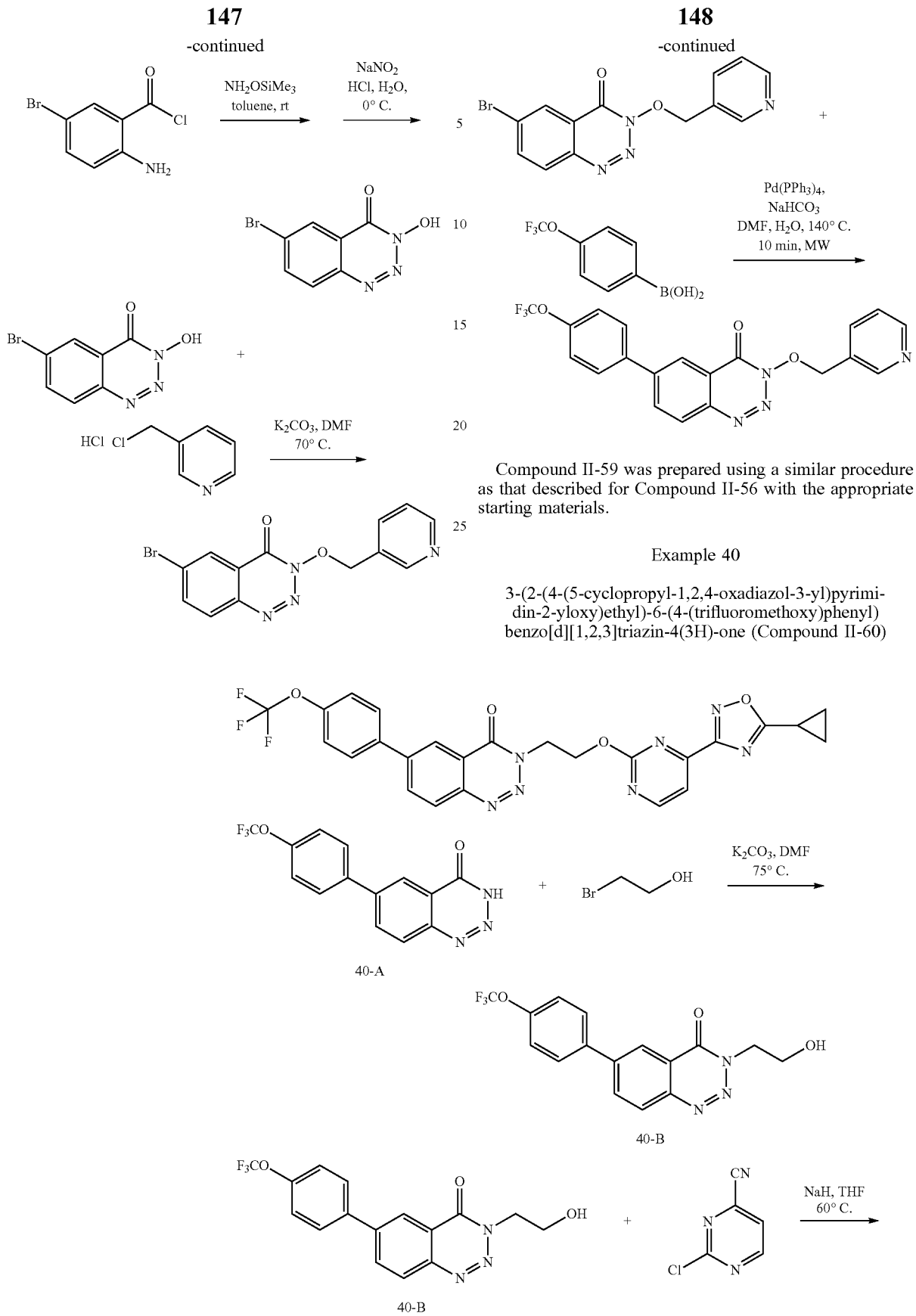
Compound II-59 was prepared using a similar procedure as that described for Compound II-56 with the appropriate starting materials.
Example 40
3-(2-(4-(5-cyclopropyl-1,2,4-oxadiazol-3-yl)pyrimidin-2-yloxy)ethyl)-6-(4-(trifluoromethoxy)phenyl)benzo[d][1,2,3]triazin-4(3H)-one (Compound II-60)

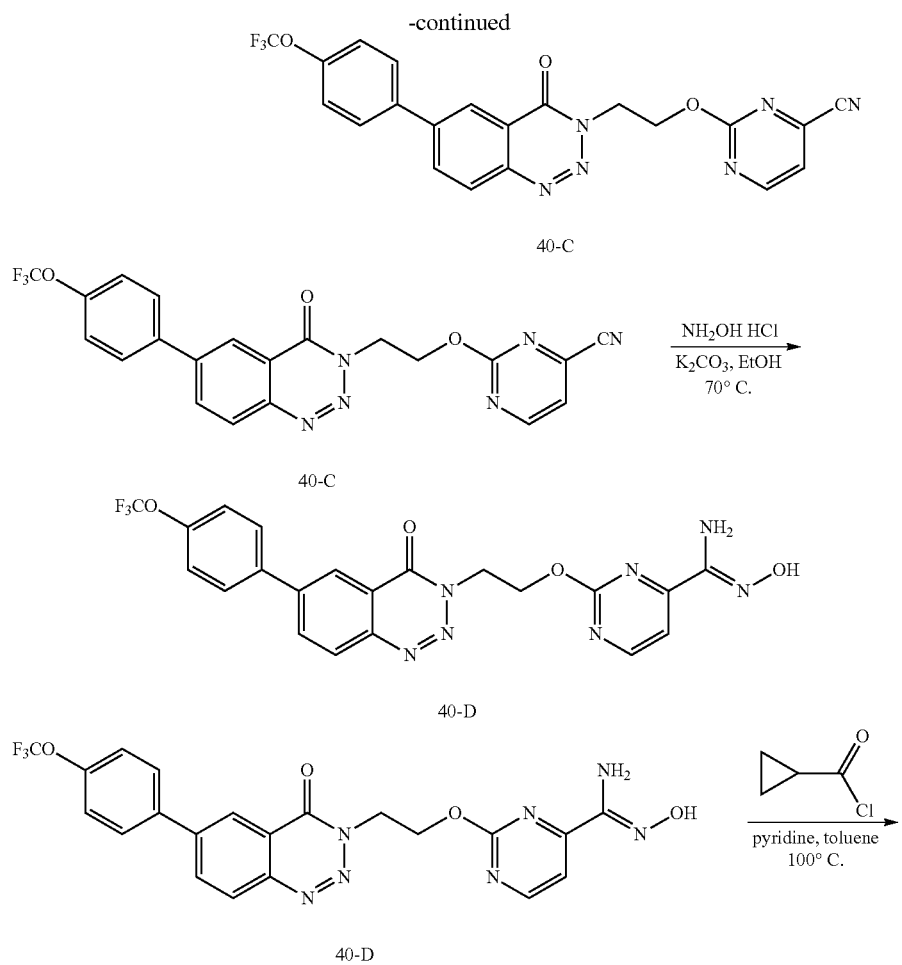

Procedure to 40-B is as described in the last step for Compound II-56

To a stirred solution of 40-B (155 mg, 0.44 mmol) in THF (10 mL) was added 60% NaH in mineral oil (26 mg, 0.66 mmol) followed by 2-chloropyrimidine-4-carbonitrile (74 mg, 0.53 mmol). The resulting mixture was stirred at 60° C. over weekend. The reaction mixture was quenched with $H_2O$ and extracted with EtOAc. The organic layer was dried over $Na_2SO_4$ and evaporated in vacuo. The residue was then purified by HPLC to afford 40-C.

Hydroxylamine hydrochloride (147 mg, 2.11 mmol) and $K_2CO_3$ (292 mg, 2.11 mmol) were stirred in EtOH (6 mL) at room temperature for half an hour. To this mixture was added 40-C (160 mg, 0.352 mmol) in EtOH (4 mL) and the resulting mixture was stirred at 70° C. overnight. After filtration of inorganic salts the filtrate was concentrated in vacuo and used directly for next step.

A solution of cyclopropanecarbonyl chloride (55 mg, 0.528 mmol) in toluene (3 mL) was added dropwise to a solution of 40-D (0.352 mmol) in pyridine (1 mL) and toluene (2 mL). The mixture was stirred at 100° C. for two days and concentrated. The residue was purified by HPLC to afford Compound II-60.

Example 41

(R)-tert-butyl 3-(4-oxo-6-(4-(trifluoromethoxy)phenyl)benzo[d][1,2,3]triazin-3(4H)-yl)pyrrolidine-1-carboxylate (Compound II-68)

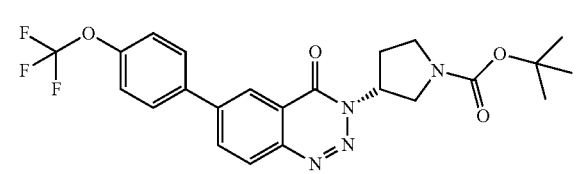

-continued

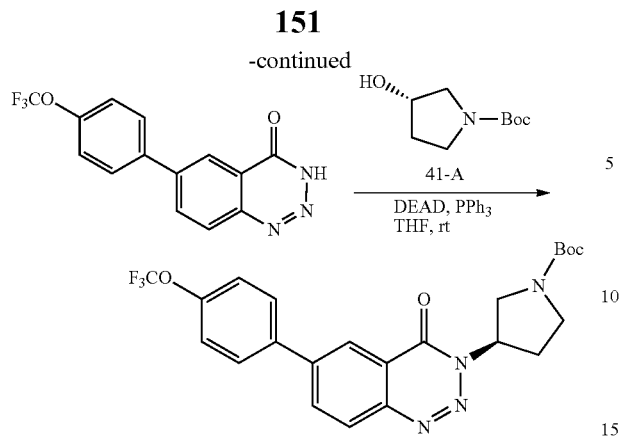

To a stirred mixture of Compound II-1 (100 mg, 0.325 mmol) and 41-A (91 mg, 0.488 mmol) in THF (8 mL) was added PPh$_3$ (170 mg, 0.65 mmol). DEAD (113 mg, 0.65 mmol) in THF (2 mL) was then added dropwise. The resulting mixture was stirred at room temperature overnight and diluted with EtOAc and washed with H$_2$O. The organic layer was dried over Na$_2$SO$_4$ and evaporated in vacuo. The residue was then purified by HPLC to afford Compound II-68.

Example 42

1-(4-oxo-6-(4-(trifluoromethoxy)phenyl)benzo[d][1,2,3]triazin-3(4H)-yl)cyclopropanecarbonitrile (Compound II-33)

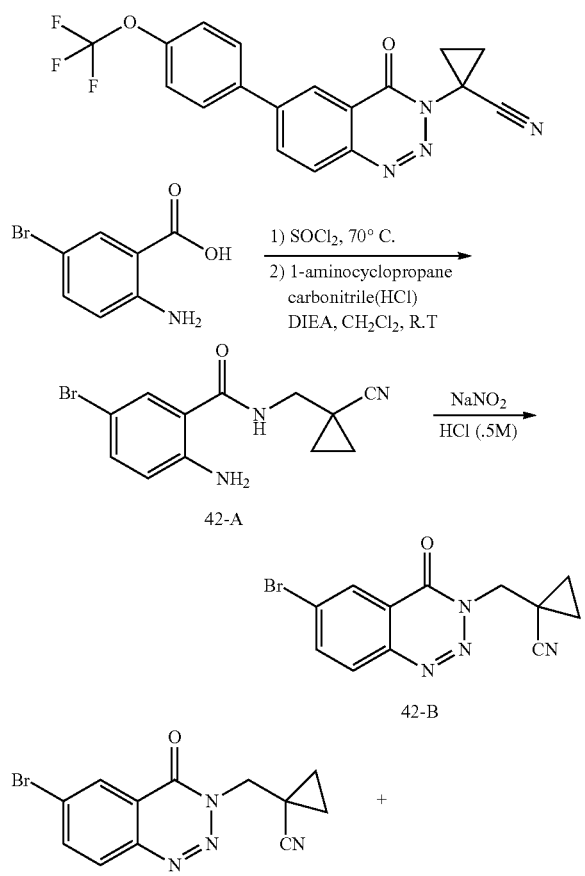

-continued

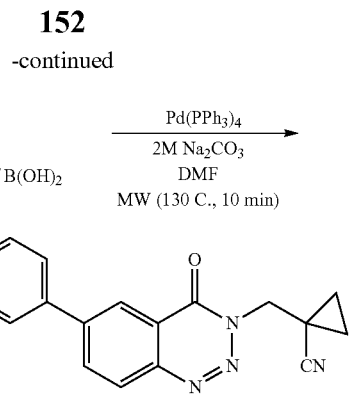

To a round bottom flask was added 2-amino-5-bromobenzoic acid (2.31 mmol), and thionyl chloride (2 mL). The mixture was heated at 70° C. for 2 hrs. The mixture was concentrated down under reduced pressure and the residue was dissolved in 15 mL of CH$_2$Cl$_2$. To this solution was added dropwise 1-aminocyclopropane carbonitrile hydrochloride salt (2.78 mmol) in CH$_2$Cl$_2$ and 2 mL of DIEA. The mixture was stirred at RT for 18 hrs and was concentrated down before purification by preparative TLC eluting with 5% methanol methylene chloride mixture to afford 42-A.

42-A was dissolved in 2 mL DMF followed by dropwise addition of NaNO$_2$ (0.714 mmol) in 0.5 M HCl (4 mL). After 2 hours the reaction mixture was concentrated down and purified by prep TLC with 5% methanol and methylene chloride mixture to give 42-B.

42-B was coupled with 4-trifluoromethoxyphenylboronic acid under previously described Suzuki conditions to give Compound II-33.

Example 43

3-((1-(morpholinomethyl)cyclopropyl)methyl)-6-(4-(trifluoromethoxy)phenyl)benzo[d][1,2,3]-triazin-4(3H)-one (Compound II-40)

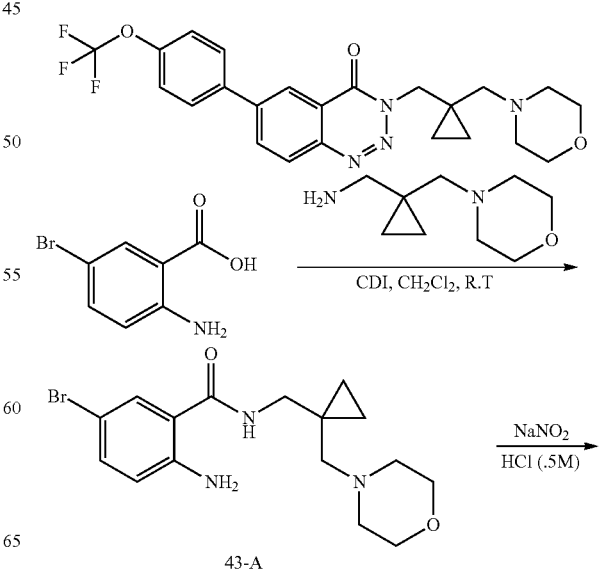

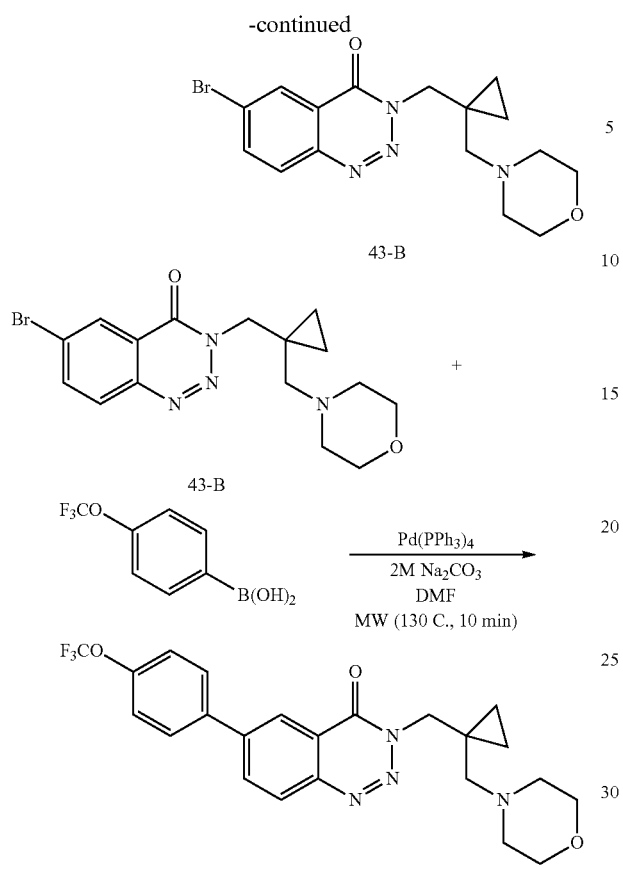

43-B

43-B

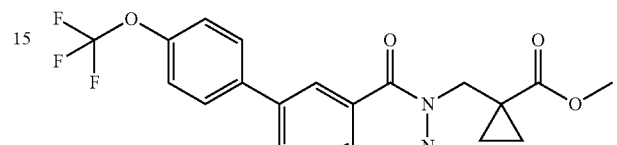

To a round bottom flask was added 2-amino-5-bromobenzoic acid (1.39 mmol), and CDI or EDCI-HCl (1.5 equiv) in CH$_2$Cl$_2$ (20 mL) and the mixture was stirred at RT for 15 min before addition of amine (1.3 equiv). The resulting reaction mixture was stirred at RT overnight. The mixture was washed with H$_2$O and the organic extract was dried over Na$_2$SO$_4$ and then concentrated down under reduced pressure before purification by preparative TLC eluting with 5% methanol methylene chloride mixture to afford 43-A.

43-A was dissolved in 2 mL DMF followed by dropwise addition of NaNO$_2$ (0.679 mmol) in 0.5 M HCl (4 mL). After 2 hours the reaction mixture was concentrated down and purified by prep TLC with 5% methanol and methylene chloride mixture to give 43-B.

43-B was coupled with 4-trifluoromethoxyphenylboronic acid under previously described Suzuki conditions to give Compound II-40.

Example 44

3-((1-((2-methyl-1H-imidazol-1-yl)methyl)cyclopropyl)methyl)-6-(4-(trifluoromethoxy)phenyl)benzo[d][1,2,3]triazin-4(3H)-one (Compound II-34)

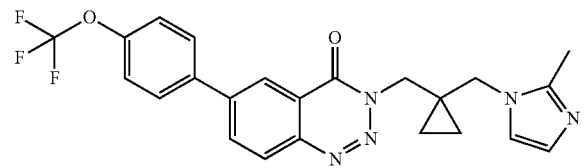 [SMILES: Cc1nccn1CC1(Cn2nnc3ccc(-c4ccc(OC(F)(F)F)cc4)cc3c2=O)CC1]

Compound II-34 was prepared using a similar procedure as that described for Compound II-40 with the appropriate starting materials.

Example 45 methyl 1-((4-oxo-6-(4-(trifluoromethoxy)phenyl)benzo[d][1,2,3]triazin-3(4H)-yl)methyl)cyclopropanecarboxylate (Compound II-55)

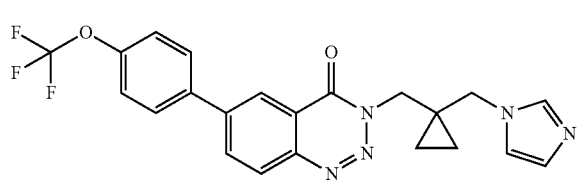 [SMILES: O=c1c2cc(-c3ccc(OC(F)(F)F)cc3)ccc2nnn1CC1(Cn2ccnc2)CC1]

Compound II-55 was prepared using a similar procedure as that described for Compound II-40 with the appropriate starting materials.

Example 46

3-((1-((1H-imidazol-1-yl)methyl)cyclopropyl)methyl)-6-(4-(trifluoromethoxy)phenyl)benzo[d][1,2,3]triazin-4(3H)-one (Compound II-58)

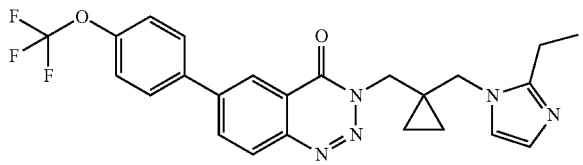 [SMILES: CCc1nccn1CC1(Cn2nnc3ccc(-c4ccc(OC(F)(F)F)cc4)cc3c2=O)CC1]

Compound II-58 was prepared using a similar procedure as that described for Compound II-40 with the appropriate starting materials.

Example 47

3-((1-((2-ethyl-1H-imidazol-1-yl)methyl)cyclopropyl)methyl)-6-(4-(trifluoromethoxy)phenyl)benzo[d][1,2,3]triazin-4(3H)-one (Compound II-57)

Compound II-57 was prepared using a similar procedure as that described for Compound II-40 with the appropriate starting materials.

Example 48

3-((1-(pyrrolidin-1-ylmethyl)cyclopropyl)methyl)-6-(4-(trifluoromethoxy)phenyl)benzo[d][1,2,3]triazin-4(3H)-one (Compound II-63)

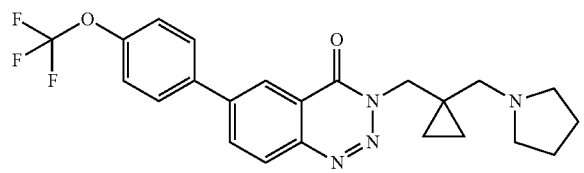 [SMILES: O=c1c2cc(-c3ccc(OC(F)(F)F)cc3)ccc2nnn1CC1(CN2CCCC2)CC1]

Compound II-63 was prepared using a similar procedure as that described for Compound II-40 with the appropriate starting materials.

Example 49

3-((1-((3,5-dimethyl-1H-pyrazol-1-yl)methyl)cyclopropyl)methyl)-6-(4-(trifluoromethoxy)phenyl)benzo[d][1,2,3]triazin-4(3H)-one (Compound II-64)

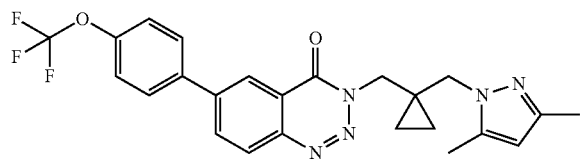 [SMILES: Cc1cc(C)n(CC2(Cn3nnc4ccc(-c5ccc(OC(F)(F)F)cc5)cc4c3=O)CC2)n1]

Compound II-64 was prepared using a similar procedure as that described for Compound II-40 with the appropriate starting materials.

Example 50

3-(3-methoxy-2,2-dimethylpropyl)-6-(4-(trifluoromethoxy)phenyl)benzo[d][1,2,3]triazin-4(3H)-one (Compound II-70)

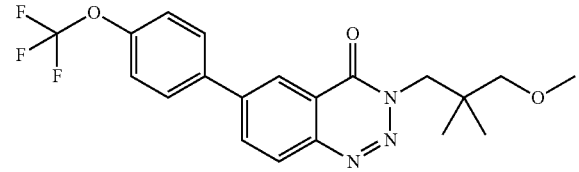 [SMILES: COCC(C)(C)Cn1nnc2ccc(-c3ccc(OC(F)(F)F)cc3)cc2c1=O]

Compound II-70 was prepared using a similar procedure as that described for Compound II-40 with the appropriate starting materials.

Example 51

3-((1-(hydroxymethyl)cyclopropyl)methyl)-6-(4-(trifluoromethoxy)phenyl)benzo[d][1,2,3]triazin-4(3H)-one (Compound II-75)

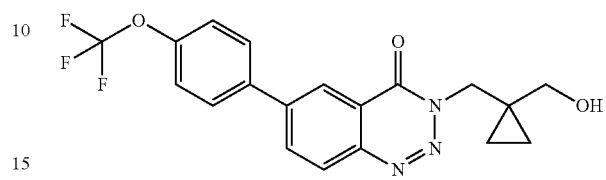

Compound II-75 was prepared using a similar procedure as that described for Compound II-40 with the appropriate starting materials.

Example 52

3-(3-hydroxy-2,2-dimethylpropyl)-6-(4-(trifluoromethoxy)phenyl)benzo[d][1,2,3]triazin-4(3H)-one (Compound II-83)

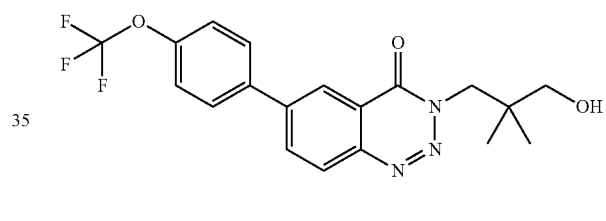

Compound II-83 was prepared using a similar procedure as that described for Compound II-40 with the appropriate starting materials.

Example 53

3-((1-(hydroxymethyl)cyclopropyl)methyl)-6-(2-(2,2,2-trifluoroethylamino)pyrimidin-5-yl)benzo[d][1,2,3]triazin-4(3H)-one (Compound V-17)

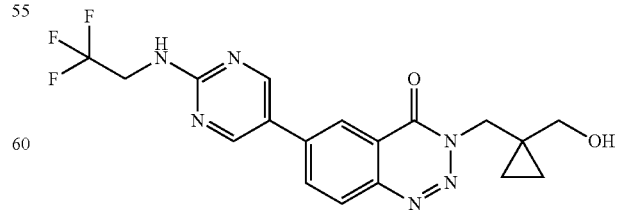

Compound V-17 was prepared using a similar procedure as that described for Compound II-40 with the appropriate starting materials.

Example 54

3-(3-hydroxy-2,2-dimethylpropyl)-6-(2-(2,2,2-trifluoroethylamino)pyrimidin-5-yl)benzo[d][1,2,3]triazin-4(3H)-one (Compound V-18)

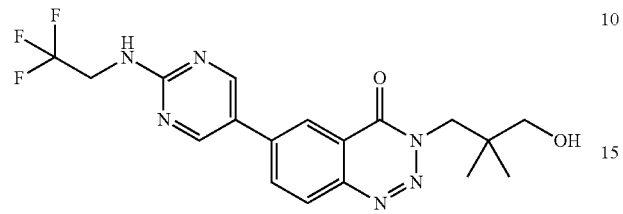

Compound V-18 was prepared using a similar procedure as that described for Compound II-40 with the appropriate starting materials.

Example 55

3-((1-((pyrimidin-2-yloxy)methyl)cyclopropyl)methyl)-6-(4-(trifluoromethoxy)phenyl)benzo[d][1,2,3]triazin-4(3H)-one (Compound II-80)

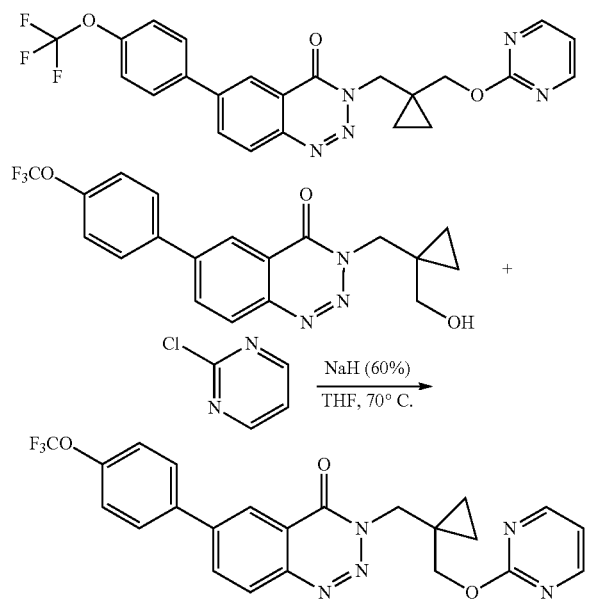

Compound II-75 (0.367 mmol) was dissolved in anhydrous THF under nitrogen followed by addition of NaH (0.551 mmol). The reaction mixture was stirred at RT for 10 min after which 2-chloropyrimidine (0.735 mmol) was added. The resulting mixture was refluxed for 18 hours. The reaction was quenched with water. Extracted with dichoromethane, dried over $Na_2SO_4$, and purified by prep TLC to afford Compound II-80.

Example 56

3-(2,2-dimethyl-3-(pyrimidin-2-yloxy)propyl)-6-(4-(trifluoromethoxy)phenyl)benzo[d][1,2,3]triazin-4(3H)-one (Compound II-84)

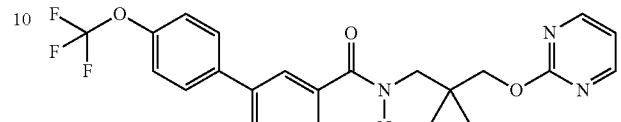

Compound II-84 was prepared using a similar procedure as that described for Compound II-80 with the appropriate starting materials.

Example 57

2-((1-(((4-oxo-6-(4-(trifluoromethoxy)phenyl)benzo[d][1,2,3]triazin-3(4H)-yl)methyl)cyclopropyl)methoxy)pyrimidine-4-carbonitrile (Compound II-88)

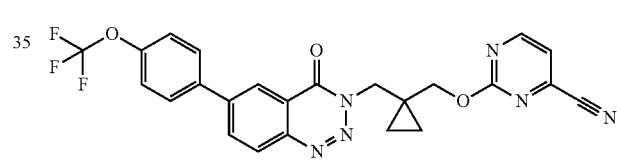

Compound II-88 was prepared using a similar procedure as that described for Compound II-80 with the appropriate starting materials.

Example 58

3-((1-(((6-chloropyridazin-3-yloxy)methyl)cyclopropyl)methyl)-6-(4-(trifluoromethoxy)phenyl)benzo[d][1,2,3]triazin-4(3H)-one (Compound II-89)

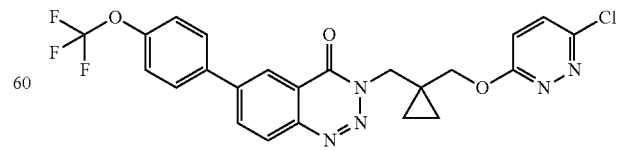

Compound II-89 was prepared using a similar procedure as that described for Compound II-80 with the appropriate starting materials.

Example 59

3-((1-((6-(2,2,2-trifluoroethoxy)pyridazin-3-yloxy)methyl)cyclopropyl)methyl)-6-(4-(trifluoromethoxy)phenyl)benzo[d][1,2,3]triazin-4(3H)-one (Compound II-90)

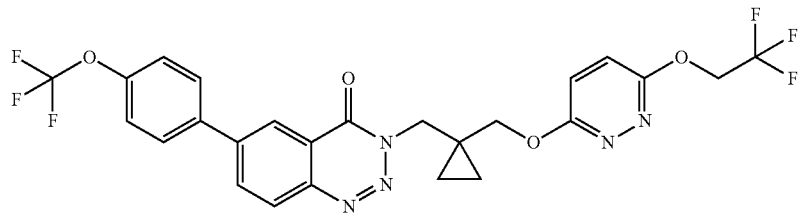 [SMILES: O=c1c2cc(-c3ccc(OC(F)(F)F)cc3)ccc2nnn1CC1(COc2ccc(OCC(F)(F)F)nn2)CC1]

Compound II-90 was prepared using a similar procedure as that described for Compound II-80 with the appropriate starting materials.

Example 60

2-(2,2-dimethyl-3-(4-oxo-6-(4-(trifluoromethoxy)phenyl)benzo[d][1,2,3]triazin-3(4H)-yl)propoxy)pyrimidine-4-carbonitrile (Compound II-92)

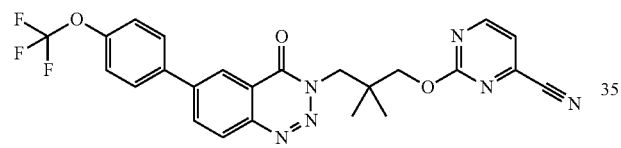

Compound II-92 was prepared using a similar procedure as that described for Compound II-80 with the appropriate starting materials.

Example 61

3-(3-(2-chloropyrimidin-4-yloxy)-2,2-dimethylpropyl)-6-(4-(trifluoromethoxy)phenyl)benzo[d][1,2,3]triazin-4(3H)-one (Compound II-93)

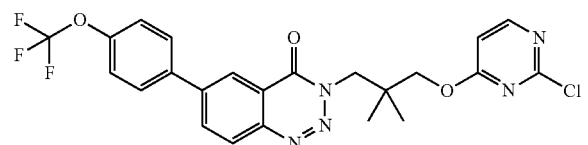

Compound II-93 was prepared using a similar procedure as that described for Compound II-80 with the appropriate starting materials.

Example 62

1-((4-oxo-6-(4-(trifluoromethoxy)phenyl)benzo[d][1,2,3]triazin-3(4H)-yl)methyl)cyclopropanecarboxylic acid (Compound II-62)

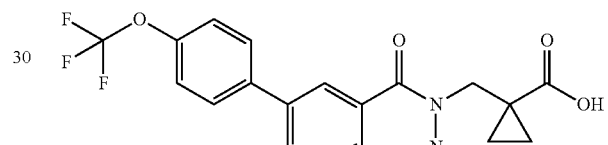

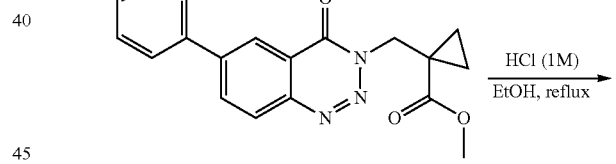

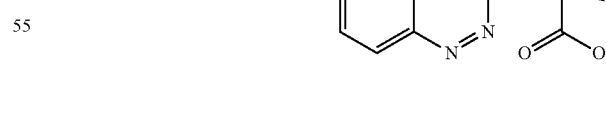

Compound II-55 (0.09 mmol) was refluxed in 1 M HCl (4 mL) and EtOH (4 mL) for 72 hours. Reaction mixture was concentrated down and purified by prep TLC to afford Compound II-62.

Example 63

3-(2-oxo-2-(4-(pyrimidin-2-yl)piperazin-1-yl)ethyl)-6-(4-(trifluoromethoxy)phenyl)benzo[d][1,2,3]triazin-4(3H)-one (Compound II-41)

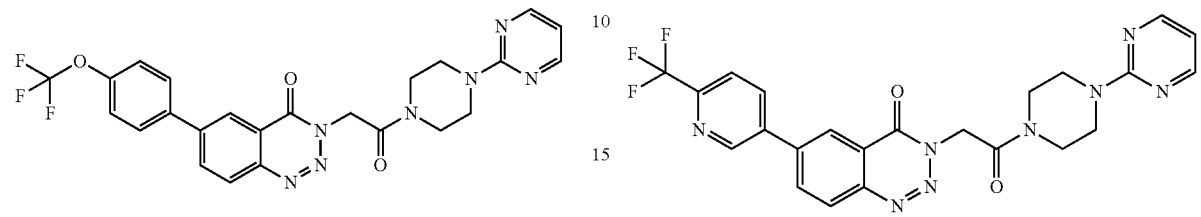

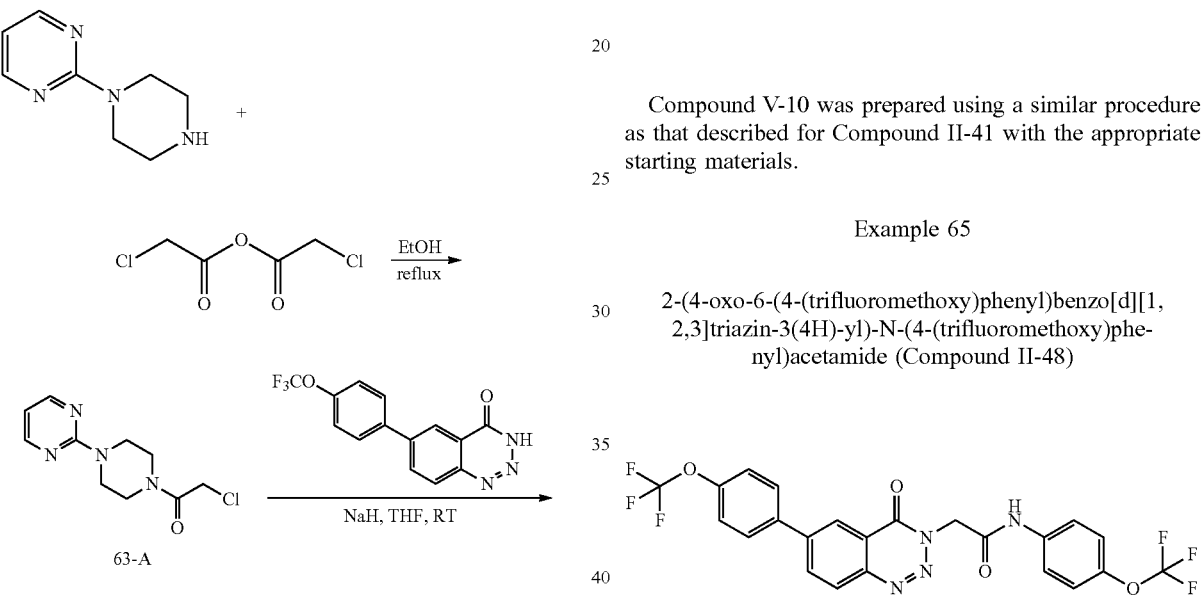

2-(Piperazin-1-yl)pyrimidine (3.96 mmol) and 2-chloroacetic anhydride (4.36 mmol) were combined and refluxed in EtOH (30 mL) for 18 hours. The reaction mixture was concentrated. The residue was dissolved in dichloromethane and washed with water. The organic extract was dried over Na$_2$SO$_4$, evaporated to afford 63-A which was used in the next step without further purifications.

Previously prepared 6-(4-trifluoromethoxy)phenyl)benzo[d][1,2,3]triazin-4(3H)-one (0.326 mmol) was dissolved in THF under nitrogen. To this was added NaH (0.977 mmol). The mixture was stirred for 10 min at RT followed by addition of 63-A (0.489 mmol). After 18 hours the reaction mixture was quenched with water and extracted with dichloromethane and purified by preparative HPLC to give Compound II-41.

Example 64

3-(2-oxo-2-(4-(pyrimidin-2-yl)piperazin-1-yl)ethyl)-6-(6-(trifluoromethyl)pyridin-3-yl)benzo[d][1,2,3]triazin-4(3H)-one (Compound V-10)

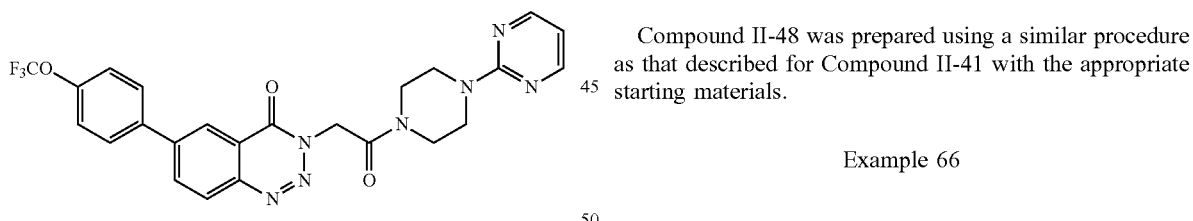

Compound V-10 was prepared using a similar procedure as that described for Compound II-41 with the appropriate starting materials.

Example 65

2-(4-oxo-6-(4-(trifluoromethoxy)phenyl)benzo[d][1,2,3]triazin-3(4H)-yl)-N-(4-(trifluoromethoxy)phenyl)acetamide (Compound II-48)

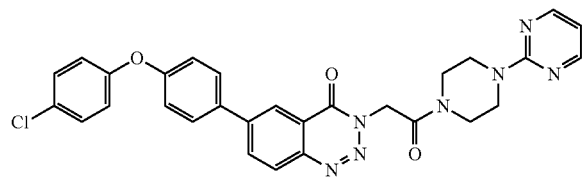 [SMILES: O=C(Cn1nnc2ccc(-c3ccc(Oc4ccc(Cl)cc4)cc3)cc2c1=O)N1CCN(c2ncccn2)CC1]

Compound II-48 was prepared using a similar procedure as that described for Compound II-41 with the appropriate starting materials.

Example 66

6-(4-(4-chlorophenoxy)phenyl)-3-(2-oxo-2-(4-(pyrimidin-2-yl)piperazin-1-yl)ethyl)benzo[d][1,2,3]triazin-4(3H)-one (Compound II-65)

Compound II-65 was prepared using a similar procedure as that described for Compound II-41 with the appropriate starting materials.

Example 67

3-((1-((4-methylpiperazin-1-yl)methyl)cyclopropyl)methyl)-6-(4-(trifluoromethoxy)phenyl)benzo[d][1,2,3]triazin-4(3H)-one (Compound II-31)

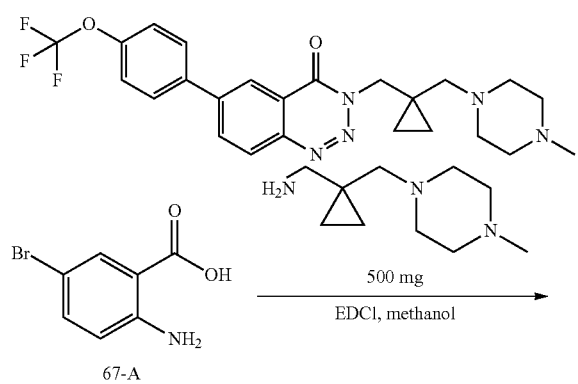

To a round bottom flask was added 2-amino-5-bromobenzoic acid (1.39 mmol), and CDI or EDCI-HCl (1.5 equiv) in CH$_2$Cl$_2$ (20 mL) and the mixture was stirred at RT for 15 min before addition of amine (1.3 equiv). The resulting reaction mixture was stirred at RT overnight. The mixture was washed with H$_2$O and the organic extract was dried over Na$_2$SO$_4$ and then concentrated down under reduced pressure before purification by preparative TLC eluting with 5% methanol methylene chloride mixture to afford 67-B.

To a cooled 0.5M HCl (10 mL), sodium nitrite (320 mg, 4.62 mmol) in 5 mL of water was added slowly at 0° C. and stirred at that temperature for 15 min. To this mixture the amide (880 mg, 2.3 mmol) dissolved in DMF (4 mL) was added slowly and stirred at room temperature for 2 h. Filtered the precipitate, washed with water and dried and the product obtained was used as such for the next step.

To the bromide 67-C (1 eq), boronic acid (1.2 eq) and tetrkistriphenyl phosphine palladium (10 mol %) in a microwave vial, DMF (2.5 mL) and 2N Na$_2$CO$_3$ (0.3 ml) were added and heated at 140° C. for 12 min. After cooling filtered through celite, concentrated and purified by prep TLC/prep HPLC. MS m/z (M$^+$)=474.2.

Example 68

3-((1-((4-methylpiperazin-1-yl)methyl)cyclopropyl)methyl)-6-(6-(trifluoromethyl)pyridin-3-yl)benzo[d][1,2,3]triazin-4(3H)-one (Compound V-5)

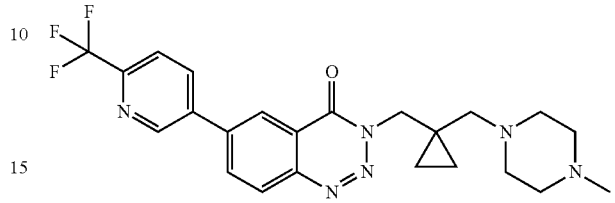

Compound V-5 was prepared using a similar procedure as that described for Compound II-31 with the appropriate starting materials. MS m/z (M$^+$)=459.2.

Example 69

6-(2-(dimethylamino)pyrimidin-5-yl)-3-((1-((4-methylpiperazin-1-yl)methyl)cyclopropyl)methyl)benzo[d][1,2,3]triazin-4(3H)-one (Compound V-6)

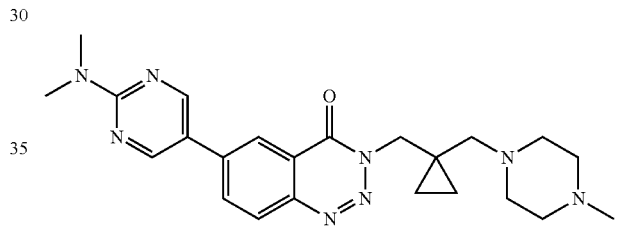

Compound V-6 was prepared using a similar procedure as that described for Compound II-31 with the appropriate starting materials. MS m/z (M$^+$)=435.1.

Example 70

1-(4-(4-oxo-3-(2-(pyrimidin-2-yloxy)ethyl)-3,4-dihydrobenzo[d][1,2,3]triazin-6-yl)phenyl)cyclopropanecarbonitrile (Compound II-50)

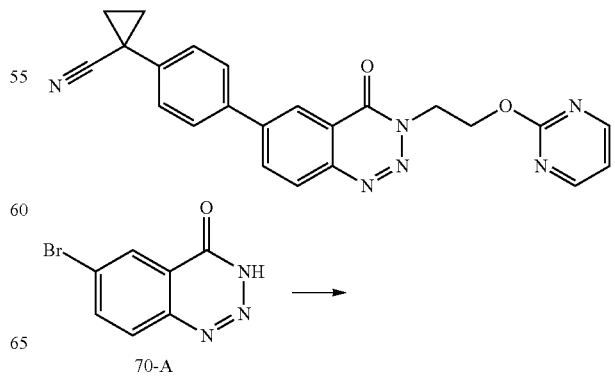

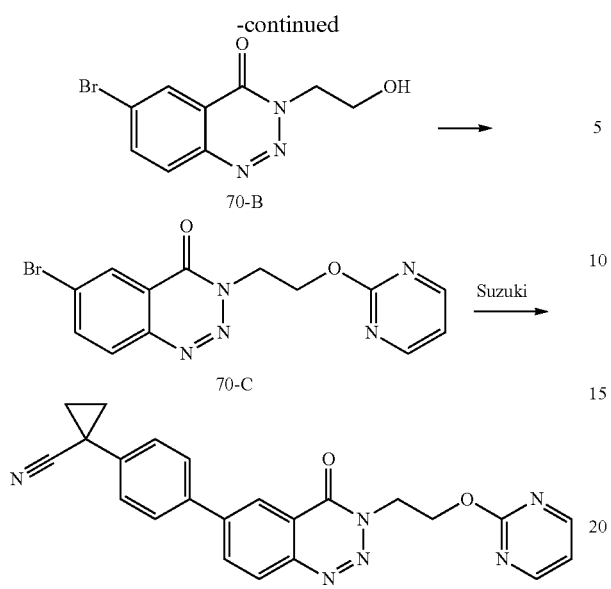

To a solution of triazenone 70-A (2.0 g, 10 mmol) in DMF (20 mL), potassium carbonate (4.1 g, 30 mmol) and bromoethanol (3.12 g, 25 mmol) were added and heated at 90° C. for 16 h. After cooling, potassium carbonate was filtered off, washed with DMF and the filtrate was concentrated. The residue was treated with water, filtered the precipitate, washed with water and dried and the alkylated triazenone 70-B was used as such for the next step.

To a solution of triazenone alcohol 70-B (1.5 g, 5.5 mmol) and 2-chloro pyrimidne (766 mg, 6.67 mmol) in THF (20 mL), sodium hydride (60% dispersion in oil, 333 mg, 8.32 mmol) was added and stirred at room temperature for 10 min, followed by heating at 80° C. for 24 h. The reaction mixture was quenched with water, extracted with ethyl acetate (100 mL). The organic layer was washed with water, brine and dried over sodium sulphate and concentrated. Purification by Flash chromatography furnished the product 70-C.

For the Suzuki coupling reaction the following conditions were applied: To a suspension of bromide 70-C (1 eq), boronic acid or boronate ester (1.2 eq) and base potassium carbonate (3 eq) in solvent (toluene:isopropanol:water in the ratio of 4:1:1) was added palladium catalyst Pd(dppf)Cl$_2$ (10 mol %) and heated at 80° C. for 2-4 h. The reaction progress was followed by LC and after completion, the reaction mixture was filtered through celite, washed with ethyl acetate, concentrated the filtrate and purified by prep TLC/prep HPLC. MS m/z (M$^+$)=410.8.

Example 71

3-(2-(pyrimidin-2-yloxy)ethyl)-6-(6-(trifluoromethyl)pyridin-3-yl)benzo[d][1,2,3]triazin-4(3H)-one (Compound V-11)

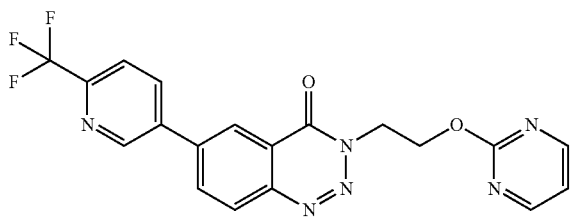 [SMILES: O=c1c2cc(-c3ccc(C(F)(F)F)nc3)ccc2nnn1CCOc1ncccn1]

Compound V-11 was prepared using a similar procedure as that described for Compound II-50 with the appropriate starting materials. MS m/z (M$^+$)=414.8.

Example 72

6-(2-(piperidin-1-yl)pyrimidin-5-yl)-3-(2-(pyrimidin-2-yloxy)ethyl)benzo[d][1,2,3]triazin-4(3H)-one (Compound V-12)

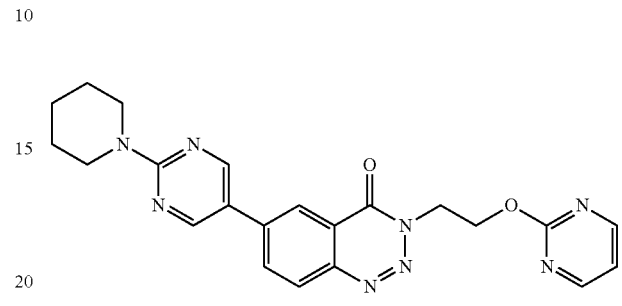

Compound V-12 was prepared using a similar procedure as that described for Compound II-50 with the appropriate starting materials. MS m/z (M$^+$)=431.2.

Example 73

3-(2-(pyrimidin-2-yloxy)ethyl)-6-(2-(pyrrolidin-1-yl)pyrimidin-5-yl)benzo[d][1,2,3]triazin-4(3H)-one (Compound V-13)

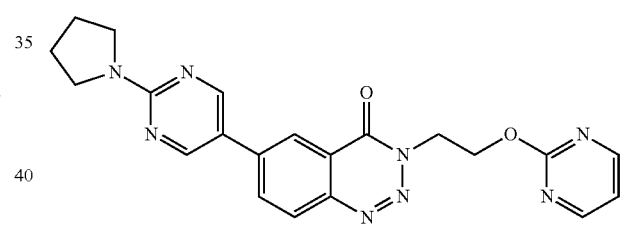

Compound V-13 was prepared using a similar procedure as that described for Compound II-50 with the appropriate starting materials. MS m/z (M$^+$)=417.2.

Example 74

6-(2-(4-methylpiperazin-1-yl)pyrimidin-5-yl)-3-(2-(pyrimidin-2-yloxy)ethyl)benzo[d][1,2,3]triazin-4(3H)-one (Compound V-14)

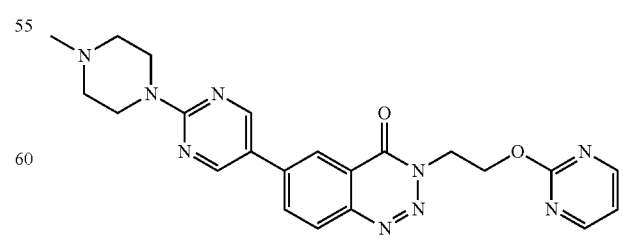

Compound V-14 was prepared using a similar procedure as that described for Compound II-50 with the appropriate starting materials. MS m/z (M$^+$)=446.1.

Example 75

3-(2-(pyrimidin-2-yloxy)ethyl)-6-(2-(2,2,2-trifluoro-ethylamino)pyrimidin-5-yl)benzo[d][1,2,3]triazin-4(3H)-one (Compound V-15)

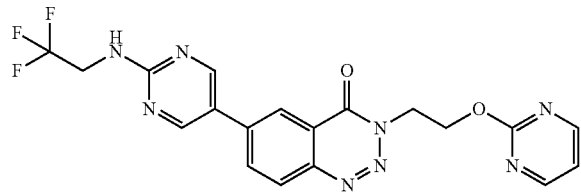 [SMILES: O=c1c2cc(-c3cnc(NCC(F)(F)F)nc3)ccc2nnn1CCOc1ncccn1]

Compound V-15 was prepared using a similar procedure as that described for Compound II-50 with the appropriate starting materials. MS m/z (M+)=445.1.

Example 76

6-(2-morpholinopyrimidin-5-yl)-3-(2-(pyrimidin-2-yloxy)ethyl)benzo[d][1,2,3]triazin-4(3H)-one (Compound V-16)

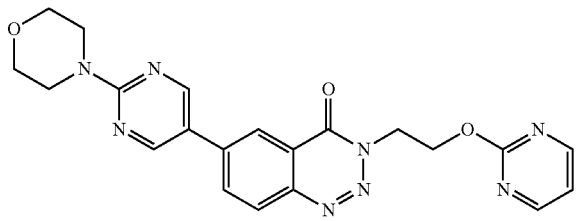 [SMILES: O=c1c2cc(-c3cnc(N4CCOCC4)nc3)ccc2nnn1CCOc1ncccn1]

Compound V-16 was prepared using a similar procedure as that described for Compound II-50 with the appropriate starting materials.

Example 77

3-(2-(5-(1H-pyrazol-3-yl)pyrimidin-2-yloxy)ethyl)-6-(4-(trifluoromethoxy)phenyl)benzo[d][1,2,3]triazin-4(3H)-one (Compound II-85)

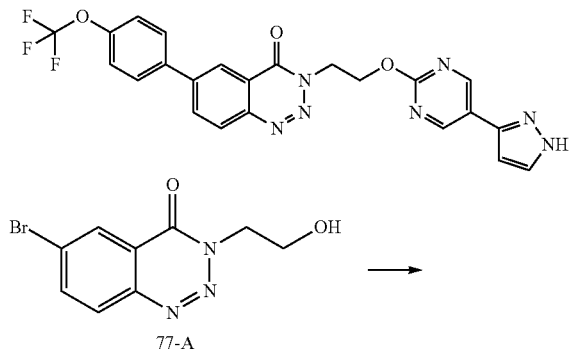

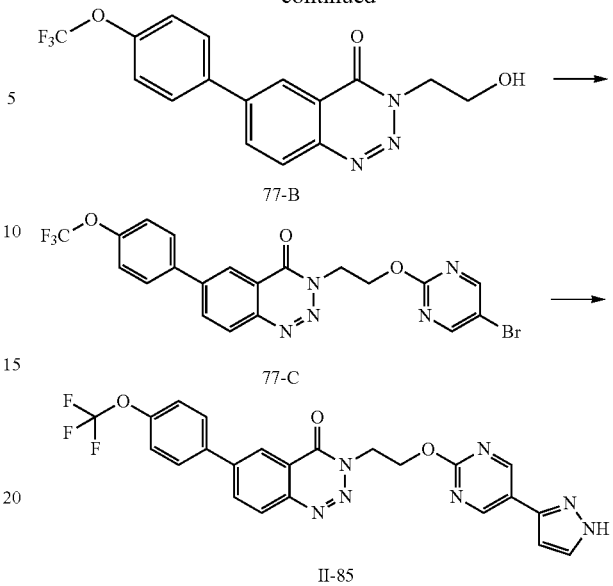

To the bromide 77-A (1 eq), boronic acid (1.2 eq) and tetrkistriphenyl phosphine palladium (10 mol %) in a microwave vial, DMF (2.5 mL) and 2N $Na_2CO_3$ (0.3 ml) were added and heated at 140° C. for 20 min. After cooling filtered through celite, concentrated and purified by column chromatography.

To a solution of triazenone alcohol 77-B (250 mg, 0.71 mmol) and 2-idodo-5-bromo pyrimidne (242 mg, 0.85 mmol) in THF (20 mL), sodium hydride (60% dispersion in oil, 50 mg, 2.13 mmol) was added and stirred at room temperature for 10 min, followed by heating at 80° C. for 3 h. The reaction mixture was quenched with water, extracted with ethyl acetate (100 mL). The organic layer was washed with water, brine and dried over sodium sulphate and concentrated. Purification by prep TLC furnished the product 77-C.

To the bromide 77-C (1 eq), boronic acid (1.2 eq) and tetrkistriphenyl phosphine palladium (10 mol %) in a microwave vial, DMF (2.5 mL) and 2N $Na_2CO_3$ (0.3 ml) were added and heated at 140° C. for 20 min. After cooling filtered through celite, concentrated and purified by column chromatography.

Example 78

3-(2-(5-(3,5-dimethylisoxazol-4-yl)pyrimidin-2-yloxy)ethyl)-6-(4-(trifluoromethoxy)phenyl)benzo[d][1,2,3]triazin-4(3H)-one (Compound II-86)

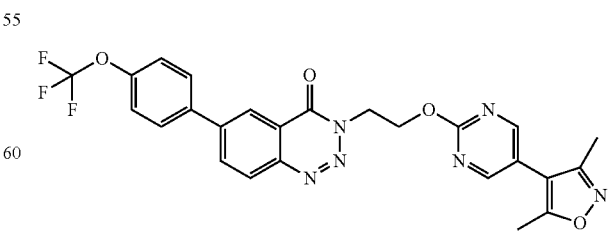

Compound II-86 was prepared using a similar procedure as that described for Compound II-85 with the appropriate starting materials.

Example 79

3-(2-(5-(pyridin-3-yl)pyrimidin-2-yloxy)ethyl)-6-(4-(trifluoromethoxy)phenyl)benzo[d][1,2,3]triazin-4(3H)-one (Compound II-87)

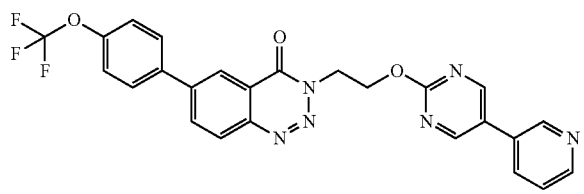 [SMILES: O=c1c2cc(-c3ccc(OC(F)(F)F)cc3)ccc2nnn1CCOc1ncc(-c2cccnc2)cn1]

Compound II-87 was prepared using a similar procedure as that described for Compound II-85 with the appropriate starting materials.

Example 80

7-(4-(trifluoromethoxy)phenyl)phthalazin-1(2H)-one (Compound III-1)

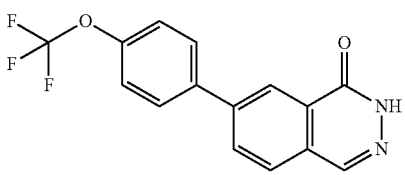

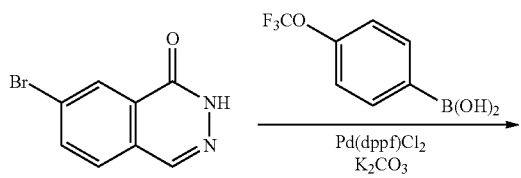

A mixture of 7-bromophthalazinone (1.09 g, 4.84 mmol), 4-trifluoromethoxyphenyl boronic acid (1.20 g, 5.81 mmol), dppf(Pd)Cl$_2$ (177 mg, 0.242 mmol), potassium carbonate (1.34 g, 9.68 mmol) in degassed toluene (4 mL), degassed water (2 mL) and degassed isopropanol (2 mL) was heated at 90° C. for 12 hours. The layers were separated, the organic layer was concentrated and the residue was purified by trituration with hexanes/ethyl acetate to provide 7-(4-(trifluoromethoxy)phenyl)phthalazin-1(2H)-one as a white powder. $C_{15}H_9F_3N_2O_2$. 307.2 (M+1).

Example 81

2-((3-methyl-1,2,4-oxadiazol-5-yl)methyl)-7-(4-(trifluoromethoxy)phenyl)phthalazin-1(2H)-one (Compound III-2)

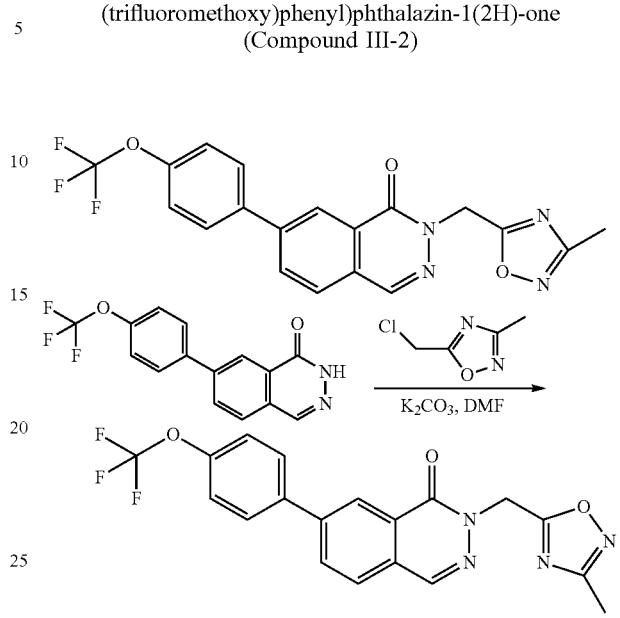

To a mixture of 7-(4-(trifluoromethoxy)phenyl)phthalazin-1(2H)-one (50 mg, 0.163 mmol), 5-(chloromethyl)-3-methyl-1,2,4-oxadiazole (47.5 mg, 0.359 mmol), and potassium carbonate (68 mg, 9.68 mmol) was added DMF (1 mL) and the reaction was heated to 80° C. overnight. The reaction was diluted with EtOAc and water, the layers were separated, and the organic layer was concentrated to an oil. The residue was purified by flash chromatography ($R_f$=0.32, 1:1 hexanes/ethyl acetate) to afford 2-((3-methyl-1,2,4-oxadiazol-5-yl)methyl)-7-(4-(trifluoromethoxy)phenyl)phthalazin-1(2H)-one as a white solid. $C_{19}H_{13}F_3N_4O_3$. 403.1 (M+1). $^1$H NMR (DMSO) δ 8.58 (s, 1H), 8.48 (d, J=2.0 Hz, 1H), 8.34 (dd, J=2.0, 8.4 Hz, 1H), 8.12 (d, J=8.4 Hz, 1H), 7.98-8.02 (m, 2H), 7.54 (d, J=8.0 Hz, 1H), 5.67 (s, 2H), 2.31 (s, 1H).

Example 82

2-(pyrimidin-2-ylmethyl)-7-(4-(trifluoromethoxy)phenyl)phthalazin-1(2H)-one (Compound III-5)

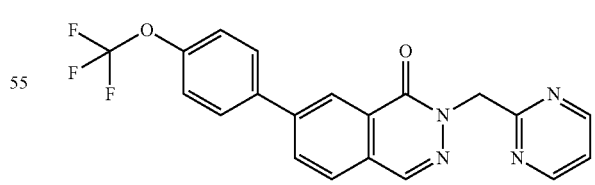

Compound III-5 was prepared using a similar procedure as that described for Compound III-2 with the appropriate starting materials. $C_{20}H_{13}F_3N_4O_2$. 399.1 (M+1). $^1$H NMR (DMSO) δ 8.73 (d, J=4.8 Hz, 2H), 8.51 (s, 1H), 8.45 (d, J=2.0 Hz, 1H), 8.30 (dd, J=2.0, 8.0 Hz, 1H), 8.09 (d, J=8.0 Hz, 1H), 7.95-7.99 (m, 2H), 7.52 (d, J=8.0 Hz, 2H), 7.40 (t, J=4.8 Hz, 1H), 5.55 (s, 2H).

Example 83

2-((5-methyl-1,2,4-oxadiazol-3-yl)methyl)-7-(4-(trifluoromethoxy)phenyl)phthalazin-1(2H)-one (Compound III-3)

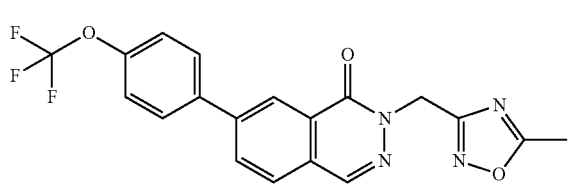 [SMILES: Cc1nc(Cn2ncc3ccc(-c4ccc(OC(F)(F)F)cc4)cc3c2=O)no1]

Compound III-3 was prepared using a similar procedure as that described for Compound III-2 with the appropriate starting materials. $C_{19}H_{13}F_3N_4O_3$. 403.0 (M+1). $^1$H NMR (DMSO) δ 8.53 (s, 1H), 8.48 (d, J=1.6 Hz, 1H), 8.32 (dd, J=2.0, 8.4 Hz, 1H), 8.10 (d, J=8.0 Hz, 1H), 7.97-8.02 (m, 2H), 7.54 (d, J=7.6 Hz, 1H), 5.48 (s, 2H), 2.56 (s, 1H).

Example 84

2-methyl-7-(4-(trifluoromethoxy)phenyl)phthalazin-1(2H)-one (Compound III-4)

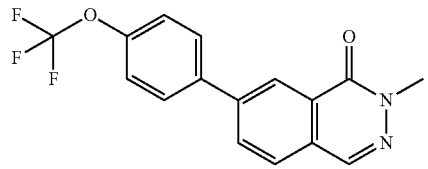 [SMILES: Cn1ncc2ccc(-c3ccc(OC(F)(F)F)cc3)cc2c1=O]

Compound III-4 was prepared using a similar procedure as that described for Compound III-2 with the appropriate starting materials. $C_{16}H_{11}F_3N_2O_2$ 321.2 (M+1)

Example 85

2-benzyl-7-(4-(trifluoromethoxy)phenyl)phthalazin-1(2H)-one (Compound III-6)

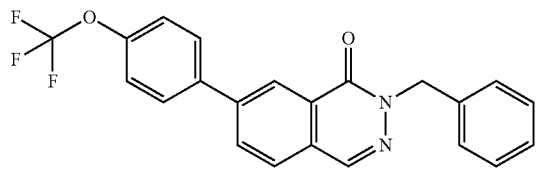 [SMILES: O=c1c2cc(-c3ccc(OC(F)(F)F)cc3)ccc2cnn1Cc1ccccc1]

Compound III-6 was prepared using a similar procedure as that described for Compound III-2 with the appropriate starting materials. $C_{22}H_{15}F_3N_2O_2$ 397.1 (M+1).

Example 86

2-((1-oxo-7-(4-(trifluoromethoxy)phenyl)phthalazin-2(1H)-yl)methyl)benzonitrile (Compound III-7)

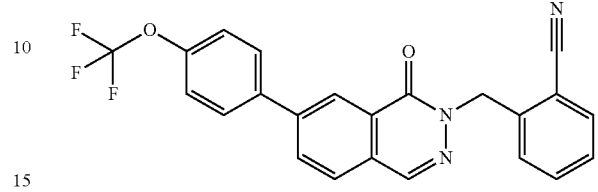

Compound III-7 was prepared using a similar procedure as that described for Compound III-2 with the appropriate starting materials. $C_{23}H_{14}F_3N_3O_2$ 422.1 (M+1).

Example 87

2-phenethyl-7-(4-(trifluoromethoxy)phenyl) phthalazin-1(2H)-one (Compound III-8)

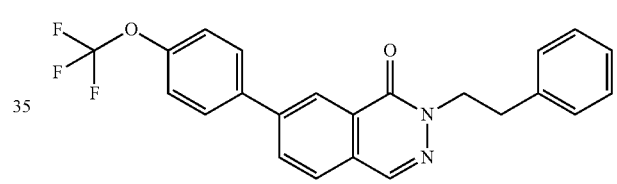

Compound III-8 was prepared using a similar procedure as that described for Compound III-2 with the appropriate starting materials. $C_{23}H_{17}F_3N_2O_2$ 411.0 (M+1).

Example 88

2-(2-(1H-pyrazol-1-yl)ethyl)-7-(4-(trifluoromethoxy)phenyl)phthalazin-1(2H)-one (Compound III-9)

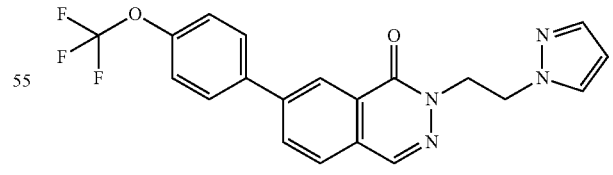

Compound III-9 was prepared using a similar procedure as that described for Compound III-2 with the appropriate starting materials. $C_{20}H_{15}F_3N_4O_2$. 401.0 (M+1). $^1$H NMR (DMSO) δ 8.43 (d, J=2.0 Hz, 1H), 8.39 (s, 1H), 8.26 (dd, J=2.0, 8.4 Hz, 1H), 8.03 (d, J=8.8 Hz, 1H), 7.94-7.97 (m, 2H), 7.52 (d, J=8.0 Hz, 2H), 7.34-7.35 (m, 1H), 6.14 (t, J=1.6 Hz, 1H), 4.50-4.56 (m, 4H).

Example 89

2-(2-(1H-pyrrol-1-yl)ethyl)-7-(4-(trifluoromethoxy)phenyl)phthalazin-1(2H)-one (Compound III-10)

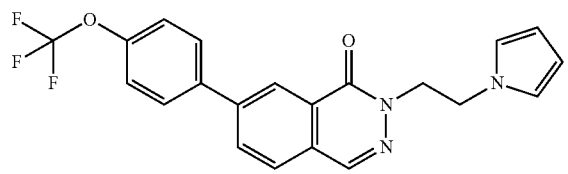 [SMILES: O=c1c2cc(-c3ccc(OC(F)(F)F)cc3)ccc2cnn1CCn1cccc1]

Compound III-10 was prepared using a similar procedure as that described for Compound III-2 with the appropriate starting materials. $C_{11}H_{16}F_3N_3O_2$. 400.0 (M+1). $^1$H NMR (DMSO) δ 8.43-8.44 (m, 1H), 8.43 (s, 1H), 8.26 (dd, J=2.0, 8.0 Hz, 1H), 8.04 (d, J=8.0 Hz, 1H), 7.95 (dt, J=2.0, 8.8 Hz, 2H), 7.51 (d, J=7.6 Hz, 2H), 6.63 (t, J=2.0 Hz, 2H), 5.89 (t, J=2.0 Hz, 2H), 4.45 (t, J=6.8 Hz, 2H), 4.32 (t, J=6.8 Hz, 2H).

Example 90

2-((4-methyl-1,2,5-oxadiazol-3-yl)methyl)-7-(4-(trifluoromethoxy)phenyl)phthalazin-1(2H)-one (Compound III-11)

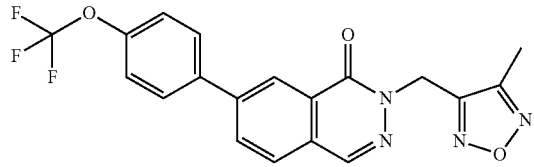 [SMILES: Cc1nonc1Cn1ncc2ccc(-c3ccc(OC(F)(F)F)cc3)cc2c1=O]

Compound III-11 was prepared using a similar procedure as that described for Compound III-2 with the appropriate starting materials. $C_{19}H_{13}F_3N_4O_3$ 403.1 (M+1).

Example 91

6-((1-oxo-7-(4-(trifluoromethoxy)phenyl)phthalazin-2(1H)-yl)methyl)picolinonitrile (Compound III-12)

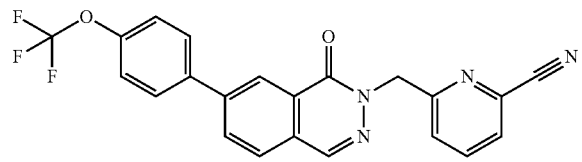 [SMILES: N#Cc1cccc(Cn2ncc3ccc(-c4ccc(OC(F)(F)F)cc4)cc3c2=O)n1]

Compound III-12 was prepared using a similar procedure as that described for Compound III-2 with the appropriate starting materials. $C_{22}H_{13}F_3N_4O_3$ 423.1 (M+1).

Example 92

7-(4-(trifluoromethoxy)phenyl)-2-((5-(3-(trifluoromethyl)phenyl)-1,2,4-oxadiazol-3-yl)methyl)phthalazin-1(2H)-one (Compound III-13)

Compound III-13 was prepared using a similar procedure as that described for Compound III-2 with the appropriate starting materials. $C_{25}H_{14}F_6N_4O_3$ 533.1 (M+1).

Example 93

2-((2-bromopyridin-3-yl)methyl)-7-(4-(trifluoromethoxy)phenyl)phthalazin-1(2H)-one (Compound III-14)

Compound III-14 was prepared using a similar procedure as that described for Compound III-2 with the appropriate starting materials. $C_{11}H_{13}BrF_3N_3O_3$ 477.9 (M+1).

Example 94

2-(3-hydroxypropyl)-7-(4-(trifluoromethoxy)phenyl)phthalazin-1(2H)-one (Compound III-15)

Compound III-15 was prepared using a similar procedure as that described for Compound III-2 with the appropriate starting materials. $C_{15}H_{15}F_3N_2O_3$ 365.0 (M+1).

Example 95

2-(2-(3-methyl-1H-pyrazol-1-yl)ethyl)-7-(4-(trifluoromethoxy)phenyl)phthalazin-1(2H)-one (Compound III-17)

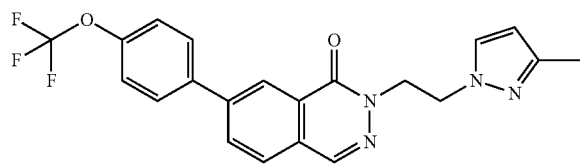 [SMILES: Cc1ccn(CCn2ncc3ccc(-c4ccc(OC(F)(F)F)cc4)cc3c2=O)n1]

Compound III-17 was prepared using a similar procedure as that described for Compound III-2 with the appropriate starting materials. $C_{11}H_{17}F_3N_4O_2$. 415.1 (M+1). $^1$H NMR (DMSO) δ 8.40-8.44 (m, 2H), 8.26 (dd, J=2.0, 8.4 Hz, 1H), 8.03 (d, J=8.8 Hz, 1H), 7.95 (d, J=8.8 Hz, 2H), 7.51 (d, J=8.0 Hz, 2H), 7.46 (d, J=2.0 Hz, 1H), 5.91 (d, J=2.4 Hz, 1H), 4.48 (t, J=1.6 Hz, 2H), 4.42 (t, J=1.6 Hz, 2H), 2.06 (s, 3H).

Example 96

7-(4-(trifluoromethoxy)phenyl)-2-((6-(trifluoromethyl)pyridin-2-yl)methyl)phthalazin-1(2H)-one (Compound III-21)

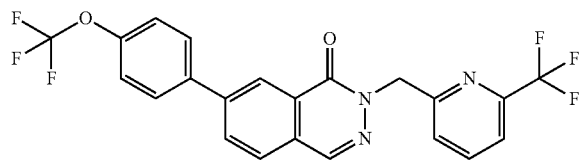 [SMILES: O=c1c2cc(-c3ccc(OC(F)(F)F)cc3)ccc2cnn1Cc1cccc(C(F)(F)F)n1]

Compound III-21 was prepared using a similar procedure as that described for Compound III-2 with the appropriate starting materials. $C_{22}H_{13}F_6N_3O_2$ 466.1 (M+1).

Example 97

2-(2-(1-methyl-1H-benzo[d]imidazol-2-yl)ethyl)-7-(4-(trifluoromethoxy)phenyl)phthalazin-1(2H)-one (Compound III-25)

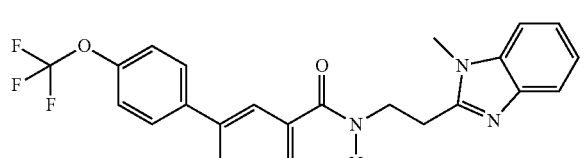

Compound III-25 was prepared using a similar procedure as that described for Compound III-2 with the appropriate starting materials. $C_{25}H_{19}F_3N_4O_2$ 465.1 (M+1).

Example 98

2-(2-(1H-1,2,4-triazol-1-yl)ethyl)-7-(4-(trifluoromethoxy)phenyl)phthalazin-1(2H)-one (Compound III-26)

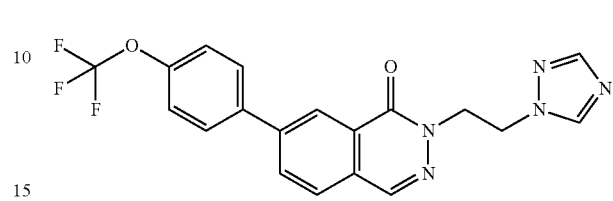

Compound III-26 was prepared using a similar procedure as that described for Compound III-2 with the appropriate starting materials. $C_{19}H_{14}F_3N_5O_2$ 401.9 (M+1).

Example 99

2-((5-chloropyrimidin-2-yl)methyl)-7-(4-(trifluoromethoxy)phenyl)phthalazin-1(2H)-one (Compound III-35)

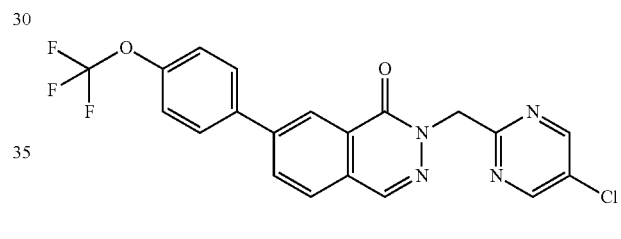

Compound III-35 was prepared using a similar procedure as that described for Compound III-2 with the appropriate starting materials. $C_{20}H_{12}ClF_3N_4O_2$. 433.1 (M+1). $^1$H NMR (DMSO) δ 8.87 (s, 2H), 8.52 (s, 1H), 8.44 (d, J=2.0 Hz, 1H), 8.30 (dd, J=2.0, 8.0 Hz, 1H), 8.09 (d, J=8.0 Hz, 1H), 7.94-7.98 (m, 2H), 7.51 (d, J=7.6 Hz, 2H), 5.56 (s, 2H).

Example 100

3-(2-(pyridin-2-yl)ethyl)-6-(4-(trifluoromethoxy)phenyl)benzo[d][1,2,3]triazin-4(3H)-one (Compound II-15)

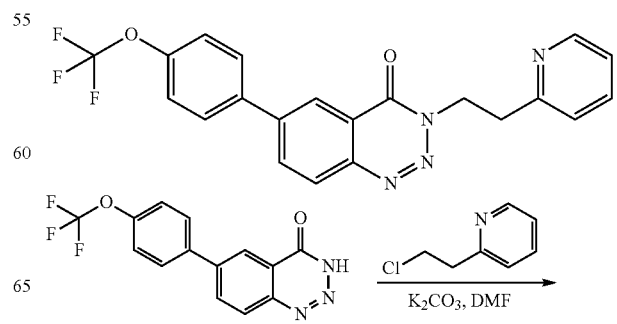

-continued

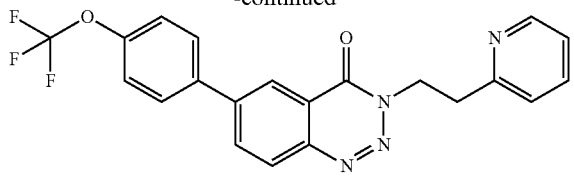

Compound II-15 was prepared using a similar procedure as that described for Compound III-2 with the appropriate starting materials. $C_{11}H_{15}F_3N_4O_2$. 413.0 (M+1). $^1$H NMR (DMSO) δ 8.38-8.44 (m, 3H), 8.26 (d, J=8.0 Hz, 1H), 8.00 (dd, J=2.4, 6.8 Hz, 2H), 7.65-7.70 (m, 1H), 7.53 (d, J=8.8 Hz, 2H), 7.30 (d, J=7.6 Hz, 1H), 7.19-7.23 (m, 1H), 4.76 (t, J=6.8 Hz, 2H), 3.30 (m, 2H).

Example 101

2-(3-(pyridin-2-yloxy)propyl)-7-(4-(trifluoromethoxy)phenyl)phthalazin-1(2H)-one (Compound III-16)

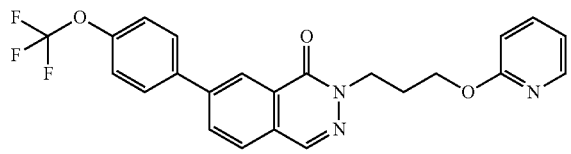

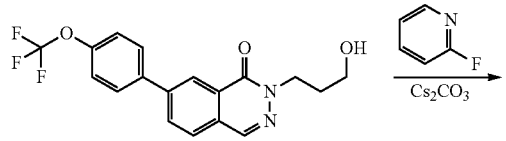

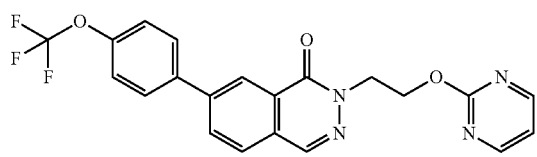 [SMILES: O=c1c2cc(-c3ccc(OC(F)(F)F)cc3)ccc2cnn1CCOc1ncccn1]

A mixture of 2-(3-hydroxypropyl)-7-(4-(trifluoromethoxy)phenyl)phthalazin-1(2H)-one (25 mg, 0.069 mmol), $Cs_2CO_3$ (67 mg, 0.21 mmol) and 2-fluoropyridine (100 μL) was heated to 155° C. overnight. The reaction was concentrated and purified by reverse phase HPLC to afford 2-(3-(pyridin-2-yloxy)propyl)-7-(4-(trifluoromethoxy)phenyl)phthalazin-1(2H)-one as a white solid. $C_{23}H_{18}F_3N_3O_3$ 441.9 (M+1).

Example 102

2-(2-(pyrimidin-2-yloxy)ethyl)-7-(4-(trifluoromethoxy)phenyl)phthalazin-1(2H)-one (Compound III-28)

Compound III-28 was prepared using a similar procedure as that described for Compound III-16 with the appropriate starting materials. $C_{21}H_{15}F_3N_4O_3$. 451.1 (M+23). $^1$H NMR (DMSO) δ 8.52 (d, J=5.2 Hz, 2H), 8.45 (s, 2H), 8.27 (dd, J=1.6, 8.4 Hz, 1H), 8.04 (d, J=8.4 Hz, 1H), 7.96 (d, J=8.4 Hz, 2H), 7.51 (d, J=8.4 Hz, 2H), 7.09 (t, J=8.8 Hz, 1H), 4.73 (t, J=5.2 Hz, 2H), 4.56 (t, J=4.8 Hz, 2H).

Example 103

2-(2-(4-cyclopropylpyrimidin-2-yloxy)ethyl)-7-(4-(trifluoromethoxy)phenyl)phthalazin-1(2H)-one (Compound III-29)

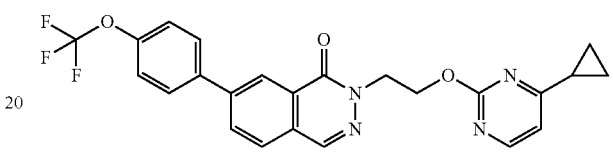

Compound III-29 was prepared using a similar procedure as that described for Compound III-16 with the appropriate starting materials. $C_{24}H_{19}F_3N_4O_3$ 468.8 (M+1).

Example 104

2-(2-(5-chloropyrimidin-2-yloxy)ethyl)-7-(4-(trifluoromethoxy)phenyl)phthalazin-1(2H)-one (Compound III-37)

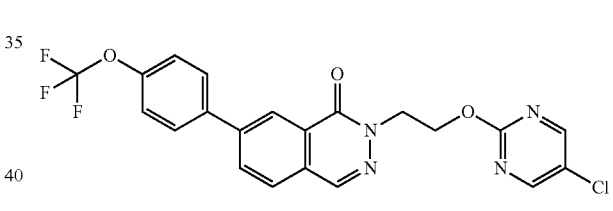

Compound III-37 was prepared using a similar procedure as that described for Compound III-16 with the appropriate starting materials. $C_{11}H_{14}ClF_3N_4O_3$. 463.0 (M+1). $^1$H NMR (DMSO) δ 8.63 (s, 2H), 8.46 (d, J=4.0 Hz, 2H), 8.27 (dd, J=2.0, 8.4 Hz, 1H), 8.04 (d, J=8.0 Hz, 1H), 7.96 (d, J=8.4 Hz, 2H), 7.51 (d, J=8.0 Hz, 2H), 4.73 (t, J=4.8 Hz, 2H), 4.56 (t, J=4.8 Hz, 2H).

Example 105

2-(2-(pyrazin-2-yloxy)ethyl)-7-(4-(trifluoromethoxy)phenyl)phthalazin-1(2H)-one (Compound III-39)

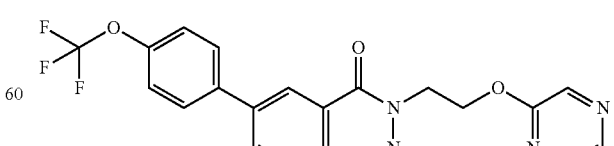

Compound III-39 was prepared using a similar procedure as that described for Compound III-16 with the appropriate starting materials. $C_{11}H_{15}F_3N_4O_3$ 428.9 (M+1). $^1$H NMR (DMSO) δ 8.44 (s, 2H), 8.26 (dd, J=1.6, 8.0 Hz, 1H), 8.21 (d, J=0.8 Hz, 1H), 8.15 (d, J=2.8 Hz, 1H), 8.09 (dd, J=1.2, 2.4 Hz, 1H), 8.03 (d, J=8.4 Hz, 1H), 7.96 (d, J=8.8 Hz, 2H), 7.51 (d, J=8.0 Hz, 2H), 4.76 (t, J=5.2 Hz, 2H), 4.56 (t, J=5.2 Hz, 2H).

Example 106

2-(2-(pyridin-2-yloxy)ethyl)-7-(4-(trifluoromethoxy) phenyl)phthalazin-1(2H)-one (Compound III-40)

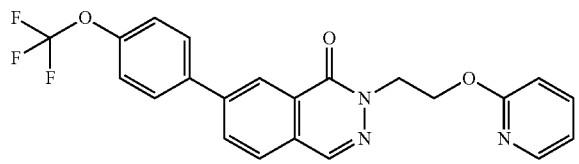 [SMILES: O=c1c2cc(-c3ccc(OC(F)(F)F)cc3)ccc2cnn1CCOc1ccccn1]

Compound III-40 was prepared using a similar procedure as that described for Compound III-16 with the appropriate starting materials. $C_{22}H_{16}F_3N_3O_3$. 427.9 (M+1). $^1$H NMR (DMSO) δ 8.45 (d, J=3.6 Hz, 2H), 8.25 (dd, J=2.0, 8.0 Hz, 1H), 8.01-8.06 (m, 2H), 7.95 (d, J=9.2 Hz, 2H), 7.61-7.66 (m, 1H), 7.50 (d, J=8.0 Hz, 2H), 6.88-6.93 (m, 1H), 6.71 (d, J=8.4 Hz, 1H), 4.68 (t, J=5.6 Hz, 2H), 4.53 (t, J=5.6 Hz, 2H).

Example 107

2-(2-(6-methylpyridin-2-yl)ethyl)-7-(4-(trifluoromethoxy)phenyl)phthalazin-1(2H)-one (Compound III-18)

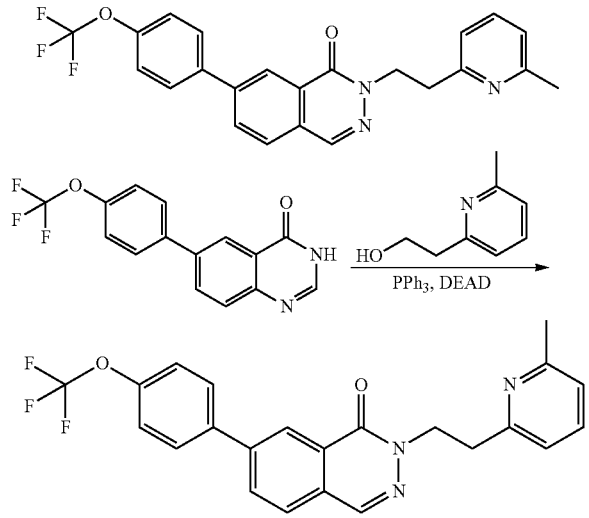

To a solution of -(4-(trifluoromethoxy)phenyl)phthalazin-1(2H)-one (52 mg, 0.17 mmol), 2-(6-methylpyridin-2-yl)ethanol (30 mg, 0.22 mmol), and triphenylphosphine (62 mg, 0.24 mmol) in THF (1 mL) was added DEAD (37 μL, 0.24 mmol) and the reaction was stirred overnight. The reaction was concentrated and purified by reverse phase HPLC to afford 2-(2-(6-methylpyridin-2-yl)ethyl)-7-(4-(trifluoromethoxy)phenyl)phthalazin-1(2H)-one.

$C_{23}H_{18}F_3N_3O_2$. 426.1 (M+1). $^1$H NMR (DMSO) δ 8.45 (s, 2H), 8.26 (dd, J=2.0, 8.0 Hz, 1H), 8.04 (d, J=8.0 Hz, 1H), 7.97 (t, J=1.6 Hz, 1H), 7.95 (t, J=2.0 Hz, 1H), 7.50-7.57 (m, 3H), 7.25 (dd, J=4.8, 8.8 Hz, 2H), 4.47 (t, J=7.6 Hz, 2H), 3.15 (t, J=7.6 Hz, 2H), 2.37 (s, 3H).

Example 108

2-((4,6-dimethoxypyrimidin-2-yl)methyl)-7-(4-(trifluoromethoxy)phenyl)phthalazin-1(2H)-one (Compound III-19)

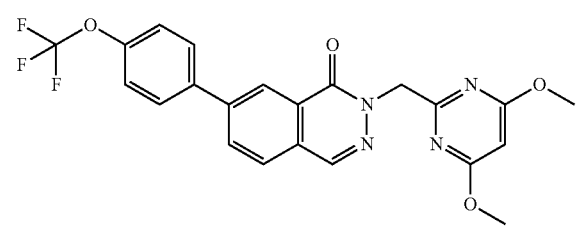 [SMILES: COc1cc(OC)nc(Cn2ncc3ccc(-c4ccc(OC(F)(F)F)cc4)cc3c2=O)n1]

Compound III-19 was prepared using a similar procedure as that described for Compound III-18 with the appropriate starting materials. $C_{22}H_{17}F_3N_4O_4$. 459.1 (M+1). $^1$H NMR (DMSO) δ 8.51 (s, 1H), 8.47 (s, 1H), 8.29 (dd, J=2.0, 8.0 Hz, 1H), 8.09 (d, J=8.0 Hz, 1H), 7.97 (d, J=8.4 Hz, 2H), 7.51 (d, J=8.0 Hz, 2H), 6.12 (s, 1H), 5.36 (s, 2H), 3.71 (s, 6H).

Example 109

2-((4,6-dimethylpyrimidin-2-yl)methyl)-7-(4-(trifluoromethoxy)phenyl)phthalazin-1(2H)-one (Compound III-22)

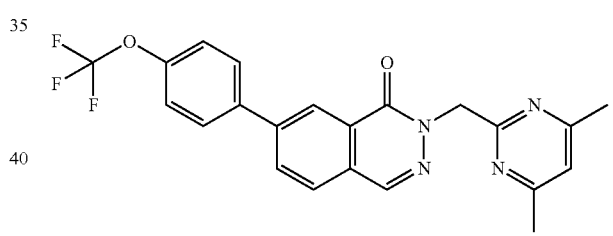

Compound III-22 was prepared using a similar procedure as that described for Compound III-18 with the appropriate starting materials. $C_{22}H_{17}F_3N_4O_2$. 427.1 (M+1). $^1$H NMR (DMSO) δ 8.49 (s, 1H), 8.46 (d, J=2.0 Hz, 1H), 8.29 (dd, J=2.0, 8.0 Hz, 1H), 8.09 (d, J=8.4 Hz, 1H), 7.98 (t, J=2.4 Hz, 1H), 7.96 (t, J=2.0 Hz, 1H), 7.52 (d, J=8.0 Hz, 2H), 7.12 (s, 1H), 5.44 (s, 2H), 2.31 (s, 6H).

Example 110

2-((4-cyclopropylpyrimidin-2-yl)methyl)-7-(4-(trifluoromethoxy)phenyl)phthalazin-1(2H)-one (Compound III-23)

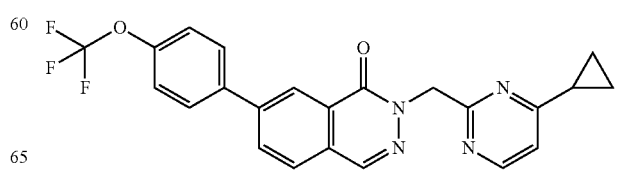

Compound III-23 was prepared using a similar procedure as that described for Compound III-18 with the appropriate starting materials. $C_{23}H_{17}F_3N_4O_2$. 439.1 (M+1). $^1$H NMR (DMSO) δ 8.49 (s, 1H), 8.45 (t, J=2.0 Hz, 1H), 8.43 (s, 1H), 8.30 (dd, J=2.0, 8.0 Hz, 1H), 8.09 (d, J=8.4 Hz, 1H), 7.97 (d, J=8.4 Hz, 2H), 7.52 (d, J=8.4 Hz, 2H), 7.26 (d, J=5.2 Hz, 1H), 5.43 (s, 2H), 2.00-2.05 (m, 1H), 0.94-0.98 (m, 2H), 0.79-0.83 (m, 2H).

Example 111

2-(2-(3,5-dimethyl-1H-pyrazol-1-yl)ethyl)-7-(4-(trifluoromethoxy)phenyl)phthalazin-1(2H)-one (Compound III-24)

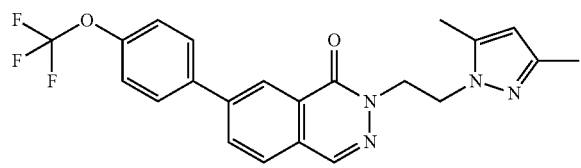 [SMILES: Cc1cc(C)n(CCn2ncc3ccc(-c4ccc(OC(F)(F)F)cc4)cc3c2=O)n1]

Compound III-24 was prepared using a similar procedure as that described for Compound III-18 with the appropriate starting materials. $C_{22}H_{19}F_3N_4O_2$ 429.1 (M+1).

Example 112

2-((4-(cyclopropylmethoxy)pyrimidin-2-yl)methyl)-7-(4-(trifluoromethoxy)phenyl)phthalazin-1(2H)-one (Compound III-27)

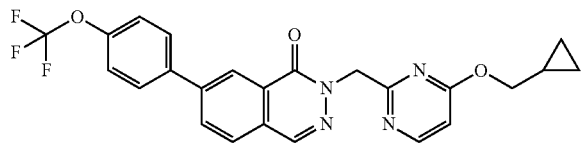 [SMILES: O=c1c2cc(-c3ccc(OC(F)(F)F)cc3)ccc2cnn1Cc1nccc(OCC2CC2)n1]

Compound III-27 was prepared using a similar procedure as that described for Compound III-18 with the appropriate starting materials. $C_{24}H_{19}F_3N_4O_3$ 469.1 (M+1).

Example 113

2-((4-methoxypyrimidin-2-yl)methyl)-7-(4-(trifluoromethoxy)phenyl)phthalazin-1(2H)-one (Compound III-30)

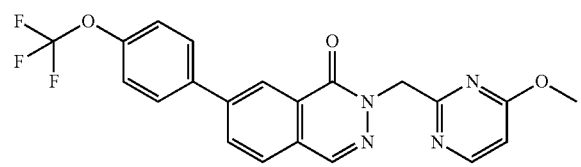 [SMILES: COc1ccnc(Cn2ncc3ccc(-c4ccc(OC(F)(F)F)cc4)cc3c2=O)n1]

Compound III-30 was prepared using a similar procedure as that described for Compound III-18 with the appropriate starting materials. $C_{21}H_{15}F_3N_4O_3$ 429.2 (M+1).

Example 114

2-(2-(4-bromo-1H-pyrazol-1-yl)ethyl)-7-(4-(trifluoromethoxy)phenyl)phthalazin-1(2H)-one (Compound III-31)

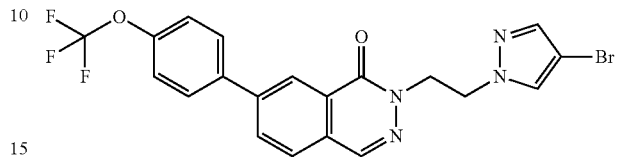

Compound III-31 was prepared using a similar procedure as that described for Compound III-18 with the appropriate starting materials. $C_{20}H_{14}BrF_3N_4O_2$ 479.0 (M+1).

Example 115

2-(2-(5-methyl-1H-pyrazol-1-yl)ethyl)-7-(4-(trifluoromethoxy)phenyl)phthalazin-1(2H)-one (Compound III-32)

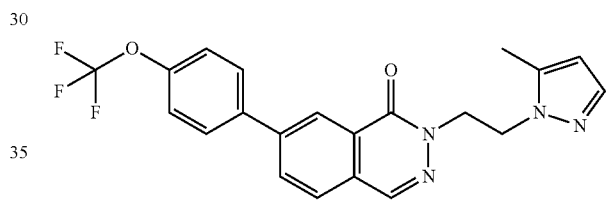

Compound III-32 was prepared using a similar procedure as that described for Compound III-18 with the appropriate starting materials. $C_{21}H_{17}F_3N_4O_2$ 415.1 (M+1).

Example 116

2-(2-(pyrimidin-4-yl)ethyl)-7-(4-(trifluoromethoxy)phenyl)phthalazin-1(2H)-one (Compound III-36)

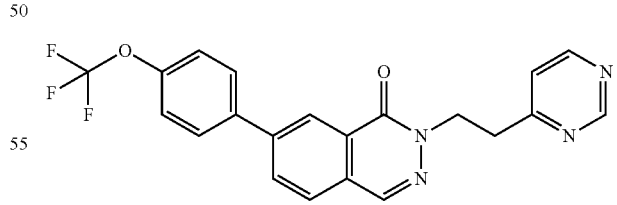

Compound III-36 was prepared using a similar procedure as that described for Compound III-18 with the appropriate starting materials. $C_{11}H_{15}F_3N_4O_2$. 413.0 (M+1). $^1$H NMR (DMSO) δ 9.04 (s, 1H), 8.65 (d, J=5.2 Hz, 1H), 8.43 (d, J=7.2 Hz, 2H), 8.26 (dd, J=2.0, 8.0 Hz, 1H), 8.04 (d, J=8.4 Hz, 1H), 7.96 (d, J=8.4 Hz, 2H), 7.52 (d, J=8.4 Hz, 2H), 7.44 (d, J=5.2 Hz, 1H), 4.54 (t, J=7.6 Hz, 2H), 3.24 (t, J=7.6 Hz, 2H).

Example 117

2-(2-(1H-pyrazol-1-yl)propyl)-7-(4-(trifluoromethoxy)phenyl)phthalazin-1(2H)-one (Compound III-38)

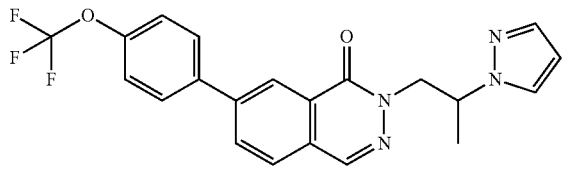 [SMILES: CC(Cn1ncc2ccc(-c3ccc(OC(F)(F)F)cc3)cc2c1=O)n1cccn1]

Compound III-38 was prepared using a similar procedure as that described for Compound III-18 with the appropriate starting materials. $C_{21}H_{17}F_3N_4O_2$. 415.1 (M+1). $^1$H NMR (DMSO) δ 8.43 (d, J=1.6 Hz, 1H), 8.35 (s, 1H), 8.25 (dd, J=2.0, 8.0 Hz, 1H), 8.01 (d, J=8.0 Hz, 1H), 7.95 (d, J=8.8 Hz, 2H), 7.68 (d, J=2.0 Hz, 1H), 7.51 (d, J=8.4 Hz, 2H), 7.34 (d, J=1.6 Hz, 1H), 6.13 (t, J=2.0 Hz, 1H) 4.91-4.97 (m, 1H), 4.39-4.49 (m, 2H), 1.50 (d, J=7.2 Hz, 3H).

Example 118

2-((5-(pyridin-2-yl)isoxazol-3-yl)methyl)-7-(4-(trifluoromethoxy)phenyl)phthalazin-1(2H)-one (Compound III-41)

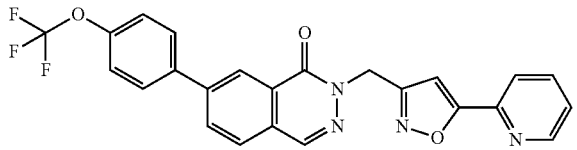 [SMILES: O=c1c2cc(-c3ccc(OC(F)(F)F)cc3)ccc2cnn1Cc1cc(-c2ccccn2)on1]

Compound III-41 was prepared using a similar procedure as that described for Compound III-18 with the appropriate starting materials. $C_{24}H_{15}F_3N_4O_3$ 465.2 (M+1).

Example 119

3-(2-(pyrimidin-4-yl)ethyl)-6-(4-(trifluoromethoxy)phenyl)benzo[d][1,2,3]triazin-4(3H)-one (Compound II-17)

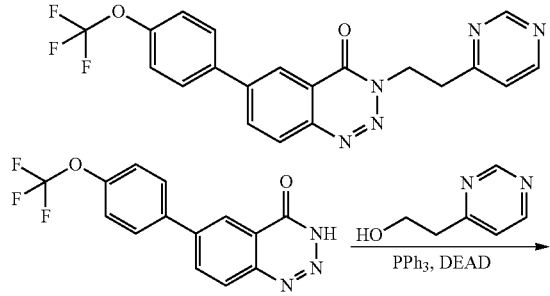

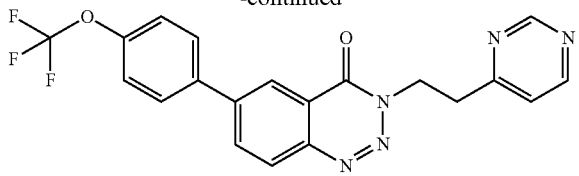

Compound II-17 was prepared using a similar procedure as that described for Compound III-18 with the appropriate starting materials. $C_{20}H_{14}F_3N_5O_2$. 413.9 (M+1). $^1$H NMR (DMSO) δ 9.04 (s, 1H), 8.67 (d, J=4.8 Hz, 1H), 8.44 (d, J=2.0 Hz, 1H), 8.41 (dd, J=2.4, 8.8 Hz, 1H), 8.26 (d, J=8.4 Hz, 1H), 8.00 (d, J=8.8 Hz, 2H), 7.48-7.54 (m, 3H), 4.80 (t, J=7.6 Hz, 2H), 3.33 (t, J=7.6 Hz, 2H).

Example 120

3-(2-(pyrimidin-2-yl)ethyl)-6-(4-(trifluoromethoxy)phenyl)benzo[d][1,2,3]triazin-4(3H)-one (Compound II-18)

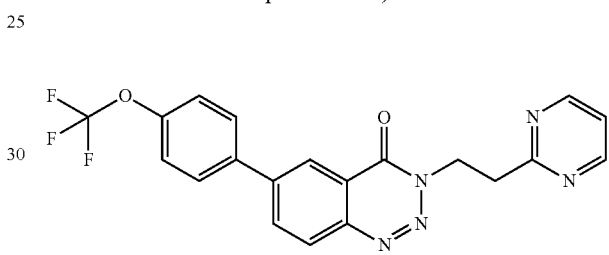

Compound II-18 was prepared using a similar procedure as that described for Compound II-17 with the appropriate starting materials. $C_{20}H_{14}F_3N_5O_2$. 413.9 (M+1). $^1$H NMR (DMSO) δ 8.69 (d, J=7.2 Hz, 2H), 8.45 (d, J=2.0 Hz, 1H), 8.40 (dd, J=2.0, 8.8 Hz, 1H), 8.26 (d, J=8.4 Hz, 1H), 8.01 (d, J=8.8 Hz, 2H), 7.53 (d, J=8.8 Hz, 2H), 7.35 (t, J=4.8 Hz, 1H), 4.84 (t, J=6.8 Hz, 2H), 3.45 (t, J=6.8 Hz, 2H).

Example 121

6-(4-(trifluoromethoxy)phenyl)-3-(2-(3-(trifluoromethyl)-1H-pyrazol-1-yl)ethyl)benzo[d][1,2,3]triazin-4(3H)-one (Compound II-52)

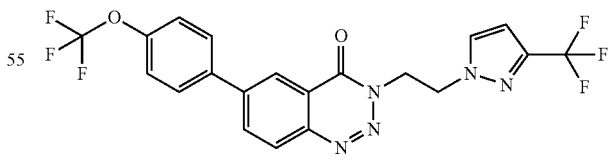

Compound II-52 was prepared using a similar procedure as that described for Compound II-17 with the appropriate starting materials. $C_{20}H_{13}F_6N_5O_2$. 469.9 (M+1). $^1$H NMR (DMSO) δ 8.42 (d, J=2.0 Hz, 1H), 8.39 (dd, J=2.0, 8.4 Hz, 1H), 8.21 (d, J=8.8 Hz, 1H), 7.94-8.01 (m, 3H), 7.51 (d, J=8.0 Hz, 2H), 6.62 (d, J=2.0 Hz, 1H), 4.78 (t, J=6.0 Hz, 2H), 4.68 (t, J=6.0 Hz, 2H).

Example 122

2-((2-cyclopropylpyridin-3-yl)methyl)-7-(4-(trifluoromethoxy)phenyl)phthalazin-1(2H)-one (Compound III-20)

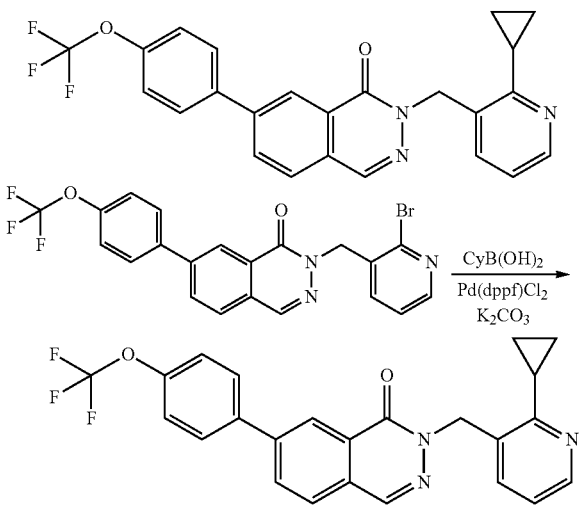

A mixture of 2-((2-bromopyridin-3-yl)methyl)-7-(4-(trifluoromethoxy)phenyl)phthalazin-1(2H)-one (25 mg, 0.053 mmol), cyclopropyl boronic acid (14 mg, 0.16 mmol), dppf(Pd)Cl$_2$ (6 mg, 0.0079 mmol), potassium carbonate (29 mg, 0.021 mmol) in degassed dioxane (1 mL) was heated at 100° C. for 3 hours. The layers were separated, the organic layer was concentrated and the residue was purified by reverse phase HPLC to provide 2-((2-cyclopropylpyridin-3-yl)methyl)-7-(4-(trifluoromethoxy)phenyl)phthalazin-1(2H)-one as a white powder. C$_{24}$H$_{18}$F$_3$N$_3$O$_2$. 438.1 (M+1).

Example 123

2-(2-(4-(2-methoxypyrimidin-5-yl)-1H-pyrazol-1-yl)ethyl)-7-(4-(trifluoromethoxy)phenyl)phthalazin-1(2H)-one (Compound III-34)

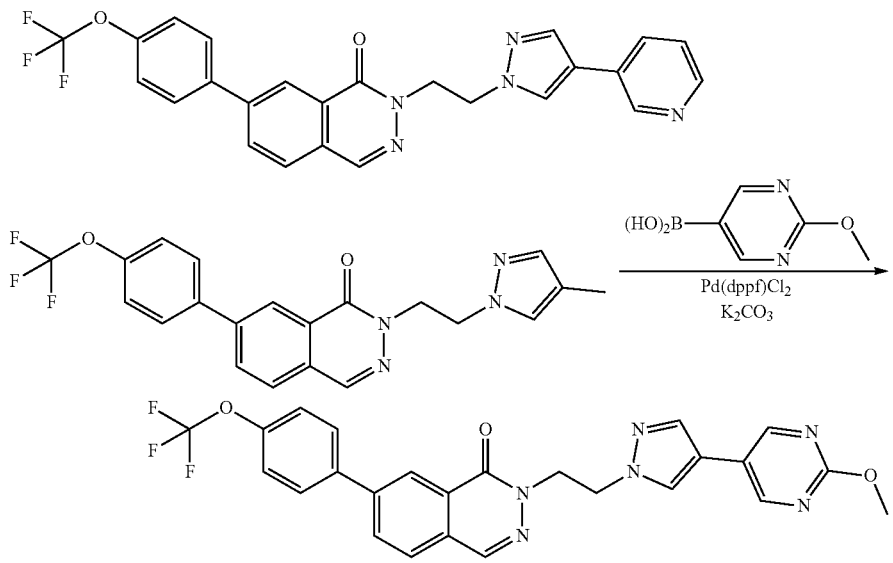

A mixture of 2-(2-(4-bromo-1H-pyrazol-1-yl)ethyl)-7-(4-(trifluoromethoxy)phenyl)phthalazin-1(2H)-one (35 mg, 0.073 mmol), 2-methoxypyrimidin-5-ylboronic acid (13 mg, 0.087 mmol), dppf(Pd)Cl$_2$ (2.7 mg, 0.0037 mmol), potassium carbonate (20 mg, 0.015 mmol) in degassed toluene (1 mL), degassed water (0.5 mL) and degassed isopropanol (0.5 mL) was heated at 85° C. for 3 hours. The layers were separated, the organic layer was concentrated and the residue was purified by reverse phase HPLC to provide 2-(2-(4-(2-methoxypyrimidin-5-yl)-1H-pyrazol-1-yl)ethyl)-7-(4-(trifluoromethoxy)phenyl)phthalazin-1(2H)-one as a white powder. C$_{25}$H$_{19}$F$_3$N$_6$O$_3$. 509.2 (M+1). $^1$H NMR (DMSO) δ 8.74 (s, 1H), 8.38-8.44 (m, 2H), 8.26 (dd, J=2.0, 8.0 Hz, 1H), 8.20 (s, 1H), 8.03 (d, J=8.4 Hz, 1H), 7.94 (d, J=8.8 Hz, 2H), 7.84 (s, 1H), 7.51 (d, J=8.4 Hz, 2H), 4.56 (s, 4H), 3.87 (s, 3H).

Example 124

2-(2-(4-(pyridin-3-yl)-1H-pyrazol-1-yl)ethyl)-7-(4-(trifluoromethoxy)phenyl)phthalazin-1(2H)-one (Compound III-33)

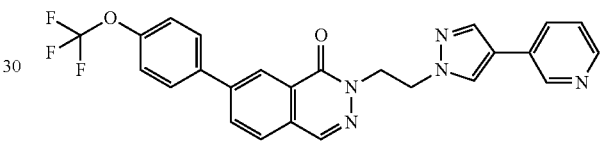

Compound III-33 was prepared using a similar procedure as that described for Compound III-34 with the appropriate starting materials. C$_{25}$H$_{18}$F$_3$N$_5$O$_2$ 478.2 (M+1).

Example 125

3-((4,6-dimethoxypyrimidin-2-yl)methyl)-6-(4-(trifluoromethoxy)phenyl)benzo[d][1,2,3]triazin-4(3H)-one (Compound II-44)

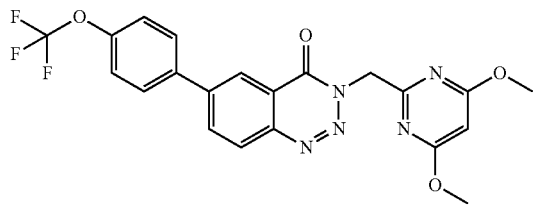

+

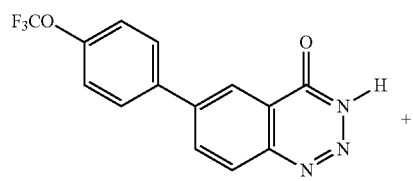

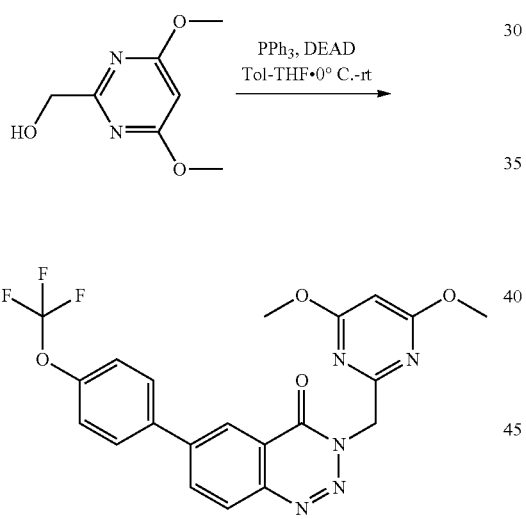

To a cooled (0° C.) solution of Compound II-1 (96 mg, 0.31 mmol), 2-Pyrimidinemethanol,4,6-dimethoxy (64 mg, 0.37 mmol), triphenylphosphine (262 mg, 1.00 mmol) in dry THF (3.0 mL) was added dropwise a 40 wt % of DEAD in toluene (205 uL, 0.45 mmol) under an atmosphere of nitrogen. After completion, the reaction mixture was stirred overnight, quenched by 30% NH$_4$Cl (1 mL), concentrated under a reduced pressure.

The crude mixture was subjected to Gilson's reverse-phase preparative HPLC with a gradient 0.1% TFA containing ACN/H$_2$O (10% to 90%) to afford additional desired product as Compound II-44. LCMS m/z 459.88 (M+H), anal HPLC >97%. $^1$H NMR (400 MHz; acetone-d$_6$) δ 8.53 (d, J=2.0 Hz, 1H); 8.44 (dd, J=8.6 and 2.0 Hz, 1H); 8.22 (d, J=8.6 Hz, 1H); 8.04 (dd, J=6.6 and 2.4 Hz, 2H); 7.54 (m, 2H); 6.00 (s, 1H); 5.69 (s, 2H); 3.76 (s, 6H). $^{19}$F NMR (400 MHz; acetone-d$_6$) δ □−59.03 (s, 3F).

Example 126

3-((5-phenyl-1H-tetrazol-1-yl)methyl)-6-(4-(trifluoromethoxy)phenyl)benzo[d][1,2,3]triazin-4(3H)-one (Compound II-21)

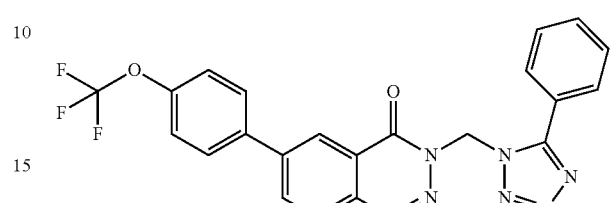

Compound II-21 was prepared using a similar procedure as that described for Compound II-44 with the appropriate starting materials.

Example 127

3-((2H-benzo[d][1,2,3]triazol-2-yl)methyl)-6-(4-(trifluoromethoxy)phenyl)benzo[d][1,2,3]triazin-4(3H)-one (Compound II-28)

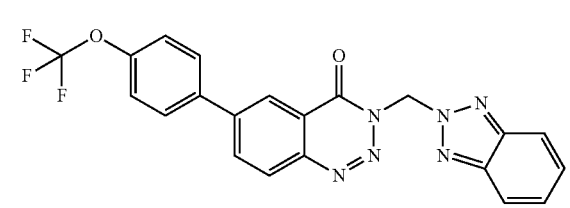 [SMILES: O=c1c2cc(-c3ccc(OC(F)(F)F)cc3)ccc2nnn1Cn1nc2ccccc2n1]

Compound II-28 was prepared using a similar procedure as that described for Compound II-44 with the appropriate starting materials.

Example 128

3-((5-(pyridin-2-yl)isoxazol-3-yl)methyl)-6-(4-(trifluoromethoxy)phenyl)benzo[d][1,2,3]triazin-4(3H)-one (Compound II-47)

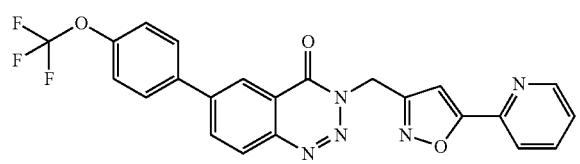

Compound II-47 was prepared using a similar procedure as that described for Compound 44 with the appropriate starting materials.

Example 129

3-((5-(pyridin-2-yl)-1,2,4-oxadiazol-3-yl)methyl)-6-(4-(trifluoromethoxy)phenyl)benzo[d][1,2,3]triazin-4(3H)-one (Compound II-54)

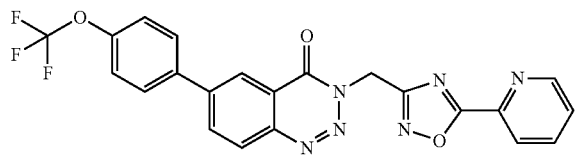 [SMILES: O=c1c2cc(-c3ccc(OC(F)(F)F)cc3)ccc2nnn1Cc1noc(-c2ccccn2)n1]

Compound II-54 was prepared using a similar procedure as that described for Compound II-44 with the appropriate starting materials.

Example 130

3-(2-(2,4-dichlorophenyl)-2-hydroxyethyl)-6-(4-(trifluoromethoxy)phenyl)benzo[d][1,2,3]triazin-4(3H)-one (Compound II-9)

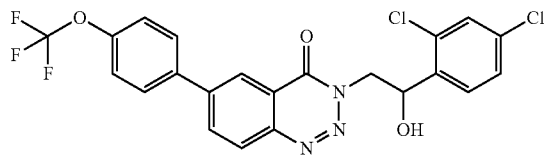

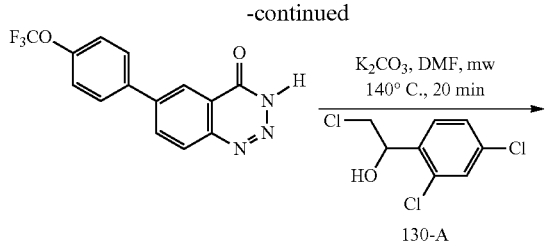

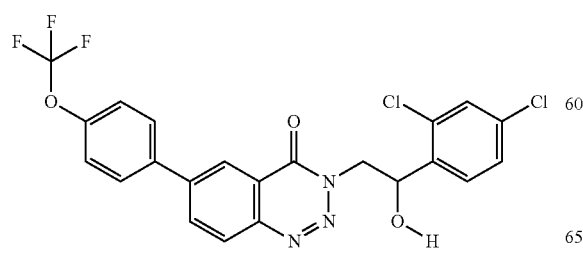

To a solution of Compound II-1 (75 mg, 0.244 mmol), 130-A (100 mg, 0.44 mmol) in DMF (3 mL) in a Biotage microwave tube (5 mL capacity) was added $K_2CO_3$ (276 mg, 2.0 mmol). The reaction mixture was sealed and subjected to microwave heating at 140° C. for 20 min. The mixture was cooled, diluted with 20% DMF in EtOAc (20 mL), filtered, washed with 20% DMF in EtOAc (10 mL). The combined filtrate was concentrated in vacuo, dissolved mostly in DMF (2 mL), subjected to Gilson's reverse-phase preparative HPLC with a gradient 0.1% TFA containing ACN/H$_2$O (5% to 95%) to afford additional desired product as Compound II-9. LCMS m/z 496.0 (M+H), anal HPLC >98%. $^1$H NMR (400 MHz; DMSO-d3) δ 8.48 (s, 1H); 8.41 (m, 1H); 8.28 (m, 1H); 8.02 (m, 2H); 7.72 (m, 1H); 7.53 (m, 4H); 5.99 (m, 1H); 5.46 (m, 1H); 4.51 (m, 2H). $^{19}$F NMR (400 MHz; DMSO-d3) δ □-57.19 (s, 3F).

Example 131

3-(2-hydroxy-3-(2-methylbenzo[d]thiazol-6-yloxy)propyl)-6-(6-(2,2,2-trifluoroethoxy)pyridin-3-yl)benzo[d][1,2,3]triazin-4(3H)-one (Compound V-3)

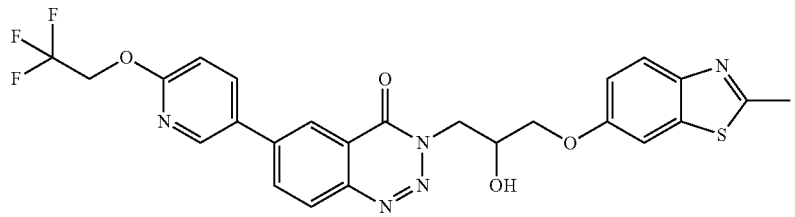 [SMILES: Cc1nc2ccc(OCC(O)Cn3nnc4ccc(-c5ccc(OCC(F)(F)F)nc5)cc4c3=O)cc2s1]

Compound V-3 was prepared using a similar procedure as that described for Compound II-9 with the appropriate starting materials.

Example 132

2,2-dimethyl-6-(4-(trifluoromethoxy)phenyl)-2H-benzo[e][1,3]oxazin-4(3H)-one (Compound VIII-17)

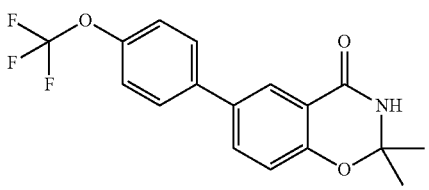

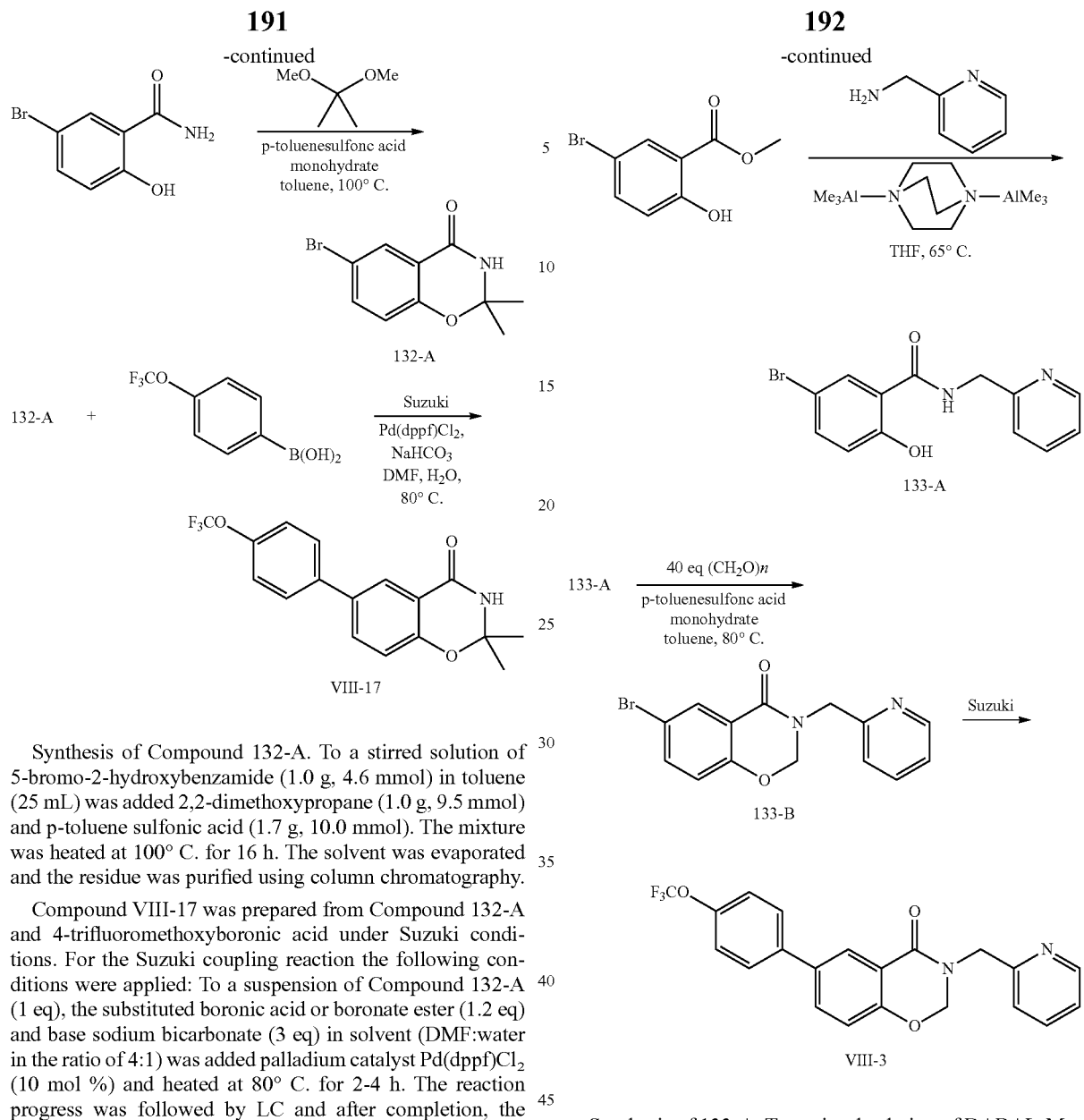

Synthesis of Compound 132-A. To a stirred solution of 5-bromo-2-hydroxybenzamide (1.0 g, 4.6 mmol) in toluene (25 mL) was added 2,2-dimethoxypropane (1.0 g, 9.5 mmol) and p-toluene sulfonic acid (1.7 g, 10.0 mmol). The mixture was heated at 100° C. for 16 h. The solvent was evaporated and the residue was purified using column chromatography.

Compound VIII-17 was prepared from Compound 132-A and 4-trifluoromethoxyboronic acid under Suzuki conditions. For the Suzuki coupling reaction the following conditions were applied: To a suspension of Compound 132-A (1 eq), the substituted boronic acid or boronate ester (1.2 eq) and base sodium bicarbonate (3 eq) in solvent (DMF:water in the ratio of 4:1) was added palladium catalyst Pd(dppf)Cl$_2$ (10 mol %) and heated at 80° C. for 2-4 h. The reaction progress was followed by LC and after completion, the reaction mixture was filtered through celite, washed with ethyl acetate. The filtrate was concentrated the filtrate and purified by prep TLC/prep HPLC or column chromatography.

Example 133

3-(pyridin-2-ylmethyl)-6-(4-(trifluoromethoxy)phenyl)-2H-benzo[e][1,3]oxazin-4(3H)-one (Compound VIII-3)

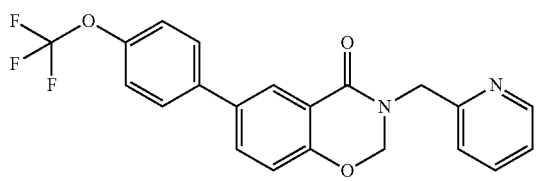

Synthesis of 133-A. To a stirred solution of DABAL-Me$_3$ (1.0 g, (4 mmol) in 15 mL THF was added 2-methylaminopyridine (0.40 g, 4 mmol). The mixture was stirred at 40° C. for 1 h. To the mixture was added 5-bromosalicylate and the mixture was heated at reflux for 16 h. the reaction was cooled to RT and quenched with aq. HCl dropwise then extracted with 2×25 mL EtOAc. The organic layer was washed with 10×2 mL water and dried over MgSO$_4$. The solvent was removed and the residue was purified using column chromatography.

Synthesis of 133-B. Same as synthesis of 132-A using para formaldehyde in place of dimethoxypropane.

Compound VIII-3 was prepared from 133-B and 4-trifluoromethoxyboronic acid under Suzuki conditions according to Example 132.

$^1$H-NMR (CDCl$_3$) δ 8.57 (d, 1H, J=5.6 Hz), 8.19 (d, 1H, J=2.4 Hz), 7.63-7.69 (m, 2H), 7.59 (dd, 2H, J=6.4, 2.0 Hz), 7.44 (d, 1H, J=8.0 Hz), 7.28 (d, 2H, J=8.4 Hz), 7.23 (t, 1H, J=4.8 Hz), 7.06 (d, 1H, J=8.0 Hz), 5.40 (s, 2H), 4.89 (s, 2H). MS m/z 401.0 (M+H).

Example 134

3-(pyridin-2-ylmethyl)-6-(4-(trifluoromethyl)phenyl)-2H-benzo[e][1,3]oxazin-4(3H)-one (Compound VIII-1)

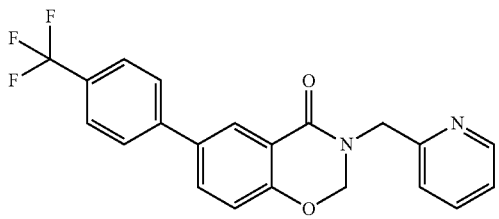

Compound VIII-1 was prepared using a similar procedure as that described for Compound VIII-3 with the appropriate starting materials. $^1$H-NMR (CD$_3$OD) δ 8.51 (d, 1H, J=4.4 Hz), 8.19 (d, 1H, J=2.4 Hz), 7.80-7.88 (m, 4H), 7.74 (d, 2H, J=8.8 Hz), 7.47 (d, 1H, J=3.8 Hz), 7.33 (dd, 1H, J=7.6, 5.2 Hz), 7.17 (d, 1H, J=8.8 Hz), 5.45 (s, 2H), 4.90 (s, 2H); MS m/z 385.1 (M+H).

Example 135

2-(pyrimidin-2-ylmethyl)-7-(4-(trifluoromethoxy)phenyl)-3,4-dihydroisoquinolin-1(2H)-one (Compound IX-1)

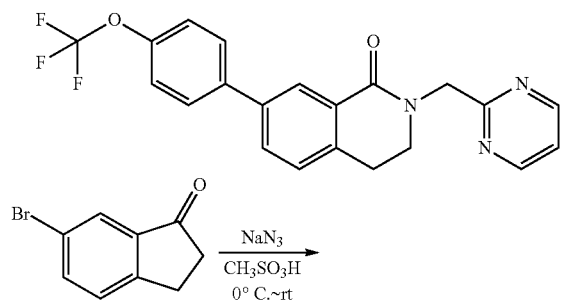

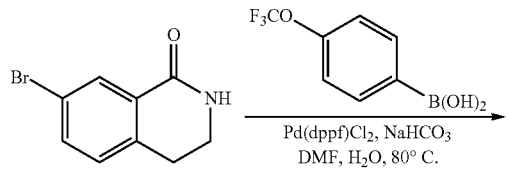

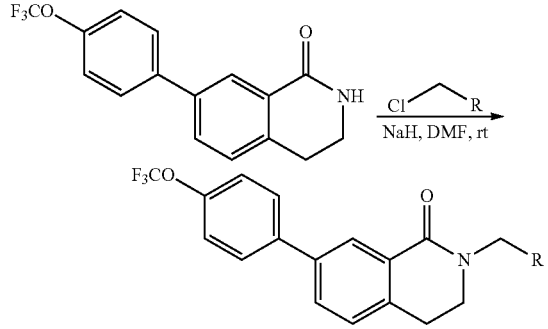

Compound IX-1 was prepared using the procedures disclosed in the above scheme using the appropriate starting materials. $^1$H-NMR (DMSO-d6) δ 8.75 (d, 2H, J=5.2 Hz), 8.17 (d, 1H, J=2.4 Hz), 7.78 (m, 3H) 7.35-7.45 (m, 4H), 4.93 (s, 1H), 3.74-3.78 (t, 2H), 3.07-3.10 (t, 2H). MS m/z 400.1 (M+H).

Example 136

2-(pyridin-2-ylmethyl)-7-(4-(trifluoromethoxy)phenyl)-3,4-dihydroisoquinolin-1(2H)-one (Compound IX-2)

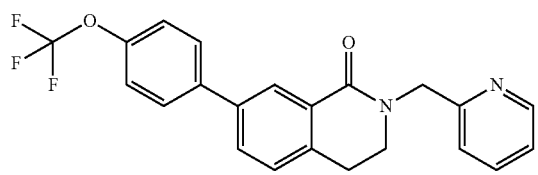 [SMILES: O=C1c2cc(-c3ccc(OC(F)(F)F)cc3)ccc2CCN1Cc1ccccn1]

Compound IX-2 was prepared using a similar procedure as that described for Compound IX-1 with the appropriate starting materials. $^1$H-NMR (DMSO-d6) δ 8.61 (d, 1H)), 8.12 (m, 1H), 7.82 (m, 1H) 7.78-7.80 (m, 4H), 7.42-7.54 (m, 4H) 4.88 (s, 1H), 3.62-3.70 (t, 2H), 3.05-3.09 (t, 2H), MS m/z 399.1 (M+H).

Example 137

3-((5-cyclopropyl-1,3,4-oxadiazol-2-yl)methyl)-2-methyl-6-(4-(trifluoromethoxy)phenyl)-2H-benzo[e][1,3]oxazin-4(3H)-one (Compound VIII-2)

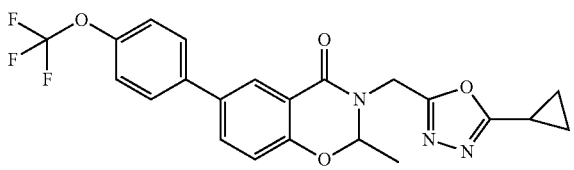 [SMILES: CC1Oc2ccc(-c3ccc(OC(F)(F)F)cc3)cc2C(=O)N1Cc1nnc(C2CC2)o1]

Compound VIII-2 was prepared using the procedures disclosed herein above with the appropriate starting materials.

Example 138

2-phenethyl-3-(pyridin-2-ylmethyl)-6-(4-(trifluoromethoxy)phenyl)-2H-benzo[e][1,3]oxazin-4(3H)-one (Compound VIII-4)

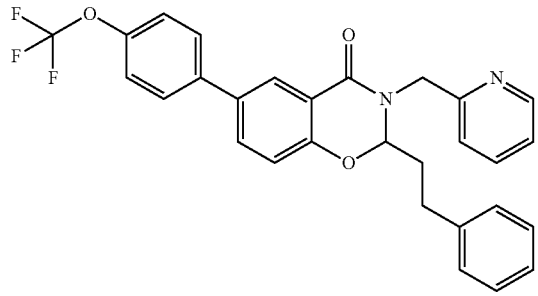 [SMILES: O=C1c2cc(-c3ccc(OC(F)(F)F)cc3)ccc2OC(CCc2ccccc2)N1Cc1ccccn1]

Compound VIII-4 was prepared using the procedures disclosed herein above with the appropriate starting materials.

Example 139

2-phenethyl-3-(pyrimidin-2-ylmethyl)-6-(4-(trifluoromethoxy)phenyl)-2H-benzo[e][1,3]oxazin-4(3H)-one (Compound VIII-5)

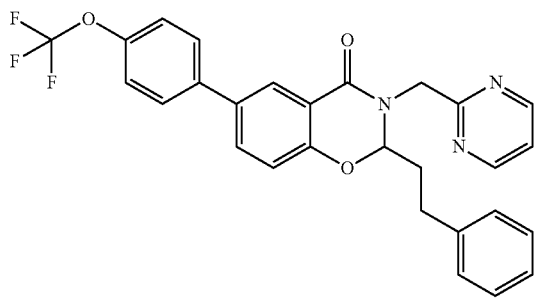 [SMILES: O=C1c2cc(-c3ccc(OC(F)(F)F)cc3)ccc2OC(CCc2ccccc2)N1Cc1ncccn1]

Compound VIII-5 was prepared using the procedures disclosed herein above with the appropriate starting materials.

Example 140

2-methyl-6-(4-(trifluoromethoxy)phenyl)-2H-benzo[e][1,3]oxazin-4(3H)-one (Compound VIII-6)

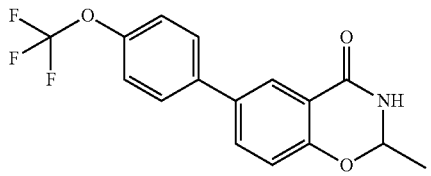 [SMILES: CC1NC(=O)c2cc(-c3ccc(OC(F)(F)F)cc3)ccc2O1]

Compound VIII-6 was prepared using the procedures disclosed herein above with the appropriate starting materials.

Example 141

2-methyl-3-(pyrimidin-2-ylmethyl)-6-(4-(trifluoromethoxy)phenyl)-2H-benzo[e][1,3]oxazin-4(3H)-one (Compound VIII-7)

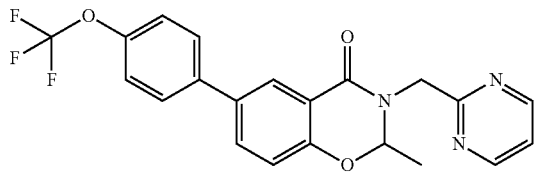 [SMILES: CC1Oc2ccc(-c3ccc(OC(F)(F)F)cc3)cc2C(=O)N1Cc1ncccn1]

Compound VIII-7 was prepared using the procedures disclosed herein above with the appropriate starting materials. MS m/z 416.0 (M+H).

Example 142

2-methyl-3-(pyridin-2-ylmethyl)-6-(4-(trifluoromethoxy)phenyl)-2H-benzo[e][1,3]oxazin-4(3H)-one (Compound VIII-8)

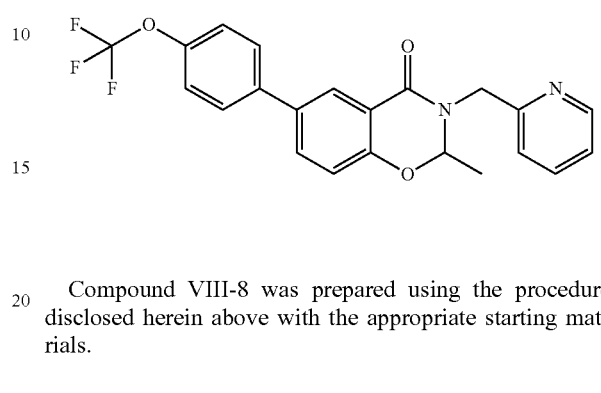

Compound VIII-8 was prepared using the procedures disclosed herein above with the appropriate starting materials.

Example 143

2-phenethyl-6-(4-(trifluoromethoxy)phenyl)-2H-benzo[e][1,3]oxazin-4(3H)-one (Compound VIII-9)

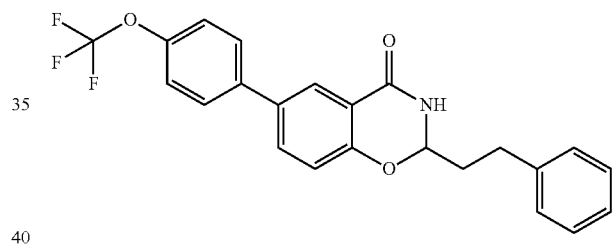

Compound VIII-9 was prepared using the procedures disclosed herein above with the appropriate starting materials.

Example 144

2,2-dimethyl-3-((3-methylisoxazol-5-yl)methyl)-6-(4-(trifluoromethoxy)phenyl)-2H-benzo[e][1,3]oxazin-4(3H)-one (Compound VIII-10)

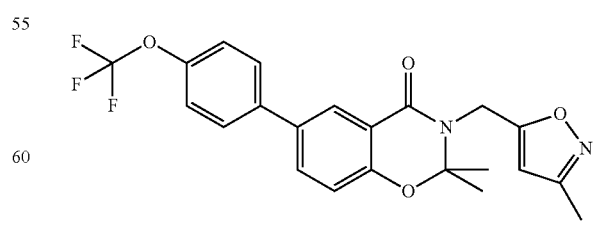

Compound VIII-10 was prepared using the procedures disclosed herein above with the appropriate starting materials. MS m/z 429.1 (M+H).

Example 145

2,2-dimethyl-3-((3-methyl-1,2,4-oxadiazol-5-yl)methyl)-6-(4-(trifluoromethoxy)phenyl)-2H-benzo[e][1,3]oxazin-4(3H)-one (Compound VIII-11)

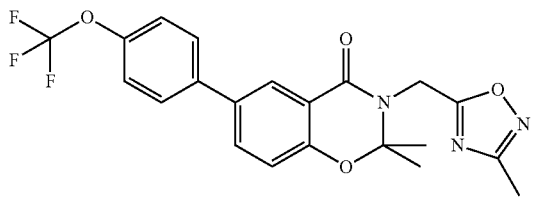 [SMILES: Cc1noc(CN2C(=O)c3cc(-c4ccc(OC(F)(F)F)cc4)ccc3OC2(C)C)n1]

Compound VIII-11 was prepared using the procedures disclosed herein above with the appropriate starting materials.

Example 146

6-(4-(trifluoromethoxy)phenyl)spiro[benzo[e][1,3]oxazine-2,3'-oxetan]-4(3H)-one (Compound VIII-12)

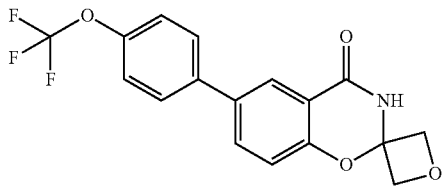 [SMILES: O=C1NC2(COC2)Oc2ccc(-c3ccc(OC(F)(F)F)cc3)cc21]

Compound VIII-12 was prepared using the procedures disclosed herein above with the appropriate starting materials.

Example 147

2,2-dimethyl-3-(pyridin-2-ylmethyl)-6-(4-(trifluoromethoxy)phenyl)-2H-benzo[e][1,3]oxazin-4(3H)-one (Compound VIII-13)

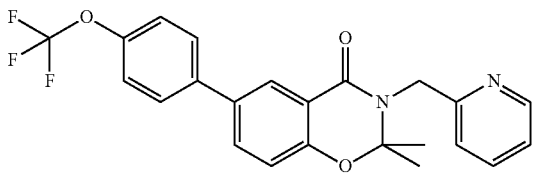 [SMILES: CC1(C)Oc2ccc(-c3ccc(OC(F)(F)F)cc3)cc2C(=O)N1Cc1ccccn1]

Compound VIII-13 was prepared using the procedures disclosed herein above with the appropriate starting materials.

Example 148

2,2-dimethyl-3-(pyrimidin-2-ylmethyl)-6-(4-(trifluoromethoxy)phenyl)-2H-benzo[e][1,3]oxazin-4(3H)-one (Compound VIII-14)

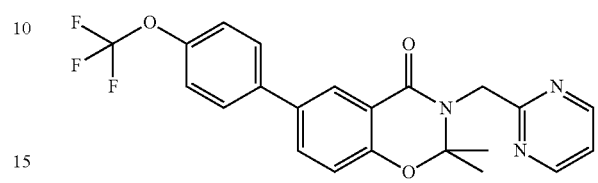

Compound VIII-14 was prepared using the procedures disclosed herein above with the appropriate starting materials.

Example 149

3-((5-cyclopropyl-1,2,4-oxadiazol-3-yl)methyl)-2,2-dimethyl-6-(4-(trifluoromethoxy)phenyl)-2H-benzo[e][1,3]oxazin-4(3H)-one (Compound VIII-15)

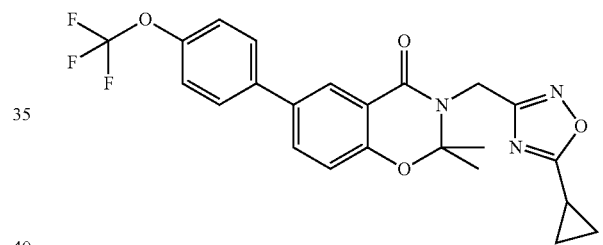

Compound VIII-15 was prepared using the procedures disclosed herein above with the appropriate starting materials.

Example 150

2,2-dimethyl-3-((5-methyl-1,2,4-oxadiazol-3-yl)methyl)-6-(4-(trifluoromethoxy)phenyl)-2H-benzo[e][1,3]oxazin-4(3H)-one (Compound VIII-16)

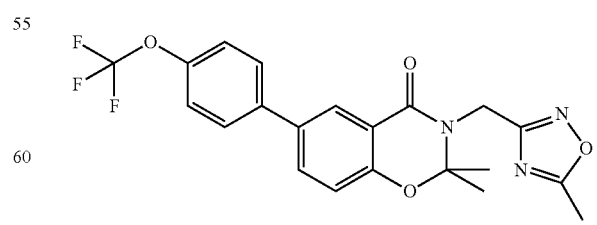

Compound VIII-16 was prepared using the procedures disclosed herein above with the appropriate starting materials.

Example 151

2-(pyrimidin-2-ylmethyl)-7-(4-(trifluoromethyl)phenyl)-3,4-dihydroisoquinolin-1(2H)-one (Compound IX-3)

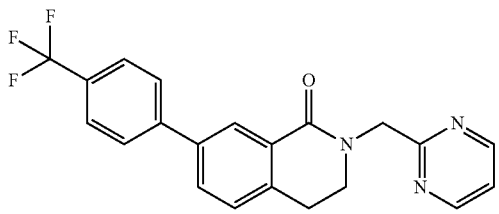 [SMILES: O=C1c2cc(-c3ccc(C(F)(F)F)cc3)ccc2CCN1Cc1ncccn1]

Compound IX-3 was prepared using the procedures disclosed herein above with the appropriate starting materials.

Example 152

2-(pyrimidin-2-ylmethyl)-7-((4-(trifluoromethyl)phenyl)ethynyl)-3,4-dihydroisoquinolin-1(2H)-one (Compound IX-4)

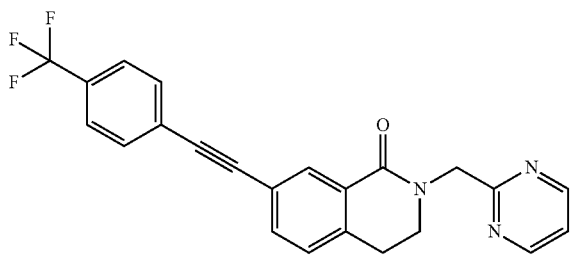 [SMILES: O=C1c2cc(C#Cc3ccc(C(F)(F)F)cc3)ccc2CCN1Cc1ncccn1]

Compound IX-4 was prepared using the procedures disclosed herein above with the appropriate starting materials. $^1$H-NMR (CD$_3$OD) δ 8.74 (d, 2H, J=4.8 Hz), 8.09 (d, 1H, J=1.6 Hz), 7.65-7.72 (m, 5H), 7.35-7.37 (m, 2H), 5.01 (s, 2H), 3.82 (t, 2H, J=6.6 Hz), 3.16 (t, 2H, J=6.6 Hz); MS m/z 408.1 (M+H).

Example 153

2-(pyrimidin-2-ylmethyl)-7-((4-(trifluoromethoxy)phenyl)ethynyl)-3,4-dihydroisoquinolin-1(2H)-one (Compound IX-5)

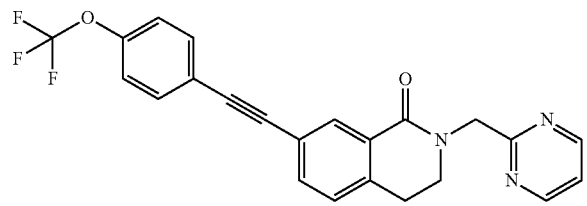 [SMILES: O=C1c2cc(C#Cc3ccc(OC(F)(F)F)cc3)ccc2CCN1Cc1ncccn1]

Compound IX-5 was prepared using the procedures disclosed herein above with the appropriate starting materials. $^1$H-NMR (CD$_3$OD) δ 8.74 (d, 2H, J=5.2 Hz), 8.06 (d, 1H, J=1.2 Hz), 7.61-7.65 (m, 3H), 7.28-7.37 (m, 4H), 7.53 (d, 1H, J=8.4 Hz), 7.48 (d, 1H, J=8.4 Hz), 7.32-7.38 (m, 3H), 5.01 (s, 2H), 3.82 (t, 2H, J=6.6 Hz), 3.15 (t, 2H, J=6.4 Hz); MS m/z 424.1 (M+H).

Example 154 pyridin-2-yl(7-(4-(trifluoromethyl)phenyl)-3,4-dihydroisoquinolin-2(1H)-yl)methanone (Compound IX-6)

To a suspension of 7-bromo-1,2,3,4-tetrahydro-isoquinoline hydrochloride (500 mgs, 2.0 mmol), pyridine-2-carboxylic acid (322 mgs, 2.61 mmol), HATU (992 mgs, 2.61 mmol), in DMF (2.5 mL) was added NMM (0.7 mL, 6.0 mmol) and the resulting solution was stirred at 23° C. for 3 h. The reaction mixture was then diluted with water/acetonitrile (15:1) and the resulting oil was then taken into EtOAc and washed with 1N HCl, NaHCO$_3$, brine and dried (MgSO$_4$). The mixture was the filtered and concentrated) to provide (7-bromo-3,4-dihydroisoquinotin-2(1H)-yl)(pyridin-2-yl)methanone.

A mixture 4-(trifluoromethyl)phenylboronic acid (90 mgs, 0.48 mmol), (7-bromo-3,4-dihydroisoquinolin-2(1H)-yl)(pyridin-2-yl)methanone (100 mgs, 0.32 mmol), potassium carbonate (87 mgs, 0.63 mmol), PdCl$_2$(dppf) (23 mgs, 0.03 mmol) in toluene/ethanol/water (2 mL/1 mL/1 mL) was heated in the microwave for 30 min at 120° C. The mixture was then concentrated and chromatographed (12 grams of SiO$_2$, 50% EtOAc/DCM) to provide the title compound.

MS found for C$_{22}$H$_{17}$F$_3$N$_2$O as (M+H)$^+$ 383.1 $^1$H NMR (400 MHz, dmso-d$_6$): mixture of rotomers (~1.5:1): major rotomer: δ 8.62 (d, J=4.8 Hz, 1H), 7.96-7.91 (m, 3H); 7.89-7.42 (m, 6H); 7.31 (m, 1H); 4.89 (s, 2H); 3.65-3.62 (m, 2H); 2.91-2.88 (m, 2H).

Example 155 pyrimidin-2-yl(7-(4-(trifluoromethyl)phenyl)-3,4-dihydroisoquinolin-2(1H)-yl)methanone (Compound IX-7)

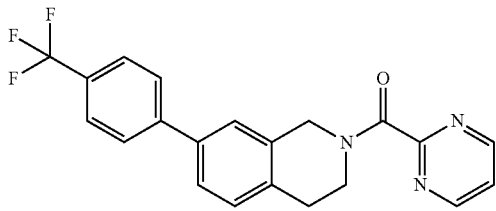 [SMILES: O=C(c1ncccn1)N1CCc2ccc(-c3ccc(C(F)(F)F)cc3)cc2C1]

Compound IX-7 was prepared using the procedures disclosed for Compound IX-6 with pyrimidine-2-carboxylic acid instead of pyridine-2-carboxylic acid. MS found for $C_{21}H_{16}F_3N_3O$ as $(M+H)^+$ 384.1 $^1$H NMR (400 MHz, dmso-$d_6$): mixture of rotomers (~1.5:1): major rotomer: δ 8.93 (m, 2H), 7.96-7.91 (m, 3H); 7.91-7.55 (m, 6H); 7.32 (m, 1H); 4.90 (s, 2H); 3.44-3.41 (m, 2H); 2.86-2.848 (m, 2H).

Example 156

(1-methyl-7-(4-(trifluoromethyl)phenyl)-3,4-dihydroisoquinolin-2(1H)-yl)(pyrimidin-2-yl)methanone (Compound IX-8)

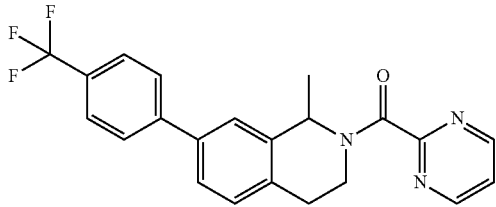 [SMILES: CC1c2cc(-c3ccc(C(F)(F)F)cc3)ccc2CCN1C(=O)c1ncccn1]

Compound IX-8 was prepared using the procedures disclosed herein above with the appropriate starting materials. MS found for $C_{22}H_{18}F_3N_3O$ 398.1 (M+1).

Example 157

3-((2-methyloxazol-5-yl)methyl)-6-(4-(trifluoromethoxy)phenyl)benzo[d][1,2,3]triazin-4(3H)-one (Compound II-95)

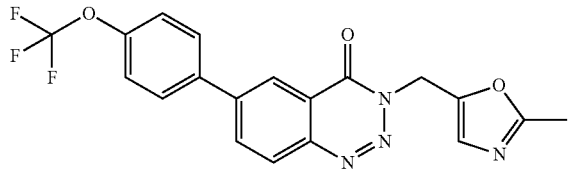 [SMILES: Cc1ncc(Cn2nnc3ccc(-c4ccc(OC(F)(F)F)cc4)cc3c2=O)o1]

Compound II-95 was prepared using the procedures disclosed herein above with the appropriate starting materials. MS 403.0 (base peak, M+H+); 425.0 (M+Na+) 827.2 (2M+Na+).

Example 158

3-((5-methyloxazol-2-yl)methyl)-6-(4-(trifluoromethoxy)phenyl)benzo[d][1,2,3]triazin-4(3H)-one (Compound II-96)

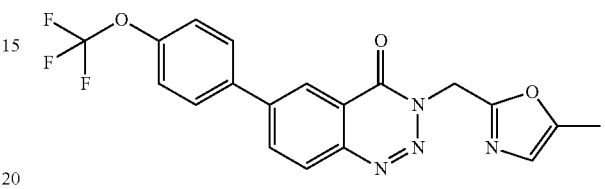

Compound II-96 was prepared using the procedures disclosed herein above with the appropriate starting materials. MS 403.0 (base peak, M+H+); 827.1 (2M+Na+). $^1$H-NMR δ 8.54 (d, 1H); 8.26 (d, 1H); 8.17 (dd, 1H); 7.72 (d, 2H); 7.36 (d, 2H); 6.70 (s, 1H); 5.73 (s, 2H); 2.29 (s, 3H). $^{19}$F NMR δ −58.28 (s).

Example 159

3-((4-methyloxazol-2-yl)methyl)-6-(4-(trifluoromethoxy)phenyl)benzo[d][1,2,3]triazin-4(3H)-one (Compound II-97)

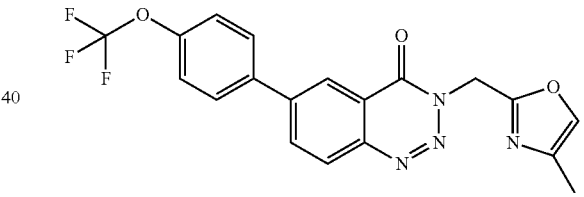

Compound II-97 was prepared using the procedures disclosed herein above with the appropriate starting materials. MS 403.1 (base peak, M+H+); 827.2 (2M+Na+).

Example 160

3-((2-cyclobutyloxazol-4-yl)methyl)-6-(4-(trifluoromethoxy)phenyl)benzo[d][1,2,3]triazin-4(3H)-one (Compound II-98)

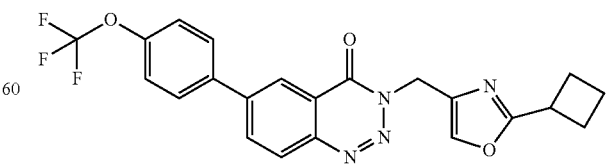

Compound II-98 was prepared using the procedures disclosed herein above with the appropriate starting materials. MS 443.1 (base peak, M+H+); 907.2 (2M+Na+).

Example 161

3-((2-methyloxazol-4-yl)methyl)-6-(4-(trifluoromethoxy)phenyl)benzo[d][1,2,3]triazin-4(3H)-one (Compound II-99)

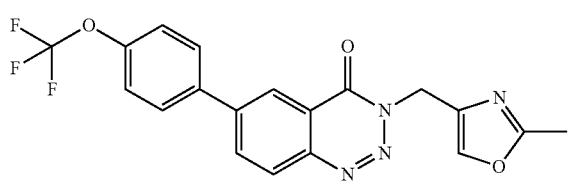

Compound II-99 was prepared using the procedures disclosed herein above with the appropriate starting materials. MS 403.1 (base peak, M+H+); 827.2 (2M+Na+). $^1$H-NMR δ 8.54 (d, 1H); 8.24 (d, 1H); 8.13 (dd, 1H); 7.72 (d, 2H); 7.65 (s, 1H); 7.38 (d, 2H); 5.55 (s, 2H); 2.42 (s, 3H). $^{19}$F NMR δ+−58.29 (s).

Example 162

3-((2-cyclopropyloxazol-4-yl)methyl)-6-(4-(trifluoromethoxy)phenyl)benzo[d][1,2,3]triazin-4(3H)-one (Compound II-100)

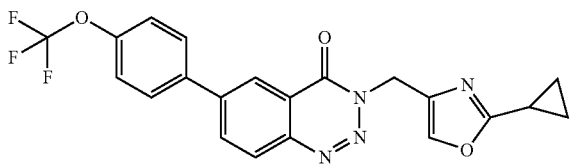 [SMILES: O=c1c2cc(-c3ccc(OC(F)(F)F)cc3)ccc2nnn1Cc1coc(C2CC2)n1]

Compound II-100 was prepared using the procedures disclosed herein above with the appropriate starting materials. $^1$H-NMR δ 8.52 (d, 1H); 8.24 (d, 1H); 8.12 (dd, 1H); 7.72 (d, 2H); 7.56 (s, 1H); 7.39 (d, 2H); 5.53 (s, 2H); 2.05 (tt, 1H); 2.06-1.98 (m, 4H). $^{19}$F NMR δ −58.29 (s).

Example 163

3-((5-tert-butyloxazol-2-yl)methyl)-6-(4-(trifluoromethoxy)phenyl)benzo[d][1,2,3]triazin-4(3H)-one (Compound II-101)

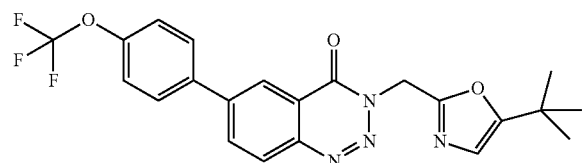

Compound II-101 was prepared using the procedures disclosed herein above with the appropriate starting materials. MS 445.1 (base peak, M+H+); 911.3 (2M+Na+).

Example 164

3-(pyrimidin-2-ylmethyl)-6-(4-(trifluoromethyl)phenyl)quinazolin-4(3H)-one (Compound IV-11)

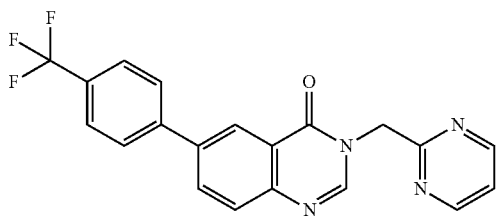 [SMILES: O=c1c2cc(-c3ccc(C(F)(F)F)cc3)ccc2ncn1Cc1ncccn1]

Compound IV-11 was prepared using the procedures disclosed herein above with the appropriate starting materials. MS (ESI+) 383.1 (base peak, M+H$^+$); 787.2 (2M+Na$^+$).

Example 165

3-((5-methyloxazol-2-yl)methyl)-6-(4-(trifluoromethyl)phenyl)quinazolin-4(3H)-one (Compound IV-12)

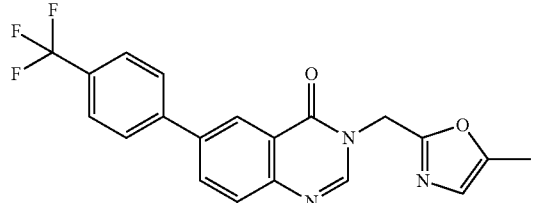

Compound IV-12 was prepared using the procedures disclosed herein above with the appropriate starting materials. $^1$H NMR 8.49 (d, 1H); 8.33 (s, 1H); 8.02 (dd, 1H); 7.86 (d, 1H); 7.76-7.80 (m, 4H); 6.71 (s, 1H); 5.33 (s, 2H); 2.30 (s, 3H). $^{19}$F NMR −63.18 (s). MS (ESI+) 386.0 (base peak, M+H$^+$); 793.2 (2M+Na$^+$).

Example 166

3-(pyrimidin-2-ylmethyl)-6-(4-(trifluoromethoxy)phenyl)quinazolin-4(3H)-one (Compound IV-13)

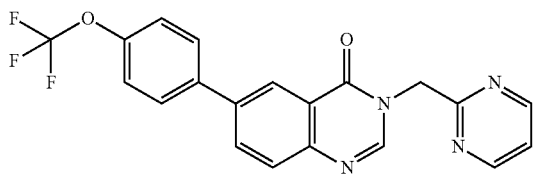 [SMILES: O=c1c2cc(-c3ccc(OC(F)(F)F)cc3)ccc2ncn1Cc1ncccn1]

Compound IV-13 was prepared using the procedures disclosed herein above with the appropriate starting materials. $^1$H NMR 8.70 (d, 2H); 8.52 (d, 1H); 8.33 (s, 1H); 8.01 (dd, 1H); 7.92 (d, 1H); 7.69 (d, 2H); 7.35 (d, 2H); 7.23 (t, 1H); 5.48 (s, 2H). $^{19}$F NMR −58.31 (s). MS (ESI+) 399.0 (base peak, M+H$^+$); 819.2 (2M+Na$^+$).

Example 167

3-((5-methyloxazol-2-yl)methyl)-6-(4-(trifluoromethoxy)phenyl)quinazolin-4(3H)-one (Compound IV-14)

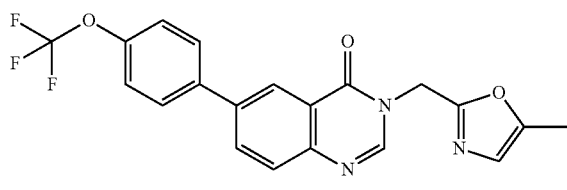 [SMILES: Cc1cnc(Cn2cnc3ccc(-c4ccc(OC(F)(F)F)cc4)cc3c2=O)o1]

Compound IV-14 was prepared using the procedures disclosed herein above with the appropriate starting materials. $^1$H NMR 8.52 (d, 1H); 8.22 (br s, 1H); 7.99 (dd, 1H); 7.83 (d, 1H); 7.69 (d, 2H); 7.32 (d, 2H); 6.71 (s, 1H); 5.31 (s, 2H); 2.30 (s, 3H). $^{19}$F NMR −58.31 (s). MS (ESI+) 402.0 (base peak, M+H$^+$); 825.2 (2M+Na$^+$).

Example 168

3-((1-methyl-1H-1,2,4-triazol-3-yl)methyl)-6-(4-(trifluoromethoxy)phenyl)quinazolin-4(3H)-one (Compound IV-15)

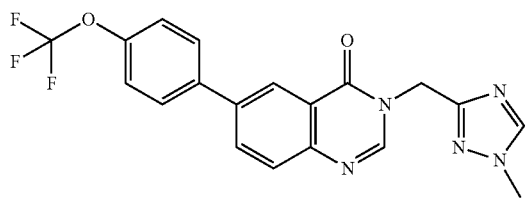 [SMILES: Cn1cnc(Cn2cnc3ccc(-c4ccc(OC(F)(F)F)cc4)cc3c2=O)n1]

Compound IV-15 was prepared using the procedures disclosed herein above with the appropriate starting materials. MS (ESI+) 391.0 (M+H$^+$); 803.1 (base peak, 2M+Na$^+$).

Example 169

3-((5-cyclopropyl-1,2,4-oxadiazol-3-yl)methyl)-6-(4-(trifluoromethoxy)phenyl)quinazolin-4(3H)-one (Compound IV-16)

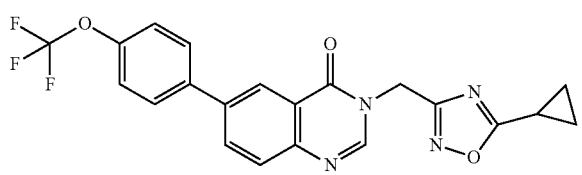 [SMILES: O=c1c2cc(-c3ccc(OC(F)(F)F)cc3)ccc2ncn1Cc1noc(C2CC2)n1]

Compound IV-16 was prepared using the procedures disclosed herein above with the appropriate starting materials. $^1$H NMR 8.51 (d, 1H); 8.18 (s, 1H); 7.99 (dd, 1H); 7.82 (d, 1H); 7.69 (d, 2H); 7.32 (d, 2H); 5.28 (s, 2H); 2.19 (quintet, 1H); 1.22 (d, 4H). MS (ESI+) 429.0 (base peak, M+H$^+$); 879.2 (2M+Na$^+$).

Example 170

3-((3-methylisoxazol-5-yl)methyl)-6-(4-(trifluoromethoxy)phenyl)quinazolin-4(3H)-one (Compound IV-17)

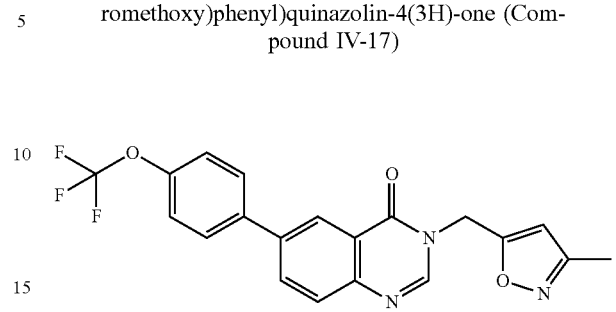

Compound IV-17 was prepared using the procedures disclosed herein above with the appropriate starting materials. MS (ESI+) 402.1 (base peak, M+H$^+$); 825.2 (2M+Na$^+$).

Example 171

3-((5-methyl-1,3,4-oxadiazol-2-yl)methyl)-6-(4-(trifluoromethoxy)phenyl)quinazolin-4(3H)-one (Compound IV-18)

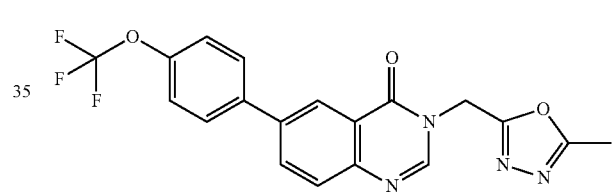

Compound IV-18 was prepared using the procedures disclosed herein above with the appropriate starting materials. MS (ESI+) 403.0 (base peak, M+H$^+$); 827.1 (2M+Na$^+$).

Example 172

3-((5-cyclopropyl-1,3,4-oxadiazol-2-yl)methyl)-6-(4-(trifluoromethoxy)phenyl)quinazolin-4(3H)-one (Compound IV-19)

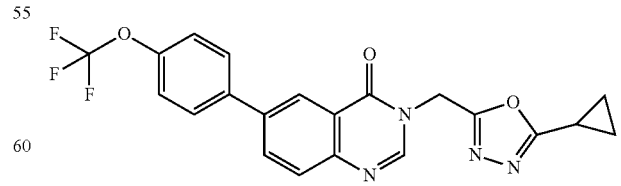

Compound IV-19 was prepared using the procedures disclosed herein above with the appropriate starting materials. MS (ESI+) 429.1 (base peak, M+H$^+$); 879.2 (2M+Na$^+$).

Example 173

3-((1-methyl-1H-pyrazol-3-yl)methyl)-6-(4-(trifluoromethoxy)phenyl)quinazolin-4(3H)-one (Compound IV-20)

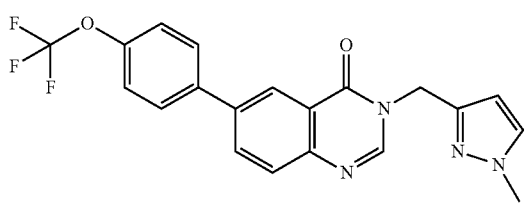 [SMILES: Cn1ccc(Cn2cnc3ccc(-c4ccc(OC(F)(F)F)cc4)cc3c2=O)n1]

Compound IV-20 was prepared using the procedures disclosed herein above with the appropriate starting materials. MS (ESI+) 401.1 (base peak, M+H+); 823.2 (2M+Na+).

Example 174

3-((5-methyl-1,2,4-oxadiazol-3-yl)methyl)-6-(4-(trifluoromethoxy)phenyl)quinazolin-4(3H)-one (Compound IV-21)

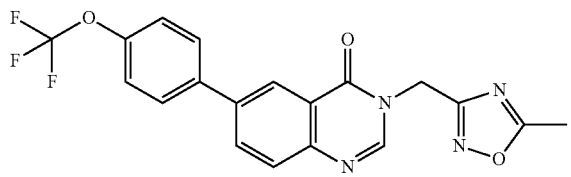 [SMILES: Cc1nc(Cn2cnc3ccc(-c4ccc(OC(F)(F)F)cc4)cc3c2=O)no1]

Compound IV-21 was prepared using the procedures disclosed herein above with the appropriate starting materials. MS (ESI+) 403.0 (base peak, M+H+); 827.1 (2M+Na+).

Example 175

3-((3-methyl-1,2,4-oxadiazol-5-yl)methyl)-6-(4-(trifluoromethoxy)phenyl)quinazolin-4(3H)-one (Compound IV-22)

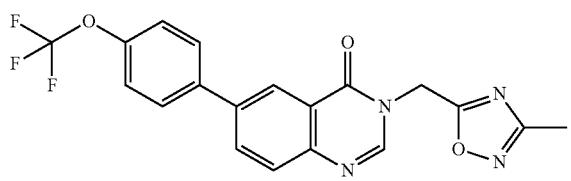 [SMILES: Cc1noc(Cn2cnc3ccc(-c4ccc(OC(F)(F)F)cc4)cc3c2=O)n1]

Compound IV-22 was prepared using the procedures disclosed herein above with the appropriate starting materials. MS (ESI+) 403.0 (base peak, M+H+); 827.1 (2M+Na+).

Example 176

2-methyl-3-((3-methyl-1,2,4-oxadiazol-5-yl)methyl)-6-(4-(trifluoromethoxy)phenyl)quinazolin-4(3H)-one (Compound IV-23)

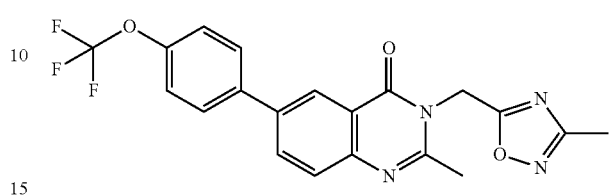

Compound IV-23 was prepared using the procedures disclosed herein above with the appropriate starting materials. MS (ESI+) 417.0 (base peak, M+H+); 855.1 (2M+Na+).

Example 177

3-((4-(hydroxymethyl)oxazol-2-yl)methyl)-6-(4-(trifluoromethoxy)phenyl)quinazolin-4(3H)-one (Compound IV-24)

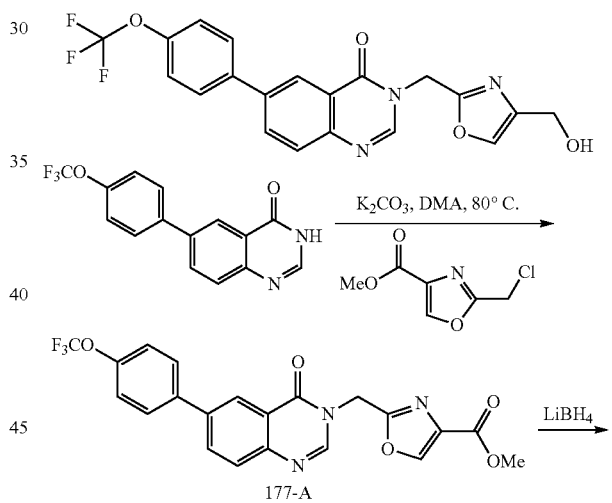

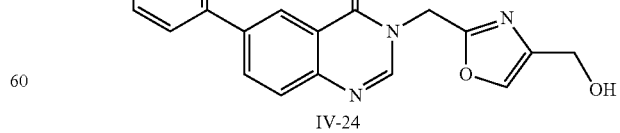

A solution of 500 mg 6-(4-(trifluoromethoxy)phenyl)quinazolin-4(3H)-one, 340 mg of methyl 2-(chloromethyl)oxazole-4-carboxylate, and 220 mg potassium carbonate in 5 mL of DMA was heated at 80° C. for 16 h. The reaction was diluted with water and dichloromethane, aqueous layer washed with dichloromethane, combined organic layers dried over sodium sulphate and concentrated. The residue was recrystallized from acetonitrile to produce methyl 2-((4-oxo-6-(4-(trifluoromethoxy)phenyl)quinazolin-3(4H)-yl)methyl)oxazole-4-carboxylate Compound 177-A as a white solid (420 mg). MS m/z (ESI)=446.0 (base peak, M+H$^+$); 891.1 (2M+H$^+$); 913.1 (2M+Na$^+$).

To a solution of methyl 2-((4-oxo-6-(4-(trifluoromethoxy)phenyl)quinazolin-3(4H)-yl)methyl)oxazole-4-carboxylate Compound 177-A (200 mg) in THF (5 mL) lithium borohydride was added (10 mg) and stirred for 1 hour. Quenched with saturated ammonium chloride and extracted with dichloromethane. Purified by gradient chromatography 0 to 5% MeOH in dichloromethane and resulting 3-(4-(hydroxymethyl)oxazol-2-yl)methyl)-6-(4-(trifluoromethoxy)phenyl)-2,3-dihydroquinazolin-4(1H)-one Compound 177-B (130 mg) submitted into next step. $^1$H NMR (δ, dmso-d$_6$, 400 MHz): 7.92 (d, 1H); 7.86 (s, 1H); 7.71 (d, 2H); 7.65 (dd, 1H); 7.38 (d, 2H); 7.03 (br s, 1H); 6.85 (d, 1H); 5.14 (t, 1H); 4.74 (s, 4H); 4.32 (d, 2H). $^{19}$F NMR (δ, dmso-d$_6$, 376 MHz): −57.29 (s). MS m/z (ESI)=420.1 (base peak, M+H$^+$); 861.2 (2M+Na$^+$).

3-((4-(Hydroxymethyl)oxazol-2-yl)methyl)-6-(4-(trifluoromethoxy)phenyl)-2,3-dihydroquinazolin-4(1H)-one Compound 177-B (120 mg) was stirred in ethyl acetate (20 mL) in the presence of palladium on carbon (10%, 120 mg) for 16 hours, then filtered through Celite® and purified by reverse-phase (ACN/H$_2$O with 0.1% TFA) followed by neutralization on resin column to produce 44 mg of 3-((4-(hydroxymethyl)oxazol-2-yl)methyl)-6-(4-(trifluoromethoxy)phenyl)quinazolin-4(3H)-one Compound IV-24 as a white solid.

$^1$H NMR (δ, CDCl$_3$, 400 MHz): 8.51 (d, 1H); 8.21 (s, 1H); 8.00 (dd, 1H); 7.83 (d, 1H); 7.70 (d, 2H); 7.59 (s, 1H); 7.27 (d, 2H); 5.33 (s, 2H); 4.58 (s, 2H); 1.90 (br s, 1H). $^{19}$F NMR (δ, CDCl$_3$, 376 MHz): −58.31. MS m/z (ESI)=418.0 (base peak, M+H$^+$); 857.2 (2M+Na$^+$).

Example 178

3-(2-(pyrimidin-2-yloxy)ethyl)-6-(4-(trifluoromethoxy)phenyl)quinazolin-4(3H)-one (Compound IV-25)

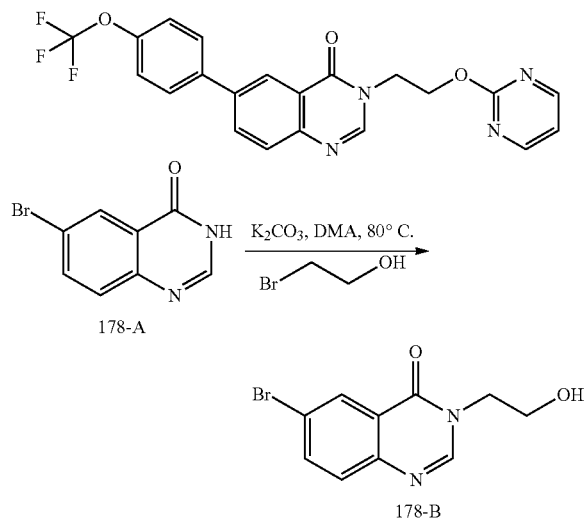

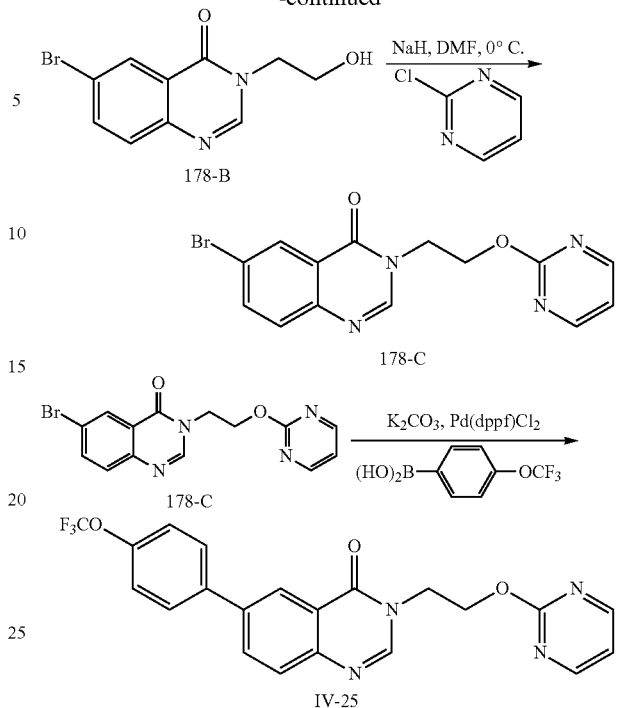

6-Bromoquinazolin-4(3H)-one Compound 178-A (1.0 g), 2-bromoethanol (1.1 g), and potassium carbonate (610 mg) were heated in DMA (10 mL) at 80° C. for 16 h. Reaction was extracted with water and dichloromethane (3 times), combined organic layers washed with brine, over sodium sulphate and concentrated. Residue was triturated with acetonitrile to yield 6-bromo-3-(2-hydroxyethyl)quinazolin-4(3H)-one Compound 178-B (810 mg) as a white solid. MS m/z (ESI)=268.9 (base peak, $^{79}$Br-M+H$^+$); 270.9 ($^{81}$Br-M+H$^+$); 290.9 ($^{79}$Br-M+Na$^+$); 292.9 ($^{81}$Br-M+Na$^+$).

In an ice bath, 6-bromo-3-(2-hydroxyethyl)quinazolin-4(3H)-one Compound 178-B (400 mg) was dissolved in DMF (10 mL) and NaH (60% suspension in oil, 120 mg) added as one portion. After 20 min, 2-chloropyridine (250 mg) was added. After 1 h, reaction was quenched by addition of water and precipitate filtered, resulting in 450 mg of 6-bromo-3-(2-(pyrimidin-2-yloxy)ethyl)quinazolin-4(3H)-one Compound 178-C as off-white solid. MS m/z (ESI)=346.6 (base peak, $^{79}$Br-M+H$^+$); 348.6 ($^{81}$Br-M+H$^+$); 368.5 ($^{79}$Br-M+Na$^+$); 370.5 ($^{81}$Br-M+Na$^+$); 714.2 ($^{79}$Br$_2$-2M+Na$^+$); 716.2 (base peak, $^{79}$Br$^{81}$Br-2M+Na$^+$); 718.3 ($^{81}$Br$_2$-M+Na$^+$).

A mixture of 60 mg 6-bromo-3-(2-(pyrimidin-2-yloxy)ethyl)quinazolin-4(3H)-one Compound 178-C (0.25 mmol), 53 mg 4-(trifluoromethoxy)phenyl boronic acid (0.38 mmol), 18 mg potassium carbonate (0.15 mmol), and 3 mg Pd(dppf)Cl$_2$ in 5 mL of degassed 9:1 DMF:water solution was heated at 90° C. After 1 h, the reaction mixture was filtered through celite and the filtrate concentrated and purified by reverse-phase (ACN/H$_2$O with 0.1% TFA) followed by neutralization on resin column to produce 56 mg of 3-(2-(pyrimidin-2-yloxy)ethyl)-6-(4-(trifluoromethoxy)phenyl)quinazolin-4(3H)-one Compound IV-25.

$^1$H NMR (δ, CDCl$_3$, 400 MHz): 8.51 (d, 1H); 8.47 (d, 2H); 8.20 (s, 1H); 7.98 (dd, 1H); 7.77 (d, 1H); 7.69 (d, 2H); 7.33 (d, 2H); 6.93 (t, 1H); 4.75 (t, 2H); 4.47 (t, 2H). $^{19}$F NMR (δ, CDCl$_3$, 376 MHz): −58.31 (s). MS m/z (ESI)=429.1 [M+H]$^+$, 879.2 [2M+Na]$^+$

Example 179

3-(2-(pyrimidin-2-yloxy)ethyl)-6-(4-(trifluoromethyl)phenyl)quinazolin-4(3H)-one (Compound IV-26)

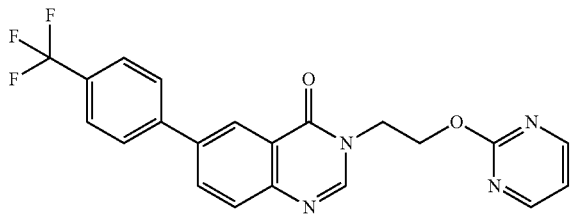 [SMILES: O=c1c2cc(-c3ccc(C(F)(F)F)cc3)ccc2ncn1CCOc1ncccn1]

Compound IV-26 was prepared using a similar procedure as that described for Compound IV-25 with the appropriate starting materials. $^1$H NMR (δ, CDCl$_3$, 400 MHz): 8.56 (d, 1H); 8.50 (d, 2H); 8.33 (s, 1H); 8.01 (dd, 1H); 7.84 (d, 1H); 7.80 (d, 2H); 7.74 (d, 2H); 6.98 (t, 1H); 4.78 (t, 2H); 4.50 (t, 2H). $^{19}$F NMR (δ, CDCl$_3$, 376 MHz): −63.03 (s). MS m/z (ESI)=413.1 [M+H]$^+$, 847.2 [2M+Na]$^+$

Example 180

3-((1-(hydroxymethyl)cyclopropyl)methyl)-6-(4-(trifluoromethoxy)phenyl)quinazolin-4(3H)-one (Compound IV-27)

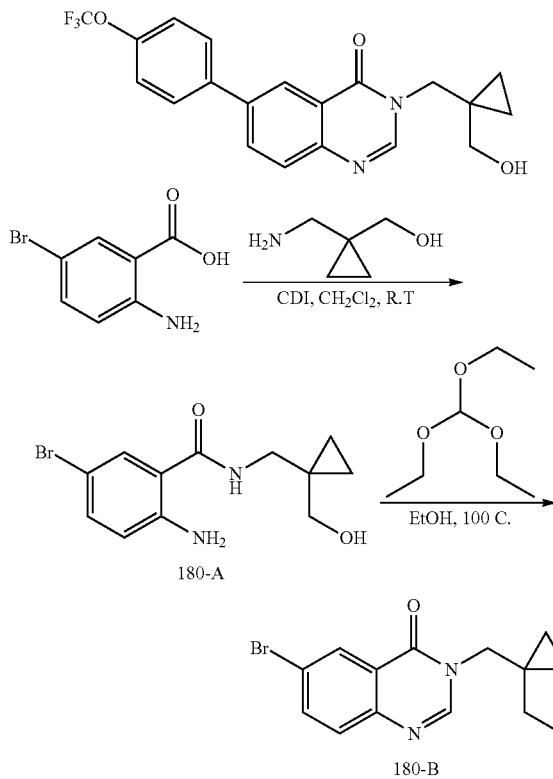

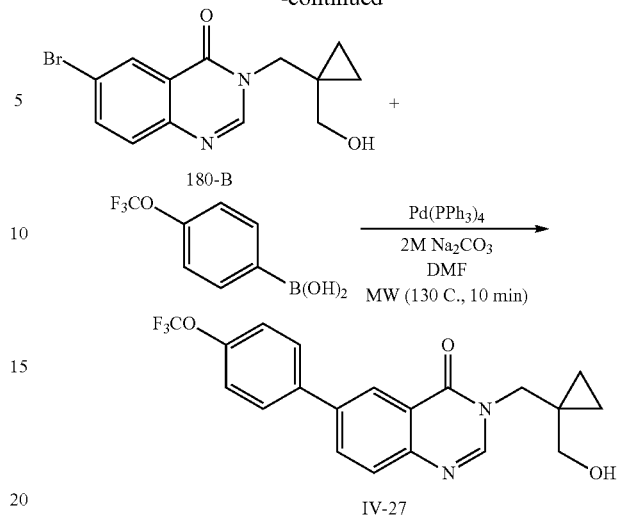

To a round bottom flask was added 2-amino-5-bromobenzoic acid (6.94 mmole), and CDI or EDCI-HCl (1.5 equiv) in CH$_2$Cl$_2$ (100 mL) and the mixture was stirred at RT for 15 min before addition of amine (1.4 equiv). The resulting reaction mixture was stirred at RT overnight. The mixture was washed with H$_2$O and the organic extract was dried over Na$_2$SO$_4$ and then concentrated down under reduced pressure before purification by biotage column chromatography eluting with 5% methanol methylene chloride mixture to afford 1.35 grams of Compound 180-A.

Compound 180-A (0.107 mmol) was dissolved in 5 mL EtOH followed by triethylorthoformate (0.7 mL). The reaction mixture was heated at 100 C overnight to give Compound 180-B. The mixture was then concentrated down and used in the next step without further purification.

Compound 180-B was coupled with 4-trifluoromethoxyphenylboronic acid under previously described Suzuki conditions to give Compound IV-27.

$^1$H-NMR (DMSO) 0.432-0.458 (m, 2H), 0.677-0.702 (m, 2H), 3.23 (s, 2H), 4.05 (s, 2H), 7.47-7.49 (d, 2H, J, =8 Hz), 7.76-7.78 (d, 1H, J, =8 Hz), 7.89-7.92 (m, 2H), 8.138.16 (m, 1H), 8.37-8.37 (s, 2H), MS m/z 391.1 (M$^+$).

Example 181

3-(3-hydroxy-2,2-dimethylpropyl)-6-(4-(trifluoromethoxy)phenyl)quinazolin-4(3H)-one (Compound IV-28)

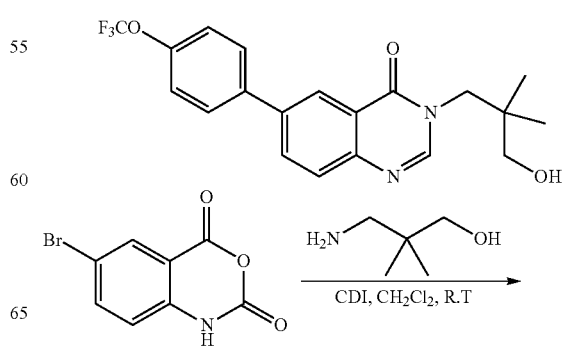

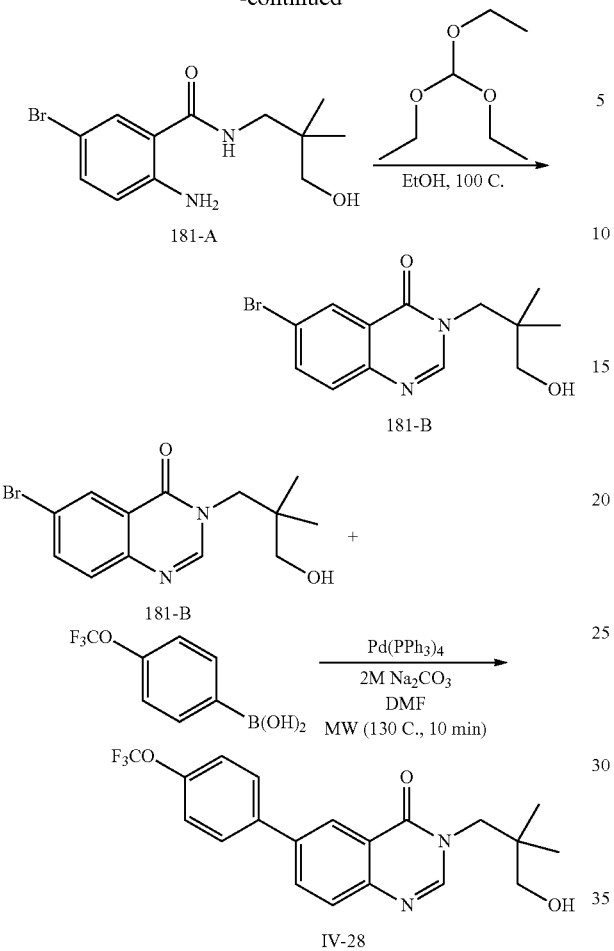

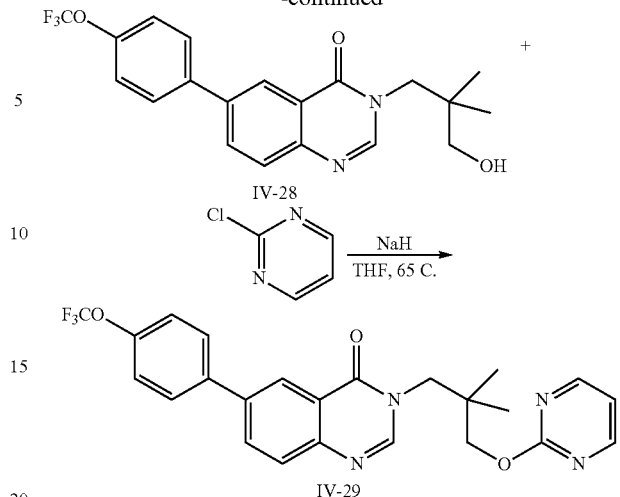

To a round bottom flask was added 5-bromoisatoic anhydride (6.20 mmole) and 3-amino-2,2-dimethylpropan-1-ol (12.4 mmole) in CH$_2$Cl$_2$ (100 mL). The resulting reaction mixture was stirred at RT overnight. The work up and purification is similar to that described above for synthesis of Compound IV-27.

Compound 181-A was dissolved in 5 mL EtOH followed by triethylorthoformate. he reaction mixture was heated at 100 C overnight to give Compound 181-B as described for Compound IV-27.

Compound 181-B was coupled with 4-trifluoromethoxyphenylboronic acid under previously described Suzuki conditions to give Compound IV-28. MS m/z 393.1 (M$^+$).

Example 182

3-(2,2-dimethyl-3-(pyrimidin-2-yloxy)propyl)-6-(4-(trifluoromethoxy)phenyl)quinazolin-4(3H)-one (Compound IV-29)

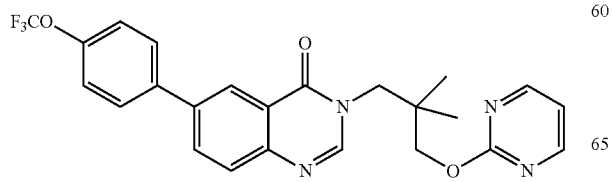

Compound IV-28 (0.367 mmole) was dissolved in THF (10 mL). To this was added NaH (0.551 mmole, 60% dispersion in mineral oil). To this suspension was added 2-chloropyrimidine (0.735 mmole) and the mixture was refluxed for 24 hours. Quenched with water and extracted with dichloromethane. Dried over Na$_2$SO$_4$ and purified by preparative TLC eluting with 2:1 Hexane:Ethyl Acetate to give Compound IV-29. MS m/z 471.1 (M$^+$).

Example 183

(1-methyl-1H-imidazol-5-yl)(7-(4-(trifluoromethyl)phenyl)-3,4-dihydroisoquinolin-2(1H)-yl)methanone (Compound IX-56)

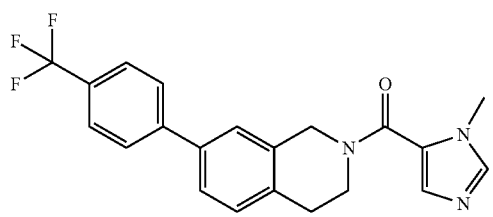 [SMILES: Cn1cncc1C(=O)N1CCc2ccc(-c3ccc(C(F)(F)F)cc3)cc2C1]

Compound IX-56 was prepared using the procedures disclosed herein above with the appropriate starting materials. Mass (M+H)$^+$ 386.1.

Example 184

(1H-imidazol-2-yl)(7-(4-(trifluoromethyl)phenyl)-3,4-dihydroisoquinolin-2(1H)-yl)methanone (Compound IX-57)

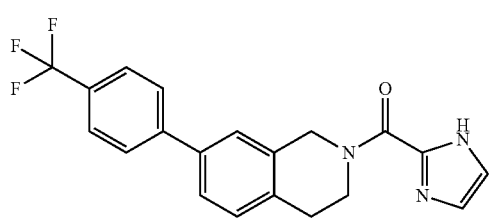 [SMILES: O=C(c1ncc[nH]1)N1CCc2ccc(-c3ccc(C(F)(F)F)cc3)cc2C1]

Compound IX-57 was prepared using the procedures disclosed herein above with the appropriate starting materials. $^1$H NMR (400 MHz; CD$_3$OD) δ 7.65-7.77 (m, 4H); 7.61 (s, 2H); 7.51 (m, 2H); 7.29 (m, 1H); 4.95 (m, 2H); 3.96 (m, 2H); 3.02 (m, 2H). $^{19}$F NMR (400 MHz; CD$_3$OD) δ −64.40 (s, 3F). Mass (M+H)$^+$ 372.1.

Example 185

(4-fluoro-1H-imidazol-5-yl)(7-(4-(trifluoromethyl)phenyl)-3,4-dihydroisoquinolin-2(1H)-yl)methanone (Compound IX-59)

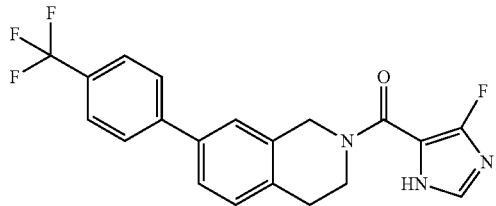 [SMILES: O=C(c1[nH]cnc1F)N1CCc2ccc(-c3ccc(C(F)(F)F)cc3)cc2C1]

Compound IX-59 was prepared using the procedures disclosed herein above with the appropriate starting materials. Mass (M+H)$^+$ 390.1.

Example 186

(1-methyl-1H-imidazol-2-yl)(7-(4-(trifluoromethyl)phenyl)-3,4-dihydroisoquinolin-2(1H)-yl)methanone (1-methyl-1H-imidazol-2-yl)(7-(4-(trifluoromethyl)phenyl)-3,4-dihydroisoquinolin-2(1H)-yl)methanone (Compound IX-80)

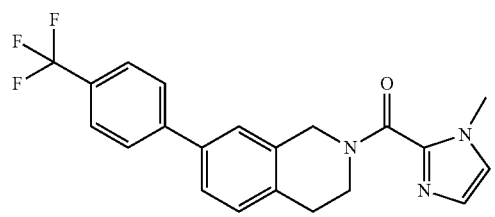 [SMILES: Cn1ccnc1C(=O)N1CCc2ccc(-c3ccc(C(F)(F)F)cc3)cc2C1]

Compound IX-80 was prepared using the procedures disclosed herein above with the appropriate starting materials. Mass (M+H)$^+$ 386.1. $^1$H NMR (400 MHz; dmso-d$_6$) δ 7.45-7.95 (m, 7H); 7.24 (s, 1H); 7.32 (m, 1H); 7.13 (m, 1H); 5.10 (s, 1H); 4.84 (m, 1H); 3.79 (m, 3H); 2.92 (m, 4H). $^{19}$F NMR (400 MHz; DMSO-d6) δ −64.40 (s, 3F).

Example 187

2-(1-methyl-1H-imidazol-4-ylsulfonyl)-7-(4-(trifluoromethyl)phenyl)-1,2,3,4-tetrahydroisoquinoline (Compound IX-98)

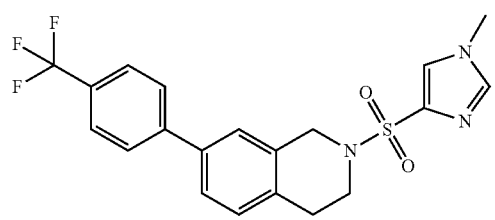 [SMILES: Cn1cnc(S(=O)(=O)N2CCc3ccc(-c4ccc(C(F)(F)F)cc4)cc3C2)c1]

Compound IX-98 was prepared using the procedures disclosed herein above with the appropriate starting materials. Mass (M+H)$^+$ 422.1.

Example 188

(R)-tert-butyl 2-(7-(4-(trifluoromethyl)phenyl)-1,2,3,4-tetrahydroisoquinoline-2-carbonyl)pyrrolidine-1-carboxylate (Compound IX-114)

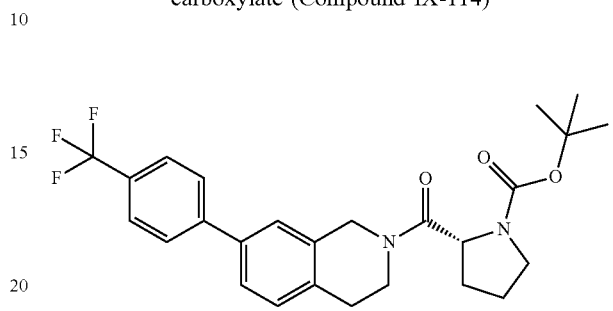

Compound IX-114 was prepared using the procedures disclosed herein above with the appropriate starting materials. Mass (M+H)$^+$ 475.1.

Example 189

(3-amino-1H-1,2,4-triazol-5-yl)(7-(4-(trifluoromethyl)phenyl)-3,4-dihydroisoquinolin-2(1H)-yl)methanone (Compound IX-111)

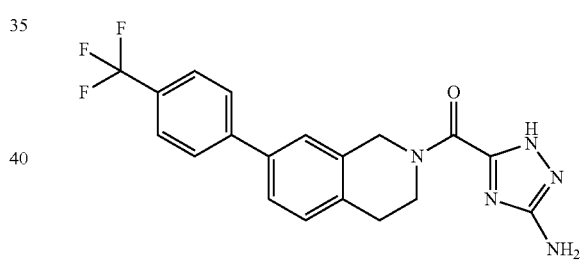

Compound IX-111 was prepared using the procedures disclosed herein above with the appropriate starting materials. Mass (M+H)$^+$ 388.1.

Example 190

(1-phenyl-1H-1,2,3-triazol-5-yl)(7-(4-(trifluoromethyl)phenyl)-3,4-dihydroisoquinolin-2(1H)-yl)methanone (Compound IX-116)

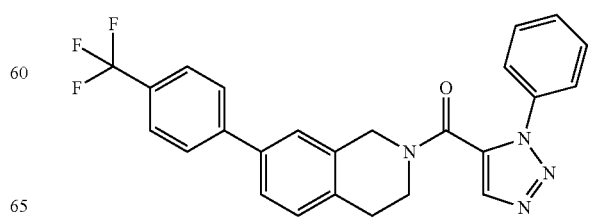

Compound IX-116 was prepared using the procedures disclosed herein above with the appropriate starting materials. Mass (M+H)+ 449.1.

Example 191 ethyl 2-(4-(7-(4-(trifluoromethyl)phenyl)-1,2,3,4-tetrahydroisoquinoline-2-carbonyl)-1H-1,2,3-triazol-1-yl)acetate (Compound IX-119)

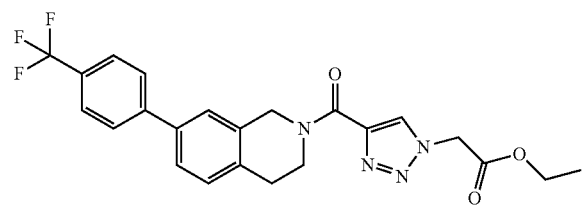 [SMILES: CCOC(=O)Cn1cc(C(=O)N2CCc3ccc(-c4ccc(C(F)(F)F)cc4)cc3C2)nn1]

Compound IX-119 was prepared using the procedures disclosed herein above with the appropriate starting materials. Mass (M+H)+ 459.1.

Example 192

(1-isopropyl-1H-pyrazol-4-yl)(7-(4-(trifluoromethyl)phenyl)-3,4-dihydroisoquinolin-2(1H)-yl)methanone (Compound IX-27)

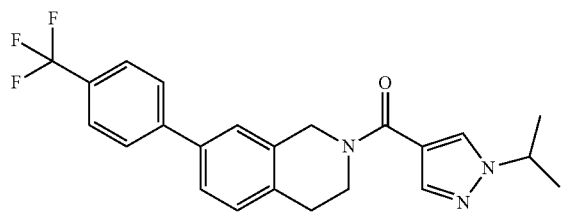 [SMILES: CC(C)n1cc(C(=O)N2CCc3ccc(-c4ccc(C(F)(F)F)cc4)cc3C2)cn1]

Compound IX-27 was prepared using the procedures disclosed herein above with the appropriate starting materials. Mass (M+H)+ 414.1.

Example 193

(1,3-dimethyl-1H-pyrazol-4-yl)(7-(4-(trifluoromethyl)phenyl)-3,4-dihydroisoquinolin-2(1H)-yl)methanone (Compound IX-28)

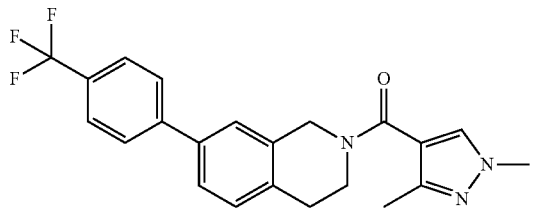 [SMILES: Cc1nn(C)cc1C(=O)N1CCc2ccc(-c3ccc(C(F)(F)F)cc3)cc2C1]

Compound IX-28 was prepared using the procedures disclosed herein above with the appropriate starting materials. Mass (M+H)+ 400.1.

Example 194

2-(pyridin-2-yl)-1-(7-(4-(trifluoromethyl)phenyl)-3,4-dihydroisoquinolin-2(1H)-yl)ethanone (Compound IX-29)

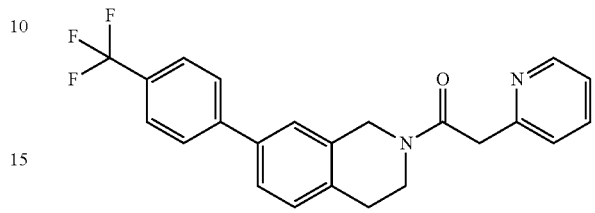

Compound IX-29 was prepared using the procedures disclosed herein above with the appropriate starting materials. Mass (M+H)+ 397.1.

Example 195

2-(pyrimidin-2-yl)-1-(7-(4-(trifluoromethyl)phenyl)-3,4-dihydroisoquinolin-2(1H)-yl)ethanone (Compound IX-30)

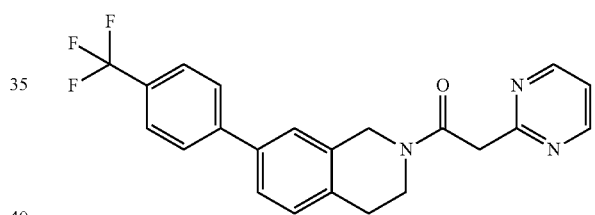

Compound IX-30 was prepared using the procedures disclosed herein above with the appropriate starting materials. Mass (M+H)+ 398.1.

Example 196

(2-isopropylpyrimidin-4-yl)(7-(4-(trifluoromethyl)phenyl)-3,4-dihydroisoquinolin-2(1H)-yl)methanone (Compound IX-31)

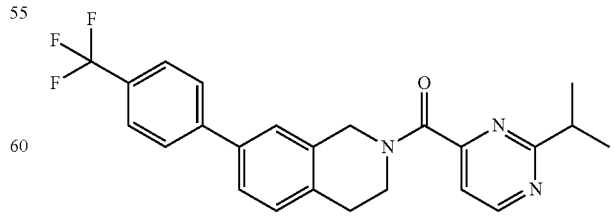

Compound IX-31 was prepared using the procedures disclosed herein above with the appropriate starting materials. Mass (M+H)+ 426.1.

Example 197 pyrimidin-4-yl(7-(4-(trifluoromethyl)phenyl)-3,4-dihydroisoquinolin-2(1H)-yl)methanone (Compound IX-32)

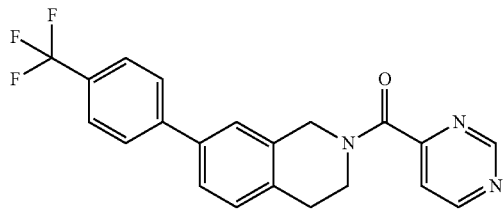 [SMILES: O=C(c1ccncn1)N1CCc2ccc(-c3ccc(C(F)(F)F)cc3)cc2C1]

Compound IX-32 was prepared using the procedures disclosed herein above with the appropriate starting materials. Mass (M+H)+ 384.1.

Example 198 pyrimidin-5-yl(7-(4-(trifluoromethyl)phenyl)-3,4-dihydroisoquinolin-2(1H)-yl)methanone (Compound IX-33)

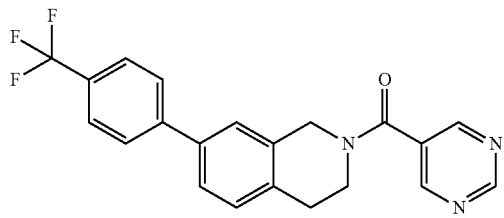 [SMILES: O=C(c1cncnc1)N1CCc2ccc(-c3ccc(C(F)(F)F)cc3)cc2C1]

Compound IX-33 was prepared using the procedures disclosed herein above with the appropriate starting materials. Mass (M+H)+ 384.1.

Example 199

(2-amino-6-methylpyrimidin-4-yl)(7-(4-(trifluoromethyl)phenyl)-3,4-dihydroisoquinolin-2(1H)-yl)methanone (Compound IX-34)

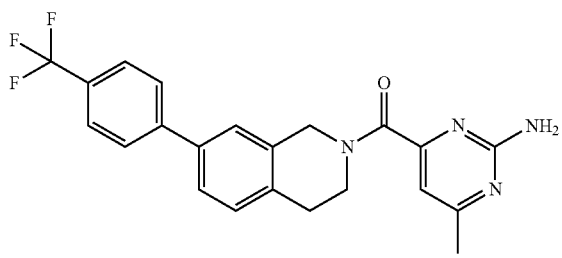 [SMILES: Cc1cc(C(=O)N2CCc3ccc(-c4ccc(C(F)(F)F)cc4)cc3C2)nc(N)n1]

Compound IX-34 was prepared using the procedures disclosed herein above with the appropriate starting materials. Mass (M+H)+ 413.1.

Example 200

(1H-pyrazol-5-yl)(7-(4-(trifluoromethyl)phenyl)-3,4-dihydroisoquinolin-2(1H)-yl)methanone (Compound IX-36)

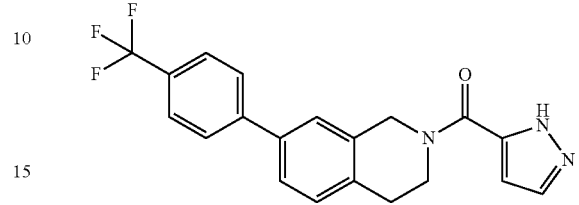

Compound IX-36 was prepared using the procedures disclosed herein above with the appropriate starting materials. Mass (M+H)+ 372.1.

Example 201

(1-methyl-1H-imidazol-4-yl)(7-(4-(trifluoromethyl)phenyl)-3,4-dihydroisoquinolin-2(1H)-yl)methanone (Compound IX-39)

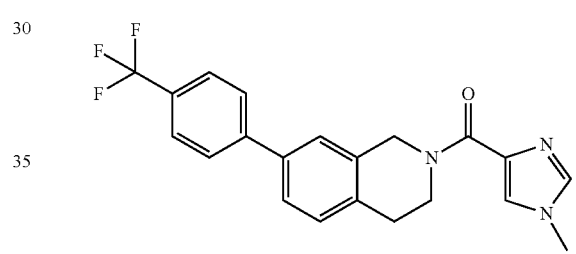

Compound IX-39 was prepared using the procedures disclosed herein above with the appropriate starting materials. Mass (M+H)+ 386.1.

Example 202 pyrimidin-2-yl(7-(4-(trifluoromethoxy)phenyl)-3,4-dihydroisoquinolin-2(1H)-yl)methanone (Compound IX-11)

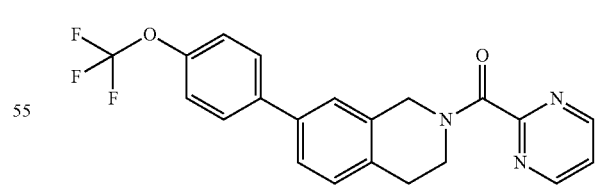

Similar procedure for the synthesis of Compound 1 was followed to obtain the title compound using 4-(trifluoromethoxy)phenylboronic acid instead of 4-(trifluoromethyl)phenylboronic acid. MS found for $C_{21}H_{16}F_3N_3O_2$ as (M+H)+ 400.1 $^1$H NMR (400 MHz, dmso-$d_6$): mixture of rotomers (~1.5:1): major rotomer: δ 8.93 (m, 2H), 7.80 (d, J=8.4 Hz, 2H); 7.96-7.91 (m, 6H); 4.89 (s, 2H); 3.44-3.41 (m, 2H); 2.85-2.848 (m, 2H).

Example 203

Compound IX-17

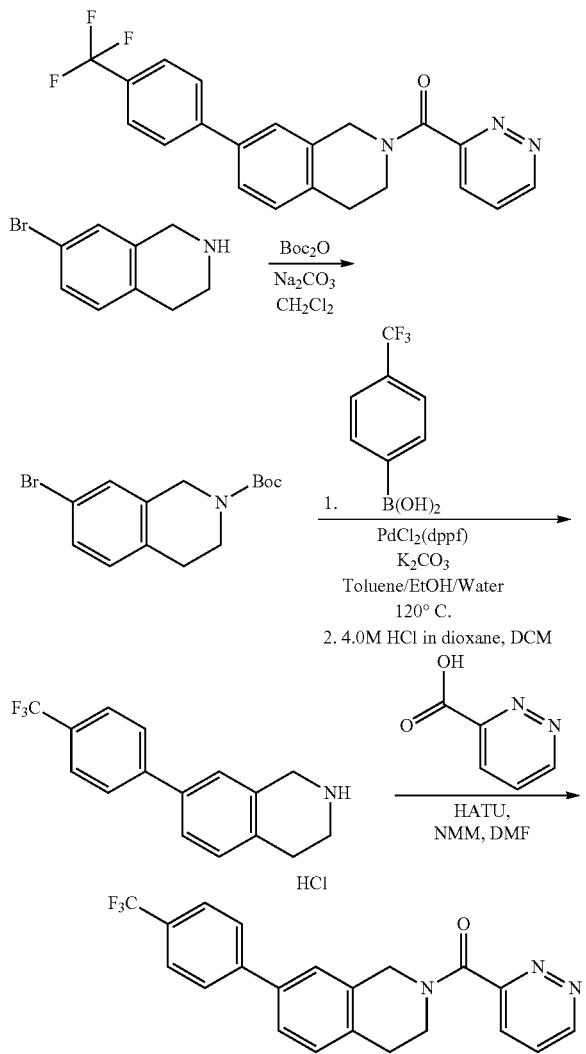

7-Bromo-3,4-dihydro-1H-isoquinoline-2-carboxylic acid test-butyl ester: To a solution of 7-bromo-1,2,3,4-tetrahydroisoquinoline hydrochloride (1.0 g, 4.0 mmol)) in DCM (18 mL) and 2M aqueous Na$_2$CO$_3$ solution (5.0 mL, 10.0 mmol) was added a solution of BOC-anhydride (1.0 g, 4.6 mmol) in DCM (7 mL). The reaction mixture was stirred at RT for 3 h and then diluted with water and DCM (1:1, 100 mL). The organic phase was then separated and washed with brine, dried (MgSO$_4$) and filtered. The solvent was evaporated and then carried to next step without purification.

tert-Butyl 7-(4-(trifluoromethyl)phenyl)-3,4-dihydroisoquinoline-2(1H)-carboxylate: A mixture 4-(trifluoromethyl) phenylboronic acid (987 mgs, 5.2 mmol), 7-Bromo-3,4-dihydro-1H-isoquinoline-2-carboxylic acid tert-butyl ester (1.2 g, 4.0 mmol), potassium carbonate (1.1 g, 8.0 mmol), PdCl$_2$(dppf) (146 mgs, 0.2 mmol) in toluene/ethanol/water (3 mL/1.5 mL/1.5 mL) was heated in pressure vessel at 120° C. for 2 h. The mixture was then concentrated and chromatographed (40 grams of SiO$_2$, 30% EtOAc/hexanes) to provide the title compound (1.4 g, 92% yield over two steps).

7-(4-(trifluoromethyl)phenyl)-1,2,3,4-tetrahydroisoquinoline hydrochloride: To a solution of tert-butyl 7-(4-(trifluoromethyl)phenyl)-3,4-dihydroisoquinoline-2(1H)-carboxylate (1.4 g, 3.7 mmol) in DCM (3 mL) was added 4.0M HCl in dioxane (4.6 mL, 18.56 mmol) and stirred at rt for 3 h. Diethyl ether (200 mL) was then added and the mixture was stirred at rt for 30 min and then filtered and washed with diethylether and dried to give the title compound (1.3 grains).

Pyridazin-3-yl(7-(4-(trifluoromethyl)phenyl)-3,4-dihydroisoquinolin-2(1H)-yl) methanone: To a suspension of 7-(4-(trifluoromethyl)phenyl)-1,2,3,4-tetrahydroisoquinoline hydrochloride (50 mgs, 0.16 mmol), pyridazine-3-carboxylic acid (30 mgs, 0.24 mmol), HATU (91 mgs, 0.24 mmol), in DMF (1.0 mL) was added NMM (0.05 mL, 0.48 mmol) and the resulting solution was stirred at 23° C. for 16 h. The reaction mixture was then diluted with water/acetonitrile (10:1) and the solid formed was then washed with water, diethylether and dried to give the title compound. MS found for C$_{21}$H$_{16}$F$_3$N$_3$O as (M+H)$^+$ 384.1 $^1$H NMR (400 MHz, dmso-d$_6$): mixture of rotomers (~1.5:1): major rotomer: δ 8.93 (m, 2H), 7.96-7.91 (m, 3H); 7.91-7.55 (m, 6H); 7.32 (m, 1H); 4.90 (s, 2H); 3.44-3.41 (m, 2H); 2.86-2.848 (m, 2H).

Example 204

(7-(2-fluoro-4-(trifluoromethyl)phenyl)-3,4-dihydroisoquinolin-2(1H)-yl)(pyrimidin-2-yl)methanone (Compound IX-22)

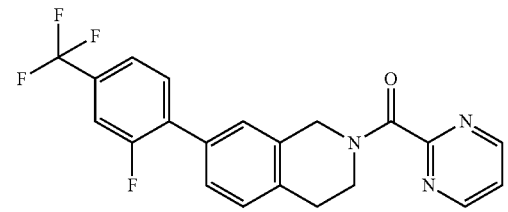 [SMILES: O=C(c1ncccn1)N1CCc2ccc(-c3ccc(C(F)(F)F)cc3F)cc2C1]

Similar procedure for the synthesis of Compound II-1 was followed to obtain the title compound using 2-fluoro-4-(trifluoromethyl)phenylboronic acid instead of 4-(trifluoromethyl)phenylboronic acid. MS found for C$_{21}$H$_{15}$F$_4$N$_3$O 402.1 (M+1).

Example 205

(7-(4-chloro-2-fluorophenyl)-3,4-dihydroisoquinolin-2(1H)-yl)(pyrimidin-2-yl)methanone (Compound IX-23)

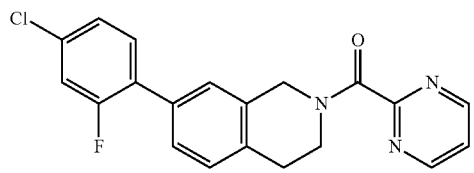 [SMILES: O=C(c1ncccn1)N1CCc2ccc(-c3ccc(Cl)cc3F)cc2C1]

Similar procedure for the synthesis of Compound II-1 was followed to obtain the title compound using 2-fluoro-4-

Chlorophenylboronic acid instead of 4-(trifluoromethyl)phenylboronic acid. MS found for $C_{20}H_{15}FN_3O$ 368.1 (M+1).

Example 206

(7-(4-chloro-3-fluorophenyl)-3,4-dihydroisoquinolin-2(1H)-yl)(pyrimidin-2-yl)methanone (Compound IX-24)

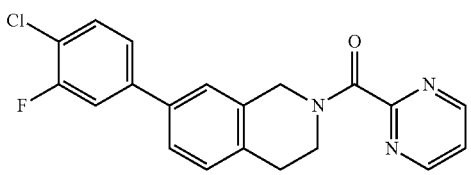 [SMILES: O=C(c1ncccn1)N1CCc2ccc(-c3ccc(Cl)c(F)c3)cc2C1]

Similar procedure for the synthesis of Compound II-1 was followed to obtain the title compound using 3-fluoro-4-Chlorophenylboronic acid instead of 4-(trifluoromethyl)phenylboronic acid. MS found for $C_{20}H_{15}FN_3O$ 368.1 (M+1).

Example 207

(3-fluoropyridin-2-yl)(7-(4-(trifluoromethyl)phenyl)-3,4-dihydroisoquinolin-2(1H)-yl)methanone (Compound IX-25)

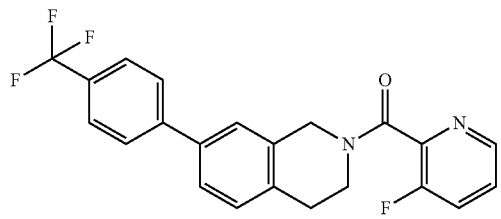 [SMILES: O=C(c1ncccc1F)N1CCc2ccc(-c3ccc(C(F)(F)F)cc3)cc2C1]

Compound IX-25 was prepared using the procedures disclosed herein above with the appropriate starting materials. Mass 401.1 (M+1).

Example 208

3-(pyridin-2-ylmethyl)-6-(4-(trifluoromethoxy)phenyl)-2H-benzo[e][1,3]thiazin-4(3H)-one (Compound X-1)

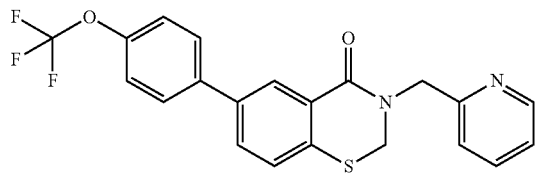 [SMILES: O=C1c2cc(-c3ccc(OC(F)(F)F)cc3)ccc2SCN1Cc1ccccn1]

Compound X-1 was prepared using the procedures disclosed herein above with the appropriate starting materials. $^1$H-NMR (CD$_3$OD) δ 8.52 (d, 1H, J=5.2 Hz), 8.30 (s, 1H), 7.81-7.85 (m, 1H), 7.75-7.77 (m, 3H), 7.53 (d, 1H, J=8.4 Hz), 7.48 (d, 1H, J=8.4 Hz), 7.32-7.38 (m, 3H), 4.99 (s, 2H), 4.89 (s, 2H); MS m/z 417.1 (M+H).

Example 209

3-(pyrimidin-2-ylmethyl)-6-(4-(trifluoromethoxy)phenyl)-2H-benzo[e][1,3]thiazin-4(3H)-one (Compound X-2)

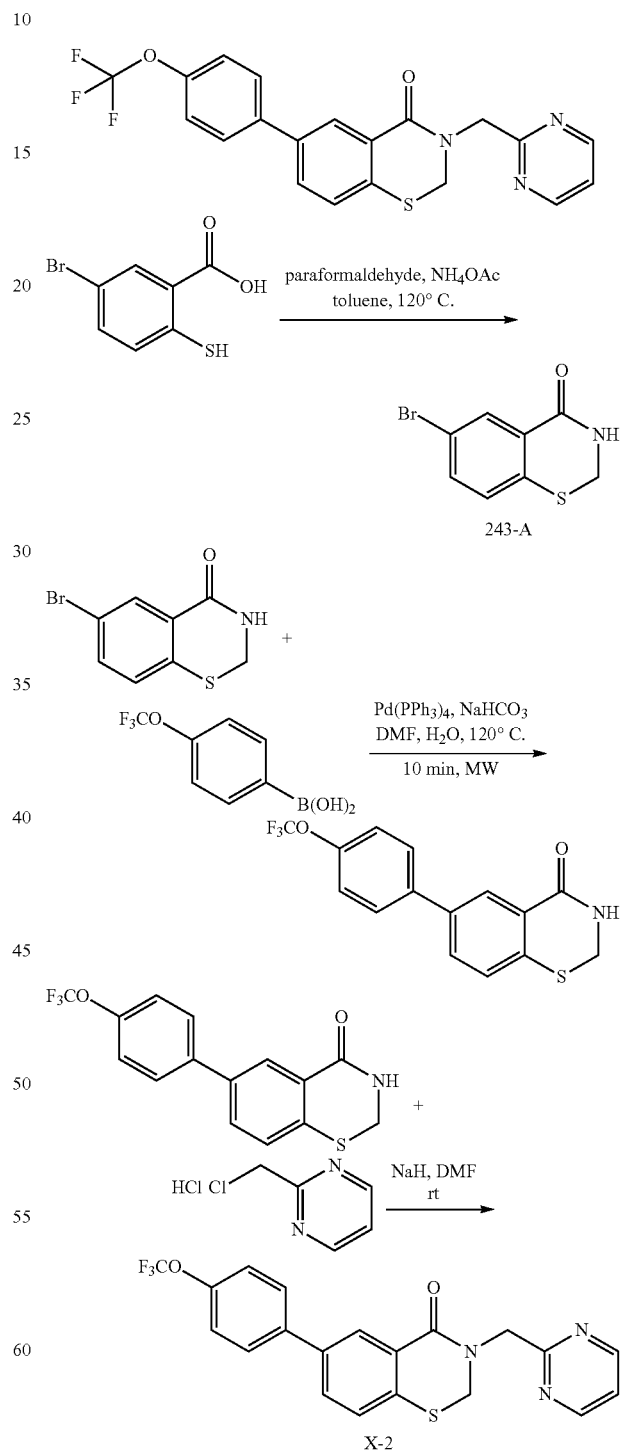

5-Bromo-2-mercaptobenzoic acid (466 mg, 2.0 mmol), paraformaldehyde (90 mg, 3.0 mmol) and ammonium acetate (308 mg, 4.0 mmol) were stirred in toluene (12 mL) at 120° C. overnight. The reaction mixture was concentrated and purified by HPLC to afford 243-A (181 mg).

Compound X-2 was prepared using the procedures disclosed above. $^1$H-NMR (CD$_3$OD) δ 8.76 (d, 2H, J=5.2 Hz), 8.27 (s, 1H), 7.74-7.76 (m, 3H), 7.49 (d, 1H, J=8.4 Hz), 7.35-7.39 (m, 3H), 5.11 (s, 2H), 5.00 (s, 2H); MS m/z. 418.1 (M+H).

Example 210

3-(pyridin-2-ylmethyl)-6-(4-(trifluoromethyl)phenyl)-2H-benzo[e][1,3]thiazin-4(3H)-one (Compound X-3)

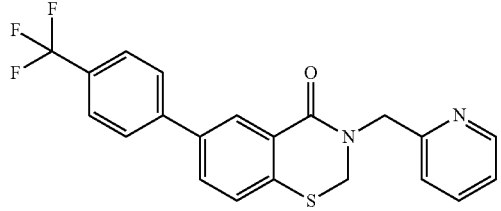 [SMILES: O=C1c2cc(-c3ccc(C(F)(F)F)cc3)ccc2SCN1Cc1ccccn1]

Compound X-3 was prepared using the procedures disclosed herein above with the appropriate starting materials. $^1$H-NMR (CD$_3$OD) δ 8.53 (d, 1H, J=5.2 Hz), 8.36 (s, 1H), 7.75-7.87 (m, 6H), 7.52 (t, 2H, J=7.8 Hz), 7.34 (t, 1H, J=6.4 Hz), 5.00 (s, 2H), 4.90 (s, 2H); MS m/z 401.0 (M+H).

Example 211

3-(pyrimidin-2-ylmethyl)-6-(4-(trifluoromethyl)phenyl)-2H-benzo[e][1,3]thiazin-4(3H)-one (Compound X-4)

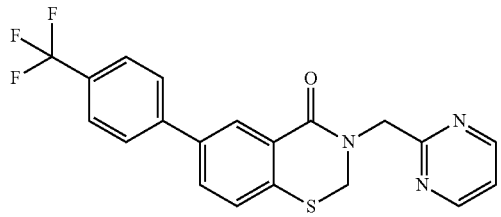 [SMILES: O=C1c2cc(-c3ccc(C(F)(F)F)cc3)ccc2SCN1Cc1ncccn1]

Compound X-4 was prepared using the procedures disclosed herein above with the appropriate starting materials. $^1$H-NMR (CD$_3$OD) δ 8.76 (d, 2H, J=7.6 Hz), 8.32 (s, 1H), 7.75-7.86 (m, 5H), 7.52 (d, 1H, J=8.0 Hz), 7.37-7.39 (m, 1H), 5.11 (s, 2H), 5.01 (s, 2H); MS m/z 402.1 (M+H).

Example 212

3-(2-chlorobenzyl)-6-(4-(trifluoromethyl)phenyl)-2H-benzo[e][1,3]thiazin-4(3H)-one (Compound X-5)

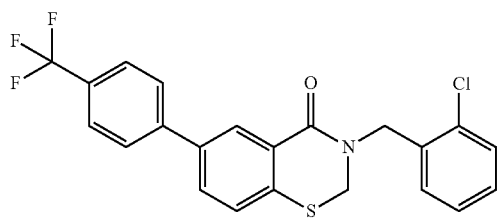 [SMILES: O=C1c2cc(-c3ccc(C(F)(F)F)cc3)ccc2SCN1Cc1ccccc1Cl]

Compound X-5 was prepared using the procedures disclosed herein above with the appropriate starting materials. $^1$H-NMR (CD$_3$OD) δ 8.37 (s, 1H), 7.87 (d, 2H, J=8.4 Hz), 7.76-7.81 (m, 3H), 7.50-7.56 (m, 2H), 7.45 (d, 1H, J=7.6 Hz), 7.30-7.40 (m, 2H), 5.00 (s, 2H), 4.85 (s, 2H); MS m/z 434.0 (M+H).

Example 213

3-((3-fluoropyridin-2-yl)methyl)-6-(4-(trifluoromethyl)phenyl)-2H-benzo[e][1,3]thiazin-4(3H)-one (Compound X-6)

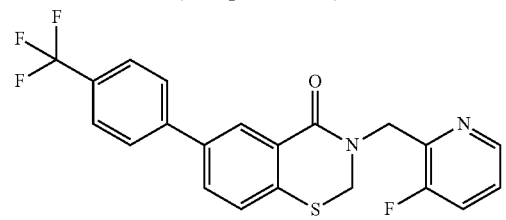

Compound X-6 was prepared using the procedures disclosed herein above with the appropriate starting materials. $^1$H-NMR (CD$_3$OD) δ 8.36 (d, 1H, J=4.4 Hz), 8.33 (s, 1H), 7.85 (d, 2H, J=8.0 Hz), 7.75-7.80 (m, 3H), 7.58-7.63 (m, 1H), 7.50 (d, 1H, J=8.4 Hz), 7.39-7.41 (m, 1H), 5.10 (s, 2H), 4.94 (s, 2H); MS m/z 419.0 (M+H).

Example 214

3-((3-fluoropyridin-2-yl)methyl)-6-(4-(trifluoromethoxy)phenyl)-2H-benzo[e][1,3]thiazin-4(3H)-one (Compound X-9)

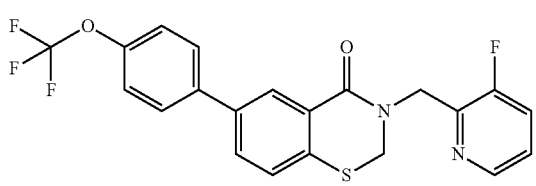 [SMILES: O=C1c2cc(-c3ccc(OC(F)(F)F)cc3)ccc2SCN1Cc1ncccc1F]

Compound X-9 was prepared using the procedures disclosed herein above with the appropriate starting materials. $^1$H-NMR (CD$_3$OD) δ 8.36 (d, 1H, J=4.4 Hz), 8.27 (s, 1H), 7.73-7.76 (m, 3H), 7.58-7.63 (m, 1H), 7.47 (d, 1H, J=8.0 Hz), 7.35-7.42 (m, 3H), 5.09 (s, 2H), 4.93 (s, 2H); MS m/z 435.1 (M+H).

Example 215

6-(2-fluoro-4-(trifluoromethyl)phenyl)-3-(pyrimidin-2-ylmethyl)-2H-benzo[e][1,3]oxazin-4(3H)-one (Compound VIII-18)

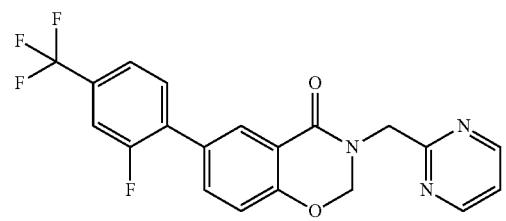 [SMILES: O=C1c2cc(-c3ccc(C(F)(F)F)cc3F)ccc2OCN1Cc1ncccn1]

Compound VIII-18 was prepared using the procedures disclosed herein above with the appropriate starting materials. $^1$H-NMR (CD$_3$OD) δ 8.76 (d, 2H, J=4.8 Hz), 8.10 (s, 1H), 7.80 (d, 1H, J=8.4 Hz), 7.73 (t, 1H, J=7.6 Hz), 7.55-7.61 (m, 2H), 7.37-7.39 (m, 1H), 7.21 (d, 1H, J=8.8 Hz), 5.61 (s, 2H), 5.04 (s, 2H); MS m/z 404.0 (M+H).

Example 216

3-(pyrimidin-2-ylmethyl)-6-(4-(trifluoromethyl)phenyl)-2H-benzo[e][1,3]oxazin-4(3H)-one (Compound VIII-19)

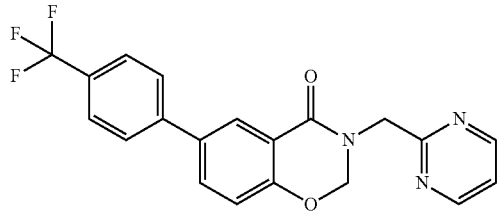 [SMILES: O=C1c2cc(-c3ccc(C(F)(F)F)cc3)ccc2OCN1Cc1ncccn1]

Compound VIII-19 was prepared using the procedures disclosed herein above with the appropriate starting materials. $^1$H-NMR (CD$_3$OD) δ 8.76 (d, 2H, J=4.4 Hz), 8.18 (d, 1H, J=2.4 Hz), 7.89 (dd, 1H, J=8.6, 2.2 Hz), 7.83 (d, 2H, J=8.4 Hz), 7.74 (d, 2H, J=8.4 Hz), 7.38 (t, 1H, J=4.8 Hz), 7.20 (d, 1H, J=8.8 Hz), 5.60 (s, 2H), 5.04 (s, 2H); MS m/z 386.0 (M+H).

Example 217

3-(pyrimidin-2-ylmethyl)-6-(4-(trifluoromethoxy)phenyl)-2H-benzo[e][1,3]oxazin-4(3H)-one (Compound VIII-20)

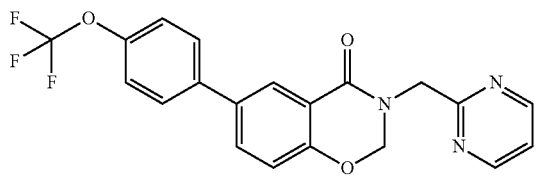 [SMILES: O=C1c2cc(-c3ccc(OC(F)(F)F)cc3)ccc2OCN1Cc1ncccn1]

Compound VIII-20 was prepared using the procedures disclosed herein above with the appropriate starting materials. $^1$H-NMR (CD$_3$OD) δ 8.76 (d, 2H, J=4.8 Hz), 8.12 (d, 1H, J=2.4 Hz), 7.83 (dd, 1H, J=8.6, 2.2 Hz), 7.72 (d, 2H, J=8.4 Hz), 7.35-7.39 (m, 3H), 7.17 (d, 1H, J=8.4 Hz), 5.58 (s, 2H), 5.04 (s, 2H); MS m/z 402.0 (M+H).

Example 218

3-benzyl-6-(4-(trifluoromethyl)phenyl)-2H-benzo[e][1,3]oxazin-4(3H)-one (Compound VIII-21)

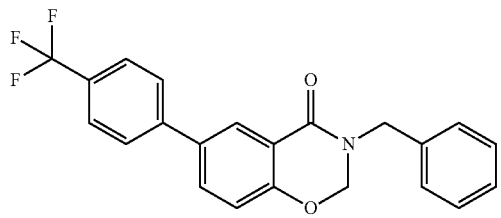 [SMILES: O=C1c2cc(-c3ccc(C(F)(F)F)cc3)ccc2OCN1Cc1ccccc1]

Compound VIII-21 was prepared using the procedures disclosed herein above with the appropriate starting materials. $^1$H-NMR (CD$_3$OD) δ 8.23 (d, 1H, J=2.4 Hz), 7.87 (dd, 1H, J=8.6, 2.2 Hz), 7.83 (d, 2H, J=8.4 Hz), 7.75 (d, 2H, J=8.0 Hz), 7.29-7.39 (m, 5H), 7.15 (d, 1H, J=8.8 Hz), 5.29 (s, 2H), 4.80 (s, 2H); MS m/z 384.0 (M+H).

Example 219

3-benzyl-6-(2-fluoro-4-(trifluoromethyl)phenyl)-2H-benzo[e][1,3]oxazin-4(3H)-one (Compound VIII-22)

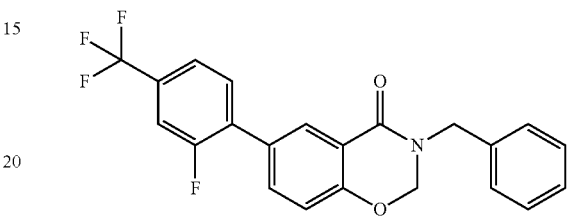

Compound VIII-22 was prepared using the procedures disclosed herein above with the appropriate starting materials. $^1$H-NMR (CD$_3$OD) δ 8.15 (s 1H), 7.72-7.78 (m, 2H), 7.56-7.61 (m, 2H), 7.30-7.38 (m, 5H), 7.136 (d, 1H, J=8.8 Hz), 5.30 (s, 2H), 4.80 (s, 2H); MS m/z 402.0 (M+H).

Example 220

3-benzyl-6-(4-(trifluoromethoxy)phenyl)-2H-benzo[e][1,3]oxazin-4(3H)-one (Compound VIII-23)

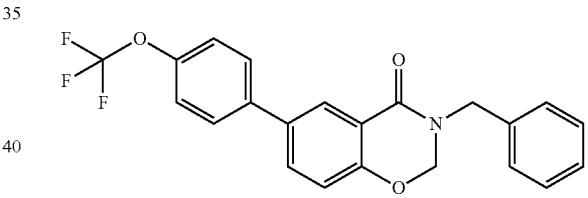

Compound VIII-23 was prepared using the procedures disclosed herein above with the appropriate starting materials. $^1$H-NMR (CD$_3$OD) δ 8.17 (d, 1H, J=2.4 Hz), 7.81 (dd, 1H, J=8.4, 2.4 Hz), 7.73 (d, 2H, J=8.4 Hz), 7.30-7.38 (m, 7H), 7.13 (d, 1H, J=8.4 Hz), 5.28 (s, 2H), 4.80 (s, 2H); MS m/z 400.0 (M+H).

Example 221

N-benzyl-7-(4-(trifluoromethyl)phenyl)-3,4-dihydroisoquinoline-2(1H)-carboxamide (Compound IX-41)

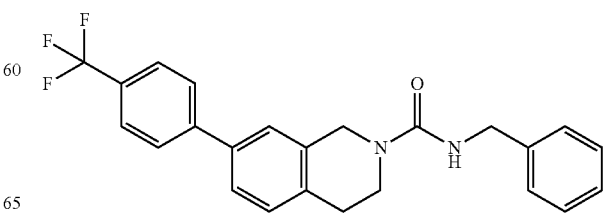

Compound IX-41 was prepared using the procedures disclosed herein above with the appropriate starting materials. MS m/z: 411 (MH⁺).

Example 222

N-phenyl-7-(4-(trifluoromethyl)phenyl)-3,4-dihydroisoquinoline-2(1H)-carboxamide (Compound IX-42)

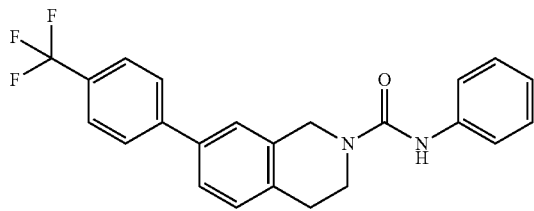 [SMILES: O=C(Nc1ccccc1)N1CCc2ccc(-c3ccc(C(F)(F)F)cc3)cc2C1]

Compound IX-42 was prepared using the procedures disclosed herein above with the appropriate starting materials. MS m/z: 397 (MH⁺).

Example 223

N-cyclopropyl-7-(4-(trifluoromethyl)phenyl)-3,4-dihydroisoquinoline-2(1H)-carboxamide (Compound IX-44)

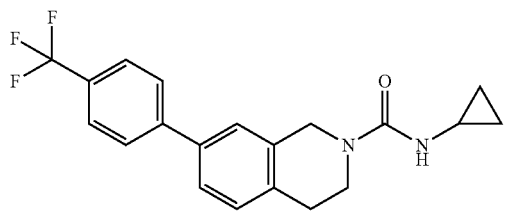 [SMILES: O=C(NC1CC1)N1CCc2ccc(-c3ccc(C(F)(F)F)cc3)cc2C1]

Compound IX-44 was prepared using the procedures disclosed herein above with the appropriate starting materials. MS m/z: 361 (MH⁺).

Example 224

N-(furan-2-ylmethyl)-7-(4-(trifluoromethyl)phenyl)-3,4-dihydroisoquinoline-2(1H)-carboxamide (Compound IX-48)

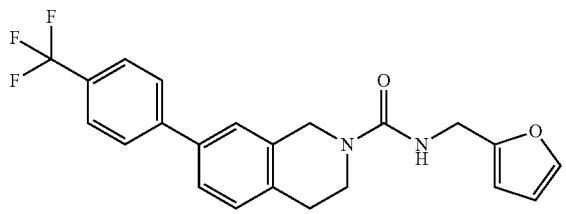 [SMILES: O=C(NCc1ccco1)N1CCc2ccc(-c3ccc(C(F)(F)F)cc3)cc2C1]

Compound IX-48 was prepared using the procedures disclosed herein above with the appropriate starting materials. MS m/z: 401 (MH⁺). ¹H NMR (DMSO-d₆): δ 7.87 (d, J=8 Hz, 2H), δ 7.80 (d, J=8.4 Hz, 2H), δ 7.57-7.51 (m, 2H), δ 7.50 (s, 1H), δ 7.50 (s, 1H), δ 7.29 (d, J=7.6 Hz, 1H), δ 7.09 (t, J=5.6 Hz, 1H), δ 6.36 (s, 1H), δ 6.18 (d, J=2.4 Hz, 1H), δ 4.60 (s, 2H), δ 4.26 (d, J=5.6 Hz, 2H), δ 3.60 (t, J=5.8 Hz, 2H), δ 2.82 (t, J=5.8 Hz, 2H).

Example 225

N-cyclopentyl-7-(4-(trifluoromethyl)phenyl)-3,4-dihydroisoquinoline-2(1H)-carboxamide (Compound IX-77)

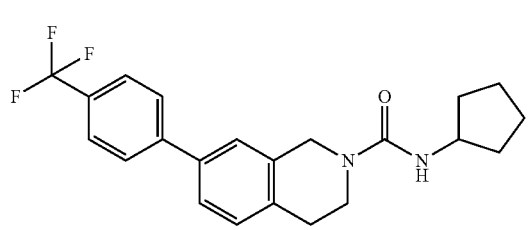 [SMILES: O=C(NC1CCCC1)N1CCc2ccc(-c3ccc(C(F)(F)F)cc3)cc2C1]

Compound IX-77 was prepared using the procedures disclosed herein above with the appropriate starting materials. MS m/z: 389 (MH⁺).

Example 226

N-methyl-N-phenyl-7-(4-(trifluoromethyl)phenyl)-3,4-dihydroisoquinoline-2(1H)-carboxamide (Compound IX-50)

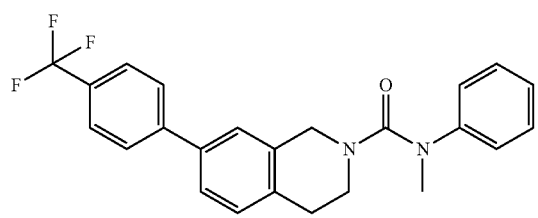 [SMILES: CN(C(=O)N1CCc2ccc(-c3ccc(C(F)(F)F)cc3)cc2C1)c1ccccc1]

Compound IX-50 was prepared using the procedures disclosed herein above with the appropriate starting materials. MS m/z: 411 (MH⁺).

Example 227 morpholino(7-(4-(trifluoromethyl)phenyl)-3,4-dihydroisoquinolin-2(1H)-yl)methanone (Compound IX-52)

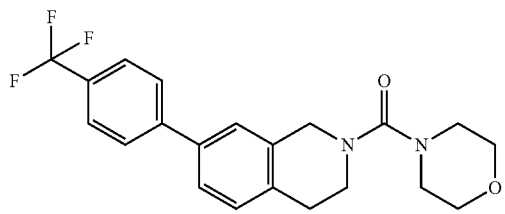 [SMILES: O=C(N1CCOCC1)N1CCc2ccc(-c3ccc(C(F)(F)F)cc3)cc2C1]

Compound IX-52 was prepared using the procedures disclosed herein above with the appropriate starting materials. MS m/z: 391 (MH⁺).

Example 228 pyrrolidin-1-yl(7-(4-(trifluoromethyl)phenyl)-3,4-dihydroisoquinolin-2(1H)-yl)methanone (Compound IX-53)

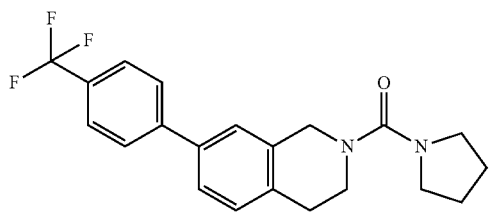 [SMILES: O=C(N1CCCC1)N1CCc2ccc(-c3ccc(C(F)(F)F)cc3)cc2C1]

Compound IX-53 was prepared using the procedures disclosed herein above with the appropriate starting materials. MS m/z: 375 (MH⁺). ¹H NMR (DMSO-d₆): δ 7.87 (d, J=8 Hz, 2H), δ 7.80 (d, J=8.4 Hz, 2H), δ 7.56 (s, 1H), δ 7.53 (d, J=7.6 Hz, 1H), δ 7.29 (d, J=7.6 Hz, 1H), δ 4.45 (s, 2H), δ 3.46 (t, J=5.6 Hz, 2H), δ 4.10-4.05 (m, 4H), δ 2.87 (t, J=5.6 Hz, 2H), δ 1.81-1.73 (m, 4H).

Example 229 azetidin-1-yl(7-(4-(trifluoromethyl)phenyl)-3,4-dihydroisoquinolin-2(1H)-yl)methanone (Compound IX-88)

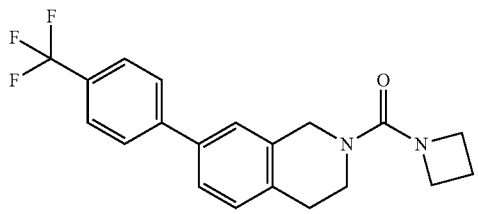 [SMILES: O=C(N1CCC1)N1CCc2ccc(-c3ccc(C(F)(F)F)cc3)cc2C1]

Compound IX-88 was prepared using the procedures disclosed herein above with the appropriate starting materials. MS m/z: 361 (MH⁺).

Example 230

N-(pyrimidin-2-ylmethyl)-7-(4-(trifluoromethyl)phenyl)-3,4-dihydroisoquinoline-2(1H)-carboxamide (Compound IX-89)

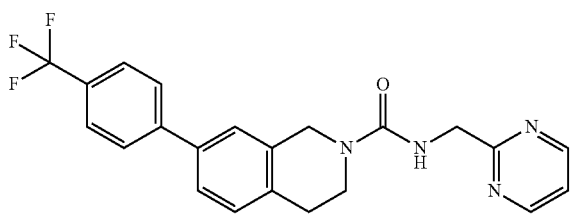 [SMILES: O=C(NCc1ncccn1)N1CCc2ccc(-c3ccc(C(F)(F)F)cc3)cc2C1]

Compound IX-89 was prepared using the procedures disclosed herein above with the appropriate starting materials. MS m/z: 413 (MH⁺). ¹H NMR (DMSO-d₆): δ 8.74 (d, J=4.8 Hz, 2H), δ 7.88 (d, J=8 Hz, 2H), δ 7.80 (d, J=8.0 Hz, 2H), δ 7.55 (d, J=8.4 Hz, 1H), δ 7.52 (s, 1H), δ 7.36 (t, J=4.8 Hz, 1H), δ 7.31 (d, J=8.0 Hz, 1H), δ 7.18 (t, J=5.4 Hz, 1H), δ 4.63 (s, 2H), δ 4.45 (d, J=5.6 Hz, 2H), δ 3.65 (t, J=5.8 Hz, 2H), δ 2.87 (t, J=5.6 Hz, 2H).

Example 231

(3-methylpyrrolidin-1-yl)(7-(4-(trifluoromethyl)phenyl)-3,4-dihydroisoquinolin-2(1H)-yl)methanone (Compound IX-90)

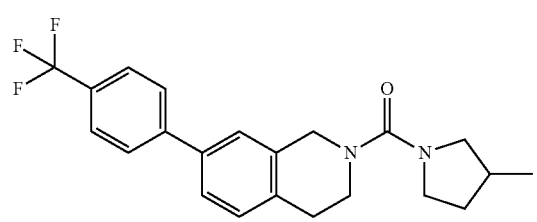 [SMILES: CC1CCN(C(=O)N2CCc3ccc(-c4ccc(C(F)(F)F)cc4)cc3C2)C1]

Compound IX-90 was prepared using the procedures disclosed herein above with the appropriate starting materials. MS m/z: 389 (MH⁺).

Example 232

(3-hydroxypyrrolidin-1-yl)(7-(4-(trifluoromethyl)phenyl)-3,4-dihydroisoquinolin-2(1H)-yl)methanoneo (Compound IX-91)

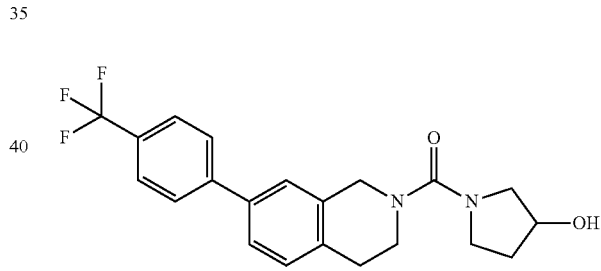

Compound IX-91 was prepared using the procedures disclosed herein above with the appropriate starting materials. MS m/z: 391 (MH⁺).

Example 233

(3,3-difluoroazetidin-1-yl)(7-(4-(trifluoromethyl)phenyl)-3,4-dihydroisoquinolin-2(1H)-yl)methanone (Compound IX-92)

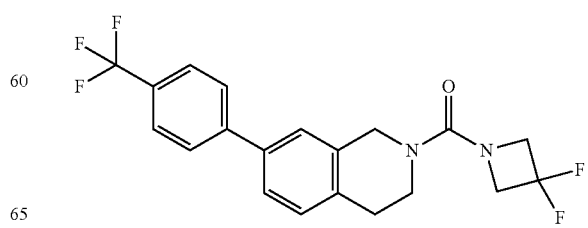

Compound IX-92 was prepared using the procedures disclosed herein above with the appropriate starting materials. MS m/z: 397 (MH+).

Example 234

(3-fluoropyrrolidin-1-yl)(7-(4-(trifluoromethyl)phenyl)-3,4-dihydroisoquinolin-2(1H)-yl)methanone (Compound IX-94)

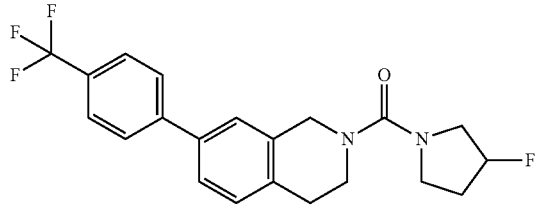 [SMILES: O=C(N1CCc2ccc(-c3ccc(C(F)(F)F)cc3)cc2C1)N1CCC(F)C1]

Compound IX-94 was prepared using the procedures disclosed herein above with the appropriate starting materials. MS m/z: 393 (MH+). $^1$H NMR (DMSO-d$_6$): δ 7.88 (d, J=8 Hz, 2H), δ 7.80 (d, J=8.0 Hz, 2H), δ 7.58 (s, 1H), δ 7.54 (d, J=7.2 Hz, 1H), δ 7.29 (d, J=8.0 Hz, 1H), δ 5.31 (d, J=52.8 Hz, 1H), δ 4.48 (s, 2H), δ 3.78-3.29 (m, 6H), δ 3.00-2.90 (m, 1H), δ 2.81 (dt, J=16.4 Hz, F=5.0 Hz, 1H), δ 2.17-1.88 (m, 2H).

Example 235

(3-fluoroazetidin-1-yl)(7-(4-(trifluoromethyl)phenyl)-3,4-dihydroisoquinolin-2(1H)-yl)methanone (Compound IX-95)

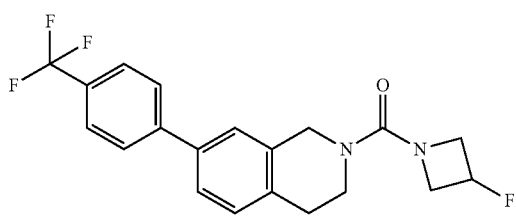

Compound IX-95 was prepared using the procedures disclosed herein above with the appropriate starting materials. MS m/z: 379 (MH+).

Example 236

(S)-(2-(hydroxymethyl)pyrrolidin-1-yl)(7-(4-(trifluoromethyl)phenyl)-3,4-dihydroisoquinolin-2(1H)-yl)methanone (Compound IX-102)

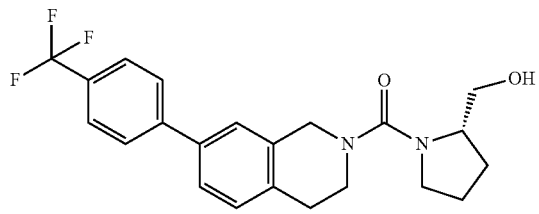 [SMILES: O=C(N1CCc2ccc(-c3ccc(C(F)(F)F)cc3)cc2C1)N1CCC[C@H]1CO]

Compound IX-102 was prepared using the procedures disclosed herein above with the appropriate starting materials. MS m/z: 405 (MH+).

Example 237

(3-(methylsulfonyl)azetidin-1-yl)(7-(4-(trifluoromethyl)phenyl)-3,4-dihydroisoquinolin-2(1H)-yl)methanone (Compound IX-104)

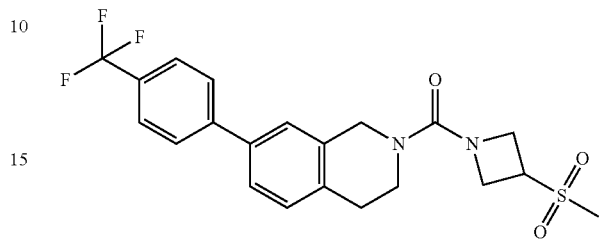

Compound IX-104 was prepared using the procedures disclosed herein above with the appropriate starting materials. MS m/z: 439 (MH+).

Example 238

(2R,5R)-2,5-dimethylpyrrolidin-1-yl)(7-(4-(trifluoromethyl)phenyl)-3,4-dihydroisoquinolin-2(1H)-yl) methanone (Compound IX-105

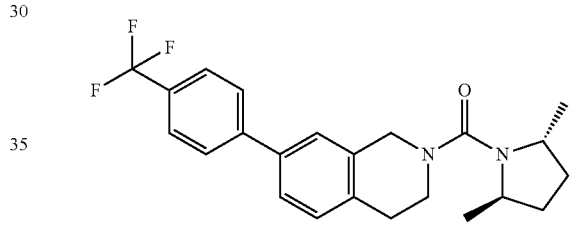

Compound IX-105 was prepared using the procedures disclosed herein above with the appropriate starting materials. MS m/z: 403 (MH+). $^1$H NMR (DMSO-d$_6$): δ 7.88 (d, J=8.4 Hz, 2H), δ 7.80 (d, J=8.0 Hz, 2H), δ 7.59 (s, 1H), δ 7.54 (d, J=7.2 Hz, 1H), δ 7.29 (d, J=8.0 Hz, 1H), δ 4.50 (d, J=16.4 Hz, 1H), δ 4.43 (d, J=16.4 Hz, 1H), δ 3.99-3.90 (m, 2H), δ 3.68 (dt, J=13.2 Hz, F=4.8 Hz, 1H), δ 3.35-3.25 (m, 1H), δ 2.98-2.88 (m, 1H), δ 2.77 (dt, J=16.8 Hz, F=4.8 Hz, 1H), δ 2.14-2.03 (m, 2H), δ 1.47-1.37 (m, 2H), δ 1.01 (d, J=6.0 Hz, 6H).

Example 239

(2R,5S)-2,5-dimethylpyrrolidin-1-yl)(7-(4-(trifluoromethyl)phenyl)-3,4-dihydroisoquinolin-2(1H)-yl) methanone (Compound IX-106

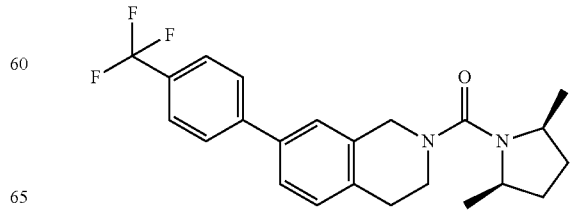

Compound IX-106 was prepared using the procedures disclosed herein above with the appropriate starting materials. MS m/z: 403 (MH+).

Example 240

(3-methylazetidin-1-yl)(7-(4-(trifluoromethyl)phenyl)-3,4-dihydroisoquinolin-2(1H)-yl)methanone (Compound IX-107)

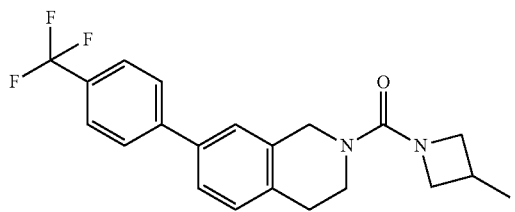 [SMILES: CC1CN(C(=O)N2CCc3ccc(-c4ccc(C(F)(F)F)cc4)cc3C2)C1]

Compound IX-107 was prepared using the procedures disclosed herein above with the appropriate starting materials. MS m/z: 375 (MH+).

Example 241

(3-hydroxyazetidin-1-yl)(7-(4-(trifluoromethyl)phenyl)-3,4-dihydroisoquinolin-2(1H)-yl)methanone (Compound IX-108)

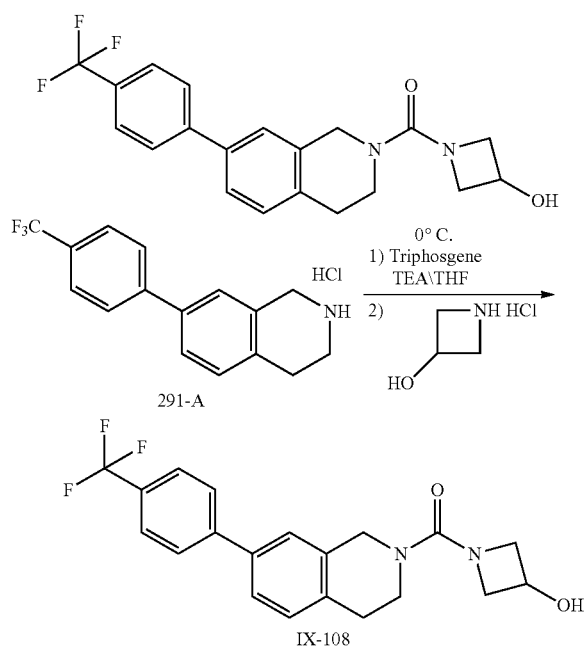

Compound 291-A (0.050 g, 0.16 mmol), Triethylamine (0.15 mL, 1.08 mmol) were dissolved in THF (1 mL). Triphosgene (0.052 g, 0.18 mmol) in THF (1 mL) was added at 0° C. with stirring in the protection of nitrogen. The resulting mixture was stirred at room temperature for several hours. Azetidin-3-ol hydrochloride (0.021 g, 0.19 mmol) and Triethylamine (0.15 mL) were added. The resulting mixture was stirred overnight, concentrated and purified by preparative HPLC to afford Compound IX-108 (0.021 g, 35%).

¹H NMR (DMSO-d₆): δ 7.88 (d, J=8.4 Hz, 2H), δ 7.80 (d, J=8.4 Hz, 2H), δ 7.59 (s, 1H), δ 7.54 (d, J=7.6 Hz, 1H), δ 7.29 (d, J=8.0 Hz, 1H), δ 5.58 (d, J=6.4 Hz, 1H), δ 4.49 (s, 2H), δ 4.46-4.36 (m, 1H), δ 4.12 (t, J=7.8 Hz, 2H), δ 3.71 (q, J=4.5 Hz, 2H), δ 3.48 (t, J=5.8 Hz, 2H),), δ 2.82 (t, J=5.8 Hz, 2H). MS m/z: 377 (MH+).

Example 242

(3-hydroxy-3-methylazetidin-1-yl)(7-(4-(trifluoromethyl)phenyl)-3,4-dihydroisoquinolin-2(1H)-yl)methanone (Compound IX-112)

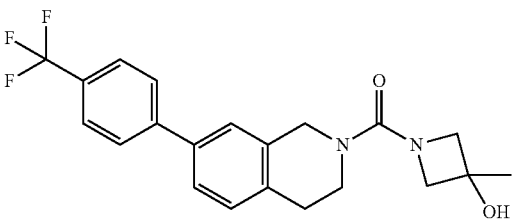 [SMILES: CC1(O)CN(C(=O)N2CCc3ccc(-c4ccc(C(F)(F)F)cc4)cc3C2)C1]

Compound IX-112 was prepared using the procedures disclosed herein above with the appropriate starting materials. MS m/z: 391 (MH+).

Example 243

(3-(hydroxymethyl)azetidin-1-yl)(7-(4-(trifluoromethyl)phenyl)-3,4-dihydroisoquinolin-2(1H)-yl)methanone (Compound IX-113)

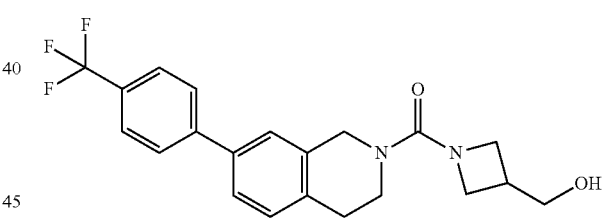

Compound IX-113 was prepared using the procedures disclosed herein above with the appropriate starting materials. MS m/z: 391 (MH+).

Example 244 pyrrolidin-1-yl(7-(4-(trifluoromethoxy)phenyl)-3,4-dihydroisoquinolin-2(1H)-yl)methanone (Compound IX-122)

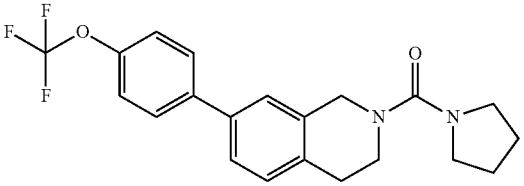 [SMILES: O=C(N1CCCC1)N1CCc2ccc(-c3ccc(OC(F)(F)F)cc3)cc2C1]

Compound IX-122 was prepared using the procedures disclosed herein above with the appropriate starting materials. MS m/z: 391 (MH+). ¹H NMR (DMSO-d₆): δ 7.77 (d, J=8.8 Hz, 2H), δ 7.49 (s, 1H), δ 7.47 (d, J=7.6 Hz, 1H), δ 7.43 (d, J=8.4 Hz, 2H), δ 7.24 (d, J=8.0 Hz, 1H), δ 4.43 (s, 2H), δ 3.46 (t, J=5.8 Hz, 2H), δ 3.37-3.28 (m, 4H), δ 2.85 (t, J=5.6 Hz, 2H), δ 1.81-1.73 (m, 4H).

Example 245

N-(pyrimidin-2-ylmethyl)-7-(4-(trifluoromethoxy)phenyl)-3,4-dihydroisoquinoline-2(1H)-carboxamide (Compound IX-123)

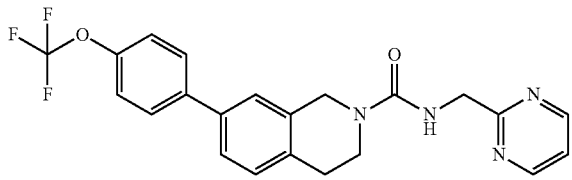 [SMILES: O=C(NCc1ncccn1)N1CCc2ccc(-c3ccc(OC(F)(F)F)cc3)cc2C1]

Compound IX-123 was prepared using the procedures disclosed herein above with the appropriate starting materials. MS m/z: 429 (MH+).

The following compounds were prepared using the procedures disclosed herein above using the appropriate starting materials.

3-(2-(4-fluorophenoxy)ethyl)-6-(4-(trifluoromethoxy)phenyl)benzo[d][1,2,3]triazin-4(3H)-one (Compound II-19)

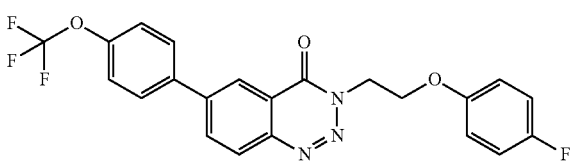 [SMILES: O=c1c2cc(-c3ccc(OC(F)(F)F)cc3)ccc2nnn1CCOc1ccc(F)cc1]

3-cyclopropyl-6-(4-(trifluoromethoxy)phenyl)benzo[d][1,2,3]triazin-4(3H)-one (Compound II-22)

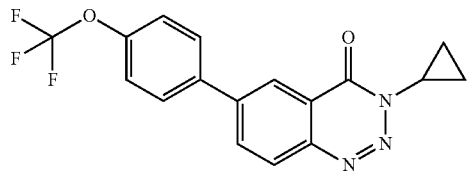 [SMILES: O=c1c2cc(-c3ccc(OC(F)(F)F)cc3)ccc2nnn1C1CC1]

3-(2-(pyrimidin-2-yloxy)ethyl)-6-(4-(trifluoromethoxy)phenyl)benzo[d][1,2,3]triazin-4(3H)-one (Compound II-32)

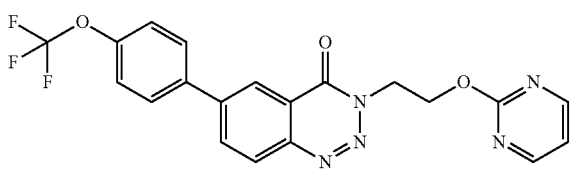 [SMILES: O=c1c2cc(-c3ccc(OC(F)(F)F)cc3)ccc2nnn1CCOc1ncccn1]

2-(2-(4-oxo-6-(4-(trifluoromethoxy)phenyl)benzo[d][1,2,3]triazin-3(4H)-yl)ethoxy)pyrimidine-4-carbonitrile (Compound II-36)

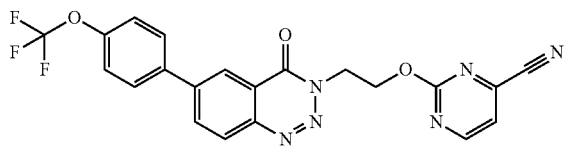 [SMILES: N#Cc1ccnc(OCCn2nnc3ccc(-c4ccc(OC(F)(F)F)cc4)cc3c2=O)n1]

tert-butyl 4-(4-oxo-6-(4-(trifluoromethoxy)phenyl)benzo[d][1,2,3]triazin-3(4H)-yl)piperidine-1-carboxylate (Compound II-37)

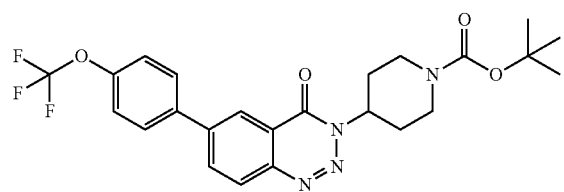 [SMILES: CC(C)(C)OC(=O)N1CCC(n2nnc3ccc(-c4ccc(OC(F)(F)F)cc4)cc3c2=O)CC1]

3-(piperidin-4-yl)-6-(4-(trifluoromethoxy)phenyl)benzo[d][1,2,3]triazin-4(3H)-one (Compound II-38)

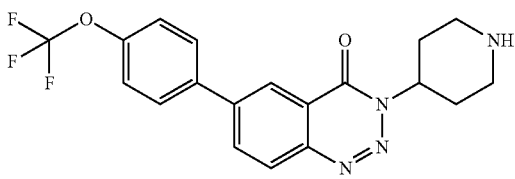 [SMILES: O=c1c2cc(-c3ccc(OC(F)(F)F)cc3)ccc2nnn1C1CCNCC1]

3-(1-(pyrimidin-2-yl)piperidin-4-yl)-6-(4-(trifluoromethoxy)phenyl)benzo[d][1,2,3]triazin-4(3H)-one (Compound II-39)

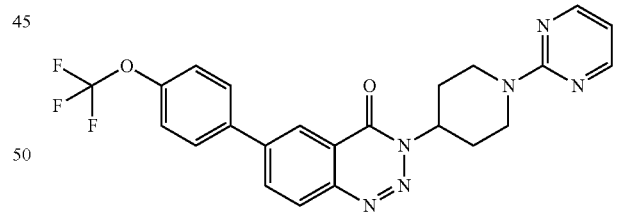

3-(2-methoxyethyl)-6-(4-(trifluoromethoxy)phenyl)benzo[d][1,2,3]triazin-4(3H)-one (Compound II-43)

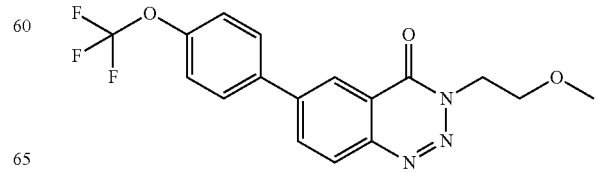

3-(2-hydroxyethyl)-6-(4-(trifluoromethoxy)phenyl) benzo[d][1,2,3]triazin-4(3H)-one (Compound II-46)

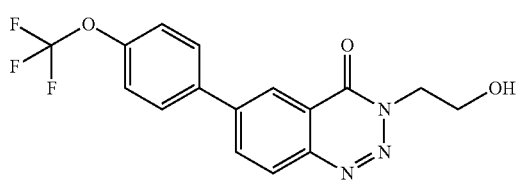 [SMILES: O=c1c2cc(-c3ccc(OC(F)(F)F)cc3)ccc2nnn1CCO]

N-cyclopropyl-2-(4-oxo-6-(4-(trifluoromethoxy) phenyl)benzo[d][1,2,3]triazin-3(4H)-yl)acetamide (Compound II-49)

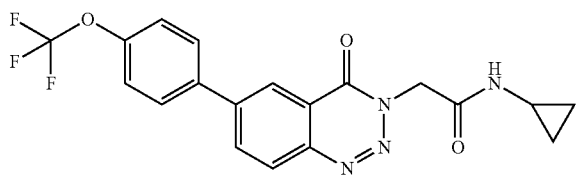 [SMILES: O=C(Cn1nnc2ccc(-c3ccc(OC(F)(F)F)cc3)cc2c1=O)NC1CC1]

2-(2-(4-oxo-6-(4-(trifluoromethoxy)phenyl)benzo[d] [1,2,3]triazin-3(4H)-yl)ethoxy)pyrimidine-5-carbonitrile (Compound II-51)

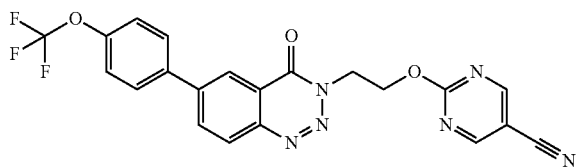 [SMILES: N#Cc1cnc(OCCn2nnc3ccc(-c4ccc(OC(F)(F)F)cc4)cc3c2=O)nc1]

3-((1-(phenoxymethyl)cyclopropyl)methyl)-6-(4-(trifluoromethoxy)phenyl)benzo[d][1,2,3]triazin-4 (3H)-one (Compound II-61)

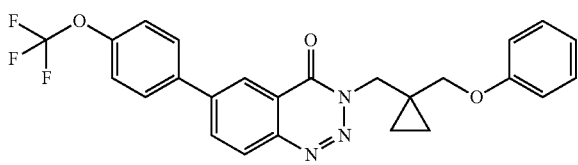 [SMILES: O=c1c2cc(-c3ccc(OC(F)(F)F)cc3)ccc2nnn1CC1(COc2ccccc2)CC1]

3-(2-(4-(2H-tetrazol-5-yl)pyrimidin-2-yloxy)ethyl)-6-(4-(trifluoromethoxy)phenyl)benzo[d][1,2,3]triazin-4(3H)-one (Compound II-69)

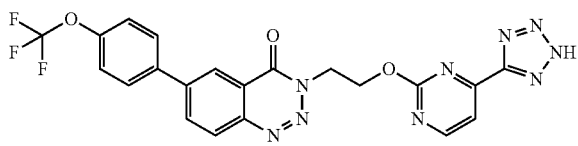 [SMILES: O=c1c2cc(-c3ccc(OC(F)(F)F)cc3)ccc2nnn1CCOc1nccc(-c2nn[nH]n2)n1]

3-(1-(2,2,2-trifluoroethyl)piperidin-4-yl)-6-(4-(trifluoromethoxy)phenyl)benzo[d][1,2,3]triazin-4(3H)-one (Compound II-71)

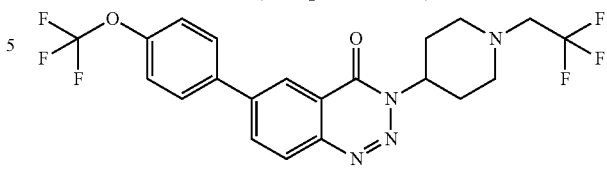

ethyl 4-oxo-3-(4-oxo-6-(4-(trifluoromethoxy)phenyl)benzo[d][1,2,3]triazin-3(4H)-yl)piperidine-1-carboxylate (Compound II-72)

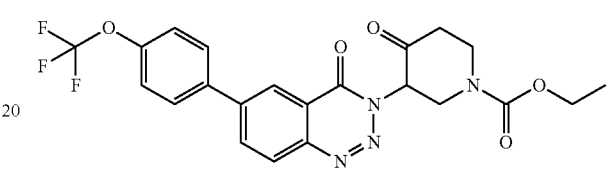

6-(4-cyclopropylphenyl)-3-((3-methyl-1,2,4-oxadiazol-5-yl)methyl)benzo[d][1,2,3]triazin-4(3H)-one (Compound II-73)

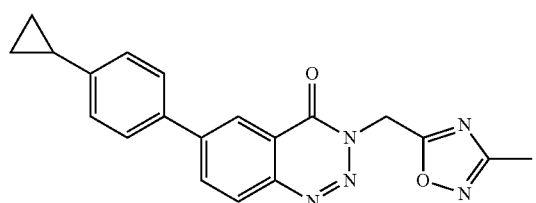

(S)-tert-butyl 3-(4-oxo-6-(4-(trifluoromethoxy)phenyl)benzo[d][1,2,3]triazin-3(4H)-yl)pyrrolidine-1-carboxylate (Compound II-74)

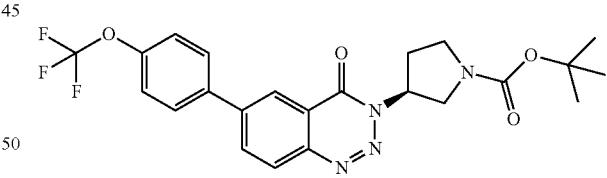

(R)-3-(pyrrolidin-3-yl)-6-(4-(trifluoromethoxy)phenyl)benzo[d][1,2,3]triazin-4(3H)-one (Compound II-76)

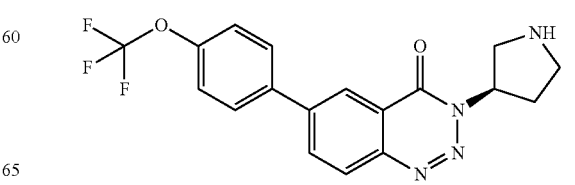

241

(S)-3-(pyrrolidin-3-yl)-6-(4-(trifluoromethoxy)phenyl)benzo[d][1,2,3]triazin-4(3H)-one (Compound II-77)

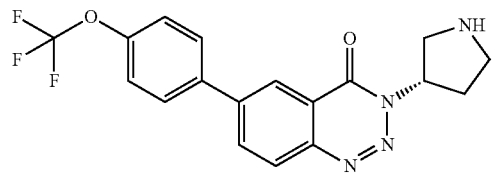 [SMILES: O=c1c2cc(-c3ccc(OC(F)(F)F)cc3)ccc2nnn1[C@H]1CCNC1]

(S)-3-(1-(2,2,2-trifluoroethyl)pyrrolidin-3-yl)-6-(4-(trifluoromethoxy)phenyl)benzo[d][1,2,3]triazin-4(3H)-one (Compound II-81)

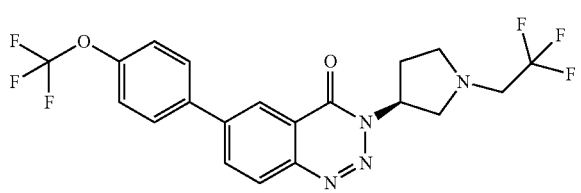 [SMILES: O=c1c2cc(-c3ccc(OC(F)(F)F)cc3)ccc2nnn1[C@H]1CCN(CC(F)(F)F)C1]

(R)-3-(1-(2,2,2-trifluoroethyl)pyrrolidin-3-yl)-6-(4-(trifluoromethoxy)phenyl)benzo[d][1,2,3]triazin-4(3H)-one (Compound II-82)

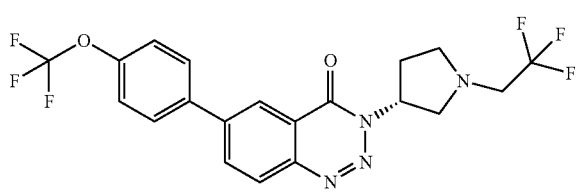 [SMILES: O=c1c2cc(-c3ccc(OC(F)(F)F)cc3)ccc2nnn1[C@@H]1CCN(CC(F)(F)F)C1]

2-((1-((4-oxo-6-(4-(trifluoromethoxy)phenyl)benzo[d][1,2,3]triazin-3(4H)-yl)methyl)cyclopropyl)methoxy)pyrimidine-4-carboxamide (Compound II-94)

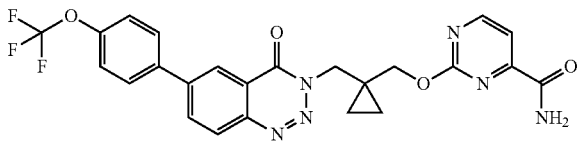 [SMILES: NC(=O)c1ccnc(OCC2(Cn3nnc4ccc(-c5ccc(OC(F)(F)F)cc5)cc4c3=O)CC2)n1]

6-(3-chloro-4-fluorophenyl)quinazolin-4(3H)-one (Compound IV-1)

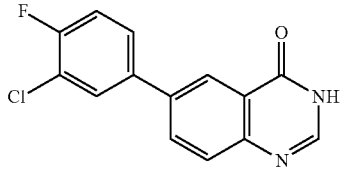 [SMILES: O=c1[nH]cnc2ccc(-c3ccc(F)c(Cl)c3)cc12]

242

6-(3'-chloro-4',6-difluorobiphenyl-3-yl)quinazolin-4(3H)-one (Compound IV-2)

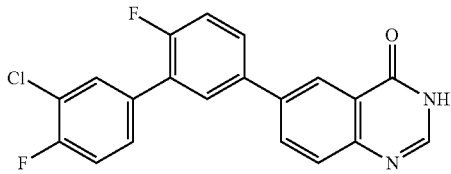 [SMILES: O=c1[nH]cnc2ccc(-c3ccc(F)c(-c4ccc(F)c(Cl)c4)c3)cc12]

3-((4-methyl-1,2,5-oxadiazol-3-yl)methyl)-6-(4-(trifluoromethoxy)phenyl)quinazolin-4(3H)-one (Compound IV-3)

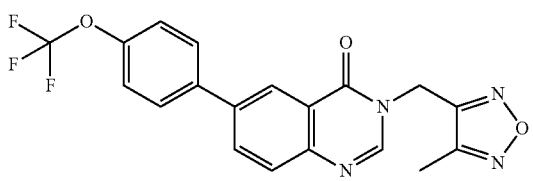 [SMILES: Cc1nonc1Cn1cnc2ccc(-c3ccc(OC(F)(F)F)cc3)cc2c1=O]

3-((4-methyl-1,2,5-oxadiazol-3-yl)methyl)-6-(3-(trifluoromethoxy)phenyl)quinazolin-4(3H)-one (Compound IV-4)

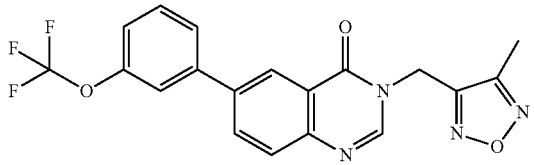 [SMILES: Cc1nonc1Cn1cnc2ccc(-c3cccc(OC(F)(F)F)c3)cc2c1=O]

2-methyl-3-((3-methyl-1,2,4-oxadiazol-5-yl)methyl)-6-(4-(trifluoromethoxy)phenyl)quinazolin-4(3H)-one (Compound IV-5)

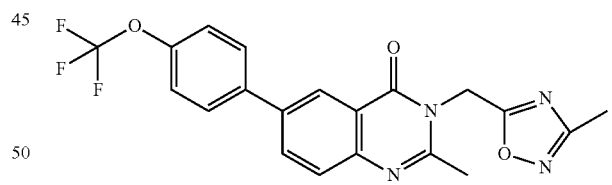

3-((3-methyl-1,2,4-oxadiazol-5-yl)methyl)-6-(4-(trifluoromethoxy)phenyl)quinazolin-4(3H)-one (Compound IV-6)

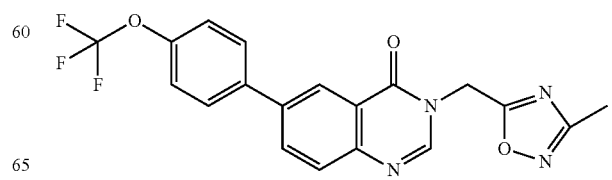

243

6-(4-(trifluoromethoxy)phenyl)quinazolin-4(3H)-one (Compound IV-7)

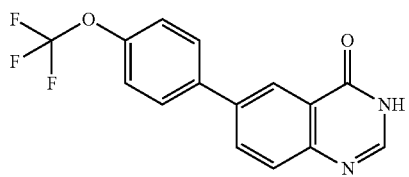 [SMILES: O=c1[nH]cnc2ccc(-c3ccc(OC(F)(F)F)cc3)cc12]

3-(2-hydroxy-3-(2-methoxyphenoxy)propyl)-6-(4-(trifluoromethoxy)phenyl)quinazolin-4(3H)-one (Compound IV-8)

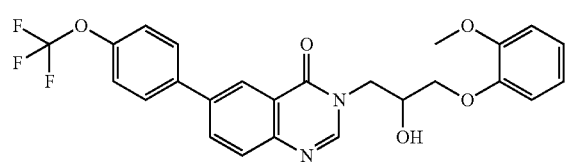 [SMILES: COc1ccccc1OCC(O)Cn1cnc2ccc(-c3ccc(OC(F)(F)F)cc3)cc2c1=O]

3-((5-methyl-1,2,4-oxadiazol-3-yl)methyl)-6-(4-(trifluoromethoxy)phenyl)quinazolin-4(3H)-one (Compound IV-9)

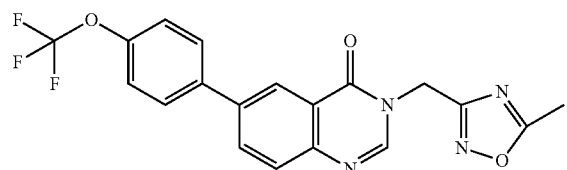

6-(4-(trifluoromethoxy)phenyl)-3-((5-(3-(trifluoromethyl)phenyl)-1,2,4-oxadiazol-3-yl)methyl)quinazolin-4(3H)-one (Compound IV-10)

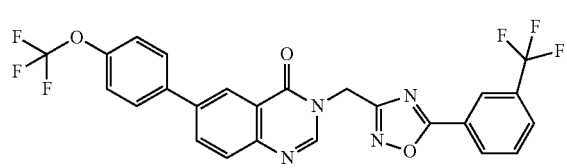 [SMILES: O=c1c2cc(-c3ccc(OC(F)(F)F)cc3)ccc2ncn1Cc1noc(-c2cccc(C(F)(F)F)c2)n1]

4-methyl-6-(4-(trifluoromethoxy)phenyl)phthalazin-1(2H)-one (Compound VI-1)

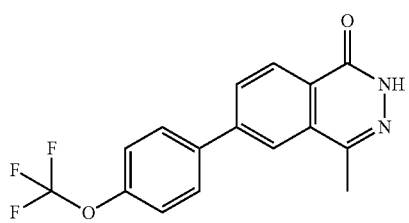 [SMILES: Cc1n[nH]c(=O)c2ccc(-c3ccc(OC(F)(F)F)cc3)cc12]

244

2-(2-(1H-pyrazol-1-yl)ethyl)-4-methyl-6-(4-(trifluoromethoxy)phenyl)phthalazin-1(2H)-one (Compound VI-2)

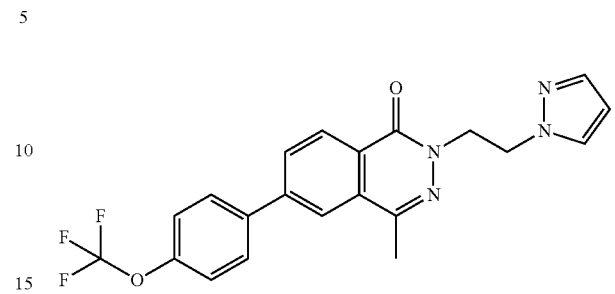

3-(2-(pyrimidin-2-yloxy)ethyl)-6-((4-(trifluoromethoxy)phenyl)ethynyl)benzo[d][1,2,3]triazin-4(3H)-one (Compound VII-1)

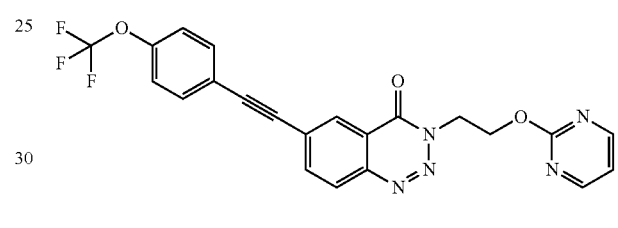

(7-(4-(trifluoromethyl)phenyl)-3,4-dihydroisoquinolin-2(1H)-yl)(1,3,5-trimethyl-1H-pyrazol-4-yl)methanone (Compound IX-26)

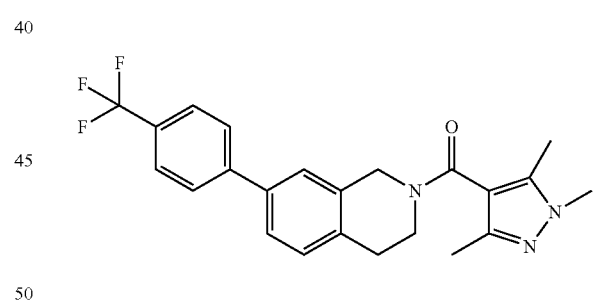

(3-(pyridin-3-yloxy)azetidin-1-yl)(7-(4-(trifluoromethyl)phenyl)-3,4-dihydroisoquinolin-2(1H)-yl)methanone (Compound IX-93)

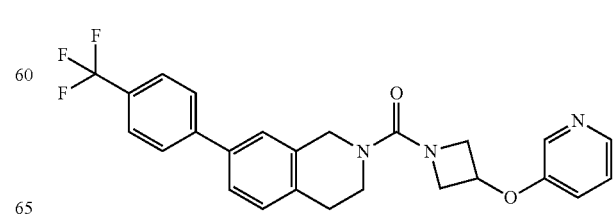

(R)-(3-(hydroxymethyl)pyrrolidin-1-yl)(7-(4-(trifluoromethyl)phenyl)-3,4-dihydroisoquinolin-2(1H)-yl)methanone (Compound IX-101)

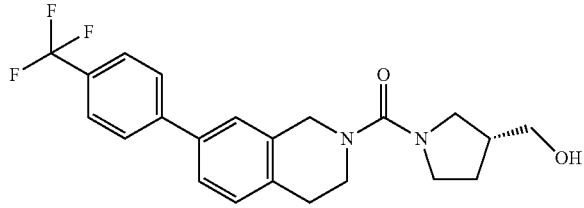 [SMILES: O=C(N1CCc2ccc(-c3ccc(C(F)(F)F)cc3)cc2C1)N1CC[C@@H](CO)C1]

Example 246

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

Example 247

A tablet Formula Is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Example 248

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Example 249

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Example 250

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 251

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Example 252

A subcutaneous formulation may be prepared as follows:

| Ingredient | Quantity |
| --- | --- |
| Active Ingredient | 5.0 mg |
| Corn Oil | 1.0 mL |

Example 253

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

Example 254

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Example 255

Sustained Release Composition

| Ingredient | Weight Range % |
| --- | --- |
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

The sustained release formulations of this disclosure are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols). The resulting tablets may be coated with an optional film-forming agent, for identification, taste-masking purposes and to improve ease of swallowing. The film forming agent will typically be present in an amount ranging from about 1% to 10%, or from about 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Example 256

Activity testing is conducted in the Examples below using methods described herein and those well known in the art.
Sodium Current Screening Assays:

The late sodium current (Late INa) and peak sodium current (Peak INa) assays are performed on an automated electrophysiology platform, QPatch 16× (Sophion Bioscience, Copenhagen, Denmark), which uses the whole cell patch clamp technique to measure currents through the cell membrane of up to 16 cells at a time. The assay uses an HEK293 (human embryonic kidney) cell line heterologously expressing the wild-type human cardiac sodium channel, hNa$_v$1.5, purchased from Millipore (Billerica, Mass.). No beta subunits were coexpressed with the Na channel alpha subunit. Cells are maintained with standard tissue culture procedures and stable channel expression is maintained with 400 µg/mL Geneticin in the culture medium. Cells isolated for use on QPatch are incubated for 5 minutes in Detachin 1× (Genlantis, San Diego, USA) at 37° C. to ensure that 80-90% of the cells are single and not part of a cell cluster. Experiments are carried out at 23-25° C.

For both the Late INa and Peak INa assays, series resistance compensation is set to 100% and series resistance and whole-cell compensation are performed automatically. Currents are digitized at 25 kHz and low-pass filtered at 12 kHz and 10 kHz for the late and peak INa assays, respectively. Currents through open sodium channels are automatically recorded and stored in the Sophion Bioscience Oracle database (Sophion Bioscience, Copenhagen, Denmark).

Analysis is performed using QPatch Assay and database software and data are compiled in Excel.

Compound stocks are routinely made by the Gilead Sample Bank in plastic vials to 10 mM in dimethyl sulfoxide (DMSO). In some cases, when compounds are not soluble in DMSO, they are made in 100% ethanol. Stocks are sonicated as necessary. The extracellular solution for screening Late INa is composed of: 140 mM NaCl, 4 mM KCl, 1.8 mM $CaCl_2$, 0.75 mM $MgCl_2$ and 5 mM HEPES with pH adjusted to 7.4 using NaOH. The intracellular solution used to perfuse the inside of the cells for both the Late INa and Peak INa assays contains: 120 mM CsF, 20 mM CsCl, 5 mM EGTA, 5 mM HEPES and pH adjusted to 7.4 with CsOH. Compounds are diluted in extracellular solution to 1 µM in glass vials and then transferred to glass well plates before robotic addition to the cells. The 0Na extracellular solution used at the end of each experiment for the Late INa and Peak INa assays to measure baseline current contains: 140 mM N-methyl-D-glucamine; 4 mM KCl; 1.8 mM $CaCl_2$; 0.75 mM $MgCl_2$; 5 mM HEPES and pH was adjusted to 7.4 with HCl.

Late INa Screening Assay:

For the Late INa assay, sodium channels are activated every 10 seconds (0.1 Hz) by depolarizing the cell membrane to −20 mV for 250 milliseconds (ms) from a holding potential of −120 mV. In response to a −20 mV voltage step, typical $hNa_v1.5$ sodium currents activate rapidly to a peak negative current and then inactivate nearly completely within 3-4 ms.

All compounds were tested to determine their activity in blocking the late sodium current. Late INa was generated by adding 10 µM Tefluthrin (pyrethroid) to the extracellular solution while recording Na currents. To confirm the block of late $I_{Na}$ observed using the automated screening method, a second late $I_{Na}$ enhancer (ATX-II) and the manual patch clamp method were used. ATX-II and tefluthrin occupy distinct, non-overlapping binding sites and modify $Na^+$ channel function differently to increase late $I_{Na}$. All compounds tested to date have been found to inhibit the enhanced late $I_{Na}$ caused by either late $I_{Na}$ enhancer. For the purposes of the screening, late INa is defined as the mean current between 225 ms and 250 ms after stepping to −20 mV to activate Na channels. After establishing the whole cell recording configuration, late INa activator is added to each well 4 times over a 16-17 minute period so that the late component of the Na current reaches a stable value. Compounds were then added (typically at 1 µM), in the presence of late INa activator, with 3 additions over the course of 7 or 8 minutes. Measurements were made at the end of exposure to the third compound addition and values were normalized to the current level when all $Na^+$ was removed from the extracellular solution after two additions of 0Na-ECF. Results are reported as percent block of late INa. When tested in the assay disclosed above with 10 µM Tefluthrin activating late INa, Compound II-3 of Example 10 inhibited (or reduced) the late sodium current by 53% (see table 1 for additional compound data).

Peak INa Screening Assay:

Compounds were also evaluated for their effect in several other assays, including their effect on Peak INa. Good separation between the concentrations of test compound to reduce late and peak $I_{Na}$ is beneficial to enable separation of the desired effect to reduce late $I_{Na}$ induced electrical and mechanical dysfunction from the undesired effect to reduce peak $I_{Na}$, which can lead to slowing or block of conduction of electrical excitation in the heart. It is contemplated that the compounds of Formula I avoid significant block of peak INa. Since the peak INa in the cells used herein can be very large, introducing artifacts in the recording, the concentration of $Na^+$ in the bath can be reduced to 20 mM and a nonpermeant cation added to compensate for the $Na^+$ that was removed to maintain the osmolarity and ionic strength of the solution (see solution details below). Analysis of peak INa generally requires correction for rundown before determining the % block of peak current by the tested compound.

A separate Peak INa screening assay was developed to allow assessment of the effect of compounds on peak INa at both low and high stimulation frequencies in order to identify compounds that are highly selective for block of late INa but do not block peak INa. A low stimulation frequency of 0.1 Hz was used to determine the effect of the test compound when the channel spent most of the time in the resting (closed) state and provides information about Tonic Block (TB). A higher stimulation frequency (3 Hz) was used to measure block of the channel when it spent more time in the activated and inactivated states and provided a measure of Use-Dependent Block (UDB). Use-dependent block refers to the accumulation of block with increased frequency of channel activation. Block of cardiac peak $I_{Na}$ by compounds of this invention is increased with an increase in the frequency of stimulation from 0.1 to 1-5 Hz (frequencies encountered either in the normal heart or during tachycardia). It is therefore expected that reduction of peak $I_{Na}$ by compounds of this invention will be greater at high heart rates, such as those during tachyarrhythmias, than at normal heart rates. As a consequence, compounds of this invention may reduce $Na^+$ and $Ca^{2+}$ overload due to late INa and abnormal electrical activity and electrical conduction in myocardium that is arrhythmic, especially during ischemia.

The −100 mV holding potential and the 3 Hz stimulation frequency were chosen so that the benchmark compound would have a small but detectable effect under experimental conditions, allowing for direct comparison of new compounds with the benchmark. The extracellular solution for screening Peak INa is composed of: 20 mM NaCl, 120 mM N-methyl-D glucamine, 4 mM KCl, 1.8 mM $CaCl_2$, 0.75 mM $MgCl_2$ and 5 mM HEPES with pH adjusted to 7.4 using HCl. The intracellular solution used for the Peak INa assay is the same as outlined for the Late INa assay (see above).

For the peak INa assay, $Na^+$ channels were activated by depolarizing the cell membrane to 0 mV for 20 ms from a holding potential of −100 mV. After establishing the whole cell recording configuration, channels were stimulated to open with low frequency stimulation (0.1 Hz) for 7 minutes so that the recording can be monitored and the extent to which the recording has stabilized can be assessed. After this stabilization period the stimulation frequency was increased to 3 Hz for 2 minutes and then returned to 0.1 Hz. Since 3 Hz stimulation causes a small decrease in the peak current even in the absence of compound, this internal control was used for each cell, when no compound is present, to correct the results from 3 Hz stimulation when compound is present. Following 3 Hz stimulation under control conditions, the cell is allowed to recover for 200 seconds before compound is added. The test compound tested at 1 or 3 µM (depending on the % block of late INa at 1 µM) was added 3 times at 60 second intervals, while stimulating the channels to open at 0.1 Hz to monitor the progression of TB. After the third compound addition, a 320 second wait period was imposed to allow for equilibration before the second period of 3 Hz stimulation begins. TB was measured before the second period of 3 Hz stimulation. Both TB and UDB were analyzed by incorporating rundown correction for the peak INa and UDB was calculated by compensating for the small use-dependent effect of the stimulation protocol on peak INa in the absence of compound. Compound II-3 of Example 10 exhibited peak INa TB of 19% and UDB of 10%, both measured at 1 This demonstrates the selectivity of Compound II-3 to block late INa compared to peak INa and suggests that Compound II-3 should show minimal to no effects on conduction through the heart (which is driven by peak INa) at concentrations that effectively block late INa (see table 1 for additional compound data).

hERG Screening Assay:

Compounds were also tested for their effect to block the hERG K$^+$ channel. At least a 3-5-fold separation, preferably 10 fold separation, of IC$_{50}$ values for compounds to inhibit late I$_{Na}$ (more potent) and hERG (less potent) indicates that a compound is unlikely to cause QT prolongation and/or proarrhythmic effects at concentrations needed to reduce late I$_{Na}$.

Compounds were screened to test their activity in blocking the hERG potassium channel at AVIVA Biosciences (San Diego, Calif., USA). The hERG channel is heterologously expressed in a CHO (Chinese Hamster Ovary) cell line. Cells were maintained with standard tissue culture procedures and stable channel expression was maintained with 500 µg/mL G418 in the culture medium. Cells were harvested for testing on the PatchXpress 7000A automated patch clamp with Accumax (Innovative Cell Technologies, San Diego, Calif.) to isolate single cells.

The following solutions were used for electrophysiological recordings. The external solution contained: 2 mM CaCl$_2$; 2 mM MgCl$_2$; 4 mM KCl; 150 mM NaCl; 10 mM Glucose; 10 mM HEPES (pH 7.4 with 1M NaOH; osmolarity, ~310 mOsm). The internal solution contained: 140 mM KCl, 10 mM MgCl$_2$, 6 mM EGTA, 5 mM HEPES, 5 mM ATP (pH adjusted to 7.25 with KOH; osmolarity, ~295 mOsm).

hERG channels were activated when the voltage was first stepped to −50 mV for 300 ms from the −80 mV holding potential and then stepped to +20 mV for 5 seconds. At +20 mV the channels open and then largely inactivate, so the currents are relatively small. Upon returning to −50 mV from +20 mV, hERG currents transiently become much larger as inactivation is rapidly removed and then the channel closes. The first step to −50 mV for 300 ms was used as a baseline for measuring the peak amplitude during the step to −50 mV after channel activation. The peak tail current at −50 mV was measured both under control conditions and after addition of compound, each cell serving as its own control.

All compounds were prepared as 10 mM DMSO stocks in glass vials. Stock solutions were mixed by vigorous vortexing and sonication for about 2 minutes at room temperature. For testing, compounds were diluted in glass vials using an intermediate dilution step in pure DMSO and then further diluted to working concentrations in external solution. Dilutions were prepared no longer than 20 minutes before use.

For the electrophysiological recordings, after achieving the whole-cell configuration, cells were monitored for 90 seconds to assess stability and washed with external solution for 66 seconds. The voltage protocol described above was then applied to the cells every 12 seconds and throughout the whole procedure. Only cells with stable recording parameters and meeting specified health criteria were allowed to enter the compound addition procedure.

External solution containing 0.1% DMSO (vehicle) was applied to the cells first to establish the control peak current amplitude. After allowing the current to stabilize for 3 to 5 minutes, 1 µM and then 10 µM test compounds were applied. Each compound concentration was added 4 times and cells were kept in test solution until the effect of the compound reached steady state or for a maximum of 12 minutes. After addition of test compound, a positive control (1 µM Cisapride) was added and must block >95% of the current for the experiment to be considered valid. Washout in the external solution compartment was performed until the recovery of the current reached steady state. Data were analyzed using DataXpress software and its associated SQL server database, Clampfit (Molecular Devices, Inc., Sunnyvale) and Origin 7 (Originlab Corp.) When tested in the assay disclosed above, Compound II-3 of Example 10 inhibited (or reduced) the activity of the hERG potassium channel by 15.5% at 1 µM and 24.5% at 10 µM (see table 2 for additional compound data).

The compounds were tested using the above described assay methods. Data are obtained by testing the listed compounds at 1 µM concentration in the late and peak INa assays (and other concentrations as needed) and at 1 µM and 10 µM for the hERG channel assay.

Microsomal Stability Assay

The micorsomal stability assay is generally performed as follows.

Format: 15 compounds (and 1 control—verapamil) in 3 different species in duplicate sets General Conditions:

Substrate: 3 uM

Protein concentration: 0.5 mg/mL (for dog, rat, and human liver microsomes)

Cofactor: 1× NADPH-Regenerating system

Time-points: 2, 12, 25, 45, and 65 minutes

Reaction composition (in each incubation well):

---

5 uL compound (150 uM stock solution, 25:75 DMSO:H2O)
25 uL NRS solution
6.25 uL 20 mg/mL liver microsomes
213.75 uL 100 mM KPO4, pH 7.4

250 uL total volume

---

TECAN program: Microsomal_Stability; Microsome_S9_Standard

Sample preparation: 25 uL at each timepoint is added to plate with 225 uL quenching solution (50% MeOH, 25% ACN, 25% H2O, and 50 nM test compound). After plates are vortexed, centrifuge for 30 minutes.

"Ideal" numbers to use for setup:

Compound plate: take 6 uL of 10 mM stock in DMSO and dilute with 394 uL 25:75 DMSO:H2O to make a 150 uM stock solution. Use tall plate and add an additional 300 uL 25:75 DMSO:H2O to the third column for the standard-making program. Shake well before use. Place this plate in "coolstack 1".

Fill the water jug in the back of TECAN and then turn on TECAN and associated cooling systems. Run through the "Flush" maintenance program and let system initialize. Standard plate: Fill 1 trough with buffer and place in trough 3, 1 trough with 70% MeoH and place in trough 2, 1 trough with Quench and place in trough 1. Label one tall plate as "Standards" and place in position 1. Place "compound plate" in position 2. Run the "Microsome_S9_Standards" program.

After the standard program is complete, label 5 tall plates for each of the 5 time-points and place them in the correct positions on the TECAN countertop. Fill the 3 "Quench" troughs 90% full with the quenching solution (located in the fridge across from TECAN) and place it in positions 1, 2, and 3. Run the "Microsomal_Stability" program through the quenching portion (steps 1-52).

While the quenching filling portion of the program is running, prepare microsomes and cofactor.

Microsomal solutions: take 400 uL of 20 mg/mL microsomes and add to 13,680 uL 100 mM KPO4 buffer. Using an 8-channel, add 650 uL of this solution to the designated two columns on a short plate. The order should be dog microsomes in columns 1 and 2, rat microsomes in columns 3 and 4, and human microsomes in columns 5 and 6. Keep on ice before use. Place this plate in incubator 1 on the TECAN countertop.

Cofactor solution: mix 3000 uL Solution A, 600 uL Solution B, and 2400 uL 100 mM KPO4 buffer in 15 mL tube/10 mL glass vial and pour solution into the "Cofactor" trough and put in position 3.

Remove the quenching troughs and place the cofactor trough in "position 3". Also fill up another trough with the 70:30 MeOH:H2O wash mixture and place in "position 2". Place the original compound plate in "coolstack 1". Place a 96-well Costar assay block on the TeShake. Once everything is setup correctly, submit the remaining portions of the Microsomal_Stability script (steps 53-312).

The assay results suggests that the compounds tested showed activity as modulators of late sodium current, for example by inhibiting (or reducing) the late sodium current. Data are shown in Table 1 below for those compounds that inhibit Late INa by at least 15% at the 1 μM concentration.

TABLE 1

Late $I_{Na}$ Assay results

| No. | Late $I_{Na}$ 1 μM | Peak TB 1 μM | Peak UDB 1 μM | MS Rat THalf | MS Dog THalf | MS Human THalf |
| --- | --- | --- | --- | --- | --- | --- |
| II-3 | 53 | 19 | 10 | 249 | 303 | 336 |
| II-4 | 41 | 9 | 4 | 135 | 61 | 270 |
| II-6 | 43 | | | 144 | 123 | 164 |
| II-7 | 75 | | | 10 | 4 | 10 |
| II-10 | 21 | | | | | |
| II-12 | 21 | | | | | |
| II-13 | 67 | | | 25 | 36 | 149 |
| II-14 | 68 | 7 | 1 | 375 | 284 | 236 |
| II-15 | 71 | | | 19 | 23 | 33 |
| II-16 | 76 | | | 102 | 31 | 74 |
| II-17 | 61 | 11 | 7 | 24 | 50 | 101 |
| II-18 | 66 | 15 | 13 | 49 | 74 | 130 |
| II-21 | 70 | | | | | |
| II-22 | 21 | | | | | |
| II-23 | 23 | | | | | |
| II-24 | 60 | 19 | 24 | 324 | 219 | >395 |
| II-25 | 50 | 9 | 2 | 298 | 117 | 363 |
| II-26 | 47 | 14 | 5 | 80 | 67 | 382 |
| II-28 | 19 | | | | | |
| II-29 | 52 | 44 | 67 | 27 | 99 | 51 |
| II-32 | 64 | 16 | 21 | 237 | 36 | 392 |
| II-33 | 26 | | | | | |
| II-34 | 48 | 27 | 34 | 2 | 2 | 2 |
| II-36 | 43 | 7 | 8 | 108 | 124 | 157 |
| II-38 | 33 | | | 298 | 68 | >395 |
| II-39 | 16 | | | | | |
| II-40 | 48 | 15 | 29 | 2 | 2 | 2 |
| II-41 | 25 | | | 16 | 80 | 28 |
| II-42 | 23 | | | | | |
| II-44 | 47 | 10 | 4 | 97 | 283 | 167 |
| II-47 | 44 | 6 | 4 | 71 | 24 | 339 |
| II-50 | 30 | | | 49 | 159 | 165 |
| II-51 | 35 | | | 197 | 93 | >395 |
| II-52 | 32 | | | 118 | 76 | 319 |
| II-53 | 29 | | | >395 | 646 | >395 |
| II-54 | 52 | 5 | 8 | 176 | 28 | 329 |
| II-55 | 58 | 7 | 3 | 2 | 2 | 14 |
| II-56 | 22 | | | | | |

TABLE 1-continued

Late $I_{Na}$ Assay results

| No. | Late $I_{Na}$ 1 μM | Peak TB 1 μM | Peak UDB 1 μM | MS Rat THalf | MS Dog THalf | MS Human THalf |
| --- | --- | --- | --- | --- | --- | --- |
| II-57 | 38 | | | | 2 | 4 | 2 |
| II-58 | 25 | | | | | |
| II-59 | 22 | | | | | |
| II-60 | 32 | | | >395 | 356 | 362 |
| II-63 | 46 | 23 | 50 | 31 | 36 | 34 |
| II-64 | 43 | 3 | 9 | 16 | 7 | 11 |
| II-65 | 19 | | | | | |
| II-66 | 39 | | | 181 | >395 | >395 |
| II-67 | 47 | 12 | 7 | >395 | 270 | >395 |
| II-71 | 25 | | | 94 | 78 | 75 |
| II-72 | 31 | | | 8 | 6 | 11 |
| II-73 | 45 | 6 | 1 | 29 | 5 | 16 |
| II-75 | 53 | 11 | 7 | 75 | 85 | 371 |
| II-79 | 54 | | | | | |
| II-80 | 42 | 8 | 7 | 34 | 85 | 49 |
| II-84 | 34 | | | 51 | 98 | 107 |
| II-95 | 36 | | | 121 | 169 | 280 |
| II-96 | 51 | 10 | 5 | 34 | 81 | 84 |
| II-97 | 54 | 12 | 7 | 24 | 63 | 206 |
| II-98 | 41 | | | 16 | 34 | 31 |
| II-99 | 47 | 9 | 0 | 42 | 62 | 128 |
| II-100 | 50 | 15 | 2 | 35 | 76 | 52 |
| III-2 | 40 | | | 222 | 68 | 333 |
| III-3 | 42 | | | 104 | 122 | >395 |
| III-5 | 44 | | | 56 | 66 | 30 |
| III-6 | 18 | | | | | |
| III-8 | 19 | | | | | |
| III-9 | 57 | 15 | 15 | 81 | 27 | 100 |
| III-10 | 33 | | | 18 | 18 | 41 |
| III-11 | 30 | | | | | |
| III-12 | 21 | | | | | |
| III-14 | 39 | | | 55 | 77 | 251 |
| III-17 | 49 | | | 22 | 28 | 34 |
| III-18 | 37 | | | 20 | 23 | 25 |
| III-19 | 56 | 14 | 19 | 72 | 129 | 130 |
| III-20 | 28 | | | 54 | 61 | 41 |
| III-22 | 35 | | | 86 | 191 | 252 |
| III-23 | 51 | 6 | 12 | 42 | 209 | 254 |
| III-24 | 28 | | | 9 | 18 | 13 |
| III-25 | 16 | | | | | |
| III-26 | 26 | | | | | |
| III-27 | 52 | 15 | 15 | 43 | 83 | 268 |
| III-28 | 75 | | | 103 | 51 | 170 |
| III-29 | 58 | 10 | 9 | 26 | 18 | 19 |
| III-30 | 56 | 11 | 12 | 70 | 167 | 205 |
| III-31 | 27 | | | | | |
| III-32 | 53 | 18 | 23 | 12 | 16 | 20 |
| III-34 | 32 | | | 41 | 46 | 50 |
| III-35 | 38 | | | 296 | 85 | >395 |
| III-36 | 39 | | | 32 | 31 | 46 |
| III-37 | 50 | 7 | 4 | 96 | 37 | 157 |
| III-38 | 52 | 9 | 11 | 24 | 31 | 54 |
| III-39 | 47 | 7 | 0 | 30 | 14 | 44 |
| III-40 | 51 | 4 | 2 | 62 | 56 | 152 |
| III-41 | 24 | | | | | |
| IV-3 | 37 | | | 219 | 54 | 366 |
| IV-6 | 49 | 12 | 7 | 190 | 158 | 280 |
| IV-9 | 42 | | | 243 | 356 | >395 |
| V-2 | 17 | | | | | |
| V-11 | 22 | | | | | |
| V-12 | 26 | | | 11 | 5 | 9 |
| VII-1 | 55 | 7 | 1 | 44 | 114 | >395 |
| VIII-1 | 52 | 35 | 26 | 211 | 210 | 125 |
| VIII-3 | 58 | 21 | 12 | 227 | 164 | 285 |
| VIII-7 | 22 | | | 152 | 392 | 221 |
| VIII-13 | 20 | | | | | |
| VIII-18 | 54 | | | | | |
| VIII-19 | 61 | | | | | |
| VIII-20 | 62 | | | | | |
| VIII-21 | 58 | | | | | |
| VIII-22 | 45 | | | | | |
| VIII-23 | 48 | | | | | |
| IX-1 | 32 | | | 150 | 157 | >395 |
| IX-2 | 40 | | | 106 | 88 | 65 |

TABLE 1-continued

Late $I_{Na}$ Assay results

| No. | Late $I_{Na}$ 1 μM | Peak TB 1 μM | Peak UDB 1 μM | MS Rat THalf | MS Dog THalf | MS Human THalf |
|---|---|---|---|---|---|---|
| IX-3 | 29 | | | 355 | 320 | 304 |
| IX-4 | 20 | | | | | |
| IX-5 | 20 | | | | | |
| IX-6 | 62 | 28 | 37 | 272 | 313 | 54 |
| IX-7 | 46 | 12 | 17 | >395 | >395 | >395 |
| IX-11 | 44 | 17 | 22 | 348 | 332 | 145 |
| IX-17 | 39 | | | 302 | >395 | 257 |
| IX-22 | 29 | | | | | |
| IX-23 | 27 | | | | | |
| IX-24 | 19 | | | | | |
| IX-25 | 57 | 28 | 33 | 170 | 97 | 320 |
| IX-26 | 15 | | | | | |
| IX-27 | 18 | | | | | |
| IX-28 | 24 | | | | | |
| IX-29 | 45 | 10 | 12 | 48 | 138 | 33 |
| IX-30 | 20 | | | | | |
| IX-31 | 25 | | | | | |
| IX-32 | 29 | | | | | |
| IX-33 | 21 | | | | | |
| IX-34 | 16 | | | | | |
| IX-36 | 20 | | | | | |
| IX-39 | 30 | | | 281 | 256 | >395 |
| IX-41 | 27 | | | | | |
| IX-42 | 25 | | | | | |
| IX-44 | 27 | | | | | |
| IX-48 | 31 | | | 37 | 149 | 80 |
| IX-50 | 29 | | | 9 | 96 | 61 |
| IX-52 | 26 | | | | | |
| IX-53 | 33 | | | 28 | 93 | 198 |
| IX-56 | 28 | | | | | |
| IX-57 | 44 | 10 | 6 | 132 | 245 | 159 |
| IX-59 | 17 | | | | | |
| IX-77 | 22 | | | | | |
| IX-80 | 40 | | | 7 | 197 | 170 |
| IX-88 | 25 | | | | | |
| IX-89 | 33 | | | 192 | 177 | 125 |
| IX-90 | 27 | | | | | |
| IX-91 | 16 | | | | | |
| IX-92 | 17 | | | | | |
| IX-93 | 15 | | | | | |
| IX-94 | 33 | | | | | |
| IX-95 | 25 | | | | | |
| IX-98 | 27 | | | | | |
| IX-101 | 15 | | | | | |
| IX-102 | 27 | | | | | |
| IX-104 | 20 | | | | | |
| IX-105 | 43 | 6 | 3 | 14 | 74 | 35 |
| IX-106 | 21 | | | | | |
| IX-107 | 24 | | | | | |
| IX-108 | 30 | | | 302 | 370 | 245 |
| IX-111 | 27 | | | | | |
| IX-112 | 18 | | | | | |
| IX-113 | 17 | | | | | |
| IX-114 | 20 | | | | | |
| IX-116 | 29 | | | | | |
| IX-119 | 15 | | | | | |
| IX-122 | 36 | | | | | |
| IX-123 | 17 | | | | | |
| IX-124 | 40 | | | 106 | 88 | 65 |
| X-1 | 47 | 14 | 22 | 58 | 107 | 74 |
| X-2 | 55 | 14 | 17 | 137 | 164 | 142 |
| X-3 | 67 | 31 | 35 | 45 | 137 | 36 |
| X-4 | 52 | 27 | 25 | 122 | 126 | 103 |
| X-5 | 57 | 12 | 35 | 57 | 55 | 48 |
| X-6 | 69 | 35 | 32 | 46 | 120 | 38 |
| X-9 | 67 | 39 | 31 | 47 | 75 | 70 |

The assay results shown in the above Table suggest that compounds tested showed activity as modulators of late sodium current, for example by inhibiting (or reducing) the late sodium current.

In some embodiments the effects of a compound of Formula I are specific for the late sodium current and show little or no activity with respect to one or more other ion channels. Thus, in some embodiments, a compound having an activity of reducing late sodium current will also exhibit little or no activity with regard to the peak sodium current. In particular embodiments, a compound having an activity of reducing late sodium current will also exhibit little or no activity with regard to the hERG potassium channel.

L-Type Ca2+ Channel Assay—ChanTest:

Selected compounds were screened for block of the cardiac L-type $Ca^{2+}$ channel (hCav1.2, encoded by the human CACNA1C gene and coexpressed with the beta 2 subunit, encoded by the human CACNB2 gene and alpha2delta1, encoded by the CACNA2D1 gene). The $Ca^{2+}$ channel is heterologously expressed in a CHO (Chinese Hamster Ovary) cell line. Cells are maintained following standard tissue culture procedures and stable channel expression is maintained with appropriate selection antibiotics in the culture medium. Cells are harvested for testing on the PatchXpress automated patch clamp (Model 7000A, Molecular Devices, Sunnyvale, Calif.) by washing twice with Hank's Balanced Salt Solution, treating the cells with trypsin and re-suspending cells in culture medium ($4-6 \times 10^6$ cells in 20 mL). Cells in suspension are allowed to recover for 10 minutes in a tissue culture incubator set at 37° C. in a humidified 95% air, 5% $CO_2$ atmosphere.

The following solutions are used for electrophysiological recordings. The external solution contains (mM): 137 NaCl, 4 KCl, 1.8 $CaCl_2$, 1 $MgCl_2$, 10 Glucose, 10 HEPES (pH 7.4 with NaOH). The internal solution contains (mM): 130 Cs Aspartate, 5 $MgCl_2$, 10 EGTA, 4 ATP, 0.5 GTP, 10 HEPES, (pH adjusted to 7.2 with N-methyl-D-glucamine).

Vehicle is applied to naive cells (n≥2, where n=the number cells), for a 5-10 minute exposure interval. Each solution exchange is performed in quadruplicate. At the end of each experiment, a saturating concentration of nifedipine (10 μM) is added to block hCav1.2 current. Leak current is digitally subtracted from the total membrane current record.

Test compound stock solutions are prepared by addition of dimethyl sulfoxide (DMSO) and stored frozen. Each test compound DMSO stock is sonicated (Model 2510/5510, Branson Ultrasonics, Danbury, Conn.), at ambient room temperature for at least 20 minutes to facilitate dissolution. Test compound concentrations are prepared fresh daily by diluting stock solutions into the standard extracellular physiological saline solution (see above). The maximum percent of DMSO added with compound is 0.1%. All test compound and control solutions are placed in a glass-lined 96-well compound plate before loading on PatchXpress.

Two concentrations (1, 10 μM) of each test compound are applied at five (5) minute intervals via disposable polyethylene micropipette tips to naïve cells (n≥2, where n=the number cells/concentration). Each test compound concentration is added to the cell in quadruplicate. Total duration of exposure to each test compound concentration is 5 minutes.

Onset and steady state block of hCav1.2 (α1C/β2/α2δ☐ channels is measured using a stimulus voltage pattern consisting of a depolarizing test pulse (duration, 200 ms; amplitude, 10 mV) at 10 s intervals from a −80 mV holding potential. Peak current is measured during a step to 10 mV.

Example 257

Compounds of this invention that block cardiac late INa may also mediate UDB of other $Na^+$ channel isoforms including the major $Na^+$ channel isoforms in peripheral nervous system pain fibers, $Na_v1.7$ and 1.8. Compounds of this invention that block these channels may also be useful to decrease neuropathic pain.

In particular embodiments, a compound will exhibit a high selectivity for the late sodium current modulatory activity as compared to the activity in one or more other ion channels. The selectivity of a compound may be determined by determining the percentage reduction in late sodium current due to the compound, as measured by the assay described above. The percentage reduction in one other ion channel activity, such as the hERG potassium channel, due to the compound is determined as described above. The selectivity is determined by taking the ratio of (percentage reduction in late sodium current) to (percentage reduction in one other ion channel activity). The assays conducted to measure activities in this regard should be performed as described above, with the compound at a concentration of 10 μM (or at the upper limit of solubility, if less). In particular embodiments, the selectivity of a compound of the disclosure will be at least 5:1, e.g. at least 6:1, at least 7:1, at least 8:1, at least 9:1, at least 10:1, at least 12:1, at least 15:1, at least 20:1, or at least 25:1, when comparing the percentage reduction in late sodium current versus percentage reduction of one of the peak sodium current, the hERG potassium channel current. Selectivity data can be calculated based on the values provided in the Examples above.

Evidence supports a role for the tetrodotoxin-sensitive $Na_v1.7$ in the pathogenesis of pain. In this assay, using whole-cell patch-clamp technique, the effects of compounds of the invention on $hNa_v1.7$ ($hNa_v1.7+\beta1$ subunits) peak $Na^+$ current ($I_{Na}$) are tested as described previously (Rajamani et al, 2009). Cells are continuously maintained using MEM (Gibco-Invitrogen, Carlsbad, Calif.) supplemented with 10% heat inactivated fetal bovine serum, 1% penicillin-streptomycin, 600 μg/mL geneticin (Gibco-Invitrogen), 2 μg/mL blastocydin (Calbiochem, N.J., USA), and are incubated at 37° C. in an atmosphere of 5% $CO_2$ in air. For recording hNav1.7 $I_{Na}$, HEK293 cells are superfused with an extracellular solution containing (in mM): 140 NaCl, 3KCl, 10 HEPES, 10 glucose, 1 $MgCl_2$, 1 $CaCl_2$, pH 7.4 (with NaOH). Patch pipettes are filled with an internal solution containing (in mM): 140 CsF, 10 NaCl, 1 EGTA, 10 HEPES, pH 7.3 (with CsOH).

Whole-cell $I_{Na}$ are recorded as described previously (Rajamani et al, 2009) using an Axopatch 200B amplifier (Molecular Devices, Sunnyvale, USA). Signals are filtered at 5 kHz and sampled at 20 kHz. Patch pipettes are formed using borosilicate glass (World Precision Instruments, Sarasota, USA) using a micropipette puller (Dagan Corporation, Minneapolis, USA). The offset potential is zeroed before the pipette is attached to the cell and the voltages are not corrected for the liquid junction potential. In all recordings, 75-80% of the series resistance compensation will be achieved, thus yielding a maximum voltage error of 5 mV and leak currents are cancelled by P/-4 subtraction. pCLAMP 10.0 software (Molecular Devices) will be used to generate voltage clamp protocols and acquire data. Hold cells at a membrane potential of −100 or −120 mV and dialyzed with pipette solution for 5-7 minutes before current is recorded, to avoid time-dependent shifts in $Na^+$ channel gating within the first several minutes after patch rupture. In all experiments, the temperature of experimental solutions will be maintained at 20±1° C. using a CL-100 bipolar temperature controller (Warner Instruments, Hamden, USA).

Analyze data using Clampfit and Microcal Origin (MicroCal, Northampton, USA) software.

Example 258

Material and Methods

Expression of Human $Na_v1.1$ cDNA

All experiments with human$Na_v1.1$ are conducted as described (Kahlig, 2008). Briefly, expression of hNav1.1 is achieved by transient transfection using Qiagen Superfect reagent (5.5 μg of DNA is transfected at a plasmid mass ratio of 10:1:1 for $\alpha_1:\beta_1:\beta_2$). The human $\beta_1$ and $\beta_2$ cDNAs are cloned into plasmids containing the marker genes DsRed (DsRed-IRES2-h$\beta_1$) or eGFP (eGFP-IRES2-h$\beta_2$) flanking an internal ribosome entry site (IRES).

Electrophysiology

Whole-cell voltage-clamp recordings are used to measure the biophysical properties of WT and mutant $Na_v1.1$ channels, as described previously (Kahlig, 2008). For recording hNav1.1 $I_{Na}$, HEK293 cells are superfused with solution containing (in mM): 145 NaCl, 4 KCl, 1.8 $CaCl_2$, 1 $MgCl_2$, 10 dextrose, 10 HEPES, with a pH of 7.35 and osmolarity of 310 mOsmol/kg. The pipette solution contains (in mM): 110 CsF, 10 NaF, 20 CsCl, 2 EGTA, 10 HEPES, with a pH of 7.35 with an osmolarity of 300 mOsmol/kg. Cells are allowed to stabilize for 10 min after establishment of the whole-cell configuration before current is measured. Series resistance is compensated 90% to assure that the command potential is reached within microseconds with a voltage error <2 mV. Leak currents are subtracted by using an online P/4 procedure and all currents are low-pass Bessel filtered at 5 kHz and digitized at 50 kHz.

For use-dependent studies, cells are stimulated with depolarizing pulse trains (−10 mV, 5 ms, 300 pulses, 10 and 25 Hz) from a holding potential of 120 mV. Currents are then normalized to the peak current recorded in response to the first pulse in each frequency train. For tonic block studies, peak and persistent currents are evaluated in response to a 200 ms depolarization to 10 mV (0.2 Hz) following digital subtraction of currents recorded in the presence and absence of 0.5 μM tetrodotoxin (TTX). Persistent current is calculated during the final 10 ms of the 200 ms step. Data analysis is performed using Clampfit 9.2 (Axon Instruments, Union City, Calif., U.S.A), Excel 2002 (Microsoft, Seattle, Wash., U.S.A.), and OriginPro 7.0 (OriginLab, Northampton, Mass., U.S.A) software. Results are presented as mean±SEM.

In Vitro Pharmacology

A stock solution of 10 mM compound of Formula I is prepared in 0.1 M HCl or DMSO. A fresh dilution of the compound of Formula I in the bath solution is prepared every experimental day and the pH is readjusted to 7.35 as necessary. The final DMSO concentration was kept at 0.1% in all solutions. Direct application of the perfusion solution to the clamped cell is achieved using the Perfusion Pencil system (Automate, Berkeley, Calif.). Direct cell perfusion is driven by gravity at a flow rate of 350 μL/min using a 250 micron tip. This system sequesters the clamped cell within a perfusion stream and enables complete solution exchange within 1 second. The clamped cell is perfused continuously starting immediately after establishing the whole-cell configuration. Control currents are measured during control solution perfusion. Where appropriate, concentration inhibition curves are fit with the Hill equation: $I/I_{max}=1/[1+10^{(\log IC_{50}-I)*k}]$, where $IC_{50}$ is the concentration that produces half inhibition and k is the Hill slope factor.

Solutions containing the compounds of the disclosure are perfused for three minutes prior to current recordings to allow equilibrium (tonic) drug block. Tonic block of peak current is measured from this steady-state condition. Use-dependent block of peak current is measured during pulse number 300 of the pulse train, (−10 mV, 5 ms, 300 pulses, 10 Hz) from a holding potential of −120 mV. Two sequential pulse train stimulations are averaged to obtain mean current traces for each recording condition.

In Vivo Pharmacology

Jugular vein cannulated male Sprague Dawley rats (250-350 g, Charles River Laboratories, Hollister, Calif.) are used to study brain penetration of the compounds of the disclosure in vivo. Animal use is approved by the Institutional Animal Care and Use Committee, Gilead Sciences. Three rats per group are infused intravenously with the compound of the disclosure in saline at 85.5 µg/kg/min. After 1, 2.5 or 5 h animals are sacrificed for plasma and brain collection, and concentrations of the compound of the disclosure are measured by liquid chromatography coupled with tandem mass spectrometry (LC-MS/MS). Brain tissue is homogenated in 1% 2N HCl acidified 5% sodium fluoride (final homogenate is diluted 3-fold). Plasma and brain homogenate samples (50 µl) are precipitated along with deuterated D3-Formula I as an internal standard, vortexed and centrifuged. The supernatant (50 µL) is transferred and diluted with water (450 µl) prior to injection (10 µl). High performance liquid chromatography was performed using a Shimadzu LC-10AD liquid chromatograph and a Luna C18(2), 3 µm, 20×2.0 mm column with a mobile phase consisting of water containing 0.1% formic acid (solution A) and acetonitrile (solution B) carried out under isocratic conditions (75% solution A, 25% solution B; flow rate 0.300 ml/min). Mass spectrometric analyses are performed using an API3000 mass spectrometer (Applied Biosystems, Foster City, Calif.) operating in positive ion mode with MRM transition 428.1>98. Brain-to-plasma ratios are calculated for each sample as ng compound/g brain divided by ng compound/ml plasma.

Results

Using the above methods it may be demonstrated that the compound of the disclosure have the ability to inhibit WT-Na$_v$1.1 and a panel of Na$_v$1.1 mutant channels associated with the epilepsy and migraine syndromes GEFS+, SMEI and FHM3 suggesting the ability of the compounds of the disclosure to preferentially block the abnormal increased persistent current carried by these mutant channels. The ability of the compounds of the disclosure to cross the blood brain barrier may also be established using the above methods.

Example 259

Material and Methods

Expression of Human Na$_v$1.2 cDNA

Wild-type (WT) cDNA stably transfected in Chinese hamster ovary (CHO) cells is used to record I$_{Na}$. Unless otherwise noted, all reagents are purchased from Sigma-Aldrich (St Louis, Mo., U.S.A.).

Electrophysiology

Whole-cell voltage-clamp recordings are used to measure the biophysical properties of WT. Briefly, the pipette solution consists of (in mM) 110 CsF, 10 NaF, 20 CsCl, 2 EGTA, 10 HEPES, with a pH of 7.35 and osmolarity of 300 mOsmol/kg. The bath (control) solution contains in (mM): 145 NaCl, 4 KCl, 1.8 CaCl$_2$, 1 MgCl$_2$, 10 dextrose, 10 HEPES, with a pH of 7.35 and osmolarity of 310 mOsmol/kg. Cells are allowed to stabilize for 10 min after establishment of the whole-cell configuration before current is measured. Series resistance is compensated 90% to assure that the command potential is reached within microseconds with a voltage error <2 mV. Leak currents are subtracted by using an online P/4 procedure and all currents are low-pass Bessel filtered at 5 kHz and digitized at 50 kHz.

For clarity, representative ramp currents are low pass filtered off-line at 50 Hz. Specific voltage-clamp protocols assessing channel activation, fast inactivation and availability during repetitive stimulation are used. Results are presented as mean±SEM Tonic block of peak current is measured using a step to −10 mV (20 ms) from a holding potential of −120 mV (0.2 Hz). Use-dependent block of peak current is measured during pulse number 300 of a pulse train (−10 mV, 5 ms, 300 pulses, 10 Hz or 25 Hz) from a holding potential of −120 mV. Two sequential pulse train stimulations are averaged to obtain mean current traces for each recording condition, which are then used for offline subtraction and analysis.

For use-dependent studies, cells are stimulated with depolarizing pulse trains (−10 mV, 5 ms, 300 pulses, 10 and 25 Hz) from a holding potential of −120 mV. Currents are then normalized to the peak current recorded in response to the first pulse in each frequency train. For tonic block studies, peak current is evaluated in response to a 20 ms depolarization to −10 mV (0.2 Hz). Data analysis is performed using Clampfit 9.2 (Axon Instruments, Union City, Calif., U.S.A), Excel 2002 (Microsoft, Seattle, Wash., U.S.A.), and OriginPro 7.0 (OriginLab, Northampton, Mass., U.S.A) software. Results are presented as mean±SEM.

In Vitro Pharmacology

A stock solution of 10 mM compound of Formula I is prepared in 0.1 M HCl or DMSO. A fresh dilution of the compound of Formula I in the bath solution is prepared every experimental day and the pH is readjusted to 7.35 as necessary. The final DMSO concentration was kept at 0.1% in all solutions. Direct application of the perfusion solution to the clamped cell is achieved using the Perfusion Pencil system (Automate, Berkeley, Calif.). Direct cell perfusion is driven by gravity at a flow rate of 350 µL/min using a 250 micron tip. This system sequesters the clamped cell within a perfusion stream and enables complete solution exchange within 1 second. The clamped cell is perfused continuously starting immediately after establishing the whole-cell configuration. Control currents are measured during control solution perfusion.

Solutions are perfused for three minutes prior to current recordings to allow equilibrium (tonic) drug block. Tonic block of peak currents is measured from this steady-state condition. Three sequential current traces are averaged to obtain a mean current for each recording. The mean current traces are utilized for offline analysis. Use-dependent block of peak current is measured during pulse number 300 of the pulse train, (−10 mV, 5 ms, 300 pulses, 10 Hz) from a holding potential of −120 mV. Two sequential pulse train stimulations are averaged to obtain mean current traces for each recording condition, which are then used for offline subtraction and analysis. Where appropriate, concentration inhibition curves are fit with the Hill equation: $I/I_{max}=1/[1+10^{(log\ IC_{50}-I)*k}]$, where $IC_{50}$ is the concentration that produces half inhibition and k is the Hill slope factor.

Results

Using the above assay it may be shown that the compounds of the disclosure have the ability to inhibit WT-Na$_v$1.2 demonstrating the ability of the compounds of the disclosure to preferentially block an abnormal increased persistent current carried by this channel.

TABLE 2

| No. | $NA_v1.5^*$-LATE- | $NA_v1.5^*$-PEAK-TB- | $NA_v1.5^*$-PEAK-UDB-3 HZ- | $NA_v1.1^*$-CHAN TEST-UDB-10 HZ- | $NA_v1.2^*$-CHAN TEST-UDB-10 HZ- | RHEART $MAPD_{90}$ ATX* | HERG* |
|---|---|---|---|---|---|---|---|
| II-3 | 53 | 19 | 10 | −6 | −3.2 | −36 | 16 |
| II-14 | 68 | 7 | 1 | 19.5 | −0.7 | −56 | <10 |
| II-17 | 61 | 11 | 7 | | | | 42 |
| II-18 | 66 | 15 | 13 | | | | 30 |
| II-32 | 64 | 16 | 21 | 21 | 16.9 | −57 | 45 |
| II-36 | 43 | 7 | 8 | 7.9 | 10.9 | | 21 |
| II-38 | 33 | | | −1 | 8 | | 58 |
| II-40 | 48 | 15 | 29 | | | | 81 |
| II-54 | 52 | 5 | 8 | | | | 23 |
| II-55 | 58 | 7 | 3 | | | | |
| II-60 | 32 | | | | | −28 | 31 |
| II-66 | 39 | | | | | | 23 |
| II-67 | 47 | 12 | 7 | | | −58 | 41 |
| II-95 | 36 | | | −0.5 | −8.2 | | <10 |
| III-2 | 40 | | | 27.6 | 5 | 6 | |
| III-5 | 44 | | | 9.3 | 5.5 | | 13 |
| III-9 | 57 | 15 | 15 | 7.1 | 3.5 | −53 | 37 |
| III-19 | 56 | 14 | 19 | 19.3 | −6 | | 23 |
| III-28 | 75 | | | 40.5 | 28.8 | −40 | 51 |
| III-35 | 38 | | | | | | 17 |
| IV-6 | 49 | 12 | 7 | 3.1 | 7.1 | | <10 |
| IV-9 | 42 | | | −6.5 | 8 | | <10 |
| VIII-1 | 52 | 35 | 26 | 4.4 | 16 | −84 | |
| VIII-3 | 58 | 21 | 12 | 3.1 | 11.7 | −57 | <10 |
| VIII-7 | 22 | | | 12.1 | 18.2 | | <10 |
| VIII-20 | 62 | 27 | 23 | 11 | 17.6 | −62 | <10 |
| IX-1 | 32 | | | −5.9 | 3.8 | −6 | 17 |
| IX-124 | 40 | | | 2.6 | 7.5 | −18 | |
| IX-3 | 29 | | | 2.9 | −4.1 | −26 | 14 |
| IX-7 | 46 | 12 | 17 | 2.025 | 8.625 | −45 | <10 |
| IX-11 | 44 | 17 | 22 | | | | |
| IX-17 | 39 | | | 1.5 | 10.4 | −35 | 76 |
| IX-25 | 57 | 28 | 32 | | | | |
| IX-29 | 45 | 10 | 12 | | | | |
| IX-39 | 30 | | | 1.5 | 16.8 | −22 | 35 |
| IX-57 | 44 | 10 | 6 | | | | |
| IX-105 | 43 | 6 | 3 | | | | |
| IX-108 | 30 | | | | | | |

* % inhibition at 1 μM

Example 260

Ischemia-Induced ST Segment Elevation in Anesthetized Rabbits

This study was undertaken to determine the anti-ischemic effects of compounds of the present invention in an in vivo rabbit model.

Methods

Female New Zealand rabbits (3.0-4.0 kg) were purchased from Western Oregon Rabbitry. Animals were housed on a 12-h light and dark cycle and received standard laboratory chow and water. All experiments were performed in accordance with the Guide for the Care and Use of Laboratory Animals published by The National Research Council and with the experimental protocol approved by the Institutional Animal Care Committee of Gilead Sciences, Inc.

Rabbits were anesthetized with ketamine (35 mg/kg) and xylazine (5 mg/kg) intramuscular injection (im). A tracheotomy was performed and the trachea was intubated with an endotracheal tube. The animal was ventilated with room air supplemented with oxygen using a pressure control animal ventilator (Kent Scientific Corp., Torrington, Conn.) at a respiratory rate of 40 strokes/min and peak inspiration pressure of 10 mmH$_2$O, which was adjusted to keep blood gases and pH within the physiological range (iSTAT clinic analyzer, Heska Corp.; Waukesha, Wis.). The left femoral artery was cannulated for the measurement of blood pressure (BP). Blood samples were also withdrawn from femoral artery. The right external jugular vein was cannulated for drug/vehicle administration. Needle electrodes were inserted subcutaneously into the limbs for recording of the surface electrocardiogram (ECG). The heart was exposed via an incision in the 4$^{th}$ intercostal space (4$^{th}$ and/or 5$^{th}$ ribs were cut for a clear surgical vision). The chest was opened and a pericardial cradle was formed using 4 retractors. A coronary artery occluder, comprised of a snare made of 5 cm PE-10 tubing with a 6-0 Prolene polypropylene suture in it, was placed loosely around the left anterior descending artery (LAD) at its origin. Two unipolar electrodes, made with teflon coated silver wire attached to a small patch of filter paper, were attached on the surface of the ischemic and normal regions of the left ventricle to record epicardial electrocardiogram. Reference electrodes were placed in the open incision of the neck. The body temperature of the animal was monitored via a rectal thermometer and maintained at 37-40° C. by adjusting the surface temperature of the surgical table. Regional ischemia (15 min) was induced by ligating the LAD followed by 15 min of reperfusion caused by releasing the ligation. The heart was excised at the end of the experiment and the LAD was re-ligated. The ischemic area was visualized by perfusing the heart with 1% Evans blue in saline and calculated as a percentage of total ventricular weight. Rabbits with ischemic area less than 10% or larger than 25% were excluded from the analysis. Animals were randomly assigned to vehicle and test compound groups. Test compounds was dissolved in 5% NMP, 30% PG, 45% PEG 400 and 20% de-ionized water (dH$_2$O). Test compound was given as an iv bolus at 0.1, 0.2 and 0.4 mg/kg. After 30 min of dosing, the heart was subjected to 15 min of ischemia followed by 15 min of reperfusion.

Results

The compound of Example II-14 dose-dependently prevented the ischemia-induced ST elevation. The area under curve (AUC) for the ST segment height was reduced (vs. control) by 19% and 75% at 0.3 and 0.7 µM plasma concentration of compound of Example II-14. At the plasma concentration levels studied, compound of Example II-14 had no significant effect on blood pressure (BP), heart rate (HR) and ECG intervals prior to the ischemia. The data suggests the compound of Example II-14 prevents ischemia-induced myocardial electrical dysfunction in a dose-dependent manner.

Example 261

Rabbit Heart (RHEART) MAPD$_{90}$ ATX

Materials and Methods

New Zealand White female rabbits weighing 2.5-3.5 kg were used in this study. Animal use was approved by the Institutional Animal Care and Use Committee of Gilead Sciences, Palo Alto. Each rabbit was sedated using an intramuscular administration of a mixture of 6 mg/kg xylazine and 40 mg/kg ketamine, and then anesthetized by i.v. administration of 15 mg/kg ketamine+4 mg/kg xylazine in 1.5 ml saline via the marginal ear vein. After anesthesia was complete, the thorax was quickly opened. The heart was excised and placed in a modified Krebs-Henseleit (K-H) solution at room temperature. The K—H solution contained (in mmol/L): NaCl 118, KCl 2.8, KH$_2$PO$_4$ 1.2, CaCl$_2$ 2.5, MgSO$_4$ 0.5, pyruvate 2.0, glucose 5.5, Na$_2$EDTA 0.57 and NaHCO$_3$ 25. The solution was continuously gassed with 95% O$_2$ and 5% CO$_2$, warmed to 36-36.5° C., and adjusted to pH 7.4. The aorta was rapidly catheterized and the heart was perfused by the method of Langendorff with K—H solution at a rate of 20 mL/min, using a roller pump (Gilson Minipuls3).

Coronary perfusion pressure was measured with a Biopac MP 150 pressure transducer from a side port of the aortic catheter and continuously recorded. To facilitate exit of fluid from the chamber of the left ventricle (LV), the leaflets of the mitral valve were trimmed with fine spring-handled scissors. The right atrial wall was partially removed to allow access to the right ventricular septum.

Complete AV block was induced by thermoablation of the AV nodal area. The spontaneous ventricular rate (i.e., the ventricular escape rhythm) was a few beats per minute after successful AV nodal ablation. A bipolar Teflon-coated electrode was placed on the right ventricular septum to pace the heart. Electrical stimuli 3 ms in width and 3-fold threshold amplitude were delivered to the pacing electrode at a frequency of 1 Hz throughout an experiment using a Grass S48 stimulator. After initiation of ventricular pacing, a 30-40 min delay was allowed for heart rhythm and perfusion pressure to achieve a steady state, an essential experimental condition for recording a good quality monophasic action potential (MAP).

Assay

The total duration of the experimental protocol was limited to 2.5 h, the time during which the preparation exhibited good stability. In experiments wherein compound concentration-response data were obtained, the compound was administered in increasing concentrations sequentially with no washout period between concentrations.

Responses were recorded after the effect of a given test drug (or drug concentration) had achieved a steady-state. Continuous left ventricular MAP and 12-lead pseudo-electrocardiogram (ECG) signals were recorded using electrodes from Harvard Apparatus, Inc. An MAP electrode was placed on the epicardial left ventricular free wall below the level of atrial-ventricular valves to record MAP signals from the base of the heart left ventricle. Electrode signals were amplified and displayed on an oscilloscope for visual monitoring throughout an experiment. The MAP duration (from onset of depolarization to 100% repolarization) was measured using an on-screen caliper throughout each drug infusion period, to ensure that each response to drug had achieved a steady state before a drug concentration was changed. Electronic signals were saved on a computer hard disk for subsequent analysis. The 12-lead pseudo-ECG was generated using an isolated-heart ECG apparatus (Harvard Apparatus) attached to Biopac amplifier system. MAPs, ECGs, and coronary perfusion pressure signals were appropriately amplified, filtered, and digitized in real time using a Biopac MP 150 signal processor and displayed on a computer screen. All signals were saved on a computer hard disk for subsequent analysis. Original MAP profiles were transferred into the software program Spike-II (Cambridge Electronic Design) to measure the duration of the MAP at the level at which repolarization is 90% completed (MAPD$_{90}$).

Data Analysis

Data were plotted and analyzed using Prism version 5 (Graph Pad Software, San Diego, Calif.) and expressed as mean±SEM. The significance of differences of measurements before and after interventions in the same heart was determined by repeated measure one-way analysis of variance (ANOVA) followed by Student-Newman-Kaul's test. When treatment values were obtained from different groups of hearts that were electrically paced at 1 Hz, two-way ANOVA with repeated measures was used. A paired or un-paired student t test was used to determine the statistical difference between values of two means obtained from the same or different experiments, respectively (see results in Table 2).

What is claimed is:
1. A compound of Formula:

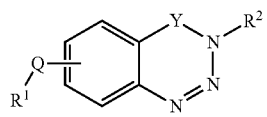

wherein:
Y is —C(R$^5$)$_2$— or —C(O)—;
Q is a covalent bond or C$_{2-4}$ alkynylene;
R$^1$ is aryl or heteroaryl;
wherein said aryl or heteroaryl are optionally substituted with trifluoromethoxy or trifluoromethyl;
R$^2$ is —R$^6$, —C$_{1-6}$ alkylene-R$^6$, —C$_{2-6}$ alkenylene-R$^6$, —C$_{2-6}$ alkynylene-R$^6$, -L-R$^6$, -L-C$_{1-6}$ alkylene-R$^6$, —C$_{1-6}$ alkylene-L-R$^6$ or —C$_{1-6}$ alkylene-L-C$_{1-6}$ alkylene-R$^6$;
L is —O—, —S—, —C(O)—, —S(O)$_2$—, —NR$^{20}$S(O)$_2$—, —S(O)$_2$NR$^{20}$—, —C(O)NR$^{20}$— or —NR$^{20}$C(O)—;

provided that when Y is —C(R$^5$)$_2$—, then L is —C(O)— or —S(O)$_2$—, and R$^2$ is -L-R$^6$, -L-C$_{1-6}$ alkylene-R$^6$, —C$_{1-6}$ alkylene-L-R$^6$ or —C$_{1-6}$ alkylene-L-C$_{1-6}$ alkylene-R$^6$;

each R$^3$ is independently hydrogen, C$_{1-6}$ alkyl, C$_{3-6}$ cycloalkyl, aryl, heteroaryl or heterocyclyl;
  wherein said C$_{1-6}$ alkyl is optionally substituted with one, two or three substituents independently selected from the group consisting of halo, —NO$_2$, C$_{3-6}$ cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;
    wherein said C$_{3-6}$ cycloalkyl, aryl, heterocyclyl and heteroaryl are optionally further substituted with one, two or three substituents independently selected from the group consisting of halo, —NO$_2$, C$_{1-6}$ alkyl, aralkyl, C$_{3-6}$ cycloalkyl, aryl, heterocyclyl, heteroaryl, —N(R$^{20}$)(R$^{22}$), —C(O)—R$^{20}$, C(O)—OR$^{20}$, —C(O)—N(R$^{20}$)(R$^{22}$), —CN and —O—R$^{20}$; and
      wherein said C$_{1-6}$ alkyl, aralkyl, C$_{3-6}$ cycloalkyl, aryl, heterocyclyl and heteroaryl are optionally further substituted with one, two or three substituents independently selected from the group consisting of halo, —NO$_2$, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

R$^4$ is hydrogen, C$_{1-6}$ alkyl, C$_{1-4}$ alkoxy, —C(O)—OR$^{20}$, —C(O)—N(R$^{20}$)(R$^{22}$), —N(R$^{20}$)—S(O)$_2$—R$^{20}$, C$_{3-6}$ cycloalkyl, aryl, heteroaryl or heterocyclyl;
  wherein said C$_{1-6}$ alkyl is optionally substituted with one, two or three substituents independently selected from the group consisting of halo, —NO$_2$, C$_{3-6}$ cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;
    wherein said C$_{3-6}$ cycloalkyl, aryl, heterocyclyl or heteroaryl are optionally further substituted with one, two or three substituents independently selected from the group consisting of halo, —NO$_2$, C$_{1-6}$ alkyl, aralkyl, C$_{3-6}$ cycloalkyl, aryl, heterocyclyl, heteroaryl, —N(R$^{20}$)(R$^{22}$), —C(O)—R$^{20}$, C(O)—OR$^{20}$, —C(O)—N(R$^{20}$)(R$^{22}$), —CN and —O—R$^{20}$; and
      wherein said C$_{1-6}$ alkyl, aralkyl, C$_{3-6}$ cycloalkyl, aryl, heterocyclyl, heteroaryl, are optionally further substituted with one, two or three substituents independently selected from the group consisting of hydroxyl, halo, —NO$_2$, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

each R$^5$ is independently hydrogen or C$_{1-6}$ alkyl;

R$^6$ is C$_{3-6}$ cycloalkyl, aryl, heteroaryl or heterocyclyl;
  wherein said C$_{3-6}$ cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, C$_{3-6}$ cycloalkyl, aryl, heterocyclyl, heteroaryl, —N(R$^{20}$)(R$^{22}$), —N(R$^{20}$)—S(O)$_2$—R$^{20}$, —N(R$^{20}$)—C(O)—R$^{22}$, —C(O)—R$^{20}$, —C(O)—OR$^{20}$, —C(O)—N(R$^{20}$)(R$^{22}$), —S(O)$_2$—R$^{20}$, —CN and —O—R$^{20}$;
    wherein said C$_{1-6}$ alkyl, C$_{3-6}$ cycloalkyl, aryl, heterocyclyl or heteroaryl are optionally further substituted with one, two or three substituents independently selected from the group consisting of halo, —NO$_2$, C$_{1-6}$ alkyl, C$_{3-6}$ cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and
      wherein said C$_{1-6}$ alkyl, C$_{3-6}$ cycloalkyl, aryl, heterocyclyl or heteroaryl are optionally further substituted with one, two or three substituents independently selected from the group consisting of C$_{1-6}$ alkyl, halo, aryl, —NO$_2$, —CF$_3$, —N(R$^{20}$)(R$^{22}$), —C(O)—R$^{20}$, —C(O)—OR$^{20}$, —C(O)—N(R$^{20}$)(R$^{22}$), —CN, —S(O)$_2$—R$^{20}$ and —O—R$^{20}$;

R$^{20}$ and R$^{22}$ are in each instance independently hydrogen, C$_{1-6}$ alkyl, C$_{2-6}$ alkenyl, C$_{2-6}$ alkynyl, C$_{3-6}$ cycloalkyl, heterocyclyl, aryl or heteroaryl; and
  wherein the C$_{1-6}$ alkyl, C$_{2-6}$ alkenyl, C$_{2-6}$ alkynyl, C$_{3-6}$ cycloalkyl, heterocyclyl, aryl or heteroaryl are optionally substituted with one, two or three substituents independently selected from the group consisting of hydroxyl, halo, C$_{1-4}$ alkyl, aralkyl, —N(R$^{26}$)(R$^{28}$), aminoacyl, —NO$_2$, —S(O)$_2$—R$^{26}$, —CN, C$_{1-3}$ alkoxy, —CF$_3$, —OCF$_3$, —OCH$_2$CF$_3$, —C(O)—NH$_2$, —C(O)—R$^{26}$, —C(O)—OR$^{26}$, aryl, C$_{3-6}$ cycloalkyl, heterocyclyl, aryl and heteroaryl;
    wherein said aralkyl, heterocyclyl or heteroaryl is optionally further substituted with C$_{1-4}$ alkyl, —CF$_3$, aryl or C$_{3-6}$ cycloalkyl; or
  when R$^{20}$ and R$^{22}$ are attached to a common nitrogen atom R$^{20}$ and R$^{22}$ may join to form a heterocyclic or heteroaryl ring which is then optionally substituted with one, two or three substituents independently selected from the group consisting of hydroxyl, halo, alkyl, aralkyl, aryl, aryloxy, aralkyloxy, heteroaryloxy, substituted amino, aminoacyl, —NO$_2$, —S(O)$_2$—R$^{26}$, —CN, C$_{1-3}$ alkoxy, hydroxymethyl, —CF$_3$, —OCF$_3$, aryl, heteroaryl and C$_{3-6}$ cycloalkyl; and R$^{26}$ and R$^{28}$ are each independently selected from the group consisting of hydrogen, C$_{1-6}$ alkyl, C$_{1-6}$ alkenyl, C$_{3-6}$ cycloalkyl, aryl and heteroaryl; and
  wherein the C$_{1-6}$ alkyl, C$_{3-6}$ cycloalkyl, aryl or heteroaryl may be further substituted with from 1 to 3 substituents independently selected from the group consisting of hydroxyl, halo, C$_{1-4}$ alkoxy, —CF$_3$, —OCF$_3$ and C$_{3-6}$ cycloalkyl;
or a pharmaceutically acceptable salt, stereoisomer, or tautomer thereof.

2. The compound of claim 1, wherein Q is a bond.

3. The compound of claim 1, wherein R$^2$ is —R$^6$, —C$_{1-6}$ alkylene-R$^6$, -L-R$^6$, -L-C$_{1-6}$ alkylene-R$^6$ or —C$_{1-6}$ alkylene-L-R$^6$;

L is —O—, —C(O)—, —S(O)$_2$—, —S(O)$_2$NR$^{20}$— or —C(O)NR$^{20}$—; provided that when Y is —C(R$^5$)$_2$—, then L is —C(O)— or —S(O)$_2$—, and R$^2$ is -L-R$^6$, -L-C$_{1-6}$ alkylene-R$^6$ or —C$_{1-6}$ alkylene-L-R$^6$; and R$^6$ is cycloalkyl, aryl, heteroaryl or heterocyclyl;
  wherein said cycloalkyl, aryl, heteroaryl or heterocyclyl are optionally substituted with one, two or three substituents independently selected from the group consisting of C$_{1-6}$ alkyl, halo, cycloalkyl, aryl, heteroaryl, —N(R$^{20}$)(R$^{22}$), —C(O)—OR$^{20}$, —S(O)$_2$—R$^{20}$, —CN and —O—R$^{20}$;
    wherein said C$_{1-6}$ alkyl or heteroaryl are optionally further substituted with one, two or three substituents independently selected from the group consisting of halo, cycloalkyl, aryl, heterocyclyl, heteroaryl, —C(O)—OR$^{20}$ and —O—R$^{20}$; and
      wherein said heteroaryl is optionally further substituted with one, two or three C$_{1-6}$ alkyl.

4. The compound of claim 3, wherein R² is
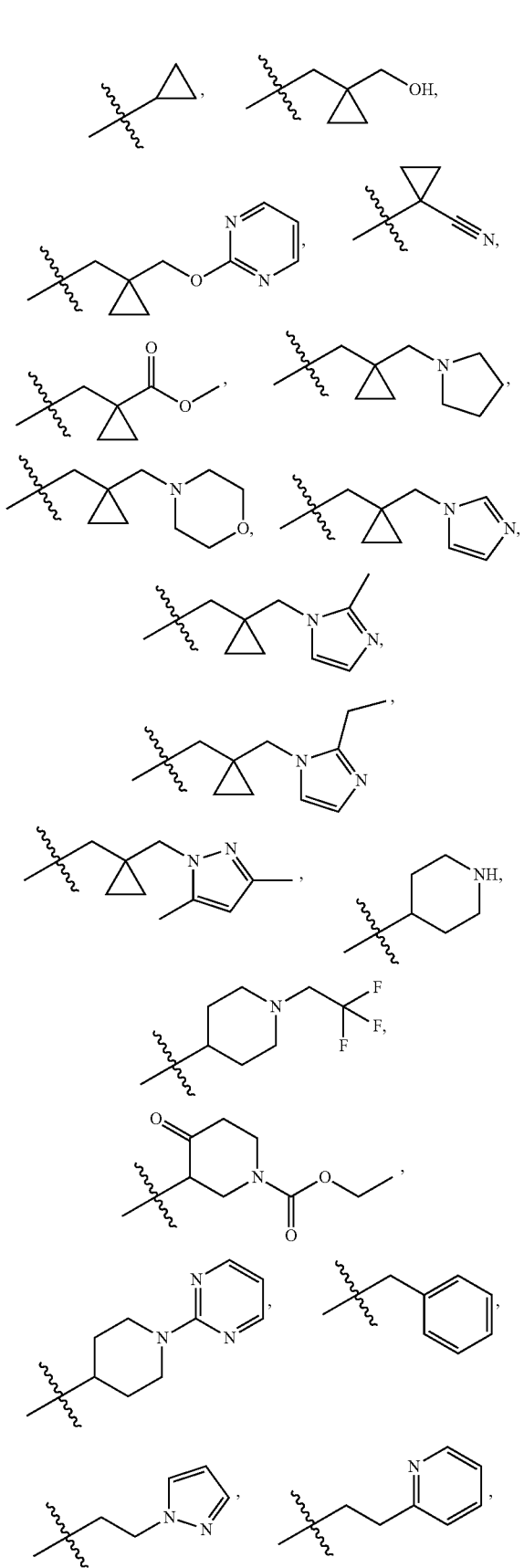
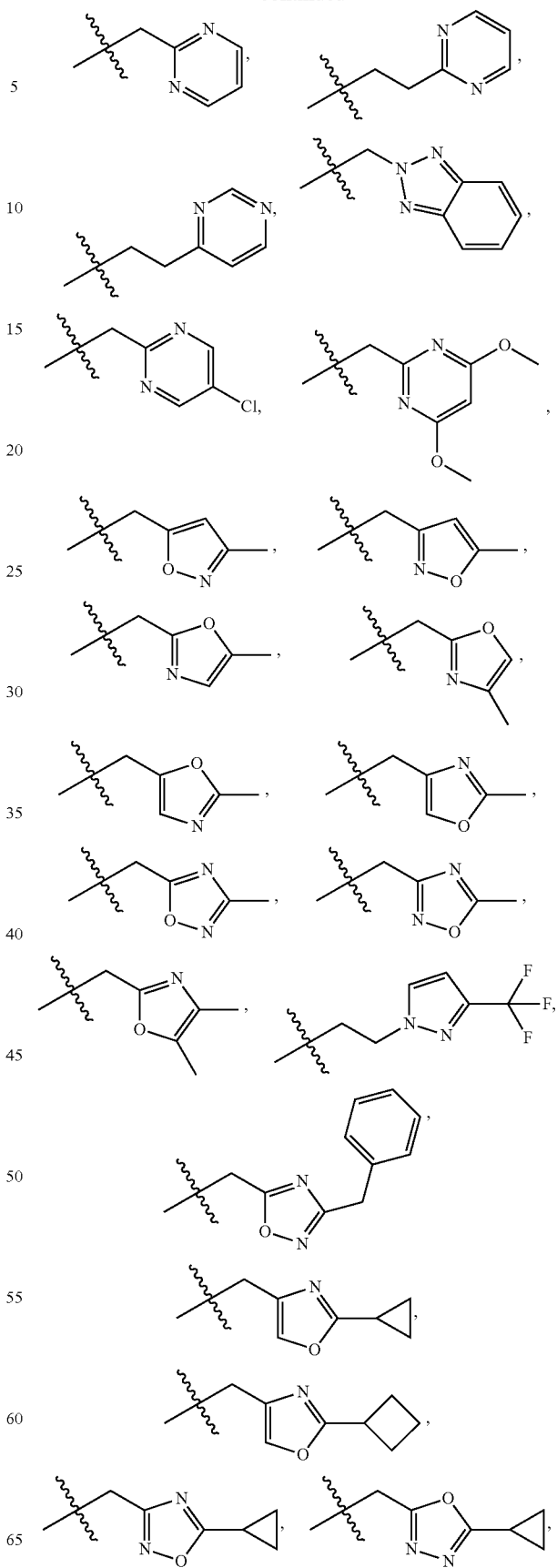

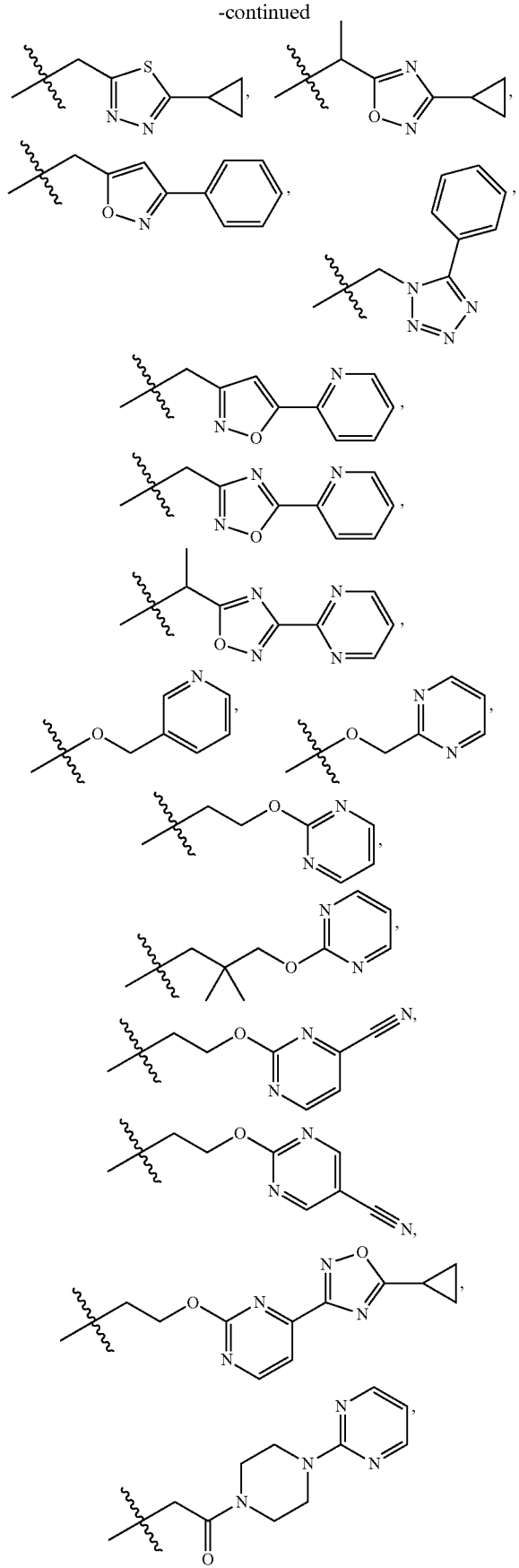
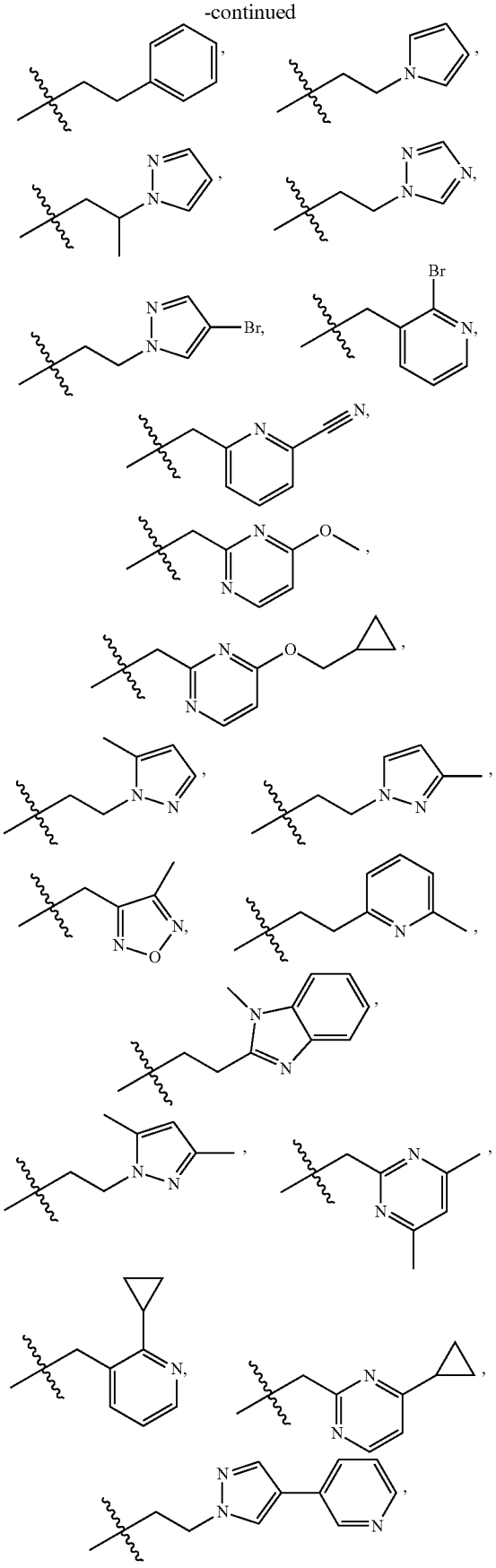

271
-continued
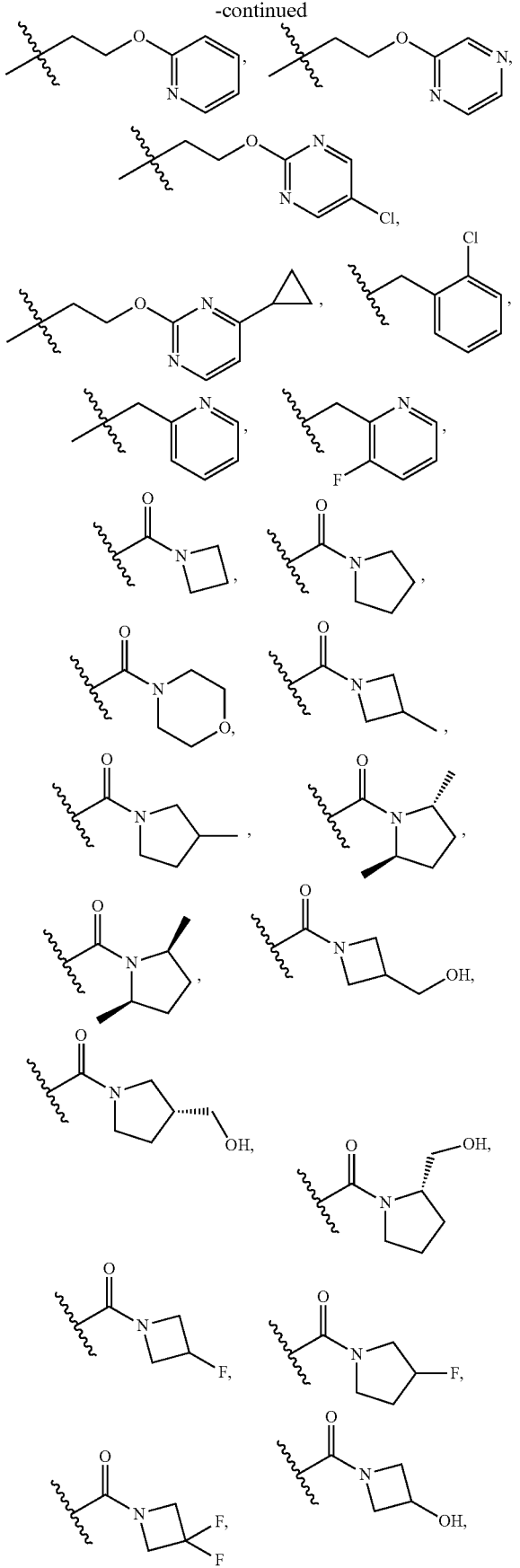
272
-continued
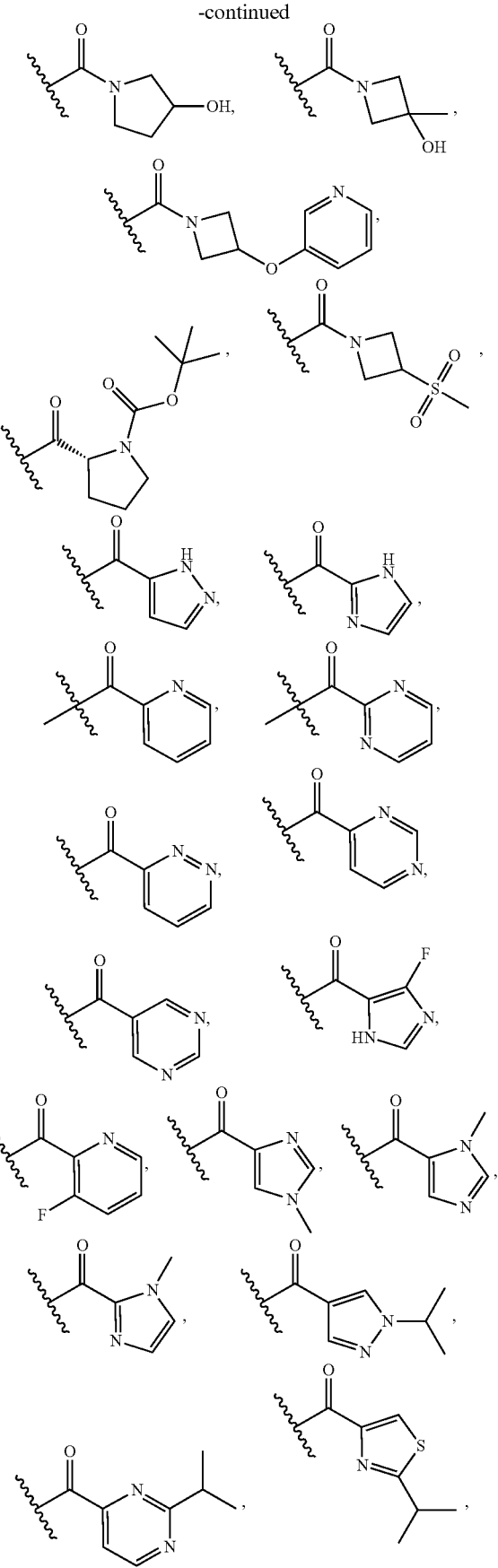

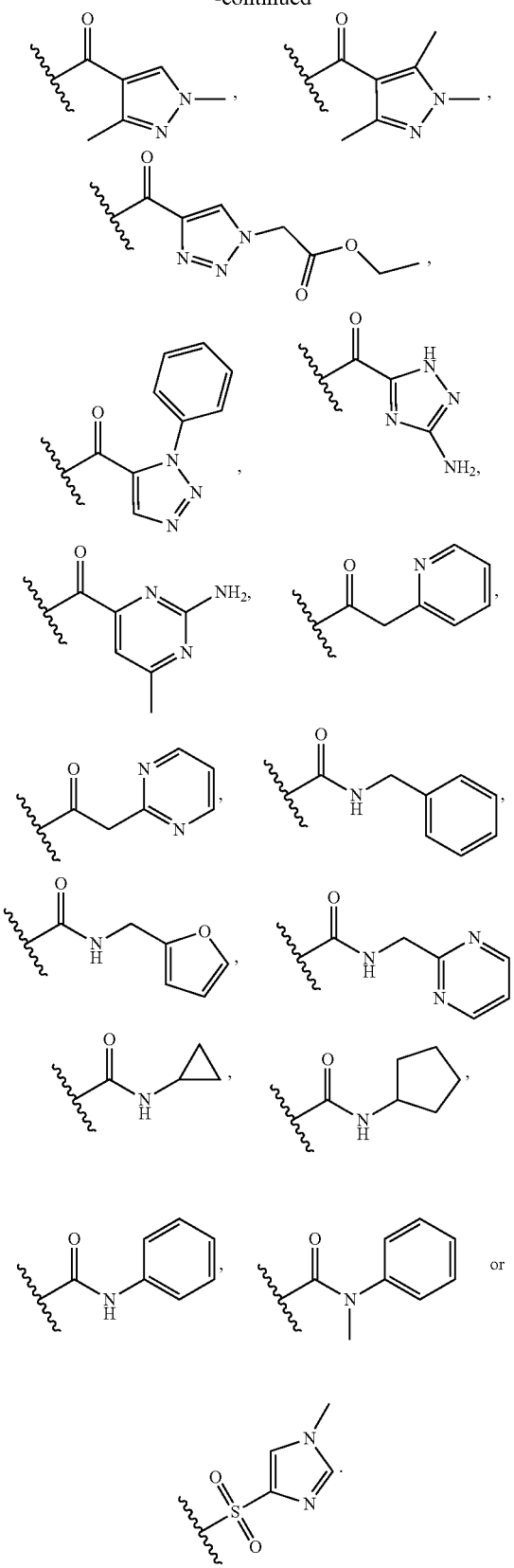

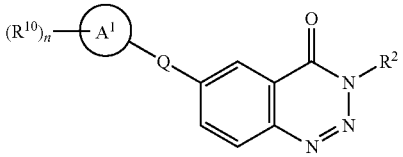

wherein Q and R² are as defined in claim 1;
A¹ is aryl or heteroaryl;
n is 0, 1, 2 or 3; and
R¹⁰ is trifluoromethoxy or trifluoromethyl.

6. The compound of claim 5, wherein Q is a bond.

7. The compound of claim 5, wherein
R² is —R⁶, —C₁₋₆ alkylene-R⁶ or -L-C₁₋₆ alkylene-R⁶;
L is —O—, —C(O)— or —C(O)— or —C(O)NR²⁰—;
R⁶ is C₃₋₆ cycloalkyl, aryl, heteroaryl or heterocyclyl;
  wherein said C₃₋₆ cycloalkyl, heteroaryl or heterocyclyl are optionally substituted with one, two or three substituents independently selected from the group consisting of C₁₋₆ alkyl, halo, C₃₋₆ cycloalkyl, aryl, heteroaryl, —C(O)—OR²⁰, —CN and —O—R²⁰;
  wherein said C₁₋₆ alkyl or heteroaryl are optionally further substituted with one, two or three substituents independently selected from the group consisting of halo, cycloalkyl, aryl, heterocyclyl, heteroaryl, and —O—R²⁰; and
  wherein said heteroaryl is optionally further substituted with one, two or three C₁₋₆ alkyl.

8. The compound of claim 5, wherein R² is

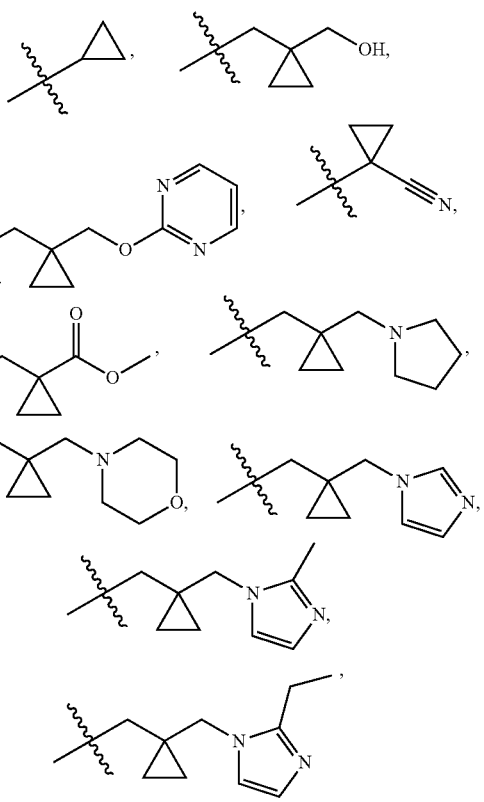

5. The compound of claim 1, wherein the compound of Formula I is represented by Formula II:

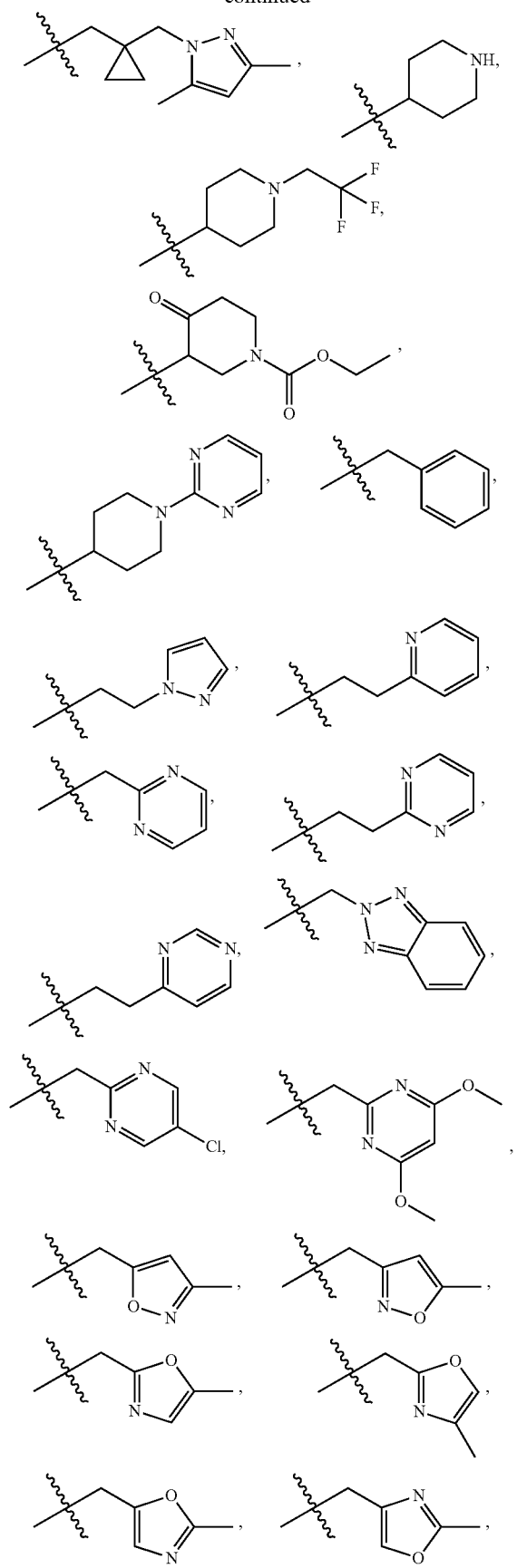
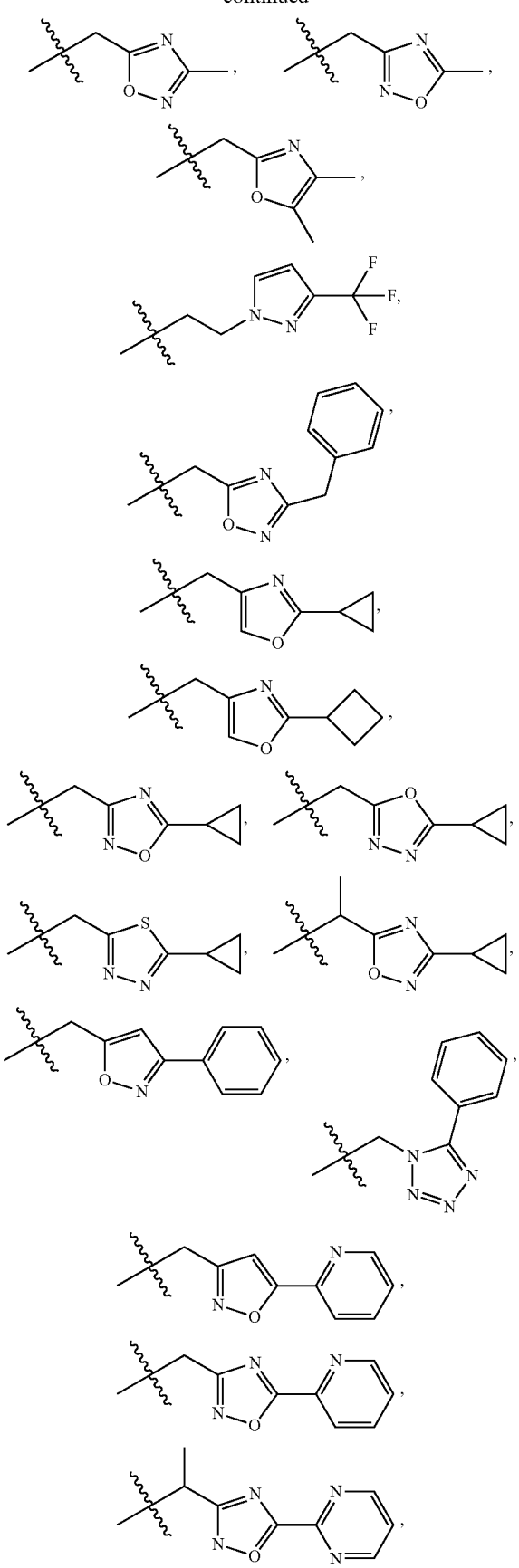

9. A compound selected from the group consisting of:

3-((3-methyl-1,2,4-oxadiazol-5-yl)methyl)-6-(4-(trifluoromethoxy)phenyl)benzo[d][1,2,3]triazin-4(3H)-one
3-((5-chloropyrimidin-2-yl)methyl)-6-(4-(trifluoromethoxy)phenyl)benzo[d][1,2,3]triazin-4(3H)-one
3-((5-methyl-1,2,4-oxadiazol-3-yl)methyl)-6-(4-(trifluoromethoxy)phenyl)benzo[d][1,2,3]triazin-4(3H)-one
3-((3-methyl-1,2,4-oxadiazol-5-yl)methyl)-6-(4-phenoxyphenyl)benzo[d][1,2,3]triazin-4(3H)-one
3-((3-phenylisoxazol-5-yl)methyl)-6-(4-(trifluoromethoxy)phenyl)benzo[d][1,2,3]triazin-4(3H)-one
3-((3-benzyl-1,2,4-oxadiazol-5-yl)methyl)-6-(4-(trifluoromethoxy)phenyl)benzo[d][1,2,3]triazin-4(3H)-one
3-(2-(1H-pyrazol-1-yl)ethyl)-6-(4-(trifluoromethoxy)phenyl)benzo[d][1,2,3]triazin-4(3H)-one
3 ((5-cyclopropyl-1,2,4-oxadiazol-3-yl)methyl)-6-(4-(trifluoromethoxy)phenyl)benzo[d][1,2,3]triazin-4(3H)-one
3-(2-(pyridin-2-yl)ethyl)-6-(4-(trifluoromethoxy)phenyl)benzo[d][1,2,3]triazin-4(3H)-one
6-(4-(4-chlorophenoxy)phenyl)-3-((3-methyl-1,2,4-oxadiazol-5-yl)methyl)benzo[d][1,2,3]triazin-4(3H)-one
3-(2-(pyrimidin-4-yl)ethyl)-6-(4-(trifluoromethoxy)phenyl)benzo[d][1,2,3]triazin-4(3H)-one
3-(2-(pyrimidin-2-yl)ethyl)-6-(4-(trifluoromethoxy)phenyl)benzo[d][1,2,3]triazin-4(3H)-one
3-((5-phenyl-1H-tetrazol-1-yl)methyl)-6-(4-(trifluoromethoxy)phenyl)benzo[d][1,2,3]triazin-4(3H)-one
3-cyclopropyl-6-(4-(trifluoromethoxy)phenyl)benzo[d][1,2,3]triazin-4(3H)-one
3-((4,5-dimethyloxazol-2-yl)methyl)-6-(4-(trifluoromethoxy)phenyl)benzo[d][1,2,3]triazin-4(3H)-one
3-(pyrimidin-2-ylmethyl)-6-(4-(trifluoromethoxy)phenyl)benzo[d][1,2,3]triazin-4(3H)-one
3-((3-methylisoxazol-5-yl)methyl)-6-(4-(trifluoromethoxy)phenyl)benzo[d][1,2,3]triazin-4(3H)-one
3-((5-methylisoxazol-3-yl)methyl)-6-(4-(trifluoromethoxy)phenyl)benzo[d][1,2,3]triazin-4(3H)-one
3-((2H-benzo[d][1,2,3]triazol-2-yl)methyl)-6-(4-(trifluoromethoxy)phenyl)benzo[d][1,2,3]triazin-4(3H)-one
3-(2-(1H-pyrazol-1-yl)ethyl)-6-(4-(4-chlorophenoxy)phenyl)benzo[d][1,2,3]triazin-4(3H)-one
3-(2-(pyrimidin-2-yloxy)ethyl)-6-(4-(trifluoromethoxy)phenyl)benzo[d][1,2,3]triazin-4(3H)-one
1-(4-oxo-6-(4-(trifluoromethoxy)phenyl)benzo[d][1,2,3]triazin-3 (4H)-yl)cyclopropanecarbonitrile
3-((1-((2-methyl-1H-imidazol-1-yl)methyl)cyclopropyl)methyl)-6-(4-(trifluoromethoxy)phenyl)benzo[d][1,2,3]triazin-4(3H)-one
2-(2-(4-oxo-6-(4-(trifluoromethoxy)phenyl)benzo[d][1,2,3]triazin-3 (4H)-yl)ethoxy)pyrimidine-4-carbonitrile
3-(piperidin-4-yl)-6-(4-(trifluoromethoxy)phenyl)benzo[d][1,2,3]triazin-4(3H)-one
3-(1-(pyrimidin-2-yl)piperidin-4-yl)-6-(4-(trifluoromethoxy)phenyl)benzo[d][1,2,3]triazin-4(3H)-one
3-((1-(morpholinomethyl)cyclopropyl)methyl)-6-(4-(trifluoromethoxy)phenyl)benzo[d][1,2,3]triazin-4(3H)-one
3-(2-oxo-2-(4-(pyrimidin-2-yl)piperazin-1-yl)ethyl)-6-(4-(trifluoromethoxy)phenyl)benzo[d][1,2,3]triazin-4(3H)-one
3-benzyl-6-(4-(trifluoromethoxy)phenyl)benzo[d][1,2,3]triazin-4(3H)-one
3-((4,6-dimethoxypyrimidin-2-yl)methyl)-6-(4-(trifluoromethoxy)phenyl)benzo[d][1,2,3]triazin-4(3H)-one
3-((5-(pyridin-2-yl)isoxazol-3-yl)methyl)-6-(4-(trifluoromethoxy)phenyl)benzo[d][1,2,3]triazin-4(3H)-one
1-(4-(4-oxo-3-(2-(pyrimidin-2-yloxy)ethyl)-3,4-dihydrobenzo[d][1,2,3]triazin-6-yl)phenyl)cyclopropanecarbonitrile
2-(2-(4-oxo-6-(4-(trifluoromethoxy)phenyl)benzo[d][1,2,3]triazin-3 (4H)-yl)ethoxy)pyrimidine-5-carbonitrile
6-(4-(trifluoromethoxy)phenyl)-3-(2-(3-(trifluoromethyl)-1H-pyrazol-1-yl)ethyl)benzo[d][1,2,3]triazin-4(3H)-one
3-(1-(3-(pyrimidin-2-yl)-1,2,4-oxadiazol-5-yl)ethyl)-6-(4-(trifluoromethoxy)phenyl)benzo[d][1,2,3]triazin-4(3H)-one
3-((5-(pyridin-2-yl)-1,2,4-oxadiazol-3-yl)methyl)-6-(4-(trifluoromethoxy)phenyl)benzo[d][1,2,3]triazin-4(3H)-one
methyl 1-((4-oxo-6-(4-(trifluoromethoxy)phenyl)benzo[d][1,2,3]triazin-3(4H)-yl)methyl)cyclopropanecarboxylate
3-(pyrimidin-2-ylmethoxy)-6-(4-(trifluoromethoxy)phenyl)benzo[d][1,2,3]triazin-4(3H)-one
3-((1-((2-ethyl-1H-imidazol-1-yl)methyl)cyclopropyl)methyl)-6-(4-(trifluoromethoxy)phenyl)benzo[d][1,2,3]triazin-4(3H)-one
3-((1-(((1H-imidazol-1-yl)methyl)cyclopropyl)methyl)-6-(4-(trifluoromethoxy)phenyl)benzo[d][1,2,3]triazin-4(3H)-one 3-(pyridin-3-ylmethoxy)-6-(4-(trifluoromethoxy)phenyl)
benzo[d][1,2,3]triazin-4(3H)-one 3-(2-(4-(5-cyclopropyl-1,2,4-oxadiazol-3-yl)pyrimidin-
2-yloxy)ethyl)-6-(4-(trifluoromethoxy)phenyl)benzo
[d][1,2,3]triazin-4(3H)-one 3-((1-(pyrrolidin-1-ylmethyl)cyclopropyl)methyl)-6-(4-
(trifluoromethoxy)phenyl)benzo[d][1,2,3]triazin-4
(3H)-one 3-((1-((3,5-dimethyl-1H-pyrazol-1-yl)methyl)cyclopro-
pyl)methyl)-6-(4-(trifluoromethoxy)phenyl)benzo[d]
[1,2,3]triazin-4(3H)-one 6-(4-(4-chlorophenoxy)phenyl)-3-(2-oxo-2-(4-(pyrimi-
din-2-yl)piperazin-1-yl)ethyl)benzo[d][1,2,3]triazin-4
(3H)-one 3-((5-cyclopropyl-1,3,4-thiadiazol-2-yl)methyl)-6-(4-(tri-
fluoromethoxy)phenyl)benzo[d][1,2,3]triazin-4(3H)-
one 3-((5-cyclopropyl-1,3,4-oxadiazol-2-yl)methyl)-6-(4-(tri-
fluoromethoxy)phenyl)benzo[d][1,2,3]triazin-4(3H)-
one 3-(1-(2,2,2-trifluoroethyl)piperidin-4-yl)-6-(4-(trifluo-
romethoxy)phenyl)benzo[d][1,2,3]triazin-4(3H)-one ethyl 4-oxo-3-(4-oxo-6-(4-(trifluoromethoxy)phenyl)
benzo[d][1,2,3]triazin-3(4H)-yl)piperidine-1-carboxy-
late 6-(4-cyclopropylphenyl)-3-((3-methyl-1,2,4-oxadiazol-5-
yl)methyl)benzo[d][1,2,3]triazin-4(3H)-one 3-((1-(hydroxymethyl)cyclopropyl)methyl)-6-(4-(trifluo-
romethoxy)phenyl)benzo[d][1,2,3]triazin-4(3H)-one 3-(1-(3-cyclopropyl-1,2,4-oxadiazol-5-yl)ethyl)-6-(4-(tri-
fluoromethoxy)phenyl)benzo[d][1,2,3]triazin-4(3H)-
one 3-((1-((pyrimidin-2-yloxy)methyl)cyclopropyl)methyl)-
6-(4-(trifluoromethoxy)phenyl)benzo[d][1,2,3]triazin-
4(3H)-one 3-(2,2-dimethyl-3-(pyrimidin-2-yloxy)propyl)-6-(4-(trif-
luoromethoxy)phenyl)benzo[d][1,2,3]triazin-4(3H)-
one 3-((2-methyloxazol-5-yl)methyl)-6-(4-(trifluoromethoxy)
phenyl)benzo[d][1,2,3]triazin-4(3H)-one 3-((5-methyloxazol-2-yl)methyl)-6-(4-(trifluoromethoxy)
phenyl)benzo[d][1,2,3]triazin-4(3H)-one 3-((4-methyloxazol-2-yl)methyl)-6-(4-(trifluoromethoxy)
phenyl)benzo[d][1,2,3]triazin-4(3H)-one 3-((2-cyclobutyloxazol-4-yl)methyl)-6-(4-(trifluo-
romethoxy)phenyl)benzo[d][1,2,3]triazin-4(3H)-one 3-((2-methyloxazol-4-yl)methyl)-6-(4-(trifluoromethoxy)
phenyl)benzo[d][1,2,3]triazin-4(3H)-one 3-((2-cyclopropyloxazol-4-yl)methyl)-6-(4-(trifluo-
romethoxy)phenyl)benzo[d][1,2,3]triazin-4(3H)-one 3-((5-methyl-1,2,4-oxadiazol-3-yl)methyl)-6-(6-(2,2,2-
trifluoroethoxy)pyridin-3-yl)benzo[d][1,2,3]triazin-4
(3H)-one 3-(2-(pyrimidin-2-yloxy)ethyl)-6-(6-(trifluoromethyl)
pyridin-3-yl)benzo[d][1,2,3]triazin-4(3H)-one 6-(2-(piperidin-1-yl)pyrimidin-5-yl)-3-(2-(pyrimidin-2-
yloxy)ethyl)benzo[d][1,2,3]triazin-4(3H)-one 3-(2-(pyrimidin-2-yloxy)ethyl)-6-((4-(trifluoromethoxy)
phenyl)ethynyl)benzo[d][1,2,3]triazin-4(3H)-one or a pharmaceutically acceptable salt, stereoisomer, or
tautomer, thereof.

10. A compound of Formula:

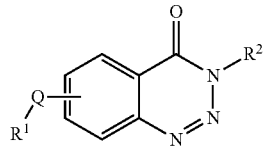

wherein:
R¹ is aryl or heteroaryl;
  wherein said aryl or heteroaryl are optionally sub-
    stituted with trifluoromethoxy or trifluoromethyl;
R² is hydrogen, $C_{1-15}$ alkyl, $C_{1-4}$ alkoxy, —C(O)—O—
  $R^{26}$, —C(O)—N($R^{26}$)($R^{28}$), —N($R^{20}$)—S(=O)$_2$—
  $R^{20}$, cycloalkyl, aryl, heteroaryl, or heterocyclyl;
  wherein said alkyl, alkoxy, cycloalkyl, and heterocyclyl
    are optionally substituted with one, two, or three
    substituents independently selected from the group
    consisting of hydroxyl, alkyl, alkoxy, alkynyl, halo,
    —NO$_2$, —O—CF$_3$, —O—CHF$_2$, aryl, heterocyclyl,
    heteroaryl, cycloalkyl, —N($R^{20}$)($R^{22}$), —C(O)—
    $R^{20}$, —C(O)—O—$R^{20}$, —C(O)—N($R^{20}$)($R^{22}$),
    —CN, oxo, and —O—$R^{20}$;
  wherein said alkyl, alkoxy, cycloalkyl, aryl, hetero-
    cyclyl, or heteroaryl are optionally further substi-
    tuted with one, two, or three substituents indepen-
    dently selected from the group consisting of
    hydroxyl, halo, —NO$_2$, —CF$_3$, —O—CF$_3$, $C_{1-6}$
    alkyl, $C_{1-4}$ alkoxy, benzyl, aryl, heterocyclyl, het-
    eroaryl, cycloalkyl, —N($R^{20}$)($R^{22}$), —C(O)—
    $R^{20}$, —C(O)—O—$R^{20}$, —C(O)—N($R^{20}$)($R^{22}$),
    —CN, and —O—$R^{20}$; and
  wherein said $C_{1-6}$ alkyl, $C_{1-4}$ alkoxy, benzyl, aryl,
    heterocyclyl, heteroaryl, cycloalkyl, are option-
    ally further substituted with one, two, or three
    substituents independently selected from the
    group consisting of hydroxyl, halo, —NO$_2$,
    —O—CF$_3$, —CF$_3$, —O—CHF$_2$, —N($R^{20}$)
    ($R^{22}$), —C(O)—$R^{20}$, —C(O)—O—$R^{20}$,
    —C(O)—N($R^{20}$)($R^{22}$), —CN, —S(O)$_2$—$R^{20}$
    and —O—$R^{20}$;
Q is a covalent bond or $C_{2-4}$ alkynylene;
R³ is hydrogen, $C_{1-15}$ alkyl, $C_{1-4}$ alkoxy, cycloalkyl, aryl,
  heteroaryl, or heterocyclyl;
  wherein said alkyl is optionally substituted with one,
    two, or three substituents independently selected
    from the group consisting of halo, —NO$_2$, aryl,
    heterocyclyl, heteroaryl, cycloalkyl, —N($R^{20}$)($R^{22}$),
    —C(O)—$R^{20}$, —C(O)—O—$R^{20}$, —C(O)—N($R^{20}$)
    ($R^{22}$), —CN, and —O—$R^{20}$;
  wherein said cycloalkyl, aryl, heterocyclyl, or het-
    eroaryl are optionally further substituted with one,
    two, or three substituents independently selected
    from the group consisting of halo, —NO$_2$, $C_{1-6}$
    alkyl, benzyl, aryl, heterocyclyl, heteroaryl,
    cycloalkyl, —N($R^{20}$)($R^{22}$), —C(O)—$R^{20}$,
    —C(O)—O$R^{20}$, —C(O)—N($R^{20}$)($R^{22}$), —CN,
    and —O—$R^{20}$; and
  wherein said $C_{1-6}$ alkyl, benzyl, aryl, heterocyclyl,
    heteroaryl, cycloalkyl, are optionally further
    substituted with one, two, or three substituents
    independently selected from the group consist-
    ing of halo, —NO$_2$, —N($R^{20}$)($R^{22}$), —C(O)—
    $R^{20}$, —C(O)—O$R^{20}$, —C(O)—N($R^{20}$)($R^{22}$),
    —CN, and —O—$R^{20}$;

$R^4$ is hydrogen, $C_{1-15}$ alkyl, $C_{1-4}$ alkoxy, —C(O)—O—$R^{26}$, —C(O)—N($R^{26}$)($R^{28}$), —N($R^{20}$)—S(=O)$_2$—$R^{20}$, cycloalkyl, aryl, heteroaryl, or heterocyclyl;

wherein said alkyl is optionally substituted with one, two, or three substituents independently selected from the group consisting of halo, —NO$_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$;

wherein said cycloalkyl, aryl, heterocyclyl, or heteroaryl are optionally further substituted with one, two, or three substituents independently selected from the group consisting of halo, —NO$_2$, $C_{1-6}$ alkyl, benzyl, aryl, heterocyclyl, heteroaryl, cycloalkyl, —N($R^{20}$)($R^{22}$), —C(O)—$R^{20}$, —C(O)—O$R^{20}$, —C(O)—N($R^{20}$)($R^{22}$), —CN, and —O—$R^{20}$; and wherein said $C_{1-6}$ alkyl, benzyl, aryl, heterocyclyl, heteroaryl, cycloalkyl, are optionally further substituted with one, two, or three substituents independently selected from the group consisting of halo, —NO$_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$;

$R^{20}$ and $R^{22}$ are in each instance independently selected from the group consisting of hydrogen, $C_1$-$C_{15}$ alkyl, $C_2$-$C_{15}$ alkenyl, $C_2$-$C_{15}$ alkynyl, cycloalkyl, heterocyclyl, aryl, and heteroaryl; and wherein the alkyl, alkenyl, alkynyl, heterocyclyl, aryl, and heteroaryl are optionally substituted with one, two, or three substituents independently selected from the group consisting of hydroxyl, halo, $C_{1-4}$ alkyl, monoalkylamino, dialkylamino, alkyl amide, aryl amide, heteroaryl amide, —NO$_2$, —SO$_2R^{26}$, —CN, $C_{1-3}$ alkoxy, —CF$_3$, —OCF$_3$, —OCH$_2$CF$_3$, —C(O)—NH$_2$, aryl, cycloalkyl, and heteroaryl;

wherein said heteroaryl is optionally further substituted with $C_{1-4}$ alkyl, or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two, or three substituents independently selected from the group consisting of hydroxyl, halo, alkyl, benzyl, phenyl, phenoxy, benzyloxy, monoalkylamino, dialkylamino, alkyl amide, aryl amide, heteroaryl amide, —NO$_2$, —SO$_2R^{26}$, —CN, $C_{1-3}$ alkoxy, —CF$_3$, —OCF$_3$, aryl, heteroaryl and cycloalkyl;

$R^{25}$ is in each instance independently a covalent bond or $C_1$-$C_3$ alkylene optionally substituted with one or two $C_1$-$C_3$ alkyl groups; and $R^{26}$ and $R^{28}$ are in each instance independently selected from the group consisting of hydrogen, alkyl, and cycloalkyl; and wherein the alkyl, phenyl and cycloalkyl may be further substituted with from 1 to 3 substituents independently selected from the group consisting of hydroxyl, halo, $C_{1-4}$ alkoxy, —CF$_3$, and —OCF$_3$;

or a pharmaceutically acceptable salt, stereoisomer, or tautomer, thereof.

11. A pharmaceutical composition comprising a compound according to claim 1 and one or more pharmaceutically acceptable carriers.

12. A method of treating epilepsy in a human, comprising administering to a human in need thereof a therapeutically effective dose of a compound of claim 1.

\* \* \* \* \*